US008878006B2

(12) United States Patent  
Lee et al.

(10) Patent No.: US 8,878,006 B2
(45) Date of Patent: Nov. 4, 2014

(54) PLANTS HAVING ENHANCED YIELD-RELATED TRAITS AND A METHOD FOR MAKING THE SAME

(75) Inventors: Sang Yeol Lee, Seoul (KR); Yang Do Choi, Seoul (KR); Ho Hee Jang, Seoul (KR); Ohkmae K. Park, Seoul (KR); Huh Sun Mi, Seoul (KR)

(73) Assignees: Crop Design N.V., Zwijnaarde (BE); Crop Functional Genomics Center, Seoul (KR)

( * ) Notice: Subject to any disclaimer, the term of this patent is extended or adjusted under 35 U.S.C. 154(b) by 616 days.

(21) Appl. No.: 12/601,023

(22) PCT Filed: May 23, 2008

(86) PCT No.: PCT/EP2008/056381
§ 371 (c)(1),
(2), (4) Date: Nov. 20, 2009

(87) PCT Pub. No.: WO2008/142163
PCT Pub. Date: Nov. 27, 2008

(65) Prior Publication Data
US 2010/0170011 A1  Jul. 1, 2010

Related U.S. Application Data

(60) Provisional application No. 60/932,226, filed on May 29, 2007, provisional application No. 60/937,994, filed on Jun. 29, 2007.

(30) Foreign Application Priority Data

May 23, 2007 (EP) ..................................... 07108768
Jun. 12, 2007 (EP) ..................................... 07110086

(51) Int. Cl.
*A01H 5/00* (2006.01)
*A01H 5/10* (2006.01)
*C12N 15/82* (2006.01)
*C07K 14/415* (2006.01)

(52) U.S. Cl.
CPC .......... *C12N 15/8261* (2013.01); *C07K 14/415* (2013.01)
USPC ........... 800/287; 800/290; 800/298; 435/468; 435/419; 435/320.1; 536/23.2

(58) Field of Classification Search
None
See application file for complete search history.

(56) References Cited

U.S. PATENT DOCUMENTS

2006/0143729 A1* 6/2006 Alexandrov et al. ......... 800/278

FOREIGN PATENT DOCUMENTS

| EP | 1217068 A2 | 6/2002 |
|---|---|---|
| JP | 2004/283028 | * 10/2004 |
| JP | 2004/283028 A | 10/2004 |
| WO | WO-99/53016 A2 | 10/1999 |
| WO | WO-01/64928 A2 | 9/2001 |
| WO | WO-2004/013304 A2 | 2/2004 |
| WO | WO 2004/035798 A | * 4/2004 |
| WO | WO-2004/035798 A2 | 4/2004 |
| WO | WO 2005/116082 | * 12/2005 |
| WO | WO-2005/116082 A1 | 12/2005 |

OTHER PUBLICATIONS

Xu et al (Plant Molecular Biology 27: 237-248 (1995) p. 237-248).*
Friedberg (Brief. Bioinformatics (2006) 7: 225-242).*
König et al, JBC, 2003, vol. 278 (27) 24409-24420.*
*Arabidopsis thaliana* 2-Cys peroxiredoxin BAS1 (AT3G11630) mRNA, complete cds NCBI Reference Sequence: NM_111995.2 (2000).*
Thornton et al (Nature structural biology, structural genomics supplement, Nov. 2000, pp. 991-994.*
Benfey et al (The EMBO Journal vol. 9 No. 6 pp. 1677-1684 (1990).*
Baier et al (The Plant Journal (1997) 12(1) 179-190).*
Klughammer, B., et al., "Inactivation by Gene Disruption of 2-Cysteine-Peroxiredoxin in *Synechocystis* sp. PCC 6803 Leads to Increased Stress Sensitivity", Physiologia Plantarum, vol. 104, (1998), pp. 699-706.
Finkemeier, I., et al., "The Mitochondrial Type II Peroxiredoxin F Is Essential for Redox Homeostasis and Root Growth of *Arabidopsis thaliana* Under Stress", The Journal of Biological Chemistry, vol. 280, No. 13, (2005), pp. 12168-12180.
Baier, M., et al., "Antisense Suppression of 2-Cysteine Peroxiredoxin in *Arabidopsis* Specifically Enhances the Activities and Expression of Enzymes Associated with Ascorbate Metabolism But Not Glutathione Metabolism", Plant Physiology, vol. 124, (2000), pp. 823-832.
Dietz, K.-J., et al., "The Function of Peroxiredoxins in Plant Organelle Redox Metabolism", Journal of Experimental Botany, vol. 57, No. 8, (2006), pp. 1697-1709.

* cited by examiner

*Primary Examiner* — Brent T Page
*Assistant Examiner* — Lee A Visone
(74) *Attorney, Agent, or Firm* — Drinker Biddle & Reath LLP

(57) ABSTRACT

The present invention relates generally to the field of molecular biology and concerns a method for enhancing plant yield-related traits relative to control plants. More specifically, the present invention concerns a method for enhancing yield related traits in plants relative to control plants, by modulating, preferably increasing, expression in the roots of a plant, of a nucleic acid sequence encoding a 2-cysteine peroxiredoxin (2-Cys PRX); or by modulating expression of a nucleic acid encoding an ANN polypeptide in a plant. The present invention also concerns plants having modulated, preferably increased, expression in the roots, of a nucleic acid sequence encoding a 2-Cys PRX, or having modulated expression of a nucleic acid encoding an ANN polypeptide, which plants have enhanced yield-related traits relative to control plants. The invention also provides constructs useful in the methods of the invention.

22 Claims, 68 Drawing Sheets

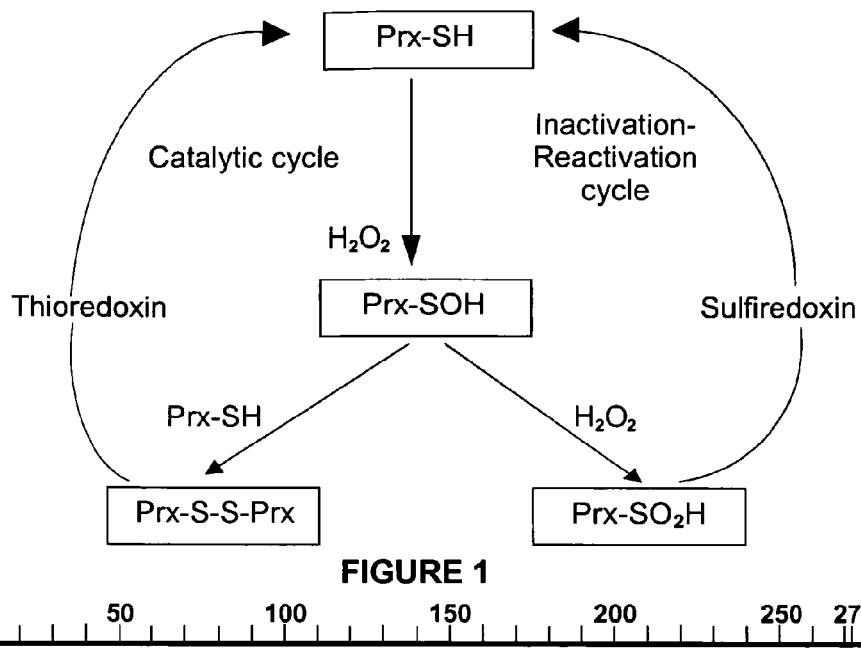

FIGURE 1

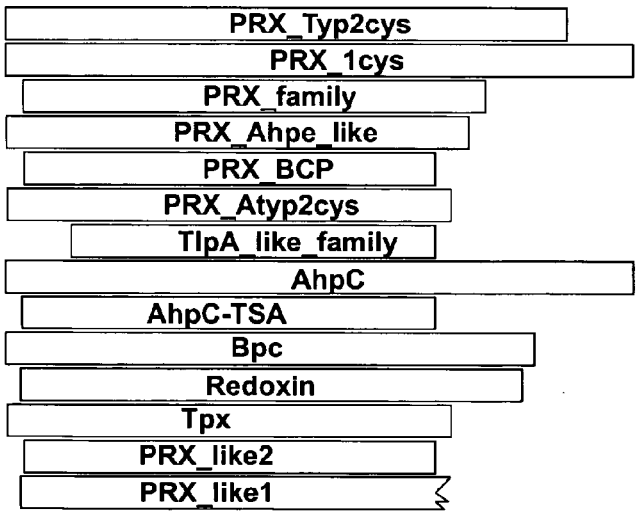

Descriptions

| + | Title | Pssmid | Multi-Dom | E-value |
|---|---|---|---|---|
| +]cd03015, PRX_Typ2cys, Peroxiredoxin (PRX) family, Typical 2-Cys PRX subfamily; PRXs ar... | | 48564 | No | 9e-73 |
| +]cd03016, PRX_1 cys, Peroxiredoxin (PRX) family, 1-Cys PRX subfamily; composed of PRXs c... | | 48565 | No | 1e-34 |
| +]cd02971, PRX_family, Peroxiredoxin (PRX) family; composed of the different classes of ... | | 48520 | No | 2e-34 |
| +]cd03018, PRX_AhpE_like, Peroxiredoxin (PRX) family, AhpE-like subfamily; composed of ... | | 48567 | No | 8e-27 |
| +]cd03017, PRX_BCP, Peroxiredoxin (PRX) family, Bacterioferritin comigratory protein (BC... | | 48566 | No | 1e-21 |
| +]cd03014, PRX_Atyp2cys, Peroxiredoxin (PRX) family, Atypical 2-Cys PRX subfamily; compo... | | 48563 | No | 2e-11 |
| +]cd02966, TlpA_like_family, TlpA-like family; composed of TlpA, ResA, DsbE, and similar... | | 48515 | No | 9e-06 |
| +]COG0450, AhpC, Peroxiredoxin [Posttranslational modification, protein turnover, chaper... | | 30799 | No | 1e-63 |
| +]pfam00578, AhpC-TSA, AhpC/TSA family. This family contains proteins related to alkyl h... | | 64443 | No | 1e-28 |
| +]COG1225, Bcp, Peroxiredoxin [Posttranslational modification, protein turnover, chapero... | | 31418 | No | 2e-25 |
| +]pfam08534, Redoxin, Redoxin family. This family of redoxins includes peroxiredoxin, thioredox... | | 71962 | No | 1e-13 |
| +]COG2077, Tpx, Peroxiredoxin [Posttranslational modification, protein turnover, chapero... | | 32260 | No | 7e-10 |

FIGURE 2

```
gi 113596153|dbj|BAF20027.1|       ----------------MAAAASTLASLSATAAAAAGKRLLLSSPSRSLS 33
gi 113535696|dbj|BAF08079.1|       ----------------MAAPTAAALSTLSTASVTSGKRFITSS----FS 29
gi 113533376|dbj|BAF05759.1|       -------------------------------------------------
gi 115439131|ref|NP_001043845.     -------------------------------------------------
gi 113532211|dbj|BAF04594.1|       ----------------MASALLRKATVGGSAAAAAAR------------ 21
gi 115435844|ref|NP_001042680.     ----------------MASALLRKATVGGSAAAAAAR------------ 21
gi 113611943|dbj|BAF22321.1|       -------------------------------------------------
gi 113611944|dbj|BAF22322.1|       -------------------------------------------------
gi 2499469|sp|Q61171|PRDX2_MOU     -------------------------------------------------
gi 8394432|ref|NP_058865.1|        -------------------------------------------------
gi 21553667 gb|AAM62760.1|         ------MASIASSSSTTLLSSSRVLLPSKSSLL-SPTVSVPRTLHSSSAS 43
gi 13265490 gb|AAG40040.2|AF32     ------MASIASSSSTTLLSSSRVLLPSKSSLL-SPTVSFPRIIPSSSAS 43
gi 11119229 gb|AAG30570.1|AF31     ------MASLAS--TTTLISSSSVLLPSKPSPF-SPAASFLRTLPSTSVS 41
gi 113564335|dbj|BAF14678.1|       ------MACAFS------VSSAAAPLAS--------------------- 16
gi 15229806 ref|NP_187769.1        ------MASVASS-TTLISSPSSRVFPAKSSLS-SPSVSFLRTLSSPSAS 42
gi 21592588 gb|AAM64537.1|         ------MASVASS-TTLISSPSSRVFPAKSSLS-SPSVSFLRTLSSPSAS 42
gi 3121825|sp|O24364|BAS1_SPIO     ------MACVASS-TTLISSPSSRVFPAKSSLS-SPSVSFLRTLSSPSAS 42
gi 1498198|emb|CAA63909.1|         ------MASVASS-TTLISSPSSRVFPAKSSLS-SPSVSFLRTLSSPSAS 42
gi 6002472|gb|AAF00001.1|AF052     ------MASVASS-TTLISSSASVLPATKSSLLPSPSLSFLPTLSSPSPS 43
gi 21912927 emb|CAC84143.2|        ------MACSASS-TALLSSNPKAASISPKSSFQAPISQCLSVPSSFNGL 43
gi 47027073 gb|AAT08751.1|         -------------------------------------------------
gi 11558242 emb|CAC17803.1|        ------MASSAPC-ASLISSNPN-ILFSPK--FPSSSFSSLSFPNSPNSL 40
gi 15131688 emb|CAC48323.1|        ------MACSAPF-ASLLYSNPN-TLFSPK--FSSPRLSSLSIPNAPNSL 40
gi 3328221|gb|AAC78473.1|          --------MACAFSASTVSTAAALVASPKPAGA----------PSACRFP 32
gi 2499477|sp|Q96468|BAS1_HORV     -------------------------------------------------
gi 2829687|sp|P80602|BAS1_WHEA     -------------------------------------------------
gi 1076722|pir||S49173             -------------------------------------------------
gi 115446541|ref|NP_001047050.     ------MAACCSSLATAVSSSSAKPLAGIPPAA----------PHSLSLP 34
gi 113536581|dbj|BAF08964.1|       ------MAACCSSLATAVSSSSAKPLAGIPPAA----------PHSLSLP 34
gi 125539780|gb|EAY86175.1|        ------MAACCSSLATAVSSSSAKPLAGIPPAS----------PHSLSLP 34
gi 7339568|emb|CAB82860.1|         ------MATACAAVSAVAVPVASVANHIASSSSGTPSLAIPRSYEGLNKS 44
gi 17232133 ref|NP_488681.1|       -------------------------------------------------
gi 119509654|ref|ZP_01628800.1     -------------------------------------------------
gi 86609696 ref|YP_478458.1|       -------------------------------------------------
gi 86605254 ref|YP_474017.1|       -------------------------------------------------
gi 22298997 ref|NP_682244.1|       -------------------------------------------------
gi 11465738 ref|NP_053882.1|       -------------------------------------------------
gi 51209959 ref|YP_063623.1|       ------MLLCCFITVILYNIDNTK------------------------- 18
gi 81301118 ref|YP_401326.1|       -------------------------------------------------
gi 33865747 ref|NP_897306.1|       -------------------------------------------------
gi 84518029 ref|ZP_01005378.1      -------------------------------------------------
gi 116059461|emb|CAL55168.1|       -------MLSASLSKSAFTPRASA------------------------- 17
gi 74272711 gb|ABA01151.1|         MAALQSASRSSAVAFSRQARVAPR------------------------- 24
gi 11995220 emb|CAC19677.1|        -------------------------------------------------
gi 115455107|ref|NP_001051154.     ----------------METVASLS--RAALAGAPAATRATASPVNRAVV 31
gi 115455105|ref|NP_001051153.     ----------------MAAAASTSLPVPRVSLPPSARPAAAPRHGLLI 33
gi 113595092|dbj|BAF18966.1|       ----------MAFAVSTACRPSLLLPPRQRSSPPRPRPLLCTPSTAAFR 39
gi 115452325|ref|NP_001049763.     ----------------MAARAPLPVPHAAATSPRPAAASSLLRARGPCA 33
gi 113610859|dbj|BAF21237.1|       ----------------MSLATAAAGAQPFVRSSSSAAAASSSRPLLAVAA 34
```

FIGURE 4

```
gi|113596153|dbj|BAF20027.1|      LSLASRGRIAVMPHLRAGILSAAPRRAVSASAPAAATIAVGDKLPD-ATL 82
gi|113535696|dbj|BAF08079.1|      LSFSSR---PLATGVRAAGARAARRSAASAST-VVATIAVGDKLPD-ATL 74
gi|113533376|dbj|BAF05759.1|      ---------------------------------MAPVAVGDILPD-GQL 15
gi|115439131|ref|NP_001043845.    ---------------------------------MAPVAVGDILPD-GQL 15
gi|113532211|dbj|BAF04594.1|      ------------------WASRGLASVGSGSDIVSAAPGVSLQK-ARS 50
gi|115435844|ref|NP_001042680.    ------------------WASRGLASVGSGSDIVSAAPGVSLQK-ARS 50
gi|113611943|dbj|BAF22321.1|      ---------------------------------MPGLTIGDIVPNLELD 16
gi|113611944|dbj|BAF22322.1|      ---------------------------------MPGLTLGDVVPDLELD 16
gi|2499469|sp|Q61171|PRDX2_MOU    -------------------------------MASGNAQIGKSAPDFTAT 18
gi|8394432|ref_NP_058865.1|       -------------------------------MASGNAHIGKPAPDFTGT 18
gi|21553667|gb|AAM62760.1|        ---SSSLCSGFSSLGSLTTSRSASRRNFAVKAQADDLPLVGNKAPDFEAE 90
gi|13265490|gb|AAG40040.2|AF32    ---SSSLCSGFSSLGSLTTNRSASRRNFAVKAQADDLPLVGNKAPDFEAE 90
gi|11119229|gb|AAG30570.1|AF31    T--SSSLRSCFSSISPLTCIRSSSRPSFAVKAQADDLPLVGNKAPDFEAE 89
gi|113564335|dbj|BAF14678.1|      ----------------------------PKGDLPLVGNKAPDFEAE 34
gi|15229806|ref_NP_187769.1|      ----ASLRSGFARRSSLS--STS-RRSFAVKAQADDLPLVGNKAPDFEAE 85
gi|21592588|gb|AAM64537.1|        ----ASLRSGFARRSSLS--STS-RRSFAVKAQADDLPLVGNKAPDFEAE 85
gi|3121825|sp|O24364|BAS1_SPIO    ----ASLRSGFARRSSLS--STS-RRSFAVKAQADDLPLVGNKAPDFEAE 85
gi|1498198|emb|CAA63909.1|        ----ASLRSGFARRSSLS--STS-RRSFAVKAQADDLPLVGNKAPDFKAE 85
gi|6002472|gb|AAF00001.1|AF052    ----ASLRSLVPLPSPQS--ASSSRRSFAVKGQTDDLPLVGNKAPDFEAE 87
gi|21912927|emb_CAC84143.2|       R--NCKPFVSRVARSLSTRVAQSQRRRFVVR-ASSELPLVGNQAPDFEAE 90
gi|47027073|gb|AAI08751.1|        ---------------------------ELPLVGNSAPGFEAE 15
gi|11558242|emb|CAC17803.1|       F--KP------LRTSLNP--SSPPLRTFVAR-ASSELPLVGNIAPDFEAE 79
gi|15131688|emb|CAC48323.1|       P--KLR---TSLPLSLNR--SSSSRRTFVVR-ASGELPLVGNSAPDFEAE 82
gi|3328221|gb|AAC78473.1|         A-----LRRGRAGLRCARLEDARARSFVARAAAEYDLPLVGNKAPDFAAE 77
gi|2499477|sp|Q96468|BAS1_HORV    -------------------DARARSFVARAAAEYDLPLVGNKAPDFAAE 30
gi|2829687|sp|P80602|BAS1_WHEA    -------------------DARARSFVARAAAEYDLPLVGNKAPDFAAE 30
gi|1076722|pir|  S49173           -------------------DARARSFVARAAAEYDLPLVGNKAPDFAAE 30
gi|115446541|ref|NP_001047050.    R----APAARPLRLSASSSRSARASSFVARAGGVDDAPLVGNKAPDFDAE 80
gi|113536581|dbj|BAF08964.1|      R----APAARPLRLSASSSRSARASSFVARAGGVDDAPLVGNKAPDFDAE 80
gi|125539780|gb|EAY86175.1|       R--SPAAAARPLRLSASSSRSARASSFVARAGGVDDAPLVGNKAPDFDAE 82
gi|7339568|emb_CAB82860.1|        FGARIAPRSTSAFRKPVTGVSLKQFSKGKVASARCASPLVGNVAPDFEAE 94
gi|17232133|ref_NP_488681.1|      -----------------------MSITYG--TQESLRVGQQAPDFTAT 23
gi|119509654|ref_ZP_01628800.1    -----------------------MSLTYA--TEGCLRVGQQAPEFTAT 23
gi|86609696|ref_YP_478458.1|      -----------------------MSQ------EGCLRVGQPAPDFSAT 19
gi|86605254|ref_YP_474017.1|      -----------------------MSQ------EGCLRVGQPAPDFSAT 19
gi|22298997|ref_NP_682244.1|      -----------------------MS--------ECLRVGQPAPDFEAV 17
gi|11465738|ref_NP_053882.1|      -----------------------MISG-----HNCLQVGQIAPDFSAT 20
gi|51209959|ref_YP_063623.1|      -----------------FYNRKCSIKMITN-----NNILRVGQQAPNFSAI 47
gi|81301118|ref_YP_401326.1|      -----------------------MTEG-------ALRVGQLAPDFEAT 18
gi|33865747|ref_NP_897306.1|      -----------------------MTET------GCLRVGQQAPDFTAT 19
gi|84518029|ref_ZP_01005378.1|    -----------------------MTN-------ECIRVGQKAPDFTAT 18
gi|116059461|emb_CAL55168.1|      ----------------LQKSVKGKNFSRSAVRVEARKPLVGYPAPEFSAE 51
gi|74272711|gb|ABA01151.1|        ----------------VASSVARRNLVVRAS--HAEKPLVGSVAPDFKAQ 56
gi|11995220|emb_CAC19677.1|       -------------------------RAS--HAEKPLVGSVAPDFKAQ 20
gi|115455107|ref|NP_001051154.    PAASRPGGRLCCRRSLTAVSAAAGASPPVSPSPSPDGGSPGVWDALGGV 81
gi|115455105|ref|NP_001051153.    PG----RRGCFRLRGSPAAPAAAASGSPSV-PSSSPEAGS-GIGDALGGV 77
gi|113595092|dbj|BAF18966.1|      RG-------------ALSATTTPTPARAALPSTTGRNRIVCGKVSKGSAA 76
gi|115452325|ref_NP_001049763.    S------LLYPRRLRFSVAPVAAAKPEAVGRAGEAAAAPVEGLAKSLQGV 77
gi|113610859|dbj|BAF21237.1|      ARHRRPHGSLAAAAAAARRRRRRPLLQVRAARTESTGVSVGFRAPQFELP 84
```

Motif 1

FIGURE 4 (continued)

Motif 1 (cont'd)    Conserved N-terminal Cys

FIGURE 4 (continued)

```
gi|113596153 dbj|BAF20027.1        GELRAKGVDAVACVSVN--DAFVMRAWKESLGVGD-EVLLLSDGNGELAR 178
gi|113535696 dbj|BAF08079.1        GELHAKGVDAIACVSVN--DAFVMRAWKESLGLGDADVLLLSDGNLELTR 171
gi|113533376 dbj|BAF05759.1        EQLKAKGVDDILLVSVN--DPFVMKAWAKSYPENK-HVKFLADGLGTYTK 110
gi|115439131 ref|NP_001043845.     EQLKAKGVDDILLVSVN--DPFVMKAWAKSYPENK-HVKFLADGLGTYTK 110
gi|113532211 dbj|BAF04594.1        DKLKAKGVDSVICVSVN--DPYALNGWAEKLQAKD-AIEFYGDFDGSFHK 145
gi|115435844 ref|NP_001042680.     DKLKAKGVDSVICVSVN--DPYALNGWAEKLQAKD-AIEFYGDFDGSFHK 145
gi|113611943 dbj|BAF22321.1        KEFDKR-GVKLLGISCD--DVQSHKDWIKDIEAYKPGNRVTYPIMADPSR 104
gi|113611944 dbj|BAF22322.1        GEFDKR-GVKLLGFSCD--DVESHKDWIKDIEAYKPGRRVGFPIVADPDR 104
gi|2499469|sp|Q61171|PRDX2_MOU     EDFRKL-GCEVLGVSVD--SQFTHLAWINTPRKEGGLGPLNIPLLADVTK 109
gi|8394432|ref|NP_058865.1|        EDFRKL-GCEVLGVSVD--SQFTHLAWINTPRKEGGLGPLNIPLLADVTK 109
gi|21553667|gb|AAM62760.1|         EEFEKL-NTEVLGVSVD--SVFSHLAWVQTDRKSGGLGDLNYPLVSDITK 182
gi|13265490|gb|AAG40040.2|AF32     EEFEKL-NTEVLGVSVD--SVFSHLAWVQTDRKSGGLGDLNYPLVSDITK 182
gi|11119229|gb|AAG30570.1|AF31     EEFEKL-NTEVLGVSVD--SVFSHLAWVQTERKSGGLGDLNYPLVSDITK 181
gi|113564335 dbj|BAF14678.1        EEFEKI-NTEVLGVSID--SV-----------------------  79
gi|15229806|ref|NP_187769.1        SEFEKL-NTEVLGVSVD--SVFSHLAWVQTDRKSGGLGDLNYPLISDVTK 177
gi|21592588|gb|AAM64537.1|         SEFEKL-NTEVLGVSVD--SVFSHLAWVQTDRKSGGLGDLNYPLISYFTK 177
gi|3121825|sp|O24364|BAS1_SPIO     SEFEKL-NTEVLGVSVD--SVFSHLAWVQTDRKSGGLGDLNYPLISDVTK 177
gi|1498198|emb|CAA63909.1|         SEFEKL-NTEVLGVSVD--SVFSHLAWVQTDRKSGGLGDLNYPLISDVTK 177
gi|6002472|gb|AAF00001.1|AF052     AEFEKL-NTEVLGVSVDSVSVFSHLAGVQTDRKFGGLGDLNYPLISDVTK 184
gi|21912927|emb|CAC84143.2|        GEFEKL-NTEILGVSVD--SVFSHLAWVQTDRKSGGLGDLNYPLISDVTK 182
gi|47020703|gb|AAT08751.1|         SEFEKV-NTEVLGVSVD--SVFSHLAWVQTDRKSGGLGDLNYPLVSDVTK 107
gi|11558242|emb|CAC17803.1|        AEFEAL-NTEILGVSVD--SVFSHLAWVQTDRKSGGLGDLNYPLISDVTK 171
gi|15131688|emb|CAC48323.1|        AEFDAI-NTEILGVSVD--SVFSHLAWVQSDRKSGGLGDLKYPLVSDVTK 174
gi|3328221|gb|AAC78473.1|          EEFEKI-NTEILGVSVD--SVFSHLAWVQTERKSGGLGDLKYPLVSDVTK 169
gi|2499477|sp|Q96468|BAS1_HORV     EEFEKI-NTEILGVSVD--SVFSHLAWVQTERKSGGLGDLKYPLVSDVTK 122
gi|2829687|sp|P80602|BAS1_WHEA     EEFEKI-NTEILGVSVD--SVFSHLAWVQTERKSGGLGDLKYPLVSDVTK 122
gi|1076722|pir||S49173             EEFEKI-NTEILGVSVD--SVFSHLAWVQTERKSGGLGDLKYPLVSDVTK 122
gi|115446541 ref|NP_001047050.     DEFEKL-NTEILGVSID--SVFSHLAWVQTDRKSGGLGDLKYPLISDVTK 172
gi|113536581 dbj|BAF08964.1        DEFEKL-NTEILGVSID--SVFSHLAWVQTDRKSGGLGDLKYPLISDVTK 172
gi|125539780 gb|EAY86175.1|        DEFEKL-NTEILGVSID--SVFSHLAWVQTDRKSGGLGDLKYPLISDVTK 174
gi|7339568|emb|CAB82860.1          EEFEKL-NTEVIGVSVD--SVFSHLAWIQTDRKSGGLGDLKYPLVSDLTK 186
gi|17232133|ref|NP_488681.1        EEFKKL-NTEILGVSVD--SEFSHLAWIQTDRKSGGVGDLNYPLVSDIKK 114
gi|119509654 ref|ZP_01628800.1     EEFKKV-NTEILGVSVD--SEFSHLAWIQTERKSGGVGDLNYPLVSDIKK 114
gi|86609696|ref|YP_478458.1        DDFAKL-DTEILGVSVD--SEYSHLAWIQTDRKAGGVGELRYPLVSDLKK 111
gi|86605254|ref|YP_474017.1        DEFAKL-DTEILGVSVD--SEYSHLAWIQTDRKAGGVGELRYPLVSDLKK 111
gi|22298997|ref|NP_682244.1        DEFAKL-NTEILGVSVD--SQFSHLAWTQTDRKAGGVGDLKYPLVSDLKK 108
gi|11465738|ref|NP_053882.1        SDFSEL-NTEILGVSVD--SEYSHLAWLQTDRESGGLGDLEYPLVSDLKK 111
gi|51209959|ref|YP_063623.1        KEIQSL-NTEVLGISVD--SEYSHLAWLQMERDIGGLGDLNYPLVSDLTK 138
gi|81301118|ref|YP_401326.1        ADFSAL-NTEILGVSVD--SQFSHLAWIQTSRKEGGLGDLAYPLVADLKK 109
gi|33865747|ref|NP_897306.1        ADFSSK-NTEILGVSVD--SQFSHLAWIQTPRNQGGLGDINYPLVADLKK 110
gi|84518029|ref|ZP_01005378.1|     SEFSSK-NTEVLGVSVD--SQFSHLAWIQTQRNDGGIGDINYPLVADLKK 109
gi|116059461 emb|CAL55168.1|       EEFAKL-NTEVLGVSVD--SKFSHLAWLQTDRNDGGLGDLAYPLVSDLKR 142
gi|74272711|gb|ABA01151.1|         KEFKDI-NTEVLGVSVD--SQFTHLAWIQTDRKEGGLGDLNYPLVADLKK 147
gi|11995220|emb|CAC19677.1|        KEFKDI-NTEVLGVSVD--SQFTHLAWIQTDRKEGGLGDLAYPLVADLKK 111
gi|115455107 ref|NP_001051154.     AKFDAA-GAKLIAIGVG----------IPDKARILADGLPFPVDSLYAD 167
gi|115455105 ref|NP_001051153.     ERFDSA-GVKLIAVGVG----------IPDKARILAERLPFPLDYLYAD 163
gi|113595092 dbj|BAF18966.1        EKFKKA-GAEVIGISGD---------DAASHKEFKKKYKLPFTLLSDEGN 163
gi|115452325 ref|NP_001049763.     DAVEAA-GVALVLIGPG---------IVEQAKAFYDQTKFKG-EVYAD 159
gi|113610859 dbj|BAF21237.1        TSFYMEKGLAAVAISSNS-IVIHPQDGPDYIAEEAKLYKYSFPYLYDESQ 174
                                    :              .. .

Motif 2
```

FIGURE 4 (continued)

```
gi|113596153|dbj|BAF20027.1      AMGVELDLSDKPA----GLGVRSRRYALLAEDGVVKVLNLEEG-GAFTTS 223
gi|113535696|dbj|BAF08079.1      ALGVEMDLSDKPM----GLGVRSRRYALLADDGVVKVLNLEEG-GAFTTS 216
gi|113533376|dbj|BAF05759.1      ALGLELDLSEK------GLGIRSRRFALLADNLKVTVANIEEG-GQFTIS 153
gi|115439131|ref|NP_001043845.   ALGLELDLSEK------GLGIRSRRFALLADNLKVTVANIEEG-GQFTIS 153
gi|113532211|dbj|BAF04594.1      SLDLEVDLSAA------LLGRRSHRWSAFVDDGKIKAFNVEVAPSDFKVS 189
gi|115435844|ref|NP_001042680.   SLDLEVDLSAA------LLGRRSHRWSAFVDDGKIKAFNVEVAPSDFKVS 189
gi|113611943|dbj|BAF22321.1      EAIKQLNMVDPDEKDSNGGHLPSRALHIVGPDKKVKLSFLYPACVGRNMD 154
gi|113611944|dbj|BAF22322.1      EAIRQLNMIDADEKDTAGGELPNRALHIVGPDKKVKLSFLFPACTGRNMA 154
gi|2499469 sp Q61171|PRDX2_MOU   SLSQNYGVLKNDE------GIAYRGLFIIDAKGVLRQITVNDLPVGRSVD 153
gi|8394432 ref|NP_058865.1|      SLSQNYGVLKNDE------GIAYRGLFIIDAKGVLRQITVNDLPVGRSVD 153
gi|21553667|gb|AAM62760.1|       SISKSFGVLIPDQ------GIALRGLFIIDKEGVIQHSTINNLGIGRSVD 226
gi|13265490|gb|AAG40040.2|AF32   SISKSFGVLIPDQ------GIALRGLFIIDKEGVIQHSPINNLGIGRSVD 226
gi|11119229|gb|AAG30570.1|AF31   SISKSFGVLIPDQ------GIALRGLFIIDKKGVIQHSTINNLGIGRSVD 225
gi|113564335|dbj|BAF14678.1      -------------------GIALRGLFIIDKEGVIQHSTINNLAIGRSVD 110
gi|15229806|ref|NP_187769.1      SISKSFGVLIHDQ------GIALRGLFIIDKEGVIQHSTINNLGIGRSVD 221
gi|21592588|gb|AAM64537.1|       SISKSFGVLIHDQ------GIALRTLFIIDKEGVIQHSTINNLGIGQSVD 221
gi|3121825 sp O24364|BAS1_SPIO   SISKSFGVLIHDQ------GIALRGLFIIDKEGVIQHSTINNLGIGRSVD 221
gi|1498198 emb|CAA63909.1|       SISKSFGVLIHDQ------GIALRGLFIIDKEGVIQHSTINNLGIGRSVD 221
gi|6002472 gb AAF00001.1|AF052   SISKSFGVLIHDQ------GIALRGLFIIDKEGVIQHSTIXNLGIGRSVD 228
gi|21912927|emb|CAC84143.2|      SISKSYNVLIPDQ------GIALRGLFIIDKEGVIQHSTINNLGIGRSVD 226
gi|47027073|gb|AAT08751.1|       SISKSYGVLIPDQ------GIALRGLFIIDKEGVIQHSTINNLGIGRSVD 151
gi|11558242|emb|CAC17803.1|      SISKSYDVLIPDQ------GIALRGLFIIDKEGVIQHSTINNLAIGRSVD 215
gi|15131688|emb|CAC48323.1|      SISESYGVLIPDQ------GIALRGLFIIDKEGVIQHSTINNLGIGRSVD 218
gi|3328221 gb AAC78473.1|        SISKSFGVLIPDQ------GIALRGLFMIDKEGVIQHSTINNLGIGRSVD 213
gi|2499477 sp Q96468|BAS1_HORV   SISKSFGVLIPDQ------GIALRGLFIIDKEGVIQHSTINNLGIGRSVD 166
gi|2829687 sp P80602|BAS1_WHEA   SISKSFGVLIPDQ------GIALRGLFIIDKEGVIQHSTINNLGIGRSVD 166
gi|1076722 pir||S49173           SISKSFGVLIPDQ------GIALRGLFIIDKEGVIQHSTINNLGIGRSVD 166
gi|115446541|ref|NP_001047050.   SISKSFGVLIPDQ------GIALRGLFIIDKEGVIQHSTINNLAIGRSVD 216
gi|113536581|dbj|BAF08964.1      SISKSFGVLIPDQ------GIALRGLFIIDKEGVIQHSTINNLGIGRSVD 216
gi|125539780|gb|EAY86175.1|      SISKSFGVLIPDQ------GIALRGLFIIDKEGVIQHSTINNLAIGRSVD 218
gi|7339568 emb|CAB82860.1|       KIAEDFGVLIPDQ------GIALRGLFIIDKEGVIQHATINNLAIGRSVE 230
gi|17232133|ref|NP_488681.1      EVSDAYNVLDPAA------GIALRGLFIIDKDGIIQHATINNLAFGRSVD 158
gi|119509654|ref|ZP_01628800.1   EISATYNVLDPAA------GIALRGLFIIDKDGIIQHSTVNNLAFGRSVD 158
gi|86609696|ref|YP_478458.1      EISAAYNVLDPEA------GVALRGLFIIDKEGIIQHATINNLAFGRSVD 155
gi|86605254|ref|YP_474017.1      EISAAYNVLDPAA------GVALRGLFIIDKEGIIQHATINNLAFGRSVD 155
gi|22298997|ref|NP_682244.1      DISTAYNVLT-EE------GVALRGLFIIDKEGIIQHATINNLAFGRSVD 151
gi|11465738|ref|NP_053882.1      EISIAYNVLN-SG------GVALRGLFIIDPKGIIQYSTVNNLEFGRSVE 154
gi|51209959|ref|YP_063623.1      QISASYNVLT-EE------GKALRGLFIVDQQGIIQYSLVNNLDFGRSIS 181
gi|81301118|ref|YP_401326.1      EISTAYNVLDPAE------GIALRGLFIIDKEGVIQHATINNLAFGRSVD 153
gi|33865747|ref|NP_897306.1      EIATAYNVLDDAE------GVALRGLFIIDPDGVIMHSTINNLPVGRNVD 154
gi|84518029|ref|ZP_01005378.1|   EISLAYNVLDDAE------GVALRGLYIIDPDGVIMHATINNLPVGRNVD 153
gi|116059461|emb|CAL55168.1      EICESYDVLY-ED------GTALRGLYIIDREGVIQHYTCNNAPFGRNVD 185
gi|74272711|gb|ABA01151.1|       EISKAYGVLT-ED------GISLRGLFIIDKEGVVQHATINNLAFGRSVD 190
gi|11995220|emb|CAC19677.1|      EISKAYGVLT-ED------GISLRGLFIIDKEGVVQHATINNLAFGRSVD 154
gi|115455107|ref|NP_001051154.   PERKAYDVLGLYH------GLGRTLISP--AKMYSGLNSIKKVIKNYTLK 209
gi|115455105|ref|NP_001051153.   PERKAYDLLGLYF------GIGRTFFNPASASVFSRFDSLKEAVKNYTIE 207
gi|113595092|dbj|BAF18966.1      KVRKEWGVPADLFG-----TLPGRQTYVLDKNGVVQYIYNNQFQPEKHIG 208
gi|115452325|ref|NP_001049763.   PSHSSYNALEFAF------GLFSTFTPSAGLKIIQLYMEGYRQDWELSFE 203
gi|113610859|dbj|BAF21237.1      EVAKAFR-----------AVCTPEFYLFKKDGRRPFELFYHGQFDDSRP 212
```

Motif 2
(cont'd)

FIGURE 4 (continued)

```
gi|113596153|dbj|BAF20027.1|    SAEEMLKAL----------------------------------------- 232
gi|113535696|dbj|BAF08079.1|    SAEEMLKAL----------------------------------------- 225
gi|113533376|dbj|BAF05759.1|    GAEEILKAL----------------------------------------- 162
gi|115439131|ref|NP_001043845.  GAEEILKAL----------------------------------------- 162
gi|113532211|dbj|BAF04594.1|    GAEVILDQI----------------------------------------- 198
gi|115435844|ref|NP_001042680.  GAEVILDQI----------------------------------------- 198
gi|113611943|dbj|BAF22321.1|    EVVRAVDA-------------LQTAAKHAVATPVNWKPGERVVIPPGVS 190
gi|113611944|dbj|BAF22322.1|    EVLRATDA-------------LLTAARHRVATPVNWKPGERVVIPPGVS 190
gi|2499469|sp|Q61171|PRDX2_MOU  EALRLVQA-------------FQYTDEHG-EVCPAGWKPGSDTIKPN--- 186
gi|8394432|ref|NP_058865.1|     EALRLVQA-------------FQYTDEHG-EVCPAGWKPGSDTIKPN--- 186
gi|21553667|gb|AAM62760.1|      ETMRTLQA-------------LQYVQENPDEVCPAGWKPGEKSMKPD--- 260
gi|13265490|gb|AAG40040.2|AF32  ETMRTLQA-------------LQYVQENPDEVCPAGWKPGEKSMKPD--- 260
gi|11119229|gb|AAG30570.1|AF31  ETMRTLQA-------------LQYVQENPDEVCPAGWKPGEKSMKPD--- 259
gi|113564335|dbj|BAF14678.1|    ETLRTLQA-------------LQYVQENPDEVCPAGWKPGEKSMKPD--- 144
gi|15229806|ref|NP_187769.1|    ETMRTLQA-------------LQYIQENPDEVCPAGWKPGEKSMKPD--- 255
gi|21592588|gb|AAM64537.1|      ETMRTLQA-------------LQYIQENPDEVCPAGWKPGEKSMKPD--- 255
gi|3121825|sp|O24364|BAS1_SPIO  ETMRTLQA-------------LQYTG-NPDEVCPAGWKPGEKSMKPD--- 254
gi|1498198|emb|CAA63909.1|      ETMRTLQA-------------LQYTG-NPDEVCPAGWKSGEKSMKPD--- 254
gi|6002472|gb|AAF00001.1 AF052  ETMRTLQA-------------LQYIQEGPGEVCPAGWKPGEKSMKPD--- 262
gi|21912927|emb|CAC84143.2|     ETLRTLQA-------------LQYVQDNPDEVCPAGWKPGEKSMKPD--- 260
gi|47027073|gb|AAT08751.1|      ETMRTLQA-------------LQYVQENPDEVCPAGWKPGEKSMKPD--- 185
gi|11558242|emb|CAC17803.1|     ETKRTLQA-------------LQYVQENPDEVCPAGWKPGEKSMKPD--- 249
gi|15131688|emb|CAC48323.1|     ETKRTLQA-------------LQYVQENPDEVCPAGWKPGEKSMKPD--- 252
gi|3328221|gb|AAC78473.1|       ETLRTLQA-------------LQYVQENPDEVCPAGWKPGEKSMKPD--- 247
gi|2499477|sp|Q96468|BAS1_HORV  ETLRTLQA-------------LQYVKK-PDEVCPAGWKPGEKSMKPD--- 199
gi|2829687|sp|P80602|BAS1_WHEA  ETLRTLRA-------------LQYVKK-PDEVCPAGWKPGEKSMKPD--- 199
gi|1076722|pir||S49173          ETLRTLQA-------------LQYVKK-PDEVCPAGWKPGEKSMKPDLG- 201
gi|115446541 ref NP_001047050.  ETMRTLQA-------------LQYVQDNPDEVCPAGWKPGDKSMKPD--- 250
gi|113536581|dbj|BAF08964.1|    ETMRTLQA-------------LQYVQDNPDEVCPAGWKPGDKSMKPD--- 250
gi|125539780|gb|EAY86175.1|     ETMRTLQASSLEYTLLSAHTALQYVQDNPDEVCPAGWKPGDKSMKPD--- 265
gi|7339568|emb|CAB82860.1|      ETLRTLQA-------------VQYVQENPDEVCPAGWKPGEKTMKPD--- 264
gi|17232133|ref|NP_488681.1|    ETLRTLQA-------------IQYVQSHPDEVCPAGWQPGEKTMIPD--- 192
gi|119509654|ref|ZP_01628800.1  ETLRTLQA-------------LQYVQSHPDEVCPAGWQPGDQTMVPD--- 192
gi|86609696|ref|YP_478458.1|    ETLRTLQA-------------IQYVQSHPDEVCPANWQPGQKTMHPD--- 189
gi|86605254|ref|YP_474017.1|    ETLRTLQA-------------IQYVQAHPDEVCPANWQPGQRTLNPD--- 189
gi|22298997|ref|NP_682244.1|    ETLRVLQA-------------IQYVQTHPDEVCPAGWHPGDKTMNPD--- 185
gi|11465738|ref|NP_053882.1|    ETLRVLQA-------------IQYVQAHPDEVCPANWKPGDRTMNPD--- 188
gi|51209959|ref|YP_063623.1|    ETIRTLKA-------------IQYVQSHPDEVCPANWQPGKATIINS--- 215
gi|81301118|ref|YP_401326.1|    ETLRVLQA-------------IQYVQSHPDEVCPANWQPGAATMNPD--- 187
gi|33865747|ref|NP_897306.1|    ETLRVLQA-------------FQYVQSNPDEVCPANWTPGEKTMKPD--- 188
gi|84518029|ref|ZP_01005378.1|  ETLRVLQA-------------FQYVQANPDEVCPANWTPGEKTMKPD--- 187
gi|116059461|emb|CAL55168.1|    ECLRVLQA-------------IQYVQNNPDEVCPAGWTPGAATMKPD--- 219
gi|74272711|gb|ABA01151.1|      ETKRVLQA-------------IQYVQSNPDEVCPAGWKPGDKTMKPD--- 224
gi|11995220|emb|CAC19677.1|     ETKRVLQA-------------IQYVQSNPDEVCPAGWKPGDKTMKPD--- 188
gi|115455107|ref|NP_001051154.  GTPADLTGILQQ---------GGMLVFRGKELLYSWKDKGTGDHAPLDDV 250
gi|115455105|ref|NP_001051153.  ATPDDRASVLQQ---------GGMFVFRGKELIYARKDEGTGDHAPLDDV 248
gi|113595092|dbj|BAF18966.1|    ETLKILQSL----------------------------------------- 217
gi|115452325|ref|NP_001049763.  KITRIKGGWYQGG--------LLVAGPGIDNILYIHKDKEAGDDPDMDDV 245
gi|113610859|dbj|BAF21237.1|    SNNVPVTG----------------RDLSRAIDCALSGQELPFVPKP--  242
```

Conserved C-terminal C

FIGURE 4 (continued)

```
gi|113596153|dbj|BAF20027.1|      ----------------------------------------
gi|113535696|dbj|BAF08079.1|      ----------------------------------------
gi|113533376|dbj|BAF05759.1|      ----------------------------------------
gi|115439131|ref|NP_001043845.    ----------------------------------------
gi|113532211|dbj|BAF04594.1|      ----------------------------------------
gi|115435844|ref|NP_001042680.    ----------------------------------------
gi|113611943|dbj|BAF22321.1|      DDEAKEKFPQGFDTADLPSGKGYLRFTKVG----------- 220
gi|113611944|dbj|BAF22322.1|      DEEAKARFPAGFETAQLPSNKCYLRFTQVD----------- 220
gi|2499469|sp|Q61171|PRDX2_MOU    VDDSKEYFSKHN----------------------------- 198
gi|8394432|ref|NP_058865.1|       VDDSKEYFSKHN----------------------------- 198
gi|21553667|gb|AAM62760.1|        PKLSKEYFSAI----------------------------- 271
gi|13265490|gb|AAG40040.2|AF32    PKLSKEYFSAI----------------------------- 271
gi|11119229|gb|AAG30570.1|AF31    PKLSKEYFSAI----------------------------- 270
gi|113564335|dbj|BAF14678.1|      PKDSKEEQEC------------------------------ 154
gi|15229806|ref|NP_187769.1|      PKLSKEYFSAI----------------------------- 266
gi|21592588|gb|AAM64537.1|        PKLSKEYFSAI----------------------------- 266
gi|3121825|sp|O24364|BAS1_SPIO    PKLSKEYFSAI----------------------------- 265
gi|1498198|emb|CAA63909.1|        PKLSKEYFSAI----------------------------- 265
gi|6002472|gb|AAF00001.1|AF052    PKLSKELFSAI----------------------------- 273
gi|21912927|emb|CAC84143.2|       PKGSKEYFASI----------------------------- 271
gi|47027073|gb|AAT08751.1|        PKRSKEYFASI----------------------------- 196
gi|11558242|emb|CAC17803.1|       PKLSKEYFSAI----------------------------- 260
gi|15131688|emb|CAC48323.1|       PKGSKEYFAAV----------------------------- 263
gi|3328221|gb|AAC78473.1|         PKGSKEYFAAI----------------------------- 258
gi|2499477|sp|Q96468|BAS1_HORV    PKGSKEYFAAI----------------------------- 210
gi|2829687|sp|P80602|BAS1_WHEA    PKGSKEYFAAI----------------------------- 210
gi|1076722|pir||S49173            PKRSTRCYLERTFALSCGVLSWPFLGYMCFCDPSCSYHAYN 242
gi|115446541|ref|NP_001047050.    PKGSKEYFAAI----------------------------- 261
gi|113536581|dbj|BAF08964.1|      PKGSKEYFAAI----------------------------- 261
gi|125539780|gb|EAY86175.1|       PKGSKEYFAAI----------------------------- 276
gi|7339568|emb|CAB82860.1|        TKLSKEYFAQV----------------------------- 275
gi|17232133|ref|NP_488681.1|      PVKSKVYFAAV----------------------------- 203
gi|119509654|ref|ZP_01628800.1    PVKSKVYFSAV----------------------------- 203
gi|86609696|ref|YP_478458.1|      PVKSKEFFAAIAK--------------------------- 202
gi|86605254|ref|YP_474017.1|      PVKSKEFFAAVAK--------------------------- 202
gi|22298997|ref|NP_682244.1|      PVKSKVYFEAVG----------------------------- 197
gi|11465738|ref|NP_053882.1|      PIKSKNYFAAA----------------------------- 199
gi|51209959|ref|YP_063623.1|      PQKSKNYFQSI----------------------------- 226
gi|81301118|ref|YP_401326.1|      PVKSKEFFAAV----------------------------- 198
gi|33865747|ref|NP_897306.1|      PKGSKEYFSAIG----------------------------- 200
gi|84518029|ref|ZP_01005378.1|    PEGSKEYFSSL----------------------------- 198
gi|116059461|emb|CAL55168.1|      PKGSKEYFKAI----------------------------- 230
gi|74272711|gb|ABA01151.1|        PKGSKEYFAAV----------------------------- 235
gi|11995220|emb|CAC19677.1|       PKGSKEYFSAV----------------------------- 199
gi|115455107|ref|NP_001051154.    LNACCNRTS------------------------------- 259
gi|115455105|ref|NP_001051153.    LNICCKAPAA------------------------------ 258
gi|113595092|dbj|BAF18966.1|      ----------------------------------------
gi|115452325|ref|NP_001049763.    LKACCS---------------------------------- 251
gi|113610859|dbj|BAF21237.1|      SVGCSIKWHP------------------------------ 252
```

FIGURE 4 (continued)

SEQ ID NO: 01 - DNA - Brassica rapa
TTGTACAAAAAAGCAGGCTTAAACAATGGCGTCTGTTGCTTCTTCAACCACTCTCATCTCCTCCTC
CGCTAGTGTTCTCCCAGCCACCAAGTCTTCGCTTCTTCCATCTCCCTCCCTCTCTTTCCTTCCAAC
CCTCTCCTCTCCTTCCCCATCCGCTTCTCTCCGGCTCCCTCGTCCCTCTCCCCTCACCTCAATCCG
CTCCTCTTCTCGCCGGAGCTTCGCTGTCAAGGCCCAAACCGATGATCTTCCATTGGTTGGAAACAA
GGCGCCTGATTTTGAGGCAGAGGCTGTGTTCGATCAGGAGTTCATCAAGGTCAAGCTCTCTGAGTA
CATTGGGAAGAAGTATGTGATTCTCTTTTTCTACCCCTTGGACTTCACTTTCGTCTGCCCAACAGA
GATTACTGCCTTCAGTGACCGATATGCAGAATTTGAGAAGCTGAACACAGAAGTGTTAGGTGTCTC
TGTTGATAGTGTGTTCTCCCACCTTGCTTGGGTTCAAACCGACAGAAAATCTGGAGGACTTGGTGA
TCTCAACTATCCACTTATATCAGATGTCACTAAATCTATCTCAAAATCTTTTGGAGTGCTCATCCA
TGATCAGGGAATAGCGTTGAGAGGGCTTTTCATAATAGACAAGGAAGGAGTGATCCAACATTCAAC
CATCAACAATCTTGGTATTGGCCGAAGTGTTGATGAGACAATGAGAACCCTTCAGGCATTACAGTA
CATCCAGGAGAACCCTGATGAAGTCTGCCCTGCAGGATGGAAACCAGGGGAGAAGTCAATGAAACC
TGACCCCAAGCTCAGCAAAGAGTACTTCTCAGCTATTTAGCTCGAACCCAGCTTTC

SEQ ID NO: 02 - protein - Brassica rapa
MASVASSTTLISSSASVLPATKSSLLPSPSLSFLPTLSSPSPSASLRLPRPSPLTSIRSSSRRSFA
VKAQTDDLPLVGNKAPDFEAEAVFDQEFIKVKLSEYIGKKYVILFFYPLDFTFVCPTEITAFSDRY
AEFEKLNTEVLGVSVDSVFSHLAWVQTDRKSGGLGDLNYPLISDVTKSISKSFGVLIHDQGIALRG
LFIIDKEGVIQHSTINNLGIGRSVDETMRTLQALQYIQENPDEVCPAGWKPGEKSMKPDPKLSKEY
FSAI

SEQ ID NO: 03 - DNA - Brassica rapa
GCCATATGGCGTCTGTTGCTTCTTCAACCACTCTCATCTCCTCCTCCGCTAGTGTTCTCCCAGCCA
CCAAGTCTTCGCTTCTTCCATCTCCCTCCCTCTCTTTCCTTCCAACCCTCTCCTCTCCTTCCCCAT
CCGCTTCTCTCCGGTCCCTCGTCCCTCTCCCCTCACCTCAATCCGCTTCCTCTTCTCGCCGGAGCT
TCGCTGTCAAGGGCCAAACCGATGATCTTCCATTGGTTGGAAACAAGGCGCCTGATTTTGAGGCAG
AGGGTGTGTTCGATCAGGAGTTCATCAAGTTCATCAAGGTCAAGCTCTCTGATTACATTGGGAAAA
AGTATGTGATTCTCTTTTTTCTACCCCTTGACTTCACTTTCGTCTGCCCAACAGAAATTACTGCCT
TCAGTGACCGATATGCAGAATTTGAGAAGCTGAATACAGAAGTGTTAGGTGTTTCTGTTGATAGTG
TGAGTGTGTTCTCCCACCTTGCTGGGGTTCAAACCGACAGAAAATTTGGAGGACTTGGTGATCTCA
ACTATCCACTTATATCAGATGTCACTAAATCTATCTCAAAATCTTTTGGAGTGCTCATCCATGATC
AGGGAATAGCGTTGAGAGGGCTTTTCATAATAGACAAGGAAGGAGTGATCCAACATTCAACCATCA
ANAATCTTGGTATTGGCCGAAGTGTTGATGAGACAATGAGAACCCTTCAGGCATTACAGTACATCC
AGGAAGGCCCTGGTGAAGTCTGCCCTGCAGGATGGAAACCAGGGGAGAAGTCAATGAAACCTGACC
CCAAGCTCAGCAAAGAGCTCTTCTCAGCTATTTAGCTCGAGGCTAAGCC

SEQ ID NO: 04 - protein - Brassica rapa
MASVASSTTLISSSASVLPATKSSLLPSPSLSFLPTLSSPSPSASLRSLVPLPSPQSASSSRRSFA
VKGQTDDLPLVGNKAPDFEAEGVFDQEFIKFIKVKLSDYIGKKYVILFFLPLDFTFVCPTEITAFS
DRYAEFEKLNTEVLGVSVDSVSVFSHLAGVQTDRKFGGLGDLNYPLISDVTKSISKSFGVLIHDQG
IALRGLFIIDKEGVIQHSTIXNLGIGRSVDETMRTLQALQYIQEGPGEVCPAGWKPGEKSMKPDPK
LSKELFSAI

SEQ ID NO: 05 - DNA - Arabidopsis thaliana
GTGATTGACAGATAGATAAGAGTGTTTGGTAGCTCAGACTCAGAGAGTCACAAAGTGTGTGTAGCA
GCAATGGCGTCTGTTGCTTCTTCAACTACTCTCATCTCTTCTCCCTCTTCTAGGGTTTTTCCAGCA
AAGTCTTCACTTTCCTCTCCATCTGTTTCTTTCCTTCGAACCCTTTCTTCTCCTTCCGCATCTGCT

FIGURE 6

```
TCTCTCCGCTCCGGATTTGCTCGACGCTCTTCCCTCAGCTCCACTTCTCGTCGGAGCTTTGCTGTC
AAAGCCCAGGCCGATGATCTTCCACTGGTTGGAAACAAGGCGCCTGATTTTGAGGCAGAGGCTGTG
TTTGATCAAGAGTTCATCAAGGTTAAGCTCTCTGATTACATTGGAAAGAAGTATGTGATTCTCTTT
TTCTACCCATTGGACTTTACTTTCGTCTGCCCAACAGAGATTACTGCCTTCAGTGACCGGCATTCA
GAATTTGAGAAGTTGAACACCGAAGTATTAGGTGTTTCTGTCGATAGTGTGTTCTCTCACCTTGCA
TGGGTCCAAACAGACAGGAAATCTGGAGGGCTTGGTGATCTGAACTATCCCCTTATTTCATATTTC
ACTAAATCAATCTCAAAGTCGTTCGGAGTGCTCATCCATGATCAGGGAATAGCACTGAGAGGACTT
TTCATAATCGACAAGGAAGGAGTGATCCAACATTCCACCATCAACAATCTTGGTATTGGCCAAAGC
GTTGATGAGACAATGAGAACCCTCCAGGCATTACAGTACATCCAGGAAAACCCGGATGAAGTCTGC
CCAGCAGGATGGAAGCCGGGTGAGAAGTCAATGAAACCCGACCCAAAACTCAGCAAAGAGTACTTC
TCAGCTATTTAGAAACTCTACTATGATAGCAAAAGGTACAATCTTTGTTATATGTGAGCAGAGTT
TTTTTTCTTGTACGCTAAAACAATCCTTTGTTTGATTCTCACTTTGTCCCCAAAATTATAATAAAA
AACTTTTTCCGC
```

SEQ ID NO: 06 - protein - Arabidopsis thaliana
```
MASVASSTTLISSPSSRVFPAKSSLSSPSVSFLRTLSSPSASASLRSGFARRSSLSSTSRRSFAVK
AQADDLPLVGNKAPDFEAEAVFDQEFIKVKLSDYIGKKYVILFFYPLDFTFVCPTEITAFSDRHSE
FEKLNTEVLGVSVDSVFSHLAWVQTDRKSGGLGDLNYPLISYFTKSISKSFGVLIHDQGIALRGLF
IIDKEGVIQHSTINNLGIGQSVDETMRTLQALQYIQENPDEVCPAGWKPGEKSMKPDPKLSKEYFS
AI
```

SEQ ID NO: 07 - DNA - Brassica napus
```
GTCGACCACGCGTCCGGAGAGAAAGAGAGAGAGAGCAGAGTTCTTCAGTCCATGGCTTCCTTAGCT
TCAACCACCACACTTATCTCTTCATCTAGCGTTCTTCTTCCCTCAAAGCCTTCTCCTTTTTCTCCC
GCCGCCTCCTTCCTCCGAACTCTTCCTTCTACCTCCGTATCTACCTCCTCTTCTCTCCGCTCCTGT
TTCTCCAGCATCAGTCCCCTCACCTGCATCCGCTCTTCCTCTCGCCCTAGCTTCGCCGTCAAGGCC
CAGGCTGATGATTTGCCACTGGTTGGTAACAAGGCGCCTGATTTTGAGGCAGAGGCTGTTTTTGAC
CAAGAGTTCATCAAGGTGAAGCTCTCAGAGTACATTGGTAAAAAGTATGTGATTCTGTTTCTCTAC
CCTTTGGACTTCACTTTTGTCTGCCCTACGGAGATTACTGCCTTCAGTGACCGTTATGAAGAATTT
GAGAAGCTAAACACGGAAGTGTTAGGTGTCTCAGTCGACAGTGTGTTCTCGCATCTTGCGTGGGTC
CAAACAGAGAGAAAGTCAGGAGGGCTGGGTGACCTGAACTACCCACTTGTCTCTGATATCACTAAA
TCCATTTCAAAATCTTTTGGAGTGCTCATCCCTGATCAGGGCATTGCACTGAGAGGGCTTTTCATC
ATCGACAAAAAGGAGTCATACAGCATTCCACAATCAACAACCTCGGTATTGGCCGAAGCGTTGAT
GAGACAATGAGAACCCTCCAGGCATTGCAGTATGTTCAAGAAACCCTGATGAGGTTTGCCCCGCG
GGATGGAAGCCTGGGGAGAAATCGATGAAGCCTGACCCCAAGCTGAGCAAAGAGTATTTTCAGCT
ATTTAAAGGCTTTTTAAACAAATGATTGGTGAAAAGCAGAGGCATGTTTTGTCTTCATTGCTTATG
TTTCTGCTATGTGTGTTTTCCTCAAAATTGAATAAAAATAATGGAATTTAAAAAAAAAAAAAAAA
```

SEQ ID NO: 8 - protein - Brassica napus
```
MASLASTTTLISSSSVLLPSKPSPFSPAASFLRTLPSTSVSTSSSLRSCFSSISPLTCIRSSSRPS
FAVKAQADDLPLVGNKAPDFEAEAVFDQEFIKVKLSEYIGKKYVILFLYPLDFTFVCPTEITAFSD
RYEEFEKLNTEVLGVSVDSVFSHLAWVQTERKSGGLGDLNYPLVSDITKSISKSFGVLIPDQGIAL
RGLFIIDKKGVIQHSTINNLGIGRSVDETMRTLQALQYVQENPDEVCPAGWKPGEKSMKPDPKLSK
EYFSAI
```

FIGURE 6 (continued)

SEQ ID NO: 9 - DNA - Arabidopsis thaliana
AGCTATTTGGTTTCTCTATCCGATTCGTCTCTCTCACGCCCTCACGTTTATCCACCTCATCCTCAA
ACCAAACCACAAGACCTCTTTTTTAAGTAACCAATCACAGAGAGATAGAGAGAGAGAACAGAGTCA
ATGTCAATGGCGTCTATAGCTTCTTCTTCTTCCACCACCCTACTCTCTTCCTCTAGGGTTCTTCTT
CCCTCCAAGTCTTCTCTTTTATCTCCTACCGTCTCTTTCCCCAGAATCATACCCTCTTCCTCGGCA
TCATCCTCTTCTCTCTGTTCCGGGTTCTCCAGTCTCGGTTCCCTCACCACCAACCGCTCCGCCTCA
CGCCGGAACTTCGCCGTCAAGGCTCAGGCTGATGATTTACCACTGGTCGGTAATAAGGCGCCTGAT
TTTGAAGCTGAGGCAGTTTTTGATCAAGAGTTCATAAAGGTGAAGCTCTCTGAGTACATTGGCAAA
AAGTATGTTATTCTATTCTTCTACCCTTTGGACTTCACTTTTGTCTGCCCCACTGAGATTACTGCC
TTCAGTGACCGTTATGAAGAATTTGAGAAGCTAAACACCGAAGTATTAGGGGTCTCTGTCGACAGT
GTGTTCTCGCATCTTGCGTGGGTCCAAACAGACAGAAAGTCGGGAGGGCTCGGTGATCTGAATTAT
CCTCTTGTTTCGGATATCACTAAATCCATTTCAAAATCGTTTGGAGTGCTCATCCCTGATCAGGGC
ATTGCACTGAGAGGGCTTTTCATCATAGACAAGGAAGGAGTCATTCAGCATTCCACCATCAACAAC
CTCGGTATTGGCCGAAGTGTTGATGAGACAATGAGAACCCTCCAGGCATTACAGTATGTTCAAGAA
AACCCGGATGAAGTGTGCCCTGCGGGATGGAAGCCAGGGGAGAAATCAATGAAACCTGACCCCAAG
CTCAGCAAAGAATACTTTTCAGCTATCTAGAGGCTAAGATTGAACACATGTTTGGTGAAAATTAGC
AATCAGAGTTGTTTTATTCGTCTTTTCAAAGTTGGAGCAGAGTTGTTATTTTTAGCCAAAGAACCT
TTGTATCTATCTCATCTTTCTCCTGTTTCTGCTATGTGATTCTCCTTAAATTGAATCAAAAATAAA
GAAATCCTTCTTTTCTTTTGCCAA

SEQ ID NO: 10 - protein - Arabidopsis thaliana
MASIASSSSTTLLSSSRVLLPSKSSLLSPTVSVPRTLHSSSASSSSLCSGFSSLGSLTTSRSASRR
NFAVKAQADDLPLVGNKAPDFEAEAVFDQEFIKVKLSEYIGKKYVILFFYPLDFTFVCPTEITAFS
DRYEEFEKLNTEVLGVSVDSVFSHLAWVQTDRKSGGLGDLNYPLVSDITKSISKSFGVLIPDQGIA
LRGLFIIDKEGVIQHSTINNLGIGRSVDETMRTLQALQYVQENPDEVCPAGWKPGEKSMKPDPKLS
KEYFSAI

SEQ ID NO: 11 - DNA - Spinacia oleracea
GTGTGTAGCAGCAATGGCGTGTGTTGCTTCTTCAACTACTCTCATCTCTTCTCCCTCTTCTAGGGT
TTTTCCAGCAAAGTCTTCACTTTCCTCTCCATCTGTTTCTTTCCTTCGAACCCTTTCTTCTCCTTC
CGCATCTGCTTCTCTCCGCTCCGGATTTGCTCGACGCTCTTCCCTCAGCTCCACTTCTCGTCGGAG
CTTTGCTGTCAAAGCCCAGGCCGATGATCTTCCACTGGTTGGAAACAAGGCGCCTGATTTTGAGGC
AGAGGCTGTGTTTGATCAAGAGTTCATCAAGGTTAAGCTCTCTGATTACATTGGAAAGAAGTATGT
GATTCTGTTTTTCTACCCATTGGACTTTACTTTCGTCTGCCCAACAGAGATTACTGCCTTCAGTGA
CCGGCATTCAGAATTTGAAGTTGAACACCGAAGTATTAGGTGTTTCTGTCGATAGTGTGTTCTC
TCACCTTGCATGGGTCCAAACAGACAGGAAATCTGGAGGGCTTGGTGATCTGAACTATCCCCTTAT
TTCAGATGTCACTAAATCAATCTCAAAGTCGTTCGGAGTGCTCATCCATGATCAGGGAATAGCACT
GAGAGGACTTTTCATAATCGACAAGGAAGGAGTGATCCAACATTCCACCATCAACAATCTTGGTAT
TGGCCGAAGCGTTGATGAGACAATGAGAACCCTCCAGGCATTACAGTACACAGGAAACCCGGATGA
AGTCTGCCCAGCAGGATGGAAGCCGGGTGAGAAGTCAATGAAACCCGACCCAAAACTCAGCAAGGA
GTACTTCTCAGCTATTTAGAACTCTACTATGATAGCAAAGGTACATCTTTGTTATATGTGAGCAGA
GTTTTTCTG

SEQ ID NO: 12 - protein - Spinacia oleracea
MACVASSTTLISSPSSRVFPAKSSLSSPSVSFLRTLSSPSASASLRSGFARRSSLSSTSRRSFAVK
AQADDLPLVGNKAPDFEAEAVFDQEFIKVKLSDYIGKKYVILFFYPLDFTFVCPTEITAFSDRHSE
FEKLNTEVLGVSVDSVFSHLAWVQTDRKSGGLGDLNYPLISDVTKSISKSFGVLIHDQGIALRGLF
IIDKEGVIQHSTINNLGIGRSVDETMRTLQALQYTGNPDEVCPAGWKPGEKSMKPDPKLSKEYFSA
I

FIGURE 6 (continued)

SEQ ID NO: 13 - DNA - Nicotiana tabacum

GGCACGAGCTCCTATCCAATGGCTTGCTCTGCTTCTTCTACAGCACTTCTTTCTTCCAACCCAAAA
GCAGCTTCCATTTCCCCCAAATCCTCCTTTCAAGCTCCCATTTCTCAATGTTTATCTGTACCTTCC
TCTTTCAATGGGCTCCGTAATTGCAAGCCTTTTGTTTCTCGTGTAGCCCGTTCCCTCTCTACTCGC
GTTGCTCAATCCCAACGCCGTCGTTTCGTTGTTCGTGCCTCTAGTGAACTTCCACTTGTTGGAAAT
CAAGCGCCAGACTTTGAGGCTGAAGCTGTTTTTGATCAAGAATTCATCAAGGTTAAACTATCTGAG
TACATTGGAAGAAGTATGTCATTCTCTTTTTCTACCCACTAGACTTTACATTTGTTTGCCCAACA
GAGATCACTGCTTTCAGTGACCGTTATGGAGAATTTGAAAAGTTGAACACAGAAATATTGGGTGTT
TCCGTAGACAGTGTGTTCTCCCACCTTGCCTGGGTTCAAACTGATAGAAAGTCTGGTGGCCTAGGT
GATCTGAACTATCCATTAATTTCCGACGTGACCAAGTCAATTTCAAAATCATACAATGTTCTGATC
CCCGATCAGGGAATTGCATTGAGAGGACTTTTCATCATTGACAAGGAAGGAGTTATTCAGCATTCA
ACCATTAACAATCTTGGAATTGGTCGTAGTGTTGATGAAACATTGAGAACTCTTCAGGCATTGCAA
TACGTTCAGGATAACCCGGATGAAGTGTGCCCAGCTGGATGGAAGCCTGGGGAGAAATCCATGAAG
CCTGACCCCAAGGGTAGCAAAGAATACTTTGCATCCATATGAGGTGATGACTGCAATTGCTTTATC
TAATTTGTTGTTTAGGAAGGCTGGAGACCCTACTTTTCTGTTACATTTTTCTAATGTACCGGCTGA
GTTTGGTCATTTTTGAGAATATATACACTTGTACACTTTTAAAAAAAAAAAAAAAAAAAAAAAAA

SEQ ID NO: 14 - protein - Nicotiana tabacum
MACSASSTALLSSNPKAASISPKSSFQAPISQCLSVPSSFNGLRNCKPFVSRVARSLSTRVAQSQR
RRFVVRASSELPLVGNQAPDFEAEAVFDQEFIKVKLSEYIGKKYVILFFYPLDFTFVCPTEITAFS
DRYGEFEKLNTEILGVSVDSVFSHLAWVQTDRKSGGLGDLNYPLISDVTKSISKSYNVLIPDQGIA
LRGLFIIDKEGVIQHSTINNLGIGRSVDETLRTLQALQYVQDNPDEVCPAGWKPGEKSMKPDPKGS
KEYFASI

SEQ ID NO: 15 - DNA - Phaseolus vulgaris
TCTATTCTATCTACACTCACTCTCTCACTCTCCCACTCTCCCATGGCTTCCTCAGCTCCCTGTGCT
TCTCTCATATCCTCAAACCCTAACATTCTCTTCTCTCCAAATTCCCTTCTTCTTCCTTTTCTTCC
CTCTCCTTCCCCAATTCCCCCAACTCTCTTTTCAAACCTTTACGCACTTCTCTCAATCCTTCATCT
CCCCCTCTCAGAACCTTCGTTGCCAGGGCTTCGAGTGAACTTCCATTAGTTGGGAACACAGCACCG
GATTTTGAAGCAGAGGCCGTTTTTGATCAGGAGTTCATCAAGGTCAAACTATCTGATTATATTGGG
AAAAAATATGTTATCCTCTTTTTCTATCCACTGGACTTCACATTCGTTTGTCCGACAGAAATCACT
GCCTTCAGTGACCGGTATGCAGAGTTTGAGGCACTAAATACAGAAATTTTGGGTGTTTCAGTTGAC
AGTGTTTTTTCACACCTTGCATGGGTTCAAACTGATAGAAAGTCGGGTGGTCTTGGCGACTTGAAT
TATCCATTGATTTCTGATGTCACCAAATCCATCTCAAAATCTTATGATGTTCTCATTCCCGATCAG
GGGATTGCATTGAGAGGATTGTTCATTATTGACAAGGAAGGGGTTATTCAGCATTCTACCATTAAC
AACCTGGCCATTGGTAGAAGTGTTGATGAGACAAAGAGAACGCTCCAGGCCTTGCAGTATGTGCAG
GAGAACCCAGATGAAGTTTGCCCAGCTGGGTGGAAGCCTGGTGAGAAGTCCATGAAACCAGACCCT
AAACTTAGCAAAGAGTACTTCTCTGCTATTTAGGGAGGATAATGGTTGAAGAGTAGCAATTGCTCA
TATGTATCAATCAATGATAATTTGTATAATGCAACGCAAGTTTATAAAGTTTTGATTGAGAGGGTC
TCATGATTATACAAAAAAA

SEQ ID NO: 16 - protein - Phaseolus vulgaris
MASSAPCASLISSNPNILFSPKFPSSSFSSLSFPNSPNSLFKPLRTSLNPSSPPLRTFVARASSEL
PLVGNTAPDFEAEAVFDQEFIKVKLSDYIGKKYVILFFYPLDFTFVCPTEITAFSDRYAEFEALNT
EILGVSVDSVFSHLAWVQTDRKSGGLGDLNYPLISDVTKSISKSYDVLIPDQGIALRGLFIIDKEG
VIQHSTINNLAIGRSVDETKRTLQALQYVQENPDEVCPAGWKPGEKSMKPDPKLSKEYFSAI

FIGURE 6 (continued)

SEQ ID NO: 17 - DNA - Pisum sativum
ATGGCTTGCTCAGCTCCATTTGCTTCTCTCCTATATTCAAACCCTAACACACTCTTCTCTCCCAAA
TTCTCTTCTCCGCGCCTCTCTTCTCTCTCAATCCCCAATGCACCCAATTCTCTCCCCAAACTACGC
ACTTCCCTCCCTCTTTCCCTCAACCGCTCCTCTTCCTCTCGCCGCACTTTCGTCGTTAGGGCTTCT
GGTGAATTACCATTAGTTGGGAACTCAGCGCCGGATTTTGAAGCTGAAGCTGTTTTCGATCAGGAG
TTTATCAAGGTCAAACTATCTGAATATATTGGGAAGAAATATGTTATCCTCTTTTTCTACCCATTG
GACTTCACGTTCGTTTGCCCAACAGAAATCACTGCTTTCAGTGACCGGCATGCAGAGTTTGATGCA
ATAAATACTGAGATTTTGGGTGTTTCAGTTGACAGTGTGTTCTCGCACCTTGCATGGGTTCAATCA
GATAGAAAGTCAGGTGGCCTTGGTGACTTGAAATATCCTCTGGTTTCTGATGTCACCAAATCCATA
TCGGAATCTTACGGTGTTCTCATTCCCGATCAGGGAATTGCATTGAGAGGATTGTTCATTATCGAT
AAGGAAGGGGTGATCCAACATTCCACCATCAACAACCTCGGAATTGGTAGAAGTGTTGACGAGACA
AAGAGAACACTCCAGGCTTTGCAGTATGTGCAGGAGAACCCAGATGAAGTTTGCCCTGCTGGGTGG
AAGCCTGGTGAGAAGTCCATGAAACCAGACCCCAAAGGTAGCAAAGAGTACTTTGCTGCTGTGTAG
AATGGCTAATAGTAAATTGCTATGAGTATTAACTACTCATCTGTATCATTTGGGATGTAAAAGGAT
TTTGTTTTATGTAATTCTATCCATTTTGAATTATGAGGCCTATGGGCTTAGCCATAAAAATAAAAA
GTATGAGGTCCAAAAGTGTGTGGTTACAGAAGCATGCTTGTGTNCCTTGATTTTGGAGTGAATTAT
GAATTGATGTATTATCTGTAAAAAAAAAAAAAAAAAAAAAAAAAAAAAAAA

SEQ ID NO: 18 - protein - Pisum sativum
MACSAPFASLLYSNPNTLFSPKFSSPRLSSLSIPNAPNSLPKLRTSLPLSLNRSSSSRRTFVVRAS
GELPLVGNSAPDFEAEAVFDQEFIKVKLSEYIGKKYVILFFYPLDFTFVCPTEITAFSDRHAEFDA
INTEILGVSVDSVFSHLAWVQSDRKSGGLGDLKYPLVSDVTKSISESYGVLIPDQGIALRGLFIID
KEGVIQHSTINNLGIGRSVDETKRTLQALQYVQENPDEVCPAGWKPGEKSMKPDPKGSKEYFAAV

SEQ ID NO: 19 - DNA - Oryza sativa
ACCCAAGCTCCCAAACCCCTCTCGCACCCAATCCAACCCAATCCCCTCCTCATCCACTCCGCTCTG
CGGCCATGGCCGCCTGCTGCTCCTCCCTCGCCACCGCCGTCTCCTCCTCCTCCGCCAAGCCCCTCG
CCGGCATCCCCCCCGCCGCGCCGCACTCCCTCTCCCTCCCCCGCGCTCCCGCCGCCAGGCCCCTCC
GCCTCTCCGCCTCCTCATCCAGATCCGCCCGGGCCAGCAGCTTCGTCGCCCGCGCCGGCGGTGTGG
ACGATGCGCCGCTGGTCGGGAACAAGGCGCCCGACTTCGATGCGGAGGCAGTCTTCGACCAGGAGT
TCATCAACGTGAAGCTGTCCGACTACATCGGGAAGAAGTACGTCATTCTCTTCTTCTACCCGTTGG
ACTTCACCTTCGTCTGCCCGACCGAGATTACCGCTTTCAGTGACAGATACGATGAGTTCGAGAAGT
TGAACACTGAGATCCTCGGTGTTTCAATTGACAGTGTGTTCTCCCATCTTGCATGGGTGCAGACAG
ACAGGAAATCTGGTGGGCTTGGTGATCTGAAATACCCATTGATTTCAGATGTTACTAAATCAATTT
CGAAGTCCTTTGGTGTCTTGATCCCTGACCAGGGAATTGCTCTGAGAGGACTTTTCATCATTGACA
AGGAGGGAGTGATTCAGCACTCTACCATTAACAACCTTGCCATTGGACGCAGTGTAGATGAGACCA
TGAGGACCCTTCAGGCGTTGCAGTACGTCCAGGACAACCCGGACGAGGTGTGCCCGGCCGGATGGA
AGCCCGGTGACAAGTCGATGAAGCCTGACCCCAAGGGAAGCAAGGAGTACTTCGCGGCCATCTAAG
CACACATATGCATATGCCTGGTGATGGATGTAGGGAGTTTTTTTGCTTTCGCGAGAGCCATTGCGT
TTCGTCTCCAAAGTGTAGTACCGTGTGCTCGTCTGATCGGATTTTGTTACTTGTTCGCCACCAGCT
GTTACTTTGTTCCCTAACAAATAAGGCTTTGTTTTGGTCGTGTTATACATGTATACATGTTAGTGC
GTTTCAAGATCGCTTCTGTTTT

SEQ ID NO: 20 - protein - Oryza sativa
MAACCSSLATAVSSSSAKPLAGIPPAAPHSLSLPRAPAARPLRLSASSSRSARASSFVARAGGVDD
APLVGNKAPDFDAEAVFDQEFINVKLSDYIGKKYVILFFYPLDFTFVCPTEITAFSDRYDEFEKLN
TEILGVSIDSVFSHLAWVQTDRKSGGLGDLKYPLISDVTKSISKSFGVLIPDQGIALRGLFIIDKE
GVIQHSTINNLAIGRSVDETMRTLQALQYVQDNPDEVCPAGWKPGDKSMKPDPKGSKEYFAAI

FIGURE 6 (continued)

SEQ ID NO: 21 - DNA - Secale cereale
TCTTCATATTCGGGAACCCTATCTATCTGGAGGCTACCGCGGCCGCCCCCGGGCACTCCCCGCCTG
ACAACCACGGCCATGGCGTGCGCCTTCTCCGCCTCCACCGTGTCCACGGCGGCCGCGCTCGTCGCG
TCCCCGAAGCCAGCCGGGGCGCCGAGTGCCTGTCGTTTCCCCGCGCTTCGCAGGGGCCGCGCAGGC
CTCCGCTGCGCGCGGCTCGAGGACGCCAGGGCCCGCAGCTTCGTCGCCCGCGCCGCAGCCGAGTAC
GACCTGCCACTGGTGGGAACAAAGCACCGGACTTCGCTGCGGAGGCCGTGTTCGACCAGGAGTTC
ATCAACGTCAAGCTATCTGATTACATTGGGAAGAAGTATGTGATTCTTTTCTTCTACCCTCTGGAC
TTCACCTTCGTCTGCCCAACTGAGATTACGGCTTTCAGCGACAGACATGAGGAGTTCGAGAAGATA
AACACTGAAATTCTTGGTGTTTCAGTTGATAGTGTGTTTTCCCATCTTGCATGGGTGCAGACAGAG
AGGAAATCTGGTGGACTTGGTGATCTTAAGTATCCTCTGGTTTCTGATGTCACCAAATCAATCTCA
AAGTCTTTTGGTGTATTGATCCCTGATCAGGGAATTGCTCTGAGAGGATTATTCATGATTGACAAG
GAGGGTGTGATTCAGCATTCCACTATTAACAACCTTGGTATTGGCCGCAGTGTGGATGAGACCTTG
AGAACCCTTCAGGCTCTGCAATACGTCCAAGAAAACCCAGACGAGGTCTGCCCGGCAGGATGGAAA
CCCGGGGAAAAGTCGATGAAGCCTGACCCTAAGGGCAGCAAGGAGTACTTCGCTGCCATCTAGATG
CGACCTTTGCGCTCACAGTCTGAGTTTTGTCATGGCCATTTCTGGTTACTTGTGTTCTTGTGACCC
GAGTTGTAGTTATCACGCGTCCAATTGCCTCTGTAATTCCTCCAATAAGGGTTTGTCTGTGTGTTG
ATTTTCCCTCCTCCAATTTGGAAAGCCCAATCCAAGATTGGAAATAAAACCTTCTGCCACCCAAAA
AAAAAAAAAA

SEQ ID NO: 22 - protein - Secale cereale
MACAFSASTVSTAAALVASPKPAGAPSACRFPALRRGRAGLRCARLEDARARSFVARAAAEYDLPL
VGNKAPDFAAEAVFDQEFINVKLSDYIGKKYVILFFYPLDFTFVCPTEITAFSDRHEEFEKINTEI
LGVSVDSVFSHLAWVQTERKSGGLGDLKYPLVSDVTKSISKSFGVLIPDQGIALRGLFMIDKEGVI
QHSTINNLGIGRSVDETLRTLQALQYVQENPDEVCPAGWKPGEKSMKPDPKGSKEYFAAI

SEQ ID NO: 23 - DNA - Riccia fluitans
GTTGGGAAAGGCAGCAAATATGGCAACCGCCTGTGCTGCAGTGTCTGCAGTGGCTGTTCCTGTGGC
CTCTGTAGCTAACCACATTGCGTCTTCATCATCTGGGACCCCATCCCTTGCCATTCCCAGGTCTTA
TGAGGGTTTAAACAAATCCTTCGGCGCTAGAATTGCACCCCGATCAACCTCCGCTTTTCGCAAGCC
CGTCACTGGTGTCTCCCTCAAGCAGTTCTCGAAGGGAAAAGTCGCTTCTGCGAGATGTGCGTCACC
TCTTGTTGGAAATGTCGCCCCGGACTTCGAGGCGGAGGCCGTTTTTGACCAAGAGTTCGTGAAGAT
CAAGCTCTCGGAGTACATTGGGAAGAGATACGTTGTTCTTTTCTTCTACCCTCTTGACTTCACCTT
CGTTTGCCCAACAGAAATTACCGCATTTAGCGACAAACACGAAGAGTTTGAAGAGTTGAACACCGA
AGTTATTGGGGTTTCTACTGACAGTGTGTTTTCCCATCTTGCCTGGATTCAAACTGACAGAAAATC
TGGAGGACTTGGTGACTTGAAGTACCCACTTGTGTCCGACTTGACCAAGAAGATCGCTGAAGATTT
TGGAGTATTGATCCCCGATCAGGGCATTGCATTGCGAGGATTGTTCATCATCGACAAGGAGGGCGT
CATTCAGCACGCAACCATTAACAATTTGGCCATCGGCAGAAGTGTGGAGGAGACGCTTCGAACTCT
GCAGGCTGTACAATATGTGCAGGAGAACCCAGACGAGGTCTGCCCCGCTGGCTGGAAGCCGGGTGA
AAAGACCATGAAGCCTGACACAAAGCTCAGCAAGGAGTACTTCGCACAAGTATAGGCCGAAAATAG
CTTCGTTTGGAATACATA

SEQ ID NO: 24 - protein - Riccia fluitans
MATACAAVSAVAVPVASVANHIASSSSGTPSLAIPRSYEGLNKSFGARIAPRSTSAFRKPVTGVSL
KQFSKGKVASARCASPLVGNVAPDFEAEAVFDQEFVKIKLSEYIGKRYVVLFFYPLDFTFVCPTEI
TAFSDKHEEFEKLNTEVIGVSTDSVFSHLAWIQTDRKSGGLGDLKYPLVSDLTKKIAEDFGVLIPD
QGIALRGLFIIDKEGVIQHATINNLAIGRSVEETLRTLQAVQYVQENPDEVCPAGWKPGEKTMKPD
TKLSKEYFAQV

FIGURE 6 (continued)

SEQ ID NO: 25 - DNA - Chlamydomonas incerta
ATGGCCGCTCTGCAGTCCGCTTCCCGCTCCTCGGCGGTGGCCTTCTCGCGCCAGGCGCGCGTGGCC
CCGCGCGTTGCCTCCAGCGTTGCTCGCCGCAACCTGGTCGTGCGCGCTTCCCACGCTGAGAAGCCT
CTGGTCGGCTCCGTCGCCCCTGACTTCAAGGCCCAGGCCGTGTTCGACCAGGAGTTCCAGGAGATT
ACCCTGAGCAAGTACCGCGGCAAGTACGTGGTGCTGTTCTTCTACCCCCTGGACTTCACCTTCGTG
TGCCCCACCGAGATCACCGCCTTCTCGGACCGCTACAAGGAGTTCAAGGACATCAACACCGAGGTC
CTGGGCGTGTCCGTGGACAGCCAGTTCACCCACCTGGCCTGGATTCAGACCGACCGCAAGGAGGGT
GGCCTGGGCGACCTGAACTACCCCCTGGTGGCTGACCTGAAGAAGGAGATCTCCAAGGCCTACGGC
GTCCTGACCGAGGACGGCATCTCCCTGCGCGGCCTGTTCATCATCGACAAGGAGGGCGTTGTGCAG
CACGCCACCATCAACAACCTGGCTTTCGGCCGCTCGGTCGACGAGACCAAGCGTGTGCTGCAGGCC
ATCCAGTACGTGCAGTCCAACCCCGATGAGGTCTGCCCCGCCGGCTGGAAGCCCGGTGACAAGACC
ATGAAGCCCGACCCCAAGGGCTCCAAGGAGTACTTCGCCGCCGTGTAAATTGACCCTTGATTGAGA
GTCAATGACACGCGAGGGCGTCATCGCAGTACTCGGGGGCATGCTGCAGATCAGCAGGCATGCGGA
CGAGACCAGTGCATTGGCAGGCTAGGCGCACACGGGAGGCAGAGCCAGTGCGGCGGCAGCGGCGAG
CGGCGGCTGTGGAAGCAGGCGCTAGCAGCAGCGGCGGCCGCGGCGGCGCTGCTCTCCATGGGTGCG
CCTGCAAGCAGCATGTGCATGTGGACTCGGTGCTTCTCGTTGATGGGTCAGGCGGCGTTGCCGGT
GGTGCGGACCGGGCGGTAATCGCACGTAGCTCAATTGTTGCGTGCGGGCGCTGTGCGGGCTGGCGT
GACGGCACGCAACCTGTGTGGGGCCTGTTGGTACGCTCGCGATAATGCAGTGCGCGGTCCGAGCGG
AGGGACGCGGCGGTGAATAGCTGCTGTAGTTTCAGGCAGGGATTTACCAGGTGACGGGTGGTTGCG
CCCACACCCGAACGGCTGTGATCCCAATTTTCCATGAGAGGGCTTGCAGATGGACGGCGTGTGATC
G

SEQ ID NO: 26 - protein - Chlamydomonas incerta
MAALQSASRSSAVAFSRQARVAPRVASSVARRNLVVRASHAEKPLVGSVAPDFKAQAVFDQEFQEI
TLSKYRGKYVVLFFYPLDFTFVCPTEITAFSDRYKEFKDINTEVLGVSVDSQFTHLAWIQTDRKEG
GLGDLNYPLVADLKKEISKAYGVLTEDGISLRGLFIIDKEGVVQHATINNLAFGRSVDETKRVLQA
IQYVQSNPDEVCPAGWKPGDKTMKPDPKGSKEYFAAV

SEQ ID NO: 27 - DNA - Nostoc sp.
ATGTCCATCACCTACGGAACACAAGAAAGCCTCCGCGTTGGTCAACAGGCTCCCGACTTTACAGCA
ACAGCTGTAGTTGATCAGGAATTCAAGACAATTAAGCTTTCCGACTATCGTGGTAAGTACGTTGTC
TTGTTCTTCTATCCCCTAGACTTTACCTTTGTTTGCCCCACGGAGATCACAGCATTTAGCGATCGC
TACGAAGAATTCAAGAAACTTAACACCGAAATTCTCGGTGTGTCCGTTGATAGCGAGTTCTCCCAC
CTAGCTTGGATTCAAACTGATCGTAAGTCTGGTGGTGTTGGCGACCTAAATTATCCCTTAGTTTCC
GATATTAAGAAAGAGGTTAGCGACGCTTACAACGTACTAGACCCAGCAGCAGGTATCGCTTTACGT
GGTCTGTTCATCATCGATAAAGATGGTATCATTCAGCACGCTACCATTAACAACCTAGCTTTTGGT
CGTAGCGTTGATGAAACCCTACGGACATTGCAAGCAATCCAGTATGTCCAGTCTCACCCAGATGAA
GTTTGCCCTGCTGGTTGGCAACCTGGGGAAAAGACCATGACTCCCGACCCTGTGAAGTCCAAAGTT
TACTTCGCTGCTGTGTAA

SEQ ID NO: 28 - protein - Nostoc sp.
MSITYGTQESLRVGQQAPDFTATAVVDQEFKTIKLSDYRGKYVVLFFYPLDFTFVCPTEITAFSDR
YEEFKKLNTEILGVSVDSEFSHLAWIQTDRKSGGVGDLNYPLVSDIKKEVSDAYNVLDPAAGIALR
GLFIIDKDGIIQHATINNLAFGRSVDETLRTLQAIQYVQSHPDEVCPAGWQPGEKTMTPDPVKSKV
YFAAV FIGURE 6 (continued)

SEQ ID NO: 29 - DNA - Synechococcus sp.
CTACTTGGCAATCGCCGCGAAGAACTCCTTGGATTTCACTGGGTCGGGGTGCATGGTTTTCTGGCC
GGGCTGCCAGTTGGCCGGGCAAACTTCATCGGGGTGAGATTGCACGTATTGGATAGCTTGCAGGGT
GCGCAAGGTTTCATCCACACTGCGGCCAAAGGCCAGGTTGTTAATGGTGGCGTGCTGGATGATCCC
TTCTTTGTCGATGATGAACAGGCCGCGCAGCGCCACACCGGCCTCCGGATCCAGAACATTGTAGGC
AGCGCTGATCTCCTTTTTCAGGTCAGAGACCAGAGGATACCTTAGCTCGCCCACCCCTCCGGCTTT
GCGGTCGGTCTGGATCCAGGCCAAGTGAGAGTATTCGCTGTCCACCGAGACGCCCAGGATCTCGGT
ATCCAGCTTGGCAAAGTCGTCATAGCGGTCGCTAAAGGCCGTGATCTCCGTTGGGCAGACAAAGGT
GAAGTCCAAGGGGTAGAAGAACAGCACCACATACTTCTTACCCCGGTAGTCGGAGAGCTTCACCGT
CTTGAATTCCATGTCATAGACGGCGGTGGCCGAAAAATCGGGAGCGGGCTGCCCCACTCGCAGGCA
TCCTTCCTGAGACAT

SEQ ID NO: 30 - protein - Synechococcus sp.
MSQEGCLRVGQPAPDFSATAVYDMEFKTVKLSDYRGKKYVVLFFYPLDFTFVCPTEITAFSDRYDD
FAKLDTEILGVSVDSEYSHLAWIQTDRKAGGVGELRYPLVSDLKKEISAAYNVLDPEAGVALRGLF
IIDKEGIIQHATINNLAFGRSVDETLRTLQAIQYVQSHPDEVCPANWQPGQKTMHPDPVKSKEFFA
AIAK

SEQ ID NO: 31 - DNA - Nodularia spumigena
ATGTCCCTCACTTACGCAACAGAAGGATGCCTCCGCGTTGGTCAACAGGCTCCTGAATTTACAGCC
ACAGCTGTGGTAGATCAAGAATTTAAGACCATTAAACTTTCCGACTATCGCGGTAAGTATGTGGTT
CTGTTTTTCTACCCCTTAGACTTTACCTTTGTTTGCCCCACTGAGATCACAGCATTTAGCGATCGC
TACGAAGAATTTAAGAAAGTTAACACAGAAGTTCTCGGTGTTTCCGTTGATAGCGAATTCTCTCAC
CTAGCCTGGATTCAAACTGAACGCAAGTCTGGTGGTGTCGGCGACCTCAATTATCCCTTAGTTTCG
GACATCAAAAAGAGATTAGCGCCACCTACAATGTCCTTGACCCAGCCGCAGGTATTGCTTTACGC
GGTTTGTTCATTATTGATAAAGATGGTATCATCCAGCATTCTACAGTGAATAACCTCGCCTTTGGT
CGCAGCGTTGATGAAACCCTGCGGACATTGCAAGCCCTTCAGTATGTTCAGTCTCACCCCGATGAA
GTTTGCCCAGCCGGTTGGCAACCTGGTGATCAAACAATGGTTCCTGACCCTGTGAAGTCGAAAGTC
TACTTCTCGGCTGTCTAG

SEQ ID NO: 32 - protein - Nodularia spumigena
MSLTYATEGCLRVGQQAPEFTATAVVDQEFKTIKLSDYRGKYVVLFFYPLDFTFVCPTEITAFSDR
YEEFKKVNTEVLGVSVDSEFSHLAWIQTERKSGGVGDLNYPLVSDIKKEISATYNVLDPAAGIALR
GLFIIDKDGIIQHSTVNNLAFGRSVDETLRTLQALQYVQSHPDEVCPAGWQPGDQTMVPDPVKSKV
YFSAV

SEQ ID NO: 33 - DNA - Thermosynechococcus elongatus
TTAGCCCACGGCTTCAAAATAGACTTTGGATTTGACAGGGTCAGGGTTCATCGTCTTGTCACCGGG
GTGCCAGCCCGCGGGGCAGACTTCATCGGGGTGAGTTTGAACGTATTGAATCGCTTGGAGTACCCG
CAGGGTCTCATCAACACTGCGGCCAAAGGCCAAGTTATTGATTGTTGCGTGTTGGATAATCCCTTC
TTTATCAATGATGAACAGACCCCGCAGGGCCACGCCTTCTTCGGTCAGGACATTGTAGGCAGTGCT
GATGTCTTTTTTCAGGTCAGACACCAAGGGATATTTAAGATCGCCGACACCACCAGCTTTGCGATC
AGTTTGTGTCCAAGCCAAGTGGGAGAACTGGCTATCCACAGACACGCCCAGGATTTCGGTGTTCAA
TTTGGCAAATTCATCGTAGCGATCGCTAAAGGCAACAATTTCGTGGGGCAGACAAAGGTAAAGTC
CAAGGGATAGAAAAGAGAACAACGTACTTACCGCGATAGTCCGAGAGCTTGATGGTTTTGAACTC
TTGGTCATAAACAGCAACCGCTTCAAAATCGGGGCGGGTTGACCGACGCGCAGACACTCAGACAT

SEQ ID NO: 34 - protein - Thermosynechococcus elongatus
MSECLRVGQPAPDFEAVAVYDQEFKTIKLSDYRGKYVVLFFYPLDFTFVCPTEIVAFSDRYDEFAK
LNTEILGVSVDSQFSHLAWTQTDRKAGGVGDLKYPLVSDLKKDISTAYNVLTEEGVALRGLFIIDK
EGIIQHATINNLAFGRSVDETLRVLQAIQYVQTHPDEVCPAGWHPGDKTMNPDPVKSKVYFEAVG

SEQ ID NO: 35 - DNA - Ostreococcus tauri
ATGTTGTCCGCGAGTTTGTCCAAGAGCGCGTTCACGCCCAGGGCGTCGGCGCTCCAGAAGAGCGTT
AAGGGGAAGAACTTCTCCCGATCCGCCGTCCGCGTGGAAGCGCGCAAGCCGCTCGTGGGCTACCCG
GCGCCGGAGTTTAGCGCCGAGGCGGTGTTCGATCAAGAGTTCCAAGACATCAAGCTCTCGGATTAC
CGCGGCAAGTACGTCGTGCTCTTCTTCTACCCGCTCGATTTTACCTTTGTGTGCCCGACGGAAATC
ACCGCCTTCTCCGATCGCTACGAAGAGTTCGCGAAGCTCAACACCGAAGTCCTCGGCGTGAGCGTT
GACTCCAAGTTCTCTCACTTGGCGTGGTTGCAAACCGACCGCAACGACGGCGGCCTCGGCGACTTG
GCCTACCCGCTCGTCAGTGACCTCAAGCGCGAAATCTGCGAATCGTACGATGTGTTGTACGAAGAC
GGCACCGCGCTCCGTGGGTTGTACATCATCGATCGTGAGGGCGTCATCCAGCACTACACATGCAAC
AACGCTCCGTTCGGCCGCAACGTCGACGAGTGCCTGCGCGTGCTTCAAGCGATCCAATACGTTCAA
AACAACCCAGACGAGGTGTGCCCGGCGGGCTGGACCCCGGGTGCGGCGACGATGAAGCCGGATCCG
AAGGGCTCGAAGGAATACTTCAAGGCGATCTAA

SEQ ID NO: 36 - protein - Ostreococcus tauri
MLSASLSKSAFTPRASALQKSVKGKNFSRSAVRVEARKPLVGYPAPEFSAEAVFDQEFQDIKLSDY
RGKYVVLFFYPLDFTFVCPTEITAFSDRYEEFAKLNTEVLGVSVDSKFSHLAWLQTDRNDGGLGDL
AYPLVSDLKREICESYDVLYEDGTALRGLYIIDREGVIQHYTCNNAPFGRNVDECLRVLQAIQYVQ
NNPDEVCPAGWTPGAATMKPDPKGSKEYFKAI

SEQ ID NO: 37 - DNA - Synechococcus sp.
CTACTTGGCAACCGCCGCGAAGAACTCCTTGGATTTCACCGGGTCGGGGTTCAGGGTTCTCTGGCC
GGGCTGCCAGTTGGCCGGGCAAACTTCATCGGGGTGAGCTTGCACGTACTGGATGGCCTGCAGGGT
GCGCAGGGTTTCATCCACGCTGCGGCCAAAGGCCAGGTTGTTGATGGTGGCGTGCTGGATGATCCC
TTCCTTGTCGATGATGAACAGGCCGCGCAAAGCCACCCCTGCCGCCGGATCCAGGACATTGTAGGC
GGCGCTGATCTCCTTTTTCAGGTCGGAGACCAGCGGATACCTCAGCTCGCCCACCCCTCCGGCTTT
GCGGTCGGTCTGAATCCAGGCCAGGTGAGAGTACTCGCTATCCACCGAGACGCCGAGGATCTCCGT
GTCCAGCTTGGCAAACTCGTCGTAGCGATCGCTGAAAGCCGTGATCTCCGTCGGGCAGACGAAGGT
GAAGTCCAAGGGGTAGAAGAACAGCACCACGTACTTCTTGCCCCGGTAGTCGGAGAGCCTCACCGT
CTTAAATTCCATGTCGTAAACGGCAGTGGCCGAAAAATCGGGAGCGGGCTGCCCCACCCGCAGACA
TCCTTCCTGAGACAT

SEQ ID NO: 38 - protein - Synechococcus sp.
MSQEGCLRVGQPAPDFSATAVYDMEFKTVRLSDYRGKKYVVLFFYPLDFTFVCPTEITAFSDRYDE
FAKLDTEILGVSVDSEYSHLAWIQTDRKAGGVGELRYPLVSDLKKEISAAYNVLDPAAGVALRGLF
IIDKEGIIQHATINNLAFGRSVDETLRTLQAIQYVQAHPDEVCPANWQPGQRTLNPDPVKSKEFFA
AVAK

SEQ ID NO: 39 - DNA - Synechococcus sp.
TCAACCGATGGCGGAGAAATACTCCTTGGAACCTTTCGGATCGGCTTCATGGTCTTTTCGCCGGG
CGTCCAGTTGGCGGGGCAGACTTCATCGGGGTTGGACTGCACGTACTGGAAGGCCTGAAGCACACG
CAGGGTTTCGTCCACATTCCGGCCAACAGGCAGGTTGTTGATCGTGGAGTGCATGATCACGCCATC
GGGATCGATGATGAACAGTCCACGCAAAGCAACGCCTTCGGCGTCGTCCAGCACGTTGTATGCGGT
GGCGATTTCCTTCTTGAGGTCAGCGACCAGGGGATAGTTGATGTCGCCCAGACCGCCCTGATTGCG FIGURE 6 (continued)

```
GGGAGTCTGAATCCAGGCCAGATGGCTGAACTGGCTGTCAACGGAAACGCCGAGGACTTCGGTGTT
CTTGCTGGAGAAATCGGCGTAGCGGTCGCTGAAGGCCGTGATTTCTGTGGGGCAGACGAAGGTGAA
ATCCAGGGGATAGAAGAAGAGCACCACGTACTTGCCGCGGTACTGGGACAGGGAGATTTCCTTGAA
TTCCTGGTCCACCACTGCAGTGGCAGTGAAATCGGGGGCCTGCTGGCCCACACGAAGGCAACCGGT
CTCGGTCAT
```

SEQ ID NO: 40 - protein - Synechococcus sp.
```
MTETGCLRVGQQAPDFTATAVVDQEFKEISLSQYRGKYVVLFFYPLDFTFVCPTEITAFSDRYADF
SSKNTEVLGVSVDSQFSHLAWIQTPRNQGGLGDINYPLVADLKKEIATAYNVLDDAEGVALRGLFI
IDPDGVIMHSTINNLPVGRNVDETLRVLQAFQYVQSNPDEVCPANWTPGEKTMKPDPKGSKEYFSA
IG
```

SEQ ID NO: 41 - DNA - Synechococcus elongatus
```
CTAGACTGCAGCGAAGAACTCTTTCGACTTAACAGGGTCGGGGTTCATCGTCGCTGCACCCGGTTG
CCAATTGGCGGGGCAAACTTCATCGGGGTGACTTTGGACGTACTGAATGGCTTGCAGCACCCGCAG
GGTTTCATCAACGCTGCGGCCAAACGCCAGGTTGTTGATGGTGGCGTGCTGGATCACACCTTCTTT
GTCGATGATGAACAGACCGCGCAGGGCAATGCCTTCAGCCGGATCAAGCACGTTGTAGGCAGTGCT
GATTTCTTTCTTGAGGTCAGCAACCAGCGGGTAAGCCAAGTCACCCAAACCACCTTCTTTACGGCT
GGTTTGAATCCAAGCCAAGTGGCTGAATTGGCTATCGACCGAGACACCCAAGATTTCGGTGTTCAG
GGCTGAAAAGTCTGCATAGCGATCGCTAAAAGCAGTAATTTCGGTCGGGCAAACAAAGGTGAAGTC
GAGGGGATAGAAGAACAGAACGACGTATTTGCCCCGGTAATTGGATAGCTTGATCGTCTGGAATTC
CTGATCAACGACTGCAGTCGCTTCAAAATCGGGGCCAATTGGCCGACGCGCAGGGCTCCTTCGGT
CAT
```

SEQ ID NO: 42 - protein - Synechococcus elongatus
```
MTEGALRVGQLAPDFEATAVVDQEFQTIKLSNYRGKYVVLFFYPLDFTFVCPTEITAFSDRYADFS
ALNTEILGVSVDSQFSHLAWIQTSRKEGGLGDLAYPLVADLKKEISTAYNVLDPAEGIALRGLFII
DKEGVIQHATINNLAFGRSVDETLRVLQAIQYVQSHPDEVCPANWQPGAATMNPDPVKSKEFFAAV
```

SEQ ID NO: 43 - DNA - Prochlorococcus marinus
```
TTATAGACTTGAGAAATACTCCTTGCTCCCTTCTGGATCTGGCTTCATTGTCTTTTCCCCTGGAGT
CCAATTGGCAGGACATACCTCGTCTGGGTTGGCTTGAACATATTGAAATGCTTGAAGAACTCTCAA
GGTCTCATCAACATTTCTTCCTACAGGTAGGTTGTTAATAGTAGCGTGCATGATCACACCATCTGG
ATCGATGATATAAAGACCTCTTAAAGCAACACCCTCTGCATCGTCGAGAACGTTATAAGCCAATGA
AATCTCTTTCTTTAAATCGGCAACCAAGGGATAATTGATATCGCCAATGCCTCCATCATTTCTTTG
AGTTTGAATCCAGGCAAGGTGGCTAAATTGACTGTCTACAGATACCCCTAAGACCTCAGTGTTCTT
ACTTGAAAATTCGGAGTATCTATCGCTAAAGCGGTAATTTCAGTTGGACATACAAAGTAAAATC
TAGAGGGTAAAAGAAAAGCACAACATATTTACCTCTGTAATTTGAAAGTGATATTTCCTTGAATTC
CTGGTCTATCACTGCAGTAGCAGTAAAATCAGGAGCTTTCTGGCCAACACGGATACATTCGTTCGT
CAT
```

SEQ ID NO: 44 - protein - Prochlorococcus marinus
```
MTNECIRVGQKAPDFTATAVIDQEFKEISLSNYRGKYVVLFFYPLDFTFVCPTEITAFSDRYSEFS
SKNTEVLGVSVDSQFSHLAWIQTQRNDGGIGDINYPLVADLKKEISLAYNVLDDAEGVALRGLYII
DPDGVIMHATINNLPVGRNVDETLRVLQAFQYVQANPDEVCPANWTPGEKTMKPDPEGSKEYFSSL
```

FIGURE 6 (continued)

SEQ ID NO: 45 - DNA - Porphyra purpurea
TTATGCAGCCGCAAAATAATTTTTAGATTTTATAGGATCCGGATTCATTGTTCTATCACCAGGTTT
CCAATTTGCTGGACATACTTCATCTGGATGGGCTTGAACATATTGAATTGCTTGCAGAACTCTTAA
AGTTTCTTCAACGCTTCTTCCAAACTCCAGATTGTTAACGGTAGAATATTGAATTATACCTTTAGG
ATCTATAATAAATAATCCCCTTAGGGCTACACCCCCACTATTTAATACATTATAGGCAATGCTAAT
TTCTTTTTTTAGATCTGATACTAAAGGATACTCAAGATCTCCTAATCCACCAGATTCTCGATCTGT
TTGCAACCAAGCTAAGTGAGAATATTCGCTATCCACAGAAACGCCTAAGATTTCTGTGTTAAGTTC
AGAAAAATCAGAATACTTATCACTGAACGCGGTTATTTCTGTAGGGCAAACAAAAGTAAAATCTAA
AGGGTAAAAAAATAAGATGACATACTTATTTTTAAAGTCAGATAATTTTATTGTTTTAAATTCTTG
GTCATAAACAGCTGTAGCTGAAAAGTCAGGCGCGATCTGGCCTACTTGAAGACAATTGTGTCCTGA
AATCAT

SEQ ID NO: 46 - protein - Porphyra purpurea
MISGHNCLQVGQIAPDFSATAVYDQEFKTIKLSDFKNKYVILFFYPLDFTFVCPTEITAFSDKYSD
FSELNTEILGVSVDSEYSHLAWLQTDRESGGLGDLEYPLVSDLKKEISIAYNVLNSGGVALRGLFI
IDPKGIIQYSTVNNLEFGRSVEETLRVLQAIQYVQAHPDEVCPANWKPGDRTMNPDPIKSKNYFAA
A

SEQ ID NO: 47 - DNA - Gracilaria tenuistipitata
ATGTTATTATGTTGTTTTATTACTGTTATTTTATATAATATAGACAATACTAAATTTTATAACAGG
AAGTGTAGTATTAAAATGATAACAAATAATAATATTTTGAGAGTTGGTCAACAAGCCCCCAATTTT
TCTGCTATTGCTGTATATGATCAAGAGTTTAAGAAAATAACACTGTCTGATTACTTGGGTAAGTAT
GTAATATTACTGTTTTATCCTTTAGATTTCACATTTGTTTGTCCAACTGAGATCACTGCTTTCAGT
GATTCATATAAAGAGATTCAAAGTCTGAATACAGAAGTTTTGGGTATATCTGTTGACAGTGAATAT
TCACATTTAGCATGGTTGCAAATGGAAAGAGATATTGGAGGCTTAGGAGATCTTAATTACCCGTTA
GTTTCTGATTTAACAAAACAGATTAGTGCTTCATATAATGTTCTAACAGAAGAAGGTAAAGCATTA
AGAGGTTTATTTATTGTTGATCAGCAAGGAATTATACAATATTCTTTAGTTAATAATTTAGACTTT
GGCCGTAGTATTAGTGAAACTATAAGAACACTTAAAGCTATCCAATATGTACAATCTCACCCAGAT
GAAGTTTGTCCAGCAAATTGGCAGCCAGGAAAAGCTACTATAATTAATAGTCCTCAAAAATCGAAA
AATTATTTTCAATCTATATAG

SEQ ID NO: 48 - protein - Gracilaria tenuistipitata
MLLCCFITVILYNIDNTKFYNRKCSIKMITNNNILRVGQQAPNFSAIAVYDQEFKKITLSDYLGKY
VILLFYPLDFTFVCPTEITAFSDSYKEIQSLNTEVLGISVDSEYSHLAWLQMERDIGGLGDLNYPL
VSDLTKQISASYNVLTEEGKALRGLFIVDQQGIIQYSLVNNLDFGRSISETIRTLKAIQYVQSHPD
EVCPANWQPGKATIINSPQKSKNYFQSI

SEQ ID NO: 49 - DNA - Mus musculus
GCCTAGGGCTCTCTCGGTTTCGAGATCTCTTTCCTGTCTCTAACCGTGTCTGGAAGTCCATGTGTC
CGGCTCTTGTTCACGCAGTAATGGCCTCCGGCAACGCGCAAATCGGAAAGTCGGCTCCTGACTTCA
CGGCCACAGCGGTGGTGGATGGTGCCTTCAAGGAAATCAAGCTTTCGGACTACAGAGGGAAGTACG
TGGTCCTCTTTTTCTACCCACTGGACTTCACTTTTGTTTGCCCCACGGAGATCATCGCTTTTAGCG
ACCATGCTGAGGACTTCCGAAAGCTAGGCTGCGAGGTGCTGGGAGTGTCTGTGGACTCTCAGTTCA
CCCACCTGGCGTGGATCAATACCCCACGGAAGAGGGAGGCTTGGGCCCCTGAATATCCCTCTGC
TTGCTGACGTGACTAAAAGCTTGTCCCAGAATTACGGCGTGTTGAAAAATGATGAGGGCATTGCTT
ACAGGGGTCTCTTTATCATCGATGCCAAGGGTGTCCTTCGCCAGATCACAGTCAATGACCTACCTG
TGGGCCGCTCTGTAGACGAGGCTCTCCGCCTAGTCCAGGCCTTTCAGTATACAGACGAGCATGGGG
AAGTCTGCCCTGCTGGCTGGAAGCCCGGCAGTGACACCATCAAGCCCAATGTGGATGACAGCAAGG

FIGURE 6 (continued)

```
AATACTTCTCCAAACACAACTGAGATGGGTAAACATCGGTGAGCCTGAAGCTTGGATTTCACCTGT
GCCCCAACCTGGATGTCCTGTGCTGGCCCAGAAAATGCTAGATTTTCCTCCACTCTCTGAAGGGGC
TGGAGTCTAGGCTGAGGCTTTCTCATTACCCACCTGGAATCTGGTGAATAGTGATCCTGCCCTGAG
CACACCTAGCTGGGCCCAGGTCTATAGGAAACCAATAAAGTATTAGGGACAGTGTAAAAAAAAAAA
```

SEQ ID NO: 50 - protein - Mus musculus
```
MASGNAQIGKSAPDFTATAVVDGAFKEIKLSDYRGKYVVLFFYPLDFTFVCPTEIIAFSDHAEDFR
KLGCEVLGVSVDSQFTHLAWINTPRKEGGLGPLNIPLLADVTKSLSQNYGVLKNDEGIAYRGLFII
DAKGVLRQITVNDLPVGRSVDEALRLVQAFQYTDEHGEVCPAGWKPGSDTIKPNVDDSKEYFSKHN
```

SEQ ID NO: 51 - DNA - Rattus norvegicus
```
GAATTCGGCACGAGGGTCGTCCGCGTGTCCGGCTCTTGCCCACGCAGTCATGGCCTCCGGCAACGC
GCACATCGGAAAGCCTGCCCCTGACTTCACGGGCACCGCCGTGGTGGATGGTGCCTTTAAGGAAAT
CAAGCTTTCAGACTACAGAGGGAAGTACGTGGTCCTCTTTTTCTATCCACTGGACTTCACTTTTGT
TTGCCCCACGGAGATCATCGCTTTTAGCGACCACGCTGAGGACTTCCGAAAGCTAGGCTGCGAGGT
GCTGGGAGTGTCTGTGGACTCTCAGTTCACCCACCTGGCCTGGATCAATACCCCACGGAAGGAGGG
AGGCTTGGGCCCACTGAATATCCCTCTGCTTGCTGATGTGACTAAAAGCTTGTCCCAGAATTACGG
CGTGTTGAAAAATGATGAGGGCATCGCTTACAGGGGCCTCTTTATCATCGATGCCAAGGGTGTCCT
TCGCCAGATCACAGTCAACGACCTACCTGTGGGACGCTCTGTAGATGAGGCTCTCCGCCTCGTCCA
GGCCTTTCAGTATACAGATGAGCATGGGGAAGTCTGTCCTGCTGGCTGGAAGCCCGGCAGTGACAC
CATCAAACCCAATGTGGATGACAGCAAGGAATACTTCTCCAAACACAACTGAGATGGGTAAACATC
GGTGAGCCTGAATCCCGGATCTCACCTGCGCCCTTACCTGGATGTCCTGTGCTGGCCCAGAAAACG
CTAGATCTTCCTCTACATTCTAAAGGGGCTGGAGGCTAGGCCGAGGCTTTCTCATTACCCACCTGG
AATCTGGTGAATAGTGACCCTGCCCTGAGCACACCCAGCTGGGCCCAGGTCTATAGGAAACCAATA
AAGTATTAGGGACAGTGTA
```

SEQ ID NO: 52 - protein - Rattus norvegicus
```
MASGNAHIGKPAPDFTGTAVVDGAFKEIKLSDYRGKYVVLFFYPLDFTFVCPTEIIAFSDHAEDFR
KLGCEVLGVSVDSQFTHLAWINTPRKEGGLGPLNIPLLADVTKSLSQNYGVLKNDEGIAYRGLFII
DAKGVLRQITVNDLPVGRSVDEALRLVQAFQYTDEHGEVCPAGWKPGSDTIKPNVDDSKEYFSKHN
```

SEQ ID NO: 53 - DNA - Oryza sativa
```
GCCTTCGTCTCGACACGTTTGCATTGCAGCAGCTCATAAGTTTCTTCTTCGTTTCTGCTCCCAGTG
CTAAGGCAGCACAGTCGTTCGTCGCCATGCCAGGGCTCACCATCGGCGACACCGTCCCCAACCTGG
AGCTGGACTCCACCCACGGCAAGATCCGCATCCACGACTTCGTCGGCGACACCTATGTCATCCTCT
TCTCCCACCCCGGCGACTTCACCCCGGTCTGCACCACGGAGCTGGCAGCCATGGCCGGCTACGCCA
AGGAGTTCGACAAGAGGGCGTCAAGCTGCTCGGCATCTCCTGCGACGACGTGCAGTCTCACAAGG
ACTGGATCAAGGACATCGAGGCCTACAAGCCTGGGAACCGCGTGACGTACCCGATCATGGCCGATC
CGAGCCGCGAGGCCATCAAGCAGCTGAACATGGTCGACCCGGACGAGAAGGATTCCAACGGCGGCC
ACCTCCCGTCCCGCGCGCTGCACATCGTCGGCCCCGACAAGAAGGTGAAGCTGAGCTTCCTGTACC
CGGCGTGCGTGGGGCGGAACATGGATGAGGTGGTGCGTGCGGTCGACGCGCTGCAGACGGCGGCGA
AGCACGCGGTGGCGACGCCGGTGAACTGGAAGCCCGGCGAGCGCGTCGTCATCCCTCCGGCGTCT
CCGACGACGAGGCGAAGGAGAAGTTCCCCCAGGGGTTCGACACCGCCGACCTGCCGTCCGGCAAGG
GCTACCTCCGCTTCACCAAGGTCGGCTAGATCATATCGATATCGACCTCGCTCTTCGTACATCATG
TGCGCCACGCGTGCGTGATAGCGTGTGCTGGCGTGATGACTATGCGAGATGCATCCCTGTGTGTGT
TGGTGTGGATAATGCCGCTACGTTTGGAACAGTAGTGCATTTACTCTGTGCTACTGTCTGAACTTT
GGCTGTTTGGCAGACTGTTTATGTACCCGTATGTTCGCCCTGTACTAATAGAGTGGGTGTTGTGG
TTGGCAAGTACTCTCCTCGGACAACATTTTAACTTTGACTACTAATAACAAACAAATTAAAAGAT
CAATCAGATGTTACTAGACATCTTAATTTTATT
```

FIGURE 6 (continued)

SEQ ID NO: 54 - protein - Oryza sativa
MPGLTIGDTVPNLELDSTHGKIRIHDFVGDTYVILFSHPGDFTPVCTTELAAMAGYAKEFDKRGVK
LLGISCDDVQSHKDWIKDIEAYKPGNRVTYPIMADPSREAIKQLNMVDPDEKDSNGGHLPSRALHI
VGPDKKVKLSFLYPACVGRNMDEVVRAVDALQTAAKHAVATPVNWKPGERVVIPPGVSDDEAKEKF
PQGFDTADLPSGKGYLRFTKVG

SEQ ID NO: 55 - DNA - Oryza sativa
ATGGCGTGCGCCTTCTCCGTCTCCTCTGCCGCGGCGCCTCTCGCCTCCCCGAAGGGGGACCTGCCG
TTGGTCGGGAACAAGGCGCCGGACTTCGAGGCGGAGGCCATGTTCGACCAGGGGTTCATCAAGTCT
AAATGCATGTTTGTAAGCTCTGCAGAGATCACTGCTTTCAGCGACAGATATGAGGAGTTTGAGAAG
ATAAATACTGAAGTTCTCGGTGTTTCGATTGACAGTGTGGGGATTGCTCTGAGAGGATTATTCATC
ATTGACAAGGAGGGTGTGATTCAGCATTCTACCATTAACAACCTTGCTATTGGCCGTAGCGTGGAT
GAGACGCTTAGGACCCTTCAGGCCCTACAGTATGTCCAAGAAAACCCGGATGAGGTTTGCCCAGCT
GGATGGAAACCTGGGGAGAAGTCAATGAAGCCTGACCCCAAGGACAGCAAGGAGGAACAAGAATGC
TGA

SEQ ID NO: 56 - protein - Oryza sativa
MACAFSVSSAAAPLASPKGDLPLVGNKAPDFEAEAMFDQGFIKSKCMFVSSAEITAFSDRYEEFEK
INTEVLGVSIDSVGIALRGLFIIDKEGVIQHSTINNLAIGRSVDETLRTLQALQYVQENPDEVCPA
GWKPGEKSMKPDPKDSKEEQEC

SEQ ID NO: 57 - DNA - Oryza sativa
CATTCCATCACAGACAGTTCGCAGAATCGCAGCAGCTTAGCTTAATTACTTTTTTCACCAACTCAA
CTTTCAGTTAATTTCCGGTTAATCCTCGATTCCTCATCATGCCTGGACTCACCCTCGGCGACGTCG
TCCCCGACCTGGAGCTCGACACCACCCACGGCAAGATCCGCCTCCACGACTTCGTCGGCGACGCCT
ACGTCATCATCTTCTCCCACCCCGCTGACTTCACGCCGGTCTGCACGACGGAGCTGTCGGAGATGG
CGGGCTACGCCGGCGAGTTCGACAAGAGGGGCGTCAAGCTCCTCGGCTTCTCCTGCGACGACGTCG
AGTCGCACAAGGACTGGATCAAGGACATCGAGGCCTACAAGCCTGGCCGCCGCGTCGGCTTCCCGA
TCGTCGCCGACCCGGACAGGGAGGCGATCAGGCAGCTCAACATGATCGACGCCGACGAGAAGGACA
CCGCCGGCGGCGAGCTCCCCAACCGGGCGCTCCACATCGTCGGGCCGGACAAGAAGGTGAAGCTGA
GCTTCCTGTTCCCGGCGTGCACGGGGCGGAACATGGCGGAGGTGCTGCGCGCGACGGACGCGCTGC
TGACGGCGGCGAGGCACCGGGTGGCGACGCCGGTGAACTGGAAGCCCGGCGAGCGCGTCGTCATCC
CCCCCGGCGTCTCCGACGAGGAGGCCAAGGCGAGGTTCCCGGCCGGGTTCGAGACCGCCCAGCTGC
CCTCCAACAAGTGCTACCTCCGCTTCACCCAGGTGGACTGAGAGACTGATGGTGAGGGAGGGAGGG
AGAGATCTGGGCCGTCGGTTTCGTGTGTAATAAACCAACGCACGACGTAGATGCTTCCACGTGTGT
GTTTCCCGTGCTGCTTCGATTGATCGATCGATCATTCGGTAAGTACTCTAGTTATGTGTAATCTGC
TGTTTGGGTGTAGTGGTGCATTTGCTGTTCTGTTGCCTGAAAGTGACGAACGGATTATGTTTGTCA
TTTGTATGTAAAATGTAACCGTATGTTTTTTATTTATCCCTTCCGAAATTACTGTGGAATATAGTG
AAGTAATGCTGTTAATAAACAGCCCGTTT

SEQ ID NO: 58 - protein - Oryza sativa
MPGLTLGDVVPDLELDTTHGKIRLHDFVGDAYVIIFSHPADFTPVCTTELSEMAGYAGEFDKRGVK
LLGFSCDDVESHKDWIKDIEAYKPGRRVGFPIVADPDREAIRQLNMIDADEKDTAGGELPNRALHI
VGPDKKVKLSFLFPACTGRNMAEVLRATDALLTAARHRVATPVNWKPGERVVIPPGVSDEEAKARF
PAGFETAQLPSNKCYLRFTQVD

FIGURE 6 (continued)

SEQ ID NO: 59 - DNA - Oryza sativa
ATCGATTCCCCCAACATATTAGGGCTCACGCCTCCCAAAGTCAAAACAGCCCAGCCCGAACAAGCA
TTTCCTCGAACACTTCGCCCTCCACCACCATGGCCGCCGCCGCCTCCACCCTCGCCTCCCTCTCCG
CCACCGCGGCCGCGGCCGCCGGCAAGCGCCTCCTCCTCTCCTCCCCCTCCCGCTCCCTCTCCCTCT
CCCTCGCCTCCCGCGGCCGCATCGCCGTCATGCCCCACCTCCGCGCTGGCATCCTCTCCGCCGCAC
CGAGGAGGGCGGTGTCGGCCTCGGCCCCGGCCGCGGCCACCATCGCGGTCGGGGACAAGCTCCCCG
ACGCGACGCTCTCCTACTTCGACTCGCCCGACGGGGAGCTGAAGACGGTGACCGTGCGCGACCTCA
CCGCCGGGAAGAAGGTGGTCCTCTTCGCGGTCCCCGGCGCGTTCACCCCGACCTGCACGCAGAAGC
ACGTCCCGGGGTTCGTCGCCAAGGCCGGGGAGCTCCGCGCCAAGGGGGTCGACGCCGTGGCCTGCG
TCTCCGTCAACGACGCGTTCGTGATGCGGGCGTGGAAGGAGAGCCTCGGCGTCGGCGACGAGGTGC
TCCTCCTCTCCGACGGCAACGGCGAGCTCGCCCGCGCCATGGGCGTCGAGCTCGACCTCTCCGACA
AGCCCGCCGGCCTCGGCGTGCGGTCCCGCCGCTACGCGCTCCTGGCGGAGGACGGCGTCGTCAAGG
TGCTCAACCTCGAGGAGGGCGGCGCCTTCACCACCAGCAGCGCCGAGGAGATGCTCAAGGCGCTCT
GAAGCGTGAACAACTCAAGCCATCCTCCACTTTTCATCTCAAATCTCCATAGCTCGGTTCGTTGCC
TACTTCTCTCAAGTGTTCGCTTCTTTTCCTGAATAATAAATCATGGCAACAATGGTGGACCGTGCA
GAGTAGTGTTGTCGTTTTGATGTGTGAAGCTTCTATAGCGAACATAGTGTGCAATTTTTAGGTAAC
ATATATGAGTCTTGGCCTTGCACTGTTTGTCAGGTAGTAACAACTTGGCACAGCTATAGACTGTAG
TAACAGAGTTCCTTTCATGTTGAATGGTGAGGCTGTGATGTGTTCTAGAGCTGAATAAACGTGCTC
TGGTAAATACTGTCACCAGATCAGACTATGGAGTAGTAGTAAGATTTTGCTTGGTTAATTGGGCAA
TGGCTATTTTTCAGGATCGTTCAGTTGAGATAAACATGTTTTGCTGTTCAGATGAGTTCG

SEQ ID NO: 60 - protein - Oryza sativa
MAAAASTLASLSATAAAAAGKRLLLSSPSRSLSLSLASRGRIAVMPHLRAGILSAAPRRAVSASAP
AAATIAVGDKLPDATLSYFDSPDGELKTVTVRDLTAGKKVVLFAVPGAFTPTCTQKHVPGFVAKAG
ELRAKGVDAVACVSVNDAFVMRAWKESLGVGDEVLLLSDGNGELARAMGVELDLSDKPAGLGVRSR
RYALLAEDGVVKVLNLEEGGAFTTSSAEEMLKAL

SEQ ID NO: 61 - DNA - Oryza sativa
ACACCCAAACCCGACGAACAGCCGCAGCTGCAGGCCACGCATCCTCGCCGTGAATCTCCCACCGCG
CTCCGGCGATGGCATTCGCGGTCTCCACCGCCTGCAGGCCGTCCCTGCTCCTGCCCCGCGCCAGC
GCTCGTCGCCGCCGCGGCCGCGGCCGCTCCTCTGCACGCCCTCCACCGCCGCCTTCCGCCGCGGCG
CCCTCAGCGCGACAACAACGCCAACGCCGGCGCGCGCAGCACTGCCGTCGACGACGGGGAGGAACA
GGATCGTCTGCGGCAAGGTGAGCAAGGGCAGCGCGGCGCCCAACTTCACGCTGAGGGACCAGGACG
GGAGGGCGGTGTCGCTGTCCAAGTTCAAGGGGAGGCCGGTGGTGGTGTACTTCTACCCCGCCGACG
AGACCCCCGGATGCACCAAGCAGGCCTGCGCCTTCCGCGACTCCTACGAGAAGTTCAAGAAGGCCG
GCGCCGAGGTCATCGGCATCAGCGGCGACGACGCCGCCTCCCACAAGGAGTTCAAGAAGAAGTACA
AGCTGCCGTTCACGCTGCTGAGCGACGAGGGGAACAAGGTGAGGAAGGAGTGGGGTGTGCCGGCTG
ACCTGTTCGGGACGCTGCCGGGAAGGCAGACGTACGTGCTCGACAAGAACGGCGTCGTCCAGTACA
TCTACAACAACCAGTTCCAGCCCGAGAAGCACATTGGCGAGACCCTCAAGATCCTCCAGAGCCTCT
GATTCTCTTCTTCTTCCTCCTTTTTAACTACAATCTCTCATGTATGATCCATCACAGTATAC
CGAGAAATTAATCCATCTGTTAATCTCTTCTCGATCGTTTTCTCCCTCGGCATGTGTATAGCTAG
TGTATCTGTAACTCTGTGAGTATATATACAGTCAAAATCGGTGGCTGCTAGCTCTGAATTTTGCC
GTAAGGCACTCTGATTTTCTCT

SEQ ID NO: 62 - protein - Oryza sativa
MAFAVSTACRPSLLLPPRQRSSPPRPRPLLCTPSTAAFRRGALSATTTPTPARAALPSTTGRNRIV
CGKVSKGSAAPNFTLRDQDGRAVSLSKFKGRPVVVYFYPADETPGCTKQACAFRDSYEKFKKAGAE
VIGISGDDAASHKEFKKKYKLPFTLLSDEGNKVRKEWGVPADLFGTLPGRQTYVLDKNGVVQYIYN
NQFQPEKHIGETLKILQSL

FIGURE 6 (continued)

SEQ ID NO: 63 - DNA - Oryza sativa
ATCTCCCTTCCCTGTCGATTACCTTCTCTCCTTCCTCTGTTCCTCCTCTCCTCCACACATCCAGGC
AGGCAACACAAGAATCATCCGGGAGAGCGACATGGCCCCGGTTGCCGTGGGCGACACCCTCCCCGA
CGGCCAGCTGGGGTGGTTCGACGGGGAGGACAAGCTGCAGCAGGTCTCCGTCCACGGCCTCGCCGC
CGGCAAGAAGGTCGTCCTCTTCGGCGTCCCCGGTGCCTTCACCCCGACCTGCAGCAATCAGCATGT
GCCAGGATTCATAAATCAGGCTGAGCAGCTCAAAGCCAAGGGTGTAGACGACATCTTGCTTGTCAG
TGTTAACGACCCCTTTGTCATGAAGGCGTGGGCAAAGTCATACCCTGAGAATAAGCATGTGAAATT
CCTTGCCGATGGTTTGGGAACATACACCAAGGCACTTGGTCTTGAGCTTGACCTTTCGGAGAAAGG
GCTTGGTATTCGTTCGAGACGGTTTGCTCTCCTTGCTGACAACCTCAAGGTTACTGTTGCAAACAT
TGAGGAAGGTGGCCAATTCACAATCTCTGGTGCTGAGGAGATCCTCAAGGCACTGTAAGAGCTTCA
GCTCTTAGGAACGGCAGCGATCACTTGGACCTATCGTGTCAATCTTGTTTAAATTTGTCTGCAAAA
TACTTGTGCGAATAAAATTGTCGATGAGCTGCCTAGTTGTGAGGACTTTATGATAATGTTTGAATC
TGTATCCACTGTTGAATCAAGTAGTAATGTTCAGTGCTCATGTT

SEQ ID NO: 64 - protein - Oryza sativa
MAPVAVGDTLPDGQLGWFDGEDKLQQVSVHGLAAGKKVVLFGVPGAFTPTCSNQHVPGFINQAEQL
KAKGVDDILLVSVNDPFVMKAWAKSYPENKHVKFLADGLGTYTKALGLELDLSEKGLGIRSRRFAL
LADNLKVTVANIEEGGQFTISGAEEILKAL

SEQ ID NO: 65 - DNA - Oryza sativa
GAGAGCCAACACGGTGCATCTCTCAGCCACACAGCCCCACCCGCGCCATGTCACTCGCCACCGCCG
CCGCCGGAGCGCAACCGTTCGTCCGCTCCTCCTCCTCCGCCGCCGCGGCGTCCTCGTCGCGGCCCC
TGCTCGCCGTCGCCGCCGCCCGCCACCGCCGCCCGCATGGATCTCTCGCCGCCGCCGCCGCCGCGG
CAAGGCGGCGTCGTCGTCGTCCGCTCCTCCAGGTGCGCGCGGCAAGGACGGAGTCCACGGGCGTCT
CCGTCGGGTTCCGCGCGCCCCAGTTCGAGCTCCCGGAGCCACTGACGGGGAAGCTCTGGACATTGG
ATGACTTCGAAGGCAACCCCGCGCTGCTGGTTATGTTTGTATGTAATCACTGTCCATTCGTAAAGC
ATCTCAAAAAGATATTGCGAAGCTCACCTCATTCTACATGGAGAAAGGGCTTGCTGCTGTTGCCA
TATCCTCGAACTCAATTGTGACACACCCACAGGATGGTCCTGATTACATAGCTGAGGAAGCAAAAT
TGTATAAATACTCTTTCCCGTATCTATATGATGAGTCTCAAGAAGTTGCTAAAGCTTTTCGAGCCG
TCTGCACGCCAGAGTTTTACTTGTTCAAAAAGGATGGACGAAGGCCATTTGAGCTTTTCTACCATG
GGCAGTTTGACGATTCAAGACCGAGTAACAACGTGCCAGTTACCGGAAGGGATTTAAGTCGTGCGA
TTGATTGTGCACTTAGTGGACAAGAGCTACCTTTTGTGCCAAAACCCAGTGTCGGGTGCAGCATCA
AATGGCACCCATGAAGAGCGTATTGCATTGTCATGTGCTGGAATATAGATGTTTTTCCCCCTTAAA
TTGAAGGTTGAACATGGGGATTGAGGTGAGCCATGCTCTCTACTACTAGAAGTATGGAAGCACACA
CATAGTAGATTTATGATAGCTAATTTCACATAGTAGATTTATGATAGCTAATTTATAATGTAATTT
TTAAGGGAAATAGATGCAGTTGAGGCCTTGTGGAGCTGATTCTTAACGTTGTGGGGCTGTTCAAC
TTGAGAGTTGCAAAACTAGACATGAATGGCGTGGATAGTGTTATGTTGTGTGCTGGTGTCTCATCT
TGGCCGGAAAAGAAAAACTGATGGATGTAACTGGTATTTGTGCAACAATGGGATAATGCACACAA
GTACAATAACCCATTATTATGGCTAACACAACACCCACGGGTGAAAATTAAAGATGAGGGC

SEQ ID NO: 66 - protein - Oryza sativa
MSLATAAAGAQPFVRSSSSAAAASSRPLLAVAAARHRRPHGSLAAAAAARRRRRRPLLQVRAAR
TESTGVSVGFRAPQFELPEPLTGKLWTLDDFEGNPALLVMFVCNHCPFVKHLKKDIAKLTSFYMEK
GLAAVAISSNSIVTHPQDGPDYIAEEAKLYKYSFPYLYDESQEVAKAFRAVCTPEFYLFKKDGRRP
FELFYHGQFDDSRPSNNVPVTGRDLSRAIDCALSGQELPFVPKPSVGCSIKWHP

FIGURE 6 (continued)

SEQ ID NO: 67 - DNA - Oryza sativa
AAATCCCAACAGAGAAGCATTTCCTCGAACACATCGCCGTCGCCGCCCTCCATGGCCGCTCCCACC
GCAGCAGCTCTCTCCACCCTCTCCACCGCCAGCGTCACCTCCGGCAAGCGCTTCATCACCTCCTCC
TTCTCCCTCTCCTTCTCCTCCCGCCCCCTCGCAACAGGCGTCCGCGCCGCGGGGGCGAGAGCGGCG
CGGAGGTCGGCGGCGTCGGCGTCCACCGTGGTGGCGACCATCGCCGTCGGAGACAAGCTCCCCGAC
GCGACGCTGTCCTACTTCGACCCGGCGGACGGCGAGCTGAAGACGGTGACGGTGGCGGAGCTGACG
GCGGGCAGGAAGGCGGTGCTGTTCGCGGTGCCCGGCGCGTTCACGCCGACGTGCTCGCAGAAGCAC
CTCCCGGGGTTCATCGAGAAGGCCGGGGAGCTCCACGCCAAGGGGGTGGACGCCATTGCCTGCGTG
TCGGTGAACGACGCGTTCGTGATGCGCGCGTGGAAGGAGAGCCTGGGCCTCGGCGACGCCGACGTG
CTCCTCCTCTCCGACGGCAACCTGGAGCTCACGCGCGCGCTCGGCGTCGAGATGGACCTCTCCGAC
AAGCCCATGGGGCTCGGCGTCAGGTCGCGCCGCTACGCGCTCCTCGCCGACGACGGCGTCGTCAAG
GTGCTCAACCTCGAGGAGGGCGGCGCCTTCACCACCAGCAGCGCCGAGGAGATGCTCAAGGCGCTC
TGAAGATGGAATCCGAGCTCTCGTAGGTGGCAACAATGGCAGGATCAGCCCGTTGCTCTCGCGCGT
TGGTGAGTAGCGTCGTCGTTGTGAAGAGGAAATTTTGTGTGTGTTTTTTTCGGTTGAATGTTGCA
TGCCATGTGCTTGACGAAATGACGGAATAACAAAAGAAAAAAAACTACTTTTATTTTTTTGTTGAA
ATTTGCAAACCATGTGTTTGACGAAATGTCGAGATATGAAAGCTGTGAAATCGCTTACGTCACGTG
CACC

SEQ ID NO: 68 - protein - Oryza sativa
MAAPTAAALSTLSTASVTSGKRFITSSFSLSFSSRPLATGVRAAGARAARRSAASASTVVATIAVG
DKLPDATLSYFDPADGELKTVTVAELTAGRKAVLFAVPGAFTPTCSQKHLPGFIEKAGELHAKGVD
AIACVSVNDAFVMRAWKESLGLGDADVLLLSDGNLELTRALGVEMDLSDKPMGLGVRSRRYALLAD
DGVVKVLNLEEGGAFTTSSAEEMLKAL

SEQ ID NO: 69 - DNA - Oryza sativa
TACCTATGGAGACGGTCGCCTCGCTCTCGCGCGCCGCGCTCGCCGGCGCGCCCGCCGCTACACGCG
CGACAGCGTCGCCCGTGAACAGGGCCGTGGTCCCTGCGGCGTCCCGGCCGCGCGGGGGACGCCTTT
GCTGCCGACGCTCGCTGACGGCCGTCTCCGCGGCGGCAGGGGCTTCCCCTCCCGTCTCCCCGTCGC
CTAGCCCCGATGGCGGCTCCCCGGCGTGTGGGACGCTCTCGGCGGCGTGTCCGTGCTCGCCGCCG
GCACCGGCGAAGCCGTTCAGCTCAGGGACCTGTGGGACCCCACCGAGGGGGTGGCCGTGGTGGCGC
TGCTCCGGCACTTCGGGTGCTTCTGCTGCTGGGAGCTGGCCTCTGTTCTGAAGGAATCCATGGCGA
AATTCGACGCTGCCGGGGCCAAGCTGATCGCCATCGGCGTCGGGACTCCTGACAAAGCTCGCATTC
TCGCCGATGGGCTGCCGTTCCCTGTTGATAGCTTGTACGCTGACCCCGAGCGCAAGGCTTACGACG
TATTGGGGCTTTACCATGGTCTGGGTCGGACATTAATCAGTCCTGCGAAGATGTACTCGGGGCTTA
ATTCCATCAAGAAGGTAACCAAGAACTACACGCTCAAGGGCACACCAGCAGACCTGACGGGTATCT
TGCAGCAGGGTGGTATGCTTGTGTTCAGAGGGAAAGAGTTGCTGTACTCATGGAAAGACAAAGGCA
CGGGTGATCATGCTCCTCTGGATGATGTCCTCAACGCTTGCTGCAATCGAACTTCTTGAGGTCTCT
AGCAGTCGGAAGATGTGTATGTAAATATATGAAATGCTCAGCATGCCAAACAGAGAGCAATTAGAC
TCAACAGTACTAGATGTTCGATTAATTATGCATTGTTGGTTTGCTTATGTACTTAGCATGATATTG
GATTAGCTACCCAATGGACATGACACTACAGTCTG

SEQ ID NO: 70 - protein - Oryza sativa
METVASLSRAALAGAPAATRATASPVNRAVVPAASRPRGGRLCCRRSLTAVSAAAGASPPVSPSPS
PDGGSPGVWDALGGVSVLAAGTGEAVQLRDLWDPTEGVAVVALLRHFGCFCCWELASVLKESMAKF
DAAGAKLIAIGVGTPDKARILADGLPFPVDSLYADPERKAYDVLGLYHGLGRTLISPAKMYSGLNS
IKKVTKNYTLKGTPADLTGILQQGGMLVFRGKELLYSWKDKGTGDHAPLDDVLNACCNRTS

FIGURE 6 (continued)

SEQ ID NO: 71 - DNA - Oryza sativa
TCCGCAACGACCTCCACACCGCAACGGTCCACTCGCTCGCCTCCGTCTCCCTCCCGCGTCTAGGGT
TTCGCCACGTCTCACGCAGCCATGGCCGCGGCGGCCGCGTCCACCTCGCTCCCCGTCCCGCGCGTC
TCCCTCCCGCCGTCCGCTCGCCCAGCCGCCGCTCCCCGGCACGGTCTCCTCATCCCCGGTCGCCGT
GGGTGCTTCCGTCTCCGCGGCTCACCAGCGGCACCGGCCGCCGCCGCCTCGGGCTCCCCTTCCGTG
CCTTCCTCTTCCCCGGAGGCTGGGTCGGGCATCGGGGATGCCCTCGGTGGCGTCGCCATCTACTCC
GCGGCCACCGGCGAGCCCGTGCTGTTCAGGGACCTGTGGGACCAGAACGAGGGAATGGCTGTTGTT
GCCCTGCTAAGGCATTTTGGGTGCCCTTGCTGTTGGGAGTTGGCCTCTGTGTTGAGGGATACAAAA
GAGAGATTTGATTCAGCTGGTGTCAAGCTAATAGCCGTTGGTGTTGGCACTCCAGATAAAGCCCGT
ATTCTTGCTGAGCGTTTACCATTTCCATTGGACTACCTCTACGCAGATCCTGAGCGCAAGGCCTAT
GATCTCTTGGGTTTGTATTTTGGTATTGGTCGCACATTCTTCAATCCAGCCAGTGCAAGTGTGTTT
TCACGATTTGACTCCCTCAAGGAGGCAGTGAAGAACTATACAATTGAAGCCACCCCAGATGATAGG
GCTAGTGTTCTACAACAGGGTGGAATGTTTGTGTTCAGAGGGAAAGAATTAATATATGCAAGGAAA
GATGAGGGCACTGGTGATCATGCACCTCTGGATGATGTCCTCAACATCTGTTGTAAAGCCCCTGCG
GCATGATATTGTGTAATCAATGTCCCATGAGAATTTTCATAGCCTGGTTCTGTTCGTGTCCCAAAG
TTGTATGCAGAAAAGCATCTCTTGATTTTGGAAGGCTGGCTTCTGCAAGGATAGTATCTCTTTGTC
TGTACGTCTGATCTACCATGCTGTTGATATGTAATATATCAGTTGAAAACTTGAGGGATGTAGGCA
GACCAAAGGACTTTCTCATGCCATAAGCTCAGCAGTTCTTTTCCTTTTCCTCATAGAAATGTACTA
ATTATAGAAGAGAATCTTACACTGTACAATAAGTTTGTGTTAAAGTTGGCGAAATTTTCCT

SEQ ID NO: 72 - protein - Oryza sativa
MAAAAASTSLPVPRVSLPPSARPAAAPRHGLLIPGRRGCFRLRGSPAAPAAAASGSPSVPSSSPEA
GSGIGDALGGVAIYSAATGEPVLFRDLWDQNEGMAVVALLRHFGCPCCWELASVLRDTKERFDSAG
VKLIAVGVGTPDKARILAERLPFPLDYLYADPERKAYDLLGLYFGIGRTFFNPASASVFSRFDSLK
EAVKNYTIEATPDDRASVLQQGGMFVFRGKELIYARKDEGTGDHAPLDDVLNICCKAPAA

SEQ ID NO: 73 - DNA - Oryza sativa
CTCGGCGCGGCCACAGCCGCAGAACCACACCTAGGCCGCTCGAAGACCCACGTAGCTTCCATCCAA
GCTTACCGCCATGGCCGCGCGCGCCGCTCCCGTACCGCACGCGGCCGCCACCAGCCCGCGACC
GGCTGCGGCGTCGAGCCTCCTCCGCGCGAGGGGCCCGTGCGCCTCCTCCTCTACCCGCCGCCGCCT
CCGCTTCTCCGTTGCGCCGGTGGCCGCCGCCAAGCCCGAGGCCGTCGGGAGGGCCGGGGAGGCAGC
TGCGGCGCCGGTGGAAGGGCTCGCGAAATCCCTGCAGGGGGTGGAGGTGTTCGATCTGAGCGGAAA
GGCGGTGCCCGTTGTTGATCTGTGGAAGGACAGGAAGGCCATCGTTGCGTTCGCCCGCCATTTTGG
ATGCGTGCTGTGCCGTAAGAGGGCCGATCTTCTCGCGGCTAAGCAGGATGCAATGGAGGCTGCAGG
GGTTGCTCTTGTTTTAATCGGACCAGGTACTGTTGAACAGGCAAAGGCATTTTATGACCAAACCAA
ATTCAAAGGAGAAGTATACGCTGATCCAAGTCACTCATCATATAATGCCCTTGAATTTGCATTTGG
GCTGTTCTCAACGTTTACTCCATCGGCCGGTTTGAAGATTATACAGTTGTACATGGAAGGATACAG
GCAGGATTGGGAACTGTCGTTCGAGAAGACCACCAGAACGAAAGGTGGATGGTATCAAGGGGCCT
ACTTGTTGCAGGACCAGGCATCGACAATATTTTGTATATCCACAAGGACAAAGAAGCAGGAGATGA
CCCTGACATGGATGATGTCTTGAAAGCTTGCTGTTCCTAGATCACTAGTATCCTATATCATTTCTG
TTAACCTCCAGACCTTGAAGACACATGTAAATATTTTGCCAAGTTAAAGTATGTTATGT

SEQ ID NO: 74 - protein - Oryza sativa
MAARAPLPVPHAAATSPRPAAASSLLRARGPCASLLYPRRLRFSVAPVAAAKPEAVGRAGEAAAAP
VEGLAKSLQGVEVFDLSGKAVPVVDLWKDRKAIVAFARHFGCVLCRKRADLLAAKQDAMEAAGVAL
VLIGPGTVEQAKAFYDQTKFKGEVYADPSHSSYNALEFAFGLFSTFTPSAGLKIIQLYMEGYRQDW
ELSFEKTTRTKGGWYQGGLLVAGPGIDNILYIHKDKEAGDDPDMDDVLKACCS

SEQ ID NO: 75 - DNA - Oryza sativa
ACGCGTGAGTTCGTGACGCGTCACGCCCCGCGGCCTTCCCCTCCCAAAAAGCGGCAGGACGCAACC
TGATCCCCATCCCCCGAGCAAGCAAAGCGGAGGAACGCGATGGCGTCGGCGCTGCTGAGGAAGGCG
ACGGTAGGCGGCTCCGCGGCGGCGGCGGCGGCGAGGTGGGCTTCCAGGGGGCTCGCGTCGGTGGGC
TCCGGCTCCGACATCGTCTCGGCGGCGCCCGGCGTGTCGCTGCAGAAGGCCCGCTCCTGGGACGAG
GGCGTCGCCACCAACTTCTCCACCACCCCTCTCAAGGACATCTTCCATGGGAAGAAAGTGGTCATC
TTCGGCCTGCCTGGTGCATACACAGGAGTCTGTTCACAGGCACACGTCCCTAGTTATAAAAATAAC
ATTGACAAGTTGAAAGCAAAAGGGGTTGACTCTGTTATCTGTGTCTCTGTGAATGACCCTTATGCC
CTGAATGGATGGGCAGAAAAGCTACAGGCAAAAGATGCTATTGAATTTTATGGTGATTTTGATGGG
AGTTTCCACAAAAGCTTGGATTTGGAAGTAGACCTCTCTGCTGCTTTGCTTGGCCGCCGTTCCCAC
AGGTGGTCAGCCTTTGTTGACGATGGGAAGATCAAGGCTTTCAATGTTGAGGTAGCTCCTTCTGAC
TTCAAGGTTTCTGGTGCCGAGGTGATCTTGGACCAAATCTGATCCGAGTAACGAAATTCTGTCGTT
GTTTGTTTTCTCATGCAGCATGCATGCTTTTGCTGTAGTAAATAAACGAAACTCGACTACTCGAG
TATCCATGTAAAGATGTTTGTAGTCTGCCTTGCTACGCCCAGAATATTTGTTTTCCTGTTACAAAT
CAGCTTGCCGGGCAACATGTTTGTCAGC

SEQ ID NO: 76 - protein - Oryza sativa
MASALLRKATVGGSAAAAAARWASRGLASVGSGSDIVSAAPGVSLQKARSWDEGVATNFSTTPLKD
IFHGKKVVIFGLPGAYTGVCSQAHVPSYKNNIDKLKAKGVDSVICVSVNDPYALNGWAEKLQAKDA
IEFYGDFDGSFHKSLDLEVDLSAALLGRRSHRWSAFVDDGKIKAFNVEVAPSDFKVSGAEVILDQI

SEQ ID NO: 77 - protein - Motif 1
PLVGNXAPDFXAE(A/G)(V/M)FDQ(E/G)F(I/V)(K/N)

where X is any amino acid

SEQ ID NO: 78 - protein - Motif 2
YPL(I/V)S(D/Y)XTK(S/K)I(S/A)(K/E)(S/D)(F/Y)(G/D/N)VLI(P/H)DQ where X is any amino acid

SEQ ID NO: 79 - DNA - Oryza sativa - GOS2 promoter
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT

FIGURE 6 (continued)

```
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTAATTATATGAAATGAACTGTAGCATAAGCAGTATT
CATTTGGATTATTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

SEQ ID NO: 80 - DNA - Oryza sativa - Rcc3 promoter
```
TCGACGCTACTCAAGTGGTGGGAGGCCACCGCATGTTCCAACGAAGCGCCAAAGAAAGCCTTGCAG
ACTCTAATGCTATTAGTCGCCTAGGATATTTGGAATGAAAGGAACCGCAGAGTTTTTCAGCACCAA
GAGCTTCCGGTGGCTAGTCTGATAGCCAAAATTAAGGAGGATGCCAAAACATGGGTCTTGGCGGGC
GCGAAACACCTTGATAGGTGGCTTACCTTTTAACATGTTCGGGCCAAAGGCCTTGAGACGGTAAAG
TTTTCTATTTGCGCTTGCGCATGTACAATTTTATTCCTCTATTCAATGAAATTGGTGGCTCACTGG
TTCATTAAAAAAAAAGAATCTAGCCTGTTCGGGAAGAAGAGGATTTTGTTCGTGAGAGAGAGAGA
GAGAGAGAGAGAGAGAGAGAGAGAAGGAGGAGGAGGATTTTCAGGCTTCGCATTGCCCAACCTC
TGCTTCTGTTGGCCCAAGAAGAATCCCAGGCGCCCATGGGCTGGCAGTTTACCACGGACCTACCTA
GCCTACCTTAGCTATCTAAGCGGGCCGACCTAGTAGCCACGTGCCTAGTGTAGATTAAAGTTGCCG
GGCCAGCAGGAAGCCACGCTGCAATGGCATCTTCCCTGTCCTTCGCGTACGTGAAAACAAACCCA
GGTAAGCTTAGAATCTTCTTGCCCGTTGGACTGGGACACCCACCAATCCCACCATGCCCCGATATT
CCTCCGGTCTCGGTTCATGTGATGTCCTCTCTTGTGTGATCACGGAGCAAGCATTCTTAAACGGCA
AAAGAAAATCACCAACTTGCTCACGCAGTCACGCTGCACCGCGCGAAGCGACGCCCGATAGGCCAA
GATCGCGAGATAAAATAACAACCAATGATCATAAGGAAACAAGCCCGCGATGTGTCGTGTGCAGCA
ATCTTGGTCATTTGCGGGATCGAGTGCTTCACAGCTAACCAAATATTCGGCCGATGATTTAACACA
TTATCAGCGTAGATGTACGTACGATTTGTTAATTAATCTACGAGCCTTGCTAGGGCAGGTGTTCTG
CCAGCCAATCCAGATCGCCCTCGTATGCACGCTCACATGATGGCAGGGCAGGGTTCACATGAGCTC
TAACGGTCGATTAATTAATCCCGGGGCTCGACTATAAATACCTCCCTAATCCCATGATCAAAACCA
TCTCAAGCAGCCTAATCATCTCCAGCTGATCAAGAGCTCTTAATTAGCTAGCTAGTGATTAGCTGC
GCTTGTGATC
```

SEQ ID NO: 81 - DNA - forward primer
```
GGGGACAAGTTTGTACAAAAAAGCAGGCTTAAACAATGGCGTCTGTTGCTTCTT
```

SEQ ID NO: 82 - DNA - reverse primer
```
GGGGACCACTTTGTACAAGAAAGCTGGGTTCGAGCTAAATAGCTGAGAAGAG
```

FIGURE 6 (continued)

MATLKVSDSVPAPSDDAEQLRTAFEGWGTNEDLIISILAHRSAEQRKVIRQAYHETY GEDLLKTLDKELSNDFERAILLWTLEPGERDALLANEATKRWTSSNQVLMEVACTRT STQLLHARQAYHARYKKSLEEDVAHHTTGDFRKLLVSLVTSYRYEGDEVNMTLAKQE AKLVHEKIKDKHYNDEDVIRILSTRSKAQINATFNRYQDDHGEEILKSLEEGDDDDK FLALLRSTIQCLTRPELYFVDVLRSAINKTGTDEGALTRIVTTRAEIDLKVIGEEYQ RRNSIPLEKAITKDTRGDYEKMLVALLGEDDA

FIGURE 7 A

MALPLELESLTEAISAGMGMGVDENALISTLGKSQKEHRKLFRKASKSFFVEDEERA FEKCHDHFVRHLKLEFSRFNTAVVMWAMHPWERDARLVKKALKKGEEAYNLIVEVSC TRSAEDLLGARKAYHSLFDQSMEEDIASHVHGPQRKLLVGLVSAYRYEGNKVKDDSA KSDAKILAEAVASSGEEAVEKDEVVRILTTRSKLHLQHLYKHFNEIKGSDLLGGVSK SSLLNEALICLLKPALYFSKILDASLNKDADKTTKKWLTRVFVTRADHSDEMNEIKE EYNNLYGETLAQRIQEKIKGNYRDFLLTLLSKSD

FIGURE 7B

CLUSTAL W (1.83) multiple sequence alignment

```
NP_001063096         ------------------------------------------MASLTLPPAPT
NP_001061839         ------------------------------------------MASLSVPPVPT
ABE65753             ------------------------------------------MATMKIPMTVP
NP_181410            ------------------------------------------MATIRVPNEVP
NP_001055408         MCCWCCCLDCIHNIPPLNLLFLHFSPHSLSSSAASAGGEAAAAAVAPMASISVPNPAP
AAC33305             ------------------------------------------MATLTVPTTVP
AAB71830             ------------------------------------------MATLTVPSTLP
CAB92956             ------------------------------------------MASLTVPAEVP
ABB55363             ------------------------------------------MASLTVPAEVP
AAC97494             ------------------------------------------MASLTVPAEVP
1DK5                 -----------------------------MAHHHHHMASLTVPAHVP
CAA75213             ------------------------------------------MASLTVPAEVP
CAA75214             ------------------------------------------MASLTVPAEVP
NP_174810            ------------------------------------------MATLKVSDSVP
AAD24540             ------------------------------------------MASLKVPTSVP
AAC97493             ------------------------------------------MSSLKVPASVP
AAB67994             ------------------------------------------TLKVPVHVP
AAR13288             ------------------------------------------MATLKVPAHVP
AAZ41833             ------------------------------------------MASLKVPTNVP
NP_201307            ------------------------------------------MASLKVPSNVP
NP_196585            ------------------------------------------MASLKVPATVP
AAZ67605             ------------------------------------------MASLKVPASVP
NP_196584            ------------------------------------------MASLKIPANIP
CAA52903             ------------------------------------------SHVP
NP_001048149         ------------------------------------------MATLTVPAAVP
NP_001057176         ------------------------------------------MATLTVPSAVP
NP_568271            ------------------------------------------MATIVSPPHFS
NP_181409            ------------------------------------------MALP
NP_001063343         ------------------------------------------MASRCLVT
NP_001061661         ----------------------------MSTTSSSKTATCPLCHADVLLPRRS
NP_001051711         ------------------------------------------
```

```
NP_001063096  ------------NPRQDAIDLHKAFKGFGCDSTTVINILTHRDSMQRALIQQEYRTMYSEDLSR
NP_001061839  ------------DPRRDAIDLHRAFKGFGCDATAVTAILAHRDASQRALIRRHYAAVYHQDLLH
ABE65753      ------------SPRVDADQLFKAFKGFGCDTSVININILAHRNATQRALIEQEYETKFSDDLRK
NP_181410     ------------SPAQDSETLKQAIRGWGTDEKAIIRVLGQRDQSQRRKIRESFREIYGKDLID
NP_001055408  ------------SPTEDAESIRKAVQGWGTDENALIEILGHRTAAQRAEIAVAYEGLYDETLLD
AAC33305      ------------SVSEDCEQLRKAFSGWGTNEGLIIDILGHRNAEQRNLIRKTYAETYGEDLLK
AAB71830      ------------SVSEDCEQLRKAFSGWGTNEDLIINILGHRNADERNSIRKAYTETHGEDLLK
CAB92956      ------------SVAEDCEQLRSAFKGWGTNEKLIISILAHRNAAQRKLIRQTYAETFGEDLLK
ABB55363      ------------SVAEDCEQLRSAFKGWGTNEKLIISILAHRNAAQRKLIRQTYAETFGEDLLK
AAC97494      ------------SVAEDCEQLRSAFKGWGTNEKLIISILAHRNAAQRKLIRQTYAETFGEDLLK
1DK5          ------------SAAEDCEQLRSAFKGWGTNEKLIISILAHRTAAQRKLIQQTYAETFGEDLLK
CAA75213      ------------SVAEDCEQLRSAFKGWGTNEKLIISILAHRNAAQRKLIQQTYAETFGEDLLK
CAA75214      ------------SVAEDCEQLRSAFKGWGTNEDLIISILAHRSAEQRKVIRQAYHETYGEDLLK
NP_174810     ------------APSDDAEQLRTAFEGWGTNEDLIISILAHRNAAQRKLIRETYAAAYGEDLLK
AAD24540      ------------EPYEDAEQLKKAFAGWGTNEALIQILAHRNAAQRKLIRDSYAAAYGEDLLK
AAC97493      ------------DPYEDAEQLKKAFKGWGTNEELIIQILAHRNARQRKLIRDSYAAAYGEDLLK
AAB67994      S-----------PSEDAEWQLRKAFEGWGTNEQLIIDILAHRNAAQRNSIRKVYGEAYGEDLLK
AAR13288      A-----------PSE-DAEQLRKAFEGWGTNEQLIIDILAHRNAAQRNLIRKTYREAYGEDLLK
AAZ41833      ------------LPEEDAEQLHKAFAGWGTNEKLIISILAHRTSAQRSLIRSAYAAAYNEDLLK
NP_201307     ------------LPEDDAEQLHKAFSGWGTNEKLIISILAHRNAAQRSLIRSVYAATYNEDLLK
NP_196585     ------------LPEEDAEQLYKAFKGWGTNERMISILAHRNATQRSFIRAVYAANYNKDLLK
AAZ67605      ------------LPEEDAEQLQKAFKGWGTNERMISILAHRNAEQRSFIRAVYAANYNKDLLK
NP_196584     ------------LPEEDSEQLHKAFKGWGTNEGMISILAHRNATQRSFIRAVYAANYNKDLLK
CAA52903      ------------SPSEDSEQLRGAFQGWGTNEGLIISILAHRNAAQRKSIRETYTQTHGEDLLK
NP_001048149  ------------PVAEDCEQLRKAFKGWGTNEKLIISILAHRDAAQRRAIRRAYAEAYGEELLR
NP_001057176  ------------PVADDCDQLRKAFQGWGTNEALISILAHRDAAQRRAIRRAYADTYGEELLR
NP_568271     ------------PVEDAENIKAACQGWGTNENAISILGHRNLFQRKLIRQAYQEIYHEDLIH
NP_181409     ------------LELESLTEAISAGMGMGVDENALISTLGKSQKEHRKLFRKASKSFFVEDEER
NP_001063343  T-----------GFEDECREIHDACN----QPRRLSVLLAHRSPSERQKIKATYRTVFGEDLAG
NP_001061661  AGSSTHRSHDLDDGPAPPSPESSCRSNAAVCGCARCRRPDLISPGTGMRMRNRFGDGPNR
NP_001051711  ------------MGGRKDNHDSSNADKGFHGAYPSGYPG-----
```

```
NP_001063096  RISS------ELSGHHKKAMLLWILDPAGRDATVLREALSGDTIDLR-----AATE
NP_001061839  RLAA------ELSGHHKRAVLLWVLDPASRDAAVLHQALNGDVTDMR-----AATE
ABE65753      RLHS------ELHGHLKKAVLLWMPEAVERDASILKRSLRGAVTDHK-----AIAE
NP_181410     VLSS------ELSGDFMKAVVSWTYDPAERDARLVNKILNEKKKKSLENLKVIVE
NP_001055408  RLHS------ELSGDFRSALMLWTMDPAARDAKLANEALKK-KKKGELRHIWVLVE
AAC33305      ALDK------ELSNDFERLVLLWALDPAERDALLANEATKRWTSSN----QVLME
AAB71830      ALDK------ELSNDFERLVLIWTLDPPERDALLANEATKRWTSSN----QVIME
CAB92956      ELDR------ELTHDFEKLVLIWTLDPSERDAYLAKEATKRWTKSN----FVLVE
ABB55363      EIGTGR----NLTHDFEKLVLIWTLDPSERDAYLAKEATKRWTKSN----FVLVE
AAC97494      ELDR------ELTHDFEKLVVVWTLDPAERDAYLAKEATKRWTKSN----FVLVE
1DK5          ELDR------ELTNDFEKLVVVWTLDPSERDAHLAKEATKRWTKSN----FVLVE
CAA75213      ELDR------ELTNDFEKLVVVWTLDPSERDAYLAKEATKRWTKSN----FVLVE
CAA75214      TLDK------ELSNDFERAILLWTLEPGERDALLANEATKRWTSSN----QVLME
NP_174810     DLDA------ELTSDFQRAVLLWTLSPAERDAYLVNEATKRLTSSN----WVILE
AAD24540      DLDS------ELTSDFQRVVLLWTLSPAERDAYLVNEATKRLTASN----WGIME
AAC97493      CLEK------ELTSDFERAVLLFTLDPAERDAHLANEATKKFTSSN----WILME
AAB67994      SLDE------ELTSDFERAVLLFTLDPAERDAFLAHEATKRFTSSH----WVLME
AAR13288      ALDK------ELSSDFERVVMLWTLDPAERDAFLAKESTKMFTKNN----WVLVE
AAZ41833      ALDK------ELSSDFERAVMLWTLDPPERDAYLAKESTKMFTKNN----WVLVE
NP_201307     ELDR------EISGDFERAVMLWTFEPAERDAYLAKESTKMFTKNN----WVLVE
NP_196585     ELDK------ELSGDFERAVILWTLDPAERDAVLANEVARKWYPGSGS--RVLVE
AAZ67605      ELDK------ELSGDFERAVMLWTLEPAERDAYLAKESTKMFTKDN----WVLVE
NP_196584     ELDG------ELSGDFERVVMLWTLDPTERDAYLANESTKLFTKNI----WVLVE
CAA52903      DLDK------ELSSDFEKAVLLWTLDPAERDAFLANQATKMLTSNN----SIIVE
NP_001048149  ALND------EIHGKFERAVIQWTLDPAERDAVLANEEARKWHPGG----RALVE
NP_001057176  SITD------EISGDFERAVILWTLDPAERDAVLANEVARKWYPGSGS--RVLVE
NP_568271     QLKS------ELSGNFERAICLWVLDPPERDALLANLALQKPIPDY-----KVLVE
NP_181409     AFEKCHDHFVRHLKLEFSRFNTAVVMWAMHPWERDARLVKKALKKGEEAYN---LIVE
NP_001063343  EVQKILMVN------QEDELCKLLYLWVLDPSERDAIMARDAVENGGATDYR--VLVE
NP_001061661  ISAQSG-----AWLCRERTAETCRSTSSRSGRYRRLQPAAVAGTRRAELIKRLQELCH
NP_001051711  ----------------------AYPLMQGYPNSPGQYPTPGGYPSAPPGQYPP-----
```

FIGURE 9 (contiued)

```
NP_001063096  IICSRTPSQLQIMKQTYHAKFG----TYLEHDIGQRT------SGDHQKLLLAYVGIPRYE
NP_001061839  VVCSRTPSQLLVVRQAYLARFGGGGGLEHDVAVRA-------SGDHQRLLLAYLRSPRYE
ABE65753      IICTRSGSQLRQIKQVYSNTFG-----VKLEEDIESEA-----SGNHKRVLLAYLNTTRYE
NP_181410     ISCTTSPNHLIAVRKAYCSLFD-----SSLEEHIASS-L----PFPLAKLLVTLASTFRYD
NP_001055408  VACASSPDHLVAVRKAYRAAYA-----SSLEEDVASCSLF---GDPLRRFLVRLVSSYRYG
AAC33305      IACTRSANQLLHARQAYHARYK-----KSLEEDVAHHT-----TGDFRKLLLPLVSSYRYE
AAB71830      IACRSSSDQLLRARQAYHVRYK-----KSLEEDVAHHT-----TGDFRKLLLPLVSSYRYE
CAB92956      IACTRSPKELVLAREAYHARNK-----KSLEEDVAYHT-----TGDHRKLLVPLVSSYRYG
ABB55363      IACTRSPKELVLAREAYHARNK-----KSLEEDVAYHT-----TGDHRKLLVPLVSSYRYG
AAC97494      IACTRSPKELVLAREAYHARNK-----KSLEEDVAYHT-----TGDHRKLLVPLVSSYRYG
1DK5          LACTRSPKELVLAREAYHARYK-----KSLEEDVAYHT-----TGDHRKLLVPLVSSYRYG
CAA75213      IACTRSPKELVLAREAYHARFK-----KSLEEDVAYHT-----TGEHPQLLVPLVSSYRYG
CAA75214      IACTRSPKELVLAREAYHAREK-----KSLEEDVAYHT-----TGEHRKLLVALVSSYRYG
NP_174810     VACTRTSTQLLHARQAYHARYK-----KSLEEDVAYHT-----TGDFRKLLVSLVTSYRYE
AAD24540      IACTRSSDDLFKARQAYHARYK-----KSLEEDVAYHT-----TGDFRKLLVPLTAFRYE
AAC97493      IACTRSSDDLFKARQAYHAPYK-----KSLEEDVAYHT-----VGDFRKLLVPLITAFRYE
AAB67994      IACSRSSHELLNVKAYHARYK------KSLEEDVAHHT-----TGEYRKLLVPLVSAFRYE
AAR13288      IACTRSSHELFNVRKAYHDLYK-----KSLEEDVAHHT-----KGDYRKLLVPLVSAFRYQ
AAZ41833      IACTRCPLDLFKVKQAYOARYK-----KSLEEDVAQHT-----SGDLRKLLLPLVSTFRYE
NP_201307     IACTRPALELIKVKQAYQARYK-----KSIEEDVAQHT-----SGDLRKLLLPLVSTFRYE
NP_196585     IACTRSALELFNAKQAYQARYK-----TSLEEDVAYHT-----SGDIRKLLVPLVSTFRYD
AAZ67605      IACTRSSLEFFKAKQAYVRYK------TSIEEDVAYHT-----SGDVRKLLVPLVSTFRYD
NP_196584     IACTRPSLEFFKTKQAYHVRYK-----TSLEEDVAYHT-----SGNIRKLLVPLVSTFRYD
CAA52903      IASTRSPLELLKAKQAYQVRFK-----KSLEEDVAYHT-----SGDIRKLLVPLVGIHRYE
NP_001048149  IACTRTPSQLFAAKQAYHERFK-----RSLEEDVAAHI-----TGDYRKLLVPLVPTVYRD
NP_001057176  IACARGPAQLFAVRQAYHERFK-----RSLEEDVAAHA-----TGDFRKLLVPLISAYRYE
NP_568271     IACMRSPEDMLAARRAYRCLYK-----HSLEEDLASRT-----IGDIRRLLVAMVSAYKYD
NP_181409     VSCTRSAEDLLGARKAYHSLFD-----QSMEEDIASHVH----GPQRKLLVGLVSAYRYE
NP_001063343  IFTRRKQNQLFFTNQAYLARFK-----KNLEQDMVTEP-----SHPYQRLLVALATSHKSH
NP_001061661  PANNLPNCSASWQPQRQKTIDRIPDSLDCGVTMERGKNKRDGSDNGLIFSNLMHGVAA
NP_001051711  ----------------------------------------------AGGYPGAQYPPSGYPPSQ
```

FIGURE 9 (contiued)

FIGURE 9 (contiuned)

```
NP_001063096   GP---EVDPTIVTHDAKDLYKAGEKR-------------------------LGTDEKTFIRIFTERSWAH
NP_001061839   GP---EVVDMAAAARDARELYRAGERR-------------------------LGTDERTFIRVFSERSAAH
ABE65753       GP---EIDNASVENDARTLKSAVARK--------------------------HKSDDQTLIQIFTDRSRTH
NP_181410      K----DRTDAEVATIEAAMLREAIEKK------------------------QLDHDHVLYILGTRSIYQ
NP_001055408   G---GGVDGELAIAEAAELHDAVVGRG------------------------Q-ALHGDDVVRIVGTRSKAQ
AAC33305       G---EEVNMNLAKTEAKLLHEKISDK--------------------------AYSDDDVIRVLATRSKAQ
AAB71830       G---DEVNMTLAKTEAKLLHEKISNK--------------------------AYSDDDVIRVLATRSKSQ
CAB92956       G---DEVDLRLAKAESKVLHEKISDK--------------------------AYSDDEVIRILATRSKAQ
ABB55363       G---DEVDLRLAKAESKVLHEKISDK--------------------------AYSDDEVIRILATRSKAQ
AAC97494       G---DEVDLRLAKAESKVLHEKISDK--------------------------AYSDDEVIRILATRSKAQ
1DK5           G---EEVDLRLAKAESKILHEKISDK--------------------------AYSDDEVIRILATRSKAQ
CAA75213       G---DEVDLRLAKAEAKILHEKISDK--------------------------AYSDDEVIRILATRSKAQ
CAA75214       G---DEVDLRLAKAEAKILHEKISDK--------------------------AYSDNEVIRILATRSKAQ
NP_174810      G---DEVNMTLAKQEAKLVHEKIKDK--------------------------HYNDEDVIRILSTRSKAQ
AAD24540       G---EEANMTLARKEANILHEKISDK--------------------------AYNDEELIRIISTRSKAQ
AAC97493       G---DEVNMTLARKGSKYLHEKISDK--------------------------AYHDEEIIRIISTRSKAQ
AAB67994       G---EEVNMTLAKSEAKILHDKISDK--------------------------HYTDEEVIRIVSTRSKAQ
AAR13288       G---EEVNMTLARSEAKILREKISDK--------------------------QYSDEEVIRIVTTRSKAQ
AAZ41833       G---DEVNMRLARSEAKLLHEKVSEK--------------------------AFSDDDFIRILTTRSKAQ
NP_201307      G---DDVNMMLARSEAKILHEKVSEK--------------------------SYSDDDFIRILTTRSKAQ
NP_196585      G---DEVNMTLARSEAKILHEKIKEK--------------------------AYADDDLIRILTTRSKAQ
AAZ67605       G---DEVNMMIAKSEAKILHEKMEAK--------------------------DYNDGDLIRILTTRSKAQ
NP_196584      GN--ADEVNVKLARSEAKTLHKKITEK-------------------------AYTDEDLIRILTTRSKAQ
CAA52903       G---DEVNMTLAKSEAKLLHEKIADK--------------------------AYNHDDLIRIVTTRSKAQ
NP_001048149   G---PEVNTSLAHSEAKILHEKIHDK--------------------------AYSDDEIIRILTTRSKAQ
NP_001057176   G---PEVNTKLAHSEAKILHEKIQHK--------------------------AYGDDEIIRILTTRSKAQ
NP_568271      G---EEIDEMLAQSEAAILHDEILGK--------------------------AVDHEETIRVLSTRSSMQ
NP_181409      G---NKVKDDSAKSDAKILAEAVASSG-------------------------EEAVEKDEVVRILTTRSKLH
NP_001063343   H---DELSRHIAKCDARRLYDAKNSGM-----------------------G-SVDEAVILEMFSKRSIPQ
NP_001061661   GIYGYPPHQGYTQAQSYLLPEAYPPPPWTYPLSSAYPPQPVGYPSGGYPPAVYSDSYLH
NP_001051711   G----------------------------------------------------GYPPGAYPPSGYPQQPGY
```

```
NP_001063096    MASVASAYHHMYDRSLEKVVKSETSG-NFELALLTILRCAENPAKYFAKVLRKSMKGMG-
NP_001061839    MAAVAAAYHHMYDRSLEKAVKSETSG-NFGFGLLTILRCAESPAKYFAKVLHEAMKGLG-
ABE65753        LVAVRSTYRSMYGKELGKAIRDETRG-NFEHVLLTILQCAENSCFYFAKALRKSMKGLG-
NP_181410       LRETFVAYKKNYGVTIDKDKDVDGCPGDADLRSLLKVAIFCIDTPEKHFAKVVRDSIEGFG-
NP_001055408    LAVTLERYRQEHGKGIDEVLDGRRGDQ-LAAVLKAALWCLTSPEKHFAEVIRTSILGLG-
AAC33305        INATLNHYKNEYGNDINKDLKADPK-DEFLALLRSTVKCLVYPEKYFEKVLRLAINRRG-
AAB71830        INERLNHYKNEYATDINKDLKADPK-DEFLALLRSTVKCLVYPEKYFEKVLRLAINKRG-
CAB92956        LNATLNHYKDEYGEDILKQLEDE---DEFVALLRATIKGLVYPEHYFVEVLRDAINRRG-
ABB55363        LNATLNHYKDEYGEDILKQLEDE---DEFVALLRATIKGLVYPEHYFVEVLRDAINRRG-
AAC97494        LNATLNHYKDEYGEDILKQLEDE---DEFVALLRATIKGLVYPEHYFVEVLRDAINRRG-
1DK5            LNATLNHYKDEHGEDILKQLEDG---DEFVGLLRATIKGLVYPEHYFVEVLRDAINRRG-
CAA75213        INATLNHYKDEYEEDILKQLEEG---DEFVGLLRATIKGLVYTEHYFVEVLRDAINRRG-
CAA75214        INATLNHYKDEYEEDILKQLEEG---DEFVGLLRATIKGLVYTEHYFVEVLRDAINRRG-
NP_174810       INATFNRYQDDHGEEILKSLEEGDDDKFLALLRSTIQCLTRPELYFVDVLRSAINKTG-
AAD24540        LNATFNHYLDQHGSEINKDLETDSDD-EYLKLLSAAIECLKTPEKHFEKVLRLAIKGTG-
AAC97493        LSATFNHYHDHHGHEIIKDLEADDDD-EYLKLLRAAIECLK--PREHFEKVLRLAIKKLG-
AAB67994        LNATLNHYNTSFGNAINKDLKADPSD-EFLKLLRAVIKCLTTPEQYFEKVLRQAINKLG-
AAR13288        LNATLNHYNTAFGNAINKDLKADPED-EFLKLLRAAIKCLTVPEKYFEKVLRQAINKLG-
AAZ41833        LGATLNHYNNEYGNAINKHLEEDSDD-EYLKLLRAAITCLTYPEKHFEKVLRLAINKMG-
NP_201307       LGATLNHYNNEYGNAINKNLKEESDDNDYMKLLRAVITCLTYPEKHFEKVLRLSINKMG-
NP_196585       ISATLNHYKNNFGTSMSKYLKEDSEN-EYIQLLKAVIKCLTYPEKYFEKVLRQAINKLG-
AAZ67605        ISATLNHFKNKFGTSITKYLKEDSDN-EYVQLLKAVIKCLTYPEKYFEKVLRQAINKMG-
NP_196584       INATLNHFKDKFGSSINKFLKEDSND-DYVQLLKTAIKCLTYPEKYFEKVLRRAINRMG-
CAA52903        LNATLNHYNNEFGNVIDKDLETDSDD-EYLKLLRAAIKGLTYPEKYFEELLRLAINKMG-
NP_001048149    LLATFNSYNDQFGHPITKDLKADPKD-EFLGTLRAIIRCFTCPDRYFEKVIRALGGMG-
NP_001057176    LIATFNRYNDEYGHPINKDLKADPKD-EFLSTLRAIIRCFCCPDRYFEKVIRLAIAGMG-
NP_568271       LSAIFNRYKDIYGTSITKDLLNHPTN-EYLSALRAAIRCIKNPTRYYAKVLRNSINTVG-
NP_181409       LQHLYKHFNEIKGSDLLGGVSKS------SLLNEALICLLKPALYFSKILDASLNKDAD
NP_001063343    LRLAFCSYKHIYGHDYTKALKKNGFG-EFEQSLRVVVKCIYNPSMYFSKLLHRSLQCSA-
NP_001061661    QGSRVAREQCPLSYSNNAVTCREDGQMNCENGTVNMEKSAMSSNKMATSLLKSCGNVMPC
NP_001051711    PPAGYPGHGHGPPMQGGGHGAGASGYGALLAGGAAVAAAVGAHMVRPGGGGHGMFGH-
```

FIGURE 9 (contuned)

```
NP_001063096  -TDDSTLIRVVTRTEIDMQY--IKAEYYKKYKKSLAEAIHSETSG-NYRTFLLSLVGSH
NP_001061839  -TNDTTLIRVVTTRAEVDMQY--IKAEYHRSYKRSLADAVHSETSG-NYRTFLLSLIGRD
ABE65753      -TDDTALIRIVVTRAEVDMQF--IITEYRKRYKKTLYNAVHSDTTS-HYRTFLLSLLGPN
NP_181410     -TDEDSLTRAIVTRAEIDLMK--VRGEYFNMYNTSMDNAITGDISG-DYKDFIITLLGSK
NP_001055408  -TDEEMLTRGIVSRAEVDMEK--VKEEYKVRYNTTVTADVRGDTSG-YYMNTLLTLVGPE
AAC33305      -TDEGALTRVVCTRAEVDLKI--IADEYQRRNSVPLTRAIVKDTHG-DYEKLLLVLAGHV
AAB71830      -TDEGALTRVVSTRAEVDLKI--IADEYQRRNSVPLTRAIVKDTNG-DYEKLLLVLAGEV
CAB92956      -TEEDHLSRVIATRAEVDLKT--IANEYQKRDSIPLGRAIAKDTGG-DYENMLVALLGQE
ABB55363      -TEEDHLSRVIATRAEVDLKT--IANEYQKRDSIPLGRAIAKDTGG-DYENMLVALLGQE
AAC97494      -TEEDHLTRVIATRAEVDLKT--IANEYQKRDSVPLGRAIAKDTGG-DYESMLLALLGQE
1DK5          -TEEDHLTRVIATRAEVDLKI--IADEYQKRDSIPLGRAIAKDTRG-DYESMLLALLGQE
CAA75213      -TEEDHLTRVIATRAEVDMKI--IADEYQKRDSIPLGRAIAKDTRG-DYESMLLALLGQE
CAA75214      -TEEDHLTRVIATRAEVDMKT--IADEYQKRDSIHLGRAIAKDTRG-DYEKMLVALLGED
NP_174810     -TDEGALTRIVTTRAEIDLKV--IGEEYQRRNSIPLEKAITKDTRG-DYERMLLALIGHG
AAD24540      -TDEWDLTRVVTTRAEVDMER--IKEEYHKRNSVPLDRAIAGDTSG-DYEKMLLALIGHG
AAC97493      -TDEWDLTRVVATRAEVDMER--IKEEYHRRNSVTLDRAIAGDTSG-DYEKMLLALIGHG
AAB67994      -SDEWALTRVVTTRAEVDMVR--IKEAYQRRNSIPLEQAIAKDTSG-DYEKFLLALIGAG
AAR13288      -TDEWALTRVVATRAEVDMVR--IKEEYQRRNSVTLEKAIAGDTSG-DYEKMLLALIGAG
AAZ41833      -TDEWALTRVVTTRTEVDMER--IKEEYQRRNSIPLHHAVAKDTSG-DYEDMLVSLLGHG
NP_201307     -TDEWGLTRVVTTRTEVDMER--IKEEYQRRNSIPLDRAIAKDTSG-DYEDMIVALLGHG
NP_196585     -TDEWGLTRVVTTRAEFDMER--IKEEYIRRNSVPLDRAIAKDTHG-DYEDILLALLGHD
AAZ67605      -TDEWGLTRVVTTRAELDMER--IKEEYLRRNSVPLDRAIAKDTHG-DYEDILLALIGHG
NP_196584     -TDEWALTRVVTTRAEVDLER--IKEEYLRRNSVPLDRAIANDTSG-DYKDMLLALLGHD
CAA52903      -TDENALTRVVTTRAEVDLQR--IAEEYQRRNSVPLDRAIDKDTSG-DYQKILLALMGHD
NP_001048149  -TDENSLTRIITTRAEVDLKL--IKEAYQKRNSVPLERAVAKDTTR-DYEDILLALLGAE
NP_001057176  -TDENSLTRIITTRAEVDLKL--ITEAYQKRNSVPLERAVAGDTSG-DYERMLLALLGQE
NP_568271     -TDEDALNRVIVTRAEKDLTN--ITGLYFKRNNVSLDQAIAKETSG-DYKAFLLALLGHG
NP_181409     KTTKKWLTRVFVTRADHSDEMNEIKEEYNNLYGETLAQRIQEKIKG-NYRDFLLTLLSKS
NP_001063343  -TNKRLVTRAILGSDDVDMDK--IKSVFKSSYGKDLEDFILESLPENDYRDFLLGAAKGS
NP_001061661  RNMERSGPAMYKVDMRGSTKQFSMGSKMMMCLIVFGCLIAALDMFRNVAQKQMFSVVSLL
NP_001051711  ------------------------HGGKFKKGKFKHGKYGKHKKFGR-KWK---------
```

FIGURE 9 (contiuned)

| | |
|---|---|
| NP_001063096 | — |
| NP_001061839 | R— |
| ABE65753 | V— |
| NP_181410 | I— |
| NP_001055408 | K— |
| AAC33305 | EN— |
| AAB71830 | EA— |
| CAB92956 | EE— |
| ABB55363 | EE— |
| AAC97494 | EE— |
| 1DK5 | ED— |
| CAA75213 | ED— |
| CAA75214 | ED— |
| NP_174810 | DA— |
| AAD24540 | DA— |
| AAC97493 | DA— |
| AAB67994 | DA— |
| AAR13288 | DV— |
| AAZ41833 | DEGTLDGSFAGDKRLGFSSSSQSSRRLALSGGSSLQQRIERTLLPLLLSGYRRQAPVNSP |
| NP_201307 | DA— |
| NP_196585 | HA— |
| AAZ67605 | HA— |
| NP_196584 | HA— |
| CAA52903 | E— |
| NP_001048149 | Q— |
| NP_001057176 | KQL— |
| NP_568271 | D— |
| NP_181409 | RAS— |
| NP_001063343 | SFVVATYVC— |
| NP_001061661 | — |
| NP_001051711 | — |

FIGURE 9 (contiuned)

| Accession | Sequence |
|---|---|
| NP_001063096 | ---------- |
| NP_001061839 | ---------- |
| ABE65753 | ---------- |
| NP_181410 | ---------- |
| NP_001055408 | ---------- |
| AAC33305 | ---------- |
| AAB71830 | ---------- |
| CAB92956 | ---------- |
| ABB55363 | ---------- |
| AAC97494 | ---------- |
| 1DK5 | ---------- |
| CAA75213 | ---------- |
| CAA75214 | ---------- |
| NP_174810 | ---------- |
| AAD24540 | ---------- |
| AAC97493 | ---------- |
| AAB67994 | ---------- |
| AAR13288 | ---------- |
| AAZ41833 | LTAPDMSRFCRSEEPSGSLGLSSFGGSFLTRAGSSVNSPAPLSSIYVNPATDVGGTPLRR |
| NP_201307 | ---------- |
| NP_196585 | ---------- |
| AAZ67605 | ---------- |
| NP_196584 | ---------- |
| CAA52903 | ---------- |
| NP_001048149 | ---------- |
| NP_001057176 | ---------- |
| NP_568271 | ---------- |
| NP_181409 | ---------- |
| NP_001063343 | ---------- |
| NP_001061661 | ---------- |
| NP_001051711 | ---------- |

FIGURE 9 (contiuned)

FIGURE 9 (continued)

FIGURE 9 (contiuned)

```
NP_001063096    ------------------------------------------------------------
NP_001061839    ------------------------------------------------------------
ABE65753        ------------------------------------------------------------
NP_181410       ------------------------------------------------------------
NP_001055408    ------------------------------------------------------------
AAC33305        ------------------------------------------------------------
AAB71830        ------------------------------------------------------------
CAB92956        ------------------------------------------------------------
ABB55363        ------------------------------------------------------------
AAC97494        ------------------------------------------------------------
1DK5            ------------------------------------------------------------
CAA75213        ------------------------------------------------------------
CAA75214        ------------------------------------------------------------
NP_174810       ------------------------------------------------------------
AAD24540        ------------------------------------------------------------
AAC97493        ------------------------------------------------------------
AAB67994        ------------------------------------------------------------
AAR13288        ------------------------------------------------------------
AAZ41833        VVEITLLPCLPSMNGENFSDSFPSFSCSLLTGLLLYGAVRTGPEGAIETTSVFLVGEDCL
NP_201307       ------------------------------------------------------------
NP_196585       ------------------------------------------------------------
AAZ67605        ------------------------------------------------------------
NP_196584       ------------------------------------------------------------
CAA52903        ------------------------------------------------------------
NP_001048149    ------------------------------------------------------------
NP_001057176    ------------------------------------------------------------
NP_568271       ------------------------------------------------------------
NP_181409       ------------------------------------------------------------
NP_001063343    ------------------------------------------------------------
NP_001061661    ------------------------------------------------------------
NP_001051711    ------------------------------------------------------------
```

FIGURE 9 (contiuned)

| | |
|---|---|
| NP_001063096 | ---------------------------------------- |
| NP_001061839 | ---------------------------------------- |
| ABE65753 | ---------------------------------------- |
| NP_181410 | ---------------------------------------- |
| NP_001055408 | ---------------------------------------- |
| AAC33305 | ---------------------------------------- |
| AAB71830 | ---------------------------------------- |
| CAB92956 | ---------------------------------------- |
| ABB55363 | ---------------------------------------- |
| AAC97494 | ---------------------------------------- |
| 1DK5 | ---------------------------------------- |
| CAA75213 | ---------------------------------------- |
| CAA75214 | ---------------------------------------- |
| NP_174810 | ---------------------------------------- |
| AAD24540 | ---------------------------------------- |
| AAC97493 | ---------------------------------------- |
| AAB67994 | ---------------------------------------- |
| AAR13288 | ---------------------------------------- |
| AAZ41833 | STSLVTISQLSNFAVEALLTHSNLIINSLSTSYEDLLCLFLIAIIVHELSTRGCLVLFWL |
| NP_201307 | ---------------------------------------- |
| NP_196585 | ---------------------------------------- |
| AAZ67605 | ---------------------------------------- |
| NP_196584 | ---------------------------------------- |
| CAA52903 | ---------------------------------------- |
| NP_001048149 | ---------------------------------------- |
| NP_001057176 | ---------------------------------------- |
| NP_568271 | ---------------------------------------- |
| NP_181409 | ---------------------------------------- |
| NP_001063343 | ---------------------------------------- |
| NP_001061661 | ---------------------------------------- |
| NP_001051711 | ---------------------------------------- |

FIGURE 9 (contiuned)

| | |
|---|---|
| NP_001063096 | --- |
| NP_001061839 | --- |
| ABE65753 | --- |
| NP_181410 | --- |
| NP_001055408 | --- |
| AAC33305 | --- |
| AAB71830 | --- |
| CAB92956 | --- |
| ABB55363 | --- |
| AAC97494 | --- |
| 1DK5 | --- |
| CAA75213 | --- |
| CAA75214 | --- |
| NP_174810 | --- |
| AAD24540 | --- |
| AAC97493 | --- |
| AAB67994 | --- |
| AAR13288 | --- |
| AAZ41833 | CSPCI |
| NP_201307 | --- |
| NP_196585 | --- |
| AAZ67605 | --- |
| NP_196584 | --- |
| CAA52903 | --- |
| NP_001048149 | --- |
| NP_001057176 | --- |
| NP_568271 | --- |
| NP_181409 | --- |
| NP_001063343 | --- |
| NP_001061661 | --- |
| NP_001051711 | --- |

FIGURE 9 (contiuned)

SEQ ID NO: 83, NM_103274.3 Arabidopsis thaliana ANNAT1 (ANNEXIN ARABIDOPSIS 1); calcium ion binding / calcium-dependent phospholipid binding (ANNAT1) mRNA, complete cds
CGGACAGGCCACGTCGTGTCCTAAACCTCTTAGCCTTTCCCTTTATAAGTCAATCTTGTGTCGGCT
TCGACTCCCAACATACACAAAACACTAAAAGTAGAAGAAAAATGGCGACTCTTAAGGTTTCTGATT
CTGTTCCTGCTCCTTCTGATGATGCTGAGCAATTGAGAACCGCTTTTGAAGGATGGGGTACGAACG
AGGACTTGATCATATCAATCTTGGCTCACAGAAGTGCTGAACAGAGGAAAGTCATCAGGCAAGCAT
ACCACGAAACCTACGGCGAAGACCTTCTCAAGACTCTTGACAAGGAGCTCTCTAACGATTTCGAGA
GAGCTATCTTGTTGTGGACTCTTGAACCCGGTGAGCGTGATGCTTTATTGGCTAATGAAGCTACAA
AAAGATGGACTTCAAGCAACCAAGTTCTTATGGAAGTTGCTTGCACAAGGACATCAACGCAGCTGC
TTCACGCTAGGCAAGCTTACCATGCTCGCTACAAGAAGTCTCTTGAAGAGGACGTTGCTCACCACA
CTACCGGTGACTTCAGAAAGCTTTTGGTTTCTCTTGTTACCTCATACAGGTACGAAGGAGATGAAG
TGAACATGACATTGGCTAAGCAAGAAGCTAAGCTGGTCCATGAGAAAATCAAGGACAAGCACTACA
ATGATGAGGATGTTATTAGAATCTTGTCCACAAGAAGCAAAGCTCAGATCAATGCTACTTTTAACC
GTTACCAAGATGATCATGGCGAGGAAATTCTCAAGAGTCTTGAGGAAGGAGATGATGATGACAAGT
TCCTTGCACTTTTGAGGTCAACCATTCAGTGCTTGACAAGACCAGAGCTTTACTTTGTCGATGTTC
TTCGTTCAGCAATCAACAAAACTGGAACTGATGAAGGAGCACTCACTAGAATTGTGACCACAAGAG
CTGAGATTGACTTGAAGGTCATTGGAGAGGAGTACCAGCGCAGGAACAGCATTCCTTTGGAGAAAG
CTATTACCAAAGACACTCGTGGAGATTACGAGAAGATGCTCGTCGCACTTCTCGGTGAAGATGATG
CTTAATCAATCAATCCTCCACAGAGAAACATAAGCTGCTCTACAGCTTCTGTTATCTCTTATCTCC
CTCTCTCTCTCTTTGATGAGTTTCAAATCGTTTGATTTTGTTTCTACAAAAACCTTGTTTGTTTCT
GTTGTGTGTTTTGAGTTCCTAAATAATGCAAAAGAGAGAGACAGAGAGAACCAGTGTGGTCTCTTA
AGTTATATATATGAAGAGCATTGGCCTAAAACACAGACTAACAAGTAGTTCTGGTTTTGAC

SEQ ID NO: 84, NP_174810.1 ANNAT1 (ANNEXIN ARABIDOPSIS 1); calcium ion binding / calcium-dependent phospholipid binding [Arabidopsis thaliana]
MATLKVSDSVPAPSDDAEQLRTAFEGWGTNEDLIISILAHRSAEQRKVIRQAYHETYGEDLLKTLD
KELSNDFERAILLWTLEPGERDALLANEATKRWTSSNQVLMEVACTRTSTQLLHARQAYHARYKKS
LEEDVAHHTTGDFRKLLVSLVTSYRYEGDEVNMTLAKQEAKLVHEKIKDKHYNDEDVIRILSTRSK
AQINATFNRYQDDHGEEILKSLEEGDDDDKFLALLRSTIQCLTRPELYFVDVLRSAINKTGTDEGA
LTRIVTTRAEIDLKVIGEEYQRRNSIPLEKAITKDTRGDYEKMLVALLGEDDA

SEQ ID NO: 85, forward primer prm08727
GGGGACAAGTTTGTACAAAAAAGCAGGCTTAAACAATGGCGACTCTTAAGGTTTCT

SEQ ID NO: 86, reverse primer prm09025
GGGGACCACTTTGTACAAGAAAGCTGGGTTTAAGCATCATCTTCACCGAG

SEQ ID NO: 87, signature sequence 1, wherein X on position 4 may be any amino acid, preferably one of L, S, I, V, Q, or M; and X on position 10 may be any amino acid, preferably one of A, V, P, G, S, T or W
(A/L/V)(M/V/L/I)(L/V/M/I/C)X(W/F)(I/V/M/T/A)(L/P/Y/M/F)(D/E/S/H)(P/A)X(G/S/E/A)RDA

FIGURE 11

SEQ ID NO: 88, signature sequence 2, wherein X in position 3 may be any amino acid, preferably one of K, R, Q, S, E, A or M; X on position 10 may be any amino acid, preferably one of T, S, K, N, G, D, A, E, Q, or R; X on position 14 may be any amino acid, preferably one of N, A, R, E, D, S, Q
A(F/I/V/C/G)XG(F/R/W/M)G(C/T/V)(D/N)(S/A/T/E)X(T/A/V/L/M)(V/I/L)(I/T)X(I/V/T)L(T/A/G)(H/Q/K)(R/S)

SEQ ID NO: 89, signature sequence 3, wherein X on position 4 may be any amino acid, preferably one of S, T, D, E, G, W, N, K; X on position 5 may be any amino acid, preferably one of T, A, S, M, H, D, G, W
(T/S)(D/N/E/T)(D/E/K)XXL(I/T/S/N)R(V/I/A/G)(V/I/F)(V/T/C/S/A)(T/S)R(T/A)(E/D)(I/V/F/L/K/H)(D/S)

SEQ ID NO: 90, signature sequence 4, wherein X on position 8 may be any amino acid, preferably one of K, E, D, T, L, S, Q, R, N, or A
(Y/H)(F/Y)(A/E/V/S)(K/E/D)(V/A/L/I)(L/V/I)(R/H/D)X(S/A)(M/I/L)

SEQ ID NO: 91, signature sequence 5
(Y/G/K/S)(L/I/M)E(H/E)(D/H)(I/V/L)(G/A/E)

SEQ ID NO: 92, signature sequence 6
(F/L/V/I/T)(I/L/V)(R/Q/Y)(I/V)(F/L/V/I)(T/S/G/A)(E/D/T)RS

SEQ ID NO: 93, signature sequence 7, wherein X on position 3 may be any amino acid, preferably one of T, D, N, K, S, R, A
Y(R/K/M/E/Q)X(F/T/L/M/I)(L/I)(L/I/V)(S/T/V/A)L(V/I/L/A/M)(G/S)

SEQ ID NO: 94, GOS2 promoter
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTTAATTATATGAAATGAACTGTAGCATAAGCAGTATT
CATTTGGATTATTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC

SEQ ID NO: 95, expansin promoter
AAAACCACCGAGGGACCTGATCTGCACCGGTTTTGATAGTTGAGGGACCCGTTGTGTCTGGTTTTC
CGATCGAGGGACGAAAATCGGATTCGGTGTAAAGTTAAGGGACCTCAGATGAACTTATTCCGGAGC
ATGATTGGGAAGGGAGGACATAAGGCCCATGTCGCATGTGTTTGGACGGTCCAGATCTCCAGATCA
CTCAGCAGGATCGGCCGCGTTCGCGTAGCACCCGCGGTTTGATTCGGCTTCCCGCAAGGCGGCGGC
CGGTGGCCGTGCCGCCGTAGCTTCCGCCGGAAGCGAGCACGCCGCCGCCGCCGACCCGGCTCTGCG
TTTGCACCGCCTTGCACGCGATACATCGGGATAGATAGCTACTACTCTCTCCGTTTCACAATGTAA
ATCATTCTACTATTTTCCACATTCATATTGATGTTAATGAATATAGACATATATATCTATTTAGAT
TCATTAACATCAATATGAATGTAGGAAATGCTAGAATGACTTACATTGTGAATTGTGAAATGGACG
AAGTACCTACGATGGATGGATGCAGGATCATGAAAGAATTAATGCAAGATCGTATCTGCCGCATGC
AAAATCTTACTAATTGCGCTGCATATATGCATGACAGCCTGCATGCGGGCGTGTAAGCGTGTTCAT
CCATTAGGAAGTAACCTTGTCATTACTTATACCAGTACTACATACTATATAGTATTGATTTCATGA
GCAAATCTACAAAACTGGAAAGCAATAAGAAATACGGGACTGGAAAAGACTCAACATTAATCACCA
AATATTTCGCCTTCTCCAGCAGAATATATATCTCTCCATCTTGATCACTGTACACACTGACAGTGT
ACGCATAAACGCAGCAGCCAGCTTAACTGTCGTCTCACCGTCGCACACTGGCCTTCCATCTCAGGC
TAGCTTTCTCAGCCACCCATCGTACATGTCAACTCGGCGCGCGCACAGGCACAAATTACGTACAAA
ACGCATGACCAAATCAAAACCACCGGAGAAGAATCGCTCCCGCGCGCGGCGGCGACGCGCACGTAC
GAACGCACGACGCACGCCCAACCCCACGACACGATCGCGCGCGACGCCGGCGACACCGGCCGTCC
ACCCGCGCCCTCACCTCGCCGACTATAAATACGTAGGCATCTGCTTGATCTTGTCATCCATCTCAC
CACCAAAAAAAAAGGAAAAAAAAACAAAACACACCAAGCCAAATAAAAGCGACAA

SEQ ID NO: 96, U89609.1, GHU89609 Gossypium hirsutum fiber annexin mRNA, complete cds
CAGATTCAGAAAGAAATAAAGGAAGAAGAAGCAATGGCCACTCTTACAGTGCCCACGACAGTTCCT
TCGGTGTCTGAAGATTGTGAACAGCTAAGAAAAGCCTTTTCAGGATGGGGAACTAATGAGGGCTTA
ATCATAGATATATTGGGTCACAGAAATGCCGAGCAACGAAACTTGATTCGAAAAACCTACGCTGAA
ACCTATGGAGAGGATCTCCTCAAGGCACTAGACAAGGAGCTCTCGAATGACTTTGAGAGGCTGGTT
TTGCTTTGGGCTCTTGATCCTGCTGAACGTGATGCCCTTTTGGCTAATGAAGCCACCAAAAGGTGG
ACTTCAAGCAATCAGGTCCTTATGGAAATAGCTTGCACAAGGTCTGCCAACCAACTGCTTCACGCA
AGGCAGGCTTATCATGCTCGTTATAAGAAGTCGCTTGAAGAGGATGTTGCTCATCACACGACTGGC FIGURE 11 (continued)

```
GACTTCCGTAAGCTCCTCCTACCTCTAGTGAGTTCATACAGATATGAGGGAGAGGAGGTGAACATG
AATCTGGCGAAAACAGAGGCGAAGTTGCTTCATGAGAAAATTTCAGACAAAGCTTACAGTGATGAC
GATGTCATAAGGGTTTTGGCTACAAGAAGCAAGGCACAGATCAATGCAACTCTGAATCACTACAAA
AATGAATATGGAAATGACATAAACAAGGACTTGAAGGCTGATCCTAAGGATGAGTTCCTTGCACTA
CTAAGGTCCACAGTGAAGTGCTTGGTCTATCCGGAAAAGTATTTTGAGAAGGTTCTTCGCCTAGCA
ATCAATAGACGAGGAACGGATGAAGGAGCTCTTACTAGAGTTGTTTGCACTAGGGCTGAGGTTGAT
CTAAAGATCATAGCAGATGAGTACCAGCGAAGGAACAGTGTCCCACTGACTCGTGCCATTGTCAAG
GACACTCATGGAGACTATGAAAAATTGCTGCTGGTACTTGCAGGACATGTGGAGAATTGAATCTGA
TATCATGAGACAATTTCCTGGTGAATAAATGTTTATGACCAAACTATAATGGTCTAGTGTGGTTAT
TGATGTTTCCTGTTTTTCTATGTAGTATTGCGAGTTATATGCTATCCAAGAATTCGAAGTCTATT
TAAAAAAAAAAAAAAAAAA
```

SEQ ID NO: 97, AAC33305.1, fiber annexin [Gossypium hirsutum]
```
MATLTVPTTVPSVSEDCEQLRKAFSGWGTNEGLIIDILGHRNAEQRNLIRKTYAETYGEDLLKALD
KELSNDFERLVLLWALDPAERDALLANEATKRWTSSNQVLMEIACTRSANQLLHARQAYHARYKKS
LEEDVAHHTTGDFRKLLLPLVSSYRYEGEEVNMNLAKTEAKLLHEKISDKAYSDDDVIRVLATRSK
AQINATLNHYKNEYGNDINKDLKADPKDEFLALLRSTVKCLVYPEKYFEKVLRLAINRRGTDEGAL
TRVVCTRAEVDLKIIADEYQRRNSVPLTRAIVKDTHGDYEKLLLVLAGHVEN
```

SEQ ID NO: 98, AF006197.1, Lavatera thuringiaca annexin (AnxLt1) mRNA, complete cds
```
AATGGCTACTCTTACAGTTCCCTCCACACTTCCGTCAGTGTCTGAAGATTGTGAACAACTCAGGAA
AGCCTTCTCAGGATGGGGAACTAATGAGGACTTAATCATAAATATATTGGGTCACCGAAATGCGGA
CGAACGAAACTCGATTCGAAAAGCTTATACTGAAACCCATGGAGAAGATCTCCTCAAGGCACTGGA
CAAGGAACTCTCAAATGACTTTGAGAGGCTGGTTCTGCTTTGGACTCTTGATCCTCCTGAACGTGA
TGCACTTTTGGCAAATGAAGCCACCAAAAGGTGGACTTCAAGCAATCAGGTAATTATGGAAATAGC
CTGCAGAAGTTCTTCTGACCAACTGCTTCGCGCGAGGCAGGCTTATCATGTTCGTTATAAGAAATC
GCTTGAAGAGGATGTTGCCCATCACACAACTGGCGACTTCCGTAAGCTTCTCCTACCTCTTGTGAG
TTCATACAGATACGAGGGAGATGAAGTGAACATGACTCTGGCGAAAACAGAGGCCAAGTTACTCCA
TGAGAAAATCTCAAACAAAGCTTACAGTGATGACGATGTCATCAGGGTTTTGGCTACGAGAAGCAA
GTCACAGATCAACGAACGTCTTAATCACTACAAAAATGAATACGCAACTGATATAAACAAGGACCT
GAAGGCTGACCCTAAGGATGAGTTCCTTGCACTGCTAAGGTCCACAGTGAAGTGCTTGGTCTACCC
TGAAAAGTATTTCGAGAAGGTTCTTCGTCTAGCAATCAATAAACGAGGAACGGATGAAGGAGCTCT
TACGAGGGTTGTTTCCACCAGGGCTGAGGTTGATCTAAAGATCATAGCAGATGAGTACCAGCGAAG
GAACAGTGTCCCACTGACTCGTGCTATTGTCAAGGACACTAATGGAGACTACGAAAAATTGCTGCT
GGTACTTGCTGGAGAGGTGGAGGCTTGAACCGGTTTTCATGAGATGATTTTGTGTTGAATAAAAAC
TTAATGACCGGAACTCTAATGGTCTAGTGTTGCTATTATGTTATCCTGTTTTTTTTCTTCTATGGT
ACTGTGAGTTTTATGCAATAAAGGCTTGTTATTTAGAAAAAAAAAAAAAAAAAAAA
```

SEQ ID NO: 99, AAB71830.1, annexin [Lavatera thuringiaca]
```
MATLTVPSTLPSVSEDCEQLRKAFSGWGTNEDLIINILGHRNADERNSIRKAYTETHGEDLLKALD
KELSNDFERLVLLWTLDPPERDALLANEATKRWTSSNQVIMEIACRSSSDQLLRARQAYHVRYKKS
LEEDVAHHTTGDFRKLLLPLVSSYRYEGDEVNMTLAKTEAKLLHEKISNKAYSDDDVIRVLATRSK
SQINERLNHYKNEYATDINKDLKADPKDEFLALLRSTVKCLVYPEKYFEKVLRLAINKRGTDEGAL
TRVVSTRAEVDLKIIADEYQRRNSVPLTRAIVKDTNGDYEKLLLVLAGEVEA
```

FIGURE 11 (continued)

SEQ ID NO: 100, Brassica rapa subsp. pekinensis clone KBrH080C09, (81215-81290, 81491-81636, 81867-82085, 82155-82367, 82548-82838, 83254-83514, 83600-84433), complete sequence
ATGGCGTCTCTCAAAGTCCCTACCAACGTTCCTCTTCCCGAGGAAGACGCCGAGCAACTCCACAAG
GCTTTTGCAGGATGGGGTACCAACGAGAAGCTGATCATATCAATCCTAGCTCACAGGACCTCAGCA
CAACGCAGCTTAATCCGCAGCGCTTATGCCGCTGCTTACAATGAGGATCTCCTCAAGGCCTTAGAC
AAAGAGCTTTCTAGTGACTTTGAGCGAGTTGTCATGTTGTGGACTCTTGATCCAGCGGAGAGAGAT
GCTTTCCTTGCTAAAGAATCTACCAAAATGTTCACCAAGAACAATTGGGTTCTTGTTGAAATCGCA
TGCACTAGGTGTCCTCTTGATCTTTTCAAGGTCAAACAAGCTTACCAAGCACGTTACAAGAAATCT
CTAGAGGAAGATGTTGCGCAACACACATCTGGTGACCTTCGTAAGCTCTTGCTTCCTCTTGTTAGT
ACTTTTAGGTACGAAGGAGATGAGGTGAACATGAGGCTTGCAAGATCCGAAGCTAAGTTACTTCAC
GAGAAGGTCTCAGAGAAAGCCTTTAGTGATGATGACTTCATCAGAATCTTGACAACAAGAAGCAAA
GCACAGCTCGGTGCAACTCTTAACCACTACAATAATGAGTACGGAAACGCTATTAACAAGCACTTG
AAGGAAGATTCAGATGATGAGTACCTGAAGCTACTAAGAGCTGCGATCACGTGTTTGACATACCCT
GAGAAGCATTTTGAGAAGGTTTTGCGTCTAGCAATTAACAAAATGGGGACTGATGAGTGGGCACTA
ACCCGAGTTGTGACTACACGAACTGAAGTTGATATGGAACGTATCAAAGAGGAATATCAACGAAGG
AACAGCATTCCTTTGCACCATGCCGTCGCTAAAGACACTTCTGGTGATTATGAGGATATGCTTGTT
TCTCTTCTCGGACATGGAGATGAAGGGACTCTCGACGGATCTTTTGCTGGAGATAAGCGCCTCGGC
TTCTCGTCTTCTTCACAGTCCTCACGTCGTCTCGCCCTATCTGGTGGGTCGTCTCTCCAACAACGA
ATCGAGAGGACTCTCTTGCCACTGCTGCTCTCGGGTATCGGAGACAAGCTCCAGTGAACTCCCCT
CTAACTGCCCCAGACATGTCTCGATTTTGCAGATCCGAAGAACCTTCTGGTTCTCTTGGTCTCTCA
TCATTTGGTGGCTCCTTCCTCACCAGAGCCGGGTCTAGCGTCAATTCACCTGCTCCTCTCATCA
ATTTATGTTAATCCGGCGACCGATGTAGGTGGAACTCCACTCCGGCGACCAGATCTGTTCCTTAAA
AGTTTGAGAAGACAAGCATCCTCCAGCGACATTCCTCTTCCCCGCTCCATCCTCTCCATCCTCCAT
GTTTGGCCTCCTCCACCCTTCAGATTGTGTAAACTTGGTTTAAAACGATTGCATGAAGATCCATAC
CACCAACCACTGCAAACATACCTTCTATCACAGCGGTTTGCAAATTTGGCGTCCGATGTAGGTGGG
AATTCACTCCGGCATACAGTTTTGAGCCATATGTTTATGAATATGACGTCTGATGTGAGTGGGAAT
CCACTCCGGCCTCCAGCTCTGAGCCATCAAAAGCTAGTAAGGCCAATTTGTCGGCGCATTATTCTC
ACCTCTTTTTCTGTTGTGGAGATCACTTTACTACCATGTCTCCCTTCTATGAATGGAGAAAATTTC
TCAGATTCTTTTCCGAGCTTCAGTTGCAGTTTACTCACTGGTTTGTTACTTTATGGAGCGGTCCGT
ACGGGGCCTGAAGGTGCAATCGAGACTACTTCGGTTTTTCTTGTTGGTGAAGACTGTCTTTCAACG
TCACTTGTGACTATCTCTCAACTATCCAACTTTGCCGTGGAAGCTTTATTGACGCATTCAAACTTG
ATATTGAATTCGCTGTCAACTTCATATGAAGATTTATTATGCTTGTTTCTAATTGCTATTATAGTT
CATGAATTGTCCACAAGAGGATGTTTAGTTCTCTTTTGGCTTTGTAGTCCTTGCATTTGA

SEQ ID NO: 101, AAZ41833.1, 80C09_22 [Brassica rapa subsp. pekinensis]
MASLKVPTNVPLPEEDAEQLHKAFAGWGTNEKLIISILAHRTSAQRSLIRSAYAAAYNEDLLKALD
KELSSDFERVVMLWTLDPAERDAFLAKESTKMFTKNNWVLVEIACTRCPLDLFKVKQAYQARYKKS
LEEDVAQHTSGDLRKLLLPLVSTFRYEGDEVNMRLARSEAKLLHEKVSEKAFSDDDFIRILTTRSK
AQLGATLNHYNNEYGNAINKHLKEDSDDEYLKLLRAAITCLTYPEKHFEKVLRLAINKMGTDEWAL
TRVVTTRTEVDMERIKEEYQRRNSIPLHHAVAKDTSGDYEDMLVSLLGHGDEGTLDGSFAGDKRLG
FSSSSQSSRRLALSGGSSLQQRIERTLLPLLLSGYRRQAPVNSPLTAPDMSRFCRSEEPSGSLGLS
SFGGSFLTRAGSSVNSPAPLSSIYVNPATDVGGTPLRRPDLFLKSLRRQASSSDIPLPRSILSILH
VWPPPPFRLCKLGLKRLHEDPYHQPLQTYLLSQRFANLASDVGGNSLRHTVLSHMFMNMTSDVSGN
PLRPPALSHQKLVRPICRRIILTSFSVVEITLLPCLPSMNGENFSDSFPSFSCSLLTGLLLYGAVR
TGPEGAIETTSVFLVGEDCLSTSLVTISQLSNFAVEALLTHSNLILNSLSTSYEDLLCLFLIAIIV
HELSTRGCLVLFWLCSPCI

FIGURE 11 (continued)

SEQ ID NO: 102, U73747.1, GHU73747 Gossypium hirsutum annexin (AnnGh2) mRNA, partial cds
CAACCCTCAAAGTTCCAGTTCACGTTCCTTCTCCTTCTGAGGATGCTGAATGGCAACTTCGGAAAG
CTTTTGAAGGCTGGGGTACGAACGAGCAATTGATTATCGACATATTGGCTCACAGGAATGCAGCAC
AGCGCAATTCAATTCGGAAAGTTTATGGTGAAGCTTATGGGGAAGATCTTCTCAAGTGTTTGGAGA
AGGAACTTACAAGTGATTTCGAGCGGGCTGTGCTGCTTTTTACGTTGGACCCTGCAGAGCGAGATG
CTCATCTGGCTAATGAAGCTACAAAGAAGTTCACATCAAGCAATTGGATTCTCATGGAGATAGCTT
GCAGTAGGTCTTCGCATGAACTACTCAATGTGAAAAAGGCGTATCATGCTCGTTATAAGAAATCCC
TTGAAGAAGATGTTGCTCACCACACTACCGGAGAGTACCGCAAGCTTTTGGTCCCTCTTGTTAGTG
CATTCCGATATGAGGGAGAGGAGGTGAACATGACATTGGCAAAATCTGAGGCTAAGATACTTCATG
ATAAAATTTCGGACAAGCATTATACCGATGAGGAGGTGATTAGGATTGTATCAACAAGGAGTAAGG
CACAGCTCAATGCAACTCTCAACCATTACAATACTTCATTCGGCAATGCTATCAACAAGGATTTGA
AGGCTGATCCCAGTGATGAATTCCTCAAATTACTAAGAGCTGTGATCAAGTGCTTGACCACCCCAG
AGCAATATTTCGAGAAGGTTTTACGTCAAGCCATCAATAAGTTGGGATCCGATGAATGGGCTCTTA
CCCGAGTCGTCACAACTCGTGCAGAGGTCGACATGGTACGTATTAAGGAGGCATATCAACGAAGAA
ACAGCATCCCTCTCGAACAAGCAATTGCTAAAGATACTTCGGGTGACTATGAGAAGTTTCTTCTTG
CCTTGATCGGAGCTGGAGATGCATGAACCGTCTTCGGTATTAAGTTCCTCTGTATGAATGTTTAGT
TTGCCTTATCCGCTATGACTTAATAATTTATGCTTGGTTTTTCATCGTTTTCATTATCTAAAGCAT
TGCTTGCTTCCATGATAGAACATTCAAAATAAATGATTGAGTTCGTTTAAAAAAAAAAAAAAAAAA
AAAAAAGGAAAAAAAAAAAAAAAA

SEQ ID NO: 103, AAB67994.1, annexin [Gossypium hirsutum]
TLKVPVHVPSPSEDAEWQLRKAFEGWGTNEQLIIDILAHRNAAQRNSIRKVYGEAYGEDLLKCLEK
ELTSDFERAVLLFTLDPAERDAHLANEATKKFTSSNWILMEIACSRSSHELLNVKKAYHARYKKSL
EEDVAHHTTGEYRKLLVPLVSAFRYEGEEVNMTLAKSEAKILHDKISDKHYTDEEVIRIVSTRSKA
QLNATLNHYNTSFGNAINKDLKADPSDEFLKLLRAVIKCLTTPEQYFEKVLRQAINKLGSDEWALT
RVVTTRAEVDMVRIKEAYQRRNSIPLEQAIAKDTSGDYEKFLLALIGAGDA

SEQ ID NO: 104, X93308.1, C.annuum mRNA for annexin
AAAAATGGCAAGTCTAACCGTTCCAGCACATGTTCCTTCGGCTGCTGAAGACTGTGAACAACTCCG
ATCTGCCTTCAAAGGATGGGGAACAAATGAGAAGTTGATCATATCAATTTTGGCTCATAGAACTGC
TGCTCAGCGCAAATTGATTCGTCAAACTTATGCTGAGACTTTCGGAGAGGATCTACTTAAAGAGTT
GGACAGAGAACTTACCCATGATTTTGAGAAATTGGTGCTAGTGTGGACGTTGGATCCTTCAGAACG
TGATGCTCATTTGGCTAAGGAAGCTACTAAGAGATGGACAAAAAGCAACTTTGTTCTTGTGGAGCT
AGCTTGTACCAGATCGCCTAAAGAACTGGTTTTGGCTAGGGAAGCTTATCATGCACGTTACAAGAA
ATCTCTTGAGAGGATGTTGCCTATCACACTACTGGGGATCACCGCAAGCTTTTGGTACCTCTTGT
GAGCTCCTACCGATATGGAGGAGAGGAGGTGGACTTGCGCCTTGCTAAAGCAGAATCTAAAATTCT
GCATGAGAAGATCTCCGATAAGGCTTACAGTGATGATGAGGTCATTAGAATTTTAGCCACAAGGAG
CAAAGCGCAACTCAATGCTACTTTGAATCATTACAAAGATGAACATGGTGAGGATATCCTAAAGCA
ATTGGAAGATGGGGATGAGTTTGTTGCACTATTGAGGGCCACCATTAAAGGTCTTGTCTACCCGGA
GCACTATTTTGTGGAGGTTCTTCGTGATGCAATCAACAGGAGAGGGACAGAGGAAGATCATCTGAC
AAGAGTTATTGCTACAAGGGCTGAGGTCGATCTGAAGATTATCGCTGATGAGTACCAGAAGAGGGA
TAGCATTCCCCTGGGTCGCGCCATTGCCAAAGATACAAGAGGAGATTATGAGAGTATGCTGTTGGC
TTTGCTTGGACAAGAGGAGGACTGAGGAGGATTTGGCCACTTATGTTTTACAATGACAAGAATAAA
TATGCCATCCCTATATGAGAATTGGCATCCGTTGTATGTTTGATGATTGAGTGTGGTCTGTTTAT
GAGCTTTTAGTCCTTTTTTCTTCTCGTGAGAAACTTCTAATATGCAACTTTGTGCTGTCTACATAT
GTTTTCTAATAATATGCATCGATTAGTTCTAAAAAAAAAAAAAAAAAAAAAAAAAAAAA FIGURE 11 (continued)

SEQ ID NO: 105, 1DK5, Chain A, Crystal Structure Of Annexin 24(Ca32) Capsicum Annuum
MAHHHHHHMASLTVPAHVPSAAEDCEQLRSAFKGWGTNEKLIISILAHRTAAQRKLIRQTYAETFG
EDLLKELDRELTHDFEKLVLVWTLDPSERDAHLAKEATKRWTKSNFVLVELACTRSPKELVLAREA
YHARYKKSLEEDVAYHTTGDHRKLLVPLVSSYRYGGEEVDLRLAKAESKILHEKISDKAYSDDEVI
RILATRSKAQLNATLNHYKDEHGEDILKQLEDGDEFVALLRATIKGLVYPEHYFVEVLRDAINRRG
TEEDHLTRVIATRAEVDLKIIADEYQKRDSIPLGRAIAKDTRGDYESMLLALLGQEED

SEQ ID NO: 106, AF113545.1, Nicotiana tabacum vacuole-associated annexin VCaB42 (Anx3) mRNA, complete cds
CATCCACAATTCTCCACAGTACAAGAAAACAAAAAATGGCGAGTCTTAAAGTTCCAACATCTGTT
CCAGAACCTTATGAAGATGCTGAGCAACTCAAAAAAGCTTTTGCTGGATGGGGTACAAATGAGGCA
CTTATTATTCAGATTCTGGCACATAGAAATGCAGCACAACGCAAGTTAATCCGAGAAACTTATGCT
GCAGCTTATGGAGAGGATCTTCTCAAGGACTTGGATGCTGAACTGACAAGTGATTTTCAGCGTGCA
GTGCTTCTGTGGACTTTGAGTCCTGCTGAGCGCGACGCCTACTTGGTTAATGAAGCTACCAAACGT
CTGACTTCTAGCAATTGGGTTATCTTGGAAATTGCTTGTACAAGGTCTTCTGATGATCTCTTTAAG
GCGAGGCAGGCCTACCATGCTCGATACAAGAAATCACTTGAAGAAGATGTTGCTTATCACACAACT
GGGGATTTCCGTAAGCTTTTGGTTCCTCTTTTAACTGCATTCAGATACGAAGGAGAAGAGGCGAAC
ATGACATTGGCAAGAAAGGAGGCAAATATACTACACGAGAAGATCTCTGACAAGGCTTACAATGAT
GAGGAGCTCATCCGAATTATTTCTACTAGGAGTAAAGCACAGCTGAATGCAACATTCAACCACTAC
CTTGACCAACATGGCAGTGAAATCAACAAGGATCTGGAAACTGATTCTGATGATGAGTACCTGAAA
TTACTCAGCGCAGCAATAGAATGCTTGAAAACCCCAGAGAAACACTTTGAGAAAGTTCTTCGATTG
GCTATCAAGGGTACAGGCACAGACGAATGGGACCTTACTAGAGTTGTCACTACTCGGGCTGAAGTT
GACATGGAACGTATCAAAGAAGAGTACCATAAGAGGAACAGTGTTCCATTGGACCGTGCAATTGCT
GGAGACACTTCAGGAGACTATGAAAGGATGCTTCTGGCTTTGATTGGGCATGGAGATGCTTGAATG
GAATATGTGTTCTAAGATTGGATAAGAAACTATTTCCTAATGTCTGAAGTTTGAATTTGTTTGATG
ATGTGTGCATGTATGCCCAGAGTTTGGTTTGCATTATATGGATTTAAATAATCCAGGTGTTGTGTT
TTGTTTTTTTCTTCACTTGTCATAGTTTGGTTCTATATATTCGGACTTCCTCAACCAGTGATCTTA
TTGTTTATC

SEQ ID NO: 107, AAD24540.1, AF113545_1 vacuole-associated annexin VCaB42 [Nicotiana tabacum]
MASLKVPTSVPEPYEDAEQLKKAFAGWGTNEALIIQILAHRNAAQRKLIRETYAAAYGEDLLKDLD
AELTSDFQRAVLLWTLSPAERDAYLVNEATKRLTSSNWVILEIACTRSSDDLFKARQAYHARYKKS
LEEDVAYHTTGDFRKLLVPLLTAFRYEGEEANMTLARKEANILHEKISDKAYNDEELIRIISTRSK
AQLNATFNHYLDQHGSEINKDLETDSDDEYLKLLSAAIECLKTPEKHFEKVLRLAIKGTGTDEWDL
TRVVTTRAEVDMERIKEEYHKRNSVPLDRAIAGDTSGDYERMLLALIGHGDA

SEQ ID NO: 108, AY351650.1, Gossypium hirsutum Anx1 (Anx1) mRNA, complete cds
GGGCAGGTTCTTCACAAAAAGAAAAGAAAATTACAGTGAAAATGGCAACCCTTAAAGTTCCAGC
TCATGTACCTGCCCCTTCTGAGGATGCTGAGCAACTTCGTAAAGCTTTTGAAGGATGGGGTACAAA
TGAGCAATTGATTATCGACATTTTGGCTCACAGGAATGCAGCTCAGCGCAATTTGATTCGTAAAAC
TTATCGTGAAGCTTATGGGGAAGATCTCCTTAAGTCTTTGGATGAGGAACTTTCAAGTGACTTTGA
GCGAGCTGTGGTGCTGTTTACTTTGGACCCTGCAGAGCGTGATGCATTTCTGGCTCATGAAGCTAC
AAAGAGGTTCACATCAAGCCATTGGGTTCTCATGGAATTGCTTGCACTAGGTCTTCACATGAACT
GTTCAATGTGAGGAAGGCGTATCACGATCTTTACAAGAAATCCCTTGAAGAAGATGTTGCGCACCA
TACCAAGGGAGACTACCGCAAGCTTTTGGTCCCACTTGTTAGTGCATTCCGATACCAGGGAGAGGA FIGURE 11 (continued)

```
GGTGAACATGACACTGGCAAGGTCGGAGGCAAAGATACTTCGTGAGAAGATATCAGACAAGCAGTA
CAGTGATGAGGAGGTCATCAGGATTGTAACAACACGGAGTAAGGCACAGTTAAATGCTACTCTGAA
TCATTACAATACTGCATTTGGGAATGCTATCAACAAGGATTTGAAGGCCGACCCTGAAGACGAATT
CCTCAAATTGCTGAGAGCTGCAATCAAGTGCTTGACTGTCCCTGAGAAATATTTTGAGAAGGTGCT
ACGTCAAGCAATCAATAAGCTGGGAACAGATGAATGGGCTCTTACTAGAGTGGTCGCCACTCGGGC
GGAGGTAGACATGGTGCGTATTAAGGAGGAATATCAGCGAAGAAACAGTGTGACCCTGGAAAAAGC
GATTGCTGGAGATACCTCTGGAGACTATGAGAAATGCTGCTTGCGTTGATTGGAGCTGGAGACGT
CTGAGCTGCTTTCCTATATTGAGTTGTTGGTATGAAAATTTAGTTTGCAATTTGAGGTGTGAGTTA
TGTTTGTTTGGTTGAGGGTGTGCCAATCGC
```

SEQ ID NO: 109, AAR13288.1, Anx1 [Gossypium hirsutum]
```
MATLKVPAHVPAPSEDAEQLRKAFEGWGTNEQLIIDILAHRNAAQRNLIRKTYREAYGEDLLKSLD
EELSSDFERAVVLFTLDPAERDAFLAHEATKRFTSSHWVLMEIACTRSSHELFNVRKAYHDLYKKS
LEEDVAHHTKGDYRKLLVPLVSAFRYQGEEVNMTLARSEAKILREKISDKQYSDEEVIRIVTTRSK
AQLNATLNHYNTAFGNAINKDLKADPEDEFLKLLRAAIKCLTVPEKYFEKVLRQAINKLGTDEWAL
TRVVATRAEVDMVRIKEEYQRRNSVTLEKAIAGDTSGDYEKMLLALIGAGDV
```

SEQ ID NO: 110, Y14972.1, Nicotiana tabacum mRNA for annexin, clone X511
```
GCATTTACGAGTTTTGACAATCATATCTTCCACAGACAGAAAAAAAATGGCTAGTCTTACTGTTCC
GGCAGAAGTTCCTTCAGTTGCTGAAGACTGTGAACAACTCCGATCTGCCTTCAAAGGATGGGGAAC
AAATGAGAAGTTGATCATATCAATTTTGGCTCATAGAAATGCTGCTCAACGCAAGTTGATTCAACA
GACTTATGCTGAGACTTTTGGTGAAGATCTCCTTAAAGAGTTGGACAGAGAACTTACCAATGATTT
TGAGAAATTGGTGGTAGTGTGGACATTGGATCCTTCAGAACGCGATGCCTATTTGGCTAAGGAAGC
TACTAAGAGATGGACAAAAGCAATTTTGTTCTTGTGGAGATTGCTTGTACCAGATCTCCTAAAGA
ATTGGTTTTGGCAAGGGAAGCTTATCATGCTCGTTTCAAGAAATCTCTTGAAGAGGACGTTGCTTA
TCACACTACTGGGGAACACCCCCAGCTTTTGGTACCTCTTGTGAGCTCCTACCGATATGGAGGGGA
CGAGGTGGACTTGCGCCTTGCTAAAGCAGAAGCTAAAATACTGCACGAGAAGATCTCCGATAAGGC
TTACAGTGACGATGAGGTCATCAGAATTCTAGCCACAAGGAGCAAAGCACAGATCAATGCTACTCT
GAACCATTACAAAGATGAATATGAAGAAGATATCCTGAAGCAATTGGAAGAGGGGGATGAGTTTGT
TGGACTATTGAGGGCAACCATAAAAGGTCTTGTCTACCCCGAGCACTACTTCGTGGAGGTTCTTCG
AGATGCAATTAACAGGAGAGGAACAGATGAAGATCATCTGACCAGAGTTATCGCTACAAGGGCTGA
GGTTGATATGAAGATTATCGCTGATGAGTACCAGAAGAGGGATAGCATCCCTCTGGGTCGGGCCAT
CGCCAAAGATACAAGAGGAGATTATGAGAGTATGTTGTTGGCTCTGCTTGGACAAGAGGAGGACTA
AGAAGGTTTTGCTTCTGTTTCATAATGACCAGAATAAACATGCTATCCCCTATATTTGAGAGTTGG
CATCCGTTGTATGCTTGATGATTAAGCGTGGTCTGTTTAACGTGAGCTTTTAGTCCTTTTCTTCTT
GTGATAAACTTTGAATGTACAACTTTATGCTATCTAAGAATGTTTTTCTAAAAAAAAAAAAAAAAA
AAAAAAAA
```

SEQ ID NO: 111, CAA75213.1, annexin [Nicotiana tabacum]
```
MASLTVPAEVPSVAEDCEQLRSAFKGWGTNEKLIISILAHRNAAQRKLIQQTYAETFGEDLLKELD
RELTNDFEKLVVVWTLDPSERDAYLAKEATKRWTKSNFVLVEIACTRSPKELVLAREAYHARFKKS
LEEDVAYHTTGEHPQLLVPLVSSYRYGGDEVDLRLAKAEAKILHEKISDKAYSDDEVIRILATRSK
AQINATLNHYKDEYEEDILKQLEEGDEFVGLLRATIKGLVYPEHYFVEVLRDAINRRGTDEDHLTR
VIATRAEVDMKIIADEYQKRDSIPLGRAIAKDTRGDYESMLLALLGQEED
```

FIGURE 11 (continued)

SEQ ID NO: 112, AJ401032.1, Solanum tuberosum mRNA for annexin p34 (an34 gene)
ATGGCAAGTCTTACAGTTCCGGCAGAAGTTCCTTCCGTAGCTGAAGACTGTGAACAACTCCGATCT
GCCTTCAAAGGATGGGGAACGAACGAGAAGTTGATTATATCAATTTTGGCTCATAGAAATGCTGCT
CAGCGCAAATTGATTCGACAGACTTATGCTGAAACTTTTGGGGAAGATCTACTTAAAGAGTTGGAC
AGAGAACTTACCCATGATTTTGAGAAATTGGTGCTAATATGGACACTGGATCCGTCAGAACGTGAT
GCCTATTTGGCTAAGGAAGCTACTAAGAGATGGACAAAAGCAACTTTGTTCTTGTGGAGATAGCT
TGTACTAGATCTCCTAAAGAACTGGTTTTGGCAAGGGAAGCTTATCATGCTCGTAACAAGAAATCT
CTTGAAGAGGACGTTGCTTATCACACTACTGGGGATCACCGCAAGCTTTTGGTACCTCTTGTGAGC
TCCTACCGATATGGAGGAGACGAGGTGGACTTGCGCCTTGCTAAAGCAGAATCTAAAGTACTGCAT
GAGAAGATCTCCGATAAGGCTTACAGTGACGATGAGGTCATTAGAATTTTAGCCACAAGGAGCAAA
GCGCAACTCAATGCTACTTTGAATCATTACAAAGATGAATATGGTGAGGATATCCTAAAGCAATTG
GAAGATGAGGATGAGTTTGTTGCACTATTGAGGGCCACCATAAAAGGTCTTGTCTACCCTGAGCAC
TATTTCGTGGAGGTTCTTCGTGATGCAATTAACAGGAGAGGAACAGAGGAAGATCATCTGAGCCGA
GTTATCGCTACAAGGGCTGAGGTGGATCTGAAGACTATCGCTAACGAGTACCAGAAGAGGGATAGC
ATTCCTCTGGGTCGCGCCATTGCCAAAGATACAGGAGGAGATTATGAGAATATGCTGGTGGCTTTA
CTTGGACAAGAGGAGGAATGA

SEQ ID NO: 113, CAB92956.1 annexin p34 [Solanum tuberosum]
MASLTVPAEVPSVAEDCEQLRSAFKGWGTNEKLIISILAHRNAAQRKLIRQTYAETFGEDLLKELD
RELTHDFEKLVLIWTLDPSERDAYLAKEATKRWTKSNFVLVEIACTRSPKELVLAREAYHARNKKS
LEEDVAYHTTGDHRKLLVPLVSSYRYGGDEVDLRLAKAESKVLHEKISDKAYSDDEVIRILATRSK
AQLNATLNHYKDEYGEDILKQLEDEDEFVALLRATIKGLVYPEHYFVEVLRDAINRRGTEEDHLSR
VIATRAEVDLKTIANEYQKRDSIPLGRAIAKDTGGDYENMLVALLGQEEE

SEQ ID NO: 114, AF079232.1, Lycopersicon esculentum annexin p34 (AN34) mRNA, complete cds
ATGGCAAGTCTTACAGTTCCGGCAGAAGTTCCTTCAGTCGCTGAAGACTGTGAACAACTCCGATCT
GCCTTCAAAGGATGGGGAACGAATGAGAAGTTGATTATATCAATTTTGGCTCATAGAAATGCGGCT
CAACGCAAATTGATTCGACAGACTTATGCTGAGACTTTTGGGGAAGATCTGCTTAAAGAGTTGGAC
AGAGAACTTACTCATGATTTTGAGAAATTGGTGGTAGTATGGACACTGGATCCTGCAGAACGTGAT
GCCTATTTGGCTAAGGAAGCTACTAAGAGATGGACAAAAGCAACTTTGTTCTTGTGGAGATAGCT
TGTACCAGATCTCCTAAAGAACTGGTTTTGGCAAGAGAAGCTTATCATGCTCGTAACAAGAAATCT
CTCGAAGAGGACGTTGCTTATCACACTACTGGGGATCACCGCAAGCTTTTGGTACCTCTTGTGAGC
TCCTACCGATATGGGGGAGATGAGGTGGACTTGCGACTTGCTAAAGCAGAATCTAAAGTGCTGCAT
GAGAAGATCTCCGATAAGGCTTACAGTGACGATGAGGTCATTAGAATTTTAGCCACAAGGAGCAAA
GCGCAACTCAATGCTACTTTGAATCATTACAAAGATGAATATGGTGAGGATATCCTAAAGCAATTA
GAAGATGAGGATGAGTTTGTTGCACTGTTAAGGGCCACCATAAAAGGTCTTGTCTACCCCGAGCAC
TATTTCGTGGAGGTTCTTCGTGATGCAATTAACAGGAGAGGAACAGAGGAAGATCATCTAACCCGA
GTTATCGCTACAAGGGCTGAGGTCGATCTGAAGACTATCGCTAACGAGTACCAGAAGAGGGATAGC
GTTCCTCTGGGTCGCGCCATTGCCAAAGATACAGGAGGAGATTATGAGAATATGCTGGTGGCTTTA
CTTGGACAAGAGGAGGAATAAGAAGCGGATTGGCTCACTTCTGTTTATAATGACCAGATAATATGC
CATTCTCCATATATTTCAGAGTTGGCATGTGTTTGATGATTGAGAGTGGTCTGTTCACATGAGCTT
TAGTCCTTTTCTTCTTGTGAGAAACTTTGAATATGAATCTTTGTGCTGTCTAAAAATGTTCTCTAA
TGATTTGCATCCACTAAAAAAAAAAAAAAAAAAAAAAAAA FIGURE 11 (continued)

SEQ ID NO: 115, AAC97494.1| annexin p34 [Lycopersicon esculentum]
MASLTVPAEVPSVAEDCEQLRSAFKGWGTNEKLIISILAHRNAAQRKLIRQTYAETFGEDLLKELD
RELTHDFEKLVVVWTLDPAERDAYLAKEATKRWTKSNFVLVEIACTRSPKELVLAREAYHARNKKS
LEEDVAYHTTGDHRKLLVPLVSSYRYGGDEVDLRLAKAESKVLHEKISDKAYSDDEVIRILATRSK
AQLNATLNHYKDEYGEDILKQLEDEDEFVALLRATIKGLVYPEHYFVEVLRDAINRRGTEEDHLTR
VIATRAEVDLKTIANEYQKRDSVPLGRAIAKDTGGDYENMLVALLGQEEE

SEQ ID NO: 116, AF079231.1, Lycopersicon esculentum annexin p35 (AN35) mRNA, complete cds
ATGTCTAGTCTTAAAGTTCCAGCATCAGTTCCAGATCCTTATGAAGATGCTGAGCAACTCAAAAAA
GCTTTTAAAGGATGGGGCACAAATGAGGAACTTATTATTCAGATTCTGGCTCATAGGAATGCCAGA
CAACGCAAGTTAATCCGAGATTCTTATGCTGCTGCTTATGGAGAGGATCTTCTCAAGGACTTGGAT
TCTGAACTGACAAGTGATTTTCAGCGTGTGGTGCTTCTCTGGACTTTGAGTCCTGCTGAGCGCGAC
GCCTACTTGGTTAATGAGGCTACCAAACGTCTGACTGCTAGCAATTGGGGTATCATGGAAATTGCT
TGTACCAGGTCTTCTGATGATCTTTTTAAGGCGAGGCAGGCCTACCATGCTCCATACAAGAAATCA
CTTGAAGAAGATGTTGCTTATCATACAGTGGGGGATTTCCGTAAGCTTTTGGTTCCTCTTATAACT
GCATTCAGATATGAAGGAGATGAGGTGAACATGACATTAGCAAGAAAGGGAAGCAAATATCTGCAT
GAGAAGATCTCTGACAAGGCTTACCATGACGAGGAGATCATCCGAATCATTTCTACTAGGAGTAAA
GCACAGCTGAGTGCTACGTTCAACCACTACCATGATCACCATGGCCATGAAATCATCAAGGATCTG
GAAGCTGATGATGACGATGAGTACCTGAAACTACTCAGAGCAGCAATAGAATGCTTGAAACCCAGA
GAACACTTTGAGAAAGTTCTTCGATTGGCTATCAAGAAGCTGGGTACAGACGAATGGGATCTTACT
AGAGTTGTTGCCACTCGGGCTGAAGTTGACATGGAGCGTATCAAAGAAGAGTACCATAGGAGGAAC
AGTGTTACATTGGACCGTGCAATTGCTGGAGACACTTCAGGAGACTATGAAAAATGCTTCTGGCT
CTGATTGGGCACGGAGATGCTTGAATTACATGTGCTGAAACCTTAAGATAATAAAAAACTCTACTT
ATTTTCTGAACTTTCATTTGCTTTTATGATCTATGGTGTGTACTCTCAGAGTTTGGTTCTGTGTTT
ATATGAACTAAAAACACTCGGGAGTTGAGTTGTGTTTTGTTTTCGCCTTCACTTTTCATTTCGGAC
TTCTACTGGTTTTGCCTGCTAAATAAGCATAGCTTCAACTTTGGCTTGAACGGATCTTGTTTCTTT
ATAACTCAGAAATAGATTATGTATCTTGGTTCGTAAAAAAAAAAAAAAAAAAAA

SEQ ID NO: 117, AAC97493.1, annexin p35 [Lycopersicon esculentum]
MSSLKVPASVPDPYEDAEQLKKAFKGWGTNEELIIQILAHRNARQRKLIRDSYAAAYGEDLLKDLD
SELTSDFQRVVLLWTLSPAERDAYLVNEATKRLTASNWGIMEIACTRSSDDLFKARQAYHAPYKKS
LEEDVAYHTVGDFRKLLVPLITAFRYEGDEVNMTLARKGSKYLHEKISDKAYHDEEIIRIISTRSK
AQLSATFNHYHDHHGHEIIKDLEADDDDEYLKLLRAAIECLKPREHFEKVLRLAIKKLGTDEWDLT
RVVATRAEVDMERIKEEYHRRNSVTLDRAIAGDTSGDYEKMLLALIGHGDA

SEQ ID NO: 118, NM_125901.3 Arabidopsis thaliana ANNAT2 (ANNEXIN ARABIDOPSIS 2); calcium ion binding / calcium-dependent phospholipid binding (ANNAT2) mRNA, complete cds
TTACTTAAGTAGGACGACGTGCGTCTGCTTCGTCTCATTACAAAGCAGAAGAAACACAAACAGAGG
CAGAGATCTTAAGAGTTAAAGACTAATCCCAACAATGGCGTCTCTCAAAGTCCCAAGCAATGTTCC
TCTTCCCGAAGATGACGCCGAGCAACTCCACAAGGCTTTTTCAGGATGGGGTACCAACGAGAAGCT
GATCATATCAATACTAGCTCACAGGAACGCAGCACAACGCAGCTTGATCCGCAGCGTTTATGCAGC
TACCTACAATGAGGATCTTCTCAAAGCATTAGACAAAGAGCTTTCTAGCGACTTTGAGAGAGCTGT
GATGTTGTGGACTCTTGATCCACCAGAGAGATGCTTATTTGGCTAAAGAATCCACCAAGATGTT
CACCAAGAACAATTGGGTTCTTGTTGAAATCGCTTGCACAAGGCCTGCTCTTGAGCTTATCAAGGT
CAAGCAAGCTTACCAAGCTCGATACAAGAAATCAATCGAGGAAGATGTCGCGCAACACACATCTGG
TGACCTTCGTAAGCTCTTGCTTCCTCTTGTGAGCACTTTCAGGTATGAAGGAGATGATGTGAACAT

```
GATGCTTGCAAGATCTGAAGCTAAGATACTTCACGAGAAGGTCTCAGAGAAATCTTACAGTGACGA
TGACTTCATCAGAATCTTGACAACAAGAAGCAAAGCACAGCTCGGTGCAACACTCAACCACTACAA
CAACGAGTATGGAAACGCCATTAACAAGAACTTGAAGGAAGAGTCGGACGACAATGACTACATGAA
ACTACTAAGAGCTGTAATCACATGTTTGACATACCCTGAGAAGCATTTTGAGAAGGTTCTTCGTCT
ATCAATCAACAAAATGGGAACAGACGAATGGGGACTAACCCGAGTCGTGACTACACGAACTGAAGT
TGACATGGAACGCATCAAGAGGAATATCAGCGAAGAAACAGCATTCCTTTGGACCGTGCTATCGC
CAAAGACACTTCTGGTGACTATGAGGACATGCTTGTTGCTCTTCTCGGACATGGCGATGCTTGAAA
CTGTTTCAACTTTCGAGTTCCTCCTTTCTCTTACTGCATGGTTTGTTTTAAATAAAAGAGTTGTGA
AACTGGTTCTGCAACTATTTATCAATGATCGTTTGAGTTTGTTAAATTTGAATCAAAATCTGTTTT
TCTTTCTTTTAAATACAATCTAAAGCACAAACTAAAGC
```

SEQ ID NO: 119, NP_201307.1, ANNAT2; calcium ion binding / calcium-dependent phospholipid binding [Arabidopsis thaliana]
```
MASLKVPSNVPLPEDDAEQLHKAFSGWGTNEKLIISILAHRNAAQRSLIRSVYAATYNEDLLKALD
KELSSDFERAVMLWTLDPPERDAYLAKESTKMFTKNNWVLVEIACTRPALELIKVKQAYQARYKKS
IEEDVAQHTSGDLRKLLLPLVSTFRYEGDDVNMMLARSEAKILHEKVSEKSYSDDDFIRILTTRSK
AQLGATLNHYNNEYGNAINKNLKEESDDNDYMKLLRAVITCLTYPEKHFEKVLRLSINKMGTDEWG
LTRVVTTRTEVDMERIKEEYQRRNSIPLDRAIAKDTSGDYEDMLVALLGHGDA
```

SEQ ID NO: 120, Y14973.1, Nicotiana tabacum mRNA for annexin, clone X671
```
CTGCTTGCATTTTCGAGTCTTGACAATCATAAAAATGGCTAGTCTTACTGTTCCGGCAGAAGTTCC
TTCAGTAGCTGAAGACTGTGAACAACTCCGATCTGCCTTCAAAGGGTGGGGAACAAACGAGAAGTT
GATCATATCAATTTTGGCTCATAGAAATGCTGCTCAACGCAAGTTGATTCAACAGACTTATGCTGA
GACTTTTGGTGAAGATCTCCTTAAAGAGTTGGACAGAGAACTTACCAATGATTTTGAGAAATTGGT
GGTAGTGTGGACATTGGATCCTTCAGAACGCGATGCCTATTTGGCTAAGGAAGCTACTAAGAGATG
GACAAAAAGCAATTTTGTTCTTGTGGAAATAGCTTGTACCAGATCTCCTAAAGAATTGGTTTTGGC
ACGGGAAGCTTATCATGCTCGTTACAAGAAATCTCTTGAAGAGGACGTTGCTTATCACACTACTGG
GGAACACCGCAAGCTTTTGGTAGCTCTTGTGAGCTCCTATCGATATGGAGGAGACGAGGTGGACTT
GCGTCTTGCTAAAGCTGAAGCTAAAATACTGCATGAGAAGATCTCCGATAAGGCTTACAGTGACAA
TGAGGTCATCAGAATTCTAGCCACAAGGAGTAAAGCACAGATCAATGCTACTCTGAATCATTACAA
AGATGAATATGAAGAGGATATCCTAAAGCAATTGGAAGAGGGGGATGAGTTTGTTGGACTATTGAG
GGCAACCATAAAAGGTCTTGTCTACACCGAGCACTACTTCGTGGAGGTTCTTCGAGATGCAATTAA
CAGGAGAGGAACAGAGGAAGATCATCTGACCAGAGTTATCGCTACAAGGGCTGAGGTTGATATGAA
GACTATCGCTGATGAGTACCAGAAGAGGGATAGCATCCATCTGGGTCGCGCCATTGCCAAAGATAC
AAGAGGAGATTATGAGAGTATGTTGTTGGCTCTGCTTGGACAAGAGGAGGACTAAGAAGGATTTGC
TTTATAATGACCGGAATAAATATGATATCCCCTATATTTGAGAGTTGGCATCCGCTGTATGTTTGA
TGATTGAGCGTGGTCTGTTTAACGTGAGCGTTGAGTCCTTTTCTTCTCACTTTGAATATGCAACTT
TATGCTATCTAAGAATATTTTTTTATAAAAAAAAAAAAAAAAAAAAAAAAA
```

SEQ ID NO: 121, CAA75214.1, annexin [Nicotiana tabacum]
```
MASLTVPAEVPSVAEDCEQLRSAFKGWGTNEKLIISILAHRNAAQRKLIQQTYAETFGEDLLKELD
RELTNDFEKLVVVWTLDPSERDAYLAKEATKRWTKSNFVLVEIACTRSPKELVLAREAYHARYKKS
LEEDVAYHTTGEHRKLLVALVSSYRYGGDEVDLRLAKAEAKILHEKISDKAYSDNEVIRILATRSK
AQINATLNHYKDEYEEDILKQLEEGDEFVGLLRATIKGLVYTEHYFVEVLRDAINRRGTEEDHLTR
VIATRAEVDMKTIADEYQKRDSIHLGRAIAKDTRGDYESMLLALLGQEED
```

FIGURE 11 (continued)

SEQ ID NO: 122, DQ252486.1, Solanum tuberosum clone 051E10 annexin p34-like protein-like mRNA, complete cds
ATCACTCTGCATTTTCGAGTCTTCACAATCATATCCTCCTAACCACACACAGAAGAAAAAAAATG
GCAAGTCTTACAGTTCCGGCAGAAGTTCCTTCCGTCGCTGAAGACTGTGAACAACTCCGATCTGCC
TTCAAAGGATGGGGAACGAACGAGAAGTTGATTATATCAATTTTGGCTCATAGAAATGCTGCTCAG
CGCAAATTGATTCGACAGACTTATGCTGAAACTTTTGGGGAAGATCTACTTAAAGAGATTGGGACA
GGAAGAAACTTAACCCATGATTTTGAGAAATTGGTGCTAATATGGACACTGGATCCGTCAGAACGT
GATGCCTATTTGGCTAAGGAAGCTACTAAGAGATGGACAAAAGCAACTTTGTTCTTGTGGAGATA
GCTTGTACTAGATCTCCTAAAGAACTGGTTTTGGCAAGGGAAGCTTATCATGCTCGTAACAAGAAA
TCTCTCGAAGAGGACGTTGCTTATCACACTACTGGGGATCACCGCAAGCTTTTGGTACCTCTTGTG
AGCTCCTACCGATATGGAGGAGACGAGGTGGACTTGCGCCTTGCTAAAGCAGAATCTAAAGTACTG
CATGAGAAGATCTCCGATAAGGCTTACAGTGACGATGAGGTCATTAGAATTTTAGCCACAAGGAGC
AAAGCGCAACTCAATGCTACTTTGAATCATTACAAAGATGAATATGGTGAGGATATCCTAAAGCAA
TTGGAAGATGAGGATGAGTTTGTTGCACTATTGAGGGCCACCATAAAAGGTCTTGTCTACCCTGAG
CACTATTTCGTGGAGGTTCTTCGTGATGCAATTAACAGGAGAGGAACAGAGGAAGATCATCTGAGC
CGAGTTATTGCTACAAGGGCTGAGGTCGATCTGAAGACTATCGCTAACGAGTACCAGAAGAGGGAT
AGCATTCCTCTGGGTCGCGCCATTGCCAAAGATACAGGAGGAGATTATGAGAATATGCTGGTGGCT
TTACTTGGACAAGAGGAGGAATGAGGAGGATTGGCTCACTTCTGTGTTATAATGACCAGAATAAAT
ATGCCATCTCCCATATATTTCAGAGTTGGCATCTGTTTGATGATTGAGTGTGGTCTGTTTTCACAT
GAGCTTTTAGTCCTTTTCTTCGTGTGAGAAACTTTGAATATGCATCTTTGTGCTGTCTAAAAATAT
TTTCTAAAAAAAAAAAAAAAAAAAAAA SEQ ID NO: 123, ABB55363.1, annexin p34-like protein-like [Solanum tuberosum]
MASLTVPAEVPSVAEDCEQLRSAFKGWGTNEKLIISILAHRNAAQRKLIRQTYAETFGEDLLKEIG
TGRNLTHDFEKLVLIWTLDPSERDAYLAKEATKRWTKSNFVLVEIACTRSPKELVLAREAYHARNK
KSLEEDVAYHTTGDHRKLLVPLVSSYRYGGDEVDLRLAKAESKVLHEKISDKAYSDDEVIRILATR
SKAQLNATLNHYKDEYGEDILKQLEDEDEFVALLRATIKGLVYPEHYFVEVLRDAINRRGTEEDHL
SRVIATRAEVDLKTIANEYQKRDSIPLGRAIAKDTGGDYENMLVALLGQEEE SEQ ID NO: 124, NM_121061.2, Arabidopsis thaliana ANN7 (ANN7, ANNEXIN ARABIDOPSIS 7); calcium ion binding / calcium-dependent phospholipid binding (ANN7) mRNA, complete cds
CATACAGAAATTTCACTTGTTCGAAAATGGCTTCTCTCAAAGTTCCCGCCACTGTTCCTCTTCCC
GAAGAAGACGCTGAGCAACTCTACAAAGCCTTTAAAGGATGGGGAACCAATGAGAGGATGATCATA
TCAATCTTGGCTCACAGAAATGCAACGCAACGTAGTTTCATTCGTGCCGTTTATGCTGCTAACTAC
AATAAGGATCTTCTCAAGGAATTAGACAGAGAGCTTTCCGGTGACTTTGAGCGAGCTGTGATGTTG
TGGACTTTTGAACCAGCGGAGAGAGATGCTTATTTGGCAAAAGAATCTACCAAAATGTTCACCAAA
AACAATTGGGTTCTTGTCGAAATCGCTTGTACTAGATCTGCTCTTGAACTCTTTAATGCCAAGCAA
GCATACCAAGCCCGCTACAAGACCTCCCTCGAGGAAGACGTCGCATACCACACATCTGGAGACATT
CGAAAGCTCTTGGTACCTCTTGTGAGCACTTTTAGGTACGATGGAGATGAAGTGAACATGACGTTA
GCTAGGTCCGAGGCTAAGATACTTCACGAGAAGATCAAGGAAAAGGCTTATGCTGATGATGATCTC
ATAAGAATCTTGACAACCAGGAGCAAAGCACAAATCAGCGCAACTCTCAATCACTACAAAACAAT
TTCGGAACTTCCATGAGCAAATACCTAAAGGAGGATTCGGAAAACGAATACATTCAATTGCTCAAA
GCCGTGATCAAATGCTTGACATATCCAGAGAAGTATTTTGAGAAAGTTCTACGTCAAGCCATCAAC
AAATTGGGAACAGATGAGTGGGGACTAACGAGAGTGGTCACTACACGAGCAGAGTTTGACATGGAA
CGGATCAAAGAGGAATATATACGTAGAAACAGTGTTCCTCTTGATCGAGCCATTGCTAAAGACACT FIGURE 11 (continued)

```
CATGGTGACTATGAGGATATACTTCTCGCTCTTCTCGGACATGACCATGCTTGAAATAACATTTGC
AAGTTTTGTTTAAGAAAAAAAACTAAATTTTATCGCTTTGTGTTTAATAAAACAGTTGTGGTTGGA
CTTGCAACTTGGTCATGTTAAGAATTTAGTGTCTTCAGTTTCATTTGTCGTCGATGTTTTCAGTTA
TTTTTTTTTTTAAATCTAAAAATTATAAAACCATATCAAAAATTATTATTGATC
```

SEQ ID NO: 125, NP_196585.1, ANN7 (annexin 7); calcium ion binding/calcium-dependent phospholipid binding [Arabidopsis thaliana]
```
MASLKVPATVPLPEEDAEQLYKAFKGWGTNERMIISILAHRNATQRSFIRAVYAANYNKDLLKELD
RELSGDFERAVMLWTFEPAERDAYLAKESTKMFTKNNWVLVEIACTRSALELFNAKQAYQARYKTS
LEEDVAYHTSGDIRKLLVPLVSTFRYDGDEVNMTLARSEAKILHEKIKEKAYADDDLIRILTTRSK
AQISATLNHYKNNFGTSMSKYLKEDSENEYIQLLKAVIKCLTYPEKYFEKVLRQAINKLGTDEWGL
TRVVTTRAEFDMERIKEEYIRRNSVPLDRAIAKDTHGDYEDILLALLGHDHA
```

SEQ ID NO: 126, X74947.1, M.sativa mRNA for annexin
```
CTCTCACGTTCCGTCTCCATCAGAAGACAGTGAACAATTGCGCGGTGCTTTTCAAGGATGGGGAAC
GAATGAAGGCTTGATAATATCGATCCTGGCTCATAGAAATGCAGCTCAGCGTAAGTCGATCCGCGA
AACTTACACGCAGACCCATGGAGAAGATCTTCTTAAAGATCTTGACAAAGAACTTTCAAGTGATTT
TGAGAAAGCTGTGCTGCTGTGGACATTGGATCCGGCCGAGCGTGATGCATTTTTAGCCAATCAAGC
AACTAAAATGTTGACTTCAAACAATTCGATCATCGTGGAAATTGCTTCCACAAGATCTCCACTTGA
ACTTCTTAAGGCAAAGCAAGCATATCAAGTCCGTTTCAAAAAGTCCCTTGAAGAAGATGTTGCCTA
TCATACTTCTGGTGACATCCGCAAGCTTTTGGTTCCTCTTGTGGGCATACACCGTTATGAGGGAGA
TGAGGTGAACATGACATTGGCAAAATCTGAAGCTAAATTGCTTCATGAGAAGATTGCGGATAAGGC
TTACAATCATGATGACCTGATCAGGATTGTAACAACAAGGAGTAAAGCGCAATTAAATGCAACTTT
GAATCACTATAACAATGAGTTTGGGAATGTAATAGACAAGGATTTGGAAACTGATTCGGATGATGA
ATATCTGAAATTATTGAGGGCAGCAATTAAGGGCTTGACCTACCCTGAGAAATATTTTGAGGAACT
CCTTAGGCTGGCTATAAACAAGATGGGAACCGATGAAAATGCTCTTACTAGAGTGGTGACAACTAG
AGCTGAGGTTGATTTGCAGCGAATTGCGGAGGAATACCAGAGAAGAAACAGTGTTCCTCTGGACCG
TGCAATTGACAAAGACACTTCTGGAGACTATCAGAAAATTCTCCTTGCACTGATGGGACATGATGA
GTAAGTTCTTAATCTGTCCAGTAGTCATGGAGTGGCTGTTTGGACTATCTGTTTTCCCTTCATCAT
CAGCGTGATTTTGCTGCGGATCTCTTGATAGTATACAGAATTCGGTGACTTGCTGTGGTAACTATG
CTTGTGATATGTATGAACTATTGTGGTTTTAAATAATATGTTTTGAATATGGACTGAAATTCAAAA
CAGAACTTTGCCTTCTTAAATAATGAAACAGCTATCATATTTCTCTCCTTAAAAAAAAAA
```

SEQ ID NO: 127, CAA52903.1, annexin [Medicago sativa]
```
SHVPSPSEDSEQLRGAFQGWGTNEGLIISILAHRNAAQRKSIRETYTQTHGEDLLKDLDKELSSDF
EKAVLLWTLDPAERDAFLANQATKMLTSNNSIIVEIASTRSPLELLKAKQAYQVRFKKSLEEDVAY
HTSGDIRKLLVPLVGIHRYEGDEVNMTLAKSEAKLLHEKIADKAYNHDDLIRIVTTRSKAQLNATL
NHYNNEFGNVIDKDLETDSDDEYLKLLRAAIKGLTYPEKYFEELLRLAINKMGTDENALTRVVTTR
AEVDLQRIAEEYQRRNSVPLDRAIDKDTSGDYQKILLALMGHDE
```

SEQ ID NO: 128, Brassica rapa subsp. pekinensis clone KBrH080A08 (c76682-76607, c75996-75851, c75753-75535, c75368-74859), complete sequence
```
ATGGCGTCTCTCAAAGTTCCTGCTAGTGTTCCTCTTCCAGAAGAAGATGCCGAGCAGCTCCAGAAG
GCCTTTAAAGGATGGGGAACCAACGAGAGGATGATCATATCAATCTTGGCTCACAGAAATGCCGAG
CAACGCAGCTTCATCCGTGCTGTTTATGCTGCTAACTACAATAAGGATCTTCTCAAGGAATTAGAC
AAAGAGCTATCCGGTGACTTCGAGCGAGCTGTGATGTTGTGGACACTTGAACCAGCGGAGAGAGAT
```

FIGURE 11 (continued)

```
GCGTATTTGGCTAAGGAATCAACAAAAATGTTCACTAAAGACAATTGGGTTCTAGTTGAAATCGCT
TGTACTAGATCTTCCCTTGAGTTTTTCAAGGCCAAGCAAGCATACCAAGTTCGCTACAAGACATCT
ATTGAGGAAGATGTCGCCTACCACACATCTGGAGATGTCCGAAAGCTCTTGGTTCCTCTTGTGAGT
ACCTTTAGGTACGATGGAGATGAAGTAAACATGATGATTGCTAAGTCTGAGGCTAAGATACTTCAC
GAGAAGATGGAGGCGAAGGATTACAATGATGGAGATCTCATTAGAATCCTGACAACAAGAAGCAAA
GCTCAAATCAGTGCAACACTCAACCACTTCAAAAATAAGTTCGGAACTTCCATTACAAAATACCTT
AAAGAGGATTCCGACAACGAATATGTTCAGCTACTTAAAGCCGTGATCAAATGCTTGACTTATCCA
GAGAAATATTTTGAGAAAGTTCTTCGTCAAGCCATCAACAAAATGGGAACTGACGAGTGGGGACTT
ACTAGAGTGGTCACCACACGAGCTGAGCTCGACATGGAACGGATCAAAGAGGAATACTTGCGCAGG
AACAGTGTCCCACTTGACCGAGCCATTGCCAAAGACACTCATGGTGACTATGAGGATATTCTTCTA
GCTCTTATCGGACATGGCCATGCTTGA
```

SEQ ID NO: 129, AAZ67605.1| 80A08_20 [Brassica rapa subsp. pekinensis]
```
MASLKVPASVPLPEEDAEQLQKAFKGWGTNERMIISILAHRNAEQRSFIRAVYAANYNKDLLKELD
KELSGDFERAVMLWTLEPAERDAYLAKESTKMFTKDNWVLVEIACTRSSLEFFKAKQAYQVRYKTS
IEEDVAYHTSGDVRKLLVPLVSTFRYDGDEVNMMIAKSEAKILHEKMEAKDYNDGDLIRILTTRSK
AQISATLNHFKNKFGTSITKYLKEDSDNEYVQLLKAVIKCLTYPEKYFEKVLRQAINKMGTDEWGL
TRVVTTRAELDMERIKEEYLRRNSVPLDRAIAKDTHGDYEDILLALIGHGHA
```

SEQ ID NO: 130, NM_129433.3, Arabidopsis thaliana ANNAT3 (ANNEXIN 3, ANNEXIN ARABIDOPSIS 3); calcium ion binding/ calcium-dependent phospholipid binding (ANNAT3) mRNA, complete cds
```
CCTTGAGGAAAAAAAACTAAAACGGCTCTAAATTGAAAACAAAAGAAGAGAGAGAGAGAGAGAC
GAAGAAACAGAGAGATTCTCTCGAAAATGGCCACCATTAGAGTACCAAACGAAGTTCCTTCTCCAG
CTCAGGATTCTGAAACTCTCAAACAAGCTATTCGCGGATGGGGAACAGATGAGAAGGCGATTATAC
GAGTTTTAGGGCAAAGAGACCAGAGCCAGAGAAGGAAGATTAGAGAAAGTTTTAGAGAGATTTATG
GCAAAGATCTTATCGATGTTCTATCCTCCGAACTGTCTGGTGATTTCATGAAAGCTGTGGTTTCGT
GGACGTATGATCCAGCAGAGAGAGACGCAAGGCTTGTGAACAAGATTTTGAACAAGGAGAAGAAGA
AGAAAAGCTTAGAGAATTTGAAGGTTATAGTAGAGATCTCTTGCACGACTTCCCCAAACCATTTGA
TTGCTGTGAGGAAAGCTTATTGTTCACTCTTTGACTCTTCTCTTGAAGAACACATTGCTTCTTCTC
TGCCTTTTCCTCTTGCAAAGTTACTGGTGACATTGGCAAGTACATTCAGATATGACAAAGATAGGA
CTGATGCAGAAGTAGCTACTATTGAGGCGGCTATGCTACGTGAAGCCATAGAGAAGAAACAATTAG
ATCATGACCATGTCCTGTACATATTAGGAACGCGTAGTATCTATCAGCTCAGAGAAACTTTTGTTG
CTTACAAGAAGAATTATGGGGTCACAATTGATAAGGATGTTGATGGATGTCCAGGAGATGCTGATC
TGAGAAGTCTATTGAAGGTGGCAATCTTTTGTATTGATACTCCTGAGAAACACTTTGCAAAGGTGG
TAAGAGATTCGATTGAGGGTTTTGGAACAGATGAGGATTCGTTGACGAGGGCGATTGTGACGCGTG
CAGAGATCGATTTGATGAAAGTAAGAGGAGAGTATTTCAACATGTATAATACAAGCATGGACAATG
CTATTACTGGTGATATTTCTGGAGACTACAAGGACTTCATTATCACCTTACTTGGATCCAAAATCT
GATCGTTCTTTCGTTTCTTTGTCAGTTGTTATATTCTTGGCTTTGCTTGTGACTTGTATAATCAAT
CAATACATTGTATTCCAACTCCAGTTTGAATTGTTTAAAAAATAATCAAATTTCTCTTGATTCTTG
CATTTTTGAATCAAAGCAAATCTATGTTTAATTTTGTTTTCAAAATT
```

FIGURE 11 (continued)

SEQ ID NO: 131, NP_181410.1, ANNAT3 (ANNEXIN 3); calcium ion binding / calcium-dependent phospholipid binding [Arabidopsis thaliana]
MATIRVPNEVPSPAQDSETLKQAIRGWGTDEKAIIRVLGQRDQSQRRKIRESFREIYGKDLIDVLS
SELSGDFMKAVVSWTYDPAERDARLVNKILNKEKKKKSLENLKVIVEISCTTSPNHLIAVRKAYCS
LFDSSLEEHIASSLPFPLAKLLVTLASTFRYDKDRTDAEVATIEAAMLREAIEKKQLDHDHVLYIL
GTRSIYQLRETFVAYKKNYGVTIDKDVDGCPGDADLRSLLKVAIFCIDTPEKHFAKVVRDSIEGFG
TDEDSLTRAIVTRAEIDLMKVRGEYFNMYNTSMDNAITGDISGDYKDFIITLLGSKI

SEQ ID NO: 132, DQ446409.1, Arabidopsis thaliana clone pENTR221-At1g68090 annexin 5 (At1g68090) mRNA, complete cds
ATGGCAACAATGAAAATACCAATGACGGTACCTTCTCCTCGAGTCGATGCTGACCAACTCTTTAAG
GCCTTCAAAGGAAGAGGCTGCGATACTTCGGTGATCATCAACATCTTAGCTCATCGCAATGCAACA
CAACGAGCTCTCATCGAACAAGAATACGAAACCAAATTCTCGGATGACCTCCGAAAACGTCTCCAC
TCTGAGCTTCATGGTCATCTCAAGAAAGCCGTTCTTTTGTGGATGCCTGAAGCAGTGGAGCGAGAC
GCTTCAATACTGAAACGCTCCTTAAGAGGAGCCGTGACTGATCATAAAGCGATTGCTGAGATTATA
TGCACACGATCTGGCTCTCAGCTTCGTCAGATCAAACAGGTCTACTCAAACACTTTCGGTGTGAAA
CTTGAAGAGGACATCGAATCCGAAGCTTCTGGCAATCACAAAGAGTTTTGCTCGCGTATTTGAAC
ACTACGCGATATGAAGGACCAGAGATCGATAATGCGAGTGTAGAGAACGATGCTAGGACTCTCAAG
AGCGCGGTTGCAAGGAAGCATAAATCTGATGACCAGACGTTGATTCAGATATTCACTGACCGAAGC
AGGACTCATTTGGTCGCTGTAAGATCTACTTACCGTTCCATGTACGGCAAAGAACTTGGAAAGGCC
ATAAGAGATGAGACTCGCGGGAACTTCGAGCATGTCCTTCTAACAATTTTACAATGTGCTGAAAAC
TCTTGTTTCTATTTCGCAAAGGCATTGAGGAAATCAATGAAAGGATTAGGAACAGATGACACGGCG
TTGATAAGAATCGTGGTGACGAGAGCAGAGGTGGATATGCAGTTCATCATCACAGAATACCGTAAG
AGATACAAGAAGACTTTGTACAATGCTGTTCATTCTGATACAACTAGTCATTACAGGACTTTTCTC
CTCTCTCTTTTAGGCCCCAACGTTTGA

SEQ ID NO: 133, ABE65753.1| annexin 5 [Arabidopsis thaliana]
MATMKIPMTVPSPRVDADQLFKAFKGRGCDTSVIINILAHRNATQRALIEQEYETKFSDDLRKRLH
SELHGHLKKAVLLWMPEAVERDASILKRSLRGAVTDHKAIAEIICTRSGSQLRQIKQVYSNTFGVK
LEEDIESEASGNHKRVLLAYLNTTRYEGPEIDNASVENDARTLKSAVARKHKSDDQTLIQIFTDRS
RTHLVAVRSTYRSMYGKELGKAIRDETRGNFEHVLLTILQCAENSCFYFAKALRKSMKGLGTDDTA
LIRIVVTRAEVDMQFIITEYRKRYKKTLYNAVHSDTTSHYRTFLLSLLGPNV

SEQ ID NO: 134, NM_129432.2, Arabidopsis thaliana ANNAT4 (ANNEXIN 4, ANNEXIN ARABIDOPSIS 4); calcium ion binding / calcium-dependent phospholipid binding (ANNAT4) mRNA, complete cds
ACAGAAACCAAACCAAGAGCCGGAAATCAAAAACAGTAATAAAAGATCAACTGCAAGAAAATGGCT
CTTCCTCTCGAGCTCGAAAGCCTCACTGAAGCCATCTCAGCTGGGATGGGAATGGGAGTTGATGAG
AATGCATTGATAAGCACACTGGGGAAATCGCAAAAGGAACATAGAAAATTGTTTAGGAAAGCAAGC
AAAAGTTTCTTTGTTGAAGATGAGGAAAGAGCTTTTGAGAAATGTCATGATCACTTCGTCAGACAC
CTCAAGCTTGAGTTCTCCCGCTTCAATACTGCGGTGGTGATGTGGGCAATGCATCCATGGGAGAGA
GATGCAAGGTTGGTGAAGAAAGCTTTGAAGAAGGAGAAGAAGCTTACAACCTCATCGTTGAGGTC
TCATGCACACGCTCTGCTGAGGATCTCCTCGGTGCACGTAAAGCTTACCACTCTCTCTTCGACCAA
TCAATGGAAGAAGACATTGCCTCTCACGTCCACGGTCCTCAGCGCAAGTTGCTTGTGGGCTCGTG
AGTGCTTATAGATACGAAGGAAATAAGGTGAAGGATGATTCTGCCAAATCCGATGCTAAGATTCTA
GCCGAAGCAGTGGCTTCTTCAGGCGAAGAAGCCGTGGAGAAGGATGAGGTTGTTAGGATTTTGACC
ACAAGAAGCAAACTTCATCTCCAACATCTCTACAAACACTTTAACGAAATCAAAGGCTCTGATCTT FIGURE 11 (continued)

```
CTTGGGGGTGTATCTAAGTCTTCTCTTCTCAATGAAGCATTGATTTGTTTGCTCAAACCGGCTCTG
TATTTCAGCAAGATTTTGGATGCGTCTCTGAACAAAGACGCAGACAAGACTACCAAGAAATGGTTG
ACAAGAGTGTTCGTTACAAGAGCAGATCATAGTGATGAGATGAATGAGATCAAAGAAGAGTACAAT
AACCTTTATGGTGAGACTTTGGCTCAAAGAATCCAAGAGAAGATAAAAGGGAACTACAGAGATTTC
TTGCTCACACTTCTCTCCAAATCCGATTGATTTCGTGTTGAGAAACCTATTACCAATACTTTTGGT
TATTGAAGATTTATGATTTCCCTTTTTATGGTTTTATGTTTCTAATTCCTAAATTTGCGTTTTCTC
TACCGTTTGGTAATAAAGACATGAAAATTTGATGAACTCGGTGAATCGAGAGTAAGAGTTTTGCGA
TTGTGACAATGAGTGATTAATACAAGGATTAAGCTCCAATAAAAAAATGTTGCATAAATCAGAAAT
GAAACTTGTAACTCTTCTTTTCTTTATGTGAAACTTGTAACTCTATTTGAAAGATTCTATGTGACC
ACTAAACCGAATTACGG
```

SEQ ID NO: 135, NP_181409.1, ANNAT4 (ANNEXIN 4); calcium ion binding / calcium-dependent phospholipid binding [Arabidopsis thaliana]
```
MALPLELESLTEAISAGMGMGVDENALISTLGKSQKEHRKLFRKASKSFFVEDEERAFEKCHDHFV
RHLKLEFSRFNTAVVMWAMHPWERDARLVKKALKKGEEAYNLIVEVSCTRSAEDLLGARKAYHSLF
DQSMEEDIASHVGPQRKLLVGLVSAYRYEGNKVKDDSAKSDAKILAEAVASSGEEAVEKDEVVRI
LTTRSKLHLQHLYKHFNEIKGSDLLGGVSKSSLLNEALICLLKPALYFSKILDASLNKDADKTTKK
WLTRVFVTRADHSDEMNEIKEEYNNLYGETLAQRIQEKIKGNYRDFLLTLLSKSD
```

SEQ ID NO: 136, NM_121060.3, Arabidopsis thaliana ANN6 (ANN6, ANNEXIN ARABIDOPSIS 6); calcium ion binding / calcium-dependent phospholipid binding (ANN6) mRNA, complete cds
```
GTCTCATCTAGAGAGCTAGAGAAATATTCAGTGGTCGGAGAATGGCGTCTCTCAAAATTCCAGCAA
ATATTCCTCTTCCCGAAGAAGACTCCGAGCAGCTCCACAAGGCATTCAAAGGATGGGGAACTAATG
AAGGGATGATCATATCAATTTTGGCTCATAGAAACGCAACGCAACGCAGTTTCATTCGTGCCGTTT
ATGCTGCTAACTACAATAAGGATCTTCTCAAGGAATTAGACGGAGAGCTTTCTGGTGACTTTGAGA
GAGTTGTGATGTTGTGGACTCTTGATCCAACGGAGAGAGATGCGTATTTGGCCAATGAATCTACCA
AATTGTTCACCAAAAACATTTGGGTCCTAGTTGAAATCGCTTGTACTAGACCTTCTCTTGAGTTTT
TCAAGACCAAGCAAGCATACCATGTTCGCTACAAGACCTCTCTCGAGGAAGATGTTGCATACCATA
CATCTGGAAATATCCGAAAGCTATTGGTTCCTCTTGTGAGCACCTTCAGGTACGATGGAAATGCTG
ATGAGGTCAACGTGAAGCTGGCTAGATCCGAAGCTAAGACACTTCACAAGAAGATCACTGAGAAGG
CTTACACTGATGAAGATCTCATCAGAATCTTGACAACAAGGAGCAAAGCACAGATCAATGCAACAC
TCAATCACTTCAAGGACAAGTTTGGAAGTTCCATTAACAAGTTTCTCAAAGAAGATTCGAACGATG
ATTATGTTCAATTACTCAAAACCGCGATCAAATGCTTGACATATCCAGAGAAGTACTTTGAGAAGG
TTCTACGTCGAGCCATCAACAGGATGGGAACAGACGAGTGGGCACTTACTAGAGTGGTCACTACAA
GAGCAGAGGTCGACCTGGAGCGGATCAAAGAAGAATACTTACGCAGGAACAGTGTTCCTCTTGATC
GAGCCATTGCTAATGACACTTCTGGTGACTACAAGGATATGCTTCTCGCCCTTCTTGGACATGACC
ATGCTTGAAACAACATCATCGTTTCATAGTCTTTTATAAGACAGTTGTTATTTGTTTTTCATTTTC
TTTGAACTTTGGTCCTTAGTTTTTACATTTTACTGCAACAACTTATTCTGGTTT
```

SEQ ID NO: 137, NP_196584.1, ANN6 (annexin 6); calcium ion binding / calcium-dependent phospholipid binding [Arabidopsis thaliana]
```
MASLKIPANIPLPEEDSEQLHKAFKGWGTNEGMIISILAHRNATQRSFIRAVYAANYNKDLLKELD
GELSGDFERVVMLWTLDPTERDAYLANESTKLFTKNIWVLVEIACTRPSLEFFKTKQAYHVRYKTS
LEEDVAYHTSGNIRKLLVPLVSTFRYDGNADEVNVKLARSEAKTLHKKITEKAYTDEDLIRILTTR
SKAQINATLNHFKDKFGSSINKFLKEDSNDDYVQLLKTAIKCLTYPEKYFEKVLRRAINRMGTDEW
ALTRVVTTRAEVDLERIKEEYLRRNSVPLDRAIANDTSGDYKDMLLALLGHDHA
```

FIGURE 11 (continued)

SEQ ID NO: 138, NM_121276.2, Arabidopsis thaliana annexin, putative (AT5G12380) mRNA, complete cds

ATGGCCACCATTGTTTCTCCTCCACATTTCTCCCCTGTCGAAGACGCTGAAAACATCAAGGCGGCT
TGTCAAGGATGGGGAACCAATGAAAATGCCATCATCTCGATCTTAGGACACCGGAATTTGTTCCAG
AGGAAGCTCATAAGACAAGCTTACCAGGAGATTTACCATGAGGATCTCATTCACCAGCTCAAATCT
GAGCTCTCTGGCAATTTTGAGAGAGCTATTTGCTTGTGGGTCTTGGATCCTCCAGAGAGAGATGCT
CTCTTGGCTAACTTGGCTCTTCAAAAGCCTATTCCTGACTACAAGGTTCTTGTCGAAATTGCCTGC
ATGAGATCCCCTGAAGATATGTTAGCTGCTAGACGTGCTTACCGTTGCCTCTACAAGCATTCTCTT
GAGGAAGACTTGGCCTCCCGTACTATTGGCGACATCAGGAGACTCTTGGTTGCAATGGTGTCTGCT
TATAAATATGATGGAGAAGAAATTGATGAGATGCTGGCGCAATCAGAGGCTGCGATTCTTCATGAT
GAAATCCTTGGTAAGGCTGTTGATCACGAAGAAACGATCAGGGTGTTAAGTACAAGGAGCAGCATG
CAGCTTAGCGCAATCTTCAACCGCTACAAGGATATATATGGCACATCGATCACTAAGGATCTCCTC
AATCACCCTACAAATGAGTACCTGAGTGCACTACGTGCAGCCATCAGGTGCATCAAAAACCCTACC
CGGTATTATGCAAAGGTTTTGCGCAATTCAATCAACACGGTGGGGACTGATGAAGATGCTCTGAAC
CGTGTGATTGTCACACGAGCAGAAAAGGACCTGACGAATATAACTGGGCTGTACTTTAAGAGGAAC
AATGTGAGTCTCGATCAAGCTATAGCAAAAGAGACATCAGGGGACTACAAGGCCTTTCTTCTAGCT
TTGCTAGGACATGGAAAACAACTTTAG

SEQ ID NO: 139, NP_568271.2, put ANN8 At5g12380 annexin, putative [Arabidopsis thaliana]

MATIVSPPHFSPVEDAENIKAACQGWGTNENAIISILGHRNLFQRKLIRQAYQEIYHEDLIHQLKS
ELSGNFERAICLWVLDPPERDALLANLALQKPIPDYKVLVEIACMRSPEDMLAARRAYRCLYKHSL
EEDLASRTIGDIRRLLVAMVSAYKYDGEEIDEMLAQSEAAILHDEILGKAVDHEETIRVLSTRSSM
QLSAIFNRYKDIYGTSITKDLLNHPTNEYLSALRAAIRCIKNPTRYYAKVLRNSINTVGTDEDALN
RVIVTRAEKDLTNITGLYFKRNNVSLDQAIAKETSGDYKAFLLALLGHGKQL

SEQ ID NO: 140, NM_001069631.1, Oryza sativa (japonica cultivar-group) Os09g0394900 (Os09g0394900) mRNA, complete cds

GTTGCAGATTACTACCACCACCTCCCCAAAATCCCAATCGAATCGAAATCGAATCGAGTCGAGTCG
CCGCCGGAGCCGGAGACGGAGGCGGCAGCGGCGCAGCGGTAATGGCGAGCCTCACCCTGCCGCCGG
CGCCCACCAACCCTCGCCAGGACGCCATCGACCTCCACAAGGCCTTCAAAGGGTTTGGCTGTGATA
GTACAACAGTTATAAATATACTTACTCATCGTGACTCGATGCAACGCGCGCTCATTCAACAGGAAT
ACAGGACTATGTATTCTGAGGATCTCTCTCGCCGTATATCATCTGAACTCAGTGGACACCACAAGA
AAGCAATGCTGCTATGGATTCTTGATCCTGCTGGACGAGATGCAACTGTTTTGAGAGAAGCTCTGA
GTGGTGATACTATTGACCTGAGAGCAGCCACTGAGATAATATGTTCCAGGACACCATCGCAGCTGC
AAATAATGAAACAGACTTATCATGCAAAATTTGGTACTTATCTTGAGCACGACATTGGTCAGCGCA
CATCAGGCGACCATCAGAAGCTCTTGCTTGCTTATGTGGGGATTCCACGCTATGAAGGTCCTGAGG
TTGATCCTACTATAGTGACACACGATGCAAAGGACCTCTATAAAGCTGGTGAGAAAAGGCTGGGCA
CTGATGAGAAGACCTTCATCCGCATTTTCACTGAACGCAGCTGGGCACACATGGCATCTGTTGCCT
CTGCTTACCATCATATGTATGATCGGTCACTGGAGAAGGTTGTGAAGAGCGAAACATCTGGAAACT
TTGAACTTGCTCTGCTAACTATCCTCAGATGCGCTGAGAATCCAGCCAAGTATTTTGCAAAGGTCT
TGCGGAAGTCCATGAAAGGTATGGGCACTGATGATAGTACACTTATAAGGGTTGTAGTAACAAGGA
CTGAGATCGACATGCAATATATCAAGGCTGAGTACTACAAGAAATACAAAAAATCATTAGCTGAAG
CTATCCATTCCGAGACCTCAGGAAATTATCGAACATTCCTCCTTTCTCTAGTTGGTAGCCATTAGG
CTACATTTCGTCGACCCTGTGGCACTTGACGTTCCATGACTATCCTAAATGCAGTGGTTCTACCTG
GAAACTGTAAAATTTCGCCATCATTGTGCTCTCTATTCGTGTGTGCTTGCTTAAAAATGTGTGTAT
ATATATAACCTGGGCATTAAATAGTTGGTGCTTAATATGGTTTGGTGGTTCCATCTGACAAGTCAC
TCGTTACTCGGTGCATTTATTCGAATAAGTGATGGTATTTGGTC

FIGURE 11 (continued)

SEQ ID NO: 141, NP_001063096.1, Os09g0394900 [Oryza sativa (japonica cultivar-group)]
MASLTLPPAPTNPRQDAIDLHKAFKGFGCDSTTVINILTHRDSMQRALIQQEYRTMYSEDLSRRIS
SELSGHHKKAMLLWILDPAGRDATVLREALSGDTIDLRAATEIICSRTPSQLQIMKQTYHAKFGTY
LEHDIGQRTSGDHQKLLLAYVGIPRYEGPEVDPTIVTHDAKDLYKAGEKRLGTDEKTFIRIFTERS
WAHMASVASAYHHMYDRSLEKVVKSETSGNFELALLTILRCAENPAKYFAKVLRKSMKGMTDDST
LIRVVVTRTEIDMQYIKAEYYKKYKKSLAEAIHSETSGNYRTFLLSLVGSH

SEQ ID NO: 142, NM_001054684.1, Oryza sativa (japonica cultivar-group) Os02g0753800 (Os02g0753800) mRNA, complete cds
CTCCCCGCCGCATAAATCCCCTTCGCCTCCCCGCCGCGCCCCGCGGCGTCGCACGATCTCACTGAG
GCATAAAGTGAGAGACCGTGATTGGATCGATCACCGGAGCGACGATCAATGGCGACGCTCACCGTG
CCCGCCGCCGTGCCGCCCGTCGCCGAGGACTGCGAGCAGCTGCGCAAGGCGTTCAAAGGGTGGGGC
ACGAACGAGAAGCTCATCATCTCCATCCTCGCCCACCGCGACGCGGCGCAGCGCCGGGCGATCCGC
CGCGCCTACGCCGAGGCGTACGGCGAGGAGCTGCTCCGCGCCCTCAACGACGAGATCCACGGCAAA
TTCGAGAGGGCGGTGATCCAGTGGACGCTGGACCCGGCGGAGCGGGACGCGGTGCTGGCGAACGAG
GAGGCGAGGAAGTGGCACCCGGGGGGCCGCGCGCTCGTCGAGATCGCGTGCACGCGCACTCCATCG
CAGCTCTTCGCTGCGAAGCAGGCGTACCACGAGCGCTTCAAGAGGTCGCTCGAGGAGGACGTCGCG
GCGCACATCACCGGCGACTACCGTAAGCTTTTGGTGCCACTTGTGACTGTATATCGCTATGATGGG
CCAGAGGTGAACACATCGTTGGCACATTCTGAAGCCAAAATACTCCATGAGAAGATCCATGACAAG
GCTTACAGTGACGATGAAATCATCAGGATTCTCACCACAAGGAGCAAAGCACAGTTACTAGCAACA
TTCAATAGTTACAATGATCAGTTCGGCCATCCAATCACTAAGGATCTTAAAGCTGATCCTAAGGAC
GAGTTCCTTGGTACACTAAGGGCGATCATAAGATGCTTCACTTGCCCTGACAGATACTTTGAGAAA
GTCATTCGATTGGCTCTAGGAGGAATGGGCACAGACGAGAACTCTCTTACAAGGATCATAACAACT
CGTGCCGAGGTAGACCTGAAGCTGATAAAGGAGGCCTACCAGAAGAGAAACAGTGTCCCATTGGAG
CGAGCTGTTGCTAAAGATACAACCAGAGACTACGAGGATATACTCCTTGCCCTCCTTGGAGCAGAG
TGAGGTGTATATCTGCTCCATCTCGTCTGTCTGATCCTCCTTGTTTGATCGGAAAATAAGATCTGC
ATAGAACTGTGTTCTATTTTGTTGTTTCTGAATGATACAAGTGAGCTAGTCTGCATAGCAGTGCTC
ATATAATAAAATCTGTCCTGCATACTGGTTTGTC

SEQ ID NO: 143, NP_001048149.1, Os02g0753800 [Oryza sativa (japonica cultivar-group)]
MATLTVPAAVPPVAEDCEQLRKAFKGWGTNEKLIISILAHRDAAQRRAIRRAYAEAYGEELLRALN
DEIHGKFERAVIQWTLDPAERDAVLANEEARKWHPGGRALVEIACTRTPSQLFAAKQAYHERFKRS
LEEDVAAHITGDYRKLLVPLVTVYRYDGPEVNTSLAHSEAKILHEKIHDKAYSDDEIIRILTTRSK
AQLLATFNSYNDQFGHPITKDLKADPKDEFLGTLRAIIRCFTCPDRYFEKVIRLALGGMGTDENSL
TRIITTRAEVDLKLIKEAYQKRNSVPLERAVAKDTTRDYEDILLALLGAE

SEQ ID NO: 144, NM_001068374.1, Oryza sativa (japonica cultivar-group) Os08g0425700 (Os08g0425700) mRNA, complete cds
AGCACAGCACAGCACACATCTCGTCCAGTCCATCCATGGCGAGCCTGAGCGTGCCGCCGGTGCCGA
CGGACCCGCGGCGCGACGCGATCGACCTCCACAGGCGTTCAAGGGGTTCGGCTGCGACGCCACGG
CGGTGACCGCCATCCTCGCCCACCGCGACGCCTCCAGCGCGCCCTAATCCGGCGCCACTACGCGG
CGGTCTACCACCAGGACCTCCTCCACCGCCTCGCCGCCGAGCTCTCGGGCCACCACAAGCGCGCCG
TCCTGCTCTGGGTGCTCGACCCGGCGTCCCGCGACGCCGCCGTCCTCACCAGGCGCTCAACGGCG
ACGTCACCGACATGAGGGCGGCCACCGAGGTGGTGTGCTCCAGGACGCCGTCGCAGCTGCTCGTGG
TGAGGCAGGCCTACCTCGCCAGGTTCGGCGGCGGCGGCGGCGGCCTCGAGCACGACGTCGCCG
TCAGGGCGTCCGGCGACCACCAGAGGCTGCTTCTGGCGTACCTGCGCTCGCCGCGGTACGAGGGC FIGURE 11 (continued)

```
CCGAGGTGGTCGACATGGCGGCGGCGGCGCGCGACGCCAGGGAGCTGTACAGGGCCGGCGAGAGGC
GGCTCGGCACCGACGAGAGGACGTTCATCCGCGTCTTCTCCGAGCGCAGCGCCGCCCACATGGCGG
CCGTCGCCGCCGCGTACCACCACATGTACGACCGCTCCCTCGAGAAGGCTGTGAAGAGTGAAACTT
CAGGGAACTTTGGGTTTGGCCTGCTGACAATCCTCAGGTGCGCCGAGAGCCCGGCCAAGTACTTCG
CCAAGGTGCTCCACGAGGCGATGAAGGGGCTGGGCACCAACGACACGACGCTGATCAGGGTGGTGA
CGACGAGGGCGGAGGTGGACATGCAGTACATCAAGGCGGAGTACCACCGGAGCTACAAGCGCTCGC
TCGCCGACGCCGTCCACTCCGAGACCTCCGGCAACTACCGCACCTTCCTCCTCTCCCTCATCGGCC
GCGACCGCTAACGTCGATTGGTTTCGGTCTCTTTGAGCGTGTGTTAAGGGACGCATTTGTTCCATA
GCGCACAAACATGGCAATTATTTATGTGCGTGTGTAGTGGTGTGTTCGAACGTTCGTTTTTCGTGT
AATAAAAAAAATTGAGTTTGCTGTCTTGTG
```

SEQ ID NO: 145, NP_001061839.1, Os08g0425700 [Oryza sativa (japonica cultivar-group)]

```
MASLSVPPVPTDPRRDAIDLHRAFKGFGCDATAVTAILAHRDASQRALIRRHYAAVYHQDLLHRLA
AELSGHHKRAVLLWVLDPASRDAAVLHQALNGDVTDMRAATEVVCSRTPSQLLVVRQAYLARFGGG
GGGGLEHDVAVRASGDHQRLLLAYLRSPRYEGPEVVDMAAAARDARELYRAGERRLGTDERTFIRV
FSERSAAHMAAVAAAYHHMYDRSLEKAVKSETSGNFGFGLLTILRCAESPAKYFAKVLHEAMKGLG
TNDTTLIRVVTTRAEVDMQYIKAEYHRSYKRSLADAVHSETSGNYRTFLLSLIGRDR
```

SEQ ID NO: 146, NM_001063711.1, Oryza sativa (japonica cultivar-group) Os06g0221200 (Os06g0221200) mRNA, complete cds

```
CGGGTCTCCTCTCCTCCCCCGCCGACGCGCACTCGATCCCCCCGCCTCCGCCTCCGCCTCCGCCT
CCGCGTCGCCCATCTCGAGATCCCCCGCATGGCGACGCTCACCGTCCCCTCCGCCGTCCCGCCCGT
CGCCGACGACTGCGACCAGCTCCGCAAGGCCTTCCAAGGGTGGGGCACGAACGAGGCGCTCATCAT
CTCCATCCTGGCCCACCGCGACGCGGCGCAGCGGCGCGCCATCCGCCGCGCCTACGCCGACACCTA
CGGCGAGGAGCTCCTCCGCAGCATCACCGACGAGATCTCCGGCGACTTCGAGAGGGCCGTGATCCT
GTGGACGCTGGACCCGGCGGAGCGCGACGCGGTGCTCGCCAACGAGGTCGCGAGGAAGTGGTACCC
AGGGAGCGGGAGCCGCGTGCTGGTCGAGATCGCGTGCGCGCGCGGCCCCGCGCAGCTGTTCGCGGT
CAGGCAGGCCTACCACGAGCGCTTCAAGCGCTCGCTCGAGGAGGACGTCGCGGCGCACGCCACTGG
TGACTTCCGCAAGCTCTTGGTGCCACTTATAAGTGCTTACCGCTATGAGGGCCGGAAGTCAACAC
AAAGTTGGCACATTCAGAAGCCAAAATTCTGCATGAGAAGATCCAGCATAAGGCATATGGTGATGA
TGAGATCATCAGAATTCTCACTACTAGGAGCAAGGCTCAGTTGATTGCGACATTCAATCGTTACAA
TGATGAATATGGTCACCCAATCAACAAGGATCTCAAGGCTGATCCCAAGGACGAGTTCCTTTCCAC
GCTGCGTGCAATCATCCGCTGCTTCTGTTGCCCTGACAGGTACTTCGAGAAAGTCATCAGGTTGGC
CATCGCAGGCATGGGAACAGACGAGAACTCCCTCACTAGGATCATTACCACTCGTGCCGAGGTGGA
TCTGAAGCTGATCACGGAGGCGTACCAGAAGAGGAACAGTGTCCCGCTGGAGCGTGCGGTCGCAGG
GGACACCTCCGGGGACTACGAGAGGATGCTTCTTGCTCTTCTGGGTCAGGAGCAGTGAGCCATGCC
TATCTTGCCCAGTCACACACTTCATGTGATCATGTCATATCAGAGAATAAACCTGTTATGCAGGGG
ACACAGCCGTGGTGATTATGATGTTGTTTTCCAGTGTACGGTACTGTTTGCTGCAGCTTGCATAA
CAGTGACGATGAAATAAATCATAGTGGAATGCGTTGGCTCATGGGACCTCACTTATTTTGCAACTT
TTTGACAGGTCTTATTTC
```

SEQ ID NO: 147, NP_001057176.1, Os06g0221200 [Oryza sativa (japonica cultivar-group)]

```
MATLTVPSAVPPVADDCDQLRKAFQGWGTNEALIISILAHRDAAQRRAIRRAYADTYGEELLRSIT
DEISGDFERAVILWTLDPAERDAVLANEVARKWYPGSGSRVLVEIACARGPAQLFAVRQAYHERFK
RSLEEDVAAHATGDFRKLLVPLISAYRYEGPEVNTKLAHSEAKILHEKIQHKAYGDDEIIRILTTR
SKAQLIATFNRYNDEYGHPINKDLKADPKDEFLSTLRAIIRCFCPDRYFEKVIRLAIAGMGTDEN
SLTRIITTRAEVDLKLITEAYQKRNSVPLERAVGDTSGDYERMLLALLGQEQ
```

FIGURE 11 (continued)

SEQ ID NO: 148, NM_001069878.1, Oryza sativa (japonica cultivar-group) Os09g0453300 (Os09g0453300) mRNA, complete cds
AGTAATACGCAAGGAATACCTGGATCATACGATACGAATATCTAGAGACAAAACATGATTTGAGTG
ATTGATGATCGAGAAGAAGCTCAAAAGGTCTTGAAAAGTCGAAACGTCCATCACTGAAATTCGGT
TTCATGCCCTCAGATCCCATTGCTGAGTAGGACGCAGATTTTCTTCCTTCCTACCATTTCCTTTCT
CTTGCTTCCTTTTTGGTCATTTGAGATAGCTTTATCCATCCTTTAGCAAAAAGGAAACCAATAGCT
AGCAATACTTGCCATCATATATACCTGGGCAATGGCCGGCCAAGCAAACTCAGTTCTCTACATTGA
ACACTTCAGGTTTGAGTAGACATGGCCTCTCGGTGTCTTGTTACCACAGGTTTTGAGGATGAGTGC
AGAGAGATCCATGATGCGTGCAACCAGCCACGCCGTTTGAGCGTTCTCTTGGCTCATCGGAGCCCA
TCGGAGAGGCAGAAAATCAAGGCGACTTACCGTACAGTGTTCGGCGAAGATCTCGCCGGAGAAGTG
CAGAAAATCCTCATGGTCAACCAGGAAGATGAGCTCTGCAAGCTGCTCTACCTGTGGGTGCTCGAC
CCGTCGGAGCGCGACGCGATCATGGCTCGGGACGCCGTCGAGAATGGCGGCGCCACGGATTACCGG
GTCCTGGTGGAGATCTTCACACGCCGGAAGCAGAACCAGCTCTTCTTCACCAATCAGGCATACCTT
GCCAGGTTCAAGAAGAACCTGGAGCAGGACATGGTCACAGAGCCGTCTCATCCTTACCAGAGGCTA
TTGGTAGCACTTGCAACCTCCCACAAGTCGCACCACGATGAACTTAGTCGGCACATTGCAAAATGT
GACGCCAGGAGGCTCTATGATGCGAAGAACAGCGGCATGGGATCGGTCGACGAGGCTGTCATTCTT
GAGATGTTCAGCAAGAGGAGCATCCCACAGCTCAGGCTAGCATTCTGCAGTTACAAGCACATATAT
GGGCATGACTACACCAAGGCACTGAAGAAAAATGGCTTCGGTGAGTTTGAACAATCTTTGAGGGTT
GTTGTGAAGTGCATCTACAATCCTTCCATGTATTTCTCCAAGCTGCTGCATAGAAGTCTGCAATGC
TCAGCGACCAATAAAAGGTTGGTTACAAGGGCTATTTTGGGCAGTGACGATGTCGATATGGACAAG
ATCAAGTCAGTGTTCAAAAGTAGTTATGGAAAGGACCTTGAGGATTTCATCCTTGAAAGCTTGCCT
GAGAATGATTACAGAGACTTTCTTTTAGGTGCGGCCAAGGGGTCAAGGGCCTCATGAAGTCTGTGG
AGAGAGATCCTTGAATTATCTAGGGAAAGTAAAGGGTGCATATACTGCTTTGCATGTAAGAGCAAA
TTGACCATCAAAAACAGCAGTTTTATGTTATCTGAGAATAGGATTTAGGTGAGAACATCATGCTCA
TTTTGTTTATTTTGGGTGAAAAAAGTTATCAGTTCAACT

SEQ ID NO: 149, NP_001063343.1, Os09g0453300 [Oryza sativa (japonica cultivar-group)]
MASRCLVTTGFEDECREIHDACNQPRRLSVLLAHRSPSERQKIKATYRTVFGEDLAGEVQKILMVN
QEDELCKLLYLWVLDPSERDAIMARDAVENGGATDYRVLVEIFTRRKQNQLFFTNQAYLARFKKNL
EQDMVTEPSHPYQRLLVALATSHKSHHDELSRHIAKCDARRLYDAKNSGMGSVDEAVILEMFSKRS
IPQLRLAFCSYKHIYGHDYTKALKKNGFGEFEQSLRVVVKCIYNPSMYFSKLLHRSLQCSATNKRL
VTRAILGSDDVDMDKIKSVFKSSYGKDLEDFILESLPENDYRDFLLGAAKGSRAS

SEQ ID NO: 150, NM_001061943.1, Oryza sativa (japonica cultivar-group) Os05g0382900 (Os05g0382900) mRNA, complete cds
ATGGAAAAATACCATGAAATACAAATGGAAAAAATAGGGTAGAGCCCAGAGCATTGGATGTGCAGA
TTAAAGCTATACTACTAGCATTCAAGTTTTTTTCAACTCTGCTGCGTAGGAGGCGTGTGTGTGCCA
TGTGTTGCTGGTGCTGCTGCCTGGACTGCATCCATAACATACCTCCACTCAATCTCCTCTTCCTCC
ATTTCTCCCCCATTCTCTCTCCTCCTCAGCTGCTTCTGCAGGTGGAGGAGAAGCAGCAGCAGCAG
CAGCTGTTGCTCCCATGGCTTCCATCTCTGTCCCAAACCCAGCTCCTTCCCCTACAGAGGATGCAG
AGAGCATAAGAAAGGCAGTGCAAGGATGGGGAACGGACGAGAATGCGCTGATCGAGATCCTCGGCC
ACCGGACGGCGGCGCAGCGGGCGGAGATCGCCGTCGCCTACGAGGGCCTCTACGACGAGACCCTCC
TCGACAGGCTCCACTCCGAGCTCTCCGGCGACTTCCGTAGCGCGTTGATGCTGTGGACGATGGACC
CGGCGGCGCGGGACGCCAAGCTGGCCAACGAGGGCCTGAAGAAGAAGAAGAAGGGCGAGCTCCGCC
ACATCTGGGTGCTCGTCGAGGTCGCCTGCGCGTCGTCGCCGGACCACCTCGTCGCCGTCAGGAAGG
CCTACCGCGCCGCCTACGCCTCGTCGCTGGAGGAGGACGTGGCGTCGTGCTCGCTGTTCGGGGACC
CGCTCAGGCGGTTCCTGGTGCGCCTCGTGAGCTCCTACCGGTACGGCGGCGGTGGCGTCGACGGCG AGCTGGCGATCGCCGAGGCGGCGGAGCTGCACGACGCGGTGGTGGGCAGGGGGCAGGCGCTGCACG
GCGACGACGTCGTCCGCATCGTCGGCACGAGGAGCAAGGCGCAGCTCGCGGTGACGCTGGAGCGGT
ACAGGCAGGAGCACGGCAAGGGCATCGACGAGGTCCTCGACGGCCGCCGCGGCGACCAGCTCGCGG
CGGTGCTCAAGGCCGCGCTCTGGTGCCTCACCTCGCCGGAGAAGCATTTCGCTGAGGTGATCCGGA
CATCGATTCTAGGGCTTGGCACCGACGAGGAGATGCTGACGAGAGGGATCGTGTCGCGGGCGGAGG
TGGACATGGAGAAGGTGAAGGAGGAGTACAAGGTCAGGTACAACACCACGGTCACCGCCGACGTCC
GCGGCGACACGTCGGGGTACTACATGAACACGCTTCTCACCCTCGTCGGCCCTGAGAAGTAGCCAT
GTAGCAGCTTGGACATTTTATTGCTTGCTCATTTGATTTGAACAAAATACACCGTGTGATGTTGCA
GTTATTAGTAAAATGCGAGTAGGATCGATGTTGTTTTCGTTGGGTGGATTAATAATGGAGCATGTT
TTATCGC

SEQ ID NO: 151, NP_001055408.1, Os05g0382900 [Oryza sativa (japonica cultivar-group)]
MCCWCCCLDCIHNIPPLNLLFLHFSPHSLSSSAASAGGGEAAAAAAVAPMASISVPNPAPSPTEDA
ESIRKAVQGWGTDENALIEILGHRTAAQRAEIAVAYEGLYDETLLDRLHSELSGDFRSALMLWTMD
PAARDAKLANEALKKKKGELRHIWVLVEVACASSPDHLVAVRKAYRAAYASSLEEDVASCSLFGD
PLRRFLVRLVSSYRYGGGGVDGELAIAEAAELHDAVVGRGQALHGDDVVRIVGTRSKAQLAVTLER
YRQEHGKGIDEVLDGRRGDQLAAVLKAALWCLTSPEKHFAEVIRTSILGLGTDEEMLTRGIVSRAE
VDMEKVKEEYKVRYNTTVTADVRGDTSGYYMNTLLTLVGPEK

SEQ ID NO: 152, NM_001068196.1, Oryza sativa (japonica cultivar-group) Os08g0372900 (Os08g0372900) mRNA, complete cds
GGTCTTTTCCGGCCGCTCCCGGCGCCCGCCGGCCATGTCAACAACAAGCTCGTCAAAAACCGCCAC
GTGCCCTCTCTGCCACGCCGACGTGCTGCTGCCACGGCGGCGGTCAGCCGGCTCCTCGACGCACAG
AAGCCACGACCTCGACGACGGCCCCGCTCCGCCGTCGCCGGAGTCCAGCTGCCGCAGCAACGCCGC
GGTGTGCGGGTGCGCCCGCTGCCGGCGCCCTGATCTGATCAGTCCCGGAACCGGCATGCGGATGAG
GAACAGATTCGGCGATGGCCCCAACAGGATATCAGCCCAGAGTGGAGCATGGCTGTGCCGAGAGCG
CACGGCGGAGACTTGCCGGAGCACAAGTAGCCGGTCCGGCCGCTACCGGCGCCTGCAGCCTGCAGC
GGTCGCCGGAACACGACGCGCCGAACTCATAAAGCGGCTGCAAGAGCTCTGCCACCCAGCAAATAA
CCTTCCAAATTGTTCTGCTTCTTGGCAACCACAGCGACAGCGGCAGAAAACAATTGATCGAATTCC
AGATAGCCTAGATTGTGGGGTGACAATGGAAAGGGGCAAGAACAAGCGTGATGGAAGTGACAATGG
GCTCATCTTCTCTAACCTAATGCACGGTGTTGCTGCCGGCATCTATGGGTATCCTCCTCACCAGGG
ATACACTCAGGCTCAGAGCTACCTACTGCTGCCGGAAGCATATCCACCTCCTCCGTGGACATACCC
TCTTTCTAGTGCTTACCCTCCTCAACCTGTTGGTTACCCTTCAGGTGGCTACCCTCCTGCAGTCTA
CTCTGACTCGTATCTGCACCAAGGTAGCAGAGTTGCGCGGGAGCAATGCCCTCTATCATATTCCAA
TAATGCTGTCACTTGCAGGGAGGATGGGCAAATGAACTGTGAAAATGGAACAGTAAATATGGAGAA
AAGTGCAATGTCCTCAAATAAGATGGCTACTAGTCTACTAAAGAGTTGCGGCAATGTGATGCCATG
CAGAAATATGGAGAGAAGTGGCCCAGCCATGTATAAGGTGGACATGCGCGGCAGTACGAAGCAATT
CTCTATGGGCAGCAAGATGATGATGTGTCTGATTGTGTTTGGATGTCTGATAGCTGCCTTGGATAT
GTTTAGAAATGTTGCACAAAAACAGATGTTTTCTGTCGTTAGTTTACTTTCTTTTGTAGTCGCGAC
CTATGTCTGCTAGGAGTCTCTACATGTACCGTAAAATTGCTCTTTGTGTAATGTGTACTTCTTCAT
CCTGTAAAAATAGAATCCCAATCAAACTATATATGGTTTGTCTGTCGGGCTTTCAATACAATCTGA
GTGTCCTCTCTTTACCTTTGT

SEQ ID NO: 153, NP_001061661.1, Os08g0372900 [Oryza sativa (japonica cultivar-group)]
MSTTSSSKTATCPLCHADVLLPRRRSAGSSTHRSHDLDDGPAPPSPESSCRSNAAVCGCARCRRPD
LISPGTGMRMRNRFGDGPNRISAQSGAWLCRERTAETCRSTSSRSGRYRRLQPAAVAGTRRAELIK
RLQELCHPANNLPNCSASWQPQRQRQKTIDRIPDSLDCGVTMERGKNKRDGSDNGLIFSNLMHGVA
AGIYGYPPHQGYTQAQSYLLLPEAYPPPPWTYPLSSAYPPQPVGYPSGGYPPAVYSDSYLHQGSRV
AREQCPLSYSNNAVTCREDGQMNCENGTVNMEKSAMSSNKMATSLLKSCGNVMPCRNMERSGPAMY
KVDMRGSTKQFSMGSKMMMCLIVFGCLIAALDMFRNVAQKQMFSVVSLLSFVVATYVC

SEQ ID NO: 154, NM_001058246.1, Oryza sativa (japonica cultivar-group) Os03g0819300 (Os03g0819300) mRNA, complete cds
ATAGGTCAACTTGAATCTTGTTCAAAAATTCTTTTCAAGTCTTAGGTAGGTCACTGTTGGTGCCAC
CTTCTTGAGAAGTTTATGATCTGCATGTTCACCTAAGATATCCAGTCAAGTGCTAAAAAGGTCACA
AAAATGGGAGGCAGAAAGGACAATCATGACTCCTCAAATGCCGACAAAGGGTTCCATGGAGCGTAT
CCAAGCGGTTACCCTGGTGCATATCCCCTAATGCAAGGATACCCTAATTCACCTGGACAATATCCG
ACTCCCGGTGGATACCCTAGTGCACCACCGGGACAATACCCACCAGCCGGTGGGTACCCTGGTGCA
CAATATCCACCAAGCGGTTACCCTCCATCACAAGGTGGGTACCCTCCAGGAGCGTATCCACCATCA
GGATATCCACAACAACCAGGCTACCCGCCAGCTGGTTACCCAGGTCATGGCCATGGTCCACCCATG
CAAGGAGGTGGGCATGGTGCAGGCGCATCTGGCTATGGAGCGCTGCTCGCCGGAGGCGCCGCGGTG
GCGGCTGCTGCGGTGGGAGCTCACATGGTACGACCCGGCGGCGGTGGCGGCCACGGGATGTTCGGC
CACCATGGTGGCAAATTCAAGAAAGGAAAGTTCAAGCATGGCAAGTACGGCAAGCACAAGAAGTTT
GGGCGCAAGTGGAAGTGATAAGCAAACTAAATTGCACTGCAGTTTGCCTCCGGTTTCTTGTTTGGT
TGAAGTGCTATAGCATGATGGGATTAAGTGTCCATTTACCATATATATATATATATATATTCATCGAA
ATATAACCATACGAGATCTTATTTTAAAGATAATTGTAATAAATATAATGGTGTAATGGATCACAA
ATTAGAAAAAAGGTTTAGGAGAAAAAACATTTTGAGCTTGCTAACAGAAAATTAAACCCACCATAA
GCAATCAGAATAGGCCACATGTGAATGGCTATATCCGGTTAAATCCGCCGAATCCAATCATCGAAC
TCTTATTTCCCACAAACCAAACTCATCCAGCCTCATGCACCTAACTAATCACATCCATCCTTAGAC
GATGCATGCGTGTGGACATTCTTGCCAAAACCAACAATTAGCCGTGAGAGCCCAAACAACTGAGTA
CTCCAGCCTACGATTGTCAGGATATTTTCTCATCTAACTTATTCTAGTATTAGGAGTTATGAAGAT
ATGAAAAGCCATTTTAGTTCAGAAAATTGTACGATAAATCATGTAACCTGTTTCTGAAATGGAAAT
AAAATATGAGAAAAGATACTA

SEQ ID NO: 155, NP_001051711.1 Os03g0819300 [Oryza sativa (japonica cultivar-group)]
MGGRKDNHDSSNADKGFHGAYPSGYPGAYPLMQGYPNSPGQYPTPGGYPSAPPGQYPPAGGYPGAQ
YPPSGYPPSQGGYPPGAYPPSGYPQQPGYPPAGYPGHGHGPPMQGGGHGAGASGYGALLAGGAAVA
AAAVGAHMVRPGGGGHGMFGHHGGKFKKGKFKHGKYGKHKKFGRKWK

FIGURE 11 (continued)

PLANTS HAVING ENHANCED YIELD-RELATED TRAITS AND A METHOD FOR MAKING THE SAME

RELATED APPLICATIONS

This application is a national stage application (under 35 U.S.C. §371) of PCT/EP2008/056381, filed May 23, 2008, which claims benefit of European Application 07108768.8, filed May 23, 2007; U.S. Provisional Application 60/932,226, filed May 29, 2007, European Application 07110086.1, filed Jun. 12, 2007, and U.S. Provisional Application 60/937,994, filed Jun. 29, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_Listing__14546__00054_US. The size of the text file is 355 KB, and the text file was created on Nov. 4, 2011.

The present invention relates generally to the field of molecular biology and concerns a method for enhancing plant yield-related traits relative to control plants. More specifically, the present invention concerns a method for enhancing yield related traits in plants relative to control plants, by modulating, preferably increasing, expression in the roots of a plant, of a nucleic acid sequence encoding a 2-cysteine peroxiredoxin (2-Cys PRX); or by modulating expression of a nucleic acid encoding an ANN polypeptide in a plant. The present invention also concerns plants having modulated, preferably increased, expression in the roots, of a nucleic acid sequence encoding a 2-Cys PRX, or having modulated expression of a nucleic acid encoding an ANN polypeptide, which plants have enhanced yield-related traits relative to control plants. The invention also provides constructs useful in the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing the above-mentioned factors may therefore contribute to increasing crop yield.

Seed yield is a particularly important trait, since the seeds of many plants are important for human and animal nutrition. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots leaves and stems into the growing seed. The endosperm, in particular, assimilates the metabolic precursors of carbohydrates, oils and proteins and synthesizes them into storage macromolecules to fill out the grain.

Another important trait for many crops is early vigour. Improving early vigour is an important objective of modern rice breeding programs in both temperate and tropical rice cultivars. Long roots are important for proper soil anchorage in water-seeded rice. Where rice is sown directly into flooded fields, and where plants must emerge rapidly through water, longer shoots are associated with vigour. Where drill-seeding is practiced, longer mesocotyls and coleoptiles are important for good seedling emergence. The ability to engineer early vigour into plants would be of great importance in agriculture. For example, poor early vigour has been a limitation to the introduction of maize (Zea mays L.) hybrids based on Corn Belt germplasm in the European Atlantic.

Plant biomass is yield for forage crops like alfalfa, silage corn and hay. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679). In this way a standard environment is used as a proxy for the diverse and dynamic environments encountered at different locations and times by crops in the field.

Harvest index, the ratio of seed yield to aboveground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73). Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

Another trait of importance is that of improved abiotic stress tolerance. Abiotic stress is a primary cause of crop loss worldwide, reducing average yields for most major crop plants by more than 50% (Wang et al. (2003) Planta 218: 1-14). Abiotic stresses may be caused by drought, salinity, extremes of temperature, chemical toxicity, excess or lack of nutrients (macroelements and/or microelements), radiation and oxidative stress. The ability to increase plant tolerance to abiotic stress would be of great economic advantage to farmers worldwide and would allow for the cultivation of crops during adverse conditions and in territories where cultivation of crops may not otherwise be possible.

Crop yield may therefore be increased by optimising one of the above-mentioned factors.

Depending on the end use, the modification of certain yield traits may be favoured over others. For example for applications such as forage or wood production, or bio-fuel resource, an increase in the vegetative parts of a plant may be desirable, and for applications such as flour, starch or oil production, an increase in seed parameters may be particularly desirable. Even amongst the seed parameters, some may be favoured over others, depending on the application. Various mechanisms may contribute to increasing seed yield, whether that is in the form of increased seed size or increased seed number.

One approach to enhance yield-related traits (for example increasing yield, in particular seed yield and/or biomass) in plants may be through modification of the inherent growth mechanisms of a plant, such as the cell cycle or various signalling pathways involved in plant growth or in defense mechanisms.

Surprisingly, it has now been found that various plant yield-related traits may be enhanced relative to control plants, by modulating, preferably increasing, expression in the roots of a plant, of a nucleic acid sequence encoding a 2-cysteine peroxiredoxin (2-Cys PRX), or by modulating expression of a nucleic acid encoding an ANN polypeptide in a plant.

According to one embodiment, there is provided a method for enhancing various yield-related traits relative to control plants, comprising modulating, preferably increasing, expression in the roots of a plant, of a nucleic acid sequence encoding a 2-cysteine peroxiredoxin (2-Cys PRX), or by modulating expression of a nucleic acid encoding an ANN polypeptide, in a plant.

BACKGROUND 1. 2-Cysteine Peroxiredoxin (2-Cys PRX)

Thiol peroxidases (PRX) are ubiquitous heme-free peroxidases, which catalyze the reduction of peroxynitrites and of various peroxides by catalytic cysteine residues and thiol-containing proteins as reductants. In plants, five different classes can be distinguished, according to the number and the position of conserved catalytic cysteines. Four classes are defined as peroxiredoxins and were already identified by phylogenetic sequence analysis, 1-Cys, 2-Cys, type II, and type Q peroxiredoxins, and the fifth is represented by glutathione peroxidases, which were recently shown to possess a thioredoxin-dependent activity in plants (Rouhier & Jacquot (2005) Free Radic Biol Med 38(11): 1413-21). The analysis of the *Arabidopsis thaliana* genome indicates that at least 17 isoforms of thioredoxin-dependent peroxidases are expressed in various plant compartments.

2-Cysteine peroxiredoxin (2-Cys PRX) are a group of proteins that participate in cell proliferation, differentiation, apoptosis, and photosynthesis. These enzymes reduce $H_2O_2$, peroxinitrite and alkyl hydroperoxide to water or alcohol, respectively (Netto et al., (1996) J Biol Chem 271(26): 15315-15321) with thioredoxin (Trx) as electron donor. By doing so, 2-Cys PRXs regulate signal transduction pathways or protect macromolecules against oxidative damage. These proteins are homodimers and each subunit has the two conserved cysteines (Choi et al., (1998) Nature Struct Biol 5:400-406). The peroxide oxidizes the N-terminal cysteine of one subunit to sulphenic acid, which reacts with the C-terminal cysteine of the other subunit to form an intermolecular disulphide. To complete the catalytic cycle the enzyme is reduced via a thiol/disulphide redox interchange (Chae et al., (1994) Proc Natl Acad Sci USA 91: 7017-7021).

Transgenic *Arabidopsis thaliana* plants (Baier et al. (2000) Plant Physiol 124(2): 823-32) with reduced levels of 2-Cys PRX were generated by antisense suppression. The suppression of 2-Cys PRX expression lead to increased expression of other anti-oxidative genes, demonstrating that the enzyme forms an integral part of the anti-oxidant network of chloroplasts and is functionally interconnected with other defense systems.

International patent application WO05/116082 describes the obtention of transgenic *Arabidopsis* plants overexpressing an *Arabidopsis* 2-Cys PRX (named BAS1) using the constitutive cauliflower mosaic virus 35S promoter. The transgenic plants are described as having more potential resistance to heat shock and pathogens than the wild type plants.

Surprisingly, it has now been found that modulating, preferably increasing, expression in the roots of a plant, of a nucleic acid sequence encoding a 2-Cys PRX polypeptide gives plants having enhanced yield-related traits relative to control plants.

According one embodiment, there is provided a method for enhancing yield related traits of a plant relative to control plants, comprising modulating, preferably increasing, expression in the roots of a plant, of a nucleic acid sequence encoding a 2-Cys PRX polypeptide. The enhanced yield related traits comprise one or more of: (i) improved early vigour; (ii) increased aboveground biomass; (iii) increased root (thick and thin) biomass; (iv) increase number of flowers per panicle; (v) increased seed fill rate; (vi) increased total seed yield per plant; (vii) increased number of (filled) seeds; (viii) increased harvest index; or (ix) increased thousand kernel weight (TKW).

2. Annexin-Like (ANN)

Annexins form a family of calcium dependent phospholipid binding proteins and are found in plants and animals. In all plant species tested, the presence of at least two different annexins has been demonstrated. Structurally, plant annexins are less divergent than animal annexins. Comparative studies revealed that plant annexins share significant homology in a core domain which comprises at least one, usually four or more conserved repeats which are approximately 70 amino acids in length. As calcium-binding proteins, annexins are postulated to play a role in calcium signalling pathways. Although the structure of annexins is well known nowadays, functionally they are not well characterised. In plants, annexins are reported to be involved in Golgi-mediated secretion, cell expansion, vacuole biogenesis, chloroplast membrane binding, cell cycle, nodulation signalling, stress signalling.

US20050089872 describes T-DNA insertion mutants (anx1 and anx4-1) for respectively the Annexin 1 and Annexin 4 encoding genes from *Arabidopsis thaliana*. The mutants were sensitive to salt stress and osmotic stress. Also abscisic acid had a negative effect on germination and growth of the anx1 and anx4-1 mutants. Expression analysis revealed that the ANX1 protein was predominantly expressed in the root, but not in flower, stem or leaf tissues. It is postulated that the ANX1 and ANX4 proteins play a role in the transduction of osmotic stress and ABA signals.

Surprisingly, it has now been found that modulating expression of a nucleic acid encoding an ANN polypeptide gives plants having enhanced yield-related traits, in particular increased yield relative to control plants.

According to one embodiment, there is provided a method for enhancing yield-related traits of a plant relative to control plants, comprising modulating expression of a nucleic acid encoding an ANN polypeptide in a plant. The improved yield related traits comprise increased seed yield.

DEFINITIONS

Polypeptide(s)/Protein(s)

The terms "polypeptide" and "protein" are used interchangeably herein and refer to amino acids in a polymeric form of any length, linked together by peptide bonds.

Polynucleotide(s)/Nucleic Acid(s)/Nucleic Acid Sequence(s)/Nucleotide Sequence(s)

The terms "polynucleotide(s)", "nucleic acid sequence(s)", "nucleotide sequence(s)", "nucleic acid(s)", "nucleic acid molecule(s)" are used interchangeably herein and refer to nucleotides, either ribonucleotides or deoxyribonucleotides or a combination of both, in a polymeric unbranched form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. A "control plant" as used herein refers not only to whole plants, but also to plant parts, including seeds and seed parts.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

Orthologue(s)/Paralogue(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acid molecules are in solution. The hybridisation process can also occur with one of the complementary nucleic acid molecules immobilised to a matrix such as magnetic beads, Sepharose beads or any other resin. The hybridisation process can furthermore occur with one of the complementary nucleic acid molecules immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acid molecules.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting 2-Cys PRXnt ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acid sequences may deviate in sequence composition and still encode a substantially identical polypeptide, due to the degeneracy of the genetic code. Therefore medium stringency hybridisation conditions may sometimes be needed to identify such nucleic acid molecules.

The Tm is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA hybrids (Meinkoth and Wahl, Anal. Biochem., 138: 267-284, 1984):

$$T_m = 81.5° C. + 16.6 \times \log_{10}[Na^+]^a + 0.41 \times \%[G/C^b] - 500 \times [L^c]^{-1} - 0.61 \times \% \text{ formamide}$$

[a] or for other monovalent cation, but only accurate in the 0.01-0.4 M range.
[b] only accurate for % GC in the 30% to 75% range.
[c] L=length of duplex in base pairs.

2) DNA-RNA or RNA-RNA hybrids:

$$Tm = 79.8 + 18.5(\log_{10}[Na^+]^a) + 0.58(\%G/C^b) + 11.8(\%G/C^b)^2 - 820/L^c$$

3) oligo-DNA or oligo-RNA[d] hybrids:

[d] oligo, oligonucleotide; $I_n$, =effective length of primer=2×(no. of G/C)+(no. of A/T).

For <20 nucleotides: $T_m = 2 (I_n)$
For 20-35 nucleotides: $T_m = 22 + 1.46 (I_n)$ Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency.

A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid molecule. When nucleic acid molecules of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 µg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3$^{rd}$ Edition, Cold Spring Harbor Laboratory Press, CSH, N.Y. or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex (2005) BMC Bioinformatics 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (IN-DELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acid sequences or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid sequence. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid sequence in a cell, tissue or organ.

A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid sequence must, as described above, be linked operably to or comprise a suitable promoter which expresses the gene at the right moment in time and with the required spatial expression pattern.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid sequence used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500,0000 transcripts per cell. Conversely, a "strong promoter" drives expression of a coding sequence at high level, or at about 1/10 transcripts to about 1/100 transcripts to about 1/1000 transcripts per cell.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table 2a below gives examples of constitutive promoters.

TABLE 2a

Examples of constitutive promoters

| Gene Source | Reference |
| --- | --- |
| Actin | McElroy et al, Plant Cell, 2: 163-171, 1990 |
| HMGB | WO 2004/070039 |
| CAMV 35S | Odell et al, Nature, 313: 810-812, 1985 |
| CaMV 19S | Nilsson et al., Physiol. Plant. 100: 456-462, 1997 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| 34S FMV | Sanger et al., Plant. Mol. Biol., 14, 1990: 433-443 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |
| nos | Shaw et al. (1984) Nucleic Acids Res. 12(20): 7831-7846 |
| V-ATPase | WO 01/14572 |
| Super promoter | WO 95/14098 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

Examples of root-specific promoters are listed in Table 2b below:

TABLE 2b

Examples of root-specific promoters

| Gene Source | Reference |
| --- | --- |
| Rice RCc3 | Xu et al (1995) Plant Mol Biol 27(2): 237-48 |
| *Arabidopsis* phosphate transporter PHT1 | Kovama et al., 2005 |
| *Medicago* phosphate transporter | Xiao et al., 2006 |
| *Arabidopsis* Pyk10 | Nitz et al. (2001) Plant Sci 161(2): 337-346 |
| Tobacco root-specific genes RB7, RD2, RD5, RH12 | Conkling et al. (1990) Plant Phys 93(3): 1203-1211 |
| Barley root-specific lectin | Lerner & Raikhel (1989) Plant Phys 91: 124-129 |
| Root-specific hydroxy-proline rich protein | Keller & Lamb (1989) Genes & Dev 3: 1639-1646 |
| *Arabidopsis* CDC27B/hobbit | Blilou et al. (2002) Genes & Dev 16: 2566-2575 |

A seed-specific promoter is transcriptionally active predominantly in seed tissue, but not necessarily exclusively in seed tissue (in cases of leaky expression). The seed-specific promoter may be active during seed development and/or during germination. The seed specific promoter may be specific to one or more of: endosperm, aleurone, or embryo specific. Examples of seed-specific promoters are shown in Tables 2c, 2d, 2e, 2f below. Further examples of seed-specific promoters are given in Qing Qu and Takaiwa (Plant Biotechnol. J. 2, 113-125, 2004), which disclosure is incorporated by reference herein as if fully set forth.

TABLE 2c

Examples of seed-specific promoters

| Gene source | Reference |
| --- | --- |
| seed-specific genes | Simon et al., Plant Mol. Biol. 5: 191, 1985; Scofield et al., J. Biol. Chem. 262: 12202, 1987.; Baszczynski et al., Plant Mol. Biol. 14: 633, 1990. |
| Brazil Nut albumin | Pearson et al., Plant Mol. Biol. 18: 235-245, 1992. |
| Legumin | Ellis et al., Plant Mol. Biol. 10: 203-214, 1988. |
| glutelin (rice) | Takaiwa et al., Mol. Gen. Genet. 208: 15-22, 1986; Takaiwa et al., FEBS Letts. 221: 43-47, 1987. |
| Zein | Matzke et al Plant Mol Biol, 14(3): 323-32 1990 |
| NapA | Stalberg et al, Planta 199: 515-519, 1996. |
| wheat LMW and HMW glutenin-1 | Mol Gen Genet 216: 81-90, 1989; NAR 17: 461-2, 1989 |
| wheat SPA | Albani et al, Plant Cell, 9: 171-184, 1997 |
| wheat α, β, γ-gliadins | EMBO J. 3: 1409-15, 1984 |
| barley Itr1 promoter | Diaz et al. (1995) Mol Gen Genet 248(5): 592-8 |
| barley B1, C, D, hordein | Theor Appl Gen 98: 1253-62, 1999; Plant J 4: 343-55, 1993; Mol Gen Genet 250: 750-60, 1996 |
| barley DOF | Mena et al, The Plant Journal, 116(1): 53-62, 1998 |
| blz2 | EP99106056.7 |

TABLE 2c-continued

Examples of seed-specific promoters

| Gene source | Reference |
|---|---|
| Synthetic promoter | Vicente-Carbajosa et al., Plant J. 13: 629-640, 1998. |
| rice prolamin NRP33 | Wu et al, Plant Cell Physiology 39(8) 885-889, 1998 |
| rice a-globulin Glb-1 | Wu et al, Plant Cell Physiology 39(8) 885-889, 1998 |
| rice OSH1 | Sato et al, Proc. Natl. Acad. Sci. USA, 93: 8117-8122, 1996 |
| rice α-globulin REB/OHP-1 | Nakase et al. Plant Mol. Biol. 33: 513-522, 1997 |
| rice ADP-glucose pyrophosphorylase | Trans Res 6: 157-68, 1997 |
| maize ESR gene family | Plant J 12: 235-46, 1997 |
| *Sorghum* α-kafirin | DeRose et al., Plant Mol. Biol 32: 1029-35, 1996 |
| KNOX | Postma-Haarsma et al, Plant Mol. Biol. 39: 257-71, 1999 |
| rice oleosin | Wu et al, J. Biochem. 123: 386, 1998 |
| sunflower oleosin | Cummins et al., Plant Mol. Biol. 19: 873-876, 1992 |
| PRO0117, putative rice 40S ribosomal protein | WO 2004/070039 |
| PRO0136, rice alanine aminotransferase | unpublished |
| PRO0147, trypsin inhibitor ITR1 (barley) | Unpublished |
| PRO0151, rice WSI18 | WO 2004/070039 |
| PRO0175, rice RAB21 | WO 2004/070039 |
| PRO005 | WO 2004/070039 |
| PRO0095 | WO 2004/070039 |
| α-amylase (Amy32b) | Lanahan et al, Plant Cell 4: 203-211, 1992; Skriver et al, Proc Natl Acad Sci USA 88: 7266-7270, 1991 |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

TABLE 2d examples of endosperm-specific promoters

| Gene source | Reference |
|---|---|
| glutelin (rice) | Takaiwa et al. (1986) Mol Gen Genet 208: 15-22; Takaiwa et al. (1987) FEBS Letts. 221: 43-47 |
| Zein | Matzke et al., (1990) Plant Mol Biol 14(3): 323-32 |
| wheat LMW and HMW glutenin-1 | Colot et al. (1989) Mol Gen Genet 216: 81-90; Anderson et al. (1989) NAR 17: 461-2 |
| wheat SPA | Albani et al. (1997) Plant Cell 9: 171-184 |
| wheat gliadins | Rafalski et al. (1984) EMBO 3: 1409-15 |
| barley Itr1 promoter | Diaz et al. (1995) Mol Gen Genet 248(5): 592-8 |
| barley B1, C, D, hordein | Cho et al. (1999) Theor Appl Genet 98: 1253-62; Muller et al. (1993) Plant J 4: 343-55; Sorenson et al. (1996) Mol Gen Genet 250: 750-60 |
| barley DOF | Mena et al, (1998) Plant J 116(1): 53-62 |
| blz2 | Onate et al. (1999) J Biol Chem 274(14): 9175-82 |
| synthetic promoter | Vicente-Carbajosa et al. (1998) Plant J 13: 629-640 |
| rice prolamin NRP33 | Wu et al, (1998) Plant Cell Physiol 39(8) 885-889 |
| rice globulin Glb-1 | Wu et al. (1998) Plant Cell Physiol 39(8) 885-889 |
| rice globulin REB/OHP-1 | Nakase et al. (1997) Plant Molec Biol 33: 513-522 |
| rice ADP-glucose pyrophosphorylase | Russell et al. (1997) Trans Res 6: 157-68 |
| maize ESR gene family | Opsahl-Ferstad et al. (1997) Plant J 12: 235-46 |
| *Sorghum kafirin* | DeRose et al. (1996) Plant Mol Biol 32: 1029-35 |

TABLE 2e

Examples of embryo specific promoters:

| Gene source | Reference |
|---|---|
| KNOX | Postma-Haarsma et al, Plant Mol. Biol. 39: 257-71, 1999 |
| PRO0151 | WO 2004/070039 |
| PRO0175 | WO 2004/070039 |
| PRO005 | WO 2004/070039 |
| PRO0095 | WO 2004/070039 |

TABLE 2f

Examples of aleurone-specific promoters:

| Gene source | Reference |
|---|---|
| α-amylase (Amy32b) | Lanahan et al, Plant Cell 4: 203-211, 1992; Skriver et al, Proc Natl Acad Sci USA 88: 7266-7270, 1991 |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

A green tissue-specific promoter as defined herein is a promoter that is transcriptionally active predominantly in green tissue, substantially to the exclusion of any other parts of a plant, whilst still allowing for any leaky expression in these other plant parts.

Examples of green tissue-specific promoters which may be used to perform the methods of the invention are shown in Table 2g below.

TABLE 2g

Examples of green tissue-specific promoters

| Gene | Expression | Reference |
| --- | --- | --- |
| Maize Orthophosphate dikinase | Leaf specific | Fukayama et al., 2001 |
| Maize Phosphoenolpyruvate carboxylase | Leaf specific | Kausch et al., 2001 |
| Rice Phosphoenolpyruvate carboxylase | Leaf specific | Liu et al., 2003 |
| Rice small subunit Rubisco | Leaf specific | Nomura et al., 2000 |
| rice beta expansin EXBP9 | Shoot specific | WO 2004/070039 |
| Pigeonpea small subunit Rubisco | Leaf specific | Panguluri et al., 2005 |
| Pea RBCS3A | Leaf specific | |

Another example of a tissue-specific promoter is a meristem-specific promoter, which is transcriptionally active predominantly in meristematic tissue, substantially to the exclusion of any other parts of a plant, whilst still allowing for any leaky expression in these other plant parts. Examples of green meristem-specific promoters which may be used to perform the methods of the invention are shown in Table 2h below.

TABLE 2h

Examples of meristem-specific promoters

| Gene source | Expression pattern | Reference |
| --- | --- | --- |
| rice OSH1 | Shoot apical meristem, from embryo globular stage to seedling stage | Sato et al. (1996) Proc. Natl. Acad. Sci. USA, 93: 8117-8122 |
| Rice metallothionein | Meristem specific | BAD87835.1 |
| WAK1 & WAK 2 | Shoot and root apical meristems, and in expanding leaves and sepals | Wagner & Kohorn (2001) Plant Cell 13(2): 303-318 |

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Modulation

The term "modulation" means in relation to expression or gene expression, a process in which the expression level is changed by said gene expression in comparison to the control plant, preferably the expression level is increased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to enhanced yield-related traits (for example, increased yield and/or increased growth) of the plants.

Increased Expression/Overexpression

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acid sequences which serve as promoter or enhancer elements may be introduced in an appropriate position (typically upstream) of a non-heterologous form of a polynucleotide so as to upregulate expression of a nucleic acid sequence encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell. biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Endogenous Gene

Reference herein to an "endogenous" gene not only refers to the gene in question as found in a plant in its natural form (i.e., without there being any human intervention), but also refers to that same gene (or a substantially homologous gene/nucleic acid sequence) in an isolated form subsequently (re) introduced into a plant (a transgene). For example, a transgenic plant containing such a transgene may encounter a substantial reduction of the transgene expression and/or substantial reduction of expression of the endogenous gene. The isolated gene may be isolated from an organism or may be manmade, for example by chemical synthesis.

Decreased Expression

Reference herein to "decreased expression" or "reduction or substantial elimination" of expression is taken to mean a decrease in endogenous gene expression and/or polypeptide levels and/or polypeptide activity relative to control plants. The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control plants.

For the reduction or substantial elimination of expression an endogenous gene in a plant, a sufficient length of substantially contiguous nucleotides of a nucleic acid sequence is required. In order to perform gene silencing, this may be as little as 20, 19, 18, 17, 16, 15, 14, 13, 12, 11, 10 or fewer nucleotides, alternatively this may be as much as the entire gene (including the 5' and/or 3' UTR, either in part or in whole). The stretch of substantially contiguous nucleotides may be derived from the nucleic acid sequence encoding the protein of interest (target gene), or from any nucleic acid sequence capable of encoding an orthologue, paralogue or homologue of the protein of interest. Preferably, the stretch of substantially contiguous nucleotides is capable of forming hydrogen bonds with the target gene (either sense or antisense strand), more preferably, the stretch of substantially contiguous nucleotides has, in increasing order of preference, 50%, 60%, 70%, 80%, 85%, 90%, 95%, 96%, 97%, 98%, 99%, 100% sequence identity to the target gene (either sense or antisense strand). A nucleic acid sequence encoding a (functional) polypeptide is not a requirement for the various methods discussed herein for the reduction or substantial elimination of expression of an endogenous gene.

This reduction or substantial elimination of expression may be achieved using routine tools and techniques. A method for the reduction or substantial elimination of endogenous gene expression is by RNA-mediated silencing using an inverted repeat of a nucleic acid sequence or a part thereof (in this case a stretch of substantially contiguous nucleotides derived from the gene of interest, or from any nucleic acid sequence capable of encoding an orthologue, paralogue or homologue of the protein of interest), preferably capable of forming a hairpin structure. Another example of an RNA silencing method involves the introduction of nucleic acid sequences or parts thereof (in this case a stretch of substantially contiguous nucleotides derived from the gene of interest, or from any nucleic acid sequence capable of encoding an orthologue, paralogue or homologue of the protein of interest) in a sense orientation into a plant. Another example of an RNA silencing method involves the use of antisense nucleic acid sequences. Gene silencing may also be achieved by insertion mutagenesis (for example, T-DNA insertion or transposon insertion) or by strategies as described by, among others, Angell and Baulcombe ((1999) Plant J 20(3): 357-62), (Amplicon VIGS WO 98/36083), or Baulcombe (WO 99/15682). Other methods, such as the use of antibodies directed to an endogenous polypeptide for inhibiting its function in planta, or interference in the signalling pathway in which a polypeptide is involved, will be well known to the skilled man. Artificial and/or natural microRNAs (miRNAs) may be used to knock out gene expression and/or mRNA translation. Endogenous miRNAs are single stranded small RNAs of typically 19-24 nucleotides long. Artificial microRNAs (amiRNAs), which are typically 21 nucleotides in length, can be genetically engineered specifically to negatively regulate gene expression of single or multiple genes of interest. Determinants of plant microRNA target selection are well known in the art. Empirical parameters for target recognition have been defined and can be used to aid in the design of specific amiRNAs (Schwab et al., (2005) Dev Cell 8(4): 517-27). Convenient tools for design and generation of amiRNAs and their precursors are also available to the public (Schwab et al., (2006) Plant Cell 18(5):1121-33).

For optimal performance, the gene silencing techniques used for reducing expression in a plant of an endogenous gene requires the use of nucleic acid sequences from monocotyledonous plants for transformation of monocotyledonous plants, and from dicotyledonous plants for transformation of dicotyledonous plants. Preferably, a nucleic acid sequence from any given plant species is introduced into that same species. For example, a nucleic acid sequence from rice is transformed into a rice plant. However, it is not an absolute requirement that the nucleic acid sequence to be introduced originates from the same plant species as the plant in which it will be introduced. It is sufficient that there is substantial homology between the endogenous target gene and the nucleic acid sequence to be introduced.

Described above are examples of various methods for the reduction or substantial elimination of expression in a plant of an endogenous gene. A person skilled in the art would readily be able to adapt the aforementioned methods for silencing so as to achieve reduction of expression of an endogenous gene in a whole plant or in parts thereof through the use of an appropriate promoter, for example.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acid sequences into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid sequence can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acid sequences have been introduced successfully, the process according to the invention for introducing the nucleic acid sequences advantageously employs techniques which enable the removal or excision of these marker genes. One such a method is what is known as co-transformation. The co-transformation method employs two vectors simultaneously for the transformation, one vector bearing the nucleic acid sequence according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid sequence (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either
 (a) the nucleic acid sequences encoding proteins useful in the methods of the invention, or
 (b) genetic control sequence(s) which is operably linked with the nucleic acid sequence according to the invention, for example a promoter, or
 (c) a) and b)
are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acid sequences used in the method of the invention are not at their natural locus in the genome of said plant, it being possible for the nucleic acid sequences to be expressed homologously or heterologously. However, as mentioned, transgenic also means that, while the nucleic acid sequences according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acid sequences according to the invention at an unnatural locus in the genome, i.e. homologous or, preferably, heterologous expression of the nucleic acid sequences takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen. Genet. 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acid sequences or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later moment in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

T-DNA Activation Tagging

T-DNA activation tagging (Hayashi et al. Science (1992) 1350-1353), involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

TILLING

The term "TILLING" is an abbreviation of "Targeted Induced Local Lesions In Genomes" and refers to a mutagenesis technology useful to generate and/or identify nucleic acid sequences encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods in Molecular Biology, Vol. 82. Humana Press, Totowa, N.J., pp 91-104); (b) DNA preparation and pooling of individuals; (c)

PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous Recombination

Homologous recombination allows introduction in a genome of a selected nucleic acid sequence at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; lida and Terada (2004) Curr Opin Biotech 15(2): 132-8); Terada et al., (2007) Plant Physiol).

Yield

The term "yield" in general means a measurable produce of economic value, typically related to a specified crop, to an area, and to a period of time. Individual plant parts directly contribute to yield based on their number, size and/or weight, or the actual yield is the yield per acre for a crop and year, which is determined by dividing total production (includes both harvested and appraised production) by planted acres. The term "yield" of a plant may relate to vegetative biomass (root and/or shoot biomass), to reproductive organs, and/or to propagules (such as seeds) of that plant.

Early Vigour

"Early vigour" refers to active healthy well-balanced growth especially during early stages of plant growth, and may result from increased plant fitness due to, for example, the plants being better adapted to their environment (i.e. optimizing the use of energy resources and partitioning between shoot and root). Plants having early vigour also show increased seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

Increase/Improve/Enhance

The terms "increase", "improve" or "enhance" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased yield may also result in modified architecture, or may occur because of modified architecture.

Greenness Index

The "greenness index" as used herein is calculated from digital images of plants. For each pixel belonging to the plant object on the image, the ratio of the green value versus the red value (in the RGB model for encoding color) is calculated. The greenness index is expressed as the percentage of pixels for which the green-to-red ratio exceeds a given threshold. Under normal growth conditions, under salt stress growth conditions, and under reduced nutrient availability growth conditions, the greenness index of plants is measured in the last imaging before flowering. In contrast, under drought stress growth conditions, the greenness index of plants is measured in the first imaging after drought.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid sequence of interest. The term "plant" also encompasses plant cells, suspension cultures, callus tissue, embryos, meristematic regions, gametophytes, sporophytes, pollen and microspores, again wherein each of the aforementioned comprises the gene/nucleic acid sequence of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria*, *Ananas comosus*, *Annona* spp., *Apium graveolens*, *Arachis* spp, *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Bambusa* sp., *Benincasa hispida*, *Bertholletia excelsea*, *Beta vulgaris*, *Brassica* spp. (e.g. *Brassica napus*, *Brassica rapa* ssp. [canola, oilseed rape, turnip rape]), *Cadaba farinosa*, *Camellia sinensis*, *Canna indica*, *Cannabis sativa*, *Capsicum* spp., *Carex elata*, *Carica papaya*, *Carissa macrocarpa*, *Carya* spp., *Carthamus tinctorius*, *Castanea* spp., *Ceiba pentandra*, *Cichorium endivia*, *Cinnamomum* spp., *Citrullus lanatus*, *Citrus* spp., *Cocos* spp., *Coffea* spp., *Colocasia esculenta*, *Cola* spp., *Corchorus* sp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g. *Elaeis guineensis*, *Elaeis oleifera*), *Eleusine coracana*, *Erianthus* sp., *Eriobotrya japonica*, *Eucalyptus* sp., *Eugenia uniflora*, *Fagopyrum* spp., *Fagus* spp., *Festuca arundinacea*, *Ficus carica*, *Fortunella* spp., *Fragaria* spp., *Ginkgo biloba*, *Glycine* spp. (e.g. *Glycine max*, *Soja hispida* or *Soja max*), *Gossypium hirsutum*, *Helianthus* spp. (e.g. *Helianthus annuus*), *Hemerocallis fulva*, *Hibiscus* spp., *Hordeum* spp. (e.g. *Hordeum vulgare*), *Ipomoea batatas*, *Juglans* spp., *Lactuca sativa*, *Lathyrus* spp., *Lens culinaris*, *Linum usitatissimum*, *Litchi chinensis*, *Lotus* spp., *Luffa acutangula*, *Lupinus* spp.,

*Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Triticosecale rimpaui, Triticale* (*Triticum secale*), *Triticum* spp. (e.g. *Triticum aestivum, Triticum durum, Triticum turgidum, Triticum hybernum, Triticum macha, Triticum sativum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

DETAILED DESCRIPTION OF THE INVENTION 1. 2-Cysteine Peroxiredoxin (2-Cys PRX)

Surprisingly, it has now been found that modulating, preferably increasing, expression in the roots of a plant, of a nucleic acid sequence encoding a 2-Cys PRX polypeptide gives plants having enhanced yield-related traits relative to control plants. According to a first embodiment, the present invention provides a method for enhancing yield-related traits in plants relative to control plants, comprising modulating, preferably increasing, expression in the roots of a plant, of a nucleic acid sequence encoding a 2-Cys PRX polypeptide.

A preferred method for modulating, preferably increasing, expression of a nucleic acid sequence encoding a 2-Cys PRX polypeptide is by introducing and expressing in the roots of a plant, a nucleic acid sequence encoding a 2-Cys PRX polypeptide.

Any reference hereinafter to a "protein useful in the methods of the invention" is taken to mean a 2-Cys PRX polypeptide as defined herein. Any reference hereinafter to a "nucleic acid sequence useful in the methods of the invention" is taken to mean a nucleic acid sequence capable of encoding such a 2-Cys PRX polypeptide. The nucleic acid sequence to be introduced into a plant (and therefore useful in performing the methods of the invention) is any nucleic acid sequence encoding the type of polypeptide, which will now be described, hereafter also named "2-Cys PRX nucleic acid sequence" or "2-Cys PRX gene".

A "2-Cys PRX polypeptide" as defined herein refers to any polypeptide comprising from N-terminus to C-terminus: (1) a plastidic transit peptide; and (2) a 2-Cys PRX conserved domain.

Additionally, a "2-Cys PRX polypeptide" comprises one or both of: (i) Motif1 as represented by SEQ ID NO: 77, or a motif having at least 50%, 55%, 60%, 65%, 70%, 75%, 80%, 85%, 90%, 95%, 98%, 99% or more amino acid sequence identity to SEQ ID NO: 77; or (ii) Motif 2 as represented by SEQ ID NO: 78, or a motif having at least 50%, 55%, 60%, 65%, 70%, 75%, 80%, 85%, 90%, 95%, 98%, 99% or more amino acid sequence identity to SEQ ID NO: 78.

Alternatively or additionally, a "2-Cys PRX polypeptide" as defined herein refers to any polypeptide sequence which when used in the construction of a phylogenetic tree, such as the one depicted in FIG. 3, tends to cluster with the 2-Cys PRX clade of polypeptides comprising the polypeptide sequence as represented by SEQ ID NO: 2, rather than with any other PRX clade.

Alternatively or additionally, a "2-Cys PRX polypeptide" as defined herein refers to any polypeptide having in increasing order of preference at least 35%, 40%, 45%, 50%, 55%, 60%, 65%, 70%, 75%, 80%, 85%, 90%, 95%, 98%, 99% or more sequence identity to the 2-Cys PRX polypeptide as represented by SEQ ID NO: 2 or to any of the polypeptide sequences given in Table A1 herein.

The term "domain" and "motif" is defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244, InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004), or Pfam (Bateman et al., Nucleic Acids Research 30(1): 276-280 (2002). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains may also be identified using routine techniques, such as by sequence alignment. Analysis of the polypeptide sequence of SEQ ID NO: 2 is presented below in Examples 2 and 4.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values, which are indicated below in Example 3 as a percentage were determined over the entire nucleic acid sequence or polypeptide sequence (Table A2 herein), but may also be determined over selected domains or conserved motif(s) (such as Motif 1 as represented by SEQ ID NO: 77, and such as Motif 2 as represented by SEQ ID NO: 78, both Motif1 and Motif2 comprised in SEQ ID NO: 2), using the programs mentioned above using the default parameters.

The task of protein subcellular localisation prediction is important and well studied. Knowing a protein's localisation helps elucidate its function. Experimental methods for protein localization range from immunolocalization to tagging of proteins using green fluorescent protein (GFP). Such methods are accurate although labor-intensive compared with computational methods. Recently much progress has been made in computational prediction of protein localisation from sequence data. Among algorithms well known to a person skilled in the art are available at the ExPASy Proteomics tools hosted by the Swiss Institute for Bioinformatics, for example, PSort, TargetP, ChloroP, Predotar, LipoP, MITOPROT, PATS, PTS1, SignalP and others. The identification of subcellular localisation of the polypeptide of the invention is shown in Example 5. In particular SEQ ID NO: 2 of the present invention is assigned to the plastidic (chloroplastic) compartment of photosynthetic (autotrophic) cells.

Methods for targeting proteins to plastids are well known in the art and include the use of transit peptides. Table 3 below shows examples of transit peptides which can be used to target any 2-Cys PRX polypeptide to a plastid, which 2-Cys PRX polypeptide is not, in its natural form, normally targeted to a plastid, or which 2-Cys PRX polypeptide in its natural form is targeted to a plastid by virtue of a different transit peptide (for example, its natural transit peptide). For example, a nucleic acid sequence encoding a cyanobacterial 2-Cys PRX polypeptide may also be suitable for use in the methods of the invention as long as the 2-Cys PRX polypeptide is targeted to a plastid, preferably to a chloroplast.

The present invention is illustrated by transforming plants with the nucleic acid sequence represented by SEQ ID NO: 1, encoding the polypeptide sequence of SEQ ID NO: 2. However, performance of the invention is not restricted to these sequences; the methods of the invention may advantageously be performed using any 2-Cys PRX-encoding nucleic acid sequence or 2-Cys PRX polypeptide sequence as defined herein.

Examples of nucleic acid sequences encoding 2-Cys PRX polypeptides are given in Table A1 of Example 1 herein. Such nucleic acid sequences are useful in performing the methods of the invention. The polypeptide sequences given in Table A1 of Example 1 are example sequences of orthologues and paralogues of the 2-Cys PRX polypeptide represented by SEQ ID NO: 2, the terms "orthologues" and "paralogues" being as defined herein. Further orthologues and paralogues may readily be identified by performing a so-called reciprocal blast search. Typically, this involves a first BLAST involving BLASTing a query sequence (for example using any of the sequences listed in Table A1 of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence.

The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against *Brassica* sequences). The results of the first and second BLASTs are then compared. A paralogue is identified if a high-ranking hit from the first blast is from the same species as from which the query sequence is derived, a BLAST back

TABLE 3

Examples of transit peptide sequences useful in targeting polypeptides to plastids

| NCBI Accession Number | Source Organism | Protein Function | Transit Peptide Sequence | SEQ ID NO: |
|---|---|---|---|---|
| P07839 | *Chlamydomonas* | Ferredoxin | MAMAMRSTFAARVGAKPAVRGARPASRMSCMA | 156 |
| AAR23425 | *Chlamydomonas* | Rubisco activase | MQVTMKSSAVSGQRVGGARVATRSVRRAQLQV | 157 |
| CAA56932 | *Arabidopsis thaliana* | Aspartate amino transferase | MASLMLSLGSTSLLPREINKDKLKLGT-SASNPFLKAK SFSRVTMTVAVKPSR | 158 |
| CAA31991 | *Arabidopsis thaliana* | Acyl carrier protein1 | MATQFSASVSLQTSCLATTRISFQKPAL-ISNHGKTNL SFNLRRSIPSRRLSVSC | 159 |
| CAB63798 | *Arabidopsis thaliana* | Acyl carrier protein2 | MASIAASASISLQARPRQLAIAASQVKS-FSNGRRSSL SFNLRQLPTRLTVSCAAKPETVDKVCAVVRKQL | 160 |
| CAB63799 | *Arabidopsis thaliana* | Acyl carrier protein3 | MASIATSASTSLQARPRQLVIGAKQVKS-FSYGSRSNL SFNLRQLPTRLTVYCAAKPETVDKVCAV-VRKQLSLKE | 161 |

A 2-Cys PRX polypeptide is targeted and active in the plastid, i.e., the 2-Cys PRX polypeptide (at least in its native form) is capable of catalyzing the removal of $H_2O_2$, in the chloroplast. Assays for testing this activity are well known in the art. Further details are provided in Example 6.

then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues (see FIG. 3).

Nucleic acid variants may also be useful in practising the methods of the invention. Examples of such variants include nucleic acid sequences encoding homologues and derivatives of any one of the polypeptide sequences given in Table A1 of Example 1, the terms "homologue" and "derivative" being as defined herein. Also useful in the methods of the invention are nucleic acid sequences encoding homologues and derivatives of orthologues or paralogues of any one of the polypeptide sequences given in Table A1 of Example 1. Homologues and derivatives useful in the methods of the present invention have substantially the same biological and functional activity as the unmodified protein from which they are derived.

Further nucleic acid variants useful in practising the methods of the invention include portions of nucleic acid sequences encoding 2-Cys PRX polypeptides, nucleic acid sequences hybridising to nucleic acid sequences encoding 2-Cys PRX polypeptides, splice variants of nucleic acid sequences encoding 2-Cys PRX polypeptides, allelic variants of nucleic acid sequences encoding 2-Cys PRX polypeptides and variants of nucleic acid sequences encoding 2-Cys PRX polypeptides obtained by gene shuffling. The terms hybridising sequence, splice variant, allelic variant and gene shuffling are as described herein.

Nucleic acid sequences encoding 2-Cys PRX polypeptides need not be full-length nucleic acid sequences, since performance of the methods of the invention does not rely on the use of full-length nucleic acid sequences. According to the present invention, there is provided a method for enhancing yield-related traits in plants, comprising introducing and expressing in the roots of a plant, a portion of any one of the nucleic acid sequences given in Table A1 of Example 1, or a portion of a nucleic acid sequence encoding an orthologue, paralogue or homologue of any of the polypeptide sequences given in Table A1 of Example 1.

A portion of a nucleic acid sequence may be prepared, for example, by making one or more deletions to the nucleic acid sequence. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode a 2-Cys PRX polypeptide as defined herein, and have substantially the same biological activity as the polypeptide sequences given in Table A1 of Example 1. Preferably, the portion is a portion of any one of the nucleic acid sequences given in Table A1 of Example 1, or is a portion of a nucleic acid sequence encoding an orthologue or paralogue of any one of the polypeptide sequences given in Table A1 of Example 1. Preferably the portion is at least 500, 550, 600, 650, 700, 750, 800, consecutive nucleotides in length, the consecutive nucleotides being of any one of the nucleic acid sequences given in Table A1 of Example 1, or of a nucleic acid sequence encoding an orthologue or paralogue of any one of the polypeptide sequences given in Table A1 of Example 1. Most preferably the portion is a portion of the nucleic acid sequence of SEQ ID NO: 1. Preferably, the portion encodes a polypeptide sequence which when used in the construction of a phylogenetic tree, such as the one depicted in FIG. 3, tends to cluster with the group of 2-Cys PRX polypeptides comprising the polypeptide sequence represented by SEQ ID NO: 2 rather than with any other group.

Another nucleic acid variant useful in the methods of the invention is a nucleic acid sequence capable of hybridising, under reduced stringency conditions, preferably under stringent conditions, with a nucleic acid sequence encoding a 2-Cys PRX polypeptide as defined herein, or with a portion as defined herein.

According to the present invention, there is provided a method for enhancing yield-related traits in plants, comprising introducing and expressing in the roots of a plant, a nucleic acid sequence capable of hybridizing to any one of the nucleic acid sequences given in Table A1 of Example 1, or comprising introducing and expressing in the roots of a plant, a nucleic acid sequence capable of hybridising to a nucleic acid sequence encoding an orthologue, paralogue or homologue of any of the nucleic acid sequences given in Table A1 of Example 1.

Hybridising sequences useful in the methods of the invention encode a 2-Cys PRX polypeptide as defined herein, having substantially the same biological activity as the polypeptide sequences given in Table A1 of Example 1. Preferably, the hybridising sequence is capable of hybridising to any one of the nucleic acid sequences given in Table A1 of Example 1, or to a portion of any of these sequences, a portion being as defined above, or the hybridising sequence is capable of hybridising to a nucleic acid sequence encoding an orthologue or paralogue of any one of the polypeptide sequences given in Table A1 of Example 1. Most preferably, the hybridising sequence is capable of hybridising to a nucleic acid sequence as represented by SEQ ID NO: 1 or to a portion thereof.

Preferably, the hybridising sequence encodes a polypeptide sequence which when used in the construction of a phylogenetic tree, such as the one depicted in FIG. 3, tends to cluster with the group of 2-Cys PRX polypeptides comprising the polypeptide sequence represented by SEQ ID NO: 2 rather than with any other group.

Another nucleic acid variant useful in the methods of the invention is a splice variant encoding a 2-Cys PRX polypeptide as defined hereinabove, a splice variant being as defined herein.

According to the present invention, there is provided a method for enhancing yield-related traits in plants, comprising introducing and expressing in the roots of a plant, a splice variant of any one of the nucleic acid sequences given in Table A1 of Example 1, or a splice variant of a nucleic acid sequence encoding an orthologue, paralogue or homologue of any of the polypeptide sequences given in Table A1 of Example 1.

Preferred splice variants are splice variants of a nucleic acid sequence represented by SEQ ID NO: 1, or a splice variant of a nucleic acid sequence encoding an orthologue or paralogue of SEQ ID NO: 2. Preferably, the polypeptide sequence encoded by the splice variant, when used in the construction of a phylogenetic tree, such as the one depicted in FIG. 3, tends to cluster with the group of 2-Cys PRX polypeptides comprising the polypeptide sequence represented by SEQ ID NO: 2 rather than with any other group.

Another nucleic acid variant useful in performing the methods of the invention is an allelic variant of a nucleic acid sequence encoding a 2-Cys PRX polypeptide as defined hereinabove, an allelic variant being as defined herein.

According to the present invention, there is provided a method for enhancing yield-related traits in plants, comprising introducing and expressing in the roots of a plant, an allelic variant of any one of the nucleic acid sequences given in Table A1 of Example 1, or comprising introducing and expressing in the roots of a plant, an allelic variant of a nucleic acid sequence encoding an orthologue, paralogue or homologue of any of the polypeptide sequences given in Table A1 of Example 1.

The allelic variants useful in the methods of the present invention have substantially the same biological activity as the 2-Cys PRX polypeptide of SEQ ID NO: 2 and any of the polypeptide sequences depicted in Table A1 of Example 1. Allelic variants exist in nature, and encompassed within the methods of the present invention is the use of these natural alleles. Preferably, the allelic variant is an allelic variant of SEQ ID NO: 1 or an allelic variant of a nucleic acid sequence encoding an orthologue or paralogue of SEQ ID NO: 2. Preferably, the polypeptide sequence encoded by the allelic variant, when used in the construction of a phylogenetic tree, such as the one depicted in FIG. 3, tends to cluster with the 2-Cys PRX polypeptides comprising the polypeptide sequence represented by SEQ ID NO: 2 rather than with any other group.

Gene shuffling or directed evolution may also be used to generate variants of nucleic acid sequences encoding 2-Cys PRX polypeptides as defined above; the term "gene shuffling" being as defined herein.

According to the present invention, there is provided a method for enhancing yield-related traits in plants, comprising introducing and expressing in the roots of a plant, a variant of any one of the nucleic acid sequences given in Table A1 of Example 1, or comprising introducing and expressing in the roots of a plant, a variant of a nucleic acid sequence encoding an orthologue, paralogue or homologue of any of the polypeptide sequences given in Table A1 of Example 1, which variant nucleic acid sequence is obtained by gene shuffling.

Preferably, the polypeptide sequence encoded by the variant nucleic acid sequence obtained by gene shuffling, when used in the construction of a phylogenetic tree such as the one depicted in FIG. 3, tends to cluster with the group of 2-Cys PRX polypeptides comprising the polypeptide sequence represented by SEQ ID NO: 2 rather than with any other group.

Furthermore, nucleic acid variants may also be obtained by site-directed mutagenesis. Several methods are available to achieve site-directed mutagenesis, the most common being PCR based methods (Current Protocols in Molecular Biology, Wiley Eds.).

Nucleic acid sequences encoding 2-Cys PRX polypeptides may be from a natural source, such as from eubacteria and eukaryotes (fungi, plants, or animals). The nucleic acid sequence derived from any artificial source, or may be modified from its native form in composition and/or genomic environment through deliberate human manipulation. Preferably the 2-Cys PRX polypeptide-encoding nucleic acid sequence is from a plant, further preferably from a dicotyledonous plant, more preferably from the family Brassicaceae, most preferably the nucleic acid sequence is from *Brassica rapa*.

Performance of the methods of the invention gives plants having enhanced yield-related traits. In particular performance of the methods of the invention gives plants having increased yield, especially increased seed yield relative to control plants. The terms "yield" and "seed yield" are described in more detail in the "definitions" section herein.

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of control plants.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for enhancing yield-related traits in plants, especially seed yield of plants, relative to control plants, which method comprises modulating, preferably increasing, expression in the roots of a plant, of a nucleic acid sequence encoding a 2-Cys PRX polypeptide as defined herein.

Since the transgenic plants according to the present invention have enhanced yield-related traits, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating, preferably increasing, expression in the roots of a plant, of a nucleic acid sequence encoding a 2-Cys PRX polypeptide as defined herein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having enhanced yield-related tarits relative to control plants grown under comparable conditions. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signalling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions enhanced yield-related traits relative to control plants grown under comparable conditions. Therefore, according to the present invention, there is provided a method for enhanced yield-related traits in plants grown under non-stress conditions or under mild drought conditions, which method comprises modulating, preferably increasing, expression in the roots a plant of a nucleic acid sequence encoding a 2-Cys PRX polypeptide.

Performance of the methods according to the present invention results in plants grown under abiotic stress conditions having enhanced yield-related traits relative to control plants grown under comparable stress conditions. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. For example, drought and/or salinisation are manifested primarily as osmotic stress, resulting in the disruption of homeostasis and ion distribution in the cell. Oxidative stress, which frequently accompanies high or low temperature, salinity or drought stress may cause denaturation of functional and structural proteins. As a consequence, these diverse environmental stresses often activate similar cell signaling pathways and cellular responses, such as the production of stress proteins, up-regulation of anti-oxidants, accumulation of compatible solutes and growth arrest. Since diverse environmental stresses activate similar pathways, the exemplification of the present invention with drought stress should not be seen as a limitation to drought stress, but more as a screen to indicate the involvement of 2-Cys PRX polypeptides as defined above, in enhancing yield-related traits relative to control plants grown in comparable stress conditions, in abiotic stresses in general.

A particularly high degree of "cross talk" is reported between drought stress and high-salinity stress (Rabbani et al. (2003) Plant Physiol 133: 1755-1767). Therefore, it would be apparent that a 2-Cys PRX polypeptides would, along with its usefulness in enhancing yield-related traits in plants, relative to control plants grown under drought stress conditions, also find use in enhancing yield-related traits in plants, relative to control plants grown under various other abiotic stress conditions.

The term "abiotic stress" as defined herein is taken to mean any one or more of: water stress (due to drought or excess water), anaerobic stress, salt stress, temperature stress (due to hot, cold or freezing temperatures), chemical toxicity stress and oxidative stress. According to one aspect of the invention, the abiotic stress is an osmotic stress, selected from water stress, salt stress, oxidative stress and ionic stress. Preferably, the water stress is drought stress. The term salt stress is not restricted to common salt (NaCl), but may be any stress caused by one or more of: NaCl, KCl, LiCl, $MgCl_2$, $CaCl_2$, amongst others.

In particular, the enhanced yield-related traits in plants grown under abiotic stress conditions (preferably under drought stress conditions) relative to control plants grown in comparable stress conditions, may include one or more of the following: (i) improved early vigour; (ii) increased above-ground biomass; (iii) increased root (thick and thin) biomass; (iv) increase number of flowers per panicle; (v) increased seed fill rate; (vi) increased total seed yield per plant; (vii) increased number of (filled) seeds; (viii) increased harvest index; or (ix) increased thousand kernel weight (TKW).

Performance of the methods of the invention gives plants having enhanced yield-related traits under abiotic stress conditions relative to control plants grown in comparable stress conditions. Therefore, according to the present invention, there is provided a method for enhancing yield-related traits in plants grown under abiotic stress conditions, which method comprises modulating, preferably increasing, expression in the roots of a plant, of a nucleic acid sequence encoding a 2-Cys PRX polypeptide. According to one aspect of the invention, the abiotic stress is an osmotic stress, selected from one or more of the following: water stress, salt stress, oxidative stress and ionic stress. Preferably, the water stress is drought stress.

Another example of abiotic environmental stress is the reduced availability of one or more nutrients that need to be assimilated by the plants for growth and development. Because of the strong influence of nutrition utilization efficiency on plant yield and product quality, a huge amount of fertilizer is poured onto fields to optimize plant growth and quality. Productivity of plants ordinarily is limited by three primary nutrients, phosphorous, potassium and nitrogen, which is usually the rate-limiting element in plant growth of these three. Therefore the major nutritional element required for plant growth is nitrogen (N). It is a constituent of numerous important compounds found in living cells, including amino acids, proteins (enzymes), nucleic acids, and chlorophyll. 1.5% to 2% of plant dry matter is nitrogen and approximately 16% of total plant protein. Thus, nitrogen availability is a major limiting factor for crop plant growth and production (Frink et al. (1999) Proc Natl Acad Sci USA 96(4): 1175-1180), and has as well a major impact on protein accumulation and amino acid composition. Therefore, of great interest are crop plants with an increased yield when grown under nitrogen-limiting conditions.

Performance of the methods of the invention gives plants grown under conditions of nutrient deficiency, particularly under conditions of nitrogen deficiency, having enhanced yield-related traits relative to control plants grown under comparable conditions. Therefore, according to the present invention, there is provided a method for enhancing yield-related traits in plants grown under conditions of nutrient deficiency, which method comprises modulating, preferably increasing, expression in the roots of a plant, of a nucleic acid sequence encoding a 2-Cys PRX polypeptide. Nutrient deficiency may result from a lack or excess of nutrients such as nitrogen, phosphates and other phosphorous-containing compounds, potassium, calcium, cadmium, magnesium, manganese, iron and boron, amongst others.

The present invention encompasses plants or parts thereof (including seeds) obtainable by the methods according to the present invention. The plants or parts thereof comprise a nucleic acid transgene encoding a 2-Cys PRX polypeptide as defined above, operably linked to a root-specific promoter.

The invention also provides genetic constructs and vectors to facilitate introduction and/or expression in plants of nucleic acid sequences encoding 2-Cys PRX polypeptides. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:
(a) a nucleic acid sequence encoding a 2-Cys PRX polypeptide as defined above;
(b) one or more control sequences capable of driving expression of the nucleic acid sequence of (a); and optionally
(c) a transcription termination sequence.

Preferably, the nucleic acid sequence encoding a 2-Cys PRX polypeptide is as defined above. The term "control sequence" and "termination sequence" are as defined herein.

In one embodiment, one of the control sequences of a construct is a organ-specific promoter, preferably a promoter for expression in the roots of a plant. An example of a root-specific promoter is a Rcc3 promoter, for example a rice Rcc3 promoter as represented by SEQ ID NO: 80.

Plants are transformed with a vector comprising any of the nucleic acid sequences described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to drive expression of the nucleic acid sequence. According to a preferred feature of the invention, the nucleic acid sequence encoding a 2-Cys PRX polypeptide is operably linked to a root-specific promoter. The root-specific promoter is preferably an RCc3 promoter (Plant Mol Biol. 1995 January; 27(2):237-48), more preferably the RCc3 promoter is from rice, further preferably the RCc3 promoter is represented by a nucleic acid sequence substantially similar to SEQ ID NO: 80, most preferably the promoter is as represented by SEQ ID NO: 80. Examples of other root-specific promoters which may also be used to perform the methods of the invention are shown in Table 2b in the "Definitions" section above.

It should be clear that the applicability of the present invention is not restricted to the 2-Cys PRX polypeptide-encoding nucleic acid sequence represented by SEQ ID NO: 1, nor is the applicability of the invention restricted to expression of a 2-Cys PRX polypeptide-encoding nucleic acid sequence when driven by a root-specific promoter.

Other organ-specific promoters, for example for preferred expression in leaves, stems, tubers, meristems, seeds (embryo and/or endosperm), are useful in performing the methods of the invention. See the "Definitions" section herein for definitions of the various promoter types.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. An intron sequence may also be added to the 5' untranslated region (UTR) or in the coding sequence to increase the amount of the mature message that accumulates in the cytosol, as described in the definitions section. Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acid sequences, it is advantageous to use marker genes (or reporter genes). Therefore, the genetic construct may optionally comprise a selectable marker gene. Selectable markers are described in more detail in the "definitions" section herein.

It is known that upon stable or transient integration of nucleic acid sequences into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid sequence can be identified for example by selection (for example, cells which have integrated the selectable marker survive whereas the other cells die). The marker genes may be removed or excised from the transgenic cell once they are no longer needed. Techniques for marker gene removal are known in the art, useful techniques are described above in the definitions section.

The invention also provides a method for the production of transgenic plants having enhanced yield-related traits relative to control plants, comprising introduction and expression in the roots of a plant, of any nucleic acid sequence encoding a 2-Cys PRX polypeptide as defined hereinabove.

More specifically, the present invention provides a method for the production of transgenic plants having enhanced yield-related traits, which method comprises:
(i) introducing and expressing in a plant, plant part, or plant cell a nucleic acid sequence encoding 2-Cys PRX polypeptide, under the control of a root-specific promoter; and
(ii) cultivating the plant cell under conditions promoting plant growth and development.

The nucleic acid sequence of (i) may be any of the nucleic acid sequences capable of encoding a 2-Cys PRX polypeptide as defined herein.

The nucleic acid sequence may be introduced directly into a plant cell or into the plant itself (including introduction into a tissue, organ or any other part of a plant). According to a preferred feature of the present invention, the nucleic acid sequence is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid sequence encoding a 2-Cys PRX polypeptide as defined hereinabove. Preferred host cells according to the invention are plant cells. Host plants for the nucleic acid sequences or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression. Methods for increasing expression of nucleic acid sequences or genes, or gene products, are well documented in the art and examples are provided in the definitions section.

As mentioned above, a preferred method for modulating, preferably increasing, expression of a nucleic acid sequence encoding a 2-Cys PRX polypeptide is by introducing and expressing in the roots of a plant, a nucleic acid sequence encoding a 2-Cys PRX polypeptide; however the effects of performing the method, i.e. enhancing yield-related traits may also be achieved using other well known techniques, including but not limited to T-DNA activation tagging, TILL-ING, homologous recombination. A description of these techniques is provided in the definitions section.

The present invention also encompasses use of nucleic acid sequences encoding 2-Cys PRX polypeptides as described herein and use of these 2-Cys PRX polypeptides in enhancing any of the aforementioned yield-related traits in plants.

Nucleic acid sequences encoding 2-Cys PRX polypeptide described herein, or the 2-Cys PRX polypeptides themselves, may find use in breeding programmes in which a DNA marker is identified which may be genetically linked to a 2-Cys PRX polypeptide-encoding gene. The genes/nucleic acid sequences, or the 2-Cys PRX polypeptides themselves may be used to define a molecular marker. This DNA or protein marker may then be used in breeding programmes to select plants having enhanced yield-related traits as defined hereinabove in the methods of the invention.

Allelic variants of a 2-Cys PRX polypeptide-encoding gene/nucleic acid sequence may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which enhance yield-related traits. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acid sequences encoding 2-Cys PRX polypeptides may also be used as probes for genetically and physically mapping the genes that they are a part of, and as markers for traits linked to those genes. Such information may be useful in plant breeding in order to develop lines with desired phenotypes. Such use of 2-Cys PRX polypeptide-encoding nucleic acid sequences requires only a nucleic acid sequence of at least 15 nucleotides in length. The 2-Cys PRX polypeptide-encoding nucleic acid sequences may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the 2-Cys PRX-encoding nucleic acid sequences. The resulting banding patterns may then be subjected to genetic analyses using computer programs such as MapMaker (Lander et al. (1987) Genomics 1: 174-181) in order to construct a genetic map. In addition, the nucleic acid sequences may be used to probe Southern blots containing restriction endonuclease-treated genomic DNAs of a set of individuals representing parent and progeny of a defined genetic cross. Segregation of the DNA polymorphisms is noted and used to calculate the position of the 2-Cys PRX polypeptide-encoding nucleic acid sequence in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acid sequences. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

2. Annexin-Like (ANN)

Surprisingly, it has now been found that modulating expression in a plant of a nucleic acid encoding an annexin-like (hereafter named ANN) polypeptide gives plants having enhanced yield-related traits relative to control plants. According to a first embodiment, the present invention provides a method for enhancing yield-related traits in plants relative to control plants, comprising modulating expression in a plant of a nucleic acid encoding an ANN polypeptide.

A preferred method for modulating (preferably, increasing) expression of a nucleic acid encoding an ANN polypeptide is by introducing and expressing in a plant a nucleic acid encoding an ANN polypeptide.

Any reference hereinafter to a "protein useful in the methods of the invention" is taken to mean an ANN polypeptide as defined herein. Any reference hereinafter to a "nucleic acid useful in the methods of the invention" is taken to mean a nucleic acid capable of encoding such an ANN polypeptide. The nucleic acid to be introduced into a plant (and therefore useful in performing the methods of the invention) is any nucleic acid encoding the type of protein which will now be described, hereafter also named "ANN nucleic acid" or "ANN gene".

An "ANN polypeptide" as defined herein refers to any polypeptide comprising in its native form (i.e. the protein as it is encoded in the genome) at least one, preferably two or more of the following conserved signature sequences:

```
Signature sequence 1
                                          (SEQ ID NO: 87)
(A/L/V) (M/V/L/I) (L/V/M/I/C) X (W/F) (I/V/M/T/A)

(L/P/Y/M/F) (D/E/S/H) (P/A) X (G/S/E/A) RDA
``` wherein X on position 4 may be any amino acid, preferably one of L, S, I, V, Q, or M; and X on position 10 may be any amino acid, preferably one of A, V, P, G, S, T or W.

Preferably, signature sequence 1 is

```
(A/L/V) (V/L/I) (L/V/M/I) X (W/F) (V/T/A)

(L/Y/M/F) (D/E/S/H) PX (E/A) RDA

Signature sequence 2 (SEQ ID NO: 88):
A (F/I/V/C/G) XG (F/R/W/M) G (C/T/V) (D/N)

(S/A/T/E) X (T/A/V/L/M) (V/I/L) (I/T) X (I/V/T) L (T/A/G) (H/Q/K) (R/S)
``` wherein X in position 3 may be any amino acid, preferably one of K, R, Q, S, E, A or M; X on position 10 may be any amino acid, preferably one of T, S, K, N, G, D, A, E, Q, or R; X on position 14 may be any amino acid, preferably one of N, A, R, E, D, S, Q, Preferably, signature sequence 2 is

```
A (F/I/V/C/G) XG (W/M) G (T/V) (D/N) EX (A/L/M)

(I/L) (I/T) X (I/V/T) L (A/G) (H/Q/K) (R/S)

Signature sequence 3 (SEQ ID NO: 89):
(T/S) (D/N/E/T) (D/E/K) XXL (I/T/S/N) R (V/I/A/G)

(V/I/F) (V/T/C/S/A) (T/S) R (T/A) (E/D)

(I/V/F/L/K/H) (D/S)
``` wherein X on position 4 may be any amino acid, preferably one of S, T, D, E, G, W, N, K; X on position 5 may be any amino acid, preferably one of T, A, S, M, H, D, G, W.

Preferably, signature sequence 3 is

```
(T/S) (D/E/T) (D/E/K) XXL (T/S/N) R (V/I/A/G)

(V/I/F) (V/T/C/S/A) (T/S) R (T/A) (E/D)

(I/V/F/L/K/H) (D/S)

Signature sequence 4 (SEQ ID NO: 90):
(Y/H) (F/Y) (A/E/V/S) (K/E/D) (V/A/L/I) (L/V/I)

(R/H/D) X (S/A) (M/I/L)
``` wherein X on position 8 may be any amino acid, preferably one of K, E, D, T, L, S, Q, R, N, or A.

Preferably, signature sequence 4 is

```
(Y/H) (F/Y) (A/E/V/S) (K/E/D) (V/L/I) (L/V/I)

(R/D) X (S/A) (I/L)

Signature sequence 5 (SEQ ID NO: 91):
(Y/G/K/S) (L/I/M) E (H/E) (D/H) (I/V/L) (G/A/E)
```

Preferably, signature sequence 5 is

```
S (L/I/M) EE (D/H) (I/V/L) A

Signature sequence 6 (SEQ ID NO: 92):
(F/L/V/I/T) (I/L/V) (R/Q/Y) (I/V) (F/L/V/I)

(T/S/G/A) (E/D/T) RS
```

Preferably, signature sequence 6 is

```
(F/L/V/I/T) (I/L/V) (R/Y) (I/V) (L/V/I) (T/S/G/A)

TRS

Signature sequence 7 (SEQ ID NO: 93):
Y (R/K/M/E/Q) X (F/T/L/M/I) (L/I) (L/I/V)

(S/T/V/A) L (V/I/L/A/M) (G/S)
``` wherein X on position 3 may be any amino acid, preferably one of T, D, N, K, S, R, A Since the ANN polypeptide is related to annexins, the ANN polypeptide useful in the methods of the invention preferably also has one or more annexin domains (Pfam entry PF00191, SMART entry SM00335, InterPro IPR001464, see also FIGS. 7 A and 7 B).

Preferably, the polypeptide sequence which when used in the construction of a phylogenetic tree, such as the one depicted in FIG. 8 (taken from Cantero et al., Plant Physiol. Biochem. 44, 13-24, 2006), tends to cluster with the group of ANN polypeptides comprising the amino acid sequence represented by SEQ ID NO: 84 and SEQ ID NO: 135, rather than with any other group.

The term "domain", "motif" and "signature" is defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244, InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004), or Pfam (Bateman et al., Nucleic Acids Research 30(1): 276-280 (2002). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters.

Furthermore, ANN polypeptides (at least in their native form) typically have calcium binding activity and capability of binding to membranes. Tools and techniques for measuring membrane binding activity are well known in the art, and include measurement of effects on membrane surface hydrophobicity, vesicle leakage or vesicle aggregation. In addition, ANN polypeptides may exhibit enzymatic activity; for example, Annexin 1 from *Arabidopsis thaliana* is reported to display peroxidase activity (Gorecka et al., Biochem. Biophys. Res. Comm. 336, 868-875, 2005). Further details are provided in Example 19.

The present invention is illustrated by transforming plants with the nucleic acid sequence represented by SEQ ID NO: 83, encoding respectively the polypeptide sequences of SEQ ID NO: 84. However, performance of the invention is not restricted to these sequences; the methods of the invention may advantageously be performed using any ANN-encoding nucleic acid or ANN polypeptide as defined herein.

Examples of nucleic acids encoding ANN polypeptides are given in Table B1 of Example 14 herein. Such nucleic acids are useful in performing the methods of the invention. The amino acid sequences given in Table B1 of Example 14 are example sequences of orthologues and paralogues of the ANN polypeptide represented by SEQ ID NO: 84, the terms "orthologues" and "paralogues" being as defined herein. Further orthologues and paralogues may readily be identified by performing a so-called reciprocal blast search. Typically, this involves a first BLAST involving BLASTing a query sequence (for example using any of the sequences listed in Table B1 of Example 14) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 83 or SEQ ID NO: 84, the second BLAST would therefore be against *Arabidopsis thaliana* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Nucleic acid variants may also be useful in practising the methods of the invention. Examples of such variants include nucleic acids encoding homologues and derivatives of any one of the amino acid sequences given in Table B1 of Example 14, the terms "homologue" and "derivative" being as defined herein. Also useful in the methods of the invention are nucleic acids encoding homologues and derivatives of orthologues or paralogues of any one of the amino acid sequences given in Table B1 of Example 14. Homologues and derivatives useful in the methods of the present invention have substantially the same biological and functional activity as the unmodified protein from which they are derived.

Further nucleic acid variants useful in practising the methods of the invention include portions of nucleic acids encoding ANN polypeptides, nucleic acids hybridising to nucleic acids encoding ANN polypeptides, splice variants of nucleic acids encoding ANN polypeptides, allelic variants of nucleic acids encoding ANN polypeptides and variants of nucleic acids encoding ANN polypeptides obtained by gene shuffling. The terms hybridising sequence, splice variant, allelic variant and gene shuffling are as described herein.

Nucleic acids encoding ANN polypeptides need not be full-length nucleic acids, since performance of the methods of the invention does not rely on the use of full-length nucleic acid sequences. According to the present invention, there is provided a method for enhancing yield-related traits in plants, comprising introducing and expressing in a plant a portion of any one of the nucleic acid sequences given in Table B1 of Example 14, or a portion of a nucleic acid encoding an orthologue, paralogue or homologue of any of the amino acid sequences given in Table B1 of Example 14.

A portion of a nucleic acid may be prepared, for example, by making one or more deletions to the nucleic acid. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode an ANN polypeptide as defined herein, and have substantially the same biological activity as the amino acid sequences given in Table B1 of Example 14. Preferably, the portion is a portion of any one of the nucleic acids given in Table B1 of Example 14, or is a portion of a nucleic acid encoding an orthologue or paralogue of any one of the amino acid sequences given in Table B1 of Example 14. Preferably the portion is at least 400, 450, 500, 550, 600, 650, 700, consecutive nucleotides in length, the consecutive nucleotides being of any one of the nucleic acid sequences given in Table B1 of Example 14, or of a nucleic acid encoding an orthologue or paralogue of any one of the amino acid sequences given in Table B1 of Example 14. Most preferably the portion is a portion of the nucleic acid of SEQ ID NO: 83. Preferably, the portion encodes an amino acid sequence which when used in the construction of a phylogenetic tree, such as the one depicted in FIG. 8, tends to cluster with the group of ANN comprising the amino acid sequence represented by SEQ ID NO: 84 and SEQ ID NO: 135 rather than with any other group.

Another nucleic acid variant useful in the methods of the invention is a nucleic acid capable of hybridising, under reduced stringency conditions, preferably under stringent conditions, with a nucleic acid encoding an ANN polypeptide as defined herein, or with a portion as defined herein.

According to the present invention, there is provided a method for enhancing yield-related traits in plants, comprising introducing and expressing in a plant a nucleic acid capable of hybridizing to any one of the nucleic acids given in Table B1 of Example 14, or comprising introducing and expressing in a plant a nucleic acid capable of hybridising to a nucleic acid encoding an orthologue, paralogue or homologue of any of the nucleic acid sequences given in Table B1 of Example 14.

Hybridising sequences useful in the methods of the invention encode an ANN polypeptide as defined herein, and have substantially the same biological activity as the amino acid sequences given in Table B1 of Example 14. Preferably, the hybridising sequence is capable of hybridising to any one of the nucleic acids given in Table B1 of Example 14, or to a portion of any of these sequences, a portion being as defined above, or wherein the hybridising sequence is capable of hybridising to a nucleic acid encoding an orthologue or paralogue of any one of the amino acid sequences given in Table B1 of Example 14. Most preferably, the hybridising sequence is capable of hybridising to a nucleic acid as represented by SEQ ID NO: 83 or to a portion thereof.

Preferably, the hybridising sequence encodes an amino acid sequence which when used in the construction of a phylogenetic tree, such as the one depicted in FIG. 8, tends to cluster with the group of ANN polypeptides comprising the amino acid sequence represented by SEQ ID NO: 84 and SEQ ID NO: 135, rather than with any other group.

Another nucleic acid variant useful in the methods of the invention is a splice variant encoding an ANN polypeptide as defined hereinabove, a splice variant being as defined herein.

According to the present invention, there is provided a method for enhancing yield-related traits in plants, comprising introducing and expressing in a plant a splice variant of any one of the nucleic acid sequences given in Table B1 of Example 14, or a splice variant of a nucleic acid encoding an orthologue, paralogue or homologue of any of the amino acid sequences given in Table B1 of Example 14.

Preferred splice variants are splice variants of a nucleic acid represented by SEQ ID NO: 83, or a splice variant of a nucleic acid encoding an orthologue or paralogue of SEQ ID NO: 84. Preferably, the amino acid sequence encoded by the splice variant, when used in the construction of a phylogenetic tree, such as the one depicted in FIG. 8, tends to cluster with the group of ANN polypeptides comprising the amino acid sequence represented by SEQ ID NO: 84 and SEQ ID NO: 135 rather than with any other group.

Another nucleic acid variant useful in performing the methods of the invention is an allelic variant of a nucleic acid encoding an ANN polypeptide as defined hereinabove, an allelic variant being as defined herein.

According to the present invention, there is provided a method for enhancing yield-related traits in plants, comprising introducing and expressing in a plant an allelic variant of any one of the nucleic acids given in Table B1 of Example 14, or comprising introducing and expressing in a plant an allelic variant of a nucleic acid encoding an orthologue, paralogue or homologue of any of the amino acid sequences given in Table B1 of Example 14.

The allelic variants useful in the methods of the present invention have substantially the same biological activity as the ANN polypeptide of SEQ ID NO: 84 and any of the amino acids depicted in Table B1 of Example 14. Allelic variants exist in nature, and encompassed within the methods of the present invention is the use of these natural alleles. Preferably, the allelic variant is an allelic variant of SEQ ID NO: 83 or an allelic variant of a nucleic acid encoding an orthologue or paralogue of SEQ ID NO: 84. Preferably, the amino acid sequence encoded by the allelic variant, when used in the construction of a phylogenetic tree, such as the one depicted in FIG. 8, tends to cluster with the ANN polypeptides comprising the amino acid sequence represented by SEQ ID NO: 84 and SEQ ID NO: 135, rather than with any other group.

Gene shuffling or directed evolution may also be used to generate variants of nucleic acids encoding ANN polypeptides as defined above; the term "gene shuffling" being as defined herein.

According to the present invention, there is provided a method for enhancing yield-related traits in plants, comprising introducing and expressing in a plant a variant of any one of the nucleic acid sequences given in Table B1 of Example 14, or comprising introducing and expressing in a plant a variant of a nucleic acid encoding an orthologue, paralogue or homologue of any of the amino acid sequences given in Table B1 of Example 14, which variant nucleic acid is obtained by gene shuffling.

Preferably, the amino acid sequence encoded by the variant nucleic acid obtained by gene shuffling, when used in the construction of a phylogenetic tree such as the one depicted in FIG. 8, tends to cluster with the group of ANN polypeptides comprising the amino acid sequence represented by SEQ ID NO: 84 and SEQ ID NO: 135, rather than with any other group.

Furthermore, nucleic acid variants may also be obtained by site-directed mutagenesis. Several methods are available to achieve site-directed mutagenesis, the most common being PCR based methods (Current Protocols in Molecular Biology. Wiley Eds).

Nucleic acids encoding ANN polypeptides may be derived from any natural or artificial source. The nucleic acid may be modified from its native form in composition and/or genomic environment through deliberate human manipulation. Preferably the ANN polypeptide-encoding nucleic acid is from a plant, further preferably from a dicotyledonous plant, more preferably from the family Brassicaceae, most preferably the nucleic acid is from *Arabidopsis thaliana*.

Performance of the methods of the invention gives plants having enhanced yield-related traits. In particular performance of the methods of the invention gives plants having increased yield, especially increased seed yield relative to control plants. The terms "yield" and "seed yield" are described in more detail in the "definitions" section herein.

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of control plants.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for increasing yield, especially seed yield of plants, relative to control plants, which method comprises modulating expression, preferably increasing expression, in a plant of a nucleic acid encoding an ANN polypeptide as defined herein.

Since the transgenic plants according to the present invention have increased yield, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding an ANN polypeptide as defined herein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signalling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield relative to control plants grown under comparable conditions. Therefore, according to the present invention, there is provided a method for increasing yield in plants grown under non-stress conditions or under mild drought conditions, which method comprises increasing expression in a plant of a nucleic acid encoding an ANN polypeptide.

Performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises increasing expression in a plant of a nucleic acid encoding an ANN polypeptide. Nutrient deficiency may result from a lack of nutrients such as nitrogen, phosphates and other phosphorous-containing compounds, potassium, calcium, cadmium, magnesium, manganese, iron and boron, amongst others.

The present invention encompasses plants or parts thereof (including seeds) obtainable by the methods according to the present invention. The plants or parts thereof comprise a nucleic acid transgene encoding an ANN polypeptide as defined above.

The invention also provides genetic constructs and vectors to facilitate introduction and/or expression in plants of nucleic acids encoding ANN polypeptides. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:
(a) a nucleic acid encoding an ANN polypeptide as defined above;
(b) one or more control sequences capable of driving expression of the nucleic acid sequence of (a); and optionally
(c) a transcription termination sequence.

Preferably, the nucleic acid encoding an ANN polypeptide is as defined above. The term "control sequence" and "termination sequence" are as defined herein.

Plants are transformed with a vector comprising any of the nucleic acids described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to drive expression of the nucleic acid sequence. A constitutive promoter is particularly useful in the methods. See the "Definitions" section herein for definitions of the various promoter types. Also useful in the methods of the invention is a green tissue-specific promoter.

It should be clear that the applicability of the present invention is not restricted to the ANN polypeptide-encoding nucleic acid represented by SEQ ID NO: 83, nor is the applicability of the invention restricted to expression of an ANN polypeptide-encoding nucleic acid when driven by a constitutive promoter, or when driven by a green tissue-specific promoter.

The constitutive promoter is preferably a GOS2 promoter, preferably a GOS2 promoter from rice. Further preferably the constitutive promoter is represented by a nucleic acid sequence substantially similar to SEQ ID NO: 94, most preferably the constitutive promoter is as represented by SEQ ID NO: 94. See Table 2a in the "Definitions" section herein for further examples of constitutive promoters.

According to another preferred feature of the invention, the nucleic acid encoding an ANN polypeptide is operably linked to a green tissue-specific promoter. The green tissue specific promoter is preferably an expansin promoter, further preferably an expansin promoter from rice. Further preferably the green tissue-specific promoter is represented by a nucleic acid sequence substantially similar to SEQ ID NO: 95, most preferably the green tissue-specific promoter is as represented by SEQ ID NO: 95. See Table 2g in the "Definitions" section herein for further examples of green tissue-specific promoters.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. An intron sequence may also be added to the 5' untranslated region (UTR) or in the coding sequence to increase the amount of the mature message that accumulates in the cytosol, as described in the definitions section. Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. Selectable markers are described in more detail in the "definitions" section herein.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die). The marker genes may be removed or excised from the transgenic cell once they are no longer needed. Techniques for marker gene removal are known in the art, useful techniques are described above in the definitions section.

The invention also provides a method for the production of transgenic plants having enhanced yield-related traits relative to control plants, comprising introduction and expression in a plant of any nucleic acid encoding an ANN polypeptide as defined hereinabove.

More specifically, the present invention provides a method for the production of transgenic plants having increased enhanced yield-related traits, particularly increased seed yield, which method comprises:
(i) introducing and expressing in a plant or plant cell an ANN polypeptide-encoding nucleic acid; and
(ii) cultivating the plant cell under conditions promoting plant growth and development.

The nucleic acid of (i) may be any of the nucleic acids capable of encoding an ANN polypeptide as defined herein.

The nucleic acid may be introduced directly into a plant cell or into the plant itself (including introduction into a tissue, organ or any other part of a plant). According to a preferred feature of the present invention, the nucleic acid is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding an ANN polypeptide as defined hereinabove. Preferred host cells according to the invention are plant cells. Host plants for the nucleic acids or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression. Methods for increasing expression of nucleic acids or genes, or gene products, are well documented in the art and examples are provided in the definitions section.

As mentioned above, a preferred method for modulating (preferably, increasing) expression of a nucleic acid encoding an ANN polypeptide is by introducing and expressing in a plant a nucleic acid encoding an ANN polypeptide; however the effects of performing the method, i.e. enhancing yield-related traits may also be achieved using other well known techniques, including but not limited to T-DNA activation tagging, TILLING, homologous recombination. A description of these techniques is provided in the definitions section.

The present invention also encompasses use of nucleic acids encoding ANN polypeptides as described herein and use of these ANN polypeptides in enhancing any of the aforementioned yield-related traits in plants.

Nucleic acids encoding ANN polypeptide described herein, or the ANN polypeptides themselves, may find use in breeding programmes in which a DNA marker is identified which may be genetically linked to an ANN polypeptide-encoding gene. The nucleic acids/genes, or the ANN polypeptides themselves may be used to define a molecular marker. This DNA or protein marker may then be used in breeding programmes to select plants having enhanced yield-related traits as defined hereinabove in the methods of the invention.

Allelic variants of an ANN polypeptide-encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acids encoding ANN polypeptides may also be used as probes for genetically and physically mapping the genes that they are a part of, and as markers for traits linked to those genes. Such information may be useful in plant breeding in order to develop lines with desired phenotypes. Such use of ANN polypeptide-encoding nucleic acids requires only a nucleic acid sequence of at least 15 nucleotides in length. The ANN polypeptide-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the ANN-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the ANN polypeptide-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

Items

1. A method for enhancing yield-related traits in plants relative to control plants, comprising modulating, preferably increasing, expression in the roots a plant, of a nucleic acid sequence encoding 2-cysteine peroxiredoxin (2-Cys PRX), which 2-Cys PRX polypeptide comprises from N-terminus to C-terminus: (1) a plastidic transit peptide; and (2) a 2-Cys PRX domain, and optionally selecting for plants having increased yield.
2. Method according to item 1, wherein said 2-Cys PRX polypeptide additionally comprise one or both of: (i) Motif 1 as represented by SEQ ID NO: 77, or a motif having at least 50%, 55%, 60%, 65%, 70%, 75%, 80%, 85%, 90%, 95%, 98%, 99% or more amino acid sequence identity to SEQ ID NO: 77; or (ii) Motif 2 as represented by SEQ ID NO: 78, or a motif having at least 50%, 55%, 60%, 65%, 70%, 75%, 80%, 85%, 90%, 95%, 98%, 99% or more amino acid sequence identity to SEQ ID NO: 78.
3. Method according to item 1 or 2, wherein said 2-Cys PRX polypeptide, when used in the construction of a phylogenetic tree, such as the one depicted in FIG. 3, tends to cluster with the 2-Cys PRX Glade of polypeptides comprising the polypeptide sequence as represented by SEQ ID NO: 2, rather than with any other PRX Glade.
4. Method according to any preceding item wherein said 2-Cys PRX polypeptide is a polypeptide having in increasing order of preference at least 35%, 40%, 45%, 50%, 55%, 60%, 65%, 70%, 75%, 80%, 85%, 90%, 95%, 98%, 99% or more sequence identity to the 2-Cys PRX polypeptide as represented by SEQ ID NO: 2 or to any of the polypeptide sequences given in Table A1 herein.
5. Method according to any preceding item, wherein said nucleic acid sequence encoding a 2-Cys PRX polypeptide is represented by any one of the nucleic acid sequences listed in Table A1, or is a portion thereof, or is a sequence capable of hybridising with any one of the nucleic acid sequences listed in Table A1.
6. Method according to any preceding item, wherein said nucleic acid sequence encodes an orthologue or paralogue of any of the polypeptides listed in Table A1.
7. Method according to any preceding item, wherein said modulated, preferably increased, expression is effected by any one or more of: T-DNA activation tagging, TILLING, or homologous recombination.
8. Method according to any preceding item, wherein said modulated, preferably increased, expression is effected by introducing and expressing in the roots of a plant a nucleic acid sequence encoding a 2-Cys PRX polypeptide.
9. Method according to any preceding item, wherein said enhanced yield-related traits is one or more of: (i) improved early vigour; (ii) increased aboveground biomass; (iii) increased root biomass; (iv) increase number of flowers per panicle; (v) increased seed fill rate; (vi) increased total seed yield per plant; (vii) increased number of (filled) seeds; (viii) increased harvest index; or (ix) increased thousand kernel weight (TKW).
10. Method according to any preceding item, wherein said enhanced yield-related traits are obtained under abiotic stress.
11. Method according to item 10, wherein said abiotic stress is osmotic stress, selected from one or more of: water stress, salt stress, oxidative stress and ionic stress; preferably wherein said water stress is drought stress and/or reduced nutrient availability, preferably reduced nitrogen availability.
12. Method according to item 10 or 11, wherein said abiotic stress tolerance is manifested as enhanced yield-related trait selected from one or more of: (i) improved early vigour; (ii) increased aboveground biomass; (iii) increased root (thick and thin) biomass; (iv) increase number of flowers per panicle; (v) increased seed fill rate; (vi) increased total seed yield per plant; (vii) increased number of (filled) seeds; (viii) increased harvest index; or (ix) increased thousand kernel weight (TKW), each relative to control plants.
13. Method according to any of items 8 to 12, wherein said nucleic acid sequence is operably linked to a root-specific promoter, preferably to an RCc3 promoter, further preferably to an RCc3 promoter substantially similar to SEQ ID NO: 80, most preferably to a promoter as represented by SEQ ID NO: 80.
14. Method according to any preceding item, wherein said nucleic acid sequence encoding a 2-Cys PRX polypeptide is of plant origin, preferably from a dicotyledonous plant, more preferably from the family Brassicaceae, most preferably from *Brassica rapa*.
15. Plant or part thereof, including seeds, obtainable by a method according to any preceding item, wherein said plant or part thereof comprises a nucleic acid transgene encoding a 2-Cys PRX polypeptide, operably linked to a root-specific promoter.
16. Construct comprising:
    (a) a nucleic acid sequence encoding a 2-Cys PRX polypeptide as defined in any one of items 1 to 6;
    (b) one or more control sequences capable of driving expression of the nucleic acid sequence of (a); and optionally
    (c) a transcription termination sequence;
    wherein at least one of the control sequences is a root-specific promoter, preferably an Rcc3 promoter.
17. Use of a construct according to item 16 in a method for making plants having enhanced yield-related traits, which enhanced yield-related traits is preferably one or more of: (i) improved early vigour; (ii) increased aboveground biomass; (iii) increased root (thick and thin) biomass; (iv) increase number of flowers per panicle; (v) increased seed fill rate; (vi) increased total seed yield per plant; (vii) increased number of (filled) seeds; (viii) increased harvest index; or (ix) increased thousand kernel weight (TKW), relative to control plants.
18. Plant, plant part or plant cell transformed with a construct according to item 16.
19. Method for the production of a transgenic plant having enhanced yield-related traits relative to control plants, comprising:
    (i) introducing and expressing in a plant, plant part or plant cell a nucleic acid sequence encoding a 2-Cys PRX polypeptide as defined in any one of items 1 to 5, under the control of a root-specific promoter; and
    (ii) cultivating the plant cell under conditions promoting plant growth and development.
20. Method according to item 19 wherein said enhanced yield-related traits occur under increased abiotic stress.
21. Transgenic plant having enhanced yield-related traits relative to control plants, resulting from modulated, preferably increased, expression in the roots, of a nucleic acid sequence encoding a 2-Cys PRX polypeptide as defined in any one of items 1 to 6, or a transgenic plant cell or plant part derived from said transgenic plant.
22. Transgenic plant according to item 15, 18 or 21, wherein said plant is a crop plant or a monocot or a cereal, such as rice, maize, wheat, barley, millet, rye, triticale, sorghum and oats, or a transgenic plant cell or plant part derived from said transgenic plant.
23. Harvestable parts of a plant comprising a nucleic acid sequence encoding a 2-Cys PRX polypeptide according to item 22, wherein said harvestable parts are preferably seeds.
24. Products derived from a plant according to item 22 and/or from harvestable parts of a plant according to item 23.
25. Use of a nucleic acid sequence encoding a 2-Cys PRX polypeptide as defined in any one of items 1 to 6 in enhancing yield-related traits in plants, preferably in increasing one or more of: (i) increased seed fill rate; (ii) increased total seed yield per plant; (iii) increased number of filled seeds; (iv) increased total number of seeds; (v) increased thousand kernel weight (TKW) or (vi) increased harvest index, relative to control plants.
26. Use according to item 25, wherein said enhanced yield-related traits occur under abiotic stress.
27. A method for enhancing yield-related traits in plants relative to control plants, comprising modulating expression in a plant of a nucleic acid encoding an ANN polypeptide, wherein said ANN polypeptide comprises one or more of the following motifs:
    (i) Signature sequence 1 (SEQ ID NO: 87),
    (ii) Signature sequence 2 (SEQ ID NO: 88),
    (iii) Signature sequence 3 (SEQ ID NO: 89),
    (iv) Signature sequence 4 (SEQ ID NO: 90),
    (v) Signature sequence 5 (SEQ ID NO: 91),
    (vi) Signature sequence 6 (SEQ ID NO: 92),
    (vii) Signature sequence 7 (SEQ ID NO: 93).
28. Method according to item 27, wherein said ANN polypeptide comprises at least an annexin domain.
29. Method according to item 27 or 28, wherein said modulated expression is effected by introducing and expressing in a plant a nucleic acid encoding an ANN polypeptide.
30. Method according to any one of items 27 to 29, wherein said nucleic acid encoding an ANN polypeptide encodes any one of the proteins listed in Table B1 or is a portion of such a nucleic acid, or a nucleic acid capable of hybridising with such a nucleic acid.

31. Method according to any one of items 27 to 30, wherein said nucleic acid sequence encodes an orthologue or paralogue of any of the proteins given in Table B1.

32. Method according to any one of items 27 to 31, wherein said enhanced yield-related traits comprise increased yield, preferably increased seed yield relative to control plants.

33. Method according to any one of items 27 to 32, wherein said enhanced yield-related traits are obtained under non-stress conditions.

34. Method according to any one of items 27 to 33, wherein said enhanced yield-related traits are obtained under conditions of drought.

35. Method according to any one of items 29 to 34, wherein said nucleic acid is operably linked to a constitutive promoter, preferably to a GOS2 promoter, most preferably to a GOS2 promoter from rice.

36. Method according to any one of items 29 to 34, wherein said nucleic acid is operably linked to a green-tissue specific promoter, preferably to an expansin promoter, most preferably to an expansin promoter from rice.

37. Method according to any preceding item, wherein said nucleic acid encoding an ANN polypeptide is of plant origin, preferably from a dicotyledonous plant, further preferably from the family Brassicaceae, more preferably from the genus *Arabidopsis*, most preferably from *Arabidopsis thaliana*.

38. Plant or part thereof, including seeds, obtainable by a method according to any preceding item, wherein said plant or part thereof comprises a recombinant nucleic acid encoding an ANN polypeptide.

39. Construct comprising:
    (i) nucleic acid encoding an ANN polypeptide as defined in items 27 or 28;
    (ii) one or more control sequences capable of driving expression of the nucleic acid sequence of (i); and optionally
    (iii) a transcription termination sequence.

40. Construct according to item 39, wherein one of said control sequences is a constitutive promoter, preferably a GOS2 promoter, most preferably a GOS2 promoter from rice.

41. Construct according to item 39, wherein one of said control sequences is a green-tissue specific promoter, preferably an expansin promoter, most preferably an expansin promoter from rice.

42. Use of a construct according to any one of items 39 to 41 in a method for making plants having increased yield, particularly increased biomass and/or increased seed yield relative to control plants.

43. Plant, plant part or plant cell transformed with a construct according to any one of items 39 to 41.

44. Method for the production of a transgenic plant having increased yield, particularly increased seed yield relative to control plants, comprising:
    (i) introducing and expressing in a plant a nucleic acid encoding an ANN polypeptide as defined in item 27 or 28; and
    (ii) cultivating the plant cell under conditions promoting plant growth and development.

45. Transgenic plant having increased yield, particularly increased seed yield, relative to control plants, resulting from increased expression of a nucleic acid encoding an ANN polypeptide as defined in item 27 or 28, or a transgenic plant cell derived from said transgenic plant.

46. Transgenic plant according to item 38, 43, or 45, or a transgenic plant cell derived thereof, wherein said plant is a crop plant or a monocot or a cereal, such as rice, maize, wheat, barley, millet, rye, triticale, sorghum and oats.

47. Harvestable parts of a plant according to item 46, wherein said harvestable parts are preferably seeds.

48. Products derived from a plant according to item 46 and/or from harvestable parts of a plant according to item 47.

49. Use of a nucleic acid encoding an ANN polypeptide in increasing yield, particularly in increasing seed yield in plants, relative to control plants.

DESCRIPTION OF FIGURES

The present invention will now be described with reference to the following Figures in which:

FIG. 1 represents the catalytic and inactivation/reactivation cycles of 2-Cys Prx enzymes, according to Rhee et al., (2005) Free radical Biology and Medicine 38: 1543-1552.

FIG. 2 represents the output of a search (using default values) of the Conserved Domains Database (CDD) at NCBI, using a 2-Cys PRX as represented by SEQ ID NO: 2. The top hit is entry CD3015, PRX_Typ2cys.

FIG. 4 shows a CLUSTAL W (1.83) multiple sequence alignment of 2-Cys PRX from eubacteria, plant algae, animals, and 1-Cys PRX from plants, using default values. Motif 1 as represented by SEQ ID NO: 77 and Motif 2 as represented by SEQ ID NO: 78 are boxed. Sequences shown are:
gi|113596153|dbj|BAF20027.1| (SEQ ID NO: 162);
gi|113535696|dbj|BAF08079.1| (SEQ ID NO: 163);
gi|113533376|dbj|BAF05759.1| (SEQ ID NO: 164);
gi|115439131|ref|NP_001043845. (SEQ ID NO: 165);
gi|113532211|dbi|BAF04594.1| (SEQ ID NO: 166);
gi|115435844|ref|NP_001042680. (SEQ ID NO: 167);
gi|113611943|dbj|BAF22321.1| (SEQ ID NO: 168);
gi|113611944|dbj|BAF22322.1| (SEQ ID NO: 169);
gi|12499469|sp|Q61171|PRDX2_MOU (SEQ ID NO: 170);
gi|8394432|ref|NP_058865.1| (SEQ ID NO: 52);
gi|21553667|gb|AAM62760.1| (SEQ ID NO: 10);
gi|13265490|gb|AAG40040.2|AF32 (SEQ ID NO: 171);
gi|11119229|gb|AAG30570.1|AF31 (SEQ ID NO: 8);
gi|113564335|dbj|BAF14678.1| (SEQ ID NO: 172)
gi|15229806|ref|NP_187769.1| (SEQ ID NO: 173);
gi|21592588|gb|AAM64537.1| (SEQ ID NO: 6);
gi|3121825|sp|O24364|BAS1_SPIO (SEQ ID NO: 174);
gi|1498198|emb|CAA63909.1| (SEQ ID NO: 175);
gi|6002472|gb|AAF00001.1|AF052 (SEQ ID NO: 4);
gi|21912927|emb|CAC84143.2| (SEQ ID NO: 14);
gi|47027073|gb|AAT08751.1| (SEQ ID NO: 176);
gi|11558242|emb|CAC17803.1| (SEQ ID NO: 16);
gi|15131688|emb|CAC48323.1| (SEQ ID NO: 18);
gi|3328221|gb|AAC78473.1| (SEQ ID NO: 177);
gi|2499477|sp|Q96468|BAS1_HORV (SEQ ID NO: 178);
gi|2829687|sp|P80602|BAS1_WHEA (SEQ ID NO: 179);
gi|1076722|pir||S49173 (SEQ ID NO: 180);
gi|115446541|ref|NP_001047050. (SEQ ID NO: 20);
gi|113536581|dbj|BAF08964.1| (SEQ ID NO: 181);
gi|125539780|gb|EAY86175.1| (SEQ ID NO: 182);
gi|7339568|emb|CAB82860.1| (SEQ ID NO: 24);

gi|17232133|ref|NP_488681.1| (SEQ ID NO: 28); gi|119509654|ref|ZP_01628800.1 (SEQ ID NO: 32); gi|86609696|ref|YP_478458.1| (SEQ ID NO: 30); gi|86605254|ref|YP_474017.1| (SEQ ID NO: 38); gi|22298997|ref|NP_682244.1| (SEQ ID NO: 34); gi|11465738|ref|NP_053882.1| (SEQ ID NO: 46); gi|51209959|ref|YP_063623.1| (SEQ ID NO: 48); gi|81301118|ref|YP_401326.1| (SEQ ID NO: 42); gi|33865747|ref|NP_897306.1| (SEQ ID NO: 40); gi|84518029|ref|ZP_01005378.1| (SEQ ID NO: 44); gi|116059461|emb|CAL55168.1| (SEQ ID NO: 36); gi|74272711|gb|ABA01151.1| (SEQ ID NO: 26); gi|11995220|emb|CAC19677.1| (SEQ ID NO: 183); gi|115455107|ref|NP_001051154. (SEQ ID NO: 184); gi|115455105|ref|NP_001051153. (SEQ ID NO: 185); gi|113595092|dbj|BAF18966.1| (SEQ ID NO: 186); gi|115452325|ref|NP_001049763. (SEQ ID NO: 187); and gi|113610859|dbj|BAF21237.1| (SEQ ID NO: 188).

Figure 5:
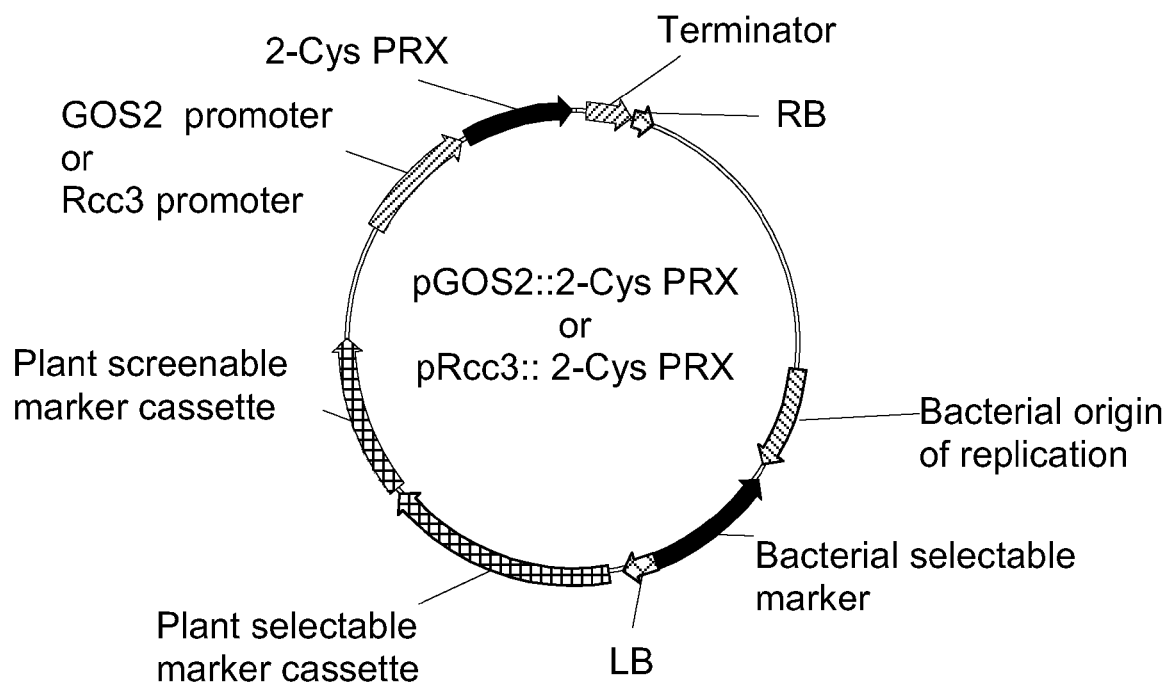

FIG. 5 represents the binary vector for increased expression in *Oryza sativa* of a 2-Cys PRX-encoding nucleic acid sequence under the control of either a rice GOS2 promoter (pGOS2; SEQ ID NO: 79), or a rice Rcc3 (pRcc3; SEQ ID NO: 80) promoter.

FIG. 6 details examples of sequences useful in performing the methods according to the present invention.

FIG. 7 A represents SEQ ID NO: 84 with the annexin domains as predicted by SMART indicated in bold underlined; FIG. 7 B shows the annexin domains (predicted by SMART) in ANNEXIN 4 of *Arabidopsis thaliana* (SEQ ID NO: 135).

Figure 8:
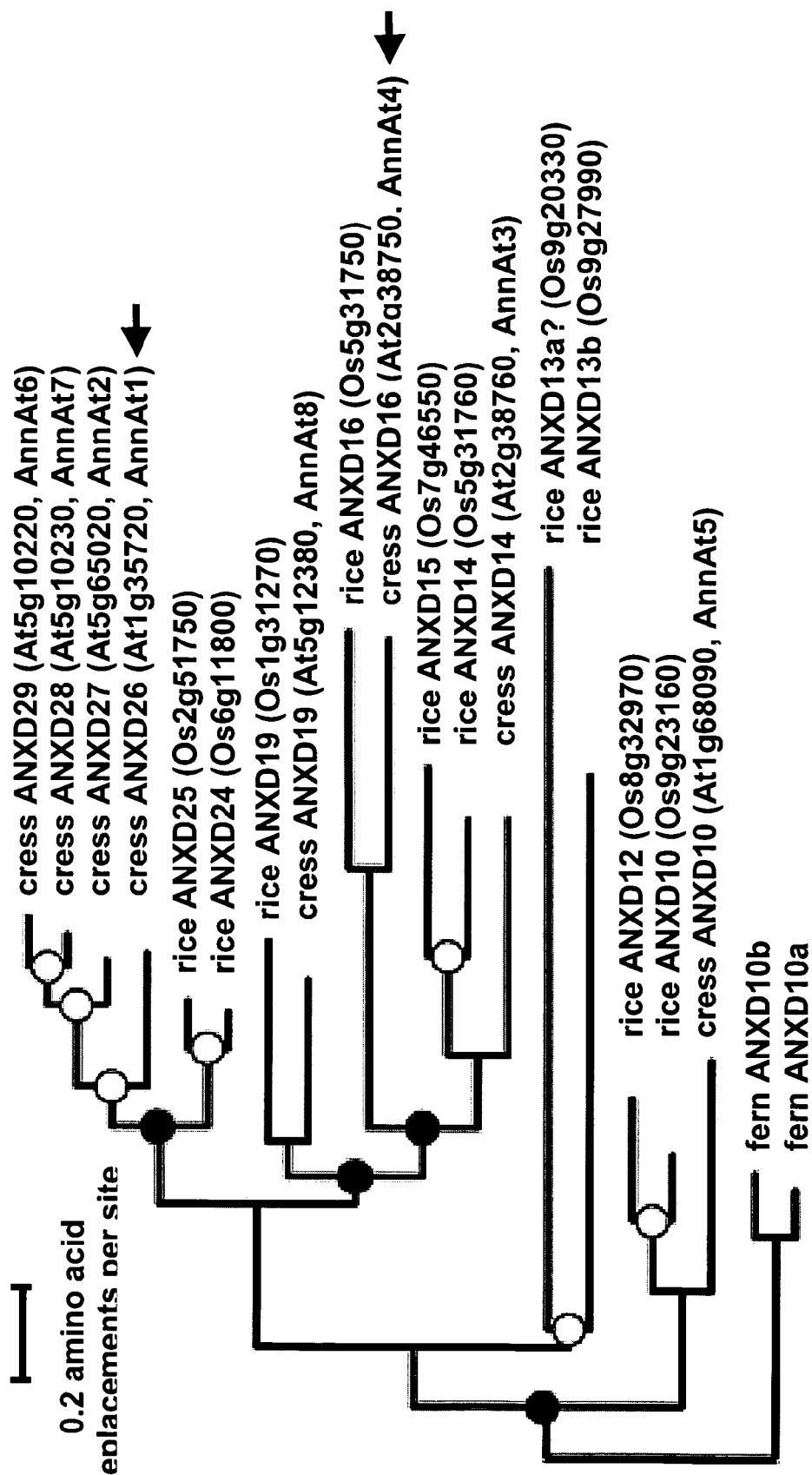

FIG. 8 shows a phylogenetic tree (Cantero et al., Plant Physiol. Biochem. 44, 13-24, 2006) of plant annexin proteins useful in the methods of the present invention. The arrows indicate annexin 1 (SEQ ID NO: 84) and annexin 4 (SEQ ID NO: 135) both from *Arabidopsis thaliana*.

Figure 9:
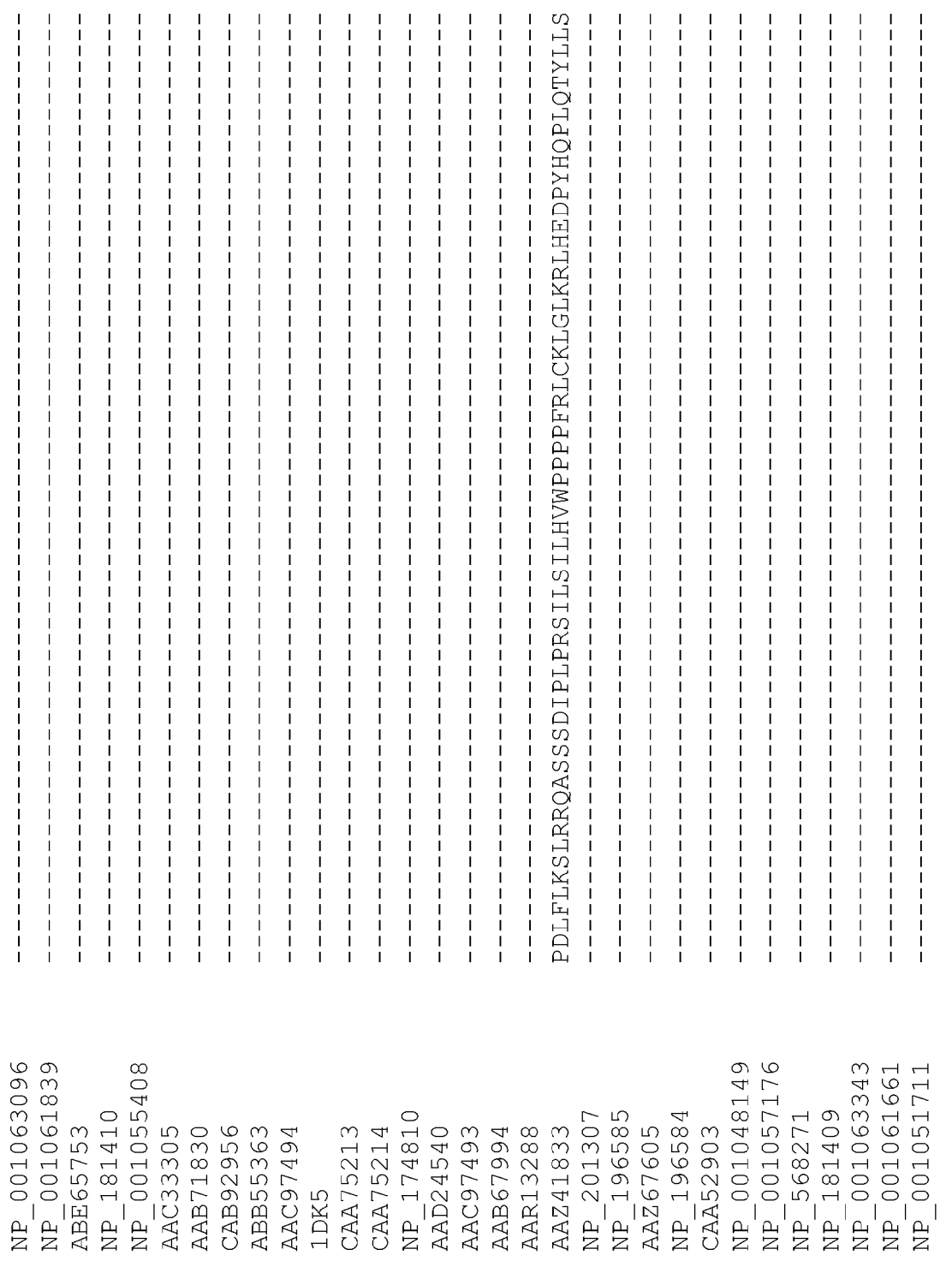
Figure 9:
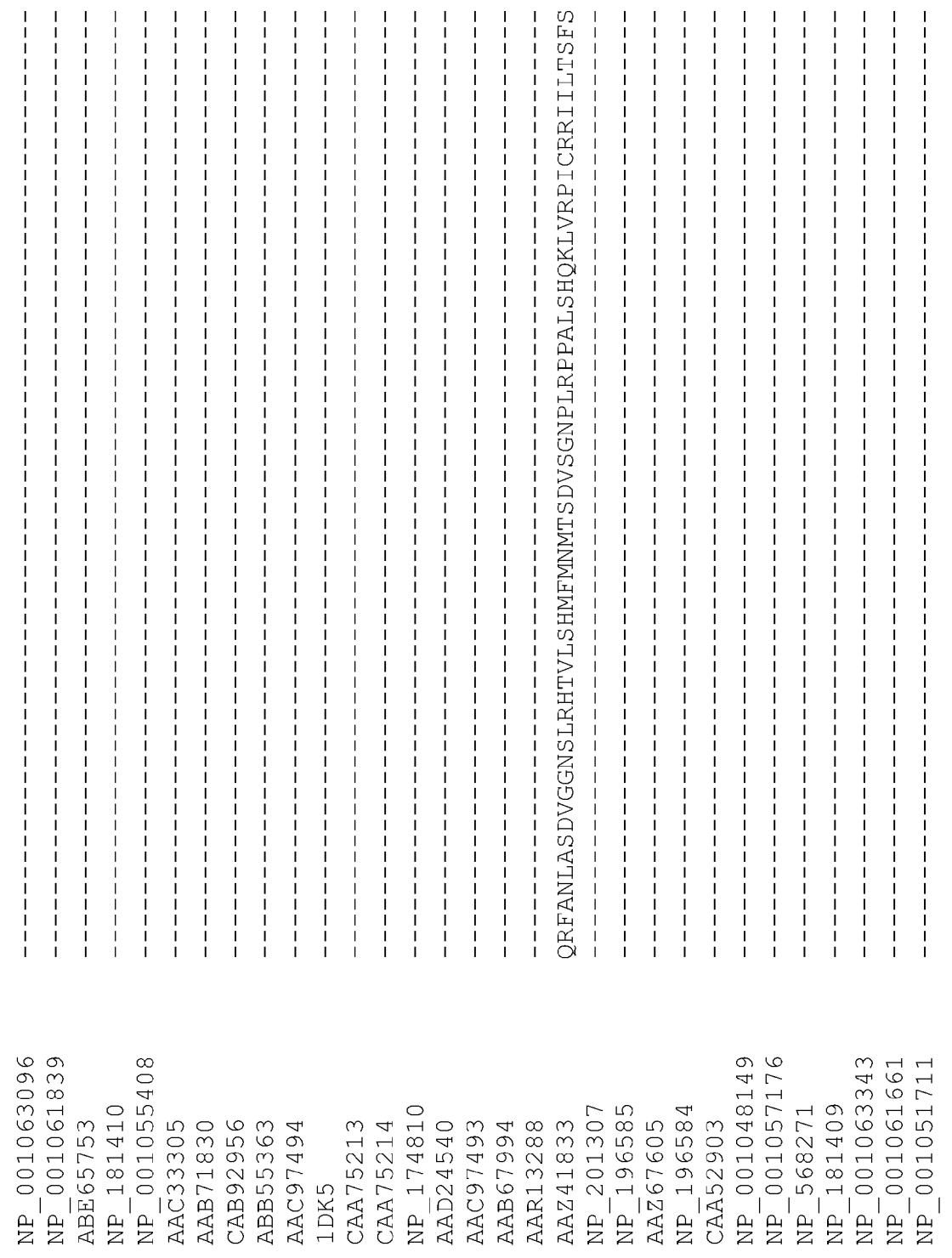

FIG. 9 represents a multiple alignment of various plant annexin proteins. The identifiers refer to the database accessions; NP_1174810 corresponds to SEQ ID NO: 84. Conserved residues are indicated by colons or dots. Sequences shown are: NP_001063096 (SEQ ID NO: 141); NP_001061839 (SEQ ID NO: 145); ABE65753 (SEQ ID NO: 133); NP_181410 (SEQ ID NO: 131); NP_001055408 (SEQ ID NO: 151); AAC33305 (SEQ ID NO: 97); AAB71830 (SEQ ID NO: 99); CAB92956 (SEQ ID NO: 113); ABB55363 (SEQ ID NO: 123); AAC97494 (SEQ ID NO: 115); 1DK5 (SEQ ID NO: 105); CAA75213 (SEQ ID NO: 111); CAA75214 (SEQ ID NO: 121); NP_174810 (SEQ ID NO: 84); AAD24540 (SEQ ID NO: 107); AAC97493 (SEQ ID NO: 117); AAB67994 (SEQ ID NO: 103); AAR13288 (SEQ ID NO: 109); AAZ41833 (SEQ ID NO: 101); NP_201307 (SEQ ID NO: 119); NP_196585 (SEQ ID NO: 125); AAZ67605 (SEQ ID NO: 129); NP_196584 (SEQ ID NO: 137); CAA52903 (SEQ ID NO: 127); NP_001048149 (SEQ ID NO: 143); NP_001057176 (SEQ ID NO: 147); NP_568271 (SEQ ID NO: 139); NP_181409 (SEQ ID NO: 135); NP_001063343 (SEQ ID NO: 149); NP_001061661 (SEQ ID NO: 153); and NP_001051711 (SEQ ID NO: 155).

Figure 10:
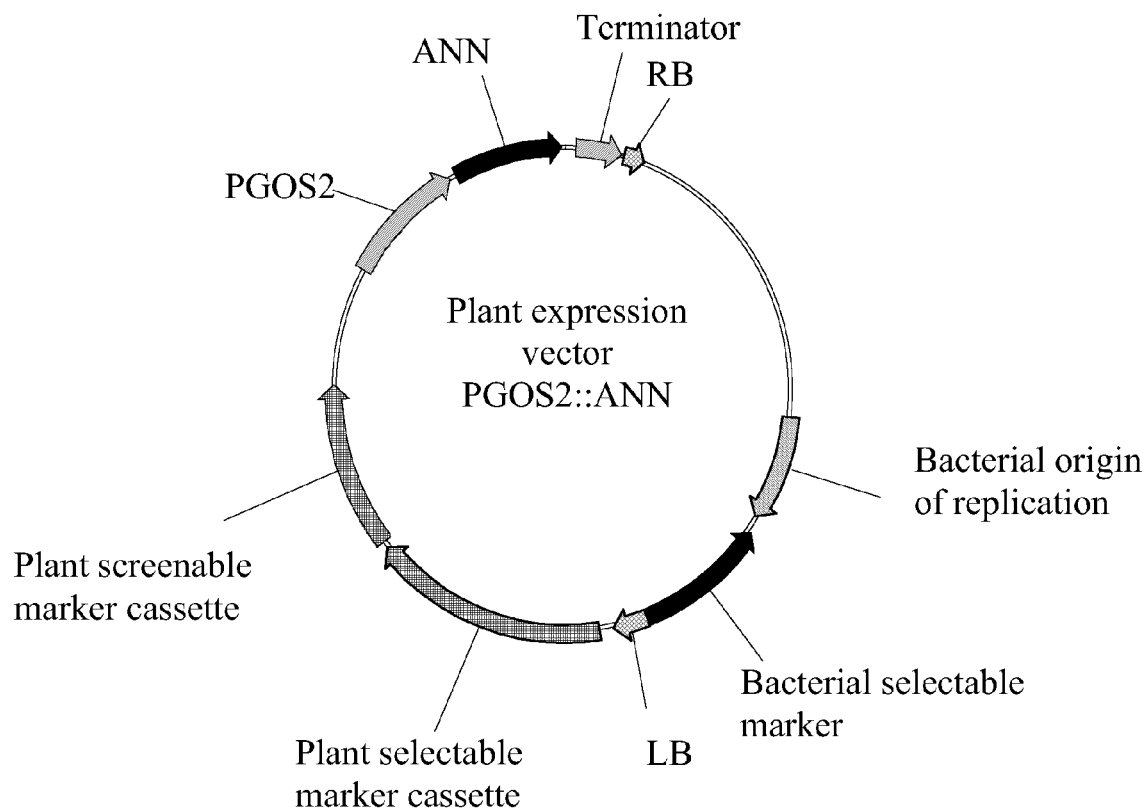

FIG. 10 represents the binary vector for increased expression in *Oryza sativa* of an ANN-encoding nucleic acid under the control of a rice GOS2 promoter (pGOS2).

FIG. 11 details examples of sequences useful in performing the methods according to the present invention.

EXAMPLES

The present invention will now be described with reference to the following examples, which are by way of illustration alone. The following examples are not intended to completely define or otherwise limit the scope of the invention.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, N.Y.) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Identification of Sequences Related to the Nucleic Acid Sequence Used in the Methods of the Invention Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acid sequence used in the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

Table A1 provides a list of nucleic acid sequences related to the nucleic acid sequence used in the methods of the present invention.

TABLE A1

Examples of 2-Cys PRX nucleic acid and polypeptide sequences:

| Species | Nucleic acid sequence NCBI accession | SEQ ID NO | Polypeptide sequence NCBI accession | SEQ ID NO |
|---|---|---|---|---|
| *Brassica* sp. | SEQ ID NO: 1 | 1 | SEQ ID NO: 2 | 2 |
| *Brassica rapa* | AF052202.1 | 3 | AAF00001.1 | 4 |
| *Arabidopsis thaliana* | AY086974.1 | 5 | AAM64537.1 | 6 |

TABLE A1-continued

Examples of 2-Cys PRX nucleic acid and polypeptide sequences:

| Species | Nucleic acid sequence NCBI accession | SEQ ID NO | Polypeptide sequence NCBI accession | SEQ ID NO |
|---|---|---|---|---|
| *Brassica napus* | AF311863.1 | 7 | AAG30570.1 | 8 |
| *Arabidopsis thaliana* | NM_120712.2 | 9 | AAM62760.1 | 10 |
| *Spinacia oleracea* | X94219.1 | 11 | O24364 | 12 |
| *Nicotiana tabacum* | AJ309009.2 | 13 | CAC84143.2 | 14 |
| *Phaseolus vulgaris* | AJ288895.1 | 15 | CAC17803.1 | 16 |
| *Pisum sativum* | AJ315851.1| | 17 | CAC48323.1 | 18 |
| *Oryza sativa* | NM_001053585.1 | 19 | NP_001047050.1 Os02g0537700 | 20 |
| *Secale cereale* | AF076920.1 | 21 | AAC78473.1 | 22 |
| *Riccia fluitans* | AJ005006.1 | 23 | CAB82860.1 | 24 |
| *Chlamydomonas incerta* | DQ122920.1 | 25 | ABA01151.1 | 26 |
| *Nostoc* | gi|17227497: 5544705-5545316 | 27 | NP_488681.1 | 28 |
| *Synechococcus* sp | gi|86607503: 2357237-2357845 | 29 | YP_478458.1 | 30 |
| *Nodularia spumigena* | gi|119509627: 35267-35878 | 31 | ZP_01628800.1 | 32 |
| *Thermosynechococcus elongatus* | gi|22297544: 1516844-1517437 | 33 | NP_682244.1 | 34 |
| *Ostreococcus tauri* | gi|118721427: 14610-14671, 14874-14913, 15068-15658 | 35 | CAL55168.1 | 36 |
| *Synechococcus* | gi|86604733: 552727-553335 | 37 | YP_474017.1 | 38 |
| *Synechococcus* | gi|33864539: 1204065-1204667 | 39 | NP_897306.1 | 40 |
| *Synechococcus elongatus* | gi|81298811: 2377107-2377703 | 41 | YP_401326.1 | 42 |
| *Prochlorococcus marinus* | gi|84517401: 555567-556163 | 43 | ZP_01005378.1 | 44 |
| *Porphyra purpurea* | gi|11465652: 76976-77575 | 45 | NP_053882.1 | 46 |
| *Gracilaria tenuistipitata* | gi|51209843: 100291-100971 | 47 | YP_063623.1 | 48 |
| *Mus musculus* | X82067.1 | 49 | Q61171 | 50 |
| *Rattus norvegicus* | NM_017169.1 | 51 | NP_058865.1 | 52 |

In some instances, related sequences have tentatively been assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid sequence or polypeptide sequence of interest.

Example 2

Alignment of 2-Cys PRX Polypeptide Sequences

Figure 4:
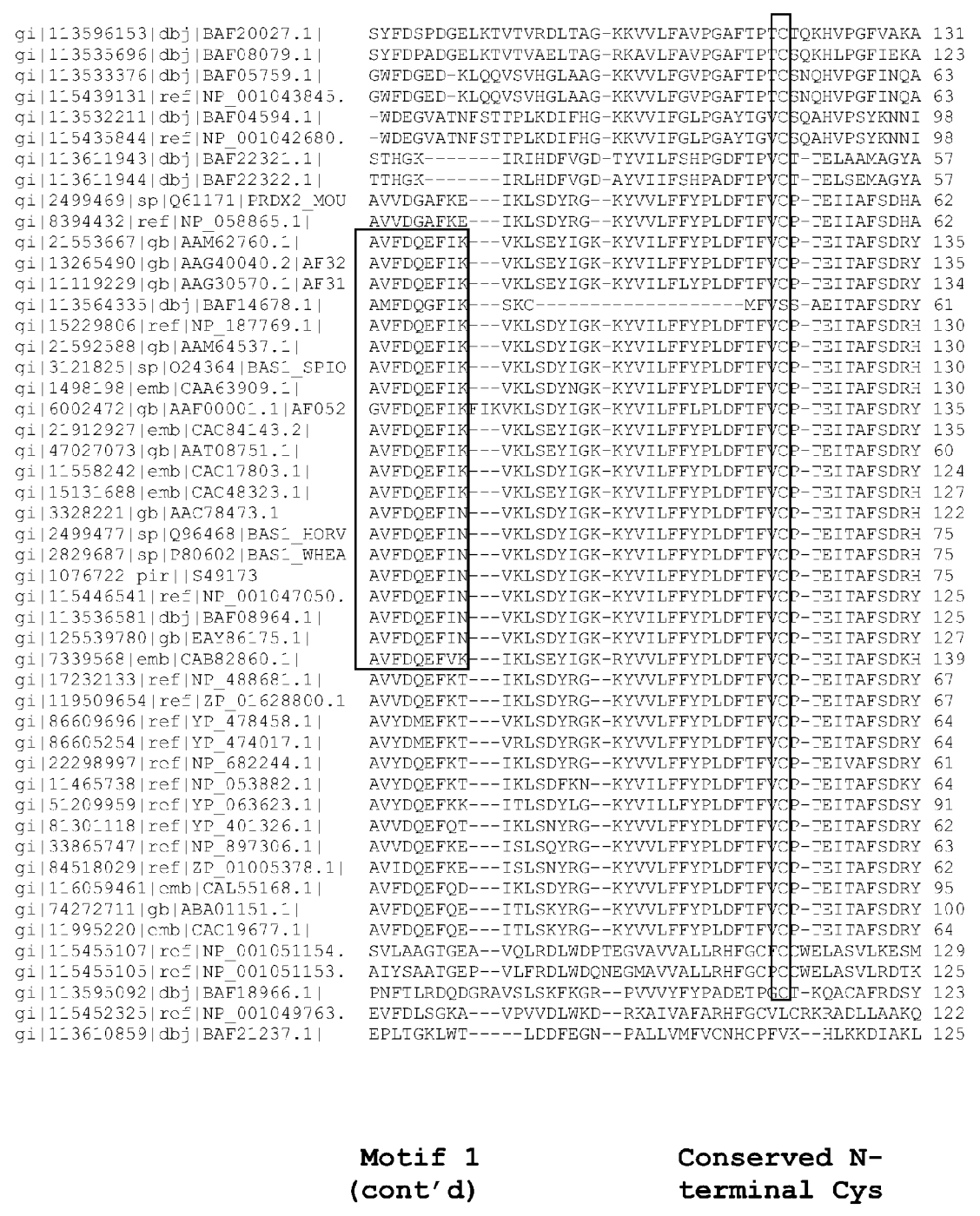

Alignment of 2-Cys PRX polypeptide sequences from eubacteria, plant algae, animals, and 1-Cys PRX polypeptide sequences from plants (as outliers) was performed the Clustal algorithm (1.83) of progressive alignment, using default values (Thompson et al. (1997) Nucleic Acids Res 25:4876-4882; Chenna et al. (2003). Nucleic Acids Res 31:3497-3500). Minor manual editing may be done to further optimise the alignment. The 2-Cys PRX polypeptides are aligned in FIG. 4. Motif 1 as represented by SEQ ID NO: 77 and Motif 2 as represented by SEQ ID NO: 78 are boxed.

Figure 3:
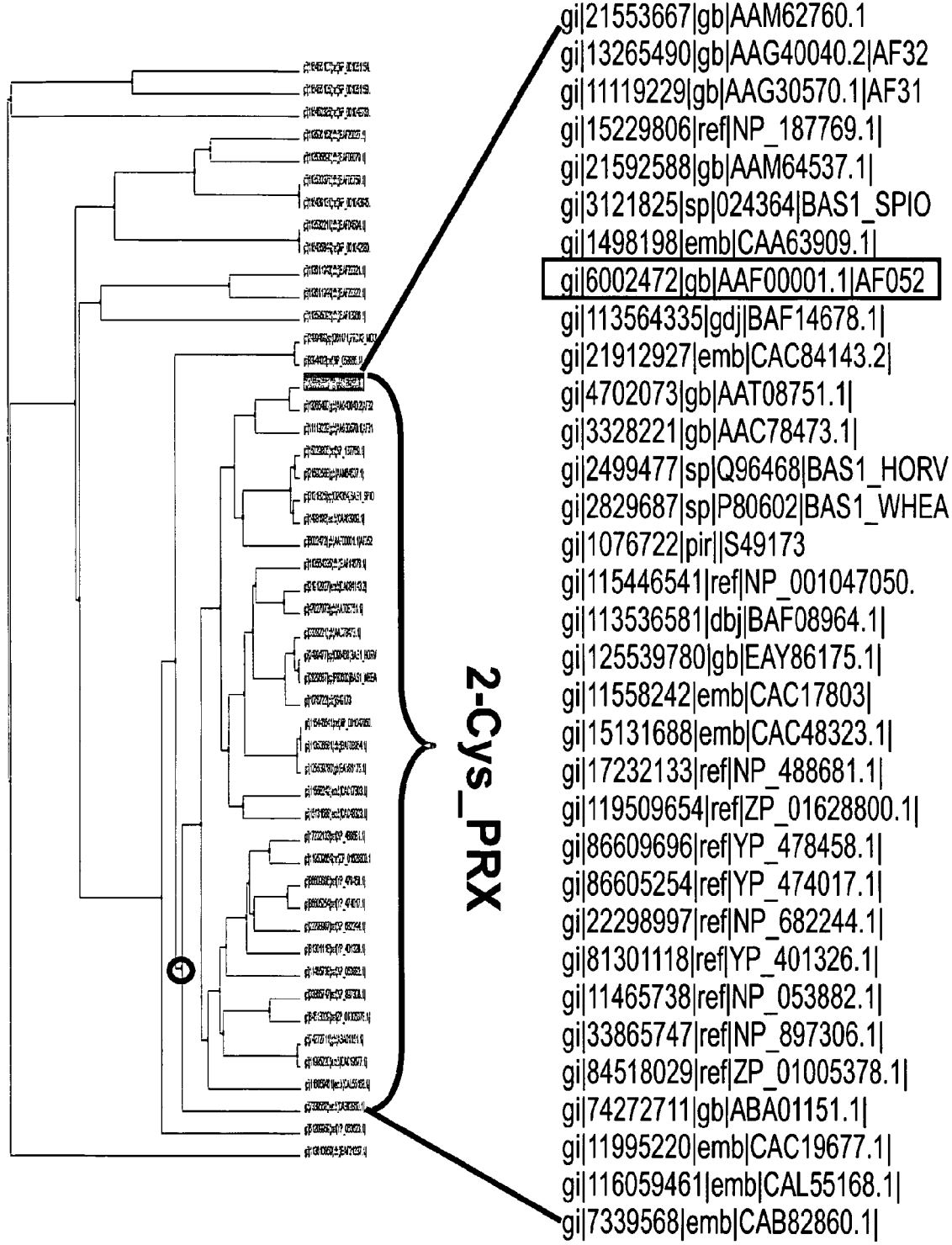
FIG. 3 shows a phylogenetic tree built using the neighbour joining clustering method, after a ClustalW (1.83) multiple sequence alignment of 2-Cys PRX from eubacteria, plant algae, animals, and 1-Cys PRX from plants. The 2-Cys PRX class is marked with an accolade. The 2-Cys PRX as represented by SEQ ID NO: 2 is boxed.

A phylogenetic tree of 2-Cys PRX polypeptide sequences from eubacteria, plant algae, animals, and 1-Cys PRX polypeptide sequences from plants (as outliers) was constructed using a neighbour-joining clustering algorithm, well known in the art (FIG. 3). The 2-Cys PRX class is marked with an accolade. The 2-Cys PRX as represented by SEQ ID NO: 2 is boxed.

Example 3

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

| Scoring matrix: | Blosum 62 |
|---|---|
| First Gap: | 12 |
| Extending gap: | 2 |

Results of the software analysis are shown in Table A2 for the global similarity and identity over the full length of the polypeptide sequences. Percentage identity is given above the diagonal in bold and percentage similarity is given below the diagonal (normal face).

The percentage identity between the 2-Cys PRX polypeptide sequences useful in performing the methods of the invention can be as low as 35% amino acid identity compared to SEQ ID NO: 2.

TABLE A2

MatGAT results for global similarity and identity over the full length of the polypeptide sequences.

|  | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 01. seqidno02 |  | 91 | 89 | 86 | 86 | 88 | 76 | 78 | 76 | 76 | 74 | 66 | 61 | 55 | 53 | 55 | 54 | 57 | 52 | 53 |
| 02. seqidno04 | 92 |  | 85 | 80 | 80 | 85 | 71 | 74 | 71 | 72 | 69 | 61 | 56 | 52 | 50 | 52 | 51 | 54 | 49 | 49 |
| 03. seqidno06 | 93 | 88 |  | 85 | 86 | 97 | 75 | 77 | 74 | 74 | 74 | 66 | 61 | 55 | 52 | 55 | 53 | 58 | 51 | 52 |
| 04. seqidno08 | 92 | 86 | 92 |  | 89 | 85 | 74 | 77 | 74 | 73 | 73 | 64 | 60 | 56 | 52 | 56 | 52 | 59 | 51 | 52 |
| 05. seqidno10 | 91 | 86 | 91 | 93 |  | 85 | 77 | 76 | 74 | 75 | 74 | 66 | 61 | 57 | 53 | 56 | 53 | 59 | 52 | 53 |
| 06. seqidno12 | 92 | 87 | 98 | 91 | 90 |  | 76 | 77 | 75 | 75 | 75 | 66 | 61 | 55 | 53 | 55 | 54 | 58 | 52 | 52 |
| 07. seqidno14 | 83 | 80 | 85 | 86 | 86 | 85 |  | 79 | 79 | 75 | 75 | 66 | 63 | 57 | 54 | 55 | 54 | 57 | 53 | 53 |
| 08. seqidno16 | 84 | 79 | 84 | 83 | 82 | 83 | 83 |  | 86 | 77 | 76 | 66 | 63 | 58 | 57 | 57 | 56 | 61 | 55 | 55 |
| 09. seqidno18 | 85 | 81 | 85 | 83 | 83 | 85 | 85 | 91 |  | 75 | 74 | 67 | 63 | 57 | 54 | 56 | 55 | 59 | 53 | 53 |
| 10. seqidno20 | 82 | 77 | 81 | 81 | 83 | 83 | 83 | 85 | 86 |  | 79 | 66 | 64 | 57 | 55 | 57 | 57 | 60 | 54 | 53 |
| 11. seqidno22 | 84 | 78 | 83 | 82 | 82 | 83 | 83 | 84 | 82 | 85 |  | 67 | 64 | 58 | 56 | 57 | 56 | 61 | 55 | 54 |
| 12. seqidno24 | 79 | 75 | 79 | 78 | 80 | 79 | 81 | 77 | 78 | 79 | 77 |  | 60 | 56 | 51 | 53 | 52 | 58 | 51 | 50 |
| 13. seqidno26 | 75 | 70 | 74 | 74 | 75 | 74 | 75 | 75 | 75 | 75 | 74 | 72 |  | 66 | 62 | 63 | 65 | 69 | 61 | 64 |
| 14. seqidno28 | 65 | 61 | 65 | 64 | 65 | 65 | 65 | 66 | 65 | 67 | 67 | 63 | 75 |  | 83 | 91 | 83 | 63 | 82 | 76 |
| 15. seqidno30 | 63 | 59 | 63 | 64 | 64 | 63 | 64 | 66 | 65 | 66 | 68 | 63 | 72 | 92 |  | 80 | 84 | 61 | 96 | 74 |
| 16. seqidno32 | 65 | 61 | 65 | 64 | 65 | 65 | 65 | 67 | 64 | 67 | 67 | 62 | 75 | 97 | 92 |  | 79 | 63 | 80 | 76 |
| 17. seqidno34 | 62 | 58 | 62 | 62 | 61 | 62 | 62 | 64 | 63 | 66 | 65 | 60 | 73 | 88 | 90 | 88 |  | 64 | 83 | 75 |
| 18. seqidno36 | 67 | 63 | 67 | 68 | 67 | 67 | 67 | 68 | 67 | 71 | 70 | 65 | 79 | 74 | 72 | 74 | 73 |  | 59 | 63 |
| 19. seqidno38 | 63 | 59 | 63 | 63 | 63 | 63 | 63 | 66 | 64 | 66 | 68 | 62 | 72 | 92 | 100 | 93 | 89 | 71 |  | 72 |
| 20. seqidno40 | 62 | 58 | 61 | 60 | 61 | 61 | 61 | 64 | 62 | 62 | 63 | 58 | 73 | 84 | 85 | 85 | 84 | 71 | 85 |  |
| 21. seqidno42 | 61 | 58 | 61 | 61 | 61 | 62 | 61 | 65 | 63 | 63 | 64 | 60 | 73 | 89 | 90 | 89 | 89 | 73 | 91 | 88 |
| 22. seqidno44 | 61 | 58 | 61 | 60 | 60 | 61 | 61 | 64 | 62 | 62 | 63 | 57 | 73 | 85 | 85 | 85 | 84 | 73 | 85 | 96 |
| 23. seqidno46 | 62 | 58 | 61 | 61 | 61 | 62 | 61 | 63 | 62 | 63 | 65 | 60 | 72 | 87 | 90 | 88 | 88 | 71 | 90 | 84 |
| 24. seqidno48 | 64 | 61 | 65 | 64 | 65 | 65 | 64 | 67 | 66 | 64 | 67 | 62 | 73 | 74 | 73 | 74 | 71 | 71 | 72 | 71 |
| 25. seqidno50 | 58 | 54 | 58 | 57 | 58 | 58 | 56 | 58 | 57 | 58 | 59 | 55 | 64 | 73 | 73 | 73 | 73 | 64 | 72 | 75 |
| 26. seqidno52 | 57 | 54 | 57 | 56 | 56 | 57 | 55 | 57 | 56 | 58 | 58 | 55 | 63 | 72 | 72 | 72 | 72 | 64 | 72 | 74 |
| 27. seqidno54 | 41 | 39 | 40 | 40 | 40 | 40 | 40 | 42 | 40 | 39 | 41 | 40 | 39 | 45 | 45 | 46 | 46 | 40 | 45 | 46 |
| 28. seqidno56 | 50 | 48 | 50 | 50 | 48 | 49 | 49 | 50 | 50 | 52 | 53 | 49 | 53 | 55 | 52 | 55 | 52 | 49 | 52 | 53 |
| 29. seqidno58 | 36 | 36 | 35 | 34 | 35 | 36 | 36 | 36 | 37 | 36 | 37 | 36 | 40 | 43 | 43 | 44 | 41 | 38 | 42 | 43 |
| 30. seqidno60 | 41 | 41 | 41 | 40 | 40 | 40 | 40 | 40 | 37 | 42 | 41 | 39 | 43 | 28 | 28 | 28 | 27 | 39 | 25 | 28 |
| 31. seqidno62 | 41 | 41 | 43 | 40 | 41 | 43 | 41 | 40 | 40 | 42 | 41 | 40 | 46 | 42 | 39 | 42 | 40 | 43 | 39 | 40 |
| 32. seqidno64 | 27 | 30 | 27 | 27 | 27 | 31 | 27 | 29 | 30 | 33 | 28 | 30 | 35 | 38 | 38 | 37 | 40 | 35 | 40 | 38 |
| 33. seqidno66 | 36 | 37 | 33 | 35 | 35 | 34 | 38 | 33 | 33 | 37 | 34 | 36 | 33 | 30 | 29 | 30 | 27 | 30 | 29 | 29 |
| 34. seqidno68 | 39 | 40 | 39 | 39 | 41 | 39 | 39 | 41 | 38 | 41 | 40 | 35 | 42 | 39 | 34 | 39 | 39 | 40 | 34 | 34 |
| 35. seqidno70 | 34 | 38 | 34 | 34 | 34 | 33 | 32 | 36 | 32 | 35 | 34 | 31 | 33 | 26 | 31 | 26 | 25 | 33 | 26 | 25 |
| 36. seqidno72 | 34 | 33 | 35 | 34 | 34 | 35 | 32 | 36 | 33 | 34 | 36 | 34 | 33 | 27 | 25 | 26 | 25 | 28 | 25 | 26 |
| 37. seqidno74 | 33 | 33 | 32 | 36 | 32 | 33 | 33 | 34 | 32 | 35 | 33 | 33 | 34 | 27 | 29 | 29 | 28 | 31 | 31 | 26 |
| 38. seqidno76 | 30 | 28 | 29 | 30 | 31 | 29 | 30 | 34 | 29 | 32 | 30 | 30 | 35 | 36 | 35 | 38 | 36 | 36 | 35 | 36 |

|  | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|
| 01. seqidno02 | 53 | 51 | 50 | 47 | 47 | 46 | 20 | 46 | 19 | 24 | 25 | 16 | 18 | 23 | 18 | 19 | 17 | 17 |
| 02. seqidno04 | 51 | 48 | 47 | 46 | 45 | 44 | 21 | 45 | 19 | 22 | 26 | 16 | 19 | 21 | 20 | 18 | 18 | 18 |
| 03. seqidno06 | 52 | 50 | 50 | 48 | 46 | 46 | 19 | 46 | 18 | 24 | 25 | 16 | 16 | 22 | 18 | 21 | 18 | 16 |
| 04. seqidno08 | 53 | 52 | 50 | 50 | 47 | 45 | 20 | 46 | 19 | 23 | 24 | 15 | 17 | 21 | 17 | 21 | 16 | 16 |
| 05. seqidno10 | 53 | 51 | 51 | 49 | 47 | 46 | 20 | 47 | 18 | 24 | 24 | 15 | 18 | 22 | 18 | 20 | 16 | 17 |
| 06. seqidno12 | 52 | 51 | 50 | 48 | 48 | 47 | 21 | 46 | 19 | 25 | 25 | 16 | 17 | 22 | 18 | 21 | 19 | 16 |
| 07. seqidno14 | 55 | 52 | 51 | 50 | 46 | 45 | 22 | 45 | 20 | 23 | 24 | 15 | 18 | 22 | 18 | 20 | 17 | 16 |
| 08. seqidno16 | 57 | 53 | 53 | 51 | 48 | 48 | 21 | 48 | 19 | 21 | 23 | 17 | 17 | 22 | 20 | 20 | 18 | 17 |
| 09. seqidno18 | 56 | 51 | 52 | 51 | 46 | 45 | 20 | 46 | 21 | 22 | 24 | 18 | 15 | 22 | 17 | 20 | 16 | 14 |
| 10. seqidno20 | 55 | 51 | 53 | 49 | 47 | 46 | 19 | 48 | 18 | 24 | 26 | 16 | 19 | 22 | 20 | 20 | 21 | 19 |
| 11. seqidno22 | 56 | 53 | 53 | 49 | 48 | 47 | 20 | 50 | 19 | 26 | 25 | 18 | 18 | 24 | 22 | 22 | 20 | 16 |
| 12. seqidno24 | 54 | 50 | 49 | 46 | 44 | 45 | 20 | 43 | 20 | 24 | 25 | 17 | 18 | 21 | 17 | 20 | 20 | 17 |
| 13. seqidno26 | 67 | 64 | 59 | 56 | 53 | 53 | 21 | 45 | 22 | 23 | 25 | 20 | 18 | 24 | 19 | 18 | 18 | 18 |
| 14. seqidno28 | 83 | 75 | 74 | 61 | 60 | 60 | 27 | 44 | 27 | 13 | 21 | 22 | 15 | 19 | 16 | 17 | 16 | 16 |
| 15. seqidno30 | 83 | 72 | 76 | 60 | 58 | 58 | 25 | 43 | 25 | 15 | 19 | 23 | 17 | 15 | 18 | 16 | 17 | 16 |
| 16. seqidno32 | 80 | 73 | 73 | 63 | 61 | 61 | 27 | 44 | 27 | 12 | 21 | 22 | 16 | 18 | 16 | 17 | 18 | 17 |
| 17. seqidno34 | 83 | 74 | 77 | 60 | 60 | 60 | 27 | 44 | 26 | 16 | 19 | 23 | 15 | 17 | 18 | 17 | 19 | 15 |
| 18. seqidno36 | 63 | 63 | 60 | 57 | 50 | 50 | 22 | 44 | 21 | 24 | 22 | 20 | 15 | 20 | 20 | 19 | 17 | 20 |
| 19. seqidno38 | 82 | 72 | 76 | 59 | 57 | 57 | 27 | 42 | 27 | 11 | 19 | 23 | 17 | 17 | 17 | 16 | 19 | 17 |
| 20. seqidno40 | 81 | 90 | 71 | 57 | 64 | 63 | 29 | 44 | 28 | 16 | 19 | 23 | 16 | 17 | 15 | 17 | 17 | 16 |
| 21. seqidno42 |  | 78 | 76 | 58 | 62 | 62 | 26 | 44 | 25 | 15 | 18 | 21 | 15 | 15 | 18 | 17 | 18 | 15 |
| 22. seqidno44 | 88 |  | 70 | 56 | 61 | 61 | 28 | 43 | 27 | 17 | 19 | 20 | 16 | 19 | 17 | 13 | 17 | 18 |
| 23. seqidno46 | 90 | 86 |  | 63 | 58 | 57 | 27 | 39 | 27 | 12 | 18 | 21 | 13 | 18 | 14 | 15 | 16 | 17 |
| 24. seqidno48 | 71 | 72 | 73 |  | 46 | 45 | 23 | 34 | 22 | 18 | 20 | 17 | 12 | 18 | 13 | 12 | 11 | 17 |
| 25. seqidno50 | 74 | 75 | 73 | 61 |  | 99 | 27 | 36 | 26 | 18 | 19 | 22 | 17 | 18 | 18 | 17 | 19 | 16 |
| 26. seqidno52 | 73 | 74 | 72 | 60 | 99 |  | 27 | 36 | 26 | 18 | 19 | 22 | 16 | 18 | 17 | 17 | 19 | 17 |
| 27. seqidno54 | 43 | 47 | 47 | 41 | 46 | 46 |  | 17 | 81 | 12 | 16 | 20 | 15 | 17 | 15 | 16 | 16 | 13 |
| 28. seqidno56 | 53 | 53 | 53 | 47 | 47 | 46 | 30 |  | 19 | 16 | 19 | 15 | 15 | 15 | 13 | 14 | 16 | 17 |
| 29. seqidno58 | 42 | 43 | 46 | 40 | 41 | 41 | 90 | 31 |  | 16 | 17 | 20 | 16 | 17 | 14 | 14 | 17 | 17 |
| 30. seqidno60 | 31 | 30 | 26 | 38 | 34 | 34 | 28 | 28 | 28 |  | 23 | 42 | 20 | 73 | 24 | 20 | 22 | 34 |
| 31. seqidno62 | 38 | 40 | 39 | 43 | 38 | 38 | 26 | 29 | 28 | 38 |  | 17 | 22 | 22 | 20 | 19 | 19 | 18 |
| 32. seqidno64 | 36 | 37 | 35 | 35 | 39 | 38 | 34 | 35 | 34 | 53 | 30 |  | 18 | 44 | 17 | 16 | 19 | 35 |
| 33. seqidno66 | 29 | 28 | 24 | 31 | 25 | 25 | 25 | 26 | 27 | 34 | 35 | 27 |  | 21 | 21 | 19 | 20 | 21 |
| 34. seqidno68 | 32 | 33 | 34 | 42 | 34 | 34 | 30 | 29 | 31 | 81 | 42 | 54 | 34 |  | 20 | 18 | 22 | 31 |
| 35. seqidno70 | 26 | 27 | 28 | 30 | 27 | 27 | 27 | 27 | 27 | 38 | 32 | 26 | 33 | 33 |  | 57 | 33 | 20 |

TABLE A2-continued

MatGAT results for global similarity and identity over the full length of the polypeptide sequences.

| 36. seqidno72 | 25 | 23 | 27 | 29 | 26 | 26 | 28 | 24 | 26 | 36 | 32 | 26 | 33 | 33 | 73 |    | 30 | 19 |
|---|---|---|---|---|---|---|---|---|---|---|---|---|---|---|---|---|---|---|
| 37. seqidno74 | 27 | 27 | 29 | 27 | 31 | 30 | 29 | 24 | 28 | 36 | 30 | 30 | 35 | 35 | 46 | 48 |    | 17 |
| 38. seqidno76 | 32 | 38 | 35 | 35 | 36 | 39 | 28 | 34 | 29 | 50 | 37 | 49 | 35 | 48 | 32 | 32 | 33 |    |

Example 4

Identification of Domains Comprised in Polypeptide Sequences Useful in Performing the Methods of the Invention The Conserved Domain Search service (CD-Search) is a web-based tool for the detection of structural and functional domains in protein sequences, hosted at NCBI. CD-Search uses BLAST® to search a comprehensive collection of domain models. Search results are displayed as domain architecture cartoons and pairwise alignments between the query and domain-model consensus sequences (Marchler-Bauer A, Bryant S H (2004), "CD-Search: protein domain annotations on the fly", Nucleic Acids Res. 32 (W) 327-331). A search (using default values) performed using a 2-Cys PRX as represented by SEQ ID NO: 2, gives as top hit is entry CD3015, PRX_Typ2cys (FIG. 2, Table A3).

TABLE A3

CDD of the polypeptide sequence as represented by SEQ ID NO: 2.

| Database | Accession number | Accession name | Description |
|---|---|---|---|
| CDD | CD3015 | PRX_Typ2cys | Peroxiredoxin (PRX) family, Typical 2-Cys PRX subfamily; PRXs are thiol-specific antioxidant (TSA) proteins, which confer a protective role in cells through its peroxidase activity by reducing hydrogen peroxide, peroxynitrite, and organic hydroperoxides |

Example 5

Subcellular Localisation Prediction of the Polypeptide Sequences Useful in Performing the Methods of the Invention TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal pre-sequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The results of TargetP 1.1 analysis of the polypeptide sequence as represented by SEQ ID NO: 2 are presented Table A4. The "plant" organism group has been selected, no cutoffs defined, and the predicted length of the transit peptide requested. The predicted subcellular localization of the polypeptide sequence as represented by SEQ ID NO: 2 is the plastidic compartment.

TABLE A4

TargetP 1.1 analysis of the polypeptide sequence as represented by SEQ ID NO: 2

| Length (AA) | 268 |
|---|---|
| Chloroplastic transit peptide | 0.987 |
| Mitochondrial transit peptide | 0.014 |
| Secretory pathway signal peptide | 0.023 |
| Other subcellular targeting | 0.018 |
| Predicted Location | Chloro |
| Reliability class | 1 |
| Predicted transit peptide length | 58 |

The predicted length according to TargetP1.1 is of 58 amino acids (starting from the N-terminus), but this can only be verified experimentally by sequencing the mature protein. Cheong et al (1999) predict a 65 amino acid transit peptide for the polypeptide as represented by SEQ ID NO: 2 (Plant Molec Biol 40: 825-834).

Many other algorithms can be used to perform such analyses, including:

- ChloroP 1.1 hosted on the server of the Technical University of Denmark;
- Protein Prowler Subcellular Localisation Predictor version 1.2 hosted on the server of the Institute for Molecular Bioscience, University of Queensland, Brisbane, Australia;
- PENCE Proteome Analyst PA-GOSUB 2.5 hosted on the server of the University of Alberta, Edmonton, Alberta, Canada;
- TMHMM, hosted on the server of the Technical University of Denmark

Example 6

Functional Assay for a 2-Cys PRX Polypeptide

2-Cys PRX polypeptides present peroxidase activity on hydrogen peroxide, for example. Enzyme assays for 2-Cys PRX proteins have been extensively described in the literature, and are well-know to a person skilled in the art. Huang et al. (2007; Appl Microbiol Biotechnol 74(1):84-92), Bernier-Villamor et al. (2004; J Exp Bot 55(406):2191-9) and Capo-raletti et al. (2007; Biochem Biophys Res Commun 355(3): 722-7) are recent publications describing the enzymatic assay of 2-Cys PRX proteins.

Example 7

Cloning of the Nucleic Acid Sequence Used in the Methods of the Invention

The nucleic acid sequence used in the methods of the invention was amplified by PCR using as template a *Brassica rapa* 2-Cys PRX clone as described in Cheong et al., (1999; Plant Molec Biol). PCR was performed using Hifi Taq DNA polymerase in standard conditions, using 200 ng of template in a 50 µl PCR mix. The primers used were prm08756 (SEQ ID NO: 81; sense, start codon in bold): 5'-ggggacaagtttgta-caaaaagcaggcttaaacaatggcgt ctgttgcttctt-3' and prm08757 (SEQ ID NO: 82; reverse, complementary): 5'-gg ggac-cactttgtacaagaaagctgggttcgagctaaatagctgagaagag-3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone", p2-Cys PRX. Plasmid pDONR201 was purchased from Invitrogen, as part of the Gateway® technology.

The entry clone comprising SEQ ID NO: 1 was then used in an LR reaction with two destination vectors used for *Oryza sativa* transformation. The vectors contained as functional elements within the T-DNA borders: a plant selectable marker; a screenable marker expression cassette; and a Gateway cassette intended for LR in vivo recombination with the nucleic acid sequence of interest already cloned in the entry clone. The first destination vector comprised upstream of this Gateway cassette the rice GOS2 promoter (SEQ ID NO: 79) for strong constitutive expression, and the second destination vector comprised the rice Rcc3 promoter for root-specific expression (SEQ ID NO: 80).

After the LR recombination step, the resulting expression vectors pGOS2::2-Cys PRX and pRcc3::2-Cys PRX (FIG. 5) were separately transformed into *Agrobacterium* strain LBA4044 according to methods well known in the art.

Example 8

Plant Transformation

Rice Transformation

The two *Agrobacterium* strains each containing one of the expression vectors as described in Example 7, used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Example 9

Phenotypic Evaluation Procedure 9.1 Evaluation Setup

Approximately 35 independent T0 rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

Drought Screen

Plants from T2 seeds from 4 events were grown in potting soil under normal conditions until they approached the heading stage. They were then transferred to a "dry" section where irrigation was withheld. Humidity probes were inserted in randomly chosen pots to monitor the soil water content (SWC). When SWC went below certain thresholds, the plants were automatically re-watered continuously until a normal level was reached again. The plants were then re-transferred again to normal conditions. The rest of the cultivation (plant maturation, seed harvest) was the same as for plants not grown under abiotic stress conditions. Growth and yield parameters were recorded as detailed for growth under normal conditions.

9.2 Statistical Analysis: F Test

A two factor ANOVA (analysis of variants) was used as a statistical model for the overall evaluation of plant phenotypic characteristics. An F test was carried out on all the parameters measured of all the plants of all the events transformed with the gene of the present invention. The F test was carried out to check for an effect of the gene over all the transformation events and to verify for an overall effect of the gene, also known as a global gene effect. The threshold for significance for a true global gene effect was set at a 5% probability level for the F test. A significant F test value points to a gene effect, meaning that it is not only the mere presence or position of the gene that is causing the differences in phenotype.

Because two experiments with overlapping events were carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P values were obtained by comparing likelihood ratio test to chi square distributions.

9.3 Parameters Measured
Biomass-Related Parameter Measurement

From the stage of sowing until the stage of maturity the plants were passed several times through a digital imaging cabinet. At each time 2-Cys PRXnt digital images (2048× 1536 pixels, 16 million colours) were taken of each plant from at least 6 different angles.

The early vigour is the plant (seedling) aboveground area three weeks post-germination. Early vigour was determined by counting the total number of pixels from aboveground plant parts discriminated from the background. This value was averaged for the pictures taken on the same time point from different angles and was converted to a physical surface value expressed in square mm by calibration. The results described below are for plants three weeks post-germination.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass.

To measure root-related parameters, plants were grown in specially designed pots with transparent bottoms to allow visualization of the roots. A digital camera recorded images through the bottom of the pot during plant growth. Root features such as total projected area (which can be correlated to total root volume), average diameter and length of roots above a certain thickness threshold (length of thick roots, or thick root length) were deduced from the picture using of appropriate software. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area ($mm^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 10

Results of the Phenotypic Evaluation of the Transgenic Plants, Grown Under Normal Growth Conditions The results of the evaluation of transgenic rice plants expressing a nucleic acid sequence encoding a 2-Cys PRX polypeptide under the control of a root-specific promoter, and grown under normal growth conditions, are presented below. Improved early vigour was observed, as well as increased seed fill rate, increased total seed yield per plant, increased number of filled seeds, increased harvest index, and increased thousand kernel weight.

TABLE A5

Results of the evaluation of transgenic rice plants expressing the nucleic acid sequence useful in performing the methods of the invention, under the control of a root-specific-promoter, grown under normal growth conditions.

| Trait | % Increase for the three best events in T1 generation | % Increase for the three best events in T2 generation |
| --- | --- | --- |
| Early vigour (seedlings) | 7% | 5% |
| Seed fill rate | 1% | 10% |
| Total seed yield per plant | 8% | 10% |
| Total numbers of filled seeds | 6% | 8% |
| Harvest index | 7% | 9% |
| Thousand kernel weight | 3% | 3% |

Transgenic rice plants expressing a nucleic acid sequence encoding a 2-Cys PRX polypeptide under the control of a constitutive promoter (a rice GOS2 promoter), and grown under normal growth conditions, showed no difference in any of the traits phenotypically examined as compared to control plants grown under comparable normal growth conditions (data not shown).

Example 11

Results of the Phenotypic Evaluation of the Transgenic Plants, Grown Under Stress Growth Conditions The results of the evaluation of transgenic rice plants expressing a nucleic acid sequence encoding a 2-Cys PRX polypeptide under the control of a root-specific promoter, and grown under drought-stress growth conditions, are presented below. Improved early vigour was observed, as well as increased aboveground biomass, increased root biomass, increased number of flowers per panicle, increased seed fill rate, increased total seed yield per plant, increased number of seeds, increased number of filled seeds, and increased harvest index.

TABLE A6

Results of the evaluation of transgenic rice plants expressing the nucleic acid sequence useful in performing the methods of the invention, under the control of a root-specific-promoter, grown under drought-stress growth conditions.

| Trait | % Increase in T2 generation (all events) |
|---|---|
| Early vigour (seedlings) | 31% |
| boveground biomass | 11% |
| Root biomass | 6% |
| Flowers per panicle | 8% |
| Seed fill rate | 8% |
| Total seed yield per plant | 18% |
| Total number of seeds | 10% |
| Total numbers of filled seeds | 17% |
| Harvest index | 8% |

Example 12

Examples of Transformation of Other Crops

Corn Transformation

Transformation of maize (Zea mays) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with Agrobacterium tumefaciens containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with Agrobacterium tumefaciens containing the expression vector, and transgenic plants are recovered through organogenesis. After incubation with Agrobacterium, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with Agrobacterium tumefaciens containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with Agrobacterium (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with Agrobacterium, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (Medicago sativa) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 μm J Bot 65:654-659). Petiole explants are cocultivated with an overnight culture of Agrobacterium tumefaciens C58C1 pMP90 (McKersie et al., 1999 Plant Physiol 119:

839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Cotton Transformation

Cotton (*Gossypium hirsutum* L.) transformation is performed using *Agrobacterium tumefaciens*, on hypocotyls explants. The commercial cultivars such as Coker 130 or Coker 312 (SeedCo, Lubbock, Tex.) are standard varieties used for transformation, but other varieties can also be used. The seeds are surface sterilized and germinated in the dark. Hypocotyl explants are cut from the germinated seedlings to lengths of about 1-1.5 centimeter. The hypotocyl explant is submersed in the *Agrobacterium tumefaciens* inoculum containing the expression vector, for 5 minutes then co-cultivated for about 48 hours on MS+1.8 mg/l KNO3+2% glucose at 24° C., in the dark. The explants are transferred the same medium containing appropriate bacterial and plant selectable markers (renewed several times), until embryogenic calli is seen. The calli are separated and subcultured until somatic embryos appear. Plantlets derived from the somatic embryos are matured on rooting medium until roots develop. The rooted shoots are transplanted to potting soil in the greenhouse. T1 seeds are produced from plants that exhibit tolerance to the selection agent and that contain a single copy of the T-DNA insert.

Example 13

Examples of Other Stress Screens

Salt Stress Screen

Plants are grown on a substrate made of coco fibers and argex (3 to 1 ratio). A normal nutrient solution is used during the first two weeks after transplanting the plantlets in the greenhouse. After the first two weeks, 25 mM of salt (NaCl) is added to the nutrient solution, until the plants were harvested.

Reduced Nutrient (Nitrogen) Availability Screen

Rice plants from T2 seeds are grown in potting soil under normal conditions except for the nutrient solution. The pots are watered from transplantation to maturation with a specific nutrient solution containing reduced N nitrogen (N) content, usually between 7 to 8 times less. The rest of the cultivation (plant maturation, seed harvest) is the same as for plants not grown under abiotic stress. Growth and yield parameters are recorded as detailed for growth under normal conditions.

Example 14

Identification of Sequences Related to the Nucleic Acid Sequence Used in the Methods of the Invention Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acid used in the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

Table B1 provides a list of nucleic acid sequences related to the nucleic acid sequence useful in the methods of the present invention.

TABLE B1

Examples of ANN polypeptides:

| Plant Source | Nucleic acid SEQ ID NO: | Protein SEQ ID NO: |
|---|---|---|
| *Arabidopsis thaliana* ANNAT1 | 83 | 84 |
| *Gossypium hirsutum* fiber annexin | 96 | 97 |
| *Lavatera thuringiaca* annexin | 98 | 99 |
| *Brassica rapa* subsp. *Pekinensis* 80C09__22 | 100 | 101 |
| *Gossypium hirsutum* annexin | 102 | 103 |
| *Capsicum annuum* Annexin 24 | 104 | 105 |
| *Nicotiana tabacum* VCaB42 | 106 | 107 |
| *Gossypium hirsutum* Anx1 | 108 | 109 |
| *Nicotiana tabacum* annexin | 110 | 111 |
| *Solanum tuberosum* annexin p34 | 112 | 113 |
| *Lycopersicon esculentum* annexin p34 | 114 | 115 |
| *Lycopersicon esculentum* annexin p35 | 116 | 117 |
| *Arabidopsis thaliana* ANNAT2 | 118 | 119 |
| *Nicotiana tabacum* annexin | 120 | 121 |
| *Solanum tuberosum* annexin p34-like | 122 | 123 |
| *Arabidopsis thaliana* ANN7 | 124 | 125 |
| *Medicago sativa* annexin | 126 | 127 |
| *Brassica rapa* subsp. *pekinensis* 80A08__20 | 128 | 129 |
| *Arabidopsis thaliana* ANNAT3 | 130 | 131 |
| *Arabidopsis thaliana* annexin 5 | 132 | 133 |
| *Arabidopsis thaliana* ANNAT4 | 134 | 135 |
| *Arabidopsis thaliana* ANN6 | 136 | 137 |
| *Arabidopsis thaliana* ANN8 At5g12380 | 138 | 139 |
| *Oryza sativa* (*japonica* cultivar-group) Os09g0394900 | 140 | 141 |
| *Oryza sativa* (*japonica* cultivar-group) Os02g0753800 | 142 | 143 |
| *Oryza sativa* (*japonica* cultivar-group) Os08g0425700 | 144 | 145 |
| *Oryza sativa* (*japonica* cultivar-group) Os06g0221200 | 146 | 147 |
| *Oryza sativa* (*japonica* cultivar-group) Os09g0453300 | 148 | 149 |
| *Oryza sativa* (*japonica* cultivar-group) Os05g0382900 | 150 | 151 |
| *Oryza sativa* (*japonica* cultivar-group) Os08g0372900 | 152 | 153 |
| *Oryza sativa* (*japonica* cultivar-group) Os03g0819300 | 154 | 155 |

In some instances, related sequences have tentatively been assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid or polypeptide sequence of interest.

Example 15

Alignment of ANN Polypeptide Sequences

Alignment of polypeptide sequences was performed using the AlignX programme from the Vector NTI (Invitrogen) which is based on the popular Clustal W algorithm of progressive alignment (Thompson et al. (1997) Nucleic Acids Res 25:4876-4882; Chenna et al. (2003). Nucleic Acids Res 31:3497-3500). Default values are for the gap open penalty of 10, for the gap extension penalty of 0, 1 and the selected weight matrix is Blosum 62 (if polypeptides are aligned). Minor manual editing was done to further optimise the alignment. Sequence conservation among ANN polypeptides is found throughout the whole sequence. The ANN polypeptides are aligned in FIG. 9.

A phylogenetic tree of ANN polypeptides (such as the one from FIG. 8) may be constructed using a neighbour-joining clustering algorithm as provided in the AlignX programme from the Vector NTI (Invitrogen).

Example 16

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

| Scoring matrix: | Blosum 62 |
|---|---|
| First Gap: | 12 |
| Extending gap: | 2 |

Results of the software analysis are shown in Table B2 for the global similarity and identity over the full length of the polypeptide sequences. Percentage identity is given above the diagonal in bold and percentage similarity is given below the diagonal (normal face).

The percentage identity between the ANN polypeptide sequences useful in performing the methods of the invention can be as low as about 30% amino acid identity compared to SEQ ID NO: 84 (NP_174810).

TABLE B2

MatGAT results for global similarity and identity over the full length of the polypeptide sequences.

| | 1 | 2 | 3 | 4 | 5 | 6 | 7 | 8 | 9 | 10 | 11 |
|---|---|---|---|---|---|---|---|---|---|---|---|
| 1. NP_174810 | | 72.6 | 71.0 | 29.9 | 68.6 | 65.2 | 67.5 | 67.8 | 65.6 | 66.2 | 65.9 |
| 2. AAC33305 | 84.5 | | 89.9 | 32.1 | 71.6 | 71.6 | 68.0 | 72.8 | 72.8 | 72.8 | 73.4 |
| 3. AAB71830 | 84.5 | 94.3 | | 30.6 | 68.8 | 67.0 | 64.2 | 68.7 | 69.0 | 68.7 | 69.0 |
| 4. AAZ41833 | 36.4 | 37.4 | 36.8 | | 32.6 | 29.4 | 33.4 | 33.9 | 29.6 | 30.0 | 30.2 |
| 5. AAB67994 | 82.3 | 84.5 | 83.2 | 38.7 | | 63.1 | 72.2 | 85.5 | 63.4 | 63.1 | 63.1 |
| 6. 1DK5 | 83.9 | 83.9 | 81.7 | 37.7 | 79.2 | | 63.6 | 64.5 | 91.0 | 91.9 | 91.6 |
| 7. AAD24540 | 81.1 | 82.6 | 81.0 | 38.7 | 83.9 | 77.6 | | 74.4 | 63.9 | 64.2 | 64.9 |
| 8. AAR13288 | 81.7 | 84.5 | 82.6 | 39.3 | 92.7 | 78.6 | 84.8 | | 65.2 | 65.2 | 66.5 |
| 9. CAA75213 | 84.2 | 85.1 | 83.2 | 37.4 | 81.0 | 95.7 | 79.1 | 80.4 | | 92.4 | 92.7 |
| 10. CAB92956 | 83.9 | 85.4 | 83.5 | 37.6 | 80.6 | 95.3 | 79.1 | 80.4 | 97.8 | | 98.4 |
| 11. AAC97494 | 83.9 | 85.4 | 83.5 | 37.6 | 80.6 | 95.3 | 79.1 | 80.4 | 97.8 | 100.0 | |
| 12. AAC97493 | 80.8 | 80.4 | 79.4 | 37.8 | 82.9 | 77.6 | 92.1 | 85.8 | 79.4 | 79.4 | 79.4 |
| 13. NP_201307 | 79.8 | 81.4 | 80.1 | 44.5 | 85.5 | 79.2 | 83.9 | 84.5 | 80.1 | 80.4 | 80.4 |
| 14. CAA75214 | 83.6 | 84.2 | 82.3 | 37.1 | 80.0 | 94.7 | 78.2 | 79.7 | 98.4 | 97.5 | 97.5 |
| 15. ABB55363 | 83.3 | 84.8 | 82.9 | 37.3 | 79.7 | 94.7 | 78.5 | 79.7 | 96.5 | 98.7 | 98.7 |
| 16. NP_196585 | 80.4 | 80.4 | 79.1 | 41.2 | 84.2 | 78.9 | 82.0 | 82.6 | 80.4 | 81.0 | 81.0 |
| 17. CAA52903 | 80.8 | 82.0 | 81.6 | 38.6 | 83.8 | 79.2 | 82.3 | 83.2 | 81.5 | 81.5 | 81.5 |
| 18. AAZ67605 | 79.2 | 79.1 | 79.1 | 41.1 | 82.6 | 78.0 | 81.6 | 82.0 | 79.4 | 79.7 | 79.7 |
| 19. NP_181410 | 59.2 | 58.6 | 58.6 | 27.8 | 61.4 | 58.4 | 61.7 | 63.2 | 58.6 | 58.9 | 58.9 |
| 20. ABE65753 | 58.4 | 56.3 | 54.7 | 27.0 | 58.5 | 54.0 | 56.6 | 59.5 | 54.7 | 55.1 | 55.1 |
| 21. NP_181409 | 56.4 | 55.2 | 53.6 | 25.3 | 53.9 | 54.7 | 54.5 | 54.2 | 55.8 | 55.8 | 55.8 |
| 22. NP_196584 | 77.4 | 78.9 | 78.6 | 41.2 | 81.8 | 78.0 | 81.1 | 81.8 | 78.3 | 79.2 | 78.9 |
| 23. NP_568271 | 69.4 | 67.1 | 67.7 | 30.9 | 68.4 | 66.5 | 66.8 | 69.0 | 66.8 | 68.0 | 67.7 |
| 24. NP_001063096 | 55.8 | 55.7 | 53.8 | 27.4 | 59.0 | 54.7 | 57.0 | 58.5 | 54.9 | 54.6 | 54.6 |
| 25. NP_001048149 | 76.0 | 78.5 | 77.5 | 35.2 | 79.4 | 74.5 | 75.3 | 79.1 | 77.1 | 77.1 | 77.1 |
| 26. NP_001061839 | 55.1 | 54.5 | 52.6 | 27.1 | 57.6 | 53.7 | 57.0 | 56.1 | 55.1 | 53.9 | 53.9 |
| 27. NP_001057176 | 78.2 | 79.8 | 80.1 | 35.2 | 79.5 | 75.8 | 77.0 | 79.5 | 76.7 | 77.0 | 77.0 |
| 28. NP_001063343 | 53.0 | 53.6 | 52.4 | 26.1 | 53.6 | 50.3 | 52.0 | 52.0 | 50.8 | 51.1 | 51.1 |
| 29. NP_001055408 | 54.3 | 52.7 | 53.0 | 30.2 | 53.8 | 55.1 | 53.8 | 54.3 | 53.0 | 53.2 | 53.2 |
| 30. NP_001061661 | 27.8 | 27.6 | 27.3 | 24.9 | 26.8 | 24.2 | 28.4 | 26.8 | 28.1 | 27.3 | 27.3 |
| 31. NP_001051711 | 17.7 | 16.8 | 17.1 | 10.2 | 16.5 | 17.4 | 14.2 | 16.8 | 17.2 | 17.5 | 17.8 |

TABLE B2-continued

MatGAT results for global similarity and identity over the full length of the polypeptide sequences.

|  | 12 | 13 | 14 | 15 | 16 | 17 | 18 | 19 | 20 | 21 | 22 |
|---|---|---|---|---|---|---|---|---|---|---|---|
| 1. NP_174810 | 65.9 | 64.0 | 65.6 | 64.9 | 63.1 | 65.0 | 62.8 | 38.5 | 34.3 | 32.3 | 60.8 |
| 2. AAC33305 | 65.5 | 67.5 | 71.8 | 71.4 | 66.5 | 69.3 | 64.9 | 41.0 | 35.6 | 34.2 | 63.8 |
| 3. AAB71830 | 63.3 | 64.4 | 68.0 | 67.3 | 63.3 | 68.4 | 62.3 | 39.8 | 34.1 | 33.0 | 61.3 |
| 4. AAZ41833 | 32.4 | 41.8 | 29.3 | 29.5 | 35.9 | 33.1 | 35.3 | 19.9 | 17.5 | 16.8 | 34.8 |
| 5. AAB67994 | 70.3 | 70.1 | 63.1 | 62.1 | 68.1 | 70.5 | 67.5 | 39.6 | 34.9 | 35.1 | 64.9 |
| 6. 1DK5 | 62.0 | 61.8 | 90.7 | 90.4 | 62.0 | 63.6 | 61.1 | 40.0 | 33.5 | 34.2 | 59.8 |
| 7. AAD24540 | 87.0 | 70.3 | 63.6 | 62.9 | 69.3 | 69.6 | 69.3 | 42.5 | 36.9 | 33.7 | 67.6 |
| 8. AAR13288 | 73.7 | 71.0 | 65.2 | 63.8 | 70.3 | 69.3 | 68.7 | 43.5 | 36.6 | 35.3 | 67.3 |
| 9. CAA75213 | 62.0 | 64.4 | 97.1 | 90.8 | 64.6 | 64.2 | 62.7 | 41.9 | 35.6 | 35.0 | 61.9 |
| 10. CAB92956 | 63.6 | 64.4 | 92.4 | 98.4 | 63.9 | 65.2 | 62.7 | 41.3 | 35.3 | 34.1 | 61.6 |
| 11. AAC97494 | 64.2 | 64.4 | 92.7 | 96.8 | 64.9 | 65.8 | 63.6 | 42.2 | 35.0 | 34.7 | 62.3 |
| 12. AAC97493 |  | 68.1 | 62.7 | 62.3 | 68.0 | 66.5 | 67.4 | 40.4 | 36.0 | 33.4 | 65.4 |
| 13. NP_201307 | 81.4 |  | 63.1 | 63.0 | 79.2 | 69.7 | 78.9 | 42.2 | 37.4 | 34.9 | 74.9 |
| 14. CAA75214 | 79.0 | 79.5 |  | 90.8 | 63.9 | 63.0 | 62.3 | 41.0 | 35.0 | 34.7 | 61.6 |
| 15. ABB55363 | 78.8 | 79.8 | 96.2 |  | 62.6 | 63.8 | 61.3 | 40.4 | 34.5 | 34.1 | 60.3 |
| 16. NP_196585 | 80.7 | 89.9 | 79.7 | 80.4 |  | 69.0 | 89.9 | 41.9 | 38.2 | 34.7 | 82.4 |
| 17. CAA52903 | 80.3 | 83.3 | 80.9 | 80.4 | 81.0 |  | 68.4 | 40.8 | 35.1 | 33.8 | 67.0 |
| 18. AAZ67605 | 80.1 | 89.9 | 78.8 | 79.1 | 95.6 | 81.3 |  | 40.4 | 36.0 | 33.8 | 82.4 |
| 19. NP_181410 | 60.1 | 57.6 | 58.3 | 58.9 | 59.5 | 58.3 | 58.3 |  | 31.9 | 33.6 | 41.4 |
| 20. ABE65753 | 55.4 | 58.0 | 55.7 | 55.1 | 58.9 | 54.7 | 58.5 | 51.7 |  | 27.4 | 36.1 |
| 21. NP_181409 | 54.9 | 53.9 | 55.8 | 55.8 | 53.0 | 51.4 | 52.0 | 54.2 | 47.6 |  | 32.6 |
| 22. NP_196584 | 80.2 | 88.4 | 77.4 | 78.6 | 91.2 | 80.8 | 91.5 | 58.6 | 58.5 | 51.7 |  |
| 23. NP_568271 | 66.5 | 66.9 | 66.8 | 68.0 | 67.7 | 68.0 | 68.4 | 63.2 | 56.6 | 55.8 | 66.0 |
| 24. NP_001063096 | 57.5 | 59.0 | 55.2 | 54.4 | 59.2 | 57.1 | 58.9 | 55.1 | 72.2 | 46.1 | 59.1 |
| 25. NP_001048149 | 74.9 | 76.0 | 76.1 | 75.9 | 76.6 | 77.1 | 75.9 | 60.1 | 57.9 | 51.1 | 74.2 |
| 26. NP_001061839 | 56.1 | 58.3 | 54.8 | 53.6 | 57.9 | 55.5 | 57.0 | 54.5 | 69.2 | 46.4 | 58.6 |
| 27. NP_001057176 | 74.8 | 76.3 | 75.7 | 76.7 | 74.8 | 76.3 | 74.4 | 60.4 | 56.8 | 48.6 | 74.2 |
| 28. NP_001063343 | 51.4 | 52.4 | 50.8 | 50.8 | 53.0 | 48.3 | 52.0 | 48.6 | 48.9 | 50.2 | 52.4 |
| 29. NP_001055408 | 53.5 | 53.8 | 53.2 | 53.2 | 53.8 | 52.4 | 53.5 | 60.2 | 44.9 | 47.3 | 53.0 |
| 30. NP_001061661 | 29.1 | 29.4 | 28.1 | 29.4 | 28.1 | 25.8 | 27.3 | 26.3 | 26.0 | 28.9 | 27.3 |
| 31. NP_001051711 | 16.8 | 16.4 | 16.2 | 17.1 | 15.2 | 19.2 | 16.8 | 16.8 | 17.1 | 17.2 | 16.7 |

|  | 23 | 24 | 25 | 26 | 27 | 28 | 29 | 30 | 31 |
|---|---|---|---|---|---|---|---|---|---|
| 1. NP_174810 | 49.4 | 35.5 | 59.6 | 36.8 | 60.2 | 28.4 | 37.2 | 12.4 | 11.3 |
| 2. AAC33305 | 51.1 | 37.4 | 63.3 | 38.8 | 64.5 | 30.2 | 38.9 | 14.1 | 10.1 |
| 3. AAB71830 | 49.2 | 35.3 | 59.8 | 36.0 | 61.8 | 29.1 | 37.8 | 15.1 | 9.2 |
| 4. AAZ41833 | 22.7 | 19.2 | 29.0 | 19.0 | 28.9 | 14.6 | 21.5 | 14.4 | 8.0 |
| 5. AAB67994 | 51.3 | 36.8 | 63.1 | 39.0 | 61.8 | 30.6 | 39.0 | 12.5 | 10.1 |
| 6. 1DK5 | 48.6 | 35.2 | 60.8 | 33.9 | 59.5 | 29.0 | 41.3 | 12.2 | 10.5 |
| 7. AAD24540 | 51.4 | 37.2 | 61.1 | 40.7 | 62.6 | 28.3 | 39.4 | 14.9 | 9.5 |
| 8. AAR13288 | 51.7 | 37.5 | 63.6 | 38.8 | 63.5 | 30.2 | 40.8 | 14.3 | 7.9 |
| 9. CAA75213 | 48.6 | 36.5 | 62.0 | 35.6 | 60.7 | 30.5 | 39.1 | 13.0 | 10.5 |
| 10. CAB92956 | 49.2 | 35.5 | 62.0 | 34.8 | 61.0 | 29.5 | 39.1 | 12.5 | 9.9 |
| 11. AAC97494 | 49.5 | 35.5 | 63.0 | 34.8 | 61.9 | 29.5 | 39.7 | 12.5 | 8.6 |
| 12. AAC97493 | 49.8 | 36.9 | 59.5 | 39.8 | 59.4 | 28.0 | 38.3 | 13.7 | 11.6 |
| 13. NP_201307 | 48.1 | 40.4 | 59.6 | 39.6 | 60.8 | 27.9 | 40.1 | 12.9 | 10.7 |
| 14. CAA75214 | 48.9 | 35.3 | 60.8 | 35.3 | 59.4 | 29.8 | 38.9 | 13.0 | 9.9 |
| 15. ABB55363 | 48.3 | 35.3 | 61.0 | 34.0 | 60.6 | 29.2 | 38.4 | 13.2 | 10.2 |
| 16. NP_196585 | 50.5 | 38.7 | 61.4 | 38.8 | 58.2 | 28.3 | 39.4 | 12.9 | 11.4 |
| 17. CAA52903 | 49.1 | 36.3 | 60.3 | 36.0 | 59.6 | 27.5 | 37.6 | 13.0 | 9.4 |
| 18. AAZ67605 | 50.2 | 37.5 | 60.1 | 37.9 | 56.6 | 28.3 | 37.5 | 12.8 | 11.1 |
| 19. NP_181410 | 45.5 | 33.4 | 41.1 | 30.3 | 42.4 | 25.5 | 41.4 | 15.0 | 11.1 |
| 20. ABE65753 | 34.3 | 53.2 | 37.0 | 50.2 | 35.5 | 27.0 | 28.8 | 14.7 | 12.3 |
| 21. NP_181409 | 34.7 | 30.1 | 33.0 | 28.2 | 31.0 | 25.4 | 30.2 | 14.1 | 10.3 |
| 22. NP_196584 | 49.5 | 37.9 | 59.1 | 37.5 | 58.1 | 29.0 | 37.6 | 12.8 | 11.3 |
| 23. NP_568271 |  | 36.5 | 51.1 | 35.9 | 52.4 | 29.2 | 38.5 | 13.3 | 12.3 |
| 24. NP_001063096 | 58.9 |  | 37.8 | 68.5 | 38.6 | 30.4 | 29.3 | 14.0 | 12.1 |
| 25. NP_001048149 | 67.1 | 59.7 |  | 37.7 | 83.9 | 29.8 | 37.4 | 14.6 | 10.8 |
| 26. NP_001061839 | 57.3 | 84.4 | 57.3 |  | 38.4 | 31.8 | 30.9 | 16.8 | 15.5 |
| 27. NP_001057176 | 69.1 | 57.4 | 90.2 | 58.3 |  | 28.1 | 39.8 | 15.4 | 11.4 |
| 28. NP_001063343 | 50.2 | 50.2 | 49.8 | 49.2 | 49.2 |  | 19.8 | 14.6 | 10.9 |
| 29. NP_001055408 | 55.6 | 46.5 | 51.6 | 46.5 | 54.8 | 38.4 |  | 15.5 | 12.1 |
| 30. NP_001061661 | 27.6 | 26.5 | 29.4 | 27.6 | 27.3 | 28.6 | 29.1 |  | 13.4 |
| 31. NP_001051711 | 19.0 | 19.0 | 17.8 | 20.6 | 17.7 | 19.4 | 16.4 | 19.6 |  |

Example 17

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Pfam is a large collection of multiple sequence alignments and hidden Markov models covering many common protein domains and families. Pfam is hosted at the Sanger Institute server in the United Kingdom. Interpro is hosted at the European Bioinformatics Institute in the United Kingdom.

The results of the InterPro scan of the polypeptide sequence as represented by SEQ ID NO: 84 are presented in Table B3.

TABLE B3

InterPro scan results (major accession numbers) of the polypeptide sequence as represented by SEQ ID NO: 84.

| Database | Accession number | Accession name | Amino acid coordinates on SEQ ID NO 84 |
|---|---|---|---|
| PRODOM | PD000143 | Annexin | [16-78]T-[88-153]T-[172-239]T-[246-313]T |
| PRINTS | PR00196 | ANNEXIN | [25-47]T-[65-81]T-[92-113]T-[255-275]T-[299-312]T |
| GENE3D | G3DSA:1.10.220.10 | Annexin | [13-82]T-[83-161]T-[166-238]T-[243-317]T |
| PANTHER | PTHR10502 | Annexin | [9-312]T |
| PFAM | PF00191 | Annexin | [15-80]T-[87-152]T-[170-236]T-[246-311]T |
| SMART | SM00335 | ANX | [28-80]T-[100-152]T-[183-232]T-[259-311]T |
| PROFILE | PS00223 | ANNEXIN | [259-311]T |
| SUPERFAMILY | SSF47874 | Annexin | [1-316]T |
| PRINTS | PR01814 | ANNEXINPLANT | [119-133]T-[161-181]T-[227-245]T |
| PANTHER | PTHR10502:SF10 | Annexin_like | [9-312]T |

Example 18

Topology Prediction of the Polypeptide Sequences Useful in Performing the Methods of the Invention TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal pre-sequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The results of TargetP 1.1 analysis of the polypeptide sequence as represented by SEQ ID NO: 84 are presented Table B4. The "plant" organism group has been selected, no cutoffs defined, and the predicted length of the transit peptide requested. The subcellular localization of the polypeptide sequence as represented by SEQ ID NO: 84 may be the cytoplasm or nucleus, no transit peptide is predicted. This prediction is in agreement with earlier reports that indicate that annexin proteins are associated to the plasma membrane, vacuole and nuclear periphery (Clark & Roux, Plant Physiol. 109, 1133-1139, 1995).

TABLE B4

TargetP 1.1 analysis of the polypeptide sequence as represented by SEQ ID NO: 84

| Length (AA) | 317 |
|---|---|
| Chloroplastic transit peptide | 0.102 |
| Mitochondrial transit peptide | 0.126 |
| Secretory pathway signal peptide | 0.045 |

TABLE B4-continued

TargetP 1.1 analysis of the polypeptide sequence as represented by SEQ ID NO: 84

| Other subcellular targeting | 0.905 |
|---|---|
| Predicted Location | / |
| Reliability class | 2 |
| Predicted transit peptide length | / |

Many other algorithms can be used to perform such analyses, including:

ChloroP 1.1 hosted on the server of the Technical University of Denmark;

Protein Prowler Subcellular Localisation Predictor version 1.2 hosted on the server of the Institute for Molecular Bioscience, University of Queensland, Brisbane, Australia;

PENCE Proteome Analyst PA-GOSUB 2.5 hosted on the server of the University of Alberta, Edmonton, Alberta, Canada;

TMHMM, hosted on the server of the Technical University of Denmark

Example 19

Functional Assay for the ANN Polypeptide

Assay for annexin-membrane interactions (Dabitz et al. Biochemistry 44, 16292-16300, 2005):
Membrane Binding Assay (Copelleting Assay).

Phospholipid vesicles are prepared following the protocol of Reeves and Dowben (J. Cell. Physiol. 73, 49-60, 1969). To assess the plant annexin-membrane binding behavior, a copelleting assay is conducted (Hofmann and Huber, Methods Enzymol. 372, 186-216, 2003).

A total amount of 0.2 µmol of phospholipids is used for each individual sample (500 µL), composed of 0.5 nmol of protein in liposome buffer and varying amounts of calcium. As a control, a sample of 0.1 nmol of protein in 100 µL of 10% SDS is prepared at this stage. All samples are centrifuged (23 000 rpm at 4° C. for 45 min), and the pellets are resuspended with 50 µL of 10% SDS and then subjected to SDS-PAGE. Gels are stained with Coomassie and analyzed densitometrically using ImageJ (Rasband, W. ImageJ, version 1.30, National Institutes of Health, Bethesda, Md., 2005). Each calcium concentration is assessed three times independently. Curve fitting is performed with SigmaPlot using a standard binding equation.

Phospholipid Vesicle Preparation.

For experiments assessing membrane surface hydrophobicity and liposome leakage, the following protocols are used. Brain phosphatidylserine (PS), egg phosphatidylcholine (PC), egg phosphatidylethanolamine (PE), nitrobenzoxadiazole phosphatidylethanolamine (NBD-PE), and lissamine rhodamine B sulfonyl phosphatidylethanolamine (Rh-PE) are from a commercial supplier. Multilamellar phospholipid vesicles (MLVs) are prepared using the method of Bangham et al. (Preparation and use of liposomes as models of biological membranes, in Methods in Membrane Biology (Korn, E. D., Ed.) pp 1-68, Plenum Press, New York, 1974). The MLVs are converted into large unilamellar vesicles (LUVs) by five freeze-thaw cycles and subsequent extrusion (five times) through 0.1 µm Nucleopore filter membranes using an extruder (Lipex Biomembranes, Vancouver, BC) at 30° C. Phosphate determination is performed according to the method of Chen et al. (Anal. Chem. 28, 1756-1758, 1956).

Membrane Surface Hydrophobicity.

An increase in membrane surface hydrophobicity is the result of dehydration of the phospholipid headgroups by either the binding of protein to the membrane surface or the creation of water-free interfaces between two vesicles, which occurs during aggregation. Changing membrane surface hydrophobicity can be observed by labeling vesicles with N-[5-(dimethylamino)-naphthalene-2-sulfonyl)-1,2-dioleoylyl-sn-glycero-3-PE (dansyl-PE), whose emission wavelength is proportional to the dielectric constant of the probe environment. In this context, pure PS, PS/PE (3:1), and PS/PC (1:1) LUVs containing 1 mol % dansyl-PE are prepared and added to a 900 µL buffer solution (final phospholipid concentration of 45 µM). The effect of annexin on these vesicles is observed at different pH values by injecting 200 nM (0.18 nmol) protein into the calcium-free sample. The samples are excited at 340 nm, and the fluorescence emission is recorded from 400 to 600 nm (23). The calcium-dependent behaviour of surface hydrophobicity is observed after monitoring the effect of protein alone.

Liposome Leakage Assay.

Annexin-phospholipid interactions may cause the destabilization of phospholipid vesicles which results in leakage of the vesicle's interior. Vesicle leakage is monitored by the fluorescence quenching of 8-aminonaphthalene-1,3,6-trisulfonic acid (ANTS) in the presence of p-xylen-bis-pyridiniumbromid (DPX). The watersoluble fluorophore ANTS and its quencher DPX are added to the buffer solution while the vesicles are prepared. Excess ANTS/DPX buffer solution is removed by gel filtration using a Sephadex G-50 column. In the undisturbed vesicles, the fluorophore and quencher are spatially close so that DPX quenches the fluorescence of ANTS. With an increasing level of vesicle leakage, ANTS and DPX are diluted into the outer buffer solution, resulting in an increase in the fluorescence of ANTS (Ellens et al., Biochemistry 24, 3099-3106, 1985).

Assay for Peroxidase Activity of Annexin 1 (Gorecka et al. 2005).

Peroxidase activity of recombinant annexin1 proteins expressed in eukaryotic or prokaryotic systems may be tested with two methods. The first method is based on the chemiluminescence of oxidized luminal. Samples containing the proteins to be analyzed, separated by non-denaturating electrophoresis, are transferred onto a nitrocellulose membrane, covered with the developing solution (ECL kit, Amersham) containing luminol, and exposed to X-ray medical film for 1 hr according to the manufacturer's protocol. Alternatively, peroxidase activity of recombinant annexin1 proteins is determined using a fluorometric method with Amplex Red reagent (Molecular Probes) on a Fluorolog 3 spectrofluorimeter (Jobin Yvon Spex, Edison, N.J.) with 1-nm slits for both excitation and emission. The assay medium (total volume of 100 µl) contains 50 mM potassium phosphate buffer, pH 7.4, 2 mM $H_2O_2$, Amplex Red reagent at a final concentration of 100 µM. Measurements are made in quartz cuvettes of optical path length of 10 mm (0.1 ml volume). Fluorescence emission of the product of Amplex Red reagent oxidation, resorufin, is recorded at $\lambda_{em}$ 590 nm ($\lambda_{exc}$ 560 nm). For the determination of the effect of protein phosphorylation on peroxidase activity AnnAt1 is prior to measurements incubated with alkaline phosphatase (Sigma, 15 U/ml) at 36° C. for 10 min in a potassium phosphate buffer, pH 7.4. A sample without AnnAt1 is used as a control.

Example 20

Cloning of the Nucleic Acid Sequence Used in the Methods of the Invention

The nucleic acid sequence used in the methods of the invention was amplified by PCR using as template a custom-made *Arabidopsis thaliana* seedlings cDNA library (in pCMV Sport 6.0; Invitrogen, Paisley, UK). PCR was performed using Hifi Taq DNA polymerase in standard conditions, using 200 ng of template in a 50 µl PCR mix. The primers used were prm08727 (SEQ ID NO: 85; sense, start codon in bold): 5'-ggggacaagtttgtacaaaaaagcaggctta aacaatg-gcgactcttaaggtttct-3' and prm09025 (SEQ ID NO: 86; reverse, complementary): 5'-ggggaccactttgtacaa-gaaagctgggtttaagcatcatcttcaccg ag-3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone", pANN. Plasmid pDONR201 was purchased from Invitrogen, as part of the Gateway® technology.

The entry clone comprising SEQ ID NO: 83 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice expansin promoter (SEQ ID NO: 95) for green-tissue specific expression was located upstream of this Gateway cassette.

In alternative embodiment, a destination vector comprising the GOS2 promoter (SEQ ID NO: 94) was used resulting in the expression vector pGOS2::ANN.

After the LR recombination step, the resulting expression vector pEXP::ANN (FIG. 10) or pGOS2::ANN was transformed into *Agrobacterium* strain LBA4044 according to methods well known in the art.

Example 21

Plant Transformation

Transformation of rice plants was carried out according to the procedure outlined in Example 8 herein.

Example 22

Phenotypic Evaluation Procedure 22.1 Evaluation setup Approximately 35 independent T0 rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

Drought Screen

Plants from T2 seeds were grown in potting soil under normal conditions until they approached the heading stage. They were then transferred to a "dry" section where irrigation was withheld. Humidity probes were inserted in randomly chosen pots to monitor the soil water content (SWC). When SWC went below certain thresholds, the plants were automatically re-watered continuously until a normal level was reached again. The plants were then re-transferred again to normal conditions. The rest of the cultivation (plant maturation, seed harvest) was the same as for plants not grown under abiotic stress conditions. Growth and yield parameters are recorded as detailed for growth under normal conditions.

Nitrogen Use Efficiency Screen

Rice plants from T2 seeds are grown in potting soil under normal conditions except for the nutrient solution. The pots are watered from transplantation to maturation with a specific nutrient solution containing reduced N nitrogen (N) content, usually between 7 to 8 times less. The rest of the cultivation (plant maturation, seed harvest) is the same as for plants not grown under abiotic stress. Growth and yield parameters are recorded as detailed for growth under normal conditions.

22.2 Statistical Analysis: F Test

A two factor ANOVA (analysis of variants) was used as a statistical model for the overall evaluation of plant phenotypic characteristics. An F test was carried out on all the parameters measured of all the plants of all the events transformed with the gene of the present invention. The F test was carried out to check for an effect of the gene over all the transformation events and to verify for an overall effect of the gene, also known as a global gene effect. The threshold for significance for a true global gene effect was set at a 5% probability level for the F test. A significant F test value points to a gene effect, meaning that it is not only the mere presence or position of the gene that is causing the differences in phenotype.

Because two experiments with overlapping events were carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P values were obtained by comparing likelihood ratio test to chi square distributions.

22.3 Parameters Measured

Biomass-Related Parameter Measurement From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass.

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area ($mm^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 23

Results of the Phenotypic Evaluation of the Transgenic Plants

Evaluation of transgenic rice plants expressing an ANN nucleic acid operably linked to a constitutive promoter, grown under non-stress conditions revealed an increase of more than 5% was observed for total seed yield, number of filled seeds, fill rate, harvest index and more than 3% for TKW. Under drought stress conditions, an increase was observed for total seed yield, number of filled seeds and fill rate.

Plants expressing an ANN nucleic acid operably linked to a green-tissue specific promoter also exhibited an increased yield, in particular increased TKW.

Example 24

Examples of Transformation of Other Crops

Transformation of other crops is described in Example 12 hereinabove.

The invention claimed is:

1. A method for enhancing seed yield in a plant relative to a control plant, comprising:
   (a) introducing and expressing in a plant, plant part, or plant cell a nucleic acid encoding a 2-cysteine peroxiredoxin (2-Cys PRX) polypeptide, wherein said nucleic acid is operably linked to a root-specific promoter; and
   (b) selecting a plant having increased seed yield relative to a control plant on the basis of said plant showing increased seed yield relative to said control plant, wherein said 2-Cys PRX polypeptide comprises from N-terminus to C-terminus:
      (1) a plastidic transit peptide; and
      (2) a 2-Cys PRX domain,
and has at least 95% sequence identity to the amino acid sequence of SEQ ID NO: 2, and wherein said 2-Cys PRX polypeptide further comprises a motif comprising the amino acid sequence of SEQ ID NO: 77 and a motif comprising the amino acid sequence of SEQ ID NO: 78.

2. The method according to claim 1, wherein said nucleic acid encoding a 2-Cys PRX polypeptide comprises the nucleic acid sequence of SEQ ID NO: 1 or a sequence capable of hybridising with the nucleic acid sequence of SEQ ID NO: 1 under conditions comprising hybridisation at 50° C. in 4×SSC or at 40° C. in 6×SSC and 50% formamide, followed by washing at 50° C. in 2×SSC.

3. The method according to claim 1, wherein said increased seed yield is one or more of: (i) increase number of flowers per panicle; (ii) increased seed fill rate; (iii) increased total seed yield per plant; (iv) increased number of (filled) seeds; (v) increased harvest index; or (vi) increased thousand kernel weight (TKW).

4. The method according to claim 1, wherein said increased seed yield is obtained under an abiotic stress.

5. The method according to claim 4, wherein said abiotic stress is osmotic stress, selected from one or more of: water stress, salt stress, oxidative stress, ionic stress, drought stress, and/or reduced nutrient availability.

6. The method according to claim 4, wherein tolerance to said abiotic stress is manifested as an enhanced yield-related trait selected from one or more of: (i) increased number of flowers per panicle; (ii) increased seed fill rate; (iii) increased total seed yield per plant; (iv) increased number of filled seeds; (v) increased harvest index; or (vi) increased thousand kernel weight (TKW), each relative to a control plant.

7. The method according to claim 1, wherein said nucleic acid encoding a 2-Cys PRX polypeptide is of plant origin.

8. A plant having increased seed yield obtained by the method according to claim 1, or a part or seed thereof, wherein said plant, or said part or seed thereof, comprises the nucleic acid encoding the 2-Cys PRX polypeptide operably linked to a root-specific promoter.

9. A method for making a plant having enhanced seed yield relative to a control plant, said method comprising the steps of:
   (i) transforming a plant, plant part, or plant cell with a DNA construct, wherein said DNA construct comprises:
      (a) a nucleic acid sequence encoding a 2-Cys PRX polypeptide comprising from N-terminus to C-terminus: (1) a plastidic transit peptide, and (2) a 2-Cys PRX domain, and having at least 95% sequence identity to the amino acid sequence of SEQ ID NO: 2;
      (b) one or more control sequences capable of driving expression of the nucleic acid sequence of (a); and optionally
      (c) a transcription termination sequence;
      wherein said 2-Cys PRX polypeptide further comprises a motif comprising the amino acid sequence of SEQ ID NO: 77 and a motif comprising the amino acid sequence of SEQ ID NO: 78;
      wherein at least one of the control sequences is a root-specific promoter; and
   (ii) selecting a plant having increased seed yield relative to a control plant on the basis of said plant showing increased seed yield relative to said control plant.

10. A plant, plant part or plant cell obtained by the method according to claim 9.

11. A transgenic plant having enhanced seed yield relative to a control plant, produced by the method of claim 9, or a transgenic plant cell or plant part derived from said transgenic plant, wherein said transgenic plant or said transgenic plant cell or plant part thereof comprises the nucleic acid encoding a 2-Cys PRX polypeptide operably linked to a root-specific promoter.

12. The transgenic plant according to claim 11, wherein said plant is a crop plant or a monocot or a cereal, or a transgenic plant cell, plant part, or harvestable part derived from said transgenic plant.

13. Products derived from the plant and/or from harvestable parts of the plant according to claim 12, wherein said harvestable parts are seeds.

14. The method according to claim 1, wherein the nucleic acid comprises the nucleic acid sequence of SEQ ID NO: 1 or a nucleic acid sequence encoding the amino acid sequence of SEQ ID NO: 2.

15. The method according to claim 9, wherein the nucleic acid sequence comprises the nucleic acid sequence of SEQ ID NO: 1 or a nucleic acid sequence encoding the amino acid sequence of SEQ ID NO: 2.

16. The plant or part thereof according to claim 8, wherein the plant is a crop plant, a monocot or a cereal.

17. A progeny of the plant according to claim 8, wherein the progeny comprises the nucleic acid transgene and has increased seed yield relative to a control plant on the basis of said progeny showing increased seed yield relative to said control plant.

18. The plant, plant part or plant cell according to claim 10, wherein the plant is a crop plant, a monocot or a cereal.

19. A progeny of the plant according to claim 10, wherein the progeny comprises the construct and has increased seed yield relative to a control plant on the basis of said progeny showing increased seed yield relative to said control plant.

20. A progeny of the transgenic plant according to claim 11, wherein the progeny comprises the nucleic acid encoding a 2-Cys PRX polypeptide operably linked to a root-specific promoter, and has increased seed yield relative to a control plant on the basis of said progeny showing increased seed yield relative to said control plant.

21. The method according to claim 9, wherein said nucleic acid sequence encoding a 2-Cys PRX polypeptide comprises the nucleic acid sequence of SEQ ID NO: 1 or a sequence capable of hybridising with the nucleic acid sequence of SEQ ID NO: 1 under conditions comprising hybridisation at 50° C. in 4×SSC or at 40° C. in 6×SSC and 50% formamide, followed by washing at 50° C. in 2×SSC.

22. The method of claim 9, wherein the increased seed yield is one or more of: (i) increased number of flowers per panicle; (ii) increased seed fill rate; (iii) increased total seed yield per plant; (iv) increased number of filled seeds; (v) increased harvest index; or (vi) increased thousand kernel weight (TKW).

* * * * *

```
                           SEQUENCE LISTING

<160> NUMBER OF SEQ ID NOS: 188

<210> SEQ ID NO 1
<211> LENGTH: 848
<212> TYPE: DNA
<213> ORGANISM: Brassica rapa

<400> SEQUENCE: 1
ttgtacaaaa aagcaggctt aaacaatggc gtctgttgct tcttcaacca ctctcatctc      60
ctcctccgct agtgttctcc cagccaccaa gtcttcgctt cttccatctc cctccctctc     120
tttccttcca accctctcct ctccttcccc atccgcttct ctccggctcc ctcgtccctc     180
tcccctcacc tcaatccgct cctcttctcg ccggagcttc gctgtcaagg cccaaaccga     240
tgatcttcca ttggttggaa acaaggcgcc tgattttgag gcagaggctg tgttcgatca     300
ggagttcatc aaggtcaagc tctctgagta cattgggaag aagtatgtga ttctctttt    360 ctaccccttg gacttcactt tcgtctgccc aacagagatt actgccttca gtgaccgata     420
tgcagaattt gagaagctga acacagaagt gttaggtgtc tctgttgata gtgtgttctc     480
ccaccttgct tgggttcaaa ccgacagaaa atctggagga cttggtgatc tcaactatcc     540
acttatatca gatgtcacta aatctatctc aaaatctttt ggagtgctca tccatgatca     600
gggaatagcg ttgagagggc ttttcataat agacaaggaa ggagtgatcc aacattcaac     660
catcaacaat cttggtattg gccgaagtgt tgatgagaca atgagaaccc ttcaggcatt     720
acagtacatc caggagaacc ctgatgaagt ctgccctgca ggatggaaac caggggagaa     780
gtcaatgaaa cctgacccca agctcagcaa agagtacttc tcagctattt agctcgaacc     840
cagctttc                                                              848

<210> SEQ ID NO 2
<211> LENGTH: 268
<212> TYPE: PRT
<213> ORGANISM: Brassica rapa

<400> SEQUENCE: 2

Met Ala Ser Val Ala Ser Ser Thr Thr Leu Ile Ser Ser Ser Ala Ser
1               5                   10                  15

Val Leu Pro Ala Thr Lys Ser Ser Leu Leu Pro Ser Pro Ser Leu Ser
            20                  25                  30

Phe Leu Pro Thr Leu Ser Ser Pro Ser Pro Ser Ala Ser Leu Arg Leu
        35                  40                  45

Pro Arg Pro Ser Pro Leu Thr Ser Ile Arg Ser Ser Ser Arg Arg Ser
    50                  55                  60

Phe Ala Val Lys Ala Gln Thr Asp Asp Leu Pro Leu Val Gly Asn Lys
65                  70                  75                  80

Ala Pro Asp Phe Glu Ala Glu Ala Val Phe Asp Gln Glu Phe Ile Lys
```

```
                    85                  90                  95
Val Lys Leu Ser Glu Tyr Ile Gly Lys Lys Tyr Val Ile Leu Phe Phe
                100                 105                 110

Tyr Pro Leu Asp Phe Thr Phe Val Cys Pro Thr Glu Ile Thr Ala Phe
            115                 120                 125

Ser Asp Arg Tyr Ala Glu Phe Glu Lys Leu Asn Thr Glu Val Leu Gly
        130                 135                 140

Val Ser Val Asp Ser Val Phe Ser His Leu Ala Trp Val Gln Thr Asp
145                 150                 155                 160

Arg Lys Ser Gly Gly Leu Gly Asp Leu Asn Tyr Pro Leu Ile Ser Asp
                165                 170                 175

Val Thr Lys Ser Ile Ser Lys Ser Phe Gly Val Leu Ile His Asp Gln
                180                 185                 190

Gly Ile Ala Leu Arg Gly Leu Phe Ile Ile Asp Lys Glu Gly Val Ile
            195                 200                 205

Gln His Ser Thr Ile Asn Asn Leu Gly Ile Gly Arg Ser Val Asp Glu
        210                 215                 220

Thr Met Arg Thr Leu Gln Ala Leu Gln Tyr Ile Gln Glu Asn Pro Asp
225                 230                 235                 240

Glu Val Cys Pro Ala Gly Trp Lys Pro Gly Glu Lys Ser Met Lys Pro
                245                 250                 255

Asp Pro Lys Leu Ser Lys Glu Tyr Phe Ser Ala Ile
            260                 265

<210> SEQ ID NO 3
<211> LENGTH: 841
<212> TYPE: DNA
<213> ORGANISM: Brassica rapa
<220> FEATURE:
<221> NAME/KEY: misc_feature
<222> LOCATION: (662)..(662)
<223> OTHER INFORMATION: n is a, c, g, or t

<400> SEQUENCE: 3
gccatatggc gtctgttgct tcttcaacca ctctcatctc ctcctccgct agtgttctcc      60
cagccaccaa gtcttcgctt cttccatctc cctccctctc tttccttcca accctctcct    120
ctccttcccc atccgcttct ctccggtccc tcgtccctct cccctcacct caatccgctt    180
cctcttctcg ccggagcttc gctgtcaagg gccaaaccga tgatcttcca ttggttggaa    240
acaaggcgcc tgattttgag gcagagggtg tgttcgatca ggagttcatc aagttcatca    300
aggtcaagct ctctgattac attgggaaaa agtatgtgat tctcttttt ctacccttg     360 acttcacttt cgtctgccca acagaaatta ctgccttcag tgaccgatat gcagaatttg    420
agaagctgaa tacagaagtg ttaggtgttt ctgttgatag tgtgagtgtg ttctcccacc    480
ttgctggggt tcaaaccgac agaaaatttg gaggacttgg tgatctcaac tatccactta    540
tatcagatgt cactaaatct atctcaaaat cttttggagt gctcatccat gatcagggaa    600
tagcgttgag agggcttttc ataatagaca aggaaggagt gatccaacat tcaaccatca    660
anaatcttgg tattggccga agtgttgatg agacaatgag aacccttcag gcattacagt    720
acatccagga aggccctggt gaagtctgcc ctgcaggatg aaaccaggg  gagaagtcaa     780 tgaaacctga ccccaagctc agcaaagagc tcttctcagc tatttagctc gaggctaagc    840
c                                                                      841

<210> SEQ ID NO 4
```

```
<211> LENGTH: 273
<212> TYPE: PRT
<213> ORGANISM: Brassica rapa
<220> FEATURE:
<221> NAME/KEY: UNSURE
<222> LOCATION: (219)..(219)
<223> OTHER INFORMATION: Xaa can be any naturally occurring amino acid

<400> SEQUENCE: 4

Met Ala Ser Val Ala Ser Ser Thr Thr Leu Ile Ser Ser Ala Ser
1               5                   10                  15

Val Leu Pro Ala Thr Lys Ser Ser Leu Leu Pro Ser Pro Ser Leu Ser
            20                  25                  30

Phe Leu Pro Thr Leu Ser Ser Pro Ser Pro Ser Ala Ser Leu Arg Ser
        35                  40                  45

Leu Val Pro Leu Pro Ser Pro Gln Ser Ala Ser Ser Arg Arg Ser
    50                  55                  60

Phe Ala Val Lys Gly Gln Thr Asp Asp Leu Pro Leu Val Gly Asn Lys
65              70                  75                  80

Ala Pro Asp Phe Glu Ala Glu Gly Val Phe Asp Gln Glu Phe Ile Lys
                85                  90                  95

Phe Ile Lys Val Lys Leu Ser Asp Tyr Ile Gly Lys Lys Tyr Val Ile
            100                 105                 110

Leu Phe Phe Leu Pro Leu Asp Phe Thr Phe Val Cys Pro Thr Glu Ile
        115                 120                 125

Thr Ala Phe Ser Asp Arg Tyr Ala Glu Phe Glu Lys Leu Asn Thr Glu
    130                 135                 140

Val Leu Gly Val Ser Val Asp Ser Val Ser Val Phe Ser His Leu Ala
145                 150                 155                 160

Gly Val Gln Thr Asp Arg Lys Phe Gly Gly Leu Gly Asp Leu Asn Tyr
                165                 170                 175

Pro Leu Ile Ser Asp Val Thr Lys Ser Ile Ser Lys Ser Phe Gly Val
            180                 185                 190

Leu Ile His Asp Gln Gly Ile Ala Leu Arg Gly Leu Phe Ile Ile Asp
        195                 200                 205

Lys Glu Gly Val Ile Gln His Ser Thr Ile Xaa Asn Leu Gly Ile Gly
    210                 215                 220

Arg Ser Val Asp Glu Thr Met Arg Thr Leu Gln Ala Leu Gln Tyr Ile
225                 230                 235                 240

Gln Glu Gly Pro Gly Glu Val Cys Pro Ala Gly Trp Lys Pro Gly Glu
                245                 250                 255

Lys Ser Met Lys Pro Asp Pro Lys Leu Ser Lys Glu Leu Phe Ser Ala
            260                 265                 270

Ile

<210> SEQ ID NO 5
<211> LENGTH: 1002
<212> TYPE: DNA
<213> ORGANISM: Arabidopsis thaliana

<400> SEQUENCE: 5
gtgattgaca gatagataag agtgtttggt agctcagact cagagagtca caaagtgtgt      60
gtagcagcaa tggcgtctgt tgcttcttca actactctca tctcttctcc ctcttctagg     120
gttttttcag caaagtcttc actttcctct ccatctgttt ctttccttcg aaccctttct     180
tctccttccg catctgcttc tctccgctcc ggatttgctc gacgctcttc cctcagctcc     240
```

```
acttctcgtc ggagctttgc tgtcaaagcc caggccgatg atcttccact ggttggaaac    300
aaggcgcctg attttgaggc agaggctgtg tttgatcaag agttcatcaa ggttaagctc    360
tctgattaca ttggaaagaa gtatgtgatt ctcttttttct acccattgga ctttactttc    420
gtctgcccaa cagagattac tgccttcagt gaccggcatt cagaatttga aagttgaac     480
accgaagtat taggtgtttc tgtcgatagt gtgttctctc accttgcatg ggtccaaaca    540
gacaggaaat ctggagggct tggtgatctg aactatcccc ttatttcata tttcactaaa    600
tcaatctcaa agtcgttcgg agtgctcatc catgatcagg gaatagcact gagaggactt    660
ttcataatcg acaaggaagg agtgatccaa cattccacca tcaacaatct tggtattggc    720
caaagcgttg atgagacaat gagaaccctc caggcattac agtacatcca ggaaaacccg    780
gatgaagtct gcccagcagg atggaagccg ggtgagaagt caatgaaacc cgacccaaaa    840
ctcagcaaag agtacttctc agctatttag aaactctact atgatagcaa aaaggtacaa    900
tctttgttat atgtgagcag agttttttttt cttgtacgct aaaacaatcc tttgtttgat    960
tctcactttg tccccaaaat tataataaaa aacttttttcc gc                     1002
```

<210> SEQ ID NO 6
<211> LENGTH: 266
<212> TYPE: PRT
<213> ORGANISM: Arabidopsis thaliana

<400> SEQUENCE: 6

```
Met Ala Ser Val Ala Ser Ser Thr Thr Leu Ile Ser Pro Ser Ser
1               5                   10                  15

Arg Val Phe Pro Ala Lys Ser Ser Leu Ser Ser Pro Ser Val Ser Phe
                20                  25                  30

Leu Arg Thr Leu Ser Ser Pro Ser Ala Ser Ala Ser Leu Arg Ser Gly
            35                  40                  45

Phe Ala Arg Arg Ser Ser Leu Ser Ser Thr Ser Arg Arg Ser Phe Ala
        50                  55                  60

Val Lys Ala Gln Ala Asp Asp Leu Pro Leu Val Gly Asn Lys Ala Pro
65                  70                  75                  80

Asp Phe Glu Ala Glu Ala Val Phe Asp Gln Glu Phe Ile Lys Val Lys
                85                  90                  95

Leu Ser Asp Tyr Ile Gly Lys Lys Tyr Val Ile Leu Phe Phe Tyr Pro
            100                 105                 110

Leu Asp Phe Thr Phe Val Cys Pro Thr Glu Ile Thr Ala Phe Ser Asp
        115                 120                 125

Arg His Ser Glu Phe Glu Lys Leu Asn Thr Glu Val Leu Gly Val Ser
    130                 135                 140

Val Asp Ser Val Phe Ser His Leu Ala Trp Val Gln Thr Asp Arg Lys
145                 150                 155                 160

Ser Gly Gly Leu Gly Asp Leu Asn Tyr Pro Leu Ile Ser Tyr Phe Thr
                165                 170                 175

Lys Ser Ile Ser Lys Ser Phe Gly Val Leu Ile His Asp Gln Gly Ile
            180                 185                 190

Ala Leu Arg Gly Leu Phe Ile Ile Asp Lys Glu Gly Val Ile Gln His
        195                 200                 205

Ser Thr Ile Asn Asn Leu Gly Ile Gly Gln Ser Val Asp Glu Thr Met
    210                 215                 220

Arg Thr Leu Gln Ala Leu Gln Tyr Ile Gln Glu Asn Pro Asp Glu Val
225                 230                 235                 240
```

```
Cys Pro Ala Gly Trp Lys Pro Gly Glu Lys Ser Met Lys Pro Asp Pro
            245                 250                 255

Lys Leu Ser Lys Glu Tyr Phe Ser Ala Ile
        260                 265

<210> SEQ ID NO 7
<211> LENGTH: 988
<212> TYPE: DNA
<213> ORGANISM: Brassica napus

<400> SEQUENCE: 7
gtcgaccacg cgtccggaga gaaagagaga gagagcagag ttcttcagtc catggcttcc    60
ttagcttcaa ccaccacact tatctcttca tctagcgttc ttcttccctc aaagccttct   120 ccttttctc ccgccgcctc cttcctccga actcttcctt ctacctccgt atctacctcc    180
tcttctctcc gctcctgttt ctccagcatc agtcccctca cctgcatccg ctcttcctct   240
cgccctagct tcgccgtcaa ggcccaggct gatgatttgc cactggttgg taacaaggcg   300
cctgattttg aggcagaggc tgtttttgac caagagttca tcaaggtgaa gctctcagag   360
tacattggta aaagtatgt gattctgttt ctctacccctt tggacttcac ttttgtctgc    420
cctacggaga ttactgcctt cagtgaccgt tatgaagaat tgagaagct aaacacggaa    480 gtgttaggtg tctcagtcga cagtgtgttc tcgcatcttg cgtgggtcca acagagaga    540 aagtcaggag ggctgggtga cctgaactac ccacttgtct ctgatatcac taaatccatt   600
tcaaaatctt ttggagtgct catccctgat cagggcattg cactgagagg cttttcatc    660 atcgacaaaa aaggagtcat acagcattcc acaatcaaca acctcggtat tggccgaagc   720
gttgatgaga caatgagaac cctccaggca ttgcagtatg ttcaagaaaa ccctgatgag   780
gtttgccccg cgggatggaa gcctggggag aaatcgatga gcctgacccc caagctgagc   840
aaagagtatt tttcagctat ttaaaggctt tttaaacaaa tgattggtga aaagcagagg   900
catgttttgt cttcattgct tatgtttctg ctatgtgtgt tttcctcaaa attgaataaa   960
aataatggaa tttaaaaaaa aaaaaaaa                                      988

<210> SEQ ID NO 8
<211> LENGTH: 270
<212> TYPE: PRT
<213> ORGANISM: Brassica napus

<400> SEQUENCE: 8

Met Ala Ser Leu Ala Ser Thr Thr Thr Leu Ile Ser Ser Ser Ser Val
1               5                   10                  15

Leu Leu Pro Ser Lys Pro Ser Pro Phe Ser Pro Ala Ala Ser Phe Leu
            20                  25                  30

Arg Thr Leu Pro Ser Thr Ser Val Ser Thr Ser Ser Ser Leu Arg Ser
        35                  40                  45

Cys Phe Ser Ser Ile Ser Pro Leu Thr Cys Ile Arg Ser Ser Ser Arg
    50                  55                  60

Pro Ser Phe Ala Val Lys Ala Gln Ala Asp Asp Leu Pro Leu Val Gly
65                  70                  75                  80

Asn Lys Ala Pro Asp Phe Glu Ala Glu Ala Val Phe Asp Gln Glu Phe
                85                  90                  95

Ile Lys Val Lys Leu Ser Glu Tyr Ile Gly Lys Lys Tyr Val Ile Leu
            100                 105                 110

Phe Leu Tyr Pro Leu Asp Phe Thr Phe Val Cys Pro Thr Glu Ile Thr
        115                 120                 125
```

```
Ala Phe Ser Asp Arg Tyr Glu Glu Phe Glu Lys Leu Asn Thr Glu Val
        130                 135                 140

Leu Gly Val Ser Val Asp Ser Val Phe Ser His Leu Ala Trp Val Gln
145                 150                 155                 160

Thr Glu Arg Lys Ser Gly Gly Leu Gly Asp Leu Asn Tyr Pro Leu Val
                165                 170                 175

Ser Asp Ile Thr Lys Ser Ile Ser Lys Ser Phe Gly Val Leu Ile Pro
            180                 185                 190

Asp Gln Gly Ile Ala Leu Arg Gly Leu Phe Ile Ile Asp Lys Lys Gly
        195                 200                 205

Val Ile Gln His Ser Thr Ile Asn Asn Leu Gly Ile Gly Arg Ser Val
    210                 215                 220

Asp Glu Thr Met Arg Thr Leu Gln Ala Leu Gln Tyr Val Gln Glu Asn
225                 230                 235                 240

Pro Asp Glu Val Cys Pro Ala Gly Trp Lys Pro Gly Glu Lys Ser Met
                245                 250                 255

Lys Pro Asp Pro Lys Leu Ser Lys Glu Tyr Phe Ser Ala Ile
                260                 265                 270

<210> SEQ ID NO 9
<211> LENGTH: 1146
<212> TYPE: DNA
<213> ORGANISM: Arabidopsis thaliana

<400> SEQUENCE: 9
agctatttgg tttctctatc cgattcgtct ctctcacgcc ctcacgttta tccacctcat      60
cctcaaacca aaccacaaga cctcttttt aagtaaccaa tcacagagag atagagagag     120
agaacagagt caatgtcaat ggcgtctata gcttcttctt cttccaccac cctactctct     180
tcctctaggg ttcttcttcc ctccaagtct tctctttat ctcctaccgt ctctttcccc     240
agaatcatac cctcttcctc ggcatcatcc tcttctctct gttccgggtt ctccagtctc     300
ggttccctca ccaccaaccg ctccgcctca cgccggaact tcgccgtcaa ggctcaggct     360
gatgatttac cactggtcgg taataaggcg cctgattttg aagctgaggc agttttgat      420 caagagttca taaaggtgaa gctctctgag tacattggca aaaagtatgt tattctattc     480
ttctaccctt tggacttcac ttttgtctgc cccactgaga ttactgcctt cagtgaccgt     540
tatgaagaat ttgagaagct aaacaccgaa gtattagggg tctctgtcga cagtgtgttc     600
tcgcatcttg cgtgggtcca aacagacaga aagtcgggag ggctcggtga tctgaattat     660
cctcttgttt cggatatcac taaatccatt tcaaaatcgt ttggagtgct catccctgat     720
cagggcattg cactgagagg gcttttcatc atagacaagg aaggagtcat tcagcattcc     780
accatcaaca acctcggtat tggccgaagt gttgatgaga caatgagaac cctccaggca     840
ttacagtatg ttcaagaaaa cccggatgaa gtgtgccctg cgggatggaa gccaggggag     900
aaatcaatga aacctgaccc caagctcagc aagaatact tttcagctat ctagaggcta     960
agattgaaca catgtttggt gaaaattagc aatcagagtt gttttattcg tcttttcaaa    1020
gttggagcag agttgttatt tttagccaaa gaacctttgt atctatctca tctttctcct    1080
gtttctgcta tgtgattctc cttaaattga atcaaaaata agaaatcct tcttttcttt    1140 tgccaa                                                                1146

<210> SEQ ID NO 10
<211> LENGTH: 271
```

<212> TYPE: PRT
<213> ORGANISM: Arabidopsis thaliana

<400> SEQUENCE: 10

```
Met Ala Ser Ile Ala Ser Ser Ser Thr Thr Leu Ser Ser
1               5                   10

Arg Val Leu Leu Pro Ser Lys Ser Ser Leu Leu Ser Pro Thr Val Ser
            20                  25                  30

Val Pro Arg Thr Leu His Ser Ser Ala Ser Ser Ser Leu Cys
        35                  40                  45

Ser Gly Phe Ser Ser Leu Gly Ser Leu Thr Thr Ser Arg Ser Ala Ser
    50                  55                  60

Arg Arg Asn Phe Ala Val Lys Ala Gln Ala Asp Asp Leu Pro Leu Val
65                  70                  75                  80

Gly Asn Lys Ala Pro Asp Phe Glu Ala Glu Ala Val Phe Asp Gln Glu
                85                  90                  95

Phe Ile Lys Val Lys Leu Ser Glu Tyr Ile Gly Lys Lys Tyr Val Ile
            100                 105                 110

Leu Phe Phe Tyr Pro Leu Asp Phe Thr Phe Val Cys Pro Thr Glu Ile
        115                 120                 125

Thr Ala Phe Ser Asp Arg Tyr Glu Glu Phe Glu Lys Leu Asn Thr Glu
    130                 135                 140

Val Leu Gly Val Ser Val Asp Ser Val Phe Ser His Leu Ala Trp Val
145                 150                 155                 160

Gln Thr Asp Arg Lys Ser Gly Gly Leu Gly Asp Leu Asn Tyr Pro Leu
                165                 170                 175

Val Ser Asp Ile Thr Lys Ser Ile Ser Lys Ser Phe Gly Val Leu Ile
            180                 185                 190

Pro Asp Gln Gly Ile Ala Leu Arg Gly Leu Phe Ile Ile Asp Lys Glu
        195                 200                 205

Gly Val Ile Gln His Ser Thr Ile Asn Asn Leu Gly Ile Gly Arg Ser
    210                 215                 220

Val Asp Glu Thr Met Arg Thr Leu Gln Ala Leu Gln Tyr Val Gln Glu
225                 230                 235                 240

Asn Pro Asp Glu Val Cys Pro Ala Gly Trp Lys Pro Gly Glu Lys Ser
                245                 250                 255

Met Lys Pro Asp Pro Lys Leu Ser Lys Glu Tyr Phe Ser Ala Ile
            260                 265                 270
```

<210> SEQ ID NO 11
<211> LENGTH: 867
<212> TYPE: DNA
<213> ORGANISM: Spinacia oleracea

<400> SEQUENCE: 11

```
gtgtgtagca gcaatggcgt gtgttgcttc ttcaactact ctcatctctt ctccctcttc    60
tagggttttt ccagcaaagt cttcactttc ctctccatct gtttctttcc ttcgaaccct   120
ttcttctcct tccgcatctg cttctctccg ctccggattt gctcgacgct cttccctcag   180
ctccacttct cgtcggagct tgctgtcaa agcccaggcc gatgatcttc cactggttgg    240
aaacaaggcg cctgattttg aggcagaggc tgtgtttgat caagagttca tcaaggttaa   300
gctctctgat tacattggaa agaagtatgt gattctgttt tctacccat tggactttac     360 tttcgtctgc ccaacagaga ttactgcctt cagtgaccgg cattcagaat tgagaagtt    420 gaacaccgaa gtattaggtg tttctgtcga tagtgtgttc tctcaccttg catgggtcca   480
```

```
aacagacagg aaatctggag ggcttggtga tctgaactat ccccttattt cagatgtcac    540
taaatcaatc tcaaagtcgt tcggagtgct catccatgat cagggaatag cactgagagg    600
acttttcata atcgacaagg aaggagtgat ccaacattcc accatcaaca atcttggtat    660
tggccgaagc gttgatgaga caatgagaac cctccaggca ttacagtaca caggaaaccc    720
ggatgaagtc tgcccagcag gatggaagcc gggtgagaag tcaatgaaac ccgacccaaa    780
actcagcaag gagtacttct cagctattta gaactctact atgatagcaa aggtacatct    840
ttgttatatg tgagcagagt ttttctg                                        867
```

<210> SEQ ID NO 12
<211> LENGTH: 265
<212> TYPE: PRT
<213> ORGANISM: Spinacia oleracea

<400> SEQUENCE: 12

```
Met Ala Cys Val Ala Ser Ser Thr Thr Leu Ile Ser Ser Pro Ser Ser
1               5                   10                  15

Arg Val Phe Pro Ala Lys Ser Ser Leu Ser Ser Pro Ser Val Ser Phe
            20                  25                  30

Leu Arg Thr Leu Ser Ser Pro Ser Ala Ser Ala Ser Leu Arg Ser Gly
        35                  40                  45

Phe Ala Arg Arg Ser Ser Leu Ser Ser Thr Ser Arg Arg Ser Phe Ala
    50                  55                  60

Val Lys Ala Gln Ala Asp Asp Leu Pro Leu Val Gly Asn Lys Ala Pro
65                  70                  75                  80

Asp Phe Glu Ala Glu Ala Val Phe Asp Gln Glu Phe Ile Lys Val Lys
                85                  90                  95

Leu Ser Asp Tyr Ile Gly Lys Lys Tyr Val Ile Leu Phe Phe Tyr Pro
            100                 105                 110

Leu Asp Phe Thr Phe Val Cys Pro Thr Glu Ile Thr Ala Phe Ser Asp
        115                 120                 125

Arg His Ser Glu Phe Glu Lys Leu Asn Thr Glu Val Leu Gly Val Ser
    130                 135                 140

Val Asp Ser Val Phe Ser His Leu Ala Trp Val Gln Thr Asp Arg Lys
145                 150                 155                 160

Ser Gly Gly Leu Gly Asp Leu Asn Tyr Pro Leu Ile Ser Asp Val Thr
                165                 170                 175

Lys Ser Ile Ser Lys Ser Phe Gly Val Leu Ile His Asp Gln Gly Ile
            180                 185                 190

Ala Leu Arg Gly Leu Phe Ile Ile Asp Lys Glu Gly Val Ile Gln His
        195                 200                 205

Ser Thr Ile Asn Asn Leu Gly Ile Gly Arg Ser Val Asp Glu Thr Met
    210                 215                 220

Arg Thr Leu Gln Ala Leu Gln Tyr Thr Gly Asn Pro Asp Glu Val Cys
225                 230                 235                 240

Pro Ala Gly Trp Lys Pro Gly Glu Lys Ser Met Lys Pro Asp Pro Lys
                245                 250                 255

Leu Ser Lys Glu Tyr Phe Ser Ala Ile
            260                 265
```

<210> SEQ ID NO 13
<211> LENGTH: 990
<212> TYPE: DNA
<213> ORGANISM: Nicotiana tabacum

<400> SEQUENCE: 13

```
ggcacgagct cctatccaat ggcttgctct gcttcttcta cagcacttct ttcttccaac      60
ccaaaagcag cttccatttc ccccaaatcc tcctttcaag ctcccatttc tcaatgttta     120
tctgtacctt cctctttcaa tgggctccgt aattgcaagc cttttgtttc tcgtgtagcc     180
cgttccctct ctactcgcgt tgctcaatcc caacgccgtc gtttcgttgt tcgtgcctct     240
agtgaacttc cacttgttgg aaatcaagcg ccagactttg aggctgaagc tgttttttgat    300
caagaattca tcaaggttaa actatctgag tacattggga agaagtatgt cattctcttt     360
ttctacccac tagactttac atttgtttgc ccaacagaga tcactgcttt cagtgaccgt     420
tatggagaat ttgaaaagtt gaacacagaa atattgggtg tttccgtaga cagtgtgttc     480
tcccaccttg cctgggttca aactgataga aagtctggtg gcctaggtga tctgaactat     540
ccattaattt ccgacgtgac caagtcaatt tcaaaatcat acaatgttct gatccccgat     600
cagggaattg cattgagagg acttttcatc attgacaagg aaggagttat tcagcattca     660
accattaaca atcttggaat tggtcgtagt gttgatgaaa cattgagaac tcttcaggca     720
ttgcaatacg ttcaggataa cccggatgaa gtgtgcccag ctggatggaa gcctggggag     780
aaatccatga agcctgaccc caagggtagc aaagaatact ttgcatccat atgaggtgat     840
gactgcaatt gctttatcta atttgttgtt taggaaggct ggagacccta cttttctgtt     900
acatttttct aatgtaccgg ctgagtttgg tcattttttga gaatatatac acttgtacac     960
ttttaaaaaa aaaaaaaaaa aaaaaaaaaa                                       990
```

<210> SEQ ID NO 14
<211> LENGTH: 271
<212> TYPE: PRT
<213> ORGANISM: Nicotiana tabacum

<400> SEQUENCE: 14

```
Met Ala Cys Ser Ala Ser Ser Thr Ala Leu Leu Ser Ser Asn Pro Lys
1               5                  10                  15

Ala Ala Ser Ile Ser Pro Lys Ser Ser Phe Gln Ala Pro Ile Ser Gln
            20                  25                  30

Cys Leu Ser Val Pro Ser Ser Phe Asn Gly Leu Arg Asn Cys Lys Pro
        35                  40                  45

Phe Val Ser Arg Val Ala Arg Ser Leu Ser Thr Arg Val Ala Gln Ser
    50                  55                  60

Gln Arg Arg Arg Phe Val Val Arg Ala Ser Ser Glu Leu Pro Leu Val
65                  70                  75                  80

Gly Asn Gln Ala Pro Asp Phe Glu Ala Glu Ala Val Phe Asp Gln Glu
                85                  90                  95

Phe Ile Lys Val Lys Leu Ser Glu Tyr Ile Gly Lys Lys Tyr Val Ile
            100                 105                 110

Leu Phe Phe Tyr Pro Leu Asp Phe Thr Phe Val Cys Pro Thr Glu Ile
        115                 120                 125

Thr Ala Phe Ser Asp Arg Tyr Gly Glu Phe Glu Lys Leu Asn Thr Glu
    130                 135                 140

Ile Leu Gly Val Ser Val Asp Ser Val Phe His Leu Ala Trp Val
145                 150                 155                 160

Gln Thr Asp Arg Lys Ser Gly Gly Leu Gly Asp Leu Asn Tyr Pro Leu
                165                 170                 175

Ile Ser Asp Val Thr Lys Ser Ile Ser Lys Ser Tyr Asn Val Leu Ile
```

```
                    180                 185                 190
Pro Asp Gln Gly Ile Ala Leu Arg Gly Leu Phe Ile Ile Asp Lys Glu
        195                 200                 205

Gly Val Ile Gln His Ser Thr Ile Asn Asn Leu Gly Ile Gly Arg Ser
    210                 215                 220

Val Asp Glu Thr Leu Arg Thr Leu Gln Ala Leu Gln Tyr Val Gln Asp
225                 230                 235                 240

Asn Pro Asp Glu Val Cys Pro Ala Gly Trp Lys Pro Gly Glu Lys Ser
                245                 250                 255

Met Lys Pro Asp Pro Lys Gly Ser Lys Glu Tyr Phe Ala Ser Ile
                260                 265                 270

<210> SEQ ID NO 15
<211> LENGTH: 944
<212> TYPE: DNA
<213> ORGANISM: Phaseolus vulgaris

<400> SEQUENCE: 15
tctattctat ctacactcac tctctcactc tcccactctc ccatggcttc ctcagctccc      60
tgtgcttctc tcatatcctc aaaccctaac attctcttct ctcccaaatt cccttcttct     120
tcctttcctt ccctctcctt ccccaattcc ccaactctc ttttcaaacc tttacgcact      180
tctctcaatc cttcatctcc ccctctcaga accttcgttg ccagggcttc gagtgaactt     240
ccattagttg ggaacacagc accggatttt gaagcagagg ccgttttga tcaggagttc      300 atcaaggtca aactatctga ttatattggg aaaaaatatg ttatcctctt tttctatcca    360
ctggacttca cattcgtttg tccgacagaa atcactgcct tcagtgaccg gtatgcagag     420
tttgaggcac taaatacaga aattttgggt gtttcagttg acagtgtttt ttcacacctt     480
gcatgggttc aaactgatag aaagtcgggt ggtcttggcg acttgaatta tccattgatt    540
tctgatgtca ccaaatccat ctcaaaatct tatgatgttc tcattcccga tcagggggatt   600 gcattgagag gattgttcat tattgacaag gaagggggtta ttcagcattc taccattaac    660
aacctggcca ttggtagaag tgttgatgag acaaagagaa cgctccaggc cttgcagtat    720
gtgcaggaga acccagatga agtttgccca gctgggtgga agcctggtga agtccatg      780 aaaccagacc ctaaacttag caaagagtac ttctctgcta tttagggagg ataatggttg     840
aagagtagca attgctcata tgtatcaatc aatgataatt tgtataatgc aacgcaagtt     900
tataaagttt tgattgagag ggtctcatga ttatacaaaa aaaa                      944

<210> SEQ ID NO 16
<211> LENGTH: 260
<212> TYPE: PRT
<213> ORGANISM: Phaseolus vulgaris

<400> SEQUENCE: 16

Met Ala Ser Ser Ala Pro Cys Ala Ser Leu Ile Ser Ser Asn Pro Asn
1               5                   10                  15

Ile Leu Phe Ser Pro Lys Phe Pro Ser Ser Ser Phe Ser Ser Leu Ser
            20                  25                  30

Phe Pro Asn Ser Pro Asn Ser Leu Phe Lys Pro Leu Arg Thr Ser Leu
        35                  40                  45

Asn Pro Ser Ser Pro Leu Arg Thr Phe Val Ala Arg Ala Ser Ser
    50                  55                  60

Glu Leu Pro Leu Val Gly Asn Thr Ala Pro Asp Phe Glu Ala Glu Ala
65                  70                  75                  80
```

Val Phe Asp Gln Glu Phe Ile Lys Val Lys Leu Ser Asp Tyr Ile Gly
            85                  90                  95

Lys Lys Tyr Val Ile Leu Phe Phe Tyr Pro Leu Asp Phe Thr Phe Val
        100                 105                 110

Cys Pro Thr Glu Ile Thr Ala Phe Ser Asp Arg Tyr Ala Glu Phe Glu
    115                 120                 125

Ala Leu Asn Thr Glu Ile Leu Gly Val Ser Val Asp Ser Val Phe Ser
130                 135                 140

His Leu Ala Trp Val Gln Thr Asp Arg Lys Ser Gly Gly Leu Gly Asp
145                 150                 155                 160

Leu Asn Tyr Pro Leu Ile Ser Asp Val Thr Lys Ser Ile Ser Lys Ser
                165                 170                 175

Tyr Asp Val Leu Ile Pro Asp Gln Gly Ile Ala Leu Arg Gly Leu Phe
            180                 185                 190

Ile Ile Asp Lys Glu Gly Val Ile Gln His Ser Thr Ile Asn Asn Leu
        195                 200                 205

Ala Ile Gly Arg Ser Val Asp Glu Thr Lys Arg Thr Leu Gln Ala Leu
    210                 215                 220

Gln Tyr Val Gln Glu Asn Pro Asp Glu Val Cys Pro Ala Gly Trp Lys
225                 230                 235                 240

Pro Gly Glu Lys Ser Met Lys Pro Asp Pro Lys Leu Ser Lys Glu Tyr
                245                 250                 255

Phe Ser Ala Ile
            260

<210> SEQ ID NO 17
<211> LENGTH: 1044
<212> TYPE: DNA
<213> ORGANISM: Pisum sativum
<220> FEATURE:
<221> NAME/KEY: misc_feature
<222> LOCATION: (968)..(968)
<223> OTHER INFORMATION: n is a, c, g, or t

<400> SEQUENCE: 17
atggcttgct cagctccatt tgcttctctc ctatattcaa accctaacac actcttctct       60
cccaaattct cttctccgcg cctctcttct ctctcaatcc ccaatgcacc caattctctc      120
cccaaactac gcacttccct ccctcttttcc ctcaaccgct cctcttcctc tcgccgcact    180
ttcgtcgtta gggcttctgg tgaattacca ttagttggga actcagcgcc ggattttgaa      240
gctgaagctg ttttcgatca ggagtttatc aaggtcaaac tatctgaata tattgggaag      300
aaatatgtta tcctcttttt ctacccattg gacttcacgt tcgtttgccc aacagaaatc      360
actgctttca gtgaccggca tgcagagttt gatgcaataa atactgagat tttgggtgtt      420
tcagttgaca gtgtgttctc gcaccttgca tgggttcaat cagatagaaa gtcaggtggc      480
cttggtgact tgaaatatcc tctggtttct gatgtcacca atccatatc ggaatcttac      540 ggtgttctca ttcccgatca gggaattgca ttgagaggat tgttcattat cgataaggaa      600
ggggtgatcc aacattccac catcaacaac ctcggaattg gtagaagtgt tgacgagaca      660
aagagaacac tccaggcttt gcagtatgtg caggagaacc cagatgaagt ttgccctgct      720
gggtggaagc ctggtgagaa gtccatgaaa ccagacccca aggtagcaa agagtacttt      780 gctgctgtgt agaatggcta atagtaaatt gctatgagta ttaactactc atctgtatca      840
tttgggatgt aaaaggattt tgttttatgt aattctatcc attttgaatt atgaggccta      900

| tgggcttagc | cataaaaata | aaaagtatga | ggtccaaaag | tgtgtggtta | cagaagcatg | 960 |
| cttgtgtncc | ttgattttgg | agtgaattat | gaattgatgt | attatctgta | aaaaaaaaaa | 1020 |
| aaaaaaaaaa | aaaaaaaaaa | aaaa | | | | 1044 |

<210> SEQ ID NO 18
<211> LENGTH: 263
<212> TYPE: PRT
<213> ORGANISM: Pisum sativum

<400> SEQUENCE: 18

```
Met Ala Cys Ser Ala Pro Phe Ala Ser Leu Leu Tyr Ser Asn Pro Asn
1               5                   10                  15

Thr Leu Phe Ser Pro Lys Phe Ser Pro Arg Leu Ser Ser Leu Ser
            20                  25                  30

Ile Pro Asn Ala Pro Asn Ser Leu Pro Lys Leu Arg Thr Ser Leu Pro
            35                  40                  45

Leu Ser Leu Asn Arg Ser Ser Ser Arg Arg Thr Phe Val Val Arg
50                  55                  60

Ala Ser Gly Glu Leu Pro Leu Val Gly Asn Ser Ala Pro Asp Phe Glu
65                  70                  75                  80

Ala Glu Ala Val Phe Asp Gln Glu Phe Ile Lys Val Lys Leu Ser Glu
                85                  90                  95

Tyr Ile Gly Lys Lys Tyr Val Ile Leu Phe Phe Tyr Pro Leu Asp Phe
                100                 105                 110

Thr Phe Val Cys Pro Thr Glu Ile Thr Ala Phe Ser Asp Arg His Ala
            115                 120                 125

Glu Phe Asp Ala Ile Asn Thr Glu Ile Leu Gly Val Ser Val Asp Ser
130                 135                 140

Val Phe Ser His Leu Ala Trp Val Gln Ser Asp Arg Lys Ser Gly Gly
145                 150                 155                 160

Leu Gly Asp Leu Lys Tyr Pro Leu Val Ser Asp Val Thr Lys Ser Ile
                165                 170                 175

Ser Glu Ser Tyr Gly Val Leu Ile Pro Asp Gln Gly Ile Ala Leu Arg
            180                 185                 190

Gly Leu Phe Ile Ile Asp Lys Glu Gly Val Ile Gln His Ser Thr Ile
        195                 200                 205

Asn Asn Leu Gly Ile Gly Arg Ser Val Asp Glu Thr Lys Arg Thr Leu
210                 215                 220

Gln Ala Leu Gln Tyr Val Gln Glu Asn Pro Asp Glu Val Cys Pro Ala
225                 230                 235                 240

Gly Trp Lys Pro Gly Glu Lys Ser Met Lys Pro Asp Pro Lys Gly Ser
                245                 250                 255

Lys Glu Tyr Phe Ala Ala Val
            260
```

<210> SEQ ID NO 19
<211> LENGTH: 1078
<212> TYPE: DNA
<213> ORGANISM: Oryza sativa

<400> SEQUENCE: 19

| acccaagctc | ccaaacccct | ctcgcaccca | atccaaccca | atccctcct | catccactcc | 60 |
| gctctgcggc | catggccgcc | tgctgctcct | ccctcgccac | cgccgtctcc | tcctcctccg | 120 |
| ccaagcccct | cgccggcatc | cccccgccg | cgccgcactc | cctctcccctc | cccgcgctc | 180 |

```
ccgccgccag gcccctccgc ctctccgcct cctcatccag atccgcccgg gccagcagct    240
tcgtcgcccg cgccggcggt gtggacgatg cgccgctggt cgggaacaag gcgcccgact    300
tcgatgcgga ggcagtcttc gaccaggagt tcatcaacgt gaagctgtcc gactacatcg    360
ggaagaagta cgtcattctc ttcttctacc cgttggactt caccttcgtc tgcccgaccg    420
agattaccgc tttcagtgac agatacgatg agttcgagaa gttgaacact gagatcctcg    480
gtgtttcaat tgacagtgtg ttctcccatc ttgcatgggt gcagacagac aggaaatctg    540
gtgggcttgg tgatctgaaa tacccattga tttcagatgt tactaaatca atttcgaagt    600
cctttggtgt cttgatccct gaccagggaa ttgctctgag aggactttc atcattgaca     660 aggagggagt gattcagcac tctaccatta caaaccttgc cattggacgc agtgtagatg    720
agaccatgag gaccctcag gcgttgcagt acgtccagga caacccggac gaggtgtgcc     780
cggccggatg gaagcccggt gacaagtcga tgaagcctga ccccaaggga agcaaggagt    840
acttcgcggc catctaagca cacatatgca tatgcctggt gatggatgta gggagttttt    900
ttgctttcgc gagagccatt gcgtttcgtc tccaaagtgt agtaccgtgt gctcgtctga    960
tcggattttg ttacttgttc gccaccagct gttactttgt tccctaacaa ataaggcttt   1020
gttttggtcg tgttatacat gtatacatgt tagtgcgttt caagatcgct tctgttttt    1078
```

<210> SEQ ID NO 20  
<211> LENGTH: 261  
<212> TYPE: PRT  
<213> ORGANISM: Oryza sativa

<400> SEQUENCE: 20

```
Met Ala Ala Cys Cys Ser Ser Leu Ala Thr Ala Val Ser Ser Ser
1               5                   10                  15

Ala Lys Pro Leu Ala Gly Ile Pro Pro Ala Ala Pro His Ser Leu Ser
            20                  25                  30

Leu Pro Arg Ala Pro Ala Ala Arg Pro Leu Arg Leu Ser Ala Ser Ser
        35                  40                      45

Ser Arg Ser Ala Arg Ala Ser Ser Phe Val Ala Arg Ala Gly Gly Val
    50                  55                      60

Asp Asp Ala Pro Leu Val Gly Asn Lys Ala Pro Asp Phe Asp Ala Glu
65                  70                  75                  80

Ala Val Phe Asp Gln Glu Phe Ile Asn Val Lys Leu Ser Asp Tyr Ile
                85                  90                  95

Gly Lys Lys Tyr Val Ile Leu Phe Phe Tyr Pro Leu Asp Phe Thr Phe
            100                 105                 110

Val Cys Pro Thr Glu Ile Thr Ala Phe Ser Asp Arg Tyr Asp Glu Phe
        115                 120                 125

Glu Lys Leu Asn Thr Glu Ile Leu Gly Val Ser Ile Asp Ser Val Phe
    130                 135                 140

Ser His Leu Ala Trp Val Gln Thr Asp Arg Lys Ser Gly Gly Leu Gly
145                 150                 155                 160

Asp Leu Lys Tyr Pro Leu Ile Ser Asp Val Thr Lys Ser Ile Ser Lys
                165                 170                 175

Ser Phe Gly Val Leu Ile Pro Asp Gln Gly Ile Ala Leu Arg Gly Leu
            180                 185                 190

Phe Ile Ile Asp Lys Glu Gly Val Ile Gln His Ser Thr Ile Asn Asn
        195                 200                 205

Leu Ala Ile Gly Arg Ser Val Asp Glu Thr Met Arg Thr Leu Gln Ala
    210                 215                 220
```

```
Leu Gln Tyr Val Gln Asp Asn Pro Asp Glu Val Cys Pro Ala Gly Trp
225                 230                 235                 240

Lys Pro Gly Asp Lys Ser Met Lys Pro Asp Pro Lys Gly Ser Lys Glu
            245                 250                 255

Tyr Phe Ala Ala Ile
            260

<210> SEQ ID NO 21
<211> LENGTH: 1067
<212> TYPE: DNA
<213> ORGANISM: Secale cereale

<400> SEQUENCE: 21
tcttcatatt cgggaaccct atctatctgg aggctaccgc ggccgccccc gggcactccc      60
cgcctgacaa ccacggccat ggcgtgcgcc ttctccgcct ccaccgtgtc cacggcggcc     120
gcgctcgtcg cgtccccgaa gccagccggg gcgccgagtg cctgtcgttt ccccgcgctt     180
cgcaggggcc gcgcaggcct ccgctgcgcg cggctcgagg acgccagggc cgcagcttc      240
gtcgcccgcg ccgcagccga gtacgacctg ccactggtgg ggaacaaagc accggacttc     300
gctgcggagg ccgtgttcga ccaggagttc atcaacgtca gctatctga ttacattggg     360
aagaagtatg tgattctttt cttctaccct ctggacttca ccttcgtctg cccaactgag     420
attacggctt tcagcgacag acatgaggag ttcgagaaga taaacactga aattcttggt     480
gtttcagttg atagtgtgtt ttcccatctt gcatgggtgc agacagagag gaaatctggt     540
ggacttggtg atcttaagta tcctctggtt tctgatgtca ccaaatcaat ctcaaagtct     600
tttggtgtat tgatccctga tcagggaatt gctctgagag gattattcat gattgacaag     660
gagggtgtga ttcagcattc cactattaac aaccttggta ttggccgcag tgtggatgag     720
accttgagaa cccttcaggc tctgcaatac gtccaagaaa cccagacga ggtctgcccg      780
gcaggatgga aacccgggga aaagtcgatg aagcctgacc ctaagggcag caaggagtac     840
ttcgctgcca tctagatgcg acctttgcgc tcacagtctg agttttgtca tggccatttc     900
tggttacttg tgttcttgtg acccgagttg tagttatcac gcgtccaatt gcctctgtaa     960
ttcctccaat aagggtttgt ctgtgtgttg attttccctc ctccaatttg gaaagcccaa    1020
tccaagattg gaaataaaac cttctgccac ccaaaaaaaa aaaaaaa                  1067

<210> SEQ ID NO 22
<211> LENGTH: 258
<212> TYPE: PRT
<213> ORGANISM: Secale cereale

<400> SEQUENCE: 22

Met Ala Cys Ala Phe Ser Ala Ser Thr Val Ser Thr Ala Ala Ala Leu
1               5                   10                  15

Val Ala Ser Pro Lys Pro Ala Gly Ala Pro Ser Ala Cys Arg Phe Pro
            20                  25                  30

Ala Leu Arg Arg Gly Arg Ala Gly Leu Arg Cys Ala Arg Leu Glu Asp
        35                  40                  45

Ala Arg Ala Arg Ser Phe Val Arg Ala Ala Glu Tyr Asp Leu
    50                  55                  60

Pro Leu Val Gly Asn Lys Ala Pro Asp Phe Ala Ala Glu Ala Val Phe
65                  70                  75                  80

Asp Gln Glu Phe Ile Asn Val Lys Leu Ser Asp Tyr Ile Gly Lys Lys
                85                  90                  95
```

Tyr Val Ile Leu Phe Tyr Pro Leu Asp Phe Thr Phe Val Cys Pro
              100                 105                 110

Thr Glu Ile Thr Ala Phe Ser Asp Arg His Glu Phe Glu Lys Ile
              115                 120                 125

Asn Thr Glu Ile Leu Gly Val Ser Val Asp Ser Val Phe Ser His Leu
        130                 135                 140

Ala Trp Val Gln Thr Glu Arg Lys Ser Gly Gly Leu Gly Asp Leu Lys
145                 150                 155                 160

Tyr Pro Leu Val Ser Asp Val Thr Lys Ser Ile Ser Lys Ser Phe Gly
                165                 170                 175

Val Leu Ile Pro Asp Gln Gly Ile Ala Leu Arg Gly Leu Phe Met Ile
            180                 185                 190

Asp Lys Glu Gly Val Ile Gln His Ser Thr Ile Asn Asn Leu Gly Ile
        195                 200                 205

Gly Arg Ser Val Asp Glu Thr Leu Arg Thr Leu Gln Ala Leu Gln Tyr
    210                 215                 220

Val Gln Glu Asn Pro Asp Glu Val Cys Pro Ala Gly Trp Lys Pro Gly
225                 230                 235                 240

Glu Lys Ser Met Lys Pro Asp Pro Lys Gly Ser Lys Glu Tyr Phe Ala
                245                 250                 255

Ala Ile

<210> SEQ ID NO 23
<211> LENGTH: 876
<212> TYPE: DNA
<213> ORGANISM: Riccia fluitans

<400> SEQUENCE: 23
gttgggaaag gcagcaaata tggcaaccgc ctgtgctgca gtgtctgcag tggctgttcc      60
tgtggcctct gtagctaacc acattgcgtc ttcatcatct gggacccat ccttgccat      120 tcccaggtct tatgagggtt taaacaaatc cttcggcgct agaattgcac cccgatcaac      180
ctccgctttt cgcaagcccg tcactggtgt ctccctcaag cagttctcga agggaaaagt      240
cgcttctgcg agatgtgcgt cacctcttgt tggaaatgtc gccccggact cgaggcgga      300 ggccgttttt gaccaagagt tcgtgaagat caagctctcg gagtacattg gaagagata      360 cgttgttctt ttcttctacc ctcttgactt caccttcgtt tgcccaacag aaattaccgc      420
atttagcgac aaacacgaag agtttgagaa gttgaacacc gaagttattg gggtttctac      480
tgacagtgtg ttttcccatc ttgcctggat tcaaactgac agaaaatctg gaggacttgg      540
tgacttgaag tacccacttg tgtccgactt gaccaagaag atcgctgaag attttggagt      600
attgatcccc gatcagggca ttgcattgcg aggattgttc atcatcgaca aggagggcgt      660
cattcagcac gcaaccatta caaatttggc catcggcaga agtgtggagg agacgcttcg      720
aactctgcag gctgtacaat atgtgcagga gaacccagac gaggtctgcc ccgctggctg      780
gaagccgggt gaaaagacca tgaagcctga cacaaagctc agcaaggagt acttcgcaca      840
agtataggcc gaaaatagct tcgtttggaa tacata                                876

<210> SEQ ID NO 24
<211> LENGTH: 275
<212> TYPE: PRT
<213> ORGANISM: Riccia fluitans

<400> SEQUENCE: 24

Met Ala Thr Ala Cys Ala Val Ser Ala Val Pro Val Ala
1               5                   10              15

Ser Val Ala Asn His Ile Ala Ser Ser Ser Gly Thr Pro Ser Leu
            20                  25                  30

Ala Ile Pro Arg Ser Tyr Glu Gly Leu Asn Lys Ser Phe Gly Ala Arg
            35                  40                  45

Ile Ala Pro Arg Ser Thr Ser Ala Phe Arg Lys Pro Val Thr Gly Val
50                  55                  60

Ser Leu Lys Gln Phe Ser Lys Gly Lys Val Ala Ser Ala Arg Cys Ala
65                  70                  75                  80

Ser Pro Leu Val Gly Asn Val Ala Pro Asp Phe Glu Ala Glu Ala Val
                85                  90                  95

Phe Asp Gln Glu Phe Val Lys Ile Lys Leu Ser Glu Tyr Ile Gly Lys
                100                 105                 110

Arg Tyr Val Val Leu Phe Phe Tyr Pro Leu Asp Phe Thr Phe Val Cys
            115                 120                 125

Pro Thr Glu Ile Thr Ala Phe Ser Asp Lys His Glu Glu Phe Glu Lys
            130                 135                 140

Leu Asn Thr Glu Val Ile Gly Val Ser Thr Asp Ser Val Phe Ser His
145                 150                 155                 160

Leu Ala Trp Ile Gln Thr Asp Arg Lys Ser Gly Gly Leu Gly Asp Leu
                165                 170                 175

Lys Tyr Pro Leu Val Ser Asp Leu Thr Lys Lys Ile Ala Glu Asp Phe
                180                 185                 190

Gly Val Leu Ile Pro Asp Gln Gly Ile Ala Leu Arg Gly Leu Phe Ile
                195                 200                 205

Ile Asp Lys Glu Gly Val Ile Gln His Ala Thr Ile Asn Asn Leu Ala
210                 215                 220

Ile Gly Arg Ser Val Glu Glu Thr Leu Arg Thr Leu Gln Ala Val Gln
225                 230                 235                 240

Tyr Val Gln Glu Asn Pro Asp Glu Val Cys Pro Ala Gly Trp Lys Pro
                245                 250                 255

Gly Glu Lys Thr Met Lys Pro Asp Thr Lys Leu Ser Lys Glu Tyr Phe
                260                 265                 270

Ala Gln Val
        275

<210> SEQ ID NO 25
<211> LENGTH: 1255
<212> TYPE: DNA
<213> ORGANISM: Chlamydomonas incerta

<400> SEQUENCE: 25
atggccgctc tgcagtccgc ttcccgctcc tcggcggtgg ccttctcgcg ccaggcgcgc      60
gtggccccgc gcgttgcctc cagcgttgct cgccgcaacc tggtcgtgcg cgcttcccac     120
gctgagaagc tctggtcgg ctccgtcgcc cctgacttca aggcccaggc cgtgttcgac     180
caggagttcc aggagattac cctgagcaag taccgcggca agtacgtggt gctgttcttc     240 tacccctgg acttcacctt cgtgtgcccc accgagatca ccgccttctc ggaccgctac     300
aaggagttca aggacatcaa caccgaggtc ctgggcgtgt ccgtggacag ccagttcacc     360
cacctggcct ggattcagac cgaccgcaag gagggtggcc tgggcgacct gaactacccc     420
ctggtggctg acctgaagaa ggagatctcc aaggcctacg cgtcctgac cgaggacggc      480 atctccctgc gcggcctgtt catcatcgac aaggagggcg ttgtgcagca cgccaccatc     540

```
aacaacctgg ctttcggccg ctcggtcgac gagaccaagc gtgtgctgca ggccatccag    600
tacgtgcagt ccaaccccga tgaggtctgc cccgccggct ggaagcccgg tgacaagacc    660
atgaagcccg accccaaggg ctccaaggag tacttcgccg ccgtgtaaat tgacccttga    720
ttgagagtca atgacacgcg agggcgtcat cgcagtactc gggggcatgc tgcagatcag    780
caggcatgcg gacgagacca gtgcattggc aggctaggcg cacacgggag gcagagccag    840
tgcggcggca gcggcgagcg gcggctgtgg aagcaggcgc tagcagcagc ggcggccgcg    900
gcggcgctgc tctccatggg tgcgcctgca agcagcatgt gcatgtggac tcggtgcttc    960
tcgttgatgg gtcagggcgg cgttgccggt ggtgcggacc gggcggtaat cgcacgtagc   1020
tcaattgttg cgtgcgggcg ctgtgcgggc tggcgtgacg gcacgcaacc tgtgtggggc   1080
ctgttggtac gctcgcgata atgcagtgcg cggtccgagc ggagggacgc ggcggtgaat   1140
agctgctgta gtttcaggca gggatttacc aggtgacggg tggttgcgcc cacacccgaa   1200
cggctgtgat cccaattttc catgagaggg cttgcagatg gacggcgtgt gatcg        1255
```

<210> SEQ ID NO 26
<211> LENGTH: 235
<212> TYPE: PRT
<213> ORGANISM: Chlamydomonas incerta

<400> SEQUENCE: 26

```
Met Ala Ala Leu Gln Ser Ala Ser Arg Ser Ala Val Ala Phe Ser
1               5                   10                  15

Arg Gln Ala Arg Val Ala Pro Arg Val Ala Ser Ser Val Ala Arg Arg
            20                  25                  30

Asn Leu Val Val Arg Ala Ser His Ala Glu Lys Pro Leu Val Gly Ser
        35                  40                  45

Val Ala Pro Asp Phe Lys Ala Gln Ala Val Phe Asp Gln Glu Phe Gln
    50                  55                  60

Glu Ile Thr Leu Ser Lys Tyr Arg Gly Lys Tyr Val Val Leu Phe Phe
65                  70                  75                  80

Tyr Pro Leu Asp Phe Thr Phe Val Cys Pro Thr Glu Ile Thr Ala Phe
                85                  90                  95

Ser Asp Arg Tyr Lys Glu Phe Lys Asp Ile Asn Thr Glu Val Leu Gly
            100                 105                 110

Val Ser Val Asp Ser Gln Phe Thr His Leu Ala Trp Ile Gln Thr Asp
        115                 120                 125

Arg Lys Glu Gly Gly Leu Gly Asp Leu Asn Tyr Pro Leu Val Ala Asp
    130                 135                 140

Leu Lys Lys Glu Ile Ser Lys Ala Tyr Gly Val Leu Thr Glu Asp Gly
145                 150                 155                 160

Ile Ser Leu Arg Gly Leu Phe Ile Ile Asp Lys Glu Gly Val Val Gln
                165                 170                 175

His Ala Thr Ile Asn Asn Leu Ala Phe Gly Arg Ser Val Asp Glu Thr
            180                 185                 190

Lys Arg Val Leu Gln Ala Ile Gln Tyr Val Gln Ser Asn Pro Asp Glu
        195                 200                 205

Val Cys Pro Ala Gly Trp Lys Pro Gly Asp Lys Thr Met Lys Pro Asp
    210                 215                 220

Pro Lys Gly Ser Lys Glu Tyr Phe Ala Ala Val
225                 230                 235
```

<210> SEQ ID NO 27
<211> LENGTH: 612
<212> TYPE: DNA
<213> ORGANISM: Nostoc sp.

<400> SEQUENCE: 27

```
atgtccatca cctacggaac acaagaaagc ctccgcgttg gtcaacaggc tcccgacttt      60
acagcaacag ctgtagttga tcaggaattc aagacaatta agctttccga ctatcgtggt     120
aagtacgttg tcttgttctt ctatccccta gactttacct tgtttgccc acggagatc       180
acagcattta gcgatcgcta cgaagaattc aagaaactta acaccgaaat tctcggtgtg     240
tccgttgata gcgagttctc ccacctagct tggattcaaa ctgatcgtaa gtctggtggt     300
gttggcgacc taaattatcc cttagtttcc gatattaaga agaggttag cgacgcttac      360
aacgtactag acccagcagc aggtatcgct ttacgtggtc tgttcatcat cgataaagat     420
ggtatcattc agcacgctac cattaacaac ctagcttttg gtcgtagcgt tgatgaaacc     480
ctacggacat tgcaagcaat ccagtatgtc cagtctcacc cagatgaagt ttgccctgct     540
ggttggcaac tggggaaaa gaccatgact cccgaccctg tgaagtccaa agtttacttc      600
gctgctgtgt aa                                                         612
```

<210> SEQ ID NO 28
<211> LENGTH: 203
<212> TYPE: PRT
<213> ORGANISM: Nostoc sp.

<400> SEQUENCE: 28

```
Met Ser Ile Thr Tyr Gly Thr Gln Glu Ser Leu Arg Val Gly Gln Gln
1               5                   10                  15

Ala Pro Asp Phe Thr Ala Thr Ala Val Val Asp Gln Glu Phe Lys Thr
            20                  25                  30

Ile Lys Leu Ser Asp Tyr Arg Gly Lys Tyr Val Val Leu Phe Phe Tyr
        35                  40                  45

Pro Leu Asp Phe Thr Phe Val Cys Pro Thr Glu Ile Thr Ala Phe Ser
    50                  55                  60

Asp Arg Tyr Glu Glu Phe Lys Lys Leu Asn Thr Glu Ile Leu Gly Val
65                  70                  75                  80

Ser Val Asp Ser Glu Phe Ser His Leu Ala Trp Ile Gln Thr Asp Arg
                85                  90                  95

Lys Ser Gly Gly Val Gly Asp Leu Asn Tyr Pro Leu Val Ser Asp Ile
            100                 105                 110

Lys Lys Glu Val Ser Asp Ala Tyr Asn Val Leu Asp Pro Ala Ala Gly
        115                 120                 125

Ile Ala Leu Arg Gly Leu Phe Ile Ile Asp Lys Asp Gly Ile Ile Gln
    130                 135                 140

His Ala Thr Ile Asn Asn Leu Ala Phe Gly Arg Ser Val Asp Glu Thr
145                 150                 155                 160

Leu Arg Thr Leu Gln Ala Ile Gln Tyr Val Gln Ser His Pro Asp Glu
                165                 170                 175

Val Cys Pro Ala Gly Trp Gln Pro Gly Glu Lys Thr Met Thr Pro Asp
            180                 185                 190

Pro Val Lys Ser Lys Val Tyr Phe Ala Ala Val
        195                 200
```

<210> SEQ ID NO 29
<211> LENGTH: 609

<212> TYPE: DNA
<213> ORGANISM: Synechococcus sp.

<400> SEQUENCE: 29

```
ctacttggca atcgccgcga agaactcctt ggatttcact gggtcggggt gcatggtttt    60
ctggccgggc tgccagttgg ccgggcaaac ttcatcgggg tgagattgca cgtattggat   120
agcttgcagg gtgcgcaagg tttcatccac actgcggcca aaggccaggt tgttaatggt   180
ggcgtgctgg atgatccctt ctttgtcgat gatgaacagg ccgcgcagcg ccacaccggc   240
ctccggatcc agaacattgt aggcagcgct gatctccttt ttcaggtcag agaccagagg   300
ataccttagc tcgcccaccc ctccggcttt gcggtcggtc tggatccagg ccaagtgaga   360
gtattcgctg tccaccgaga cgcccaggat ctcggtatcc agcttggcaa agtcgtcata   420
gcggtcgcta aaggccgtga tctccgttgg gcagacaaag gtgaagtcca aggggtagaa   480
gaacagcacc acatacttct taccccggta gtcggagagc ttcaccgtct tgaattccat   540
gtcatagacg gcggtggccg aaaaatcggg agcgggctgc cccactcgca ggcatccttc   600
ctgagacat                                                          609
```

<210> SEQ ID NO 30
<211> LENGTH: 202
<212> TYPE: PRT
<213> ORGANISM: Synechococcus sp.

<400> SEQUENCE: 30

```
Met Ser Gln Glu Gly Cys Leu Arg Val Gly Gln Pro Ala Pro Asp Phe
1               5                   10                  15
Ser Ala Thr Ala Val Tyr Asp Met Glu Phe Lys Thr Val Lys Leu Ser
                20                  25                  30
Asp Tyr Arg Gly Lys Lys Tyr Val Val Leu Phe Tyr Pro Leu Asp
            35                  40                  45
Phe Thr Phe Val Cys Pro Thr Glu Ile Thr Ala Phe Ser Asp Arg Tyr
 50                 55                  60
Asp Asp Phe Ala Lys Leu Asp Thr Glu Ile Leu Gly Val Ser Val Asp
 65                 70                  75                  80
Ser Glu Tyr Ser His Leu Ala Trp Ile Gln Thr Asp Arg Lys Ala Gly
                85                  90                  95
Gly Val Gly Glu Leu Arg Tyr Pro Leu Val Ser Asp Leu Lys Lys Glu
            100                 105                 110
Ile Ser Ala Ala Tyr Asn Val Leu Asp Pro Glu Ala Gly Val Ala Leu
        115                 120                 125
Arg Gly Leu Phe Ile Ile Asp Lys Glu Gly Ile Ile Gln His Ala Thr
130                 135                 140
Ile Asn Asn Leu Ala Phe Gly Arg Ser Val Asp Glu Thr Leu Arg Thr
145                 150                 155                 160
Leu Gln Ala Ile Gln Tyr Val Gln Ser His Pro Asp Glu Val Cys Pro
                165                 170                 175
Ala Asn Trp Gln Pro Gly Gln Lys Thr Met His Pro Asp Pro Val Lys
            180                 185                 190
Ser Lys Glu Phe Phe Ala Ala Ile Ala Lys
        195                 200
```

<210> SEQ ID NO 31
<211> LENGTH: 612
<212> TYPE: DNA
<213> ORGANISM: Nodularia spumigena

<400> SEQUENCE: 31

```
atgtccctca cttacgcaac agaaggatgc ctccgcgttg gtcaacaggc tcctgaattt      60
acagccacag ctgtggtaga tcaagaattt aagaccatta aactttccga ctatcgcggt     120
aagtatgtgg ttctgttttt ctaccccta gactttacct tgtttgccc cactgagatc      180
acagcattta gcgatcgcta cgaagaattt aagaaagtta acacagaagt tctcggtgtt     240
tccgttgata gcgaattctc tcacctagcc tggattcaaa ctgaacgcaa gtctggtggt     300
gtcggcgacc tcaattatcc cttagtttcg gacatcaaaa aagagattag cgccacctac     360
aatgccttg acccagccgc aggtattgct ttacgcggtt tgttcattat tgataaagat     420
ggtatcatcc agcattctac agtgaataac ctcgcctttg gtcgcagcgt tgatgaaacc     480
ctgcggacat tgcaagccct tcagtatgtt cagtctcacc ccgatgaagt ttgcccagcc     540
ggttggcaac tggtgatca aacaatggtt cctgaccctg tgaagtcgaa agtctacttc     600
tcggctgtct ag                                                         612
```

<210> SEQ ID NO 32
<211> LENGTH: 203
<212> TYPE: PRT
<213> ORGANISM: Nodularia spumigena

<400> SEQUENCE: 32

```
Met Ser Leu Thr Tyr Ala Thr Glu Gly Cys Leu Arg Val Gly Gln Gln
1               5                   10                  15

Ala Pro Glu Phe Thr Ala Thr Ala Val Val Asp Gln Glu Phe Lys Thr
            20                  25                  30

Ile Lys Leu Ser Asp Tyr Arg Gly Lys Tyr Val Val Leu Phe Phe Tyr
        35                  40                  45

Pro Leu Asp Phe Thr Phe Val Cys Pro Thr Glu Ile Thr Ala Phe Ser
    50                  55                  60

Asp Arg Tyr Glu Glu Phe Lys Lys Val Asn Thr Glu Val Leu Gly Val
65                  70                  75                  80

Ser Val Asp Ser Glu Phe Ser His Leu Ala Trp Ile Gln Thr Glu Arg
                85                  90                  95

Lys Ser Gly Gly Val Gly Asp Leu Asn Tyr Pro Leu Val Ser Asp Ile
            100                 105                 110

Lys Lys Glu Ile Ser Ala Thr Tyr Asn Val Leu Asp Pro Ala Ala Gly
        115                 120                 125

Ile Ala Leu Arg Gly Leu Phe Ile Ile Asp Lys Asp Gly Ile Ile Gln
    130                 135                 140

His Ser Thr Val Asn Asn Leu Ala Phe Gly Arg Ser Val Asp Glu Thr
145                 150                 155                 160

Leu Arg Thr Leu Gln Ala Leu Gln Tyr Val Gln Ser His Pro Asp Glu
                165                 170                 175

Val Cys Pro Ala Gly Trp Gln Pro Gly Asp Gln Thr Met Val Pro Asp
            180                 185                 190

Pro Val Lys Ser Lys Val Tyr Phe Ser Ala Val
        195                 200
```

<210> SEQ ID NO 33
<211> LENGTH: 594
<212> TYPE: DNA
<213> ORGANISM: Thermosynechococcus elongatus

<400> SEQUENCE: 33

```
ttagcccacg gcttcaaaat agactttgga tttgacaggg tcaggggttca tcgtcttgtc        60 accggggtgc cagcccgcgg ggcagacttc atcggggtga gtttgaacgt attgaatcgc       120
ttggagtacc cgcagggtct catcaacact gcggccaaag ccaagttat tgattgttgc       180 gtgttggata atcccttctt tatcaatgat gaacagaccc cgcagggcca cgccttcttc       240
ggtcaggaca ttgtaggcag tgctgatgtc tttttttcagg tcagacacca agggatattt       300
aagatcgccg acaccaccag ctttgcgatc agtttgtgtc caagccaagt gggagaactg       360
gctatccaca gacacgccca ggatttcggt gttcaatttg gcaaattcat cgtagcgatc       420
gctaaaggca caatttccg tggggcagac aaaggtaaag tccaagggat agaaaaagag       480
aacaacgtac ttaccgcgat agtccgagag cttgatggtt ttgaactctt ggtcataaac       540
agcaaccgct tcaaaatcgg gggcgggttg accgacgcgc agacactcag acat            594
```

<210> SEQ ID NO 34
<211> LENGTH: 197
<212> TYPE: PRT
<213> ORGANISM: Thermosynechococcus elongatus

<400> SEQUENCE: 34

```
Met Ser Glu Cys Leu Arg Val Gly Gln Pro Ala Pro Asp Phe Glu Ala
1               5                   10                  15

Val Ala Val Tyr Asp Gln Glu Phe Lys Thr Ile Lys Leu Ser Asp Tyr
            20                  25                  30

Arg Gly Lys Tyr Val Val Leu Phe Phe Tyr Pro Leu Asp Phe Thr Phe
        35                  40                  45

Val Cys Pro Thr Glu Ile Val Ala Phe Ser Asp Arg Tyr Asp Glu Phe
    50                  55                  60

Ala Lys Leu Asn Thr Glu Ile Leu Gly Val Ser Val Asp Ser Gln Phe
65                  70                  75                  80

Ser His Leu Ala Trp Thr Gln Thr Asp Arg Lys Ala Gly Gly Val Gly
                85                  90                  95

Asp Leu Lys Tyr Pro Leu Val Ser Asp Leu Lys Lys Asp Ile Ser Thr
            100                 105                 110

Ala Tyr Asn Val Leu Thr Glu Glu Gly Val Ala Leu Arg Gly Leu Phe
        115                 120                 125

Ile Ile Asp Lys Glu Gly Ile Ile Gln His Ala Thr Ile Asn Asn Leu
    130                 135                 140

Ala Phe Gly Arg Ser Val Asp Glu Thr Leu Arg Val Leu Gln Ala Ile
145                 150                 155                 160

Gln Tyr Val Gln Thr His Pro Asp Glu Val Cys Pro Ala Gly Trp His
                165                 170                 175

Pro Gly Asp Lys Thr Met Asn Pro Asp Pro Val Lys Ser Lys Val Tyr
            180                 185                 190

Phe Glu Ala Val Gly
        195
```

<210> SEQ ID NO 35
<211> LENGTH: 693
<212> TYPE: DNA
<213> ORGANISM: Ostreococcus tauri

<400> SEQUENCE: 35

```
atgttgtccg cgagtttgtc caagagcgcg ttcacgccca gggcgtcggc gctccagaag        60
agcgttaagg ggaagaactt ctcccgatcc gccgtccgcg tggaagcgcg caagccgctc       120
```

```
gtgggctacc cggcgccgga gtttagcgcc gaggcggtgt tcgatcaaga gttccaagac    180
atcaagctct cggattaccg cggcaagtac gtcgtgctct tcttctaccc gctcgatttt    240
acctttgtgt gcccgacgga aatcaccgcc ttctccgatc gctacgaaga gttcgcgaag    300
ctcaacaccg aagtcctcgg cgtgagcgtt gactccaagt tctctcactt ggcgtggttg    360
caaaccgacc gcaacgacgg cggcctcggc gacttggcct acccgctcgt cagtgacctc    420
aagcgcgaaa tctgcgaatc gtacgatgtg ttgtacgaag acggcaccgc gctccgtggg    480
ttgtacatca tcgatcgtga gggcgtcatc cagcactaca catgcaacaa cgctccgttc    540
ggccgcaacg tcgacgagtg cctgcgcgtg cttcaagcga tccaatacgt tcaaaacaac    600
ccagacgagg tgtgcccggc gggctggacc ccgggtgcgg cgacgatgaa gccggatccg    660
aagggctcga aggaatactt caaggcgatc taa                                 693
```

<210> SEQ ID NO 36
<211> LENGTH: 230
<212> TYPE: PRT
<213> ORGANISM: Ostreococcus tauri

<400> SEQUENCE: 36

```
Met Leu Ser Ala Ser Leu Ser Lys Ser Ala Phe Thr Pro Arg Ala Ser
1               5                   10                  15

Ala Leu Gln Lys Ser Val Lys Gly Lys Asn Phe Ser Arg Ser Ala Val
            20                  25                  30

Arg Val Glu Ala Arg Lys Pro Leu Val Gly Tyr Pro Ala Pro Glu Phe
        35                  40                  45

Ser Ala Glu Ala Val Phe Asp Gln Glu Phe Gln Asp Ile Lys Leu Ser
    50                  55                  60

Asp Tyr Arg Gly Lys Tyr Val Val Leu Phe Phe Tyr Pro Leu Asp Phe
65                  70                  75                  80

Thr Phe Val Cys Pro Thr Glu Ile Thr Ala Phe Ser Asp Arg Tyr Glu
                85                  90                  95

Glu Phe Ala Lys Leu Asn Thr Glu Val Leu Gly Val Ser Val Asp Ser
            100                 105                 110

Lys Phe Ser His Leu Ala Trp Leu Gln Thr Asp Arg Asn Asp Gly Gly
        115                 120                 125

Leu Gly Asp Leu Ala Tyr Pro Leu Val Ser Asp Leu Lys Arg Glu Ile
    130                 135                 140

Cys Glu Ser Tyr Asp Val Leu Tyr Glu Asp Gly Thr Ala Leu Arg Gly
145                 150                 155                 160

Leu Tyr Ile Ile Asp Arg Glu Gly Val Ile Gln His Tyr Thr Cys Asn
                165                 170                 175

Asn Ala Pro Phe Gly Arg Asn Val Asp Glu Cys Leu Arg Val Leu Gln
            180                 185                 190

Ala Ile Gln Tyr Val Gln Asn Asn Pro Asp Glu Val Cys Pro Ala Gly
        195                 200                 205

Trp Thr Pro Gly Ala Ala Thr Met Lys Pro Asp Pro Lys Gly Ser Lys
    210                 215                 220

Glu Tyr Phe Lys Ala Ile
225                 230
```

<210> SEQ ID NO 37
<211> LENGTH: 609
<212> TYPE: DNA
<213> ORGANISM: Synechococcus sp.

<400> SEQUENCE: 37

```
ctacttggca accgccgcga agaactcctt ggatttcacc gggtcggggt tcagggttct      60
ctggccgggc tgccagttgg ccgggcaaac ttcatcgggg tgagcttgca cgtactggat     120
ggcctgcagg gtgcgcaggg tttcatccac gctgcggcca aaggccaggt tgttgatggt     180
ggcgtgctgg atgatccctt ccttgtcgat gatgaacagg ccgcgcaaag ccacccctgc     240
cgccggatcc aggacattgt aggcggcgct gatctccttt ttcaggtcgg agaccagcgg     300
atacctcagc tcgcccaccc ctccggcttt gcggtcggtc tgaatccagg ccaggtgaga     360
gtactcgcta tccaccgaga cgccgaggat ctccgtgtcc agcttggcaa actcgtcgta     420
gcgatcgctg aaagccgtga tctccgtcgg gcagacgaag gtgaagtcca aggggtagaa     480
gaacagcacc acgtacttct tgccccggta gtcggagagc ctcaccgtct taaattccat     540
gtcgtaaacg gcagtggccg aaaaatcggg agcgggctgc cccacccgca gacatccttc     600
ctgagacat                                                             609
```

<210> SEQ ID NO 38
<211> LENGTH: 202
<212> TYPE: PRT
<213> ORGANISM: Synechococcus sp.

<400> SEQUENCE: 38

```
Met Ser Gln Glu Gly Cys Leu Arg Val Gly Gln Pro Ala Pro Asp Phe
 1               5                  10                  15
Ser Ala Thr Ala Val Tyr Asp Met Glu Phe Lys Thr Val Arg Leu Ser
            20                  25                  30
Asp Tyr Arg Gly Lys Lys Tyr Val Val Leu Phe Phe Tyr Pro Leu Asp
        35                  40                  45
Phe Thr Phe Val Cys Pro Thr Glu Ile Thr Ala Phe Ser Asp Arg Tyr
    50                  55                  60
Asp Glu Phe Ala Lys Leu Asp Thr Glu Ile Leu Gly Val Ser Val Asp
65                  70                  75                  80
Ser Glu Tyr Ser His Leu Ala Trp Ile Gln Thr Asp Arg Lys Ala Gly
                85                  90                  95
Gly Val Gly Glu Leu Arg Tyr Pro Leu Val Ser Asp Leu Lys Lys Glu
            100                 105                 110
Ile Ser Ala Ala Tyr Asn Val Leu Asp Pro Ala Ala Gly Val Ala Leu
        115                 120                 125
Arg Gly Leu Phe Ile Ile Asp Lys Glu Gly Ile Ile Gln His Ala Thr
    130                 135                 140
Ile Asn Asn Leu Ala Phe Gly Arg Ser Val Asp Glu Thr Leu Arg Thr
145                 150                 155                 160
Leu Gln Ala Ile Gln Tyr Val Gln Ala His Pro Asp Glu Val Cys Pro
                165                 170                 175
Ala Asn Trp Gln Pro Gly Gln Arg Thr Leu Asn Pro Asp Pro Val Lys
            180                 185                 190
Ser Lys Glu Phe Phe Ala Ala Val Ala Lys
        195                 200
```

<210> SEQ ID NO 39
<211> LENGTH: 603
<212> TYPE: DNA
<213> ORGANISM: Synechococcus sp.

<400> SEQUENCE: 39

```
tcaaccgatg gcggagaaat actccttgga acctttcgga tcgggcttca tggtcttttc     60
gccgggcgtc cagttggcgg ggcagacttc atcggggttg gactgcacgt actggaaggc    120
ctgaagcaca cgcagggttt cgtccacatt ccggccaaca ggcaggttgt tgatcgtgga    180
gtgcatgatc acgccatcgg gatcgatgat gaacagtcca cgcaaagcaa cgccttcggc    240
gtcgtccagc acgttgtatg cggtggcgat ttccttcttg aggtcagcga ccagggata     300 gttgatgtcg cccagaccgc cctgattgcg gggagtctga atccaggcca gatggctgaa    360
ctggctgtca acggaaacgc cgaggacttc ggtgttcttg ctggagaaat cggcgtagcg    420
gtcgctgaag gccgtgattt ctgtggggca gacgaaggtg aaatccaggg gatagaagaa    480
gagcaccacg tacttgccgc ggtactggga cagggagatt tccttgaatt cctggtccac    540
cactgcagtg gcagtgaaat cggggggcctg ctggcccaca cgaaggcaac cggtctcggt    600
cat                                                                  603
```

<210> SEQ ID NO 40
<211> LENGTH: 200
<212> TYPE: PRT
<213> ORGANISM: Synechococcus sp.

<400> SEQUENCE: 40

```
Met Thr Glu Thr Gly Cys Leu Arg Val Gly Gln Gln Ala Pro Asp Phe
1               5                   10                  15

Thr Ala Thr Ala Val Asp Gln Glu Phe Lys Glu Ile Ser Leu Ser
            20                  25                  30

Gln Tyr Arg Gly Lys Tyr Val Val Leu Phe Phe Tyr Pro Leu Asp Phe
        35                  40                  45

Thr Phe Val Cys Pro Thr Glu Ile Thr Ala Phe Ser Asp Arg Tyr Ala
    50                  55                  60

Asp Phe Ser Ser Lys Asn Thr Glu Val Leu Gly Val Ser Val Asp Ser
65                  70                  75                  80

Gln Phe Ser His Leu Ala Trp Ile Gln Thr Pro Arg Asn Gln Gly Gly
                85                  90                  95

Leu Gly Asp Ile Asn Tyr Pro Leu Val Ala Asp Leu Lys Lys Glu Ile
            100                 105                 110

Ala Thr Ala Tyr Asn Val Leu Asp Asp Ala Glu Gly Val Ala Leu Arg
        115                 120                 125

Gly Leu Phe Ile Ile Asp Pro Asp Gly Val Ile Met His Ser Thr Ile
    130                 135                 140

Asn Asn Leu Pro Val Gly Arg Asn Val Asp Glu Thr Leu Arg Val Leu
145                 150                 155                 160

Gln Ala Phe Gln Tyr Val Gln Ser Asn Pro Asp Glu Val Cys Pro Ala
                165                 170                 175

Asn Trp Thr Pro Gly Glu Lys Thr Met Lys Pro Asp Pro Lys Gly Ser
            180                 185                 190

Lys Glu Tyr Phe Ser Ala Ile Gly
        195                 200
```

<210> SEQ ID NO 41
<211> LENGTH: 597
<212> TYPE: DNA
<213> ORGANISM: Synechococcus elongatus

<400> SEQUENCE: 41

```
ctagactgca gcgaagaact ctttcgactt aacagggtcg gggttcatcg tcgctgcacc     60
```

```
cggttgccaa ttggcggggc aaacttcatc ggggtgactt tggacgtact gaatggcttg      120
cagcacccgc agggtttcat caacgctgcg gccaaacgcc aggttgttga tggtggcgtg      180
ctggatcaca ccttctttgt cgatgatgaa cagaccgcgc agggcaatgc cttcagccgg      240
atcaagcacg ttgtaggcag tgctgatttc tttcttgagg tcagcaacca gcgggtaagc      300
caagtcaccc aaaccacctt ctttacggct ggtttgaatc caagccaagt ggctgaattg      360
gctatcgacc gagacaccca agatttcggt gttcagggct gaaaagtctg catagcgatc      420
gctaaaagca gtaatttcgg tcgggcaaac aaaggtgaag tcgagggggat agaagaacag      480 aacgacgtat ttgccccggt aattggatag cttgatcgtc tggaattcct gatcaacgac      540
tgcagtcgct tcaaaatcgg gggccaattg ccgacgcgc agggctcctt cggtcat          597
```

<210> SEQ ID NO 42
<211> LENGTH: 198
<212> TYPE: PRT
<213> ORGANISM: Synechococcus elongatus

<400> SEQUENCE: 42

Met Thr Glu Gly Ala Leu Arg Val Gly Gln Leu Ala Pro Asp Phe Glu
1               5                   10                  15

Ala Thr Ala Val Val Asp Gln Glu Phe Gln Thr Ile Lys Leu Ser Asn
            20                  25                  30

Tyr Arg Gly Lys Tyr Val Val Leu Phe Phe Tyr Pro Leu Asp Phe Thr
        35                  40                  45

Phe Val Cys Pro Thr Glu Ile Thr Ala Phe Ser Asp Arg Tyr Ala Asp
    50                  55                  60

Phe Ser Ala Leu Asn Thr Glu Ile Leu Gly Val Ser Val Asp Ser Gln
65                  70                  75                  80

Phe Ser His Leu Ala Trp Ile Gln Thr Ser Arg Lys Glu Gly Gly Leu
                85                  90                  95

Gly Asp Leu Ala Tyr Pro Leu Val Ala Asp Leu Lys Lys Glu Ile Ser
            100                 105                 110

Thr Ala Tyr Asn Val Leu Asp Pro Ala Glu Gly Ile Ala Leu Arg Gly
        115                 120                 125

Leu Phe Ile Ile Asp Lys Glu Gly Val Ile Gln His Ala Thr Ile Asn
    130                 135                 140

Asn Leu Ala Phe Gly Arg Ser Val Asp Glu Thr Leu Arg Val Leu Gln
145                 150                 155                 160

Ala Ile Gln Tyr Val Gln Ser His Pro Asp Glu Val Cys Pro Ala Asn
                165                 170                 175

Trp Gln Pro Gly Ala Ala Thr Met Asn Pro Asp Pro Val Lys Ser Lys
            180                 185                 190

Glu Phe Phe Ala Ala Val
        195

<210> SEQ ID NO 43
<211> LENGTH: 597
<212> TYPE: DNA
<213> ORGANISM: Prochlorococcus marinus

<400> SEQUENCE: 43

```
ttatagactt gagaaatact ccttgctccc ttctggatct ggcttcattg tcttttcccc       60
tggagtccaa ttggcaggac atacctcgtc tgggttggct tgaacatatt gaatgcttg       120 aagaactctc aaggtctcat caacatttct tcctacaggt aggttgttaa tagtagcgtg      180
```

```
catgatcaca ccatctggat cgatgatata agacctctt aaagcaacac cctctgcatc      240
gtcgagaacg ttataagcca atgaaatctc tttctttaaa tcggcaacca agggataatt      300
gatatcgcca atgcctccat catttctttg agtttgaatc caggcaaggt ggctaaattg      360
actgtctaca gataccccta agacctcagt gttcttactt gaaaattcgg agtatctatc      420
gctaaaagcg taatttcag ttggacatac aaaagtaaaa tctagagggt aaaagaaaag      480
cacaacatat ttacctctgt aatttgaaag tgatatttcc ttgaattcct ggtctatcac      540
tgcagtagca gtaaaatcag gagctttctg ccaacacgg atacattcgt tcgtcat          597
```

<210> SEQ ID NO 44
<211> LENGTH: 198
<212> TYPE: PRT
<213> ORGANISM: Prochlorococcus marinus

<400> SEQUENCE: 44

```
Met Thr Asn Glu Cys Ile Arg Val Gly Gln Lys Ala Pro Asp Phe Thr
1               5                   10                  15

Ala Thr Ala Val Ile Asp Gln Glu Phe Lys Glu Ile Ser Leu Ser Asn
            20                  25                  30

Tyr Arg Gly Lys Tyr Val Val Leu Phe Phe Tyr Pro Leu Asp Phe Thr
        35                  40                  45

Phe Val Cys Pro Thr Glu Ile Thr Ala Phe Ser Asp Arg Tyr Ser Glu
    50                  55                  60

Phe Ser Ser Lys Asn Thr Glu Val Leu Gly Val Ser Val Asp Ser Gln
65                  70                  75                  80

Phe Ser His Leu Ala Trp Ile Gln Thr Gln Arg Asn Asp Gly Gly Ile
                85                  90                  95

Gly Asp Ile Asn Tyr Pro Leu Val Ala Asp Leu Lys Lys Glu Ile Ser
            100                 105                 110

Leu Ala Tyr Asn Val Leu Asp Asp Ala Glu Gly Val Ala Leu Arg Gly
        115                 120                 125

Leu Tyr Ile Ile Asp Pro Asp Gly Val Ile Met His Ala Thr Ile Asn
    130                 135                 140

Asn Leu Pro Val Gly Arg Asn Val Asp Glu Thr Leu Arg Val Leu Gln
145                 150                 155                 160

Ala Phe Gln Tyr Val Gln Ala Asn Pro Asp Glu Val Cys Pro Ala Asn
                165                 170                 175

Trp Thr Pro Gly Glu Lys Thr Met Lys Pro Asp Pro Glu Gly Ser Lys
            180                 185                 190

Glu Tyr Phe Ser Ser Leu
        195
```

<210> SEQ ID NO 45
<211> LENGTH: 600
<212> TYPE: DNA
<213> ORGANISM: Porphyra purpurea

<400> SEQUENCE: 45

```
ttatgcagcc gcaaaataat ttttagattt tataggatcc ggattcattg ttctatcacc       60
aggtttccaa tttgctggac atacttcatc tggatgggct tgaacatatt gaattgcttg      120
cagaactctt aaagtttctt caacgcttct tccaaactcc agattgttaa cggtagaata      180
ttgaattata cctttaggat ctataataaa taatccccctt agggctacac ccccactatt      240
taatacatta taggcaatgc taatttcttt ttttagatct gatactaaag gatactcaag      300
```

```
atctcctaat ccaccagatt ctcgatctgt ttgcaaccaa gctaagtgag aatattcgct      360
atccacagaa acgcctaaga tttctgtgtt aagttcagaa aaatcagaat acttatcact      420
gaacgcggtt atttctgtag ggcaaacaaa agtaaaatct aaagggtaaa aaataagat       480 gacatactta tttttaaagt cagataattt tattgtttta aattcttggt cataaacagc      540
tgtagctgaa aagtcaggcg cgatctggcc tacttgaaga caattgtgtc ctgaaatcat      600
```

<210> SEQ ID NO 46
<211> LENGTH: 199
<212> TYPE: PRT
<213> ORGANISM: Porphyra purpurea

<400> SEQUENCE: 46

```
Met Ile Ser Gly His Asn Cys Leu Gln Val Gly Gln Ile Ala Pro Asp
1               5                   10                  15

Phe Ser Ala Thr Ala Val Tyr Asp Gln Glu Phe Lys Thr Ile Lys Leu
            20                  25                  30

Ser Asp Phe Lys Asn Lys Tyr Val Ile Leu Phe Phe Tyr Pro Leu Asp
        35                  40                  45

Phe Thr Phe Val Cys Pro Thr Glu Ile Thr Ala Phe Ser Asp Lys Tyr
    50                  55                  60

Ser Asp Phe Ser Glu Leu Asn Thr Glu Ile Leu Gly Val Ser Val Asp
65                  70                  75                  80

Ser Glu Tyr Ser His Leu Ala Trp Leu Gln Thr Asp Arg Glu Ser Gly
                85                  90                  95

Gly Leu Gly Asp Leu Glu Tyr Pro Leu Val Ser Asp Leu Lys Lys Glu
            100                 105                 110

Ile Ser Ile Ala Tyr Asn Val Leu Asn Ser Gly Gly Val Ala Leu Arg
        115                 120                 125

Gly Leu Phe Ile Ile Asp Pro Lys Gly Ile Ile Gln Tyr Ser Thr Val
    130                 135                 140

Asn Asn Leu Glu Phe Gly Arg Ser Val Glu Glu Thr Leu Arg Val Leu
145                 150                 155                 160

Gln Ala Ile Gln Tyr Val Gln Ala His Pro Asp Glu Val Cys Pro Ala
                165                 170                 175

Asn Trp Lys Pro Gly Asp Arg Thr Met Asn Pro Asp Pro Ile Lys Ser
            180                 185                 190

Lys Asn Tyr Phe Ala Ala Ala
        195
```

<210> SEQ ID NO 47
<211> LENGTH: 681
<212> TYPE: DNA
<213> ORGANISM: Gracilaria tenuistipitata

<400> SEQUENCE: 47

```
atgttattat gttgttttat tactgttatt ttatataata tagacaatac taaattttat      60
aacaggaagt gtagtattaa aatgataaca aataataata ttttgagagt tggtcaacaa      120
gcccccaatt tttctgctat tgctgtatat gatcaagagt ttaagaaaat aacactgtct      180
gattacttgg gtaagtatgt aatattactg ttttatcctt tagatttcac atttgtttgt      240
ccaactgaga tcactgcttt cagtgattca tataaagaga ttcaaagtct gaatacagaa      300
gttttgggta tatctgttga cagtgaatat tcacatttag catggttgca aatggaaaga      360
gatattggag gcttaggaga tcttaattac ccgttagttt ctgatttaac aaaacagatt      420
```

```
agtgcttcat ataatgttct aacagaagaa ggtaaagcat taagaggttt atttattgtt      480
gatcagcaag gaattataca atattcttta gttaataatt tagactttgg ccgtagtatt      540
agtgaaacta taagaacact taaagctatc caatatgtac aatctcaccc agatgaagtt      600
tgtccagcaa attggcagcc aggaaaagct actataatta atagtcctca aaaatcgaaa      660
aattattttc aatctatata g                                                681
```

<210> SEQ ID NO 48
<211> LENGTH: 226
<212> TYPE: PRT
<213> ORGANISM: Gracilaria tenuistipitata

<400> SEQUENCE: 48

```
Met Leu Leu Cys Cys Phe Ile Thr Val Ile Leu Tyr Asn Ile Asp Asn
1               5                   10                  15

Thr Lys Phe Tyr Asn Arg Lys Cys Ser Ile Lys Met Ile Thr Asn Asn
            20                  25                  30

Asn Ile Leu Arg Val Gly Gln Gln Ala Pro Asn Phe Ser Ala Ile Ala
        35                  40                  45

Val Tyr Asp Gln Glu Phe Lys Lys Ile Thr Leu Ser Asp Tyr Leu Gly
    50                  55                  60

Lys Tyr Val Ile Leu Leu Phe Tyr Pro Leu Asp Phe Thr Phe Val Cys
65                  70                  75                  80

Pro Thr Glu Ile Thr Ala Phe Ser Asp Ser Tyr Lys Glu Ile Gln Ser
                85                  90                  95

Leu Asn Thr Glu Val Leu Gly Ile Ser Val Asp Ser Glu Tyr Ser His
            100                 105                 110

Leu Ala Trp Leu Gln Met Glu Arg Asp Ile Gly Gly Leu Gly Asp Leu
        115                 120                 125

Asn Tyr Pro Leu Val Ser Asp Leu Thr Lys Gln Ile Ser Ala Ser Tyr
    130                 135                 140

Asn Val Leu Thr Glu Glu Gly Lys Ala Leu Arg Gly Leu Phe Ile Val
145                 150                 155                 160

Asp Gln Gln Gly Ile Ile Gln Tyr Ser Leu Val Asn Asn Leu Asp Phe
                165                 170                 175

Gly Arg Ser Ile Ser Glu Thr Ile Arg Thr Leu Lys Ala Ile Gln Tyr
            180                 185                 190

Val Gln Ser His Pro Asp Glu Val Cys Pro Ala Asn Trp Gln Pro Gly
        195                 200                 205

Lys Ala Thr Ile Ile Asn Ser Pro Gln Lys Ser Lys Asn Tyr Phe Gln
    210                 215                 220

Ser Ile
225
```

<210> SEQ ID NO 49
<211> LENGTH: 924
<212> TYPE: DNA
<213> ORGANISM: Mus musculus

<400> SEQUENCE: 49

```
gcctagggct ctctcggttt cgagatctct ttcctgtctc taaccgtgtc tggaagtcca      60
tgtgtccggc tcttgttcac gcagtaatgg cctccggcaa cgcgcaaatc ggaaagtcgg     120
ctcctgactt cacggccaca gcggtggtgg atggtgcctt caaggaaatc aagctttcgg     180
actacagagg gaagtacgtg gtcctctttt tctacccact ggacttcact tttgtttgcc     240
```

```
ccacggagat catcgctttt agcgaccatg ctgaggactt ccgaaagcta ggctgcgagg      300
tgctgggagt gtctgtggac tctcagttca cccacctggc gtggatcaat accccacgga      360
aagagggagg cttgggcccc ctgaatatcc ctctgcttgc tgacgtgact aaaagcttgt      420
cccagaatta cggcgtgttg aaaaatgatg agggcattgc ttacaggggt ctctttatca      480
tcgatgccaa gggtgtcctt cgccagatca cagtcaatga cctacctgtg gccgctctg       540 tagacgaggc tctccgccta gtccaggcct ttcagtatac agacgagcat ggggaagtct      600
gccctgctgg ctggaagccc ggcagtgaca ccatcaagcc caatgtggat gacagcaagg      660
aatacttctc caaacacaac tgagatgggt aaacatcggt gagcctgaag cttggatttc      720
acctgtgccc caacctggat gtcctgtgct ggcccagaaa atgctagatt ttcctccact      780
ctctgaaggg gctggagtct aggctgaggc tttctcatta cccacctgga atctggtgaa      840
tagtgatcct gccctgagca cacctagctg ggcccaggtc tataggaaac caataaagta      900
ttagggacag tgtaaaaaaa aaaa                                             924
```

<210> SEQ ID NO 50
<211> LENGTH: 198
<212> TYPE: PRT
<213> ORGANISM: Mus musculus

<400> SEQUENCE: 50

```
Met Ala Ser Gly Asn Ala Gln Ile Gly Lys Ser Ala Pro Asp Phe Thr
1               5                   10                  15

Ala Thr Ala Val Val Asp Gly Ala Phe Lys Glu Ile Lys Leu Ser Asp
            20                  25                  30

Tyr Arg Gly Lys Tyr Val Val Leu Phe Phe Tyr Pro Leu Asp Phe Thr
        35                  40                  45

Phe Val Cys Pro Thr Glu Ile Ile Ala Phe Ser Asp His Ala Glu Asp
    50                  55                  60

Phe Arg Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Lys Ser Leu Ser
            100                 105                 110

Gln Asn Tyr Gly Val Leu Lys Asn Asp Glu Gly Ile Ala Tyr Arg Gly
        115                 120                 125

Leu Phe Ile Ile Asp Ala Lys Gly Val Leu Arg Gln Ile Thr Val Asn
    130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
        195
```

<210> SEQ ID NO 51
<211> LENGTH: 877
<212> TYPE: DNA
<213> ORGANISM: Rattus norvegicus

<400> SEQUENCE: 51

```
gaattcggca cgagggtcgt ccgcgtgtcc ggctcttgcc cacgcagtca tggcctccgg    60
caacgcgcac atcggaaagc ctgcccctga cttcacgggc accgccgtgg tggatggtgc   120
ctttaaggaa atcaagcttt cagactacag agggaagtac gtggtcctct ttttctatcc   180
actggacttc acttttgttt gccccacgga gatcatcgct tttagcgacc acgctgagga   240
cttccgaaag ctaggctgcg aggtgctggg agtgtctgtg gactctcagt tcacccacct   300
ggcctggatc aataccccac ggaaggaggg aggcttgggc ccactgaata tccctctgct   360
tgctgatgtg actaaaagct tgtcccagaa ttacggcgtg ttgaaaaatg atgagggcat   420
cgcttacagg ggcctcttta tcatcgatgc caagggtgtc cttcgccaga tcacagtcaa   480
cgacctacct gtgggacgct ctgtagatga ggctctccgc ctcgtccagg cctttcagta   540
tacagatgag catggggaag tctgtcctgc tggctggaag cccggcagtg acaccatcaa   600
acccaatgtg gatgacagca aggaatactt ctccaaacac aactgagatg ggtaaacatc   660
ggtgagcctg aatcccggat ctcacctgcg cccttacctg gatgtcctgt gctggcccag   720
aaaacgctag atcttcctct acattctaaa ggggctggag gctaggccga ggctttctca   780
ttacccacct ggaatctggt gaatagtgac cctgccctga gcacacccag ctgggcccag   840
gtctatagga aaccaataaa gtattaggga cagtgta                            877
```

<210> SEQ ID NO 52
<211> LENGTH: 198
<212> TYPE: PRT
<213> ORGANISM: Rattus norvegicus

<400> SEQUENCE: 52

```
Met Ala Ser Gly Asn Ala His Ile Gly Lys Pro Ala Pro Asp Phe Thr
1               5                   10                  15

Gly Thr Ala Val Val Asp Gly Ala Phe Lys Glu Ile Lys Leu Ser Asp
            20                  25                  30

Tyr Arg Gly Lys Tyr Val Val Leu Phe Phe Tyr Pro Leu Asp Phe Thr
        35                  40                  45

Phe Val Cys Pro Thr Glu Ile Ile Ala Phe Ser Asp His Ala Glu Asp
    50                  55                  60

Phe Arg Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Lys Ser Leu Ser
            100                 105                 110

Gln Asn Tyr Gly Val Leu Lys Asn Asp Glu Gly Ile Ala Tyr Arg Gly
        115                 120                 125

Leu Phe Ile Ile Asp Ala Lys Gly Val Leu Arg Gln Ile Thr Val Asn
    130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
        195
```

<210> SEQ ID NO 53
<211> LENGTH: 1089
<212> TYPE: DNA
<213> ORGANISM: Oryza sativa

<400> SEQUENCE: 53

```
gccttcgtct cgacacgttt gcattgcagc agctcataag tttcttcttc gtttctgctc      60
ccagtgctaa ggcagcacag tcgttcgtcg ccatgccagg gctcaccatc ggcgacaccg     120
tccccaacct ggagctggac tccacccacg gcaagatccg catccacgac ttcgtcggcg     180
acacctatgt catcctcttc tcccaccccg gcgacttcac cccggtctgc accacggagc     240
tggcagccat ggccggctac gccaaggagt cgacaagag gggcgtcaag ctgctcggca     300
tctcctgcga cgacgtgcag tctcacaagg actggatcaa ggacatcgag gcctacaagc     360
ctgggaaccg cgtgacgtac ccgatcatgg ccgatccgag ccgcgaggcc atcaagcagc     420
tgaacatggt cgacccggac gagaaggatt ccaacggcgg ccacctcccg tcccgcgcgc     480
tgcacatcgt cggccccgac aagaaggtga agctgagctt cctgtacccg gcgtgcgtgg     540
gcggaacat ggatgaggtg gtgcgtgcgg tcgacgcgct gcagacggcg gcgaagcacg     600
cggtggcgac gccggtgaac tggaagcccg gcgagcgcgt cgtcatccct ccgcggcgtct     660
ccgacgacga ggcgaaggag aagttccccc agggggttcga caccgccgac ctgccgtccg     720
gcaagggcta cctccgcttc accaaggtcg gctagatcat atcgatatcg acctcgctct     780
tcgtacatca tgtgcgccac gcgtgcgtga tagcgtgtgc tggcgtgatg actatgcgag     840
atgcatccct gtgtgtgttg gtgtggataa tgccgctacg tttggaacag tagtgcattt     900
actctgtgct actgtctgaa ctttggctgt ttggcagact gtttatgtac ccgtatgttc     960
gccctgtac taatagagtg ggtgttgtgg ttggcaagta ctctcctcgg acaacatttt    1020
aactttgact actaataaca aacaaattaa aaagatcaat cagatgttac tagacatctt    1080
aatttttatt                                                           1089
```

<210> SEQ ID NO 54
<211> LENGTH: 220
<212> TYPE: PRT
<213> ORGANISM: Oryza sativa

<400> SEQUENCE: 54

```
Met Pro Gly Leu Thr Ile Gly Asp Thr Val Pro Asn Leu Glu Leu Asp
1               5                  10                  15

Ser Thr His Gly Lys Ile Arg Ile His Asp Phe Val Gly Asp Thr Tyr
            20                  25                  30

Val Ile Leu Phe Ser His Pro Gly Asp Phe Thr Pro Val Cys Thr Thr
        35                  40                  45

Glu Leu Ala Ala Met Ala Gly Tyr Ala Lys Glu Phe Asp Lys Arg Gly
    50                  55                  60

Val Lys Leu Leu Gly Ile Ser Cys Asp Asp Val Gln Ser His Lys Asp
65                  70                  75                  80

Trp Ile Lys Asp Ile Glu Ala Tyr Lys Pro Gly Asn Arg Val Thr Tyr
                85                  90                  95

Pro Ile Met Ala Asp Pro Ser Arg Glu Ala Ile Lys Gln Leu Asn Met
            100                 105                 110

Val Asp Pro Asp Glu Lys Asp Ser Asn Gly Gly His Leu Pro Ser Arg
        115                 120                 125

Ala Leu His Ile Val Gly Pro Asp Lys Lys Val Lys Leu Ser Phe Leu
    130                 135                 140
```

```
Tyr Pro Ala Cys Val Gly Arg Asn Met Asp Glu Val Val Arg Ala Val
145                 150                 155                 160

Asp Ala Leu Gln Thr Ala Ala Lys His Ala Val Ala Thr Pro Val Asn
                165                 170                 175

Trp Lys Pro Gly Glu Arg Val Val Ile Pro Pro Gly Val Ser Asp Asp
            180                 185                 190

Glu Ala Lys Glu Lys Phe Pro Gln Gly Phe Asp Thr Ala Asp Leu Pro
        195                 200                 205

Ser Gly Lys Gly Tyr Leu Arg Phe Thr Lys Val Gly
    210                 215                 220

<210> SEQ ID NO 55
<211> LENGTH: 465
<212> TYPE: DNA
<213> ORGANISM: Oryza sativa

<400> SEQUENCE: 55
atggcgtgcg ccttctccgt ctcctctgcc gcggcgcctc tcgcctcccc gaaggggac     60 ctgccgttgg tcgggaacaa ggcgccggac ttcgaggcgg aggccatgtt cgaccagggg   120
ttcatcaagt ctaaatgcat gtttgtaagc tctgcagaga tcactgcttt cagcgacaga   180
tatgaggagt ttgagaagat aaatactgaa gttctcggtg tttcgattga cagtgtgggg   240
attgctctga gaggattatt catcattgac aaggagggtg tgattcagca ttctaccatt   300
aacaaccttg ctattggccg tagcgtggat gagacgctta ggacccttca ggccctacag   360
tatgtccaag aaaacccgga tgaggtttgc ccagctggat ggaaacctgg ggagaagtca   420
atgaagcctg accccaagga cagcaaggag gaacaagaat gctga                   465

<210> SEQ ID NO 56
<211> LENGTH: 154
<212> TYPE: PRT
<213> ORGANISM: Oryza sativa

<400> SEQUENCE: 56

Met Ala Cys Ala Phe Ser Val Ser Ser Ala Ala Pro Leu Ala Ser
1               5                   10                  15

Pro Lys Gly Asp Leu Pro Leu Val Gly Asn Lys Ala Pro Asp Phe Glu
            20                  25                  30

Ala Glu Ala Met Phe Asp Gln Gly Phe Ile Lys Ser Lys Cys Met Phe
        35                  40                  45

Val Ser Ser Ala Glu Ile Thr Ala Phe Ser Asp Arg Tyr Glu Glu Phe
    50                  55                  60

Glu Lys Ile Asn Thr Glu Val Leu Gly Val Ser Ile Asp Ser Val Gly
65                  70                  75                  80

Ile Ala Leu Arg Gly Leu Phe Ile Ile Asp Lys Glu Gly Val Ile Gln
                85                  90                  95

His Ser Thr Ile Asn Asn Leu Ala Ile Gly Arg Ser Val Asp Glu Thr
            100                 105                 110

Leu Arg Thr Leu Gln Ala Leu Gln Tyr Val Gln Glu Asn Pro Asp Glu
        115                 120                 125

Val Cys Pro Ala Gly Trp Lys Pro Gly Glu Lys Ser Met Lys Pro Asp
    130                 135                 140

Pro Lys Asp Ser Lys Glu Glu Gln Glu Cys
145                 150
```

<210> SEQ ID NO 57
<211> LENGTH: 1085
<212> TYPE: DNA
<213> ORGANISM: Oryza sativa

<400> SEQUENCE: 57

```
cattccatca cagacagttc gcagaatcgc agcagcttag cttaattact ttttcacca      60
actcaactt  cagttaattt ccggttaatc ctcgattcct catcatgcct ggactcaccc    120
tcggcgacgt cgtccccgac ctggagctcg acaccaccca cggcaagatc cgcctccacg    180
acttcgtcgg cgacgcctac gtcatcatct ctcccaccc  cgctgacttc acgccggtct    240
gcacgacgga gctgtcggag atggcgggct acgccggcga gttcgacaag aggggcgtca    300
agctcctcgg cttctcctgc gacgacgtcg agtcgcacaa ggactggatc aaggacatcg    360
aggcctacaa gcctggccgc cgcgtcggct cccgatcgt  cgccgacccg gacagggagg    420
cgatcaggca gctcaacatg atcgacgccg acgagaagga caccgccggc ggcgagctcc    480
ccaaccgggc gctccacatc gtcggccgga caagaaggt  gaagctgagc ttcctgttcc    540
cggcgtgcac ggggcggaac atggcggagg tgctgcgcgc gacggacgcg ctgctgacgg    600
cggcgaggca ccgggtggcg acgccggtga actggaagcc cggcgagcgc gtcgtcatcc    660
ccccggcgt  ctccgacgag gaggccaagg cgaggttccc ggccgggttc gagaccgccc    720
agctgccctc caacaagtgc tacctccgct tcacccaggt ggactgagag actgatggtg    780
agggagggag ggagagatct gggccgtcgg tttcgtgtgt aataaaccaa cgcacgacgt    840
agatgcttcc acgtgtgtgt ttcccgtgct gcttcgattg atcgatcgat cattcggtaa    900
gtactctagt tatgtgtaat ctgctgtttg ggtgtagtgg tgcatttgct gttctgttgc    960
ctgaaagtga cgaacggatt atgtttgtca tttgtatgta aaatgtaacc gtatgttttt   1020
tatttatccc ttccgaaatt actgtggaat atagtgaagt aatgctgtta ataaacagcc   1080
cgttt                                                               1085
```

<210> SEQ ID NO 58
<211> LENGTH: 220
<212> TYPE: PRT
<213> ORGANISM: Oryza sativa

<400> SEQUENCE: 58

```
Met Pro Gly Leu Thr Leu Gly Asp Val Val Pro Asp Leu Glu Leu Asp
1               5                   10                  15

Thr Thr His Gly Lys Ile Arg Leu His Asp Phe Val Gly Asp Ala Tyr
            20                  25                  30

Val Ile Ile Phe Ser His Pro Ala Asp Phe Thr Pro Val Cys Thr Thr
        35                  40                  45

Glu Leu Ser Glu Met Ala Gly Tyr Ala Gly Glu Phe Asp Lys Arg Gly
    50                  55                  60

Val Lys Leu Leu Gly Phe Ser Cys Asp Asp Val Glu Ser His Lys Asp
65                  70                  75                  80

Trp Ile Lys Asp Ile Glu Ala Tyr Lys Pro Gly Arg Arg Val Gly Phe
                85                  90                  95

Pro Ile Val Ala Asp Pro Asp Arg Glu Ala Ile Arg Gln Leu Asn Met
            100                 105                 110

Ile Asp Ala Asp Glu Lys Asp Thr Ala Gly Gly Glu Leu Pro Asn Arg
        115                 120                 125

Ala Leu His Ile Val Gly Pro Asp Lys Lys Val Lys Leu Ser Phe Leu
    130                 135                 140
```

```
Phe Pro Ala Cys Thr Gly Arg Asn Met Ala Glu Val Leu Arg Ala Thr
145                 150                 155                 160

Asp Ala Leu Leu Thr Ala Ala Arg His Arg Val Ala Thr Pro Val Asn
                165                 170                 175

Trp Lys Pro Gly Glu Arg Val Val Ile Pro Pro Gly Val Ser Asp Glu
            180                 185                 190

Glu Ala Lys Ala Arg Phe Pro Ala Gly Phe Glu Thr Ala Gln Leu Pro
        195                 200                 205

Ser Asn Lys Cys Tyr Leu Arg Phe Thr Gln Val Asp
    210                 215                 220
```

<210> SEQ ID NO 59
<211> LENGTH: 1248
<212> TYPE: DNA
<213> ORGANISM: Oryza sativa

<400> SEQUENCE: 59

```
atcgattccc caacatatt  agggctcacg cctcccaaag tcaaaacagc ccagcccgaa      60
caagcatttc ctcgaacact tcgccctcca ccaccatggc cgccgccgcc tccaccctcg     120
cctccctctc cgccaccgcg gccgcggcg  ccggcaagcg cctcctcctc tcctccccct    180
cccgctccct ctccctctcc ctcgcctccc gcggccgcat cgccgtcatg ccccacctcc    240
gcgctggcat cctctccgcc gcaccgagga gggcggtgtc ggcctcggcc ccggccgcgg    300
ccaccatcgc ggtcggggac aagctccccg acgcgacgct ctcctacttc gactcgcccg    360
acggggagct gaagacggtg accgtgcgcg acctcaccgc cgggaagaag gtggtcctct    420
tcgcggtccc cggcgcgttc accccgacct gcacgcagaa gcacgtcccg gggttcgtcg    480
ccaaggccgg ggagctccgc gccaagggg  tcgacgccgt ggcctgcgtc tccgtcaacg    540
acgcgttcgt gatgcgggcg tggaaggaga gcctcggcgt cggcgacgag gtgctcctcc    600
tctccgacgg caacggcgag ctcgcccgcg ccatggcgt  cgagctcgac ctctccgaca    660
agcccgccgg cctcggcgtg cggtcccgcc gctacgcgct cctggcggag gacggcgtcg    720
tcaaggtgct caacctcgag gagggcggcg ccttcaccac cagcagcgcc gaggagatgc    780
tcaaggcgct ctgaagcgtg aacaactcaa gccatcctcc acttttcatc tcaaatctcc    840
atagctcggt tcgttgccta cttctctcaa gtgttcgctt cttttcctga ataataaatc    900
atggcaacaa tggtggaccg tgcagagtag tgttgtcgtt ttgatgtgtg aagcttctat    960
agcgaacata gtgtgcaatt tttaggtaac atatatgagt cttggccttg cactgtttgt   1020
caggtagtaa caacttggca cagctataga ctgtagtaac agagttcctt tcatgttgaa   1080
tggtgaggct gtgatgtgtt ctagagctga ataaacgtgc tctggtaaat actgtcacca   1140
gatcagacta tggagtagta gtaagatttt gcttggttaa ttgggcaatg ctatttttc    1200
aggatcgttc agttgagata aacatgtttt gctgttcaga tgagttcg                1248
```

<210> SEQ ID NO 60
<211> LENGTH: 232
<212> TYPE: PRT
<213> ORGANISM: Oryza sativa

<400> SEQUENCE: 60

```
Met Ala Ala Ala Ala Ser Thr Leu Ala Ser Leu Ser Ala Thr Ala Ala
1               5                   10                  15

Ala Ala Ala Gly Lys Arg Leu Leu Leu Ser Ser Pro Ser Arg Ser Leu
            20                  25                  30
```

```
Ser Leu Ser Leu Ala Ser Arg Gly Arg Ile Ala Val Met Pro His Leu
         35                  40                  45

Arg Ala Gly Ile Leu Ser Ala Ala Pro Arg Arg Ala Val Ser Ala Ser
 50                  55                  60

Ala Pro Ala Ala Ala Thr Ile Ala Val Gly Asp Lys Leu Pro Asp Ala
 65                  70                  75                  80

Thr Leu Ser Tyr Phe Asp Ser Pro Asp Gly Glu Leu Lys Thr Val Thr
                 85                  90                  95

Val Arg Asp Leu Thr Ala Gly Lys Lys Val Val Leu Phe Ala Val Pro
                100                 105                 110

Gly Ala Phe Thr Pro Thr Cys Thr Gln Lys His Val Pro Gly Phe Val
             115                 120                 125

Ala Lys Ala Gly Glu Leu Arg Ala Lys Gly Val Asp Ala Val Ala Cys
130                 135                 140

Val Ser Val Asn Asp Ala Phe Val Met Arg Ala Trp Lys Glu Ser Leu
145                 150                 155                 160

Gly Val Gly Asp Glu Val Leu Leu Leu Ser Asp Gly Asn Gly Glu Leu
                165                 170                 175

Ala Arg Ala Met Gly Val Glu Leu Asp Leu Ser Asp Lys Pro Ala Gly
            180                 185                 190

Leu Gly Val Arg Ser Arg Arg Tyr Ala Leu Leu Ala Glu Asp Gly Val
            195                 200                 205

Val Lys Val Leu Asn Leu Glu Glu Gly Gly Ala Phe Thr Thr Ser Ser
            210                 215                 220

Ala Glu Glu Met Leu Lys Ala Leu
225                 230

<210> SEQ ID NO 61
<211> LENGTH: 946
<212> TYPE: DNA
<213> ORGANISM: Oryza sativa

<400> SEQUENCE: 61
acacccaaac cgacgaaca gccgcagctg caggccacgc atcctcgccg tgaatctccc       60
accgcgctcc ggcgatggca ttcgcggtct ccaccgcctg caggccgtcc ctgctcctgc      120
ccccgcgcca gcgctcgtcg ccgccgcggc cgcggccgct cctctgcacg ccctccaccg      180
ccgccttccg ccgcggcgcc ctcagcgcga caacaacgcc aacgccggcg cgcgcagcac      240
tgccgtcgac gacggggagg aacaggatcg tctgcggcaa ggtgagcaag ggcagcgcgg      300
cgcccaactt cacgctgagg gaccaggacg ggagggcggt gtcgctgtcc aagttcaagg      360
ggaggccggt ggtggtgtac ttctaccccg ccgacgagac ccccggatgc accaagcagg      420
cctgcgcctt ccgcgactcc tacgagaagt tcaagaaggc cggcgccgag gtcatcggca      480
tcagcggcga cgacgccgcc tcccacaagg agttcaagaa gaagtacaag ctgccgttca      540
cgctgctgag cgacgagggg aacaaggtga ggaaggagtg gggtgtgccg gctgacctgt      600
tcgggacgct gccgggaagg cagacgtacg tgctcgacaa gaacggcgtc gtccagtaca      660
tctacaacaa ccagttccag cccgagaagc acattggcga gaccctcaag atcctccaga      720
gcctctgatt ctcttcttct tcttcctcct tttttaacta caatctctca tgtatgatcc      780
atcacagtat accgagaaat taatccatct gttaatctct tctcgatcgt ttttctccct      840
cggcatgtgt atagctagtg tatctgtaac tctgtgagta tatatacagt caaaatcggt      900
gggctgctag ctctgaattt tgccgtaagg cactctgatt ttctct                     946
```

<210> SEQ ID NO 62
<211> LENGTH: 217
<212> TYPE: PRT
<213> ORGANISM: Oryza sativa

<400> SEQUENCE: 62

Met Ala Phe Ala Val Ser Thr Ala Cys Arg Pro Ser Leu Leu Leu Pro
1               5                   10                  15

Pro Arg Gln Arg Ser Ser Pro Pro Arg Pro Leu Leu Cys Thr
            20                  25                  30

Pro Ser Thr Ala Ala Phe Arg Arg Gly Ala Leu Ser Ala Thr Thr Thr
            35                  40                  45

Pro Thr Pro Ala Arg Ala Ala Leu Pro Ser Thr Thr Gly Arg Asn Arg
        50                  55                  60

Ile Val Cys Gly Lys Val Ser Lys Gly Ser Ala Ala Pro Asn Phe Thr
65                  70                  75                  80

Leu Arg Asp Gln Asp Gly Arg Ala Val Ser Leu Ser Lys Phe Lys Gly
                85                  90                  95

Arg Pro Val Val Val Tyr Phe Tyr Pro Ala Asp Glu Thr Pro Gly Cys
            100                 105                 110

Thr Lys Gln Ala Cys Ala Phe Arg Asp Ser Tyr Glu Lys Phe Lys Lys
        115                 120                 125

Ala Gly Ala Glu Val Ile Gly Ile Ser Gly Asp Asp Ala Ala Ser His
    130                 135                 140

Lys Glu Phe Lys Lys Tyr Lys Leu Pro Phe Thr Leu Leu Ser Asp
145                 150                 155                 160

Glu Gly Asn Lys Val Arg Lys Glu Trp Gly Val Pro Ala Asp Leu Phe
                165                 170                 175

Gly Thr Leu Pro Gly Arg Gln Thr Tyr Val Leu Asp Lys Asn Gly Val
            180                 185                 190

Val Gln Tyr Ile Tyr Asn Asn Gln Phe Gln Pro Glu Lys His Ile Gly
        195                 200                 205

Glu Thr Leu Lys Ile Leu Gln Ser Leu
    210                 215

<210> SEQ ID NO 63
<211> LENGTH: 770
<212> TYPE: DNA
<213> ORGANISM: Oryza sativa

<400> SEQUENCE: 63
atctcccttc cctgtcgatt accttctctc cttcctctgt tcctcctctc ctccacacat      60
ccaggcaggc aacacaagaa tcatccggga gagcgacatg ccccggttg ccgtgggcga      120 caccctcccc gacggccagc tggggtggtt cgacggggag acaagctgc agcaggtctc      180 cgtccacggc ctcgccgccg gcaagaaggt cgtcctcttc ggcgtccccg gtgccttcac      240
cccgacctgc agcaatcagc atgtgccagg attcataaat caggctgagc agctcaaagc      300
caagggtgta gacgacatct tgcttgtcag tgttaacgac cccttgtca tgaaggcgtg      360 ggcaaagtca taccctgaga ataagcatgt gaaattcctt gccgatggtt tgggaacata      420
caccaaggca cttggtcttg agcttgacct ttcggagaaa gggcttggta ttcgttcgag      480
acggtttgct ctccttgctg acaacctcaa ggttactgtt gcaaacattg aggaaggtgg      540
ccaattcaca atctctggtg ctgaggagat cctcaaggca ctgtaagagc ttcagctctt      600

| aggaacggca gcgatcactt ggacctatcg tgtcaatctt gtttaaattt gtctgcaaaa | 660 |
| tacttgtgcg aataaaattg tcgatgagct gcctagttgt gaggacttta tgataatgtt | 720 |
| tgaatctgta tccactgttg aatcaagtag taatgttcag tgctcatgtt | 770 |

<210> SEQ ID NO 64
<211> LENGTH: 162
<212> TYPE: PRT
<213> ORGANISM: Oryza sativa

<400> SEQUENCE: 64

Met Ala Pro Val Ala Val Gly Asp Thr Leu Pro Asp Gly Gln Leu Gly
1               5                   10                  15

Trp Phe Asp Gly Glu Asp Lys Leu Gln Gln Val Ser Val His Gly Leu
            20                  25                  30

Ala Ala Gly Lys Lys Val Val Leu Phe Gly Val Pro Gly Ala Phe Thr
        35                  40                  45

Pro Thr Cys Ser Asn Gln His Val Pro Gly Phe Ile Asn Gln Ala Glu
    50                  55                  60

Gln Leu Lys Ala Lys Gly Val Asp Asp Ile Leu Leu Val Ser Val Asn
65                  70                  75                  80

Asp Pro Phe Val Met Lys Ala Trp Ala Lys Ser Tyr Pro Glu Asn Lys
                85                  90                  95

His Val Lys Phe Leu Ala Asp Gly Leu Gly Thr Tyr Thr Lys Ala Leu
            100                 105                 110

Gly Leu Glu Leu Asp Leu Ser Glu Lys Gly Leu Gly Ile Arg Ser Arg
        115                 120                 125

Arg Phe Ala Leu Leu Ala Asp Asn Leu Lys Val Thr Val Ala Asn Ile
    130                 135                 140

Glu Glu Gly Gly Gln Phe Thr Ile Ser Gly Ala Glu Glu Ile Leu Lys
145                 150                 155                 160

Ala Leu

<210> SEQ ID NO 65
<211> LENGTH: 1249
<212> TYPE: DNA
<213> ORGANISM: Oryza sativa

<400> SEQUENCE: 65

| gagagccaac acggtgcatc tctcagccac acagcccac ccgcgccatg tcactcgcca | 60 |
| ccgccgccgc cggagcgcaa ccgttcgtcc gctcctcctc ctccgccgcc gcggcgtcct | 120 |
| cgtcgcggcc cctgctcgcc gtcgccgccg cccgccaccg ccgcccgcat ggatctctcg | 180 |
| ccgccgccgc cgccgcggca aggcggcgtc gtcgtcgtcc gctcctccag gtgcgcgcgg | 240 |
| caaggacgga gtccacgggc gtctccgtcg ggttccgcgc gccccagttc gagctcccgg | 300 |
| agccactgac ggggaagctc tggacattgg atgacttcga aggcaacccc gcgctgctgg | 360 |
| ttatgtttgt atgtaatcac tgtccattcg taaagcatct caaaaaagat attgcgaagc | 420 |
| tcacctcatt ctacatggag aaagggcttg ctgctgttgc catatcctcg aactcaattg | 480 |
| tgacacaccc acaggatggt cctgattaca tagctgagga agcaaaattg tataaatact | 540 |
| ctttcccgta tctatatgat gagtctcaag aagttgctaa agcttttcga gccgtctgca | 600 |
| cgccagagtt ttacttgttc aaaaaggatg gacgaaggcc atttgagctt ttctaccatg | 660 |
| ggcagtttga cgattcaaga ccgagtaaca acgtgccagt taccggaagg gatttaagtc | 720 |
| gtgcgattga ttgtgcactt agtggacaag agctaccttt tgtgccaaaa cccagtgtcg | 780 |

-continued

```
ggtgcagcat caaatggcac ccatgaagag cgtattgcat tgtcatgtgc tggaatatag    840 atgttttcc cccttaaatt gaaggttgaa catggggatt gaggtgagcc atgctctcta    900
ctactagaag tatggaagca cacacatagt agatttatga tagctaattt cacatagtag    960
atttatgata gctaatttat aatgtaattt taaggaaa tagatgcagt tgaggccttg   1020
tggagctgat tcttaacgtt gtggggctg ttcaacttga gagttgcaaa actagacatg   1080
aatggcgtgg atagtgttat gttgtgtgct ggtgtctcat cttggccgga aaagaaaaa   1140 ctgatggatg taactggtat ttgtgcaaca atgggataat gcacacaagt acaataaccc   1200
attattatgg ctaacacaac acccacgggt gaaaattaaa gatgagggc              1249
```

<210> SEQ ID NO 66
<211> LENGTH: 252
<212> TYPE: PRT
<213> ORGANISM: Oryza sativa

<400> SEQUENCE: 66

```
Met Ser Leu Ala Thr Ala Ala Gly Ala Gln Pro Phe Val Arg Ser
1               5                   10                  15

Ser Ser Ser Ala Ala Ala Ser Ser Arg Pro Leu Leu Ala Val
            20                  25                  30

Ala Ala Ala Arg His Arg Arg Pro His Gly Ser Leu Ala Ala Ala
            35                  40                  45

Ala Ala Ala Arg Arg Arg Arg Arg Pro Leu Leu Gln Val Arg Ala
        50                  55                  60

Ala Arg Thr Glu Ser Thr Gly Val Ser Val Gly Phe Arg Ala Pro Gln
65                  70                  75                  80

Phe Glu Leu Pro Glu Pro Leu Thr Gly Lys Leu Trp Thr Leu Asp Asp
                85                  90                  95

Phe Glu Gly Asn Pro Ala Leu Leu Val Met Phe Val Cys Asn His Cys
                100                 105                 110

Pro Phe Val Lys His Leu Lys Lys Asp Ile Ala Lys Leu Thr Ser Phe
            115                 120                 125

Tyr Met Glu Lys Gly Leu Ala Ala Val Ala Ile Ser Ser Asn Ser Ile
        130                 135                 140

Val Thr His Pro Gln Asp Gly Pro Asp Tyr Ile Ala Glu Glu Ala Lys
145                 150                 155                 160

Leu Tyr Lys Tyr Ser Phe Pro Tyr Leu Tyr Asp Glu Ser Gln Glu Val
                165                 170                 175

Ala Lys Ala Phe Arg Ala Val Cys Thr Pro Glu Phe Tyr Leu Phe Lys
            180                 185                 190

Lys Asp Gly Arg Arg Pro Phe Glu Leu Phe Tyr His Gly Gln Phe Asp
        195                 200                 205

Asp Ser Arg Pro Ser Asn Asn Val Pro Val Thr Gly Arg Asp Leu Ser
    210                 215                 220

Arg Ala Ile Asp Cys Ala Leu Ser Gly Gln Glu Leu Pro Phe Val Pro
225                 230                 235                 240

Lys Pro Ser Val Gly Cys Ser Ile Lys Trp His Pro
                245                 250
```

<210> SEQ ID NO 67
<211> LENGTH: 994
<212> TYPE: DNA
<213> ORGANISM: Oryza sativa

```
<400> SEQUENCE: 67
aaatcccaac agagaagcat ttcctcgaac acatcgccgt cgccgccctc catggccgct      60
cccaccgcag cagctctctc caccctctcc accgccagcg tcacctccgg caagcgcttc     120
atcacctcct ccttctccct ctccttctcc tcccgccccc tcgcaacagg cgtccgcgcc     180
gcgggggcga gagcggcgcg gaggtcggcg gcgtcggcgt ccaccgtggt ggcgaccatc     240
gccgtcggag acaagctccc cgacgcgacg ctgtcctact cgacccggc ggacggcgag      300
ctgaagacgg tgacggtggc ggagctgacg gcgggcagga aggcggtgct gttcgcggtg     360
cccgcgcgt tcacgccgac gtgctcgcag aagcacctcc cggggttcat cgagaaggcc      420
ggggagctcc acgccaaggg ggtggacgcc attgcctgcg tgtcggtgaa cgacgcgttc     480
gtgatgcgcg cgtggaagga gagcctgggc ctcggcgacg ccgacgtgct cctcctctcc     540
gacggcaacc tggagctcac gcgcgcgctc ggcgtcgaga tggacctctc cgacaagccc     600
atggggctcg gcgtcaggtc gcgccgctac gcgctcctcg ccgacgacgg cgtcgtcaag     660
gtgctcaacc tcgaggaggg cggcgccttc accaccagca gcgccgagga gatgctcaag     720
gcgctctgaa gatggaatcc gagctctcgt aggtggcaac aatggcagga tcagcccgtt     780
gctctcgcgc gttggtgagt agcgtcgtcg ttgtgaagag gaaattttgt gtgtgttttt     840
tttcggttga atgttgcatg ccatgtgctt gacgaaatga cggaataaca aagaaaaaa     900
aactacttt atttttttgt tgaaatttgc aaaccatgtg tttgacgaaa tgtcgagata     960
tgaaagctgt gaaatcgctt acgtcacgtg cacc                                994

<210> SEQ ID NO 68
<211> LENGTH: 225
<212> TYPE: PRT
<213> ORGANISM: Oryza sativa

<400> SEQUENCE: 68

Met Ala Ala Pro Thr Ala Ala Ala Leu Ser Thr Leu Ser Thr Ala Ser
1               5                   10                  15

Val Thr Ser Gly Lys Arg Phe Ile Thr Ser Ser Phe Ser Leu Ser Phe
                20                  25                  30

Ser Ser Arg Pro Leu Ala Thr Gly Val Arg Ala Ala Gly Ala Arg Ala
            35                  40                  45

Ala Arg Arg Ser Ala Ala Ser Ala Ser Thr Val Ala Thr Ile Ala
        50                  55                  60

Val Gly Asp Lys Leu Pro Asp Ala Thr Leu Ser Tyr Phe Asp Pro Ala
65                  70                  75                  80

Asp Gly Glu Leu Lys Thr Val Thr Val Ala Glu Leu Thr Ala Gly Arg
                85                  90                  95

Lys Ala Val Leu Phe Ala Val Pro Gly Ala Phe Thr Pro Thr Cys Ser
            100                 105                 110

Gln Lys His Leu Pro Gly Phe Ile Glu Lys Ala Gly Glu Leu His Ala
        115                 120                 125

Lys Gly Val Asp Ala Ile Ala Cys Val Ser Val Asn Asp Ala Phe Val
    130                 135                 140

Met Arg Ala Trp Lys Glu Ser Leu Gly Leu Gly Asp Ala Asp Val Leu
145                 150                 155                 160

Leu Leu Ser Asp Gly Asn Leu Glu Leu Thr Arg Ala Leu Gly Val Glu
                165                 170                 175

Met Asp Leu Ser Asp Lys Pro Met Gly Leu Gly Val Arg Ser Arg Arg
            180                 185                 190
```

```
Tyr Ala Leu Leu Ala Asp Asp Gly Val Val Lys Val Leu Asn Leu Glu
        195                 200                 205

Glu Gly Gly Ala Phe Thr Thr Ser Ser Ala Glu Glu Met Leu Lys Ala
    210                 215                 220

Leu
225

<210> SEQ ID NO 69
<211> LENGTH: 959
<212> TYPE: DNA
<213> ORGANISM: Oryza sativa

<400> SEQUENCE: 69
tacctatgga gacggtcgcc tcgctctcgc gcgccgcgct cgccggcgcg cccgccgcta    60
cacgcgcgac agcgtcgccc gtgaacaggg ccgtggtccc tgcggcgtcc cggccgcgcg   120
ggggacgcct ttgctgccga cgctcgctga cggccgtctc cgcggcggca ggggcttccc   180
ctcccgtctc cccgtcgcct agccccgatg gcggctcccc cggcgtgtgg gacgctctcg   240
gcggcgtgtc cgtgctcgcc gccggcaccg gcgaagccgt tcagctcagg gacctgtggg   300
accccaccga ggggtggcc gtggtggcgc tgctccggca cttcgggtgc ttctgctgct   360
gggagctggc ctctgttctg aaggaatcca tggcgaaatt cgacgctgcc ggggccaagc   420
tgatcgccat cggcgtcggg actcctgaca agctcgcat tctcgccgat gggctgccgt   480
tccctgttga tagcttgtac gctgaccccg agcgcaaggc ttacgacgta ttggggcttt   540
accatggtct gggtcggaca ttaatcagtc ctgcgaagat gtactcgggg cttaattcca   600
tcaagaaggt aaccaagaac tacacgctca agggcacacc agcagacctg acgggtatct   660
tgcagcaggg tggtatgctt tgttcagag ggaaagagtt gctgtactca tggaaagaca   720
aaggcacggg tgatcatgct cctctggatg atgtcctcaa cgcttgctgc aatcgaactt   780
cttgaggtct ctagcagtcg gaagatgtgt atgtaaatat atgaaatgct cagcatgcca   840
aacagagagc aattagactc aacagtacta gatgttcgat taattatgca ttgttggttt   900
gcttatgtac ttagcatgat attggattag ctacccaatg gacatgacac tacagtctg    959

<210> SEQ ID NO 70
<211> LENGTH: 259
<212> TYPE: PRT
<213> ORGANISM: Oryza sativa

<400> SEQUENCE: 70

Met Glu Thr Val Ala Ser Leu Ser Arg Ala Ala Leu Ala Gly Ala Pro
1               5                   10                  15

Ala Ala Thr Arg Ala Thr Ala Ser Pro Val Asn Arg Ala Val Val Pro
            20                  25                  30

Ala Ala Ser Arg Pro Arg Gly Gly Arg Leu Cys Cys Arg Arg Ser Leu
        35                  40                  45

Thr Ala Val Ser Ala Ala Ala Gly Ala Ser Pro Val Ser Pro Ser
    50                  55                  60

Pro Ser Pro Asp Gly Gly Ser Pro Gly Val Trp Asp Ala Leu Gly Gly
65                  70                  75                  80

Val Ser Val Leu Ala Ala Gly Thr Gly Glu Ala Val Gln Leu Arg Asp
                85                  90                  95

Leu Trp Asp Pro Thr Glu Gly Val Ala Val Val Ala Leu Leu Arg His
            100                 105                 110
```

```
Phe Gly Cys Phe Cys Cys Trp Glu Leu Ala Ser Val Leu Lys Glu Ser
            115                 120                 125

Met Ala Lys Phe Asp Ala Ala Gly Ala Lys Leu Ile Ala Ile Gly Val
        130                 135                 140

Gly Thr Pro Asp Lys Ala Arg Ile Leu Ala Asp Gly Leu Pro Phe Pro
145                 150                 155                 160

Val Asp Ser Leu Tyr Ala Asp Pro Glu Arg Lys Ala Tyr Asp Val Leu
                165                 170                 175

Gly Leu Tyr His Gly Leu Gly Arg Thr Leu Ile Ser Pro Ala Lys Met
            180                 185                 190

Tyr Ser Gly Leu Asn Ser Ile Lys Lys Val Thr Lys Asn Tyr Thr Leu
        195                 200                 205

Lys Gly Thr Pro Ala Asp Leu Thr Gly Ile Leu Gln Gln Gly Gly Met
210                 215                 220

Leu Val Phe Arg Gly Lys Glu Leu Leu Tyr Ser Trp Lys Asp Lys Gly
225                 230                 235                 240

Thr Gly Asp His Ala Pro Leu Asp Asp Val Leu Asn Ala Cys Cys Asn
                245                 250                 255

Arg Thr Ser

<210> SEQ ID NO 71
<211> LENGTH: 1183
<212> TYPE: DNA
<213> ORGANISM: Oryza sativa

<400> SEQUENCE: 71
tccgcaacga cctccacacc gcaacggtcc actcgctcgc ctccgtctcc ctcccgcgtc      60
tagggtttcg ccacgtctca cgcagccatg gccgcggcgg ccgcgtccac ctcgctcccc     120
gtcccgcgcg tctccctccc gccgtccgct cgcccagccg ccgctccccg gcacggtctc     180
ctcatccccg gtcgccgtgg gtgcttccgt ctccgcggct caccagcggc accggccgcc     240
gccgcctcgg gctcccottc cgtgccttcc tcttccccgg aggctgggtc gggcatcggg     300
gatgccctcg gtggcgtcgc catctactcc gcggccaccg gcgagcccgt gctgttcagg     360
gacctgtggg accagaacga gggaatggct gttgttgccc tgctaaggca ttttgggtgc     420
ccttgctgtt gggagttggc ctctgtgttg agggatacaa agagagatt tgattcagct      480 ggtgtcaagc taatagccgt tggtgttggc actccagata aagcccgtat tcttgctgag     540
cgtttaccat ttccattgga ctacctctac gcagatcctg agcgcaaggc ctatgatctc     600
ttgggtttgt attttggtat tggtcgcaca ttcttcaatc cagccagtgc aagtgtgttt     660
tcacgatttg actccctcaa ggaggcagtg aagaactata caattgaagc caccccagat     720
gatagggcta tgttctaca acagggtgga atgtttgtgt tcagagggaa agaattaata     780
tatgcaagga agatgagggg cactggtgat catgcacctc tggatgatgt cctcaacatc     840
tgttgtaaag cccctgcggc atgatattgt gtaatcaatg tcccatgaga attttcatag     900
cctggttctg ttcgtgtccc aaagttgtat gcagaaaagc atctcttgat tttggaaggc     960
tggcttctgc aaggatagta tctctttgtc tgtacgtctg atctaccatg ctgttgatat    1020
gtaatatatc agttgaaaac ttgagggatg taggcagacc aaaggacttt ctcatgccat    1080
aagctcagca gttctttttcc ttttcctcat agaaatgtac taattataga agagaatctt    1140
acactgtaca ataagtttgt gttaaagttg gcgaaatttt cct                      1183

<210> SEQ ID NO 72
```

```
<211> LENGTH: 258
<212> TYPE: PRT
<213> ORGANISM: Oryza sativa

<400> SEQUENCE: 72

Met Ala Ala Ala Ala Ser Thr Ser Leu Pro Val Pro Arg Val Ser
1               5                   10                  15

Leu Pro Pro Ser Ala Arg Pro Ala Ala Pro Arg His Gly Leu Leu
                20                  25                  30

Ile Pro Gly Arg Arg Gly Cys Phe Arg Leu Arg Gly Ser Pro Ala Ala
            35                  40                  45

Pro Ala Ala Ala Ala Ser Gly Ser Pro Ser Val Pro Ser Ser Ser Pro
    50                  55                  60

Glu Ala Gly Ser Gly Ile Gly Asp Ala Leu Gly Gly Val Ala Ile Tyr
65                  70                  75                  80

Ser Ala Ala Thr Gly Glu Pro Val Leu Phe Arg Asp Leu Trp Asp Gln
                85                  90                  95

Asn Glu Gly Met Ala Val Val Ala Leu Leu Arg His Phe Gly Cys Pro
                100                 105                 110

Cys Cys Trp Glu Leu Ala Ser Val Leu Arg Asp Thr Lys Glu Arg Phe
        115                 120                 125

Asp Ser Ala Gly Val Lys Leu Ile Ala Val Gly Val Gly Thr Pro Asp
130                 135                 140

Lys Ala Arg Ile Leu Ala Glu Arg Leu Pro Phe Pro Leu Asp Tyr Leu
145                 150                 155                 160

Tyr Ala Asp Pro Glu Arg Lys Ala Tyr Asp Leu Leu Gly Leu Tyr Phe
                165                 170                 175

Gly Ile Gly Arg Thr Phe Phe Asn Pro Ala Ser Ala Ser Val Phe Ser
            180                 185                 190

Arg Phe Asp Ser Leu Lys Glu Ala Val Lys Asn Tyr Thr Ile Glu Ala
        195                 200                 205

Thr Pro Asp Asp Arg Ala Ser Val Leu Gln Gln Gly Gly Met Phe Val
210                 215                 220

Phe Arg Gly Lys Glu Leu Ile Tyr Ala Arg Lys Asp Glu Gly Thr Gly
225                 230                 235                 240

Asp His Ala Pro Leu Asp Asp Val Leu Asn Ile Cys Cys Lys Ala Pro
                245                 250                 255

Ala Ala

<210> SEQ ID NO 73
<211> LENGTH: 917
<212> TYPE: DNA
<213> ORGANISM: Oryza sativa

<400> SEQUENCE: 73
ctcggcgcgg ccacagccgc agaaccacac ctaggccgct cgaagaccca cgtagcttcc      60
atccaagctt accgccatgg ccgcgcgcgc gccgctcccc gtaccgcacg cggccgccac     120
cagcccgcga ccggctgcgg cgtcgagcct cctccgcgcg aggggcccgt gcgcctccct     180
cctctacccg cgccgcctcc gcttctccgt tgcgccggtg gccgccgcca agcccgaggc     240
cgtcgggagg gccggggagg cagctgcggc gccggtggaa gggctcgcga aatccctgca     300 ggggtggag tgttcgatc tgagcggaaa ggcggtgccc gttgttgatc tgtggaagga     360
caggaaggcc atcgttgcgt tcgcccgcca ttttggatgc gtgctgtgcc gtaagagggc     420
cgatcttctc gcggctaagc aggatgcaat ggaggctgca ggggttgctc ttgttttaat     480
```

```
cggaccaggt actgttgaac aggcaaaggc attttatgac caaaccaaat tcaaaggaga     540
agtatacgct gatccaagtc actcatcata taatgccctt gaatttgcat ttgggctgtt     600
ctcaacgttt actccatcgg ccggtttgaa gattatacag ttgtacatgg aaggatacag     660
gcaggattgg gaactgtcgt tcgagaagac caccagaacg aaaggtggat ggtatcaagg     720
gggcctactt gttgcaggac caggcatcga caatattttg tatatccaca aggacaaaga     780
agcaggagat gaccctgaca tggatgatgt cttgaaagct tgctgttcct agatcactag     840
tatcctatat catttctgtt aacctccaga ccttgaagac acatgtaaat attttgccaa     900
gttaaagtat gttatgt                                                    917
```

<210> SEQ ID NO 74
<211> LENGTH: 251
<212> TYPE: PRT
<213> ORGANISM: Oryza sativa

<400> SEQUENCE: 74

Met Ala Ala Arg Ala Pro Leu Pro Val Pro His Ala Ala Thr Ser
1               5                   10                  15

Pro Arg Pro Ala Ala Ser Ser Leu Leu Arg Ala Arg Gly Pro Cys
            20                  25                  30

Ala Ser Leu Leu Tyr Pro Arg Arg Leu Arg Phe Ser Val Ala Pro Val
        35                  40                      45

Ala Ala Ala Lys Pro Glu Ala Val Gly Arg Ala Gly Glu Ala Ala
    50                  55                  60

Ala Pro Val Glu Gly Leu Ala Lys Ser Leu Gln Gly Val Glu Val Phe
65                  70                  75                  80

Asp Leu Ser Gly Lys Ala Val Pro Val Val Asp Leu Trp Lys Asp Arg
                    85                  90                  95

Lys Ala Ile Val Ala Phe Ala Arg His Phe Gly Cys Val Leu Cys Arg
                100                 105                 110

Lys Arg Ala Asp Leu Leu Ala Ala Lys Gln Asp Ala Met Glu Ala Ala
            115                 120                 125

Gly Val Ala Leu Val Leu Ile Gly Pro Gly Thr Val Glu Gln Ala Lys
    130                 135                 140

Ala Phe Tyr Asp Gln Thr Lys Phe Lys Gly Glu Val Tyr Ala Asp Pro
145                 150                 155                 160

Ser His Ser Ser Tyr Asn Ala Leu Glu Phe Ala Phe Gly Leu Phe Ser
                    165                 170                 175

Thr Phe Thr Pro Ser Ala Gly Leu Lys Ile Ile Gln Leu Tyr Met Glu
                180                 185                 190

Gly Tyr Arg Gln Asp Trp Glu Leu Ser Phe Glu Lys Thr Thr Arg Thr
            195                 200                 205

Lys Gly Gly Trp Tyr Gln Gly Gly Leu Leu Val Ala Gly Pro Gly Ile
    210                 215                 220

Asp Asn Ile Leu Tyr Ile His Lys Asp Lys Glu Ala Gly Asp Asp Pro
225                 230                 235                 240

Asp Met Asp Asp Val Leu Lys Ala Cys Cys Ser
                    245                 250

<210> SEQ ID NO 75
<211> LENGTH: 886
<212> TYPE: DNA
<213> ORGANISM: Oryza sativa

```
<400> SEQUENCE: 75
acgcgtgagt tcgtgacgcg tcacgccccg cggccttccc ctcccaaaaa gcggcaggac    60
gcaacctgat ccccatcccc cgagcaagca aagcggagga acgcgatggc gtcggcgctg   120
ctgaggaagg cgacggtagg cggctccgcg gcggcggcgg cggcgaggtg ggcttccagg   180
gggctcgcgt cggtgggctc cggctccgac atcgtctcgg cggcgcccgg cgtgtcgctg   240
cagaaggccc gctcctggga cgagggcgtc gccaccaact tctccaccac ccctctcaag   300
gacatcttcc atgggaagaa agtggtcatc ttcggcctgc ctggtgcata cacaggagtc   360
tgttcacagg cacacgtccc tagttataaa aataacattg acaagttgaa agcaaaaggg   420
gttgactctg ttatctgtgt ctctgtgaat gacccttatg ccctgaatgg atgggcagaa   480
aagctacagg caaaagatgc tattgaattt tatggtgatt ttgatgggag tttccacaaa   540
agcttggatt tggaagtaga cctctctgct gctttgcttg gccgccgttc ccacaggtgg   600
tcagcctttg ttgacgatgg gaagatcaag gctttcaatg ttgaggtagc tccttctgac   660
ttcaaggttt ctggtgccga ggtgatcttg gaccaaatct gatccgagta acgaaattct   720
gtcgttgttt gttttctcat gcagcatgca tgcttttgct gtagtaaata aacgaaaact   780
cgactactcg agtatccatg taaagatgtt tgtagtctgc cttgctacgc ccagaatatt   840
tgttttcctg ttacaaatca gcttgccggg caacatgttt gtcagc                  886

<210> SEQ ID NO 76
<211> LENGTH: 198
<212> TYPE: PRT
<213> ORGANISM: Oryza sativa

<400> SEQUENCE: 76

Met Ala Ser Ala Leu Leu Arg Lys Ala Thr Val Gly Gly Ser Ala Ala
1               5                  10                  15

Ala Ala Ala Ala Arg Trp Ala Ser Arg Gly Leu Ala Ser Val Gly Ser
            20                  25                  30

Gly Ser Asp Ile Val Ser Ala Ala Pro Gly Val Ser Leu Gln Lys Ala
        35                  40                  45

Arg Ser Trp Asp Glu Gly Val Ala Thr Asn Phe Ser Thr Thr Pro Leu
    50                  55                  60

Lys Asp Ile Phe His Gly Lys Lys Val Val Ile Phe Gly Leu Pro Gly
65                  70                  75                  80

Ala Tyr Thr Gly Val Cys Ser Gln Ala His Val Pro Ser Tyr Lys Asn
                85                  90                  95

Asn Ile Asp Lys Leu Lys Ala Lys Gly Val Asp Ser Val Ile Cys Val
            100                 105                 110

Ser Val Asn Asp Pro Tyr Ala Leu Asn Gly Trp Ala Glu Lys Leu Gln
        115                 120                 125

Ala Lys Asp Ala Ile Glu Phe Tyr Gly Asp Phe Asp Gly Ser Phe His
    130                 135                 140

Lys Ser Leu Asp Leu Glu Val Asp Leu Ser Ala Ala Leu Leu Gly Arg
145                 150                 155                 160

Arg Ser His Arg Trp Ser Ala Phe Val Asp Asp Gly Lys Ile Lys Ala
                165                 170                 175

Phe Asn Val Glu Val Ala Pro Ser Asp Phe Lys Val Ser Gly Ala Glu
            180                 185                 190

Val Ile Leu Asp Gln Ile
        195
```

```
<210> SEQ ID NO 77
<211> LENGTH: 22
<212> TYPE: PRT
<213> ORGANISM: Artificial sequence
<220> FEATURE:
<223> OTHER INFORMATION: motif 1
<220> FEATURE:
<221> NAME/KEY: UNSURE
<222> LOCATION: (6)..(6)
<223> OTHER INFORMATION: Xaa can be any naturally occurring amino acid
<220> FEATURE:
<221> NAME/KEY: UNSURE
<222> LOCATION: (11)..(11)
<223> OTHER INFORMATION: Xaa can be any naturally occurring amino acid
<220> FEATURE:
<221> NAME/KEY: VARIANT
<222> LOCATION: (14)..(14)
<223> OTHER INFORMATION: Xaa is Gly or Ala
<220> FEATURE:
<221> NAME/KEY: VARIANT
<222> LOCATION: (15)..(15)
<223> OTHER INFORMATION: Xaa is Met or Val
<220> FEATURE:
<221> NAME/KEY: VARIANT
<222> LOCATION: (19)..(19)
<223> OTHER INFORMATION: Xaa is Gly or Glu
<220> FEATURE:
<221> NAME/KEY: VARIANT
<222> LOCATION: (21)..(21)
<223> OTHER INFORMATION: Xaa is Ile or Val
<220> FEATURE:
<221> NAME/KEY: VARIANT
<222> LOCATION: (22)..(22)
<223> OTHER INFORMATION: Xaa is Asn or Lys

<400> SEQUENCE: 77

Pro Leu Val Gly Asn Xaa Ala Pro Asp Phe Xaa Ala Glu Xaa Xaa Phe
1               5                   10                  15

Asp Gln Xaa Phe Xaa Xaa
            20

<210> SEQ ID NO 78
<211> LENGTH: 22
<212> TYPE: PRT
<213> ORGANISM: Artificial sequence
<220> FEATURE:
<223> OTHER INFORMATION: motif 2
<220> FEATURE:
<221> NAME/KEY: VARIANT
<222> LOCATION: (4)..(4)
<223> OTHER INFORMATION: Xaa is Val or Ile
<220> FEATURE:
<221> NAME/KEY: VARIANT
<222> LOCATION: (6)..(6)
<223> OTHER INFORMATION: Xaa is Tyr or Asp
<220> FEATURE:
<221> NAME/KEY: UNSURE
<222> LOCATION: (7)..(7)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: Xaa is Lys or Ser
<220> FEATURE:
<221> NAME/KEY: VARIANT
<222> LOCATION: (12)..(12)
<223> OTHER INFORMATION: Xaa is Ala or Ser
<220> FEATURE:
<221> NAME/KEY: VARIANT
<222> LOCATION: (13)..(13)
<223> OTHER INFORMATION: Xaa is Glu or Lys
<220> FEATURE:
<221> NAME/KEY: VARIANT
<222> LOCATION: (14)..(14)
<223> OTHER INFORMATION: Xaa is Asp or Ser
```

<220> FEATURE:
<221> NAME/KEY: VARIANT
<222> LOCATION: (15)..(15)
<223> OTHER INFORMATION: Xaa is Tyr or Phe
<220> FEATURE:
<221> NAME/KEY: VARIANT
<222> LOCATION: (16)..(16)
<223> OTHER INFORMATION: Xaa is Asp, Asn or Gly
<220> FEATURE:
<221> NAME/KEY: VARIANT
<222> LOCATION: (20)..(20)
<223> OTHER INFORMATION: Xaa is His or Pro

<400> SEQUENCE: 78

Tyr Pro Leu Xaa Ser Xaa Xaa Thr Lys Xaa Ile Xaa Xaa Xaa Xaa Xaa
1               5                   10                  15

Val Leu Ile Xaa Asp Gln
            20

<210> SEQ ID NO 79
<211> LENGTH: 2194
<212> TYPE: DNA
<213> ORGANISM: Oryza sativa

<400> SEQUENCE: 79

| | | | | |
|---|---|---|---|---|
| aatccgaaaa | gtttctgcac | cgttttcacc | ccctaactaa | caatataggg | aacgtgtgct | 60 |
| aaatataaaa | tgagacctta | tatatgtagc | gctgataact | agaactatgc | aagaaaaact | 120 |
| catccaccta | ctttagtggc | aatcgggcta | aataaaaag | agtcgctaca | ctagtttcgt | 180 |
| tttccttagt | aattaagtgg | gaaaatgaaa | tcattattgc | ttagaatata | cgttcacatc | 240 |
| tctgtcatga | agttaaatta | ttcgaggtag | ccataattgt | catcaaactc | ttcttgaata | 300 |
| aaaaaatctt | tctagctgaa | ctcaatgggt | aaagagagag | attttttta | aaaaaataga | 360 |
| atgaagatat | tctgaacgta | ttggcaaaga | tttaaacata | taattatata | attttatagt | 420 |
| ttgtgcattc | gtcatatcgc | acatcattaa | ggacatgtct | tactccatcc | caatttttat | 480 |
| ttagtaatta | aagacaattg | acttatttt | attatttatc | tttttttcgat | tagatgcaag | 540 |
| gtacttacgc | acacactttg | tgctcatgtg | catgtgtgag | tgcacctcct | caatacacgt | 600 |
| tcaactagca | acacatctct | aatatcactc | gcctatttaa | tacatttagg | tagcaatatc | 660 |
| tgaattcaag | cactccacca | tcaccagacc | actttttaata | atatctaaaa | tacaaaaaat | 720 |
| aattttacag | aatagcatga | aaagtatgaa | acgaactatt | taggttttc | acatacaaaa | 780 |
| aaaaaagaa | ttttgctcgt | gcgcgagcgc | caatctccca | tattgggcac | acaggcaaca | 840 |
| acagagtggc | tgcccacaga | acaacccaca | aaaaacgatg | atctaacgga | ggacagcaag | 900 |
| tccgcaacaa | ccttttaaca | gcaggctttg | cggccaggag | agaggaggag | aggcaaagaa | 960 |
| aaccaagcat | cctccttctc | ccatctataa | attcctcccc | ccttttcccc | tctctatata | 1020 |
| ggaggcatcc | aagccaagaa | gagggagagc | accaaggaca | cgcgactagc | agaagccgag | 1080 |
| cgaccgcctt | ctcgatccat | atcttccggt | cgagttcttg | gtcgatctct | tccctcctcc | 1140 |
| acctcctcct | cacagggtat | gtgcctccct | tcggttgttc | ttggatttat | tgttctaggt | 1200 |
| tgtgtagtac | gggcgttgat | gttaggaaag | gggatctgta | tctgtgatga | ttcctgttct | 1260 |
| tggatttggg | atagaggggt | tcttgatgtt | gcatgttatc | ggttcggttt | gattagtagt | 1320 |
| atggttttca | atcgtctgga | gagctctatg | gaaatgaaat | ggtttaggga | tcggaatctt | 1380 |
| gcgattttgt | gagtaccttt | tgtttgaggt | aaaatcagag | caccggtgat | tttgcttggt | 1440 |
| gtaataaagt | acggttgttt | ggtcctcgat | tctggtagtg | atgcttctcg | atttgacgaa | 1500 |

```
gctatccttt gtttattccc tattgaacaa aataatcca actttgaaga cggtcccgtt    1560
gatgagattg aatgattgat tcttaagcct gtccaaaatt tcgcagctgg cttgtttaga    1620
tacagtagtc cccatcacga aattcatgga aacagttata atcctcagga acaggggatt    1680
ccctgttctt ccgatttgct ttagtcccag aatttttttt cccaaatatc ttaaaaagtc    1740
actttctggt tcagttcaat gaattgattg ctacaaataa tgcttttata gcgttatcct    1800
agctgtagtt cagttaatag gtaataccc tatagtttag tcaggagaag aacttatccg    1860
atttctgatc tccatttta attatatgaa atgaactgta gcataagcag tattcatttg    1920
gattattttt tttattagct ctcaccccct cattattctg agctgaaagt ctggcatgaa    1980
ctgtcctcaa ttttgttttc aaattcacat cgattatcta tgcattatcc tcttgtatct    2040
acctgtagaa gtttcttttt ggttattcct tgactgcttg attacagaaa gaaatttatg    2100
aagctgtaat cgggatagtt atactgcttg ttcttatgat tcatttcctt tgtgcagttc    2160
ttggtgtagc ttgccacttt caccagcaaa gttc                                2194
```

<210> SEQ ID NO 80
<211> LENGTH: 1264
<212> TYPE: DNA
<213> ORGANISM: Oryza sativa

<400> SEQUENCE: 80

```
tcgacgctac tcaagtggtg ggaggccacc gcatgttcca acgaagcgcc aaagaaagcc      60
ttgcagactc taatgctatt agtcgcctag gatatttgga atgaaaggaa ccgcagagtt     120
tttcagcacc aagagcttcc ggtggctagt ctgatagcca aaattaagga ggatgccaaa     180
acatgggtct ggcgggcgc gaaacaccct gataggtggc ttaccttta acatgttcgg      240 gccaaaggcc ttgagacggt aaagttttct atttgcgctt gcgcatgtac aatttattc      300 ctctattcaa tgaaattggt ggctcactgg ttcattaaaa aaaaagaat ctagcctgtt      360 cgggaagaag aggattttgt tcgtgagaga gagagagaga gagagagaga gagagagaga     420
gaaggaggag gaggattttc aggcttcgca ttgcccaacc tctgcttctg ttggcccaag     480
aagaatccca ggcgcccatg ggctggcagt ttaccacgga cctacctagc taccttagc     540 tatctaagcg ggccgaccta gtagccacgt gcctagtgta gattaaagtt gccgggccag     600
caggaagcca cgctgcaatg gcatcttccc ctgtccttcg cgtacgtgaa acaaaccca     660 ggtaagctta gaatcttctt gcccgttgga ctgggacacc caccaatccc accatgcccc     720
gatattcctc cggtctcggt tcatgtgatg tcctctcttg tgtgatcacg gagcaagcat     780
tcttaaacgg caaaagaaaa tcaccaactt gctcacgcag tcacgctgca ccgcgcgaag     840
cgacgcccga taggccaaga tcgcgagata aaataacaac caatgatcat aaggaaacaa     900
gcccgcgatg tgtcgtgtgc agcaatcttg gtcatttgcg ggatcgagtg cttcacagct     960
aaccaaatat tcggccgatg atttaacaca ttatcagcgt agatgtacgt acgatttgtt    1020
aattaatcta cgagccttgc tagggcaggt gttctgccag ccaatccaga tcgccctcgt    1080
atgcacgctc acatgatggc agggcagggt tcacatgagc tctaacggtc gattaattaa    1140
tcccggggct cgactataaa tacctcccta atcccatgat caaaaccatc tcaagcagcc    1200
taatcatctc cagctgatca agagctctta attagctagc tagtgattag ctgcgcttgt    1260
gatc                                                                 1264
```

<210> SEQ ID NO 81
<211> LENGTH: 54

```
<212> TYPE: DNA
<213> ORGANISM: Artificial sequence
<220> FEATURE:
<223> OTHER INFORMATION: primer: forward primer prm8756

<400> SEQUENCE: 81
ggggacaagt ttgtacaaaa aagcaggctt aaacaatggc gtctgttgct tctt         54

<210> SEQ ID NO 82
<211> LENGTH: 52
<212> TYPE: DNA
<213> ORGANISM: Artificial sequence
<220> FEATURE:
<223> OTHER INFORMATION: primer: reverse primer prm8757

<400> SEQUENCE: 82
ggggaccact ttgtacaaga aagctgggtt cgagctaaat agctgagaag ag           52

<210> SEQ ID NO 83
<211> LENGTH: 1317
<212> TYPE: DNA
<213> ORGANISM: Arabidopsis thaliana

<400> SEQUENCE: 83
cggacaggcc acgtcgtgtc ctaaacctct tagcctttcc ctttataagt caatcttgtg    60
tcggcttcga ctcccaacat acacaaaaca ctaaaagtag aagaaaaatg gcgactctta   120
aggtttctga ttctgttcct gctccttctg atgatgctga gcaattgaga accgcttttg   180
aaggatgggg tacgaacgag gacttgatca tatcaatctt ggctcacaga agtgctgaac   240
agaggaaagt catcaggcaa gcataccacg aaacctacgg cgaagacctt ctcaagactc   300
ttgacaagga gctctctaac gatttcgaga gagctatctt gttgtggact cttgaacccg   360
gtgagcgtga tgcttttattg gctaatgaag ctacaaaaag atggacttca agcaaccaag   420
ttcttatgga agttgcttgc acaaggacat caacgcagct gcttcacgct aggcaagctt   480
accatgctcg ctacaagaag tctcttgaag aggacgttgc tcaccacact accggtgact   540
tcagaaagct tttggtttct cttgttacct catacaggta cgaaggagat gaagtgaaca   600
tgacattggc taagcaagaa gctaagctgg tccatgagaa aatcaaggac aagcactaca   660
atgatgagga tgttattaga atcttgtcca caagaagcaa agctcagatc aatgctactt   720
ttaaccgtta ccaagatgat catggcgagg aaattctcaa gagtcttgag gaaggagatg   780
atgatgacaa gttccttgca cttttgaggt caaccattca gtgcttgaca agaccagagc   840
tttactttgt cgatgttctt cgttcagcaa tcaacaaaac tggaactgat gaaggagcac   900
tcactagaat tgtgaccaca agagctgaga ttgacttgaa ggtcattgga gaggagtacc   960
agcgcaggaa cagcattcct ttggagaaag ctattaccaa agacactcgt ggagattacg  1020
agaagatgct cgtcgcactt ctcggtgaag atgatgctta atcaatcaat cctccacaga  1080
gaaacataag ctgctctaca gcttctgtta tctcttatct ccctctctct ctctttgatg  1140
agtttcaaat cgtttgattt tgtttctaca aaaaccttgt ttgtttctgt tgtgtgtttt  1200
gagttcctaa ataatgcaaa agagagagac agagagaacc agtgtggtct cttaagttat  1260
atatatatga agagcattgg cctaaaacac agactaacaa gtagttctgg ttttgac     1317

<210> SEQ ID NO 84
<211> LENGTH: 317
<212> TYPE: PRT
<213> ORGANISM: Arabidopsis thaliana
```

<400> SEQUENCE: 84

```
Met Ala Thr Leu Lys Val Ser Asp Ser Val Pro Ala Pro Ser Asp Asp
1               5                   10                  15
Ala Glu Gln Leu Arg Thr Ala Phe Glu Gly Trp Gly Thr Asn Glu Asp
            20                  25                  30
Leu Ile Ile Ser Ile Leu Ala His Arg Ser Ala Glu Gln Arg Lys Val
        35                  40                  45
Ile Arg Gln Ala Tyr His Glu Thr Tyr Gly Glu Asp Leu Leu Lys Thr
    50                  55                  60
Leu Asp Lys Glu Leu Ser Asn Asp Phe Glu Arg Ala Ile Leu Leu Trp
65                  70                  75                  80
Thr Leu Glu Pro Gly Glu Arg Asp Ala Leu Leu Ala Asn Glu Ala Thr
                85                  90                  95
Lys Arg Trp Thr Ser Ser Asn Gln Val Leu Met Glu Val Ala Cys Thr
            100                 105                 110
Arg Thr Ser Thr Gln Leu Leu His Ala Arg Gln Ala Tyr His Ala Arg
        115                 120                 125
Tyr Lys Lys Ser Leu Glu Glu Asp Val Ala His His Thr Thr Gly Asp
    130                 135                 140
Phe Arg Lys Leu Leu Val Ser Leu Val Thr Ser Tyr Arg Tyr Glu Gly
145                 150                 155                 160
Asp Glu Val Asn Met Thr Leu Ala Lys Gln Glu Ala Lys Leu Val His
                165                 170                 175
Glu Lys Ile Lys Asp Lys His Tyr Asn Asp Glu Asp Val Ile Arg Ile
            180                 185                 190
Leu Ser Thr Arg Ser Lys Ala Gln Ile Asn Ala Thr Phe Asn Arg Tyr
        195                 200                 205
Gln Asp Asp His Gly Glu Glu Ile Leu Lys Ser Leu Glu Glu Gly Asp
    210                 215                 220
Asp Asp Asp Lys Phe Leu Ala Leu Leu Arg Ser Thr Ile Gln Cys Leu
225                 230                 235                 240
Thr Arg Pro Glu Leu Tyr Phe Val Asp Val Leu Arg Ser Ala Ile Asn
                245                 250                 255
Lys Thr Gly Thr Asp Glu Gly Ala Leu Thr Arg Ile Val Thr Thr Arg
            260                 265                 270
Ala Glu Ile Asp Leu Lys Val Ile Gly Glu Tyr Gln Arg Arg Asn
        275                 280                 285
Ser Ile Pro Leu Glu Lys Ala Ile Thr Lys Asp Thr Arg Gly Asp Tyr
    290                 295                 300
Glu Lys Met Leu Val Ala Leu Leu Gly Glu Asp Asp Ala
305                 310                 315
```

<210> SEQ ID NO 85
<211> LENGTH: 56
<212> TYPE: DNA
<213> ORGANISM: Artificial sequence
<220> FEATURE:
<223> OTHER INFORMATION: forward primer: P08727

<400> SEQUENCE: 85
ggggacaagt ttgtacaaaa aagcaggctt aaacaatggc gactcttaag gtttct      56

<210> SEQ ID NO 86
<211> LENGTH: 50
<212> TYPE: DNA
<213> ORGANISM: Artificial sequence
<220> FEATURE:
<223> OTHER INFORMATION: reverse primer: P09025

<400> SEQUENCE: 86
ggggaccact tgtacaaga aagctgggtt taagcatcat cttcaccgag        50

<210> SEQ ID NO 87
<211> LENGTH: 14
<212> TYPE: PRT
<213> ORGANISM: Artificial sequence
<220> FEATURE:
<223> OTHER INFORMATION: signature sequence 1
<220> FEATURE:
<221> NAME/KEY: VARIANT
<222> LOCATION: (1)..(1)
<223> OTHER INFORMATION: Xaa is Leu, Val or Ala
<220> FEATURE:
<221> NAME/KEY: VARIANT
<222> LOCATION: (2)..(2)
<223> OTHER INFORMATION: Xaa is Val, Leu, Ile or Met
<220> FEATURE:
<221> NAME/KEY: VARIANT
<222> LOCATION: (3)..(3)
<223> OTHER INFORMATION: Xaa is Val, Met, Ile, Cys or Leu
<220> FEATURE:
<221> NAME/KEY: UNSURE
<222> LOCATION: (4)..(4)
<223> OTHER INFORMATION: Xaa can be any naturally occurring amino acid,
      preferably one of Leu, Ser, Ile, Val, Gln or Met
<220> FEATURE:
<221> NAME/KEY: VARIANT
<222> LOCATION: (5)..(5)
<223> OTHER INFORMATION: Xaa is Phe or Trp
<220> FEATURE:
<221> NAME/KEY: VARIANT
<222> LOCATION: (6)..(6)
<223> OTHER INFORMATION: Xaa is Val, Met, Thr, Ala or Ile
<220> FEATURE:
<221> NAME/KEY: VARIANT
<222> LOCATION: (7)..(7)
<223> OTHER INFORMATION: Xaa is Pro, Tyr, Met, Phe or Leu
<220> FEATURE:
<221> NAME/KEY: VARIANT
<222> LOCATION: (8)..(8)
<223> OTHER INFORMATION: Xaa is Glu, Ser, His or Asp
<220> FEATURE:
<221> NAME/KEY: VARIANT
<222> LOCATION: (9)..(9)
<223> OTHER INFORMATION: Xaa is Ala or Pro
<220> FEATURE:
<221> NAME/KEY: UNSURE
<222> LOCATION: (10)..(10)
<223> OTHER INFORMATION: Xaa can be any naturally occurring amino acid,
      preferably one of Ala, Val, Pro, Gly, Ser, Thr or Trp
<220> FEATURE:
<221> NAME/KEY: VARIANT
<222> LOCATION: (11)..(11)
<223> OTHER INFORMATION: Xaa is Ser, Glu, Ala or Gly

<400> SEQUENCE: 87

Xaa Xaa Xaa Xaa Xaa Xaa Xaa Xaa Xaa Xaa Xaa Arg Asp Ala
1               5                   10

<210> SEQ ID NO 88
<211> LENGTH: 19
<212> TYPE: PRT
<213> ORGANISM: Artificial sequence
<220> FEATURE:
<223> OTHER INFORMATION: signature sequence 2
<220> FEATURE:
<221> NAME/KEY: VARIANT
<222> LOCATION: (2)..(2)
<223> OTHER INFORMATION: Xaa is Ile, Val, Cys, Gly or Phe
<220> FEATURE:
<221> NAME/KEY: UNSURE

```
<222> LOCATION: (3)..(3)
<223> OTHER INFORMATION: Xaa can be any naturally occurring amino acid,
      preferably one of Lys, Arg, Gln, Ser, Glu, Ala or Met
<220> FEATURE:
<221> NAME/KEY: VARIANT
<222> LOCATION: (5)..(5)
<223> OTHER INFORMATION: Xaa is Arg, Trp, Met or Phe
<220> FEATURE:
<221> NAME/KEY: VARIANT
<222> LOCATION: (7)..(7)
<223> OTHER INFORMATION: Xaa is Thr, Val or Cys
<220> FEATURE:
<221> NAME/KEY: VARIANT
<222> LOCATION: (8)..(8)
<223> OTHER INFORMATION: Xaa is Asn or Asp
<220> FEATURE:
<221> NAME/KEY: VARIANT
<222> LOCATION: (9)..(9)
<223> OTHER INFORMATION: Xaa is Ala, Thr, Glu or Ser
<220> FEATURE:
<221> NAME/KEY: UNSURE
<222> LOCATION: (10)..(10)
<223> OTHER INFORMATION: Xaa can be any naturally occurring amino acid,
      preferably one of Thr, Ser, Lys, Asn, Gly, Asp, Ala, Glu, Gln, or
      Arg
<220> FEATURE:
<221> NAME/KEY: VARIANT
<222> LOCATION: (11)..(11)
<223> OTHER INFORMATION: Xaa is Ala, Val, Leu, Met or Thr
<220> FEATURE:
<221> NAME/KEY: VARIANT
<222> LOCATION: (12)..(12)
<223> OTHER INFORMATION: Xaa is Ile, Leu or Val
<220> FEATURE:
<221> NAME/KEY: VARIANT
<222> LOCATION: (13)..(13)
<223> OTHER INFORMATION: Xaa is Thr or Ile
<220> FEATURE:
<221> NAME/KEY: UNSURE
<222> LOCATION: (14)..(14)
<223> OTHER INFORMATION: Xaa can be any naturally occurring amino acid,
      preferably one of Asn, Ala, Arg, Glu, Asp, Ser or Gln
<220> FEATURE:
<221> NAME/KEY: VARIANT
<222> LOCATION: (15)..(15)
<223> OTHER INFORMATION: Xaa is Val, Thr or Ile
<220> FEATURE:
<221> NAME/KEY: VARIANT
<222> LOCATION: (17)..(17)
<223> OTHER INFORMATION: Xaa is Ala, Gly or Thr
<220> FEATURE:
<221> NAME/KEY: VARIANT
<222> LOCATION: (18)..(18)
<223> OTHER INFORMATION: Xaa is Gln, Lys or His
<220> FEATURE:
<221> NAME/KEY: VARIANT
<222> LOCATION: (19)..(19)
<223> OTHER INFORMATION: Xaa is Ser or Arg

<400> SEQUENCE: 88

Ala Xaa Xaa Gly Xaa Gly Xaa Xaa Xaa Xaa Xaa Xaa Xaa Xaa Xaa Leu
1               5                   10                  15

Xaa Xaa Xaa

<210> SEQ ID NO 89
<211> LENGTH: 17
<212> TYPE: PRT
<213> ORGANISM: Artificial sequence
<220> FEATURE:
<223> OTHER INFORMATION: signature sequence 3
<220> FEATURE:
<221> NAME/KEY: VARIANT
<222> LOCATION: (1)..(1)
<223> OTHER INFORMATION: Xaa is Ser or Thr
<220> FEATURE:
<221> NAME/KEY: VARIANT
```

```
<222> LOCATION: (2)..(2)
<223> OTHER INFORMATION: Xaa is Asn, Glu, Thr or Asp
<220> FEATURE:
<221> NAME/KEY: VARIANT
<222> LOCATION: (3)..(3)
<223> OTHER INFORMATION: Xaa is Glu, Lys or Asp
<220> FEATURE:
<221> NAME/KEY: UNSURE
<222> LOCATION: (4)..(4)
<223> OTHER INFORMATION: Xaa can be any naturally occurring amino acid,
      preferably one of Ser Thr, Asp, Glu, Trp, Asn or Lys
<220> FEATURE:
<221> NAME/KEY: UNSURE
<222> LOCATION: (5)..(5)
<223> OTHER INFORMATION: Xaa can be any naturally occurring amino acid,
      preferably one of Thr, Ala, Ser, Met, His, Asp, Gly, or Trp
<220> FEATURE:
<221> NAME/KEY: VARIANT
<222> LOCATION: (7)..(7)
<223> OTHER INFORMATION: Xaa is Thr, Ser, Asn or Ile
<220> FEATURE:
<221> NAME/KEY: VARIANT
<222> LOCATION: (9)..(9)
<223> OTHER INFORMATION: Xaa is Ile, Ala, Gly or Val
<220> FEATURE:
<221> NAME/KEY: VARIANT
<222> LOCATION: (10)..(10)
<223> OTHER INFORMATION: Xaa is Ile, Phe or Val
<220> FEATURE:
<221> NAME/KEY: VARIANT
<222> LOCATION: (11)..(11)
<223> OTHER INFORMATION: Xaa is Thr, Cys, Ser, Ala or Val
<220> FEATURE:
<221> NAME/KEY: VARIANT
<222> LOCATION: (12)..(12)
<223> OTHER INFORMATION: Xaa is Ser or Thr
<220> FEATURE:
<221> NAME/KEY: VARIANT
<222> LOCATION: (14)..(14)
<223> OTHER INFORMATION: Xaa is Ala or Thr
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Val, Phe, Leu, Lys, His or Ile
<220> FEATURE:
<221> NAME/KEY: VARIANT
<222> LOCATION: (17)..(17)
<223> OTHER INFORMATION: Xaa is Ser or Asp

<400> SEQUENCE: 89

Xaa Xaa Xaa Xaa Xaa Leu Xaa Arg Xaa Xaa Xaa Xaa Arg Xaa Xaa Xaa
1               5                   10                  15

Xaa

<210> SEQ ID NO 90
<211> LENGTH: 10
<212> TYPE: PRT
<213> ORGANISM: Artificial sequence
<220> FEATURE:
<223> OTHER INFORMATION: signature sequence 4
<220> FEATURE:
<221> NAME/KEY: VARIANT
<222> LOCATION: (1)..(1)
<223> OTHER INFORMATION: Xaa is His or Tyr
<220> FEATURE:
<221> NAME/KEY: VARIANT
<222> LOCATION: (2)..(2)
<223> OTHER INFORMATION: Xaa is Tyr or Phe
<220> FEATURE:
<221> NAME/KEY: VARIANT
<222> LOCATION: (3)..(3)
<223> OTHER INFORMATION: Xaa is Glu, Val, Ser or Ala
```

```
<220> FEATURE:
<221> NAME/KEY: VARIANT
<222> LOCATION: (4)..(4)
<223> OTHER INFORMATION: Xaa is Glu, Asp or Lys
<220> FEATURE:
<221> NAME/KEY: VARIANT
<222> LOCATION: (5)..(5)
<223> OTHER INFORMATION: Xaa is Ala, Leu, Ile or Val
<220> FEATURE:
<221> NAME/KEY: VARIANT
<222> LOCATION: (6)..(6)
<223> OTHER INFORMATION: Xaa is Val, Ile or Leu
<220> FEATURE:
<221> NAME/KEY: VARIANT
<222> LOCATION: (7)..(7)
<223> OTHER INFORMATION: Xaa is His, Asp or Arg
<220> FEATURE:
<221> NAME/KEY: UNSURE
<222> LOCATION: (8)..(8)
<223> OTHER INFORMATION: Xaa can be any naturally occurring amino acid,
      preferably one of Lys, Glu, Asp, Thr, Leu, Ser, Gln, Arg, Asn or
      Ala
<220> FEATURE:
<221> NAME/KEY: VARIANT
<222> LOCATION: (9)..(9)
<223> OTHER INFORMATION: Xaa is Ala or Ser
<220> FEATURE:
<221> NAME/KEY: VARIANT
<222> LOCATION: (10)..(10)
<223> OTHER INFORMATION: Xaa is Ile, Leu or Met

<400> SEQUENCE: 90

Xaa Xaa Xaa Xaa Xaa Xaa Xaa Xaa Xaa Xaa
1               5                   10

<210> SEQ ID NO 91
<211> LENGTH: 7
<212> TYPE: PRT
<213> ORGANISM: Artificial sequence
<220> FEATURE:
<223> OTHER INFORMATION: signature sequence 5
<220> FEATURE:
<221> NAME/KEY: VARIANT
<222> LOCATION: (1)..(1)
<223> OTHER INFORMATION: Xaa is Gly, Lys, Ser or Tyr
<220> FEATURE:
<221> NAME/KEY: VARIANT
<222> LOCATION: (2)..(2)
<223> OTHER INFORMATION: Xaa is Ile, Met or Leu
<220> FEATURE:
<221> NAME/KEY: VARIANT
<222> LOCATION: (4)..(4)
<223> OTHER INFORMATION: Xaa is Glu or His
<220> FEATURE:
<221> NAME/KEY: VARIANT
<222> LOCATION: (5)..(5)
<223> OTHER INFORMATION: Xaa is His or Asp
<220> FEATURE:
<221> NAME/KEY: VARIANT
<222> LOCATION: (6)..(6)
<223> OTHER INFORMATION: Xaa is Val, Leu or Ile
<220> FEATURE:
<221> NAME/KEY: VARIANT
<222> LOCATION: (7)..(7)
<223> OTHER INFORMATION: Xaa is Ala, Glu or Gly

<400> SEQUENCE: 91

Xaa Xaa Glu Xaa Xaa Xaa Xaa
1               5

<210> SEQ ID NO 92
<211> LENGTH: 9
<212> TYPE: PRT
<213> ORGANISM: Artificial sequence
<220> FEATURE:
```

```
<223> OTHER INFORMATION: signature sequence 6
<220> FEATURE:
<221> NAME/KEY: VARIANT
<222> LOCATION: (1)..(1)
<223> OTHER INFORMATION: Xaa is Leu, Val, Ile, Thr or Phe
<220> FEATURE:
<221> NAME/KEY: VARIANT
<222> LOCATION: (2)..(2)
<223> OTHER INFORMATION: Xaa is Leu, Val or Ile
<220> FEATURE:
<221> NAME/KEY: VARIANT
<222> LOCATION: (3)..(3)
<223> OTHER INFORMATION: Xaa is Gln, Tyr or Arg
<220> FEATURE:
<221> NAME/KEY: VARIANT
<222> LOCATION: (4)..(4)
<223> OTHER INFORMATION: Xaa is Val or Ile
<220> FEATURE:
<221> NAME/KEY: VARIANT
<222> LOCATION: (5)..(5)
<223> OTHER INFORMATION: Xaa is Leu, Val, Ile or Phe
<220> FEATURE:
<221> NAME/KEY: VARIANT
<222> LOCATION: (6)..(6)
<223> OTHER INFORMATION: Xaa is Ser, Gly, Ala or Thr
<220> FEATURE:
<221> NAME/KEY: VARIANT
<222> LOCATION: (7)..(7)
<223> OTHER INFORMATION: Xaa is Asp, Thr or Glu

<400> SEQUENCE: 92

Xaa Xaa Xaa Xaa Xaa Xaa Xaa Arg Ser
1               5

<210> SEQ ID NO 93
<211> LENGTH: 10
<212> TYPE: PRT
<213> ORGANISM: Artificial sequence
<220> FEATURE:
<223> OTHER INFORMATION: signature sequence 7
<220> FEATURE:
<221> NAME/KEY: VARIANT
<222> LOCATION: (2)..(2)
<223> OTHER INFORMATION: Xaa is Lys, Met, Glu, Gln or Arg
<220> FEATURE:
<221> NAME/KEY: UNSURE
<222> LOCATION: (3)..(3)
<223> OTHER INFORMATION: Xaa can be any naturally occurring amino acid,
      preferably one of Thr, Asp, Asn, Lys, Ser, Arg or Ala
<220> FEATURE:
<221> NAME/KEY: VARIANT
<222> LOCATION: (4)..(4)
<223> OTHER INFORMATION: Xaa is Thr, Leu, Met, Ile or Phe
<220> FEATURE:
<221> NAME/KEY: VARIANT
<222> LOCATION: (5)..(5)
<223> OTHER INFORMATION: Xaa is Ile or Leu
<220> FEATURE:
<221> NAME/KEY: VARIANT
<222> LOCATION: (6)..(6)
<223> OTHER INFORMATION: Xaa is Ile, Val or Leu
<220> FEATURE:
<221> NAME/KEY: VARIANT
<222> LOCATION: (7)..(7)
<223> OTHER INFORMATION: Xaa is Thr, Val, Ala or Ser
<220> FEATURE:
<221> NAME/KEY: VARIANT
<222> LOCATION: (9)..(9)
<223> OTHER INFORMATION: Xaa is Ile, Leu, Ala, Met or Val
<220> FEATURE:
<221> NAME/KEY: VARIANT
<222> LOCATION: (10)..(10)
<223> OTHER INFORMATION: Xaa is Ser or Gly

<400> SEQUENCE: 93

Tyr Arg Xaa Phe Leu Leu Ser Leu Val Gly
```

<210> SEQ ID NO 94
<211> LENGTH: 2194
<212> TYPE: DNA
<213> ORGANISM: Oryza sativa

<400> SEQUENCE: 94

| | | | | | |
|---|---|---|---|---|---|
| aatccgaaaa | gtttctgcac | cgttttcacc | ccctaactaa | caatataggg | aacgtgtgct | 60 |
| aaatataaaa | tgagacctta | tatatgtagc | gctgataact | agaactatgc | aagaaaaact | 120 |
| catccaccta | ctttagtggc | aatcgggcta | aataaaaaag | agtcgctaca | ctagtttcgt | 180 |
| tttccttagt | aattaagtgg | gaaaatgaaa | tcattattgc | ttagaatata | cgttcacatc | 240 |
| tctgtcatga | agttaaatta | ttcgaggtag | ccataattgt | catcaaactc | ttcttgaata | 300 |
| aaaaaatctt | tctagctgaa | ctcaatgggt | aaagagagag | atttttttta | aaaaaataga | 360 |
| atgaagatat | tctgaacgta | ttggcaaaga | tttaaacata | taattatata | attttatagt | 420 |
| ttgtgcattc | gtcatatcgc | acatcattaa | ggacatgtct | tactccatcc | caattttat | 480 |
| ttagtaatta | aagacaattg | acttattttt | attatttatc | tttttcgat | tagatgcaag | 540 |
| gtacttacgc | acacactttg | tgctcatgtg | catgtgtgag | tgcacctcct | caatacacgt | 600 |
| tcaactagca | acacatctct | aatatcactc | gcctatttaa | tacatttagg | tagcaatatc | 660 |
| tgaattcaag | cactccacca | tcaccagacc | acttttaata | atatctaaaa | tacaaaaat | 720 |
| aattttacag | aatagcatga | aaagtatgaa | acgaactatt | taggttttc | acatacaaaa | 780 |
| aaaaaagaa | ttttgctcgt | gcgcgagcgc | caatctccca | tattgggcac | acaggcaaca | 840 |
| acagagtggc | tgcccacaga | acaacccaca | aaaaacgatg | atctaacgga | ggacagcaag | 900 |
| tccgcaacaa | ccttttaaca | gcaggctttg | cggccaggag | agaggaggag | aggcaaagaa | 960 |
| aaccaagcat | cctccttctc | ccatctataa | attcctcccc | ccttttcccc | tctctatata | 1020 |
| ggaggcatcc | aagccaagaa | gagggagagc | accaaggaca | cgcgactagc | agaagccgag | 1080 |
| cgaccgcctt | ctcgatccat | atcttccggt | cgagttcttg | gtcgatctct | tccctcctcc | 1140 |
| acctcctcct | cacagggtat | gtgcctccct | tcggttgttc | ttggatttat | tgttctaggt | 1200 |
| tgtgtagtac | gggcgttgat | gttaggaaag | gggatctgta | tctgtgatga | ttcctgttct | 1260 |
| tggatttggg | atagagggt | tcttgatgtt | gcatgttatc | ggttcggttt | gattagtagt | 1320 |
| atggttttca | atcgtctgga | gagctctatg | gaaatgaaat | ggtttaggga | tcggaatctt | 1380 |
| gcgattttgt | gagtaccttt | tgtttgaggt | aaaatcagag | caccggtgat | tttgcttggt | 1440 |
| gtaataaagt | acggttgttt | ggtcctcgat | tctggtagtg | atgcttctcg | atttgacgaa | 1500 |
| gctatccttt | gtttattccc | tattgaacaa | aaataatcca | actttgaaga | cggtcccgtt | 1560 |
| gatgagattg | aatgattgat | tcttaagcct | gtccaaaatt | tcgcagctgg | cttgtttaga | 1620 |
| tacagtagtc | cccatcacga | aattcatgga | aacagttata | atcctcagga | acaggggatt | 1680 |
| ccctgttctt | ccgatttgct | ttagtcccag | aattttttt | cccaaatatc | ttaaaaagtc | 1740 |
| actttctggt | tcagttcaat | gaattgattg | ctacaaataa | tgcttttata | gcgttatcct | 1800 |
| agctgtagtt | cagttaatag | gtaatacccc | tatagtttag | tcaggagaag | aacttatccg | 1860 |
| atttctgatc | tccattttta | attatatgaa | atgaactgta | gcataagcag | tattcatttg | 1920 |
| gattattttt | tttattagct | ctcacccctt | cattattctg | agctgaaagt | ctggcatgaa | 1980 |
| ctgtcctcaa | ttttgttttc | aaattcacat | cgattatcta | tgcattatcc | tcttgtatct | 2040 |
| acctgtagaa | gtttctttt | ggttattcct | tgactgcttg | attacagaaa | gaaatttatg | 2100 |

```
aagctgtaat cgggatagtt atactgcttg ttcttatgat tcatttcctt tgtgcagttc   2160
ttggtgtagc ttgccacttt caccagcaaa gttc                              2194

<210> SEQ ID NO 95
<211> LENGTH: 1244
<212> TYPE: DNA
<213> ORGANISM: Oryza sativa

<400> SEQUENCE: 95
aaaaccaccg agggacctga tctgcaccgg ttttgatagt tgagggaccc gttgtgtctg     60
gttttccgat cgagggacga aaatcggatt cggtgtaaag ttaagggacc tcagatgaac    120
ttattccgga gcatgattgg gaagggagga cataaggccc atgtcgcatg tgtttggacg    180
gtccagatct ccagatcact cagcaggatc ggccgcgttc gcgtagcacc cgcggtttga    240
ttcggcttcc cgcaaggcgg cggccggtgg ccgtgccgcc gtagcttccg ccggaagcga    300
gcacgccgcc gccgccgacc cggctctgcg tttgcaccgc cttgcacgcg atacatcggg    360
atagatagct actactctct ccgtttcaca atgtaaatca ttctactatt ttccacattc    420
atattgatgt taatgaatat agacatatat atctatttag attcattaac atcaatatga    480
atgtaggaaa tgctagaatg acttacattg tgaattgtga aatggacgaa gtacctacga    540
tggatggatg caggatcatg aaagaattaa tgcaagatcg tatctgccgc atgcaaaatc    600
ttactaattg cgctgcatat atgcatgaca gcctgcatgc gggcgtgtaa gcgtgttcat    660
ccattaggaa gtaaccttgt cattacttat accagtacta catactatat agtattgatt    720
tcatgagcaa atctacaaaa ctggaaagca ataagaaata cgggactgga aaagactcaa    780
cattaatcac caaatatttc gccttctcca gcagaatata tatctctcca tcttgatcac    840
tgtacacact gacagtgtac gcataaacgc agcagccagc ttaactgtcg tctcaccgtc    900
gcacactggc cttccatctc aggctagctt tctcagccac ccatcgtaca tgtcaactcg    960
gcgcgcgcac aggcacaaat tacgtacaaa acgcatgacc aaatcaaaac caccggagaa   1020
gaatcgctcc cgcgcgcggc ggcgacgcgc acgtacgaac gcacgcacgc acgcccaacc   1080
ccacgacacg atcgcgcgcg acgccggcga caccggccgt ccaccgcgc cctcacctcg    1140 ccgactataa atacgtaggc atctgcttga tcttgtcatc catctcacca ccaaaaaaaa   1200
aaggaaaaaa aaacaaaaca caccaagcca aataaaagcg acaa                   1244

<210> SEQ ID NO 96
<211> LENGTH: 1141
<212> TYPE: DNA
<213> ORGANISM: Gossypium hirsutum

<400> SEQUENCE: 96
cagattcaga aagaaataaa ggaagaagaa gcaatggcca ctcttacagt gcccacgaca     60
gttccttcgg tgtctgaaga ttgtgaacag ctaagaaaag cctttcagg atggggaact    120 aatgagggct taatcataga tatattgggt cacagaaatg ccgagcaacg aaacttgatt    180
cgaaaaacct acgctgaaac ctatggagag gatctcctca aggcactaga caaggagctc    240
tcgaatgact ttgagaggct ggttttgctt tgggctcttg atcctgctga acgtgatgcc    300
cttttggcta atgaagccac caaaaggtgg acttcaagca atcaggtcct tatggaaata    360
gcttgcacaa ggtctgccaa ccaactgctt cacgcaaggc aggcttatca tgctcgttat    420
aagaagtcgc ttgaagagga tgttgctcat cacacgactg gcgacttccg taagctcctc    480
```

```
ctacctctag tgagttcata cagatatgag ggagaggagg tgaacatgaa tctggcgaaa    540
acagaggcga agttgcttca tgagaaaatt tcagacaaag cttacagtga tgacgatgtc    600
ataagggttt tggctacaag aagcaaggca cagatcaatg caactctgaa tcactacaaa    660
aatgaatatg gaaatgacat aaacaaggac ttgaaggctg atcctaagga tgagttcctt    720
gcactactaa ggtccacagt gaagtgcttg gtctatccgg aaaagtattt tgagaaggtt    780
cttcgcctag caatcaatag acgaggaacg gatgaaggag ctcttactag agttgtttgc    840
actagggctg aggttgatct aaagatcata gcagatgagt accagcgaag gaacagtgtc    900
ccactgactc gtgccattgt caaggacact catggagact atgaaaaatt gctgctggta    960
cttgcaggac atgtggagaa ttgaatctga tatcatgaga caatttcctg gtgaataaat   1020
gtttatgacc aaactataat ggtctagtgt ggttattgat gttttcctgt ttttctatgt   1080
agtattgcga gttatatgct atccaagaat tcgaagtcta tttaaaaaaa aaaaaaaaaa   1140
a                                                                    1141
```

<210> SEQ ID NO 97
<211> LENGTH: 316
<212> TYPE: PRT
<213> ORGANISM: Gossypium hirsutum

<400> SEQUENCE: 97

```
Met Ala Thr Leu Thr Val Pro Thr Thr Val Pro Ser Val Ser Glu Asp
1               5                   10                  15

Cys Glu Gln Leu Arg Lys Ala Phe Ser Gly Trp Gly Thr Asn Glu Gly
            20                  25                  30

Leu Ile Ile Asp Ile Leu Gly His Arg Asn Ala Glu Gln Arg Asn Leu
        35                  40                  45

Ile Arg Lys Thr Tyr Ala Glu Thr Tyr Gly Glu Asp Leu Leu Lys Ala
    50                  55                  60

Leu Asp Lys Glu Leu Ser Asn Asp Phe Glu Arg Leu Val Leu Leu Trp
65                  70                  75                  80

Ala Leu Asp Pro Ala Glu Arg Asp Ala Leu Leu Ala Asn Glu Ala Thr
                85                  90                  95

Lys Arg Trp Thr Ser Ser Asn Gln Val Leu Met Glu Ile Ala Cys Thr
            100                 105                 110

Arg Ser Ala Asn Gln Leu Leu His Ala Arg Gln Ala Tyr His Ala Arg
        115                 120                 125

Tyr Lys Lys Ser Leu Glu Glu Asp Val Ala His His Thr Thr Gly Asp
    130                 135                 140

Phe Arg Lys Leu Leu Leu Pro Leu Val Ser Ser Tyr Arg Tyr Glu Gly
145                 150                 155                 160

Glu Glu Val Asn Met Asn Leu Ala Lys Thr Glu Ala Lys Leu Leu His
                165                 170                 175

Glu Lys Ile Ser Asp Lys Ala Tyr Ser Asp Asp Val Ile Arg Val
            180                 185                 190

Leu Ala Thr Arg Ser Lys Ala Gln Ile Asn Ala Thr Leu Asn His Tyr
        195                 200                 205

Lys Asn Glu Tyr Gly Asn Asp Ile Asn Lys Asp Leu Lys Ala Asp Pro
    210                 215                 220

Lys Asp Glu Phe Leu Ala Leu Leu Arg Ser Thr Val Lys Cys Leu Val
225                 230                 235                 240

Tyr Pro Glu Lys Tyr Phe Glu Lys Val Leu Arg Leu Ala Ile Asn Arg
                245                 250                 255
```

```
Arg Gly Thr Asp Glu Gly Ala Leu Thr Arg Val Cys Thr Arg Ala
            260                 265                 270

Glu Val Asp Leu Lys Ile Ile Ala Asp Glu Tyr Gln Arg Arg Asn Ser
        275                 280                 285

Val Pro Leu Thr Arg Ala Ile Val Lys Asp Thr His Gly Asp Tyr Glu
    290                 295                 300

Lys Leu Leu Leu Val Leu Ala Gly His Val Glu Asn
305                 310                 315

<210> SEQ ID NO 98
<211> LENGTH: 1112
<212> TYPE: DNA
<213> ORGANISM: Lavatera thuringiaca

<400> SEQUENCE: 98
aatggctact cttacagttc cctccacact tccgtcagtg tctgaagatt gtgaacaact      60
caggaaagcc ttctcaggat ggggaactaa tgaggactta atcataaata tattgggtca    120
ccgaaatgcg gacgaacgaa actcgattcg aaaagcttat actgaaaccc atggagaaga    180
tctcctcaag gcactggaca aggaactctc aaatgacttt gagaggctgg ttctgctttg    240
gactcttgat cctcctgaac gtgatgcact tttggcaaat gaagccacca aaggtggac     300
ttcaagcaat caggtaatta tggaaatagc ctgcagaagt tcttctgacc aactgcttcg    360
cgcgaggcag gcttatcatg ttcgttataa gaatcgctt aagaggatg ttgcccatca     420
cacaactggc gacttccgta agcttctcct acctcttgtg agttcataca gatacgaggg    480
agatgaagtg aacatgactc tggcgaaaac agaggccaag ttactccatg agaaaatctc    540
aaacaaagct tacagtgatg acgatgtcat cagggttttg gctacgagaa gcaagtcaca    600
gatcaacgaa cgtcttaatc actacaaaaa tgaatacgca actgatataa acaaggacct    660
gaaggctgac cctaaggatg agttccttgc actgctaagg tccacagtga agtgcttggt    720
ctaccctgaa aagtatttcg agaaggttct tcgtctagca atcaataaac gaggaacgga    780
tgaaggagct cttacgaggg ttgtttccac cagggctgag gttgatctaa agatcatagc    840
agatgagtac cagcgaagga acagtgtccc actgactcgt gctattgtca aggacactaa    900
tggagactac gaaaaattgc tgctggtact tgctggagag gtggaggctt gaaccggttt    960
tcatgagatg attttgtgtt gaataaaaac ttaatgaccg gaactctaat ggtctagtgt   1020
tgctattatg ttatcctgtt ttttttcttc tatggtactg tgagttttat gcaataaagg   1080
cttgttattt agaaaaaaaa aaaaaaaaa aa                                    1112

<210> SEQ ID NO 99
<211> LENGTH: 316
<212> TYPE: PRT
<213> ORGANISM: Lavatera thuringiaca

<400> SEQUENCE: 99

Met Ala Thr Leu Thr Val Pro Ser Thr Leu Pro Ser Val Ser Glu Asp
1               5                   10                  15

Cys Glu Gln Leu Arg Lys Ala Phe Ser Gly Trp Gly Thr Asn Glu Asp
            20                  25                  30

Leu Ile Ile Asn Ile Leu Gly His Arg Asn Ala Asp Glu Arg Asn Ser
        35                  40                  45

Ile Arg Lys Ala Tyr Thr Glu Thr His Gly Glu Asp Leu Leu Lys Ala
    50                  55                  60
```

| | | | | | | | | | | | |
|---|---|---|---|---|---|---|---|---|---|---|---|
|Leu|Asp|Lys|Glu|Leu|Ser|Asn|Asp|Phe|Glu|Arg|Leu|Val|Leu|Leu|Trp|
|65| | | |70| | | |75| | | |  | | |80|

Leu Asp Lys Glu Leu Ser Asn Asp Phe Glu Arg Leu Val Leu Leu Trp
65                  70                  75                  80

Thr Leu Asp Pro Pro Glu Arg Asp Ala Leu Leu Ala Asn Glu Ala Thr
                85                  90                  95

Lys Arg Trp Thr Ser Ser Asn Gln Val Ile Met Glu Ile Ala Cys Arg
            100                 105                 110

Ser Ser Ser Asp Gln Leu Leu Arg Ala Arg Gln Ala Tyr His Val Arg
            115                 120                 125

Tyr Lys Lys Ser Leu Glu Glu Asp Val Ala His His Thr Thr Gly Asp
            130                 135                 140

Phe Arg Lys Leu Leu Leu Pro Leu Val Ser Ser Tyr Arg Tyr Glu Gly
145                 150                 155                 160

Asp Glu Val Asn Met Thr Leu Ala Lys Thr Glu Ala Lys Leu Leu His
                165                 170                 175

Glu Lys Ile Ser Asn Lys Ala Tyr Ser Asp Asp Val Ile Arg Val
            180                 185                 190

Leu Ala Thr Arg Ser Lys Ser Gln Ile Asn Glu Arg Leu Asn His Tyr
            195                 200                 205

Lys Asn Glu Tyr Ala Thr Asp Ile Asn Lys Asp Leu Lys Ala Asp Pro
210                 215                 220

Lys Asp Glu Phe Leu Ala Leu Arg Ser Thr Val Lys Cys Leu Val
225                 230                 235                 240

Tyr Pro Glu Lys Tyr Phe Glu Lys Val Leu Arg Leu Ala Ile Asn Lys
            245                 250                 255

Arg Gly Thr Asp Glu Gly Ala Leu Thr Arg Val Val Ser Thr Arg Ala
            260                 265                 270

Glu Val Asp Leu Lys Ile Ile Ala Asp Glu Tyr Gln Arg Arg Asn Ser
            275                 280                 285

Val Pro Leu Thr Arg Ala Ile Val Lys Asp Thr Asn Gly Asp Tyr Glu
            290                 295                 300

Lys Leu Leu Leu Val Leu Ala Gly Glu Val Glu Ala
305                 310                 315

<210> SEQ ID NO 100
<211> LENGTH: 2040
<212> TYPE: DNA
<213> ORGANISM: Brassica rapa

<400> SEQUENCE: 100

```
atggcgtctc tcaaagtccc taccaacgtt cctcttcccg aggaagacgc cgagcaactc    60
cacaaggctt ttgcaggatg gggtaccaac gagaagctga tcatatcaat cctagctcac   120
aggacctcag cacaacgcag cttaatccgc agcgcttatg ccgctgctta caatgaggat   180
ctcctcaagg ccttagacaa agagctttct agtgactttg agcgagttgt catgttgtgg   240
actcttgatc agcgggagag agatgctttc cttgctaaag aatctaccaa aatgttcacc   300
aagaacaatt gggttcttgt tgaaatcgca tgcactaggt gtcctcttga tcttttcaag   360
gtcaaacaag cttaccaagc acgttacaag aaatctctag aggaagatgt tgcgcaacac   420
acatctggtg accttcgtaa gctcttgctt cctcttgtta gtactttag gtacgaagga   480
gatgaggtga acatgaggct tgcaagatcc gaagctaagt acttcacga gaaggtctca   540
gagaaagcct ttagtgatga tgacttcatc agaatcttga caacaagaag caaagcacag   600
ctcggtgcaa ctcttaacca ctacaataat gagtacggaa acgctattaa caagcacttg   660
aaggaagatt cagatgatga gtacctgaag ctactaagag ctgcgatcac gtgtttgaca   720
```

```
taccctgaga agcattttga gaaggttttg cgtctagcaa ttaacaaaat ggggactgat      780
gagtgggcac taacccgagt tgtgactaca cgaactgaag ttgatatgga acgtatcaaa      840
gaggaatatc aacgaaggaa cagcattcct ttgcaccatg ccgtcgctaa agacacttct      900
ggtgattatg aggatatgct tgtttctctt ctcggacatg gagatgaagg gactctcgac      960
ggatcttttg ctggagataa gcgcctcggc ttctcgtctt cttcacagtc ctcacgtcgt     1020
ctcgccctat ctggtgggtc gtctctccaa caacgaatcg agaggactct cttgccactg     1080
ctgctctcgg gttatcggag acaagctcca gtgaactccc ctctaactgc cccagacatg     1140
tctcgatttt gcagatccga agaaccttct ggttctcttg gtctctcatc atttggtggc     1200
tccttcctca ccagagccgg gtctagcgtc aattcacctg ctcctctctc atcaatttat     1260
gttaatccgg cgaccgatgt aggtggaact ccactccggc gaccagatct gttccttaaa     1320
agtttgagaa gacaagcatc ctccagcgac attcctcttc cccgctccat cctctccatc     1380
ctccatgttt ggcctcctcc acccttcaga ttgtgtaaac ttggttttaaa acgattgcat     1440
gaagatccat accaccaacc actgcaaaca taccttctat cacagcggtt tgcaaatttg     1500
gcgtccgatg taggtgggaa ttcactccgg catacagttt tgagccatat gtttatgaat     1560
atgacgtctg atgtgagtgg gaatccactc cggcctccag ctctgagcca tcaaaagcta     1620
gtaaggccaa tttgtcggcg cattattctc acctcttttt ctgttgtgga gatcacttta     1680
ctaccatgtc tcccttctat gaatggagaa aatttctcag attctttttcc gagcttcagt     1740
tgcagtttac tcactggttt gttactttat ggagcggtcc gtacgggggcc tgaaggtgca     1800
atcgagacta cttcggtttt tcttgttggt gaagactgtc tttcaacgtc acttgtgact     1860
atctctcaac tatccaactt tgccgtggaa gctttattga cgcattcaaa cttgatattg     1920
aattcgctgt caacttcata tgaagattta ttatgcttgt ttctaattgc tattatagtt     1980
catgaattgt ccacaagagg atgtttagtt ctcttttggc tttgtagtcc ttgcatttga     2040
```

<210> SEQ ID NO 101
<211> LENGTH: 679
<212> TYPE: PRT
<213> ORGANISM: Brassica rapa

<400> SEQUENCE: 101

```
Met Ala Ser Leu Lys Val Pro Thr Asn Val Pro Leu Pro Glu Glu Asp
1               5                   10                  15

Ala Glu Gln Leu His Lys Ala Phe Ala Gly Trp Gly Thr Asn Glu Lys
            20                  25                  30

Leu Ile Ile Ser Ile Leu Ala His Arg Thr Ser Ala Gln Arg Ser Leu
        35                  40                  45

Ile Arg Ser Ala Tyr Ala Ala Tyr Asn Glu Asp Leu Leu Lys Ala
    50                  55                  60

Leu Asp Lys Glu Leu Ser Ser Asp Phe Glu Arg Val Val Met Leu Trp
65                  70                  75                  80

Thr Leu Asp Pro Ala Glu Arg Asp Ala Phe Leu Ala Lys Glu Ser Thr
                85                  90                  95

Lys Met Phe Thr Lys Asn Asn Trp Val Leu Val Glu Ile Ala Cys Thr
            100                 105                 110

Arg Cys Pro Leu Asp Leu Phe Lys Val Lys Gln Ala Tyr Gln Ala Arg
        115                 120                 125

Tyr Lys Lys Ser Leu Glu Glu Asp Val Ala Gln His Thr Ser Gly Asp
    130                 135                 140
```

```
Leu Arg Lys Leu Leu Leu Pro Leu Val Ser Thr Phe Arg Tyr Glu Gly
145                 150                 155                 160

Asp Glu Val Asn Met Arg Leu Ala Arg Ser Glu Ala Lys Leu Leu His
            165                 170                 175

Glu Lys Val Ser Glu Lys Ala Phe Ser Asp Asp Phe Ile Arg Ile
            180                 185                 190

Leu Thr Thr Arg Ser Lys Ala Gln Leu Gly Ala Thr Leu Asn His Tyr
        195                 200                 205

Asn Asn Glu Tyr Gly Asn Ala Ile Asn Lys His Leu Lys Glu Asp Ser
    210                 215                 220

Asp Asp Glu Tyr Leu Lys Leu Leu Arg Ala Ala Ile Thr Cys Leu Thr
225                 230                 235                 240

Tyr Pro Glu Lys His Phe Glu Lys Val Leu Arg Leu Ala Ile Asn Lys
                245                 250                 255

Met Gly Thr Asp Glu Trp Ala Leu Thr Arg Val Val Thr Thr Arg Thr
            260                 265                 270

Glu Val Asp Met Glu Arg Ile Lys Glu Glu Tyr Gln Arg Arg Asn Ser
        275                 280                 285

Ile Pro Leu His His Ala Val Ala Lys Asp Thr Ser Gly Asp Tyr Glu
    290                 295                 300

Asp Met Leu Val Ser Leu Leu Gly His Gly Asp Glu Gly Thr Leu Asp
305                 310                 315                 320

Gly Ser Phe Ala Gly Asp Lys Arg Leu Gly Phe Ser Ser Ser Ser Gln
                325                 330                 335

Ser Ser Arg Arg Leu Ala Leu Ser Gly Gly Ser Ser Leu Gln Gln Arg
            340                 345                 350

Ile Glu Arg Thr Leu Leu Pro Leu Leu Ser Gly Tyr Arg Arg Gln
        355                 360                 365

Ala Pro Val Asn Ser Pro Leu Thr Ala Pro Asp Met Ser Arg Phe Cys
    370                 375                 380

Arg Ser Glu Glu Pro Ser Gly Ser Leu Gly Leu Ser Ser Phe Gly Gly
385                 390                 395                 400

Ser Phe Leu Thr Arg Ala Gly Ser Ser Val Asn Ser Pro Ala Pro Leu
                405                 410                 415

Ser Ser Ile Tyr Val Asn Pro Ala Thr Asp Val Gly Gly Thr Pro Leu
            420                 425                 430

Arg Arg Pro Asp Leu Phe Leu Lys Ser Leu Arg Arg Gln Ala Ser Ser
        435                 440                 445

Ser Asp Ile Pro Leu Pro Arg Ser Ile Leu Ser Ile Leu His Val Trp
    450                 455                 460

Pro Pro Pro Pro Phe Arg Leu Cys Lys Leu Gly Leu Lys Arg Leu His
465                 470                 475                 480

Glu Asp Pro Tyr His Gln Pro Leu Gln Thr Tyr Leu Leu Ser Gln Arg
                485                 490                 495

Phe Ala Asn Leu Ala Ser Asp Val Gly Gly Asn Ser Leu Arg His Thr
            500                 505                 510

Val Leu Ser His Met Phe Met Asn Met Thr Ser Asp Val Ser Gly Asn
        515                 520                 525

Pro Leu Arg Pro Pro Ala Leu Ser His Gln Lys Leu Val Arg Pro Ile
    530                 535                 540

Cys Arg Arg Ile Ile Leu Thr Ser Phe Ser Val Val Glu Ile Thr Leu
545                 550                 555                 560
```

Leu Pro Cys Leu Pro Ser Met Asn Gly Glu Asn Phe Ser Asp Ser Phe
              565                 570                 575

Pro Ser Phe Ser Cys Ser Leu Leu Thr Gly Leu Leu Leu Tyr Gly Ala
            580                 585                 590

Val Arg Thr Gly Pro Glu Gly Ala Ile Glu Thr Thr Ser Val Phe Leu
        595                 600                 605

Val Gly Glu Asp Cys Leu Ser Thr Ser Leu Val Thr Ile Ser Gln Leu
    610                 615                 620

Ser Asn Phe Ala Val Glu Ala Leu Leu Thr His Ser Asn Leu Ile Leu
625                 630                 635                 640

Asn Ser Leu Ser Thr Ser Tyr Glu Asp Leu Leu Cys Leu Phe Leu Ile
            645                 650                 655

Ala Ile Ile Val His Glu Leu Ser Thr Arg Gly Cys Leu Val Leu Phe
            660                 665                 670

Trp Leu Cys Ser Pro Cys Ile
        675

<210> SEQ ID NO 102
<211> LENGTH: 1146
<212> TYPE: DNA
<213> ORGANISM: Gossypium hirsutum

<400> SEQUENCE: 102
caaccctcaa agttccagtt cacgttcctt ctccttctga ggatgctgaa tgcaacttc      60 ggaaagcttt tgaaggctgg ggtacgaacg agcaattgat tatcgacata ttggctcaca    120
ggaatgcagc acagcgcaat tcaattcgga agtttatgg tgaagcttat ggggaagatc     180
ttctcaagtg tttggagaag gaacttacaa gtgatttcga gcgggctgtg ctgcttttta    240
cgttggaccc tgcagagcga gatgctcatc tggctaatga agctacaaag aagttcacat    300
caagcaattg gattctcatg gagatagctt gcagtaggtc ttcgcatgaa ctactcaatg    360
tgaaaaaggc gtatcatgct cgttataaga aatcccttga agaagatgtt gctcaccaca    420
ctaccggaga gtaccgcaag cttttggtcc ctcttgttag tgcattccga tatgagggag    480
aggaggtgaa catgacattg gcaaaatctg aggctaagat acttcatgat aaaatttcgg    540
acaagcatta taccgatgag gaggtgatta ggattgtatc aacaaggagt aaggcacagc    600
tcaatgcaac tctcaaccat acaatactt cattcggcaa tgctatcaac aaggatttga    660
aggctgatcc cagtgatgaa ttcctcaaat tactaagagc tgtgatcaag tgcttgacca    720
ccccagagca atatttcgag aaggttttac gtcaagccat caataagttg ggatccgatg    780
aatgggctct taccgagtc gtcacaactc gtgcagaggt cgacatggta cgtattaagg     840
aggcatatca acgaagaaac agcatccctc tcgaacaagc aattgctaaa gatacttcgg    900
gtgactatga gaagtttctt cttgccttga tcggagctgg agatgcatga accgtcttcg    960
gtattaagtt cctctgtatg aatgtttagt ttgccttatc cgctatgact taataattta   1020
tgcttggttt ttcatcgttt tcattatcta aagcattgct tgcttccatg atagaacatt   1080 caaaataaa tgattgagtt cgtttaaaaa aaaaaaaaa aaaaaaaagg aaaaaaaaaa     1140
aaaaaa                                                                1146

<210> SEQ ID NO 103
<211> LENGTH: 315
<212> TYPE: PRT
<213> ORGANISM: Gossypium hirsutum

<400> SEQUENCE: 103

Thr Leu Lys Val Pro Val His Val Pro Ser Pro Ser Glu Asp Ala Glu
1               5                   10                  15

Trp Gln Leu Arg Lys Ala Phe Glu Gly Trp Gly Thr Asn Glu Gln Leu
            20                  25                  30

Ile Ile Asp Ile Leu Ala His Arg Asn Ala Ala Gln Arg Asn Ser Ile
        35                  40                  45

Arg Lys Val Tyr Gly Glu Ala Tyr Gly Glu Asp Leu Leu Lys Cys Leu
    50                  55                  60

Glu Lys Glu Leu Thr Ser Asp Phe Glu Arg Ala Val Leu Leu Phe Thr
65                  70                  75                  80

Leu Asp Pro Ala Glu Arg Asp Ala His Leu Ala Asn Glu Ala Thr Lys
                85                  90                  95

Lys Phe Thr Ser Ser Asn Trp Ile Leu Met Glu Ile Ala Cys Ser Arg
            100                 105                 110

Ser Ser His Glu Leu Leu Asn Val Lys Lys Ala Tyr His Ala Arg Tyr
        115                 120                 125

Lys Lys Ser Leu Glu Glu Asp Val Ala His His Thr Thr Gly Glu Tyr
    130                 135                 140

Arg Lys Leu Leu Val Pro Leu Val Ser Ala Phe Arg Tyr Glu Gly Glu
145                 150                 155                 160

Glu Val Asn Met Thr Leu Ala Lys Ser Glu Ala Lys Ile Leu His Asp
                165                 170                 175

Lys Ile Ser Asp Lys His Tyr Thr Asp Glu Glu Val Ile Arg Ile Val
            180                 185                 190

Ser Thr Arg Ser Lys Ala Gln Leu Asn Ala Thr Leu Asn His Tyr Asn
        195                 200                 205

Thr Ser Phe Gly Asn Ala Ile Asn Lys Asp Leu Lys Ala Asp Pro Ser
    210                 215                 220

Asp Glu Phe Leu Lys Leu Leu Arg Ala Val Ile Lys Cys Leu Thr Thr
225                 230                 235                 240

Pro Glu Gln Tyr Phe Glu Lys Val Leu Arg Gln Ala Ile Asn Lys Leu
                245                 250                 255

Gly Ser Asp Glu Trp Ala Leu Thr Arg Val Val Thr Thr Arg Ala Glu
            260                 265                 270

Val Asp Met Val Arg Ile Lys Glu Ala Tyr Gln Arg Arg Asn Ser Ile
        275                 280                 285

Pro Leu Glu Gln Ala Ile Ala Lys Asp Thr Ser Gly Asp Tyr Glu Lys
    290                 295                 300

Phe Leu Leu Ala Leu Ile Gly Ala Gly Asp Ala
305                 310                 315

<210> SEQ ID NO 104
<211> LENGTH: 1180
<212> TYPE: DNA
<213> ORGANISM: Capsicum annuum

<400> SEQUENCE: 104
aaaaatggca agtctaaccg ttccagcaca tgttccttcg gctgctgaag actgtgaaca      60
actccgatct gccttcaaag gatggggaac aaatgagaag ttgatcatat caattttggc     120
tcatagaact gctgctcagc gcaaattgat tcgtcaaact tatgctgaga ctttcggaga     180
ggatctactt aaagagttgg acagagaact tacccatgat tttgagaaat tggtgctagt     240
gtggacgttg gatccttcag aacgtgatgc tcatttggct aaggaagcta ctaagagatg     300

-continued

```
gacaaaaagc aactttgttc ttgtggagct agcttgtacc agatcgccta agaactggt    360 tttggctagg gaagcttatc atgcacgtta caagaaatct cttgaagagg atgttgccta    420
tcacactact ggggatcacc gcaagctttt ggtacctctt gtgagctcct accgatatgg    480
aggagaggag gtggacttgc gccttgctaa agcagaatct aaaattctgc atgagaagat    540
ctccgataag gcttacagtg atgatgaggt cattagaatt ttagccacaa ggagcaaagc    600
gcaactcaat gctactttga atcattacaa agatgaacat ggtgaggata tcctaaagca    660
attggaagat ggggatgagt tgttgcact attgagggcc accattaaag gtcttgtcta    720
cccggagcac tattttgtgg aggttcttcg tgatgcaatc aacaggagag gacagagga    780 agatcatctg acaagagtta ttgctacaag ggctgaggtc gatctgaaga ttatcgctga    840
tgagtaccag aagagggata gcattcccct gggtcgcgcc attgccaaag atacaagagg    900
agattatgag agtatgctgt tggctttgct tggacaagag gaggactgag gaggatttgg    960
ccacttatgt tttacaatga caagaataaa tatgccatcc cctatatgag aattggcatc   1020
cgttgtatgt ttgatgattg agtgtggtct gtttatgagc ttttagtcct ttttcttct   1080 cgtgagaaac ttctaatatg caactttgtg ctgtctacat atgttttcta ataatatgca   1140
tcgattagtt ctaaaaaaaa aaaaaaaaaa aaaaaaaaa                          1180
```

<210> SEQ ID NO 105
<211> LENGTH: 322
<212> TYPE: PRT
<213> ORGANISM: Capsicum annuum

<400> SEQUENCE: 105

```
Met Ala His His His His His Met Ala Ser Leu Thr Val Pro Ala
1               5                   10                  15

His Val Pro Ser Ala Ala Glu Asp Cys Glu Gln Leu Arg Ser Ala Phe
            20                  25                  30

Lys Gly Trp Gly Thr Asn Glu Lys Leu Ile Ile Ser Ile Leu Ala His
        35                  40                  45

Arg Thr Ala Ala Gln Arg Lys Leu Ile Arg Gln Thr Tyr Ala Glu Thr
    50                  55                  60

Phe Gly Glu Asp Leu Leu Lys Glu Leu Asp Arg Glu Leu Thr His Asp
65                  70                  75                  80

Phe Glu Lys Leu Val Leu Val Trp Thr Leu Asp Pro Ser Glu Arg Asp
                85                  90                  95

Ala His Leu Ala Lys Glu Ala Thr Lys Arg Trp Thr Lys Ser Asn Phe
            100                 105                 110

Val Leu Val Glu Leu Ala Cys Thr Arg Ser Pro Lys Glu Leu Val Leu
        115                 120                 125

Ala Arg Glu Ala Tyr His Ala Arg Tyr Lys Lys Ser Leu Glu Glu Asp
    130                 135                 140

Val Ala Tyr His Thr Thr Gly Asp His Arg Lys Leu Leu Val Pro Leu
145                 150                 155                 160

Val Ser Ser Tyr Arg Tyr Gly Gly Glu Glu Val Asp Leu Arg Leu Ala
                165                 170                 175

Lys Ala Glu Ser Lys Ile Leu His Glu Lys Ile Ser Asp Lys Ala Tyr
            180                 185                 190

Ser Asp Asp Glu Val Ile Arg Ile Leu Ala Thr Arg Ser Lys Ala Gln
        195                 200                 205

Leu Asn Ala Thr Leu Asn His Tyr Lys Asp Glu His Gly Glu Asp Ile
    210                 215                 220
```

```
Leu Lys Gln Leu Glu Asp Gly Asp Glu Phe Val Ala Leu Leu Arg Ala
225                 230                 235                 240

Thr Ile Lys Gly Leu Val Tyr Pro Glu His Tyr Phe Val Glu Val Leu
                245                 250                 255

Arg Asp Ala Ile Asn Arg Arg Gly Thr Glu Glu Asp His Leu Thr Arg
            260                 265                 270

Val Ile Ala Thr Arg Ala Glu Val Asp Leu Lys Ile Ile Ala Asp Glu
        275                 280                 285

Tyr Gln Lys Arg Asp Ser Ile Pro Leu Gly Arg Ala Ile Ala Lys Asp
    290                 295                 300

Thr Arg Gly Asp Tyr Glu Ser Met Leu Leu Ala Leu Leu Gly Gln Glu
305                 310                 315                 320

Glu Asp

<210> SEQ ID NO 106
<211> LENGTH: 1197
<212> TYPE: DNA
<213> ORGANISM: Nicotiana tabacum

<400> SEQUENCE: 106
catccacaat tctccacagt acaagaaaac aaaaaaatgg cgagtcttaa agttccaaca      60
tctgttccag aaccttatga agatgctgag caactcaaaa aagcttttgc tggatggggt     120
acaaatgagg cacttattat tcagattctg gcacatagaa atgcagcaca acgcaagtta     180
atccgagaaa cttatgctgc agcttatgga gaggatcttc tcaaggactt ggatgctgaa     240
ctgacaagtg attttcagcg tgcagtgctt ctgtggactt tgagtcctgc tgagcgcgac     300
gcctacttgg ttaatgaagc taccaaacgt ctgacttcta gcaattgggt tatcttggaa     360
attgcttgta caaggtcttc tgatgatctc tttaaggcga ggcaggccta ccatgctcga     420
tacaagaaat cacttgaaga gatgttgct tatcacacaa ctggggatttt ccgtaagctt     480
ttggttcctc tttttaactgc attcagatac gaaggagaag aggcgaacat gacattggca     540
agaaaggagg caaatatact acacgagaag atctctgaca aggcttacaa tgatgaggag     600
ctcatccgaa ttatttctac taggagtaaa gcacagctga atgcaacatt caaccactac     660
cttgaccaac atggcagtga atcaacaag gatctggaaa ctgattctga tgatgagtac     720
ctgaaattac tcagcgcagc aatagaatgc ttgaaaaccc cagagaaaca ctttgagaaa     780
gttcttcgat tggctatcaa gggtacaggc acagacgaat gggaccttac tagagttgtc     840
actactcggg ctgaagttga catggaacgt atcaaagaag agtaccataa gaggaacagt     900
gttccattgg accgtgcaat tgctggagac acttcaggag actatgaaag gatgcttctg     960
gctttgattg ggcatggaga tgcttgaatg gaatatgtgt tctaagattg ataagaaac    1020
tatttcctaa tgtctgaagt ttgaatttgt ttgatgatgt gtgcatgtat gcccagagtt    1080
tggtttgcat tatatggatt taaataatcc aggtgttgtg ttttgttttt ttcttcactt    1140
gtcatagttt ggttctatat attcggactt cctcaaccag tgatcttatt gtttatc       1197

<210> SEQ ID NO 107
<211> LENGTH: 316
<212> TYPE: PRT
<213> ORGANISM: Nicotiana tabacum

<400> SEQUENCE: 107

Met Ala Ser Leu Lys Val Pro Thr Ser Val Pro Glu Pro Tyr Glu Asp
1               5                   10                  15
```

Ala Glu Gln Leu Lys Lys Ala Phe Ala Gly Trp Gly Thr Asn Glu Ala
            20                  25                  30

Leu Ile Ile Gln Ile Leu Ala His Arg Asn Ala Ala Gln Arg Lys Leu
            35                  40                  45

Ile Arg Glu Thr Tyr Ala Ala Tyr Gly Glu Asp Leu Leu Lys Asp
50                      55                  60

Leu Asp Ala Glu Leu Thr Ser Asp Phe Gln Arg Ala Val Leu Leu Trp
65                  70                  75                  80

Thr Leu Ser Pro Ala Glu Arg Asp Ala Tyr Leu Val Asn Glu Ala Thr
                85                  90                  95

Lys Arg Leu Thr Ser Ser Asn Trp Val Ile Leu Glu Ile Ala Cys Thr
            100                 105                 110

Arg Ser Ser Asp Asp Leu Phe Lys Ala Arg Gln Ala Tyr His Ala Arg
            115                 120                 125

Tyr Lys Lys Ser Leu Glu Glu Asp Val Ala Tyr His Thr Thr Gly Asp
            130                 135                 140

Phe Arg Lys Leu Leu Val Pro Leu Leu Thr Ala Phe Arg Tyr Glu Gly
145                 150                 155                 160

Glu Glu Ala Asn Met Thr Leu Ala Arg Lys Glu Ala Asn Ile Leu His
                165                 170                 175

Glu Lys Ile Ser Asp Lys Ala Tyr Asn Asp Glu Glu Leu Ile Arg Ile
            180                 185                 190

Ile Ser Thr Arg Ser Lys Ala Gln Leu Asn Ala Thr Phe Asn His Tyr
            195                 200                 205

Leu Asp Gln His Gly Ser Glu Ile Asn Lys Asp Leu Glu Thr Asp Ser
            210                 215                 220

Asp Asp Glu Tyr Leu Lys Leu Leu Ser Ala Ala Ile Glu Cys Leu Lys
225                 230                 235                 240

Thr Pro Glu Lys His Phe Glu Lys Val Leu Arg Leu Ala Ile Lys Gly
                245                 250                 255

Thr Gly Thr Asp Glu Trp Asp Leu Thr Arg Val Val Thr Thr Arg Ala
            260                 265                 270

Glu Val Asp Met Glu Arg Ile Lys Glu Glu Tyr His Lys Arg Asn Ser
            275                 280                 285

Val Pro Leu Asp Arg Ala Ile Ala Gly Asp Thr Ser Gly Asp Tyr Glu
            290                 295                 300

Arg Met Leu Leu Ala Leu Ile Gly His Gly Asp Ala
305                 310                 315

<210> SEQ ID NO 108
<211> LENGTH: 1086
<212> TYPE: DNA
<213> ORGANISM: Gossypium hirsutum

<400> SEQUENCE: 108
gggcaggttc ttcacaaaaa agaaaagaaa aattacagtg aaaatggcaa cccttaaagt    60
tccagctcat gtacctgccc cttctgagga tgctgagcaa cttcgtaaag cttttgaagg   120
atggggtaca aatgagcaat tgattatcga cattttggct cacaggaatg cagctcagcg   180
caatttgatt cgtaaaactt atcgtgaagc ttatggggaa gatctcctta agtctttgga   240
tgaggaactt tcaagtgact tgagcgagc tgtggtgctg tttactttgg accctgcaga   300
gcgtgatgca tttctggctc atgaagctac aaagaggttc acatcaagcc attgggttct   360
catggaaatt gcttgcacta ggtcttcaca tgaactgttc aatgtgagga aggcgtatca   420

```
cgatctttac aagaaatccc ttgaagaaga tgttgcgcac ataccaagg gagactaccg    480 caagcttttg gtcccacttg ttagtgcatt ccgataccag ggagaggagg tgaacatgac    540
actggcaagg tcggaggcaa agatacttcg tgaagagata tcagacaagc agtacagtga    600
tgaggaggtc atcaggattg taacaacacg gagtaaggca cagttaaatg ctactctgaa    660
tcattacaat actgcatttg gaatgctat caacaaggat ttgaaggccg accctgaaga    720
cgaattcctc aaattgctga gagctgcaat caagtgcttg actgtccctg agaaatattt    780
tgagaaggtg ctacgtcaag caatcaataa gctgggaaca gatgaatggg ctcttactag    840
agtggtcgcc actcgggcgg aggtagacat ggtgcgtatt aaggaggaat atcagcgaag    900
aaacagtgtg accctggaaa aagcgattgc tggagatacc tctggagact atgagaaaat    960
gctgcttgcg ttgattggag ctggagacgt ctgagctgct ttcctatatt gagttgttgg    1020
tatgaaaatt tagtttgcaa tttgaggtgt gagttatgtt tgtttggttg agggtgtgcc    1080
aatcgc                                                              1086
```

<210> SEQ ID NO 109
<211> LENGTH: 316
<212> TYPE: PRT
<213> ORGANISM: Gossypium hirsutum

<400> SEQUENCE: 109

```
Met Ala Thr Leu Lys Val Pro Ala His Val Pro Ala Pro Ser Glu Asp
1               5                   10                  15

Ala Glu Gln Leu Arg Lys Ala Phe Glu Gly Trp Gly Thr Asn Glu Gln
            20                  25                  30

Leu Ile Ile Asp Ile Leu Ala His Arg Asn Ala Ala Gln Arg Asn Leu
        35                  40                  45

Ile Arg Lys Thr Tyr Arg Glu Ala Tyr Gly Glu Asp Leu Leu Lys Ser
    50                  55                  60

Leu Asp Glu Glu Leu Ser Ser Asp Phe Glu Arg Ala Val Val Leu Phe
65                  70                  75                  80

Thr Leu Asp Pro Ala Glu Arg Asp Ala Phe Leu Ala His Glu Ala Thr
                85                  90                  95

Lys Arg Phe Thr Ser Ser His Trp Val Leu Met Glu Ile Ala Cys Thr
            100                 105                 110

Arg Ser Ser His Glu Leu Phe Asn Val Arg Lys Ala Tyr His Asp Leu
        115                 120                 125

Tyr Lys Lys Ser Leu Glu Glu Asp Val Ala His His Thr Lys Gly Asp
    130                 135                 140

Tyr Arg Lys Leu Leu Val Pro Leu Val Ser Ala Phe Arg Tyr Gln Gly
145                 150                 155                 160

Glu Glu Val Asn Met Thr Leu Ala Arg Ser Glu Ala Lys Ile Leu Arg
                165                 170                 175

Glu Lys Ile Ser Asp Lys Gln Tyr Ser Asp Glu Val Ile Arg Ile
            180                 185                 190

Val Thr Thr Arg Ser Lys Ala Gln Leu Asn Ala Thr Leu Asn His Tyr
        195                 200                 205

Asn Thr Ala Phe Gly Asn Ala Ile Asn Lys Asp Leu Lys Ala Asp Pro
    210                 215                 220

Glu Asp Glu Phe Leu Lys Leu Leu Arg Ala Ala Ile Lys Cys Leu Thr
225                 230                 235                 240

Val Pro Glu Lys Tyr Phe Glu Lys Val Leu Arg Gln Ala Ile Asn Lys
```

Leu Gly Thr Asp Glu Trp Ala Leu Thr Arg Val Val Ala Thr Arg Ala
            245                 250                 255
Glu Val Asp Met Val Arg Ile Lys Glu Glu Tyr Gln Arg Arg Asn Ser
        260                 265                 270
Val Thr Leu Glu Lys Ala Ile Ala Gly Asp Thr Ser Gly Asp Tyr Glu
    275                 280                 285
Lys Met Leu Leu Ala Leu Ile Gly Ala Gly Asp Val
290                 295                 300

305                 310                 315

<210> SEQ ID NO 110
<211> LENGTH: 1196
<212> TYPE: DNA
<213> ORGANISM: Nicotiana tabacum

<400> SEQUENCE: 110

| | | | | | |
|---|---|---|---|---|---|
| gcatttacga | gttttgacaa | tcatatcttc | cacagacaga | aaaaaaatgg | ctagtcttac | 60 |
| tgttccggca | gaagttcctt | cagttgctga | agactgtgaa | caactccgat | ctgccttcaa | 120 |
| aggatgggga | acaaatgaga | agttgatcat | atcaattttg | gctcatagaa | atgctgctca | 180 |
| acgcaagttg | attcaacaga | cttatgctga | gacttttggt | gaagatctcc | ttaaagagtt | 240 |
| ggacagagaa | cttaccaatg | attttgagaa | attggtggta | gtgtggacat | ggatccttc | 300 |
| agaacgcgat | gcctatttgg | ctaaggaagc | tactaagaga | tggacaaaaa | gcaattttgt | 360 |
| tcttgtggag | attgcttgta | ccagatctcc | taaagaattg | ttttggcaa | gggaagctta | 420 |
| tcatgctcgt | ttcaagaaat | ctcttgaaga | ggacgttgct | tatcacacta | ctggggaaca | 480 |
| ccccccagctt | ttggtacctc | ttgtgagctc | ctaccgatat | ggaggggacg | aggtggactt | 540 |
| gcgccttgct | aaagcagaag | ctaaaatact | gcacagaaag | atctccgata | aggcttacag | 600 |
| tgacgatgag | gtcatcagaa | ttctagccac | aaggagcaaa | gcacagatca | atgctactct | 660 |
| gaaccattac | aaagatgaat | atgaagaaga | tatcctgaag | caattggaag | aggggatga | 720 |
| gtttgttgga | ctattgaggg | caaccataaa | aggtcttgtc | taccccgagc | actacttcgt | 780 |
| ggaggttctt | cgagatgcaa | ttaacaggag | aggaacagat | gaagatcatc | tgaccagagt | 840 |
| tatcgctaca | agggctgagg | ttgatatgaa | gattatcgct | gatgagtacc | agaagaggga | 900 |
| tagcatccct | ctgggtcggg | ccatcgccaa | agatacaaga | ggagattatg | agagtatgtt | 960 |
| gttggctctg | cttggacaag | aggaggacta | agaaggtttt | gcttctgttt | cataatgacc | 1020 |
| agaataaaca | tgctatcccc | tatatttgag | agttggcatc | cgttgtatgc | ttgatgatta | 1080 |
| agcgtggtct | gtttaacgtg | agcttttagt | ccttttcttc | ttgtgataaa | ctttgaatgt | 1140 |
| acaactttat | gctatctaag | aatgtttttc | taaaaaaaaa | aaaaaaaaa | aaaaaa | 1196 |

<210> SEQ ID NO 111
<211> LENGTH: 314
<212> TYPE: PRT
<213> ORGANISM: Nicotiana tabacum

<400> SEQUENCE: 111

Met Ala Ser Leu Thr Val Pro Ala Glu Val Pro Ser Val Ala Glu Asp
1               5                   10                  15
Cys Glu Gln Leu Arg Ser Ala Phe Lys Gly Trp Gly Thr Asn Glu Lys
            20                  25                  30
Leu Ile Ile Ser Ile Leu Ala His Arg Asn Ala Ala Gln Arg Lys Leu
        35                  40                  45

| | | | | | | | | | | | | |
|---|---|---|---|---|---|---|---|---|---|---|---|---|
|Ile|Gln|Gln|Thr|Tyr|Ala|Glu|Thr|Phe|Gly|Glu|Asp|Leu|Leu|Lys|Glu|
|  50|   |   |   |   |  55|   |   |   |   |  60|   |   |   |   |   |

Ile Gln Gln Thr Tyr Ala Glu Thr Phe Gly Glu Asp Leu Leu Lys Glu
 50                  55                  60

Leu Asp Arg Glu Leu Thr Asn Asp Phe Glu Lys Leu Val Val Val Trp
 65                  70                  75                  80

Thr Leu Asp Pro Ser Glu Arg Asp Ala Tyr Leu Ala Lys Glu Ala Thr
                 85                  90                  95

Lys Arg Trp Thr Lys Ser Asn Phe Val Leu Val Glu Ile Ala Cys Thr
                100                 105                 110

Arg Ser Pro Lys Glu Leu Val Leu Ala Arg Glu Ala Tyr His Ala Arg
                115                 120                 125

Phe Lys Lys Ser Leu Glu Glu Asp Val Ala Tyr His Thr Thr Gly Glu
130                 135                 140

His Pro Gln Leu Leu Val Pro Leu Val Ser Ser Tyr Arg Tyr Gly Gly
145                 150                 155                 160

Asp Glu Val Asp Leu Arg Leu Ala Lys Ala Glu Ala Lys Ile Leu His
                165                 170                 175

Glu Lys Ile Ser Asp Lys Ala Tyr Ser Asp Asp Glu Val Ile Arg Ile
                180                 185                 190

Leu Ala Thr Arg Ser Lys Ala Gln Ile Asn Ala Thr Leu Asn His Tyr
                195                 200                 205

Lys Asp Glu Tyr Glu Glu Asp Ile Leu Lys Gln Leu Glu Glu Gly Asp
210                 215                 220

Glu Phe Val Gly Leu Leu Arg Ala Thr Ile Lys Gly Leu Val Tyr Pro
225                 230                 235                 240

Glu His Tyr Phe Val Glu Val Leu Arg Asp Ala Ile Asn Arg Arg Gly
                245                 250                 255

Thr Asp Glu Asp His Leu Thr Arg Val Ile Ala Thr Arg Ala Glu Val
                260                 265                 270

Asp Met Lys Ile Ile Ala Asp Glu Tyr Gln Lys Arg Asp Ser Ile Pro
                275                 280                 285

Leu Gly Arg Ala Ile Ala Lys Asp Thr Arg Gly Asp Tyr Glu Ser Met
290                 295                 300

Leu Leu Ala Leu Leu Gly Gln Glu Glu Asp
305                 310

<210> SEQ ID NO 112
<211> LENGTH: 945
<212> TYPE: DNA
<213> ORGANISM: Solanum tuberosum

<400> SEQUENCE: 112

```
atggcaagtc ttacagttcc ggcagaagtt ccttccgtag ctgaagactg tgaacaactc      60
cgatctgcct tcaaaggatg gggaacgaac gagaagttga ttatatcaat tttggctcat     120
agaaatgctg ctcagcgcaa attgattcga cagacttatg ctgaaacttt tggggaagat     180
ctacttaaag agttggacag agaacttacc catgattttg agaaattggt gctaatatgg     240
acactggatc cgtcagaacg tgatgcctat ttggctaagg aagctactaa agatggaca      300
aaaagcaact tgttcttgt ggagatagct tgtactagat ctcctaaaga actggttttg      360
gcaagggaag cttatcatgc tcgtaacaag aaatctcttg aaggacgt tgcttatcac      420
actactgggg atcaccgcaa gcttttggta cctcttgtga gctcctaccg atatggagga     480
gacgaggtgg acttgcgcct tgctaaagca gaatctaaag tactgcatga gaagatctcc     540
gataaggctt acagtgacga tgaggtcatt agaattttag ccacaaggag caaagcgcaa     600
```

```
ctcaatgcta ctttgaatca ttacaaagat gaatatggtg aggatatcct aaagcaattg    660
gaagatgagg atgagtttgt tgcactattg agggccacca taaaaggtct tgtctaccct    720
gagcactatt tcgtggaggt tcttcgtgat gcaattaaca ggagaggaac agaggaagat    780
catctgagcc gagttatcgc tacaagggct gaggtggatc tgaagactat cgctaacgag    840
taccagaaga gggatagcat tcctctgggt cgcgccattg ccaaagatac aggaggagat    900
tatgagaata tgctggtggc tttacttgga caagaggagg aatga                   945

<210> SEQ ID NO 113
<211> LENGTH: 314
<212> TYPE: PRT
<213> ORGANISM: Solanum tuberosum

<400> SEQUENCE: 113
```

Met Ala Ser Leu Thr Val Pro Ala Glu Val Pro Ser Val Ala Glu Asp
1               5                   10                  15

Cys Glu Gln Leu Arg Ser Ala Phe Lys Gly Trp Gly Thr Asn Glu Lys
            20                  25                  30

Leu Ile Ile Ser Ile Leu Ala His Arg Asn Ala Ala Gln Arg Lys Leu
        35                  40                  45

Ile Arg Gln Thr Tyr Ala Glu Thr Phe Gly Glu Asp Leu Leu Lys Glu
    50                  55                  60

Leu Asp Arg Glu Leu Thr His Asp Phe Glu Lys Leu Val Leu Ile Trp
65                  70                  75                  80

Thr Leu Asp Pro Ser Glu Arg Asp Ala Tyr Leu Ala Lys Glu Ala Thr
                85                  90                  95

Lys Arg Trp Thr Lys Ser Asn Phe Val Leu Val Glu Ile Ala Cys Thr
            100                 105                 110

Arg Ser Pro Lys Glu Leu Val Leu Ala Arg Glu Ala Tyr His Ala Arg
        115                 120                 125

Asn Lys Lys Ser Leu Glu Glu Asp Val Ala Tyr His Thr Thr Gly Asp
    130                 135                 140

His Arg Lys Leu Leu Val Pro Leu Val Ser Ser Tyr Arg Tyr Gly Gly
145                 150                 155                 160

Asp Glu Val Asp Leu Arg Leu Ala Lys Ala Glu Ser Lys Val Leu His
                165                 170                 175

Glu Lys Ile Ser Asp Lys Ala Tyr Ser Asp Asp Glu Val Ile Arg Ile
            180                 185                 190

Leu Ala Thr Arg Ser Lys Ala Gln Leu Asn Ala Thr Leu Asn His Tyr
        195                 200                 205

Lys Asp Glu Tyr Gly Glu Asp Ile Leu Lys Gln Leu Glu Asp Glu Asp
    210                 215                 220

Glu Phe Val Ala Leu Leu Arg Ala Thr Ile Lys Gly Leu Val Tyr Pro
225                 230                 235                 240

Glu His Tyr Phe Val Glu Val Leu Arg Asp Ala Ile Asn Arg Arg Gly
                245                 250                 255

Thr Glu Glu Asp His Leu Ser Arg Val Ile Ala Thr Arg Ala Glu Val
            260                 265                 270

Asp Leu Lys Thr Ile Ala Asn Glu Tyr Gln Lys Arg Asp Ser Ile Pro
        275                 280                 285

Leu Gly Arg Ala Ile Ala Lys Asp Thr Gly Gly Asp Tyr Glu Asn Met
    290                 295                 300

Leu Val Ala Leu Leu Gly Gln Glu Glu Glu
305                 310

<210> SEQ ID NO 114
<211> LENGTH: 1160
<212> TYPE: DNA
<213> ORGANISM: Lycopersicon esculentum

<400> SEQUENCE: 114

```
atggcaagtc ttacagttcc ggcagaagtt ccttcagtcg ctgaagactg tgaacaactc    60
cgatctgcct tcaaaggatg gggaacgaat gagaagttga ttatatcaat tttggctcat   120
agaaatgcgg ctcaacgcaa attgattcga cagacttatg ctgagacttt ggggaagat   180
ctgcttaaag agttggacag agaacttact catgattttg agaaattggt ggtagtatgg   240
acactggatc ctgcagaacg tgatgcctat ttggctaagg aagctactaa gagatggaca   300
aaaagcaact ttgttcttgt ggagatagct tgtaccagat ctcctaaaga actggttttg   360
gcaagagaag cttatcatgc tcgtaacaag aaatctctcg aagaggacgt tgcttatcac   420
actactgggg atcaccgcaa acttttggta cctcttgtga ctcctaccg atatggggga   480
gatgaggtgg acttgcgact tgctaaagca gaatctaaag tgctgcatga agatctcc    540
gataaggctt acagtgacga tgaggtcatt agaattttag ccacaaggag caaagcgcaa   600
ctcaatgcta ctttgaatca ttacaaagat gaatatggtg aggatatcct aaagcaatta   660
gaagatgagg atgagtttgt tgcactgtta agggccacca taaaaggtct tgtctacccc   720
gagcactatt tcgtggaggt tcttcgtgat gcaattaaca ggagaggaac agaggaagat   780
catctaaccc gagttatcgc tacaagggct gaggtcgatc tgaagactat cgctaacgag   840
taccagaaga gggatagcgt tcctctgggt cgcgccattg ccaaagatac aggaggagat   900
tatgagaata tgctggtggc tttacttgga caagaggagg aataagaagc ggattggctc   960
acttctgttt ataatgacca gataatatgc cattctccat atatttcaga gttggcatgt  1020
gtttgatgat tgagagtggt ctgttcacat gagctttagt ccttttcttc ttgtgagaaa  1080
cttttgaatat gaatctttgt gctgtctaaa aatgttctct aatgatttgc atccactaaa  1140
aaaaaaaaaa aaaaaaaaaa                                              1160
```

<210> SEQ ID NO 115
<211> LENGTH: 314
<212> TYPE: PRT
<213> ORGANISM: Lycopersicon esculentum

<400> SEQUENCE: 115

Met Ala Ser Leu Thr Val Pro Ala Glu Val Pro Ser Val Ala Glu Asp
1               5                   10                  15

Cys Glu Gln Leu Arg Ser Ala Phe Lys Gly Trp Gly Thr Asn Glu Lys
            20                  25                  30

Leu Ile Ile Ser Ile Leu Ala His Arg Asn Ala Ala Gln Arg Lys Leu
        35                  40                  45

Ile Arg Gln Thr Tyr Ala Glu Thr Phe Gly Glu Asp Leu Leu Lys Glu
    50                  55                  60

Leu Asp Arg Glu Leu Thr His Asp Phe Glu Lys Leu Val Val Val Trp
65                  70                  75                  80

Thr Leu Asp Pro Ala Glu Arg Asp Ala Tyr Leu Ala Lys Glu Ala Thr
                85                  90                  95

Lys Arg Trp Thr Lys Ser Asn Phe Val Leu Val Glu Ile Ala Cys Thr
            100                 105                 110

Arg Ser Pro Lys Glu Leu Val Leu Ala Arg Glu Ala Tyr His Ala Arg

|     | 115 |     |     |     | 120 |     |     |     | 125 |     |     |     |
| --- | --- | --- | --- | --- | --- | --- | --- | --- | --- | --- | --- | --- |

Asn Lys Lys Ser Leu Glu Glu Asp Val Ala Tyr His Thr Thr Gly Asp
    130                 135                 140

His Arg Lys Leu Leu Val Pro Leu Val Ser Ser Tyr Arg Tyr Gly Gly
145                 150                 155                 160

Asp Glu Val Asp Leu Arg Leu Ala Lys Ala Glu Ser Lys Val Leu His
                165                 170                 175

Glu Lys Ile Ser Asp Lys Ala Tyr Ser Asp Asp Glu Val Ile Arg Ile
            180                 185                 190

Leu Ala Thr Arg Ser Lys Ala Gln Leu Asn Ala Thr Leu Asn His Tyr
        195                 200                 205

Lys Asp Glu Tyr Gly Glu Asp Ile Leu Lys Gln Leu Glu Asp Glu Asp
    210                 215                 220

Glu Phe Val Ala Leu Leu Arg Ala Thr Ile Lys Gly Leu Val Tyr Pro
225                 230                 235                 240

Glu His Tyr Phe Val Glu Val Leu Arg Asp Ala Ile Asn Arg Arg Gly
                245                 250                 255

Thr Glu Glu Asp His Leu Thr Arg Val Ile Ala Thr Arg Ala Glu Val
            260                 265                 270

Asp Leu Lys Thr Ile Ala Asn Glu Tyr Gln Lys Arg Asp Ser Val Pro
        275                 280                 285

Leu Gly Arg Ala Ile Ala Lys Asp Thr Gly Gly Asp Tyr Glu Asn Met
    290                 295                 300

Leu Val Ala Leu Leu Gly Gln Glu Glu Glu
305                 310

<210> SEQ ID NO 116
<211> LENGTH: 1242
<212> TYPE: DNA
<213> ORGANISM: Lycopersicon esculentum

<400> SEQUENCE: 116

```
atgtctagtc ttaaagttcc agcatcagtt ccagatcctt atgaagatgc tgagcaactc      60
aaaaaagctt ttaaggatg  gggcacaaat gaggaactta ttattcagat tctggctcat    120
aggaatgcca gacaacgcaa gttaatccga gattcttatg ctgctgctta tggagaggat    180
cttctcaagg acttggattc tgaactgaca agtgattttc agcgtgtggt gcttctctgg    240
actttgagtc ctgctgagcg cgacgcctac ttggttaatg aggctaccaa acgtctgact    300
gctagcaatt ggggtatcat ggaaattgct tgtaccaggt cttctgatga tctttttaag    360
gcgaggcagg cctaccatgc tccatacaag aaatcacttg aagaagatgt tgcttatcat    420
acagtggggg atttccgtaa gcttttggtt cctcttataa ctgcattcag atatgaagga    480
gatgaggtga acatgacatt agcaagaaag ggaagcaaat atctgcatga aagatctct     540
gacaaggctt accatgacga ggagatcatc cgaatcattt ctactaggag taaagcacag    600
ctgagtgcta cgttcaacca ctaccatgat caccatggcc atgaaatcat caaggatctg    660
gaagctgatg atgacgatga gtacctgaaa ctactcagag cagcaataga atgcttgaaa    720
cccagagaac actttgagaa agttcttcga ttggctatca agaagctggg tacagacgaa    780
tgggatctta ctagagttgt tgccactcgg gctgaagttg acatggagcg tatcaaagaa    840
gagtaccata ggaggaacag tgttacattg gaccgtgcaa ttgctggaga cacttcagga    900
gactatgaaa aatgcttct  ggctctgatt gggcacggag atgcttgaat tacatgtgct    960
gaaaccttaa gataataaaa aactctactt attttctgaa ctttcatttg cttttatgat   1020
```

```
ctatggtgtg tactctcaga gtttggttct gtgtttatat gaactaaaaa cactcgggag    1080
ttgagttgtg ttttgttttc gccttcactt ttcatttcgg acttctactg gttttgcctg    1140
ctaaataagc atagcttcaa ctttggcttg aacggatctt gtttctttat aactcagaaa    1200
tagattatgt atcttggttc gtaaaaaaaa aaaaaaaaa aa                        1242
```

<210> SEQ ID NO 117
<211> LENGTH: 315
<212> TYPE: PRT
<213> ORGANISM: Lycopersicon esculentum

<400> SEQUENCE: 117

```
Met Ser Ser Leu Lys Val Pro Ala Ser Val Pro Asp Pro Tyr Glu Asp
1               5                   10                  15

Ala Glu Gln Leu Lys Lys Ala Phe Lys Gly Trp Gly Thr Asn Glu Glu
                20                  25                  30

Leu Ile Ile Gln Ile Leu Ala His Arg Asn Ala Arg Gln Arg Lys Leu
            35                  40                  45

Ile Arg Asp Ser Tyr Ala Ala Tyr Gly Glu Asp Leu Leu Lys Asp
        50                  55                  60

Leu Asp Ser Glu Leu Thr Ser Asp Phe Gln Arg Val Val Leu Leu Trp
65                  70                  75                  80

Thr Leu Ser Pro Ala Glu Arg Asp Ala Tyr Leu Val Asn Glu Ala Thr
                85                  90                  95

Lys Arg Leu Thr Ala Ser Asn Trp Gly Ile Met Glu Ile Ala Cys Thr
            100                 105                 110

Arg Ser Ser Asp Asp Leu Phe Lys Ala Arg Gln Ala Tyr His Ala Pro
        115                 120                 125

Tyr Lys Lys Ser Leu Glu Glu Asp Val Ala Tyr His Thr Val Gly Asp
    130                 135                 140

Phe Arg Lys Leu Leu Val Pro Leu Ile Thr Ala Phe Arg Tyr Glu Gly
145                 150                 155                 160

Asp Glu Val Asn Met Thr Leu Ala Arg Lys Gly Ser Lys Tyr Leu His
                165                 170                 175

Glu Lys Ile Ser Asp Lys Ala Tyr His Asp Glu Ile Ile Arg Ile
            180                 185                 190

Ile Ser Thr Arg Ser Lys Ala Gln Leu Ser Ala Thr Phe Asn His Tyr
        195                 200                 205

His Asp His His Gly His Glu Ile Ile Lys Asp Leu Glu Ala Asp Asp
    210                 215                 220

Asp Asp Glu Tyr Leu Lys Leu Leu Arg Ala Ala Ile Glu Cys Leu Lys
225                 230                 235                 240

Pro Arg Glu His Phe Glu Lys Val Leu Arg Leu Ala Ile Lys Lys Leu
                245                 250                 255

Gly Thr Asp Glu Trp Asp Leu Thr Arg Val Val Ala Thr Arg Ala Glu
            260                 265                 270

Val Asp Met Glu Arg Ile Lys Glu Glu Tyr His Arg Arg Asn Ser Val
        275                 280                 285

Thr Leu Asp Arg Ala Ile Ala Gly Asp Thr Ser Gly Asp Tyr Glu Lys
    290                 295                 300

Met Leu Leu Ala Leu Ile Gly His Gly Asp Ala
305                 310                 315
```

<210> SEQ ID NO 118

<211> LENGTH: 1226
<212> TYPE: DNA
<213> ORGANISM: Arabidopsis thaliana

<400> SEQUENCE: 118

```
ttacttaagt aggacgacgt gcgtctgctt cgtctcatta caaagcagaa gaaacacaaa      60
cagaggcaga gatcttaaga gttaaagact aatcccaaca atggcgtctc tcaaagtccc     120
aagcaatgtt cctcttcccg aagatgacgc cgagcaactc cacaaggctt ttcaggatg      180
gggtaccaac gagaagctga tcatatcaat actagctcac aggaacgcag cacaacgcag     240
cttgatccgc agcgtttatg cagctaccta caatgaggat cttctcaaag cattagacaa     300
agagctttct agcgactttg agagagctgt gatgttgtgg actcttgatc caccagagag     360
agatgcttat ttggctaaag aatccaccaa gatgttcacc aagaacaatt gggttcttgt     420
tgaaatcgct tgcacaaggc ctgctcttga gcttatcaag gtcaagcaag cttaccaagc     480
tcgatacaag aaatcaatcg aggaagatgt cgcgcaacac acatctggtg accttcgtaa     540
gctcttgctt cctcttgtga gcactttcag gtatgaagga gatgatgtga acatgatgct     600
tgcaagatct gaagctaaga tacttcacga gaaggtctca gagaaatctt acagtgacga     660
tgacttcatc agaatcttga caacaagaag caaagcacag ctcggtgcaa cactcaacca     720
ctacaacaac gagtatggaa acgccattaa caagaacttg aaggaagagt cggacgacaa     780
tgactacatg aaactactaa gagctgtaat cacatgtttg atatacctg agaagcatt      840
tgagaaggtt cttcgtctat caatcaacaa aatgggaaca gacgaatggg gactaacccg     900
agtcgtgact acacgaactg aagttgacat ggaacgcatc aaagaggaat atcagcgaag     960
aaacagcatt cctttggacc gtgctatcgc caaagacact tctggtgact atgaggacat    1020
gcttgttgct cttctcggac atggcgatgc ttgaaactgt ttcaactttc gagttcctcc    1080
tttctcttac tgcatggttt gttttaaata aaagagttgt gaaactggtt ctgcaactat    1140
ttatcaatga tcgtttgagt ttgttaaatt tgaatcaaaa tctgtttttc tttcttttaa    1200
atacaatcta aagcacaaac taaagc                                        1226
```

<210> SEQ ID NO 119
<211> LENGTH: 317
<212> TYPE: PRT
<213> ORGANISM: Arabidopsis thaliana

<400> SEQUENCE: 119

```
Met Ala Ser Leu Lys Val Pro Ser Asn Val Pro Leu Pro Glu Asp Asp
1               5                   10                  15

Ala Glu Gln Leu His Lys Ala Phe Ser Gly Trp Gly Thr Asn Glu Lys
            20                  25                  30

Leu Ile Ile Ser Ile Leu Ala His Arg Asn Ala Ala Gln Arg Ser Leu
        35                  40                  45

Ile Arg Ser Val Tyr Ala Ala Thr Tyr Asn Glu Asp Leu Leu Lys Ala
    50                  55                  60

Leu Asp Lys Glu Leu Ser Ser Asp Phe Glu Arg Ala Val Met Leu Trp
65                  70                  75                  80

Thr Leu Asp Pro Pro Glu Arg Asp Ala Tyr Leu Ala Lys Glu Ser Thr
                85                  90                  95

Lys Met Phe Thr Lys Asn Asn Trp Val Leu Val Glu Ile Ala Cys Thr
            100                 105                 110

Arg Pro Ala Leu Glu Leu Ile Lys Val Lys Gln Ala Tyr Gln Ala Arg
        115                 120                 125
```

```
Tyr Lys Lys Ser Ile Glu Glu Asp Val Ala Gln His Thr Ser Gly Asp
            130                 135                 140

Leu Arg Lys Leu Leu Leu Pro Leu Val Ser Thr Phe Arg Tyr Glu Gly
145                 150                 155                 160

Asp Asp Val Asn Met Met Leu Ala Arg Ser Glu Ala Lys Ile Leu His
                165                 170                 175

Glu Lys Val Ser Glu Lys Ser Tyr Ser Asp Asp Phe Ile Arg Ile
            180                 185                 190

Leu Thr Thr Arg Ser Lys Ala Gln Leu Gly Ala Thr Leu Asn His Tyr
            195                 200                 205

Asn Asn Glu Tyr Gly Asn Ala Ile Asn Lys Asn Leu Lys Glu Glu Ser
210                 215                 220

Asp Asp Asn Asp Tyr Met Lys Leu Leu Arg Ala Val Ile Thr Cys Leu
225                 230                 235                 240

Thr Tyr Pro Glu Lys His Phe Glu Lys Val Leu Arg Leu Ser Ile Asn
                245                 250                 255

Lys Met Gly Thr Asp Glu Trp Gly Leu Thr Arg Val Val Thr Thr Arg
            260                 265                 270

Thr Glu Val Asp Met Glu Arg Ile Lys Glu Glu Tyr Gln Arg Arg Asn
            275                 280                 285

Ser Ile Pro Leu Asp Arg Ala Ile Ala Lys Asp Thr Ser Gly Asp Tyr
            290                 295                 300

Glu Asp Met Leu Val Ala Leu Leu Gly His Gly Asp Ala
305                 310                 315

<210> SEQ ID NO 120
<211> LENGTH: 1172
<212> TYPE: DNA
<213> ORGANISM: Nicotiana tabacum

<400> SEQUENCE: 120
ctgcttgcat tttcgagtct tgacaatcat aaaaatggct agtcttactg ttccggcaga      60
agttccttca gtagctgaag actgtgaaca actccgatct gccttcaaag ggtggggaac    120
aaacgagaag ttgatcatat caattttggc tcatagaaat gctgctcaac gcaagttgat    180
tcaacagact tatgctgaga cttttggtga agatctcctt aaagagttgg acagagaact    240
taccaatgat tttgagaaat tggtggtagt gtggacattg gatccttcag aacgcgatgc    300
ctatttggct aaggaagcta ctaagagatg gacaaaaagc aattttgttc ttgtggaaat    360
agcttgtacc agatctccta agaattggt tttggcacgg gaagcttatc atgctcgtta    420
caagaaatct cttgaagagg acgttgctta tcacactact ggggaacacc gcaagctttt    480
ggtagctctt gtgagctcct atcgatatgg aggagacgag gtggacttgc gtcttgctaa    540
agctgaagct aaaatactgc atgagaagat ctccgataag gcttacagtg acaatgaggt    600
catcagaatt ctagccacaa ggagtaaagc acagatcaat gctactctga atcattacaa    660
agatgaatat gaagaggata tcctaaagca attggaagag ggggatgagt tgttggact    720 attgagggca accataaaag gtcttgtcta caccgagcac tacttcgtgg aggttcttcg    780
agatgcaatt aacaggagag aacagagga agatcatctg accagagtta tcgctacaag    840
ggctgaggtt gatatgaaga ctatcgctga tgagtaccag aagagggata gcatccatct    900
gggtcgcgcc attgccaaag atacaagagg agattatgag agtatgttgt tggctctgct    960
tggacaagag gaggactaag aaggatttgc tttataatga ccggaataaa tatgatatcc   1020
```

```
cctatatttg agagttggca tccgctgtat gtttgatgat tgagcgtggt ctgtttaacg    1080
tgagcgttga gtccttttct tctcactttg aatatgcaac tttatgctat ctaagaatat    1140
ttttttataa aaaaaaaaaa aaaaaaaaaa aa                                  1172
```

<210> SEQ ID NO 121
<211> LENGTH: 314
<212> TYPE: PRT
<213> ORGANISM: Nicotiana tabacum

<400> SEQUENCE: 121

```
Met Ala Ser Leu Thr Val Pro Ala Glu Val Pro Ser Val Ala Glu Asp
1               5                   10                  15

Cys Glu Gln Leu Arg Ser Ala Phe Lys Gly Trp Gly Thr Asn Glu Lys
            20                  25                  30

Leu Ile Ile Ser Ile Leu Ala His Arg Asn Ala Ala Gln Arg Lys Leu
        35                  40                  45

Ile Gln Gln Thr Tyr Ala Glu Thr Phe Gly Glu Asp Leu Leu Lys Glu
    50                  55                  60

Leu Asp Arg Glu Leu Thr Asn Asp Phe Glu Lys Leu Val Val Val Trp
65                  70                  75                  80

Thr Leu Asp Pro Ser Glu Arg Asp Ala Tyr Leu Ala Lys Glu Ala Thr
                85                  90                  95

Lys Arg Trp Thr Lys Ser Asn Phe Val Leu Val Glu Ile Ala Cys Thr
            100                 105                 110

Arg Ser Pro Lys Glu Leu Val Leu Ala Arg Glu Ala Tyr His Ala Arg
        115                 120                 125

Tyr Lys Lys Ser Leu Glu Glu Asp Val Ala Tyr His Thr Thr Gly Glu
    130                 135                 140

His Arg Lys Leu Leu Val Ala Leu Val Ser Ser Tyr Arg Tyr Gly Gly
145                 150                 155                 160

Asp Glu Val Asp Leu Arg Leu Ala Lys Ala Glu Ala Lys Ile Leu His
                165                 170                 175

Glu Lys Ile Ser Asp Lys Ala Tyr Ser Asp Asn Glu Val Ile Arg Ile
            180                 185                 190

Leu Ala Thr Arg Ser Lys Ala Gln Ile Asn Ala Thr Leu Asn His Tyr
        195                 200                 205

Lys Asp Glu Tyr Glu Glu Asp Ile Leu Lys Gln Leu Glu Glu Gly Asp
    210                 215                 220

Glu Phe Val Gly Leu Leu Arg Ala Thr Ile Lys Gly Leu Val Tyr Thr
225                 230                 235                 240

Glu His Tyr Phe Val Glu Val Leu Arg Asp Ala Ile Asn Arg Arg Gly
                245                 250                 255

Thr Glu Glu Asp His Leu Thr Arg Val Ile Ala Thr Arg Ala Glu Val
            260                 265                 270

Asp Met Lys Thr Ile Ala Asp Glu Tyr Gln Lys Arg Asp Ser Ile His
        275                 280                 285

Leu Gly Arg Ala Ile Ala Lys Asp Thr Arg Gly Asp Tyr Glu Ser Met
    290                 295                 300

Leu Leu Ala Leu Leu Gly Gln Glu Glu Asp
305                 310
```

<210> SEQ ID NO 122
<211> LENGTH: 1215
<212> TYPE: DNA
<213> ORGANISM: Solanum tuberosum

<400> SEQUENCE: 122

```
atcactctgc attttcgagt cttcacaatc atatcctcct aaccacacac agaagaaaaa      60
aaaatggcaa gtcttacagt tccggcagaa gttccttccg tcgctgaaga ctgtgaacaa     120
ctccgatctg ccttcaaagg atggggaacg aacgagaagt tgattatatc aattttggct     180
catagaaatg ctgctcagcg caaattgatt cgacagactt atgctgaaac ttttggggaa     240
gatctactta aagagattgg gacaggaaga aacttaaccc atgattttga gaaattggtg     300
ctaatatgga cactggatcc gtcagaacgt gatgcctatt tggctaagga agctactaag     360
agatggacaa aaagcaactt tgttcttgtg gagatagctt gtactagatc tcctaaagaa     420
ctggttttgg caagggaagc ttatcatgct cgtaacaaga aatctctcga gaggacgtt      480
gcttatcaca ctactgggga tcaccgcaag cttttggtac ctcttgtgag ctcctaccga     540
tatggaggag acgaggtgga cttgcgcctt gctaaagcag aatctaaagt actgcatgag     600
aagatctccg ataaggctta cagtgacgat gaggtcatta gaattttagc cacaaggagc     660
aaagcgcaac tcaatgctac tttgaatcat tacaaagatg aatatggtga ggatatccta     720
aagcaattgg aagatgagga tgagtttgtt gcactattga gggccaccat aaaaggtctt     780
gtctaccctg agcactattt cgtggaggtt cttcgtgatg caattaacag agaggaaca      840
gaggaagatc atctgagccg agttattgct acaagggctg aggtcgatct gaagactatc     900
gctaacgagt accagaagag ggatagcatt cctctgggtc gcgccattgc caaagataca     960
ggaggagatt atgagaatat gctggtggct ttacttggac aagaggagga atgaggagga    1020
ttggctcact tctgtgttat aatgaccaga ataaatatgc catctcccat atatttcaga    1080
gttggcatct gtttgatgat tgagtgtggt ctgttttcac atgagctttt agtccttttc    1140
ttcgtgtgag aaactttgaa tatgcatctt tgtgctgtct aaaaatattt tctaaaaaaa    1200
aaaaaaaaaa aaaaa                                                    1215
```

<210> SEQ ID NO 123
<211> LENGTH: 316
<212> TYPE: PRT
<213> ORGANISM: Solanum tuberosum

<400> SEQUENCE: 123

```
Met Ala Ser Leu Thr Val Pro Ala Glu Val Pro Ser Val Ala Glu Asp
1               5                   10                  15

Cys Glu Gln Leu Arg Ser Ala Phe Lys Gly Trp Gly Thr Asn Glu Lys
            20                  25                  30

Leu Ile Ile Ser Ile Leu Ala His Arg Asn Ala Ala Gln Arg Lys Leu
        35                  40                  45

Ile Arg Gln Thr Tyr Ala Glu Thr Phe Gly Glu Asp Leu Leu Lys Glu
    50                  55                  60

Ile Gly Thr Gly Arg Asn Leu Thr His Asp Phe Glu Lys Leu Val Leu
65                  70                  75                  80

Ile Trp Thr Leu Asp Pro Ser Glu Arg Asp Ala Tyr Leu Ala Lys Glu
                85                  90                  95

Ala Thr Lys Arg Trp Thr Lys Ser Asn Phe Val Leu Val Glu Ile Ala
            100                 105                 110

Cys Thr Arg Ser Pro Lys Glu Leu Val Leu Ala Arg Glu Ala Tyr His
        115                 120                 125

Ala Arg Asn Lys Lys Ser Leu Glu Glu Asp Val Ala Tyr His Thr Thr
    130                 135                 140
```

Gly Asp His Arg Lys Leu Leu Val Pro Leu Val Ser Ser Tyr Arg Tyr
145                 150                 155                 160

Gly Gly Asp Glu Val Asp Leu Arg Leu Ala Lys Ala Glu Ser Lys Val
                165                 170                 175

Leu His Glu Lys Ile Ser Asp Lys Ala Tyr Ser Asp Asp Glu Val Ile
            180                 185                 190

Arg Ile Leu Ala Thr Arg Ser Lys Ala Gln Leu Asn Ala Thr Leu Asn
        195                 200                 205

His Tyr Lys Asp Glu Tyr Gly Glu Asp Ile Leu Lys Gln Leu Glu Asp
    210                 215                 220

Glu Asp Glu Phe Val Ala Leu Leu Arg Ala Thr Ile Lys Gly Leu Val
225                 230                 235                 240

Tyr Pro Glu His Tyr Phe Val Glu Val Leu Arg Asp Ala Ile Asn Arg
                245                 250                 255

Arg Gly Thr Glu Glu Asp His Leu Ser Arg Val Ile Ala Thr Arg Ala
                260                 265                 270

Glu Val Asp Leu Lys Thr Ile Ala Asn Glu Tyr Gln Lys Arg Asp Ser
            275                 280                 285

Ile Pro Leu Gly Arg Ala Ile Ala Lys Asp Thr Gly Gly Asp Tyr Glu
        290                 295                 300

Asn Met Leu Val Ala Leu Leu Gly Gln Glu Glu Glu
305                 310                 315

<210> SEQ ID NO 124
<211> LENGTH: 1176
<212> TYPE: DNA
<213> ORGANISM: Arabidopsis thaliana

<400> SEQUENCE: 124
catacagaaa tttcacttgt tcgaaaaatg gcttctctca agttcccgc cactgttcct      60 cttcccgaag aagacgctga gcaactctac aaagccttta aaggatgggg aaccaatgag    120
aggatgatca tatcaatctt ggctcacaga aatgcaacgc aacgtagttt cattcgtgcc    180
gtttatgctg ctaactacaa taaggatctt ctcaaggaat tagacagaga gctttccggt    240
gactttgagc gagctgtgat gttgtggact tttgaaccag cggagagaga tgcttatttg    300
gcaaaagaat ctaccaaaat gttcaccaaa acaattgggt tcttgtcga atcgcttgt     360 actagatctg ctcttgaact ctttaatgcc aagcaagcat accagcccg ctacaagacc    420 tccctcgagg aagacgtcgc ataccacaca tctggagaca ttcgaaagct cttggtacct    480
cttgtgagca ctttaggta cgatggagat gaagtgaaca tgacgttagc taggtccgag    540
gctaagatac ttcacgagaa gatcaaggaa aaggcttatg ctgatgatga tctcataaga    600
atcttgacaa ccaggagcaa agcacaaatc agcgcaactc tcaatcacta caaaaacaat    660
ttcggaactt ccatgagcaa ataccctaaag gaggattcgg aaaacgaata cattcaattg    720
ctcaaagccg tgatcaaatg cttgacatat ccagagaagt attttgagaa agttctacgt    780
caagccatca acaaattggg aacagatgag tggggactaa cgagagtggt cactacacga    840
gcagagtttg acatggaacg gatcaaagag gaatatatac gtagaaacag tgttcctctt    900
gatcgagcca ttgctaaaga cactcatggt gactatgagg atatacttct cgctcttctc    960
ggacatgacc atgcttgaaa taacatttgc aagttttgtt taagaaaaaa aactaaattt   1020
tatcgctttg tgtttaataa aacagttgtg gttggacttg caacttggtc atgttaagaa   1080
tttagtgtct tcagtttcat ttgtcgtcga tgttttcagt tattttttttt tttaaatcta   1140 aaaattataa aaccatatca aaaattatta ttgatc        1176

<210> SEQ ID NO 125
<211> LENGTH: 316
<212> TYPE: PRT
<213> ORGANISM: Arabidopsis thaliana

<400> SEQUENCE: 125

Met Ala Ser Leu Lys Val Pro Ala Thr Val Pro Leu Pro Glu Glu Asp
1               5                   10                  15

Ala Glu Gln Leu Tyr Lys Ala Phe Lys Gly Trp Gly Thr Asn Glu Arg
            20                  25                  30

Met Ile Ile Ser Ile Leu Ala His Arg Asn Ala Thr Gln Arg Ser Phe
        35                  40                  45

Ile Arg Ala Val Tyr Ala Ala Asn Tyr Asn Lys Asp Leu Leu Lys Glu
    50                  55                  60

Leu Asp Arg Glu Leu Ser Gly Asp Phe Glu Arg Ala Val Met Leu Trp
65                  70                  75                  80

Thr Phe Glu Pro Ala Glu Arg Asp Ala Tyr Leu Ala Lys Glu Ser Thr
                85                  90                  95

Lys Met Phe Thr Lys Asn Asn Trp Val Leu Val Glu Ile Ala Cys Thr
            100                 105                 110

Arg Ser Ala Leu Glu Leu Phe Asn Ala Lys Gln Ala Tyr Gln Ala Arg
        115                 120                 125

Tyr Lys Thr Ser Leu Glu Glu Asp Val Ala Tyr His Thr Ser Gly Asp
    130                 135                 140

Ile Arg Lys Leu Leu Val Pro Leu Val Ser Thr Phe Arg Tyr Asp Gly
145                 150                 155                 160

Asp Glu Val Asn Met Thr Leu Ala Arg Ser Glu Ala Lys Ile Leu His
                165                 170                 175

Glu Lys Ile Lys Glu Lys Ala Tyr Ala Asp Asp Asp Leu Ile Arg Ile
            180                 185                 190

Leu Thr Thr Arg Ser Lys Ala Gln Ile Ser Ala Thr Leu Asn His Tyr
        195                 200                 205

Lys Asn Asn Phe Gly Thr Ser Met Ser Lys Tyr Leu Lys Glu Asp Ser
    210                 215                 220

Glu Asn Glu Tyr Ile Gln Leu Leu Lys Ala Val Ile Lys Cys Leu Thr
225                 230                 235                 240

Tyr Pro Glu Lys Tyr Phe Glu Lys Val Leu Arg Gln Ala Ile Asn Lys
                245                 250                 255

Leu Gly Thr Asp Glu Trp Gly Leu Thr Arg Val Val Thr Thr Arg Ala
            260                 265                 270

Glu Phe Asp Met Glu Arg Ile Lys Glu Glu Tyr Ile Arg Arg Asn Ser
        275                 280                 285

Val Pro Leu Asp Arg Ala Ile Ala Lys Asp Thr His Gly Asp Tyr Glu
    290                 295                 300

Asp Ile Leu Leu Ala Leu Leu Gly His Asp His Ala
305                 310                 315

<210> SEQ ID NO 126
<211> LENGTH: 1182
<212> TYPE: DNA
<213> ORGANISM: Medicago sativa

<400> SEQUENCE: 126

```
ctctcacgtt ccgtctccat cagaagacag tgaacaattg cgcggtgctt ttcaaggatg      60
gggaacgaat gaaggcttga taatatcgat cctggctcat agaaatgcag ctcagcgtaa     120
gtcgatccgc gaaacttaca cgcagaccca tggagaagat cttcttaaag atcttgacaa     180
agaactttca agtgattttg agaaagctgt gctgctgtgg acattggatc cggccgagcg     240
tgatgcattt ttagccaatc aagcaactaa aatgttgact tcaaacaatt cgatcatcgt     300
ggaaattgct tccacaagat ctccacttga acttcttaag gcaaagcaag catatcaagt     360
ccgtttcaaa aagtcccttg aagaagatgt tgcctatcat acttctggtg acatccgcaa     420
gcttttggtt cctcttgtgg gcatacaccg ttatgaggga gatgaggtga acatgacatt     480
ggcaaaatct gaagctaaat tgcttcatga aaagattgcg gataaggctt acaatcatga     540
tgacctgatc aggattgtaa caacaaggag taaagcgcaa ttaaatgcaa ctttgaatca     600
ctataacaat gagtttggga atgtaataga caaggatttg gaaactgatt cggatgatga     660
atatctgaaa ttattgaggg cagcaattaa gggcttgacc taccctgaga aatattttga     720
ggaactcctt aggctggcta taaacaagat gggaaccgat gaaaatgctc ttactagagt     780
ggtgacaact agagctgagg ttgatttgca gcgaattgcg gaggaatacc agagaagaaa     840
cagtgttcct ctggaccgtg caattgacaa agacacttct ggagactatc agaaaattct     900
ccttgcactg atgggacatg atgagtaagt tcttaatctg tccagtagtc atggagtggc     960
tgtttggact atctgttttc ccttcatcat cagcgtgatt ttgctgcgga tctcttgata    1020
gtatacagaa ttcggtgact tgctgtggta actatgcttg tgatatgtat gaactattgt    1080
ggttttaaat aatatgtttt gaatatggac tgaaattcaa aacagaactt tgccttctta    1140
aataatgaaa cagctatcat atttctctcc ttaaaaaaaa aa                       1182

<210> SEQ ID NO 127
<211> LENGTH: 308
<212> TYPE: PRT
<213> ORGANISM: Medicago sativa

<400> SEQUENCE: 127

Ser His Val Pro Ser Pro Ser Glu Asp Ser Glu Gln Leu Arg Gly Ala
1               5                   10                  15

Phe Gln Gly Trp Gly Thr Asn Glu Gly Leu Ile Ile Ser Ile Leu Ala
            20                  25                  30

His Arg Asn Ala Ala Gln Arg Lys Ser Ile Arg Glu Thr Tyr Thr Gln
        35                  40                  45

Thr His Gly Glu Asp Leu Leu Lys Asp Leu Asp Lys Glu Leu Ser Ser
    50                  55                  60

Asp Phe Glu Lys Ala Val Leu Leu Trp Thr Leu Asp Pro Ala Glu Arg
65                  70                  75                  80

Asp Ala Phe Leu Ala Asn Gln Ala Thr Lys Met Leu Thr Ser Asn Asn
                85                  90                  95

Ser Ile Ile Val Glu Ile Ala Ser Thr Arg Ser Pro Leu Glu Leu Leu
            100                 105                 110

Lys Ala Lys Gln Ala Tyr Gln Val Arg Phe Lys Ser Leu Glu Glu
        115                 120                 125

Asp Val Ala Tyr His Thr Ser Gly Asp Ile Arg Lys Leu Leu Val Pro
    130                 135                 140

Leu Val Gly Ile His Arg Tyr Glu Gly Asp Glu Val Asn Met Thr Leu
145                 150                 155                 160

Ala Lys Ser Glu Ala Lys Leu Leu His Glu Lys Ile Ala Asp Lys Ala
```

```
            165                 170                 175
Tyr Asn His Asp Asp Leu Ile Arg Ile Val Thr Thr Arg Ser Lys Ala
            180                 185                 190

Gln Leu Asn Ala Thr Leu Asn His Tyr Asn Asn Glu Phe Gly Asn Val
            195                 200                 205

Ile Asp Lys Asp Leu Glu Thr Asp Ser Asp Asp Glu Tyr Leu Lys Leu
            210                 215                 220

Leu Arg Ala Ala Ile Lys Gly Leu Thr Tyr Pro Glu Lys Tyr Phe Glu
225                 230                 235                 240

Glu Leu Leu Arg Leu Ala Ile Asn Lys Met Gly Thr Asp Glu Asn Ala
                245                 250                 255

Leu Thr Arg Val Val Thr Thr Arg Ala Glu Val Asp Leu Gln Arg Ile
                260                 265                 270

Ala Glu Glu Tyr Gln Arg Arg Asn Ser Val Pro Leu Asp Arg Ala Ile
                275                 280                 285

Asp Lys Asp Thr Ser Gly Asp Tyr Gln Lys Ile Leu Leu Ala Leu Met
                290                 295                 300

Gly His Asp Glu
305

<210> SEQ ID NO 128
<211> LENGTH: 951
<212> TYPE: DNA
<213> ORGANISM: Brassica rapa

<400> SEQUENCE: 128
atggcgtctc tcaaagttcc tgctagtgtt cctcttccag aagaagatgc cgagcagctc      60
cagaaggcct ttaaaggatg gggaaccaac gagaggatga tcatatcaat cttggctcac     120
agaaatgccg agcaacgcag cttcatccgt gctgtttatg ctgctaacta caataaggat     180
cttctcaagg aattagacaa agagctatcc ggtgacttcg agcgagctgt gatgttgtgg     240
acacttgaac cagcggagag agatgcgtat ttggctaagg aatcaacaaa atgttcact     300 aaagacaatt gggttctagt tgaaatcgct tgtactagat cttcccttga gttttttcaag     360 gccaagcaag cataccaagt tcgctacaag acatctattg aggaagatgt cgcctaccac     420
acatctggag atgtccgaaa gctcttggtt cctcttgtga gtaccttttag gtacgatgga     480 gatgaagtaa acatgatgat tgctaagtct gaggctaaga tacttcacga aagatggag     540 gcgaaggatt acaatgatgg agatctcatt agaatcctga caacaagaag caaagctcaa     600
atcagtgcaa cactcaacca cttcaaaaat aagttcggaa cttccattac aaaatacctt     660
aaagaggatt ccgacaacga atatgttcag ctacttaaag ccgtgatcaa atgcttgact     720
tatccagaga aatattttga gaaagttctt cgtcaagcca tcaacaaaat gggaactgac     780
gagtggggac ttactagagt ggtcaccaca cgagctgagc tcgacatgga acggatcaaa     840
gaggaatact gcgcaggaa cagtgtccca cttgaccgag ccattgccaa agacactcat     900
ggtgactatg aggatattct tctagctctt atcggacatg ccatgcttg a               951

<210> SEQ ID NO 129
<211> LENGTH: 316
<212> TYPE: PRT
<213> ORGANISM: Brassica rapa

<400> SEQUENCE: 129

Met Ala Ser Leu Lys Val Pro Ala Ser Val Pro Leu Pro Glu Glu Asp
1               5                   10                  15
```

```
Ala Glu Gln Leu Gln Lys Ala Phe Lys Gly Trp Gly Thr Asn Glu Arg
         20                  25                  30

Met Ile Ile Ser Ile Leu Ala His Arg Asn Ala Glu Gln Arg Ser Phe
         35                  40                  45

Ile Arg Ala Val Tyr Ala Ala Asn Tyr Asn Lys Asp Leu Leu Lys Glu
 50                  55                  60

Leu Asp Lys Glu Leu Ser Gly Asp Phe Glu Arg Ala Val Met Leu Trp
 65                  70                  75                  80

Thr Leu Glu Pro Ala Glu Arg Asp Ala Tyr Leu Ala Lys Glu Ser Thr
                 85                  90                  95

Lys Met Phe Thr Lys Asp Asn Trp Val Leu Val Glu Ile Ala Cys Thr
                100                 105                 110

Arg Ser Ser Leu Glu Phe Phe Lys Ala Lys Gln Ala Tyr Gln Val Arg
                115                 120                 125

Tyr Lys Thr Ser Ile Glu Glu Asp Val Ala Tyr His Thr Ser Gly Asp
130                 135                 140

Val Arg Lys Leu Leu Val Pro Leu Val Ser Thr Phe Arg Tyr Asp Gly
145                 150                 155                 160

Asp Glu Val Asn Met Met Ile Ala Lys Ser Ala Lys Ile Leu His
                165                 170                 175

Glu Lys Met Glu Ala Lys Asp Tyr Asn Asp Gly Asp Leu Ile Arg Ile
                180                 185                 190

Leu Thr Thr Arg Ser Lys Ala Gln Ile Ser Ala Thr Leu Asn His Phe
                195                 200                 205

Lys Asn Lys Phe Gly Thr Ser Ile Thr Lys Tyr Leu Lys Glu Asp Ser
                210                 215                 220

Asp Asn Glu Tyr Val Gln Leu Leu Lys Ala Val Ile Lys Cys Leu Thr
225                 230                 235                 240

Tyr Pro Glu Lys Tyr Phe Glu Lys Val Leu Arg Gln Ala Ile Asn Lys
                245                 250                 255

Met Gly Thr Asp Glu Trp Gly Leu Thr Arg Val Val Thr Thr Arg Ala
                260                 265                 270

Glu Leu Asp Met Glu Arg Ile Lys Glu Glu Tyr Leu Arg Arg Asn Ser
                275                 280                 285

Val Pro Leu Asp Arg Ala Ile Ala Lys Asp Thr His Gly Asp Tyr Glu
                290                 295                 300

Asp Ile Leu Leu Ala Leu Ile Gly His Gly His Ala
305                 310                 315

<210> SEQ ID NO 130
<211> LENGTH: 1235
<212> TYPE: DNA
<213> ORGANISM: Arabidopsis thaliana

<400> SEQUENCE: 130
ccttgaggaa aaaaactaa acggctcta aattgaaaac aaagaagag agagagagag      60 agagacgaag aaacagagag attctctcga aaatggccac cattagagta ccaaacgaag    120
ttccttctcc agctcaggat tctgaaactc tcaaacaagc tattcgcgga tggggaacag    180
atgagaaggc gattatacga gttttagggc aaagagacca gagccagaga aggaagatta    240
gagaaagttt tagagagatt tatggcaaag atcttatcga tgttctatcc tccgaactgt    300
ctggtgattt catgaaagct gtggtttcgt ggacgtatga tccagcagag agagacgcaa    360
ggcttgtgaa caagatttg aacaaggaga agaagaagaa aagcttagag aatttgaagg    420
```

-continued

```
ttatagtaga gatctcttgc acgacttccc caaaccattt gattgctgtg aggaaagctt    480
attgttcact ctttgactct tctcttgaag aacacattgc ttcttctctg ccttttcctc    540
ttgcaaagtt actggtgaca ttggcaagta cattcagata tgacaaagat aggactgatg    600
cagaagtagc tactattgag gcggctatgc tacgtgaagc catagagaag aaacaattag    660
atcatgacca tgtcctgtac atattaggaa cgcgtagtat ctatcagctc agagaaactt    720
ttgttgctta caagaagaat tatggggtca caattgataa ggatgttgat ggatgtccag    780
gagatgctga tctgagaagt ctattgaagg tggcaatctt ttgtattgat actcctgaga    840
aacactttgc aaaggtggta agagattcga ttgagggttt tggaacagat gaggattcgt    900
tgacgagggc gattgtgacg cgtgcagaga tcgatttgat gaaagtaaga ggagagtatt    960
tcaacatgta taatacaagc atggacaatg ctattactgg tgatatttct ggagactaca   1020
aggacttcat tatcacctta cttggatcca aaatctgatc gttctttcgt ttctttgtca   1080
gttgttatat tcttggcttt gcttgtgact tgtataatca atcaatacat tgtattccaa   1140
ctccagtttg aattgtttaa aaataatca aatttctctt gattcttgca ttttttgaatc   1200 aaagcaaatc tatgtttaat tttgttttca aaatt                              1235
```

<210> SEQ ID NO 131
<211> LENGTH: 321
<212> TYPE: PRT
<213> ORGANISM: Arabidopsis thaliana

<400> SEQUENCE: 131

```
Met Ala Thr Ile Arg Val Pro Asn Glu Val Pro Ser Pro Ala Gln Asp
1               5                   10                  15

Ser Glu Thr Leu Lys Gln Ala Ile Arg Gly Trp Gly Thr Asp Glu Lys
            20                  25                  30

Ala Ile Ile Arg Val Leu Gly Gln Arg Asp Gln Ser Gln Arg Arg Lys
        35                  40                  45

Ile Arg Glu Ser Phe Arg Glu Ile Tyr Gly Lys Asp Leu Ile Asp Val
    50                  55                  60

Leu Ser Ser Glu Leu Ser Gly Asp Phe Met Lys Ala Val Val Ser Trp
65                  70                  75                  80

Thr Tyr Asp Pro Ala Glu Arg Asp Ala Arg Leu Val Asn Lys Ile Leu
                85                  90                  95

Asn Lys Glu Lys Lys Lys Ser Leu Glu Asn Leu Lys Val Ile Val
            100                 105                 110

Glu Ile Ser Cys Thr Thr Ser Pro Asn His Leu Ile Ala Val Arg Lys
        115                 120                 125

Ala Tyr Cys Ser Leu Phe Asp Ser Ser Leu Glu Glu His Ile Ala Ser
    130                 135                 140

Ser Leu Pro Phe Pro Leu Ala Lys Leu Leu Val Thr Leu Ala Ser Thr
145                 150                 155                 160

Phe Arg Tyr Asp Lys Asp Arg Thr Asp Ala Glu Val Ala Thr Ile Glu
                165                 170                 175

Ala Ala Met Leu Arg Glu Ala Ile Glu Lys Lys Gln Leu Asp His Asp
            180                 185                 190

His Val Leu Tyr Ile Leu Gly Thr Arg Ser Ile Tyr Gln Leu Arg Glu
        195                 200                 205

Thr Phe Val Ala Tyr Lys Lys Asn Tyr Gly Val Thr Ile Asp Lys Asp
    210                 215                 220
```

Val Asp Gly Cys Pro Gly Asp Ala Asp Leu Arg Ser Leu Leu Lys Val
225                 230                 235                 240

Ala Ile Phe Cys Ile Asp Thr Pro Glu Lys His Phe Ala Lys Val Val
            245                 250                 255

Arg Asp Ser Ile Glu Gly Phe Gly Thr Asp Glu Asp Ser Leu Thr Arg
        260                 265                 270

Ala Ile Val Thr Arg Ala Glu Ile Asp Leu Met Lys Val Arg Gly Glu
    275                 280                 285

Tyr Phe Asn Met Tyr Asn Thr Ser Met Asp Asn Ala Ile Thr Gly Asp
290                 295                 300

Ile Ser Gly Asp Tyr Lys Asp Phe Ile Ile Thr Leu Leu Gly Ser Lys
305                 310                 315                 320

Ile

<210> SEQ ID NO 132
<211> LENGTH: 951
<212> TYPE: DNA
<213> ORGANISM: Arabidopsis thaliana

<400> SEQUENCE: 132
atggcaacaa tgaaaatacc aatgacggta ccttctcctc gagtcgatgc tgaccaactc     60 tttaaggcct␣caaaggaag aggctgcgat acttcggtga tcatcaacat cttagctcat    120
cgcaatgcaa cacaacgagc tctcatcgaa caagaatacg aaaccaaatt ctcggatgac    180
ctccgaaaac gtctccactc tgagcttcat ggtcatctca agaaagccgt tcttttgtgg    240
atgcctgaag cagtggagcg agacgcttca atactgaaac gctccttaag␣ggagccgtg    300 actgatcata aagcgattgc tgagattata tgcacacgat ctggctctca gcttcgtcag    360
atcaaacagg tctactcaaa cactttcggt gtgaaacttg aagaggacat cgaatccgaa    420
gcttctggca atcacaaaag agttttgctc gcgtatttga acactacgcg atatgaagga    480
ccagagatcg ataatgcgag tgtagagaac gatgctagga ctctcaagag cgcggttgca    540 aggaagcata␣atctgatga ccagacgttg attcagatat␣cactgaccg aagcaggact    600 catttggtcg ctgtaagatc tacttaccgt tccatgtacg␣caaagaact tggaaaggcc    660 ataagagatg agactcgcgg gaacttcgag catgtccttc taacaatttt acaatgtgct    720
gaaaactctt gtttctattt cgcaaaggca ttgaggaaat caatgaaagg␣attaggaaca    780 gatgacacgg cgttgataag aatcgtggtg acgagagcag aggtggatat gcagttcatc    840
atcacagaat accgtaagag atacaagaag actttgtaca atgctgttca ttctgataca    900 actagtcatt␣acaggacttt␣tctcctctct␣cttttaggcc␣ccaacgtttg␣a            951

<210> SEQ ID NO 133
<211> LENGTH: 316
<212> TYPE: PRT
<213> ORGANISM: Arabidopsis thaliana

<400> SEQUENCE: 133

Met Ala Thr Met Lys Ile Pro Met Thr Val Pro Ser Pro Arg Val Asp
1               5                   10                  15

Ala Asp Gln Leu Phe Lys Ala Phe Lys Gly Arg Gly Cys Asp Thr Ser
            20                  25                  30

Val Ile Ile Asn Ile Leu Ala His Arg Asn Ala Thr Gln Arg Ala Leu
        35                  40                  45

Ile Glu Gln Glu Tyr Glu Thr Lys Phe Ser Asp Asp Leu Arg Lys Arg
    50                  55                  60

```
Leu His Ser Glu Leu His Gly His Leu Lys Lys Ala Val Leu Leu Trp
 65                  70                  75                  80

Met Pro Glu Ala Val Glu Arg Asp Ala Ser Ile Leu Lys Arg Ser Leu
                 85                  90                  95

Arg Gly Ala Val Thr Asp His Lys Ala Ile Ala Glu Ile Ile Cys Thr
            100                 105                 110

Arg Ser Gly Ser Gln Leu Arg Gln Ile Lys Gln Val Tyr Ser Asn Thr
        115                 120                 125

Phe Gly Val Lys Leu Glu Glu Asp Ile Glu Ser Glu Ala Ser Gly Asn
    130                 135                 140

His Lys Arg Val Leu Leu Ala Tyr Leu Asn Thr Thr Arg Tyr Glu Gly
145                 150                 155                 160

Pro Glu Ile Asp Asn Ala Ser Val Glu Asn Asp Ala Arg Thr Leu Lys
                165                 170                 175

Ser Ala Val Ala Arg Lys His Lys Ser Asp Asp Gln Thr Leu Ile Gln
            180                 185                 190

Ile Phe Thr Asp Arg Ser Arg Thr His Leu Val Ala Val Arg Ser Thr
        195                 200                 205

Tyr Arg Ser Met Tyr Gly Lys Glu Leu Gly Lys Ala Ile Arg Asp Glu
    210                 215                 220

Thr Arg Gly Asn Phe Glu His Val Leu Leu Thr Ile Leu Gln Cys Ala
225                 230                 235                 240

Glu Asn Ser Cys Phe Tyr Phe Ala Lys Ala Leu Arg Lys Ser Met Lys
                245                 250                 255

Gly Leu Gly Thr Asp Asp Thr Ala Leu Ile Arg Ile Val Thr Arg
            260                 265                 270

Ala Glu Val Asp Met Gln Phe Ile Ile Thr Glu Tyr Arg Lys Arg Tyr
        275                 280                 285

Lys Lys Thr Leu Tyr Asn Ala Val His Ser Asp Thr Thr Ser His Tyr
    290                 295                 300

Arg Thr Phe Leu Leu Ser Leu Leu Gly Pro Asn Val
305                 310                 315

<210> SEQ ID NO 134
<211> LENGTH: 1337
<212> TYPE: DNA
<213> ORGANISM: Arabidopsis thaliana

<400> SEQUENCE: 134
acagaaacca aaccaagagc cggaaatcaa aaacagtaat aaaagatcaa ctgcaagaaa      60
atggctcttc ctctcgagct cgaaagcctc actgaagcca tctcagctgg gatgggaatg     120
ggagttgatg agaatgcatt gataagcaca ctggggaaat cgcaaaagga acatagaaaa     180
ttgtttagga aagcaagcaa aagtttcttt gttgaagatg aggaaagagc ttttgagaaa     240
tgtcatgatc acttcgtcag acacctcaag cttgagttct cccgcttcaa tactgcggtg     300
gtgatgtggg caatgcatcc atgggagaga gatgcaaggt tggtgaagaa agctttgaag     360
aaaggagaag aagcttacaa cctcatcgtt gaggtctcat gcacacgctc tgctgaggat     420
ctcctcggtg cacgtaaagc ttaccactct ctcttcgacc aatcaatgga agaagacatt     480
gcctctcacg tccacggtcc tcagcgcaag ttgcttgtgg ggctcgtgag tgcttataga     540
tacgaaggaa ataaggtgaa ggatgattct gccaaatccg atgctaagat tctagccgaa     600
gcagtggctt cttcaggcga agaagccgtg gagaaggatg aggttgttag gattttgacc     660
```

```
acaagaagca aacttcatct ccaacatctc tacaaacact ttaacgaaat caaaggctct    720
gatcttcttg ggggtgtatc taagtcttct cttctcaatg aagcattgat ttgtttgctc    780
aaaccggctc tgtatttcag caagattttg gatgcgtctc tgaacaaaga cgcagacaag    840
actaccaaga aatggttgac aagagtgttc gttacaagag cagatcatag tgatgagatg    900
aatgagatca agaagagta caataacctt tatggtgaga ctttggctca agaatccaa     960 gagaagataa aagggaacta cagagatttc ttgctcacac ttctctccaa atccgattga   1020
tttcgtgttg agaaacctat taccaatact tttggttatt gaagatttat gatttccctt   1080
tttatggttt tatgtttcta attcctaaat ttgcgttttc tctaccgttt ggtaataaag   1140
acatgaaaat ttgatgaact cggtgaatcg agagtaagag ttttgcgatt gtgacaatga   1200
gtgattaata caaggattaa gctccaataa aaaaatgttg cataaatcag aaatgaaact   1260
tgtaactctt cttttctttta tgtgaaactt gtaactctat ttgaaagatt ctatgtgacc   1320
actaaaccga attacgg                                                  1337
```

<210> SEQ ID NO 135
<211> LENGTH: 319
<212> TYPE: PRT
<213> ORGANISM: Arabidopsis thaliana

<400> SEQUENCE: 135

```
Met Ala Leu Pro Leu Glu Leu Glu Ser Leu Thr Glu Ala Ile Ser Ala
1               5                   10                  15

Gly Met Gly Met Gly Val Asp Glu Asn Ala Leu Ile Ser Thr Leu Gly
            20                  25                  30

Lys Ser Gln Lys Glu His Arg Lys Leu Phe Arg Lys Ala Ser Lys Ser
        35                  40                  45

Phe Phe Val Glu Asp Glu Glu Arg Ala Phe Glu Lys Cys His Asp His
    50                  55                  60

Phe Val Arg His Leu Lys Leu Glu Phe Ser Arg Phe Asn Thr Ala Val
65                  70                  75                  80

Val Met Trp Ala Met His Pro Trp Glu Arg Asp Ala Arg Leu Val Lys
                85                  90                  95

Lys Ala Leu Lys Lys Gly Glu Glu Ala Tyr Asn Leu Ile Val Glu Val
            100                 105                 110

Ser Cys Thr Arg Ser Ala Glu Asp Leu Leu Gly Ala Arg Lys Ala Tyr
        115                 120                 125

His Ser Leu Phe Asp Gln Ser Met Glu Glu Asp Ile Ala Ser His Val
    130                 135                 140

His Gly Pro Gln Arg Lys Leu Leu Val Gly Leu Val Ser Ala Tyr Arg
145                 150                 155                 160

Tyr Glu Gly Asn Lys Val Lys Asp Asp Ser Ala Lys Ser Asp Ala Lys
                165                 170                 175

Ile Leu Ala Glu Ala Val Ala Ser Ser Gly Glu Glu Ala Val Glu Lys
            180                 185                 190

Asp Glu Val Val Arg Ile Leu Thr Thr Arg Ser Lys Leu His Leu Gln
        195                 200                 205

His Leu Tyr Lys His Phe Asn Glu Ile Lys Gly Ser Asp Leu Leu Gly
    210                 215                 220

Gly Val Ser Lys Ser Ser Leu Leu Asn Glu Ala Leu Ile Cys Leu Leu
225                 230                 235                 240

Lys Pro Ala Leu Tyr Phe Ser Lys Ile Leu Asp Ala Ser Leu Asn Lys
                245                 250                 255
```

Asp Ala Asp Lys Thr Thr Lys Lys Trp Leu Thr Arg Val Phe Val Thr
                260                 265                 270

Arg Ala Asp His Ser Asp Glu Met Asn Glu Ile Lys Glu Glu Tyr Asn
            275                 280                 285

Asn Leu Tyr Gly Glu Thr Leu Ala Gln Arg Ile Gln Glu Lys Ile Lys
        290                 295                 300

Gly Asn Tyr Arg Asp Phe Leu Leu Thr Leu Leu Ser Lys Ser Asp
305                 310                 315

<210> SEQ ID NO 136
<211> LENGTH: 1110
<212> TYPE: DNA
<213> ORGANISM: Arabidopsis thaliana

<400> SEQUENCE: 136
gtctcatcta gagagctaga gaaatattca gtggtcggag aatggcgtct ctcaaaattc     60
cagcaaatat tcctcttccc gaagaagact ccgagcagct ccacaaggca ttcaaaggat    120
ggggaactaa tgaagggatg atcatatcaa ttttggctca tagaaacgca acgcaacgca    180
gtttcattcg tgccgtttat gctgctaact acaataagga tcttctcaag gaattagacg    240
gagagctttc tggtgacttt gagagagttg tgatgttgtg gactcttgat ccaacggaga    300
gagatgcgta tttggccaat gaatctacca aattgttcac caaaaacatt tgggtcctag    360
ttgaaatcgc ttgtactaga ccttctcttg agttttcaa gaccaagcaa gcataccatg    420
ttcgctacaa gacctctctc gaggaagatg ttgcatacca tacatctgga aatatccgaa    480
agctattggt tcctcttgtg agcaccttca ggtacgatgg aaatgctgat gaggtcaacg    540
tgaagctggc tagatccgaa gctaagacac ttcacaagaa gatcactgag aaggcttaca    600
ctgatgaaga tctcatcaga atcttgacaa caaggagcaa agcacagatc aatgcaacac    660
tcaatcactt caaggacaag tttggaagtt ccattaacaa gtttctcaaa gaagattcga    720
acgatgatta tgttcaatta ctcaaaaccg cgatcaaatg cttgacatat ccagagaagt    780
actttgagaa ggttctacgt cgagccatca caggatggg aacagacgag tgggcactta    840
ctagagtggt cactacaaga gcagaggtcg acctggagcg atcaaagaa gaatacttac    900 gcaggaacag tgttcctctt gatcgagcca ttgctaatga cacttctggt gactacaagg    960
atatgcttct cgcccttctt ggacatgacc atgcttgaaa caacatcatc gtttcatagt   1020
cttttataag acagttgtta tttgttttc attttctttg aactttggtc cttagttttt   1080
acattttact gcaacaactt attctggttt                                    1110

<210> SEQ ID NO 137
<211> LENGTH: 318
<212> TYPE: PRT
<213> ORGANISM: Arabidopsis thaliana

<400> SEQUENCE: 137

Met Ala Ser Leu Lys Ile Pro Ala Asn Ile Pro Leu Pro Glu Glu Asp
1               5                   10                  15

Ser Glu Gln Leu His Lys Ala Phe Lys Gly Trp Gly Thr Asn Glu Gly
            20                  25                  30

Met Ile Ile Ser Ile Leu Ala His Arg Asn Ala Thr Gln Arg Ser Phe
        35                  40                  45

Ile Arg Ala Val Tyr Ala Ala Asn Tyr Asn Lys Asp Leu Leu Lys Glu
    50                  55                  60

```
Leu Asp Gly Glu Leu Ser Gly Asp Phe Glu Arg Val Val Met Leu Trp
 65                  70                  75                  80

Thr Leu Asp Pro Thr Glu Arg Asp Ala Tyr Leu Ala Asn Glu Ser Thr
                 85                  90                  95

Lys Leu Phe Thr Lys Asn Ile Trp Val Leu Val Glu Ile Ala Cys Thr
            100                 105                 110

Arg Pro Ser Leu Glu Phe Phe Lys Thr Lys Gln Ala Tyr His Val Arg
        115                 120                 125

Tyr Lys Thr Ser Leu Glu Glu Asp Val Ala Tyr His Thr Ser Gly Asn
    130                 135                 140

Ile Arg Lys Leu Leu Val Pro Leu Val Ser Thr Phe Arg Tyr Asp Gly
145                 150                 155                 160

Asn Ala Asp Glu Val Asn Val Lys Leu Ala Arg Ser Glu Ala Lys Thr
                165                 170                 175

Leu His Lys Lys Ile Thr Glu Lys Ala Tyr Thr Asp Glu Asp Leu Ile
            180                 185                 190

Arg Ile Leu Thr Thr Arg Ser Lys Ala Gln Ile Asn Ala Thr Leu Asn
        195                 200                 205

His Phe Lys Asp Lys Phe Gly Ser Ser Ile Asn Lys Phe Leu Lys Glu
    210                 215                 220

Asp Ser Asn Asp Asp Tyr Val Gln Leu Leu Lys Thr Ala Ile Lys Cys
225                 230                 235                 240

Leu Thr Tyr Pro Glu Lys Tyr Phe Glu Lys Val Leu Arg Arg Ala Ile
                245                 250                 255

Asn Arg Met Gly Thr Asp Glu Trp Ala Leu Thr Arg Val Val Thr Thr
            260                 265                 270

Arg Ala Glu Val Asp Leu Glu Arg Ile Lys Glu Glu Tyr Leu Arg Arg
        275                 280                 285

Asn Ser Val Pro Leu Asp Arg Ala Ile Ala Asn Asp Thr Ser Gly Asp
    290                 295                 300

Tyr Lys Asp Met Leu Leu Ala Leu Leu Gly His Asp His Ala
305                 310                 315

<210> SEQ ID NO 138
<211> LENGTH: 951
<212> TYPE: DNA
<213> ORGANISM: Arabidopsis thaliana

<400> SEQUENCE: 138
atggccacca ttgtttctcc tccacatttc tcccctgtcg aagacgctga aaacatcaag     60
gcggcttgtc aaggatgggg aaccaatgaa atgccatca tctcgatctt aggacaccgg    120
aatttgttcc agaggaagct cataagacaa gcttaccagg agatttacca tgaggatctc    180
attcaccagc tcaaatctga gctctctggc aattttgaga gagctatttg cttgtgggtc    240
ttggatcctc cagagagaga tgctctcttg gctaacttgg ctcttcaaaa gcctattcct    300
gactacaagg ttcttgtcga aattgcctgc atgagatccc ctgaagatat gttagctgct    360
agacgtgctt accgttgcct ctacaagcat tctcttgagg aagacttggc ctcccgtact    420
attggcgaca tcaggagact cttggttgca atggtgtctg cttataaata tgatggagaa    480
gaaattgatg agatgctggc gcaatcagag gctgcgattc ttcatgatga aatccttggt    540
aaggctgttg atcacgaaga aacgatcagg gtgttaagta caaggagcag catgcagctt    600
agcgcaatct tcaaccgcta caaggatata tatggcacat cgatcactaa ggatctcctc    660
aatcacccta caaatgagta cctgagtgca ctacgtgcag ccatcaggtg catcaaaaac    720
```

```
cctacccggt attatgcaaa ggttttgcgc aattcaatca acacggtggg gactgatgaa    780
gatgctctga accgtgtgat tgtcacacga gcagaaaagg acctgacgaa tataactggg    840
ctgtacttta agaggaacaa tgtgagtctc gatcaagcta tagcaaaaga gacatcaggg    900
gactacaagg cctttcttct agctttgcta ggacatggaa acaactttag                951

<210> SEQ ID NO 139
<211> LENGTH: 316
<212> TYPE: PRT
<213> ORGANISM: Arabidopsis thaliana

<400> SEQUENCE: 139

Met Ala Thr Ile Val Ser Pro Pro His Phe Ser Pro Val Glu Asp Ala
1               5                   10                  15

Glu Asn Ile Lys Ala Ala Cys Gln Gly Trp Gly Thr Asn Glu Asn Ala
            20                  25                  30

Ile Ile Ser Ile Leu Gly His Arg Asn Leu Phe Gln Arg Lys Leu Ile
        35                  40                  45

Arg Gln Ala Tyr Gln Glu Ile Tyr His Glu Asp Leu Ile His Gln Leu
    50                  55                  60

Lys Ser Glu Leu Ser Gly Asn Phe Glu Arg Ala Ile Cys Leu Trp Val
65                  70                  75                  80

Leu Asp Pro Pro Glu Arg Asp Ala Leu Leu Ala Asn Leu Ala Leu Gln
                85                  90                  95

Lys Pro Ile Pro Asp Tyr Lys Val Leu Val Glu Ile Ala Cys Met Arg
            100                 105                 110

Ser Pro Glu Asp Met Leu Ala Ala Arg Arg Ala Tyr Arg Cys Leu Tyr
        115                 120                 125

Lys His Ser Leu Glu Glu Asp Leu Ala Ser Arg Thr Ile Gly Asp Ile
    130                 135                 140

Arg Arg Leu Leu Val Ala Met Val Ser Ala Tyr Lys Tyr Asp Gly Glu
145                 150                 155                 160

Glu Ile Asp Glu Met Leu Ala Gln Ser Glu Ala Ala Ile Leu His Asp
                165                 170                 175

Glu Ile Leu Gly Lys Ala Val Asp His Glu Glu Thr Ile Arg Val Leu
            180                 185                 190

Ser Thr Arg Ser Ser Met Gln Leu Ser Ala Ile Phe Asn Arg Tyr Lys
        195                 200                 205

Asp Ile Tyr Gly Thr Ser Ile Thr Lys Asp Leu Leu Asn His Pro Thr
    210                 215                 220

Asn Glu Tyr Leu Ser Ala Leu Arg Ala Ala Ile Arg Cys Ile Lys Asn
225                 230                 235                 240

Pro Thr Arg Tyr Tyr Ala Lys Val Leu Arg Asn Ser Ile Asn Thr Val
                245                 250                 255

Gly Thr Asp Glu Asp Ala Leu Asn Arg Val Ile Val Thr Arg Ala Glu
            260                 265                 270

Lys Asp Leu Thr Asn Ile Thr Gly Leu Tyr Phe Lys Arg Asn Asn Val
        275                 280                 285

Ser Leu Asp Gln Ala Ile Ala Lys Glu Thr Ser Gly Asp Tyr Lys Ala
    290                 295                 300

Phe Leu Leu Ala Leu Leu Gly His Gly Lys Gln Leu
305                 310                 315

<210> SEQ ID NO 140
```

<211> LENGTH: 1298
<212> TYPE: DNA
<213> ORGANISM: Oryza sativa

<400> SEQUENCE: 140

```
gttgcagatt actaccacca cctccccaaa atcccaatcg aatcgaaatc gaatcgagtc    60
gagtcgccgc cggagccgga gacggaggcg gcagcggcgc agcggtaatg gcgagcctca   120
ccctgccgcc ggcgcccacc aaccctcgcc aggacgccat cgacttccac aaggccttca   180
aagggtttgg ctgtgatagt acaacagtta taaatatact tactcatcgt gactcgatgc   240
aacgcgcgct cattcaacag gaatacagga ctatgtattc tgaggatctc tctcgccgta   300
tatcatctga actcagtgga caccacaaga aagcaatgct gctatggatt cttgatcctg   360
ctggacgaga tgcaactgtt ttgagagaag ctctgagtgg tgatactatt gacctgagag   420
cagccactga gataatatgt tccaggacac catcgcagct gcaataatg aaacagactt   480
atcatgcaaa atttggtact tatcttgagc acgacattgg tcagcgcaca tcaggcgacc   540
atcagaagct cttgcttgct tatgtgggga ttccacgcta tgaaggtcct gaggttgatc   600
ctactatagt gacacacgat gcaaaggacc tctataaagc tggtgagaaa aggctgggca   660
ctgatgagaa gaccttcatc cgcattttca ctgaacgcag ctgggcacac atggcatctg   720
ttgcctctgc ttaccatcat atgtatgatc ggtcactgga gaaggttgtg aagagcgaaa   780
catctggaaa ctttgaactt gctctgctaa ctatcctcag atgcgctgag aatccagcca   840
agtattttgc aaaggtcttg cggaagtcca tgaaggtat gggcactgat gatagtacac   900
ttataagggt tgtagtaaca aggactgaga tcgacatgca atatatcaag gctgagtact   960
acaagaaata caaaaaatca ttagctgaag ctatccattc cgagacctca ggaaattatc  1020
gaacattcct ccttttctcta gttggtagcc attaggctac atttcgtcga ccctgtggca  1080
cttgacgttc catgactatc ctaaatgcag tggttctacc tggaaactgt aaaatttcgc  1140
catcattgtg ctctctattc gtgtgtgctt gcttaaaaat gtgtgtatat atataacctg  1200
ggcattaaat agttggtgct taatatggtt tggtggttcc atctgacaag tcactcgtta  1260
ctcggtgcat ttattcgaat aagtgatggt atttggtc                          1298
```

<210> SEQ ID NO 141
<211> LENGTH: 315
<212> TYPE: PRT
<213> ORGANISM: Oryza sativa

<400> SEQUENCE: 141

```
Met Ala Ser Leu Thr Leu Pro Pro Ala Pro Thr Asn Pro Arg Gln Asp
  1               5                  10                  15

Ala Ile Asp Leu His Lys Ala Phe Lys Gly Phe Gly Cys Asp Ser Thr
             20                  25                  30

Thr Val Ile Asn Ile Leu Thr His Arg Asp Ser Met Gln Arg Ala Leu
         35                  40                  45

Ile Gln Gln Glu Tyr Arg Thr Met Tyr Ser Glu Asp Leu Ser Arg Arg
     50                  55                  60

Ile Ser Ser Glu Leu Ser Gly His His Lys Lys Ala Met Leu Leu Trp
 65                  70                  75                  80

Ile Leu Asp Pro Ala Gly Arg Asp Ala Thr Val Leu Arg Glu Ala Leu
                 85                  90                  95

Ser Gly Asp Thr Ile Asp Leu Arg Ala Ala Thr Glu Ile Ile Cys Ser
            100                 105                 110
```

```
Arg Thr Pro Ser Gln Leu Gln Ile Met Lys Gln Thr Tyr His Ala Lys
            115                 120                 125

Phe Gly Thr Tyr Leu Glu His Asp Ile Gly Arg Thr Ser Gly Asp
        130                 135                 140

His Gln Lys Leu Leu Leu Ala Tyr Val Gly Ile Pro Arg Tyr Glu Gly
145                 150                 155                 160

Pro Glu Val Asp Pro Thr Ile Val Thr His Asp Ala Lys Asp Leu Tyr
                165                 170                 175

Lys Ala Gly Glu Lys Arg Leu Gly Thr Asp Glu Lys Thr Phe Ile Arg
            180                 185                 190

Ile Phe Thr Glu Arg Ser Trp Ala His Met Ala Ser Val Ala Ser Ala
        195                 200                 205

Tyr His His Met Tyr Asp Arg Ser Leu Glu Lys Val Val Lys Ser Glu
    210                 215                 220

Thr Ser Gly Asn Phe Glu Leu Ala Leu Leu Thr Ile Leu Arg Cys Ala
225                 230                 235                 240

Glu Asn Pro Ala Lys Tyr Phe Ala Lys Val Leu Arg Lys Ser Met Lys
                245                 250                 255

Gly Met Gly Thr Asp Asp Ser Thr Leu Ile Arg Val Val Thr Arg
            260                 265                 270

Thr Glu Ile Asp Met Gln Tyr Ile Lys Ala Glu Tyr Tyr Lys Lys Tyr
        275                 280                 285

Lys Lys Ser Leu Ala Glu Ala Ile His Ser Glu Thr Ser Gly Asn Tyr
    290                 295                 300

Arg Thr Phe Leu Leu Ser Leu Val Gly Ser His
305                 310                 315

<210> SEQ ID NO 142
<211> LENGTH: 1222
<212> TYPE: DNA
<213> ORGANISM: Oryza sativa

<400> SEQUENCE: 142
ctccccgccg cataaatccc cttcgcctcc ccgccgcgcc ccgcggcgtc gcacgatctc      60
actgaggcat aaagtgagag accgtgattg gatcgatcac cggagcgacg atcaatggcg    120
acgctcaccg tgcccgccgc cgtgccgccc gtcgccgagg actgcgagca gctgcgcaag    180
gcgttcaaag ggtggggcac gaacgagaag ctcatcatct ccatcctcgc ccaccgcgac    240
gcggcgcagc gccgggcgat ccgccgcgcc tacgccgagg cgtacggcga ggagctgctc    300
cgcgccctca cgacgagat ccacggcaaa ttcgagaggg cggtgatcca gtggacgctg    360
gacccggcgg agcgggacgc ggtgctggcg aacgaggagg cgaggaagtg gcacccgggg    420
ggccgcgcgc tcgtcgagat cgcgtgcacg cgcactccat cgcagctctt cgctgcgaag    480
caggcgtacc acgagcgctt caagaggtcg ctcgaggagg acgtcgcggc gcacatcacc    540
ggcgactacc gtaagctttt ggtgccactt gtgactgtat atcgctatga tgggccagag    600
gtgaacacat cgttggcaca ttctgaagcc aaaatactcc atgagaagat ccatgacaag    660
gcttacagtg acgatgaaat catcaggatt ctcaccacaa ggagcaaagc acagttacta    720
gcaacattca atagttacaa tgatcagttc ggccatccaa tcactaagga tcttaaagct    780
gatcctaagg acgagttcct tggtacacta agggcgatca agatgcttt cacttgccct    840
gacagatact tgagaaagt cattcgattg gctctaggag gaatgggcac agacgagaac    900
tctcttacaa ggatcataac aactcgtgcc gaggtagacc tgaagctgat aaaggaggcc    960
```

```
taccagaaga gaaacagtgt cccattggag cgagctgttg ctaaagatac aaccagagac    1020
tacgaggata tactccttgc cctccttgga gcagagtgag gtgtatatct gctccatctc    1080
gtctgtctga tcctccttgt ttgatcggaa aataagatct gcatagaact gtgttctatt    1140
ttgttgtttc tgaatgatac aagtgagcta gtctgcatag cagtgctcat ataataaaat    1200
ctgtcctgca tactggtttg tc                                              1222

<210> SEQ ID NO 143
<211> LENGTH: 314
<212> TYPE: PRT
<213> ORGANISM: Oryza sativa

<400> SEQUENCE: 143

Met Ala Thr Leu Thr Val Pro Ala Ala Val Pro Pro Val Ala Glu Asp
1               5                   10                  15

Cys Glu Gln Leu Arg Lys Ala Phe Lys Gly Trp Gly Thr Asn Glu Lys
                20                  25                  30

Leu Ile Ile Ser Ile Leu Ala His Arg Asp Ala Ala Gln Arg Arg Ala
            35                  40                  45

Ile Arg Arg Ala Tyr Ala Glu Ala Tyr Gly Glu Glu Leu Leu Arg Ala
        50                  55                  60

Leu Asn Asp Glu Ile His Gly Lys Phe Glu Arg Ala Val Ile Gln Trp
65                  70                  75                  80

Thr Leu Asp Pro Ala Glu Arg Asp Ala Val Leu Ala Asn Glu Glu Ala
                85                  90                  95

Arg Lys Trp His Pro Gly Gly Arg Ala Leu Val Glu Ile Ala Cys Thr
            100                 105                 110

Arg Thr Pro Ser Gln Leu Phe Ala Ala Lys Gln Ala Tyr His Glu Arg
        115                 120                 125

Phe Lys Arg Ser Leu Glu Glu Asp Val Ala Ala His Ile Thr Gly Asp
    130                 135                 140

Tyr Arg Lys Leu Leu Val Pro Leu Val Thr Val Tyr Arg Tyr Asp Gly
145                 150                 155                 160

Pro Glu Val Asn Thr Ser Leu Ala His Ser Glu Ala Lys Ile Leu His
                165                 170                 175

Glu Lys Ile His Asp Lys Ala Tyr Ser Asp Glu Ile Ile Arg Ile
            180                 185                 190

Leu Thr Thr Arg Ser Lys Ala Gln Leu Leu Ala Thr Phe Asn Ser Tyr
        195                 200                 205

Asn Asp Gln Phe Gly His Pro Ile Thr Lys Asp Leu Lys Ala Asp Pro
    210                 215                 220

Lys Asp Glu Phe Leu Gly Thr Leu Arg Ala Ile Ile Arg Cys Phe Thr
225                 230                 235                 240

Cys Pro Asp Arg Tyr Phe Glu Lys Val Ile Arg Leu Ala Leu Gly Gly
                245                 250                 255

Met Gly Thr Asp Glu Asn Ser Leu Thr Arg Ile Ile Thr Arg Ala
            260                 265                 270

Glu Val Asp Leu Lys Leu Ile Lys Glu Ala Tyr Gln Lys Arg Asn Ser
        275                 280                 285

Val Pro Leu Glu Arg Ala Val Ala Lys Asp Thr Thr Arg Asp Tyr Glu
    290                 295                 300

Asp Ile Leu Leu Ala Leu Leu Gly Ala Glu
305                 310
```

<210> SEQ ID NO 144
<211> LENGTH: 1152
<212> TYPE: DNA
<213> ORGANISM: Oryza sativa

<400> SEQUENCE: 144

```
agcacagcac agcacacatc tcgtccagtc catccatggc gagcctgagc gtgccgccgg      60
tgccgacgga cccgcggcgc gacgcgatcg acctccacag ggcgttcaag gggttcggct     120
gcgacgccac ggcggtgacc gccatcctcg cccaccgcga cgcctcccag cgcgccctaa     180
tccggcgcca ctacgcggcg gtctaccacc aggacctcct ccaccgcctc gccgccgagc     240
tctcgggcca ccacaagcgc gccgtcctgc tctgggtgct cgacccggcg tcccgcgacg     300
ccgccgtcct ccaccaggcg ctcaacggcg acgtcaccga catgagggcg ccaccgagg     360
tggtgtgctc caggacgccg tcgcagctgc tcgtggtgag gcaggcctac ctcgccaggt     420
tcggcggcgg cggcggcggc ggcctcgagc acgacgtcgc cgtcagggcg tccggcgacc     480
accagaggct gcttctggcg tacctgcgct cgccgcggta cgaggggccc gaggtggtcg     540
acatggcggc ggcggcgcgc gacgccaggg agctgtacag ggccggcgag aggcggctcg     600
gcaccgacga ggacgttc atccgcgtct ctccgagcg cagcgccgcc cacatggcgg     660
ccgtcgccgc cgcgtaccac cacatgtacg accgctccct cgagaaggct gtgaagagtg     720
aaacttcagg gaactttggg tttggcctgc tgacaatcct caggtgcgcc gagagcccgg     780
ccaagtactt cgccaaggtg ctccacgagg cgatgaaggg gctgggcacc aacgacacga     840
cgctgatcag ggtggtgacg acgagggcgg aggtggacat gcagtacatc aaggcggagt     900
accaccggag ctacaagcgc tcgctcgccg acgccgtcca ctccgagacc tccggcaact     960
accgcacctt cctcctctcc ctcatcggcc gcgaccgcta acgtcgattg gtttcggtct    1020
ctttgagcgt gtgttaaggg acgcatttgt tccatagcgc acaaacatgg caattattta    1080
tgtgcgtgtg tagtggtgtg ttcgaacgtt cgttttttcgt gtaataaaaa aaattgagtt    1140
tgctgtcttg tg                                                        1152
```

<210> SEQ ID NO 145
<211> LENGTH: 321
<212> TYPE: PRT
<213> ORGANISM: Oryza sativa

<400> SEQUENCE: 145

```
Met Ala Ser Leu Ser Val Pro Pro Val Pro Thr Asp Pro Arg Arg Asp
1               5                   10                  15

Ala Ile Asp Leu His Arg Ala Phe Lys Gly Phe Gly Cys Asp Ala Thr
            20                  25                  30

Ala Val Thr Ala Ile Leu Ala His Arg Asp Ala Ser Gln Arg Ala Leu
        35                  40                  45

Ile Arg Arg His Tyr Ala Ala Val Tyr His Gln Asp Leu Leu His Arg
    50                  55                  60

Leu Ala Ala Glu Leu Ser Gly His His Lys Arg Ala Val Leu Leu Trp
65                  70                  75                  80

Val Leu Asp Pro Ala Ser Arg Asp Ala Ala Val Leu His Gln Ala Leu
                85                  90                  95

Asn Gly Asp Val Thr Asp Met Arg Ala Ala Thr Glu Val Val Cys Ser
            100                 105                 110

Arg Thr Pro Ser Gln Leu Leu Val Val Arg Gln Ala Tyr Leu Ala Arg
        115                 120                 125
```

```
Phe Gly Gly Gly Gly Gly Gly Leu Glu His Asp Val Ala Val Arg
    130             135                 140
Ala Ser Gly Asp His Gln Arg Leu Leu Ala Tyr Leu Arg Ser Pro
145                 150                 155                 160
Arg Tyr Glu Gly Pro Glu Val Val Asp Met Ala Ala Ala Arg Asp
                165                 170                 175
Ala Arg Glu Leu Tyr Arg Ala Gly Glu Arg Leu Gly Thr Asp Glu
            180                 185                 190
Arg Thr Phe Ile Arg Val Phe Ser Glu Arg Ser Ala His Met Ala
        195                 200                 205
Ala Val Ala Ala Ala Tyr His His Met Tyr Asp Arg Ser Leu Glu Lys
210                 215                 220
Ala Val Lys Ser Glu Thr Ser Gly Asn Phe Gly Phe Gly Leu Leu Thr
225                 230                 235                 240
Ile Leu Arg Cys Ala Glu Ser Pro Ala Lys Tyr Phe Ala Lys Val Leu
                245                 250                 255
His Glu Ala Met Lys Gly Leu Gly Thr Asn Asp Thr Thr Leu Ile Arg
            260                 265                 270
Val Val Thr Thr Arg Ala Glu Val Asp Met Gln Tyr Ile Lys Ala Glu
        275                 280                 285
Tyr His Arg Ser Tyr Lys Arg Ser Leu Ala Asp Ala Val His Ser Glu
    290                 295                 300
Thr Ser Gly Asn Tyr Arg Thr Phe Leu Leu Ser Leu Ile Gly Arg Asp
305                 310                 315                 320
Arg
```

<210> SEQ ID NO 146
<211> LENGTH: 1272
<212> TYPE: DNA
<213> ORGANISM: Oryza sativa

<400> SEQUENCE: 146

| | | | | | |
|---|---|---|---|---|---|
| cgggtctcct | ctcctccccc | gccgacgcgc | actcgatccc | cccgcctcc | gcctccgcct | 60 |
| ccgcctccgc | gtcgcccatc | tcgagatccc | ccgcatggcg | acgctcaccg | tccctccgc | 120 |
| cgtcccgccc | gtcgccgacg | actgcgacca | gctccgcaag | gccttccaag | ggtggggcac | 180 |
| gaacgaggcg | ctcatcatct | ccatcctggc | ccaccgcgac | gcggcgcagc | ggcgcgccat | 240 |
| ccgccgcgcc | tacgccgaca | cctacggcga | ggagctcctc | cgcagcatca | ccgacgagat | 300 |
| ctccggcgac | ttcgagaggg | ccgtgatcct | gtggacgctg | acccggcgg | agcgcgacgc | 360 |
| ggtgctcgcc | aacgaggtcg | cgaggaagtg | gtacccaggg | agcgggagcc | gcgtgctggt | 420 |
| cgagatcgcg | tgcgcgcgcg | gccccgcgca | gctgttcgcg | gtcaggcagg | cctaccacga | 480 |
| gcgcttcaag | cgctcgctcg | aggaggacgt | cgcggcgcac | gccactggtg | acttccgcaa | 540 |
| gctcttggtg | ccacttataa | gtgcttaccg | ctatgagggg | ccggaagtca | acacaaagtt | 600 |
| ggcacattca | gaagccaaaa | ttctgcatga | gaagatccag | cataaggcat | atggtgatga | 660 |
| tgagatcatc | agaattctca | ctactaggag | caaggctcag | ttgattgcga | cattcaatcg | 720 |
| ttacaatgat | gaatatggtc | acccaatcaa | caaggatctc | aaggctgatc | caaggacga | 780 |
| gttcctttcc | acgctgcgtg | caatcatccg | ctgcttctgt | tgccctgaca | ggtacttcga | 840 |
| gaaagtcatc | aggttggcca | tcgcaggcat | gggaacagac | gagaactccc | tcactaggat | 900 |
| cattaccact | cgtgccgagg | tggatctgaa | gctgatcacg | gaggcgtacc | agaagaggaa | 960 |
| cagtgtcccg | ctggagcgtg | cggtcgcagg | ggacacctcc | ggggactacg | agaggatgct | 1020 |

```
tcttgctctt ctgggtcagg agcagtgagc catgcctatc ttgcccagtc acacacttca    1080
tgtgatcatg tcatatcaga gaataaacct gttatgcagg ggacacagcc gtggtgatta    1140
tgatgttgtt tttccagtgt acggtactgt ttgctgcagc ttgcataaca gtgacgatga    1200
aataaatcat agtggaatgc gttggctcat gggacctcac ttattttgca acttttttgac   1260 aggtcttatt tc                                                         1272
```

```
<210> SEQ ID NO 147
<211> LENGTH: 317
<212> TYPE: PRT
<213> ORGANISM: Oryza sativa

<400> SEQUENCE: 147
```

```
Met Ala Thr Leu Thr Val Pro Ser Ala Val Pro Val Ala Asp Asp
1               5                   10                  15

Cys Asp Gln Leu Arg Lys Ala Phe Gln Gly Trp Gly Thr Asn Glu Ala
            20                  25                  30

Leu Ile Ile Ser Ile Leu Ala His Arg Asp Ala Ala Gln Arg Arg Ala
        35                  40                  45

Ile Arg Arg Ala Tyr Ala Asp Thr Tyr Gly Glu Glu Leu Leu Arg Ser
    50                  55                  60

Ile Thr Asp Glu Ile Ser Gly Asp Phe Glu Arg Ala Val Ile Leu Trp
65                  70                  75                  80

Thr Leu Asp Pro Ala Glu Arg Asp Ala Val Leu Ala Asn Glu Val Ala
                85                  90                  95

Arg Lys Trp Tyr Pro Gly Ser Gly Ser Arg Val Leu Val Glu Ile Ala
            100                 105                 110

Cys Ala Arg Gly Pro Ala Gln Leu Phe Ala Val Arg Gln Ala Tyr His
        115                 120                 125

Glu Arg Phe Lys Arg Ser Leu Glu Glu Asp Val Ala Ala His Ala Thr
    130                 135                 140

Gly Asp Phe Arg Lys Leu Leu Val Pro Leu Ile Ser Ala Tyr Arg Tyr
145                 150                 155                 160

Glu Gly Pro Glu Val Asn Thr Lys Leu Ala His Ser Glu Ala Lys Ile
                165                 170                 175

Leu His Glu Lys Ile Gln His Lys Ala Tyr Gly Asp Asp Glu Ile Ile
            180                 185                 190

Arg Ile Leu Thr Thr Arg Ser Lys Ala Gln Leu Ile Ala Thr Phe Asn
        195                 200                 205

Arg Tyr Asn Asp Glu Tyr Gly His Pro Ile Asn Lys Asp Leu Lys Ala
    210                 215                 220

Asp Pro Lys Asp Glu Phe Leu Ser Thr Leu Arg Ala Ile Ile Arg Cys
225                 230                 235                 240

Phe Cys Cys Pro Asp Arg Tyr Phe Glu Lys Val Ile Arg Leu Ala Ile
                245                 250                 255

Ala Gly Met Gly Thr Asp Glu Asn Ser Leu Thr Arg Ile Ile Thr Thr
            260                 265                 270

Arg Ala Glu Val Asp Leu Lys Leu Ile Thr Glu Ala Tyr Gln Lys Arg
        275                 280                 285

Asn Ser Val Pro Leu Glu Arg Ala Val Ala Gly Asp Thr Ser Gly Asp
    290                 295                 300

Tyr Glu Arg Met Leu Leu Ala Leu Leu Gly Gln Glu Gln
305                 310                 315
```

<210> SEQ ID NO 148
<211> LENGTH: 1491
<212> TYPE: DNA
<213> ORGANISM: Oryza sativa

<400> SEQUENCE: 148

| | | | | | |
|---|---|---|---|---|---|
| agtaatacgc | aaggaatacc | tggatcatac | gatacgaata | tctagagaca | aacatgatt | 60 |
| tgagtgattg | atgatcgaga | agaagctca | aaaggtcttg | aaaagtcgaa | acgtccatca | 120 |
| ctgaaattcg | gtttcatgcc | ctcagatccc | attgctgagt | aggacgcaga | ttttcttcct | 180 |
| tcctaccatt | tcctttctct | tgcttccttt | tggtcattt | gagatagctt | tatccatcct | 240 |
| ttagcaaaaa | ggaaaccaat | agctagcaat | acttgccatc | atatatacct | gggcaatggc | 300 |
| cggccaagca | aactcagttc | tctacattga | acacttcagg | tttgagtaga | catggcctct | 360 |
| cggtgtcttg | ttaccacagg | ttttgaggat | gagtgcagag | agatccatga | tgcgtgcaac | 420 |
| cagccacgcc | gtttgagcgt | tctcttggct | catcggagcc | catcggagag | gcagaaaatc | 480 |
| aaggcgactt | accgtacagt | gttcggcgaa | gatctcgccg | gagaagtgca | gaaaatcctc | 540 |
| atggtcaacc | aggaagatga | gctctgcaag | ctgctctacc | tgtgggtgct | cgacccgtcg | 600 |
| gagcgcgacg | cgatcatggc | tcgggacgcc | gtcgagaatg | gcggcgccac | ggattaccgg | 660 |
| gtcctggtgg | agatcttcac | acgccggaag | cagaaccagc | tcttcttcac | caatcaggca | 720 |
| taccttgcca | ggttcaagaa | gaacctggag | caggacatgg | tcacagagcc | gtctcatcct | 780 |
| taccagaggc | tattggtagc | acttgcaacc | tcccacaagt | cgcaccacga | tgaacttagt | 840 |
| cggcacattg | caaaatgtga | cgccaggagg | ctctatgatg | cgaagaacag | cggcatggga | 900 |
| tcggtcgacg | aggctgtcat | tcttgagatg | ttcagcaaga | ggagcatccc | acagctcagg | 960 |
| ctagcattct | gcagttacaa | gcacatatat | gggcatgact | acaccaaggc | actgaagaaa | 1020 |
| aatggcttcg | gtgagtttga | acaatctttg | agggttgttg | tgaagtgcat | ctacaatcct | 1080 |
| tccatgtatt | tctccaagct | gctgcataga | agtctgcaat | gctcagcgac | caataaaagg | 1140 |
| ttggttacaa | gggctatttt | gggcagtgac | gatgtcgata | tggacaagat | caagtcagtg | 1200 |
| ttcaaaagta | gttatggaaa | ggaccttgag | gatttcatcc | ttgaaagctt | gcctgagaat | 1260 |
| gattacagag | actttctttt | aggtgcggcc | aaggggtcaa | gggcctcatg | aagtctgtgg | 1320 |
| agagagatcc | ttgaattatc | tagggaaagt | aaagggtgca | tatactgctt | tgcatgtaag | 1380 |
| agcaaattga | ccatcaaaaa | cagcagtttt | atgttatctg | agaataggat | ttaggtgaga | 1440 |
| acatcatgct | cattttgttt | attttgggtg | aaaaaagtta | tcagttcaac | t | 1491 |

<210> SEQ ID NO 149
<211> LENGTH: 319
<212> TYPE: PRT
<213> ORGANISM: Oryza sativa

<400> SEQUENCE: 149

Met Ala Ser Arg Cys Leu Val Thr Thr Gly Phe Glu Asp Glu Cys Arg
1               5                   10                  15

Glu Ile His Asp Ala Cys Asn Gln Pro Arg Arg Leu Ser Val Leu Leu
            20                  25                  30

Ala His Arg Ser Pro Ser Glu Arg Gln Lys Ile Lys Ala Thr Tyr Arg
        35                  40                  45

Thr Val Phe Gly Glu Asp Leu Ala Gly Glu Val Gln Lys Ile Leu Met
    50                  55                  60

Val Asn Gln Glu Asp Glu Leu Cys Lys Leu Leu Tyr Leu Trp Val Leu

```
                65                  70                  75                  80
Asp Pro Ser Glu Arg Asp Ala Ile Met Ala Arg Asp Ala Val Glu Asn
                    85                  90                  95

Gly Gly Ala Thr Asp Tyr Arg Val Leu Val Glu Ile Phe Thr Arg Arg
                100                 105                 110

Lys Gln Asn Gln Leu Phe Phe Thr Asn Gln Ala Tyr Leu Ala Arg Phe
                115                 120                 125

Lys Lys Asn Leu Glu Gln Asp Met Val Thr Pro Ser His Pro Tyr
            130                 135                 140

Gln Arg Leu Leu Val Ala Leu Ala Thr Ser His Lys Ser His His Asp
145                 150                 155                 160

Glu Leu Ser Arg His Ile Ala Lys Cys Asp Ala Arg Arg Leu Tyr Asp
                165                 170                 175

Ala Lys Asn Ser Gly Met Gly Ser Val Asp Glu Ala Val Ile Leu Glu
            180                 185                 190

Met Phe Ser Lys Arg Ser Ile Pro Gln Leu Arg Leu Ala Phe Cys Ser
                195                 200                 205

Tyr Lys His Ile Tyr Gly His Asp Tyr Thr Lys Ala Leu Lys Lys Asn
            210                 215                 220

Gly Phe Gly Glu Phe Glu Gln Ser Leu Arg Val Val Lys Cys Ile
225                 230                 235                 240

Tyr Asn Pro Ser Met Tyr Phe Ser Lys Leu Leu His Arg Ser Leu Gln
                245                 250                 255

Cys Ser Ala Thr Asn Lys Arg Leu Val Thr Arg Ala Ile Leu Gly Ser
                260                 265                 270

Asp Asp Val Asp Met Asp Lys Ile Lys Ser Val Phe Lys Ser Ser Tyr
            275                 280                 285

Gly Lys Asp Leu Glu Asp Phe Ile Leu Glu Ser Leu Pro Glu Asn Asp
                290                 295                 300

Tyr Arg Asp Phe Leu Leu Gly Ala Ala Lys Gly Ser Arg Ala Ser
305                 310                 315

<210> SEQ ID NO 150
<211> LENGTH: 1393
<212> TYPE: DNA
<213> ORGANISM: Oryza sativa

<400> SEQUENCE: 150
atggaaaaat accatgaaat acaaatggaa aaatagggt agagcccaga gcattggatg      60
tgcagattaa agctatacta ctagcattca agtttttttc aactctgctg cgtaggaggc     120
gtgtgtgtgc catgtgttgc tggtgctgct gcctggactg catccataac atacctccac     180
tcaatctcct cttcctccat ttctcccccc attctctctc ctcctcagct gcttctgcag     240
gtggaggaga agcagcagca gcagcagctg ttgctcccat ggcttccatc tctgtcccaa     300
acccagctcc ttcccctaca gaggatgcag agagcataag aaaggcagtg caaggatggg     360
gaacggacga gaatgcgctg atcgagatcc tcggccaccg gacggcggcg cagcgggcgg     420
agatcgccgt cgcctacgag ggcctctacg acgagaccct cctcgacagg ctccactccg     480
agctctccgg cgacttccgt agcgcgttga tgctgtggac gatggacccg gcggcgcggg     540
acgccaagct ggccaacgag gccctgaaga agaagaagaa gggcgagctc cgccacatct     600
gggtgctcgt cgaggtcgcc tgcgcgtcgt cgccggacca cctcgtcgcc gtcaggaagg     660
cctaccgcgc cgcctacgcc tcgtcgctgg aggaggacgt ggcgtcgtgc tcgctgttcg     720
```

```
gggacccgct caggcggttc ctggtgcgcc tcgtgagctc ctaccggtac ggcggcggtg    780
gcgtcgacgg cgagctggcg atcgccgagg cggcggagct gcacgacgcg gtggtgggca    840
gggggcaggc gctgcacggc gacgacgtcg tccgcatcgt cggcacgagg agcaaggcgc    900
agctcgcggt gacgctggag cggtacaggc aggagcacgg caagggcatc gacgaggtcc    960
tcgacggccg ccgcggcgac cagctcgcgg cggtgctcaa ggccgcgctc tggtgcctca   1020
cctcgccgga gaagcatttc gctgaggtga tccggacatc gattctaggg cttggcaccg   1080
acgaggagat gctgacgaga gggatcgtgt cgcgggcgga ggtggacatg gagaaggtga   1140
aggaggagta caaggtcagg tacaacacca cggtcaccgc cgacgtccgc ggcgacacgt   1200
cggggtacta catgaacacg cttctcaccc tcgtcggccc tgagaagtag ccatgtagca   1260
gcttggacat tttattgctt gctcatttga tttgaacaaa atacaccgtg tgatgttgca   1320
gttattagta aaatgcgagt aggatcgatg ttgttttcgt tgggtggatt aataatggag   1380
catgttttat cgc                                                     1393

<210> SEQ ID NO 151
<211> LENGTH: 372
<212> TYPE: PRT
<213> ORGANISM: Oryza sativa

<400> SEQUENCE: 151

Met Cys Cys Trp Cys Cys Cys Leu Asp Cys Ile His Asn Ile Pro Pro
1               5                   10                  15

Leu Asn Leu Leu Phe Leu His Phe Ser Pro His Ser Leu Ser Ser Ser
            20                  25                  30

Ala Ala Ser Ala Gly Gly Gly Glu Ala Ala Ala Ala Ala Val Ala
        35                  40                  45

Pro Met Ala Ser Ile Ser Val Pro Asn Pro Ala Pro Ser Pro Thr Glu
    50                  55                  60

Asp Ala Glu Ser Ile Arg Lys Ala Val Gln Gly Trp Gly Thr Asp Glu
65                  70                  75                  80

Asn Ala Leu Ile Glu Ile Leu Gly His Arg Thr Ala Ala Gln Arg Ala
                85                  90                  95

Glu Ile Ala Val Ala Tyr Glu Gly Leu Tyr Asp Glu Thr Leu Leu Asp
            100                 105                 110

Arg Leu His Ser Glu Leu Ser Gly Asp Phe Arg Ser Ala Leu Met Leu
        115                 120                 125

Trp Thr Met Asp Pro Ala Ala Arg Asp Ala Lys Leu Ala Asn Glu Ala
    130                 135                 140

Leu Lys Lys Lys Lys Gly Glu Leu Arg His Ile Trp Val Leu Val
145                 150                 155                 160

Glu Val Ala Cys Ala Ser Ser Pro Asp His Leu Val Ala Val Arg Lys
                165                 170                 175

Ala Tyr Arg Ala Ala Tyr Ala Ser Ser Leu Glu Glu Asp Val Ala Ser
            180                 185                 190

Cys Ser Leu Phe Gly Asp Pro Leu Arg Arg Phe Leu Val Arg Leu Val
        195                 200                 205

Ser Ser Tyr Arg Tyr Gly Gly Gly Val Asp Gly Glu Leu Ala Ile
    210                 215                 220

Ala Glu Ala Ala Glu Leu His Asp Ala Val Val Gly Arg Gly Gln Ala
225                 230                 235                 240

Leu His Gly Asp Asp Val Val Arg Ile Val Gly Thr Arg Ser Lys Ala
                245                 250                 255
```

```
Gln Leu Ala Val Thr Leu Glu Arg Tyr Arg Gln Glu His Gly Lys Gly
                260                 265                 270
Ile Asp Glu Val Leu Asp Gly Arg Gly Asp Gln Leu Ala Ala Val
            275                 280                 285
Leu Lys Ala Ala Leu Trp Cys Leu Thr Ser Pro Glu Lys His Phe Ala
        290                 295                 300
Glu Val Ile Arg Thr Ser Ile Leu Gly Leu Gly Thr Asp Glu Glu Met
305                 310                 315                 320
Leu Thr Arg Gly Ile Val Ser Arg Ala Glu Val Asp Met Glu Lys Val
                325                 330                 335
Lys Glu Glu Tyr Lys Val Arg Tyr Asn Thr Thr Val Thr Ala Asp Val
                340                 345                 350
Arg Gly Asp Thr Ser Gly Tyr Tyr Met Asn Thr Leu Leu Thr Leu Val
            355                 360                 365
Gly Pro Glu Lys
    370

<210> SEQ ID NO 152
<211> LENGTH: 1341
<212> TYPE: DNA
<213> ORGANISM: Oryza sativa

<400> SEQUENCE: 152
ggtcttttcc ggccgctccc ggcgcccgcc ggccatgtca caacaagct cgtcaaaaac      60 cgccacgtgc cctctctgcc acgccgacgt gctgctgcca cggcggcggt cagccggctc     120
ctcgacgcac agaagccacg acctcgacga cggcccccgct ccgccgtcgc cggagtccag    180
ctgccgcagc aacgccgcgg tgtgcgggtg cgcccgctgc cggcgccctg atctgatcag     240
tcccggaacc ggcatgcgga tgaggaacag attcggcgat ggccccaaca ggatatcagc     300
ccagagtgga gcatggctgt gccgagagcg cacggcggag acttgccgga gcacaagtag     360
ccggtccggc cgctaccggc gcctgcagcc tgcagcggtc gccggaacac gacgcgccga     420
actcataaag cggctgcaag agctctgcca cccagcaaat aaccttccaa attgttctgc     480
ttcttggcaa ccacagcgac agcggcagaa acaattgat cgaattccag atagcctaga     540
ttgtggggtg acaatggaaa ggggcaagaa caagcgtgat ggaagtgaca atgggctcat     600
cttctctaac ctaatgcacg tgttgctgc cggcatctat gggtatcctc ctcaccaggg     660
atacactcag gctcagagct acctactgct gccggaagca tatccacctc ctccgtggac     720
ataccctctt tctagtgctt accctcctca acctgttggt tacccttcag gtggctaccc     780
tcctgcagtc tactctgact cgtatctgca ccaaggtagc agagttgcgc gggagcaatg     840
ccctctatca tattccaata atgctgtcac ttgcagggag gatgggcaaa tgaactgtga     900
aaatggaaca gtaaatatgg agaaagtgc aatgtcctca aataagatgg ctactagtct      960
actaaagagt tgcggcaatg tgatgccatg cagaaatatg gagagaagtg gcccagccat    1020
gtataaggtg gacatgcgcg gcagtacgaa gcaattctct atgggcagca agatgatgat    1080
gtgtctgatt gtgtttggat gtctgatagc tgccttggat atgtttagaa atgttgcaca    1140
aaaacagatg ttttctgtcg ttagtttact ttctttttgta gtcgcgacct atgtctgcta    1200
ggagtctcta catgtaccgt aaaattgctc tttgtgtaat gtgtacttct tcatcctgta    1260
aaaatagaat cccaatcaaa ctatatatgg tttgtctgtc gggctttcaa tacaatctga    1320
gtgtcctctc tttacccttttg t                                             1341
```

```
<210> SEQ ID NO 153
<211> LENGTH: 388
<212> TYPE: PRT
<213> ORGANISM: Oryza sativa

<400> SEQUENCE: 153

Met Ser Thr Thr Ser Ser Lys Thr Ala Thr Cys Pro Leu Cys His
1               5                   10                  15

Ala Asp Val Leu Leu Pro Arg Arg Ser Ala Gly Ser Ser Thr His
            20                  25                  30

Arg Ser His Asp Leu Asp Asp Gly Pro Ala Pro Pro Ser Pro Glu Ser
        35                  40                  45

Ser Cys Arg Ser Asn Ala Ala Val Cys Gly Cys Ala Arg Cys Arg Arg
    50                  55                  60

Pro Asp Leu Ile Ser Pro Gly Thr Gly Met Arg Met Arg Asn Arg Phe
65                  70                  75                  80

Gly Asp Gly Pro Asn Arg Ile Ser Ala Gln Ser Gly Ala Trp Leu Cys
                85                  90                  95

Arg Glu Arg Thr Ala Glu Thr Cys Arg Ser Thr Ser Ser Arg Ser Gly
            100                 105                 110

Arg Tyr Arg Arg Leu Gln Pro Ala Ala Val Ala Gly Thr Arg Arg Ala
        115                 120                 125

Glu Leu Ile Lys Arg Leu Gln Glu Leu Cys His Pro Ala Asn Asn Leu
    130                 135                 140

Pro Asn Cys Ser Ala Ser Trp Gln Pro Gln Arg Gln Arg Gln Lys Thr
145                 150                 155                 160

Ile Asp Arg Ile Pro Asp Ser Leu Asp Cys Gly Val Thr Met Glu Arg
                165                 170                 175

Gly Lys Asn Lys Arg Asp Gly Ser Asp Asn Gly Leu Ile Phe Ser Asn
            180                 185                 190

Leu Met His Gly Val Ala Ala Gly Ile Tyr Gly Tyr Pro Pro His Gln
        195                 200                 205

Gly Tyr Thr Gln Ala Gln Ser Tyr Leu Leu Pro Glu Ala Tyr Pro
    210                 215                 220

Pro Pro Pro Trp Thr Tyr Pro Leu Ser Ser Ala Tyr Pro Gln Pro
225                 230                 235                 240

Val Gly Tyr Pro Ser Gly Gly Tyr Pro Ala Val Tyr Ser Asp Ser
                245                 250                 255

Tyr Leu His Gln Gly Ser Arg Val Ala Arg Glu Gln Cys Pro Leu Ser
            260                 265                 270

Tyr Ser Asn Asn Ala Val Thr Cys Arg Glu Asp Gly Gln Met Asn Cys
        275                 280                 285

Glu Asn Gly Thr Val Asn Met Glu Lys Ser Ala Met Ser Ser Asn Lys
    290                 295                 300

Met Ala Thr Ser Leu Leu Lys Ser Cys Gly Asn Val Met Pro Cys Arg
305                 310                 315                 320

Asn Met Glu Arg Ser Gly Pro Ala Met Tyr Lys Val Asp Met Arg Gly
                325                 330                 335

Ser Thr Lys Gln Phe Ser Met Gly Ser Lys Met Met Cys Leu Ile
            340                 345                 350

Val Phe Gly Cys Leu Ile Ala Ala Leu Asp Met Phe Arg Asn Val Ala
        355                 360                 365

Gln Lys Gln Met Phe Ser Val Val Ser Leu Leu Ser Phe Val Val Ala
    370                 375                 380
```

Thr Tyr Val Cys
385

<210> SEQ ID NO 154
<211> LENGTH: 1276
<212> TYPE: DNA
<213> ORGANISM: Oryza sativa

<400> SEQUENCE: 154

```
ataggtcaac ttgaatcttg ttcaaaaatt cttttcaagt cttaggtagg tcactgttgg      60
tgccaccttc ttgagaagtt tatgatctgc atgttcacct aagatatcca gtcaagtgct     120
aaaaaggtca caaaaatggg aggcagaaag gacaatcatg actcctcaaa tgccgacaaa     180
gggttccatg gagcgtatcc aagcggttac cctggtgcat atcccctaat gcaaggatac     240
cctaattcac ctggacaata tccgactccc ggtggatacc ctagtgcacc accgggacaa     300
tacccaccag ccggtgggta ccctggtgca caatatccac caagcggtta ccctccatca     360
caaggtgggt accctccagg agcgtatcca ccatcaggat atccacaaca accaggctac     420
ccgccagctg gttacccagg tcatggccat ggtccaccca tgcaaggagg tgggcatggt     480
gcaggcgcat ctggctatgg agcgctgctc gccgaggcg ccgcggtggc ggctgctgcg      540
gtgggagctc acatggtacg acccggcggc ggtggcggcc acgggatgtt cggccaccat     600
ggtggcaaat tcaagaaagg aaagttcaag catggcaagt acggcaagca caagaagttt     660
gggcgcaagt ggaagtgata agcaaactaa attgcactgc agtttgcctc cggtttcttg     720
tttggttgaa gtgctatagc atgatgggat taagtgtcca tttaccatat atatatatat     780
atattcatcg aaatataacc atacgagatc ttattttaaa gataattgta ataaatataa     840
tggtgtaatg gatcacaaat tagaaaaaag gtttaggaga aaaacatttt tgagcttgct     900
aacagaaaat taaacccacc ataagcaatc agaataggcc acatgtgaat ggctatatcc     960
ggttaaatcc gccgaatcca atcatcgaac tcttatttcc cacaaaccaa actcatccag    1020
cctcatgcac ctaactaatc acatccatcc ttagacgatg catgcgtgtg acattcttg     1080
ccaaaaccaa caattagccg tgagagccca aacaactgag tactccagcc tacgattgtc    1140
aggatatttt ctcatctaac ttattctagt attaggagtt atgaagatat gaaaagccat    1200
tttagttcag aaaattgtac gataaatcat gtaacctgtt tctgaaatgg aaataaaata    1260
tgagaaaaag atacta                                                    1276
```

<210> SEQ ID NO 155
<211> LENGTH: 180
<212> TYPE: PRT
<213> ORGANISM: Oryza sativa

<400> SEQUENCE: 155

Met Gly Gly Arg Lys Asp Asn His Asp Ser Ser Asn Ala Asp Lys Gly
1               5                   10                  15

Phe His Gly Ala Tyr Pro Ser Gly Tyr Pro Gly Ala Tyr Pro Leu Met
                20                  25                  30

Gln Gly Tyr Pro Asn Ser Pro Gly Gln Tyr Pro Thr Pro Gly Gly Tyr
            35                  40                  45

Pro Ser Ala Pro Pro Gly Gln Tyr Pro Pro Ala Gly Gly Tyr Pro Gly
        50                  55                  60

Ala Gln Tyr Pro Pro Ser Gly Tyr Pro Pro Ser Gln Gly Gly Tyr Pro
65                  70                  75                  80

```
Pro Gly Ala Tyr Pro Pro Ser Gly Tyr Pro Gln Gln Pro Gly Tyr Pro
                85                  90                  95

Pro Ala Gly Tyr Pro Gly His Gly His Gly Pro Pro Met Gln Gly Gly
            100                 105                 110

Gly His Gly Ala Gly Ala Ser Gly Tyr Gly Ala Leu Leu Ala Gly Gly
        115                 120                 125

Ala Ala Val Ala Ala Ala Val Gly Ala His Met Val Arg Pro Gly
    130                 135                 140

Gly Gly Gly Gly His Gly Met Phe Gly His His Gly Gly Lys Phe Lys
145                 150                 155                 160

Lys Gly Lys Phe Lys His Gly Lys Tyr Gly Lys His Lys Lys Phe Gly
                165                 170                 175

Arg Lys Trp Lys
            180

<210> SEQ ID NO 156
<211> LENGTH: 32
<212> TYPE: PRT
<213> ORGANISM: Chlamydomonas sp.

<400> SEQUENCE: 156

Met Ala Met Ala Met Arg Ser Thr Phe Ala Ala Arg Val Gly Ala Lys
1               5                   10                  15

Pro Ala Val Arg Gly Ala Arg Pro Ala Ser Arg Met Ser Cys Met Ala
            20                  25                  30

<210> SEQ ID NO 157
<211> LENGTH: 32
<212> TYPE: PRT
<213> ORGANISM: Chlamydomonas sp.

<400> SEQUENCE: 157

Met Gln Val Thr Met Lys Ser Ser Ala Val Ser Gly Gln Arg Val Gly
1               5                   10                  15

Gly Ala Arg Val Ala Thr Arg Ser Val Arg Arg Ala Gln Leu Gln Val
            20                  25                  30

<210> SEQ ID NO 158
<211> LENGTH: 52
<212> TYPE: PRT
<213> ORGANISM: Arabidopsis thaliana

<400> SEQUENCE: 158

Met Ala Ser Leu Met Leu Ser Leu Gly Ser Thr Ser Leu Leu Pro Arg
1               5                   10                  15

Glu Ile Asn Lys Asp Lys Leu Lys Leu Gly Thr Ser Ala Ser Asn Pro
            20                  25                  30

Phe Leu Lys Ala Lys Ser Phe Ser Arg Val Thr Met Thr Val Ala Val
        35                  40                  45

Lys Pro Ser Arg
    50

<210> SEQ ID NO 159
<211> LENGTH: 54
<212> TYPE: PRT
<213> ORGANISM: Arabidopsis thaliana

<400> SEQUENCE: 159

Met Ala Thr Gln Phe Ser Ala Ser Val Ser Leu Gln Thr Ser Cys Leu
1               5                   10                  15
```

```
Ala Thr Thr Arg Ile Ser Phe Gln Lys Pro Ala Leu Ile Ser Asn His
            20                  25                  30

Gly Lys Thr Asn Leu Ser Phe Asn Leu Arg Arg Ser Ile Pro Ser Arg
        35                  40                  45

Arg Leu Ser Val Ser Cys
    50
```

<210> SEQ ID NO 160
<211> LENGTH: 70
<212> TYPE: PRT
<213> ORGANISM: Arabidopsis thaliana

<400> SEQUENCE: 160

```
Met Ala Ser Ile Ala Ala Ser Ala Ser Ile Ser Leu Gln Ala Arg Pro
1               5                   10                  15

Arg Gln Leu Ala Ile Ala Ala Ser Gln Val Lys Ser Phe Ser Asn Gly
            20                  25                  30

Arg Arg Ser Ser Leu Ser Phe Asn Leu Arg Gln Leu Pro Thr Arg Leu
        35                  40                  45

Thr Val Ser Cys Ala Ala Lys Pro Glu Thr Val Asp Lys Val Cys Ala
    50                  55                  60

Val Val Arg Lys Gln Leu
65                  70
```

<210> SEQ ID NO 161
<211> LENGTH: 74
<212> TYPE: PRT
<213> ORGANISM: Arabidopsis thaliana

<400> SEQUENCE: 161

```
Met Ala Ser Ile Ala Thr Ser Ala Ser Thr Ser Leu Gln Ala Arg Pro
1               5                   10                  15

Arg Gln Leu Val Ile Gly Ala Lys Gln Val Lys Ser Phe Ser Tyr Gly
            20                  25                  30

Ser Arg Ser Asn Leu Ser Phe Asn Leu Arg Gln Leu Pro Thr Arg Leu
        35                  40                  45

Thr Val Tyr Cys Ala Ala Lys Pro Glu Thr Val Asp Lys Val Cys Ala
    50                  55                  60

Val Val Arg Lys Gln Leu Ser Leu Lys Glu
65                  70
```

<210> SEQ ID NO 162
<211> LENGTH: 232
<212> TYPE: PRT
<213> ORGANISM: Unknown
<220> FEATURE:
<223> OTHER INFORMATION: PRX protein

<400> SEQUENCE: 162

```
Met Ala Ala Ala Ala Ser Thr Leu Ala Ser Leu Ser Thr Ala Ala
1               5                   10                  15

Ala Ala Ala Gly Lys Arg Leu Leu Ser Ser Pro Ser Arg Ser Leu
            20                  25                  30

Ser Leu Ser Leu Ala Ser Arg Gly Arg Ile Ala Val Met Pro His Leu
        35                  40                  45

Arg Ala Gly Ile Leu Ser Ala Ala Pro Arg Arg Ala Val Ser Ala Ser
    50                  55                  60

Ala Pro Ala Ala Ala Thr Ile Ala Val Gly Asp Lys Leu Pro Asp Ala
```

```
                65                  70                  75                  80
Thr Leu Ser Tyr Phe Asp Ser Pro Asp Gly Glu Leu Lys Thr Val Thr
                    85                  90                  95

Val Arg Asp Leu Thr Ala Gly Lys Lys Val Leu Phe Ala Val Pro
                100                 105                 110

Gly Ala Phe Thr Pro Thr Cys Thr Gln Lys His Val Pro Gly Phe Val
                115                 120                 125

Ala Lys Ala Gly Glu Leu Arg Ala Lys Gly Val Asp Ala Val Ala Cys
                130                 135                 140

Val Ser Val Asn Asp Ala Phe Val Met Arg Ala Trp Lys Glu Ser Leu
145                 150                 155                 160

Gly Val Gly Asp Glu Val Leu Leu Leu Ser Asp Gly Asn Gly Glu Leu
                165                 170                 175

Ala Arg Ala Met Gly Val Glu Leu Asp Leu Ser Asp Lys Pro Ala Gly
                180                 185                 190

Leu Gly Val Arg Ser Arg Arg Tyr Ala Leu Leu Ala Glu Asp Gly Val
                195                 200                 205

Val Lys Val Leu Asn Leu Glu Glu Gly Gly Ala Phe Thr Thr Ser Ser
210                 215                 220

Ala Glu Glu Met Leu Lys Ala Leu
225                 230

<210> SEQ ID NO 163
<211> LENGTH: 225
<212> TYPE: PRT
<213> ORGANISM: Unknown
<220> FEATURE:
<223> OTHER INFORMATION: PRX protein

<400> SEQUENCE: 163

Met Ala Ala Pro Thr Ala Ala Ala Leu Ser Thr Leu Ser Thr Ala Ser
1               5                   10                  15

Val Thr Ser Gly Lys Arg Phe Ile Thr Ser Ser Phe Ser Leu Ser Phe
                20                  25                  30

Ser Ser Arg Pro Leu Ala Thr Gly Val Arg Ala Ala Gly Ala Arg Ala
                35                  40                  45

Ala Arg Arg Ser Ala Ala Ser Ala Ser Thr Val Val Ala Thr Ile Ala
                50                  55                  60

Val Gly Asp Lys Leu Pro Asp Ala Thr Leu Ser Tyr Phe Asp Pro Ala
65                  70                  75                  80

Asp Gly Glu Leu Lys Thr Val Thr Val Ala Glu Leu Thr Ala Gly Arg
                85                  90                  95

Lys Ala Val Leu Phe Ala Val Pro Gly Ala Phe Thr Pro Thr Cys Ser
                100                 105                 110

Gln Lys His Leu Pro Gly Phe Ile Glu Lys Ala Gly Glu Leu His Ala
                115                 120                 125

Lys Gly Val Asp Ala Ile Ala Cys Val Ser Val Asn Asp Ala Phe Val
                130                 135                 140

Met Arg Ala Trp Lys Glu Ser Leu Gly Leu Gly Asp Ala Asp Val Leu
145                 150                 155                 160

Leu Leu Ser Asp Gly Asn Leu Glu Leu Thr Arg Ala Leu Gly Val Glu
                165                 170                 175

Met Asp Leu Ser Asp Lys Pro Met Gly Leu Gly Val Arg Ser Arg Arg
                180                 185                 190

Tyr Ala Leu Leu Ala Asp Asp Gly Val Val Lys Val Leu Asn Leu Glu
```

```
                195                 200                 205
Glu Gly Gly Ala Phe Thr Thr Ser Ser Ala Glu Glu Met Leu Lys Ala
    210                 215                 220

Leu
225

<210> SEQ ID NO 164
<211> LENGTH: 162
<212> TYPE: PRT
<213> ORGANISM: Unknown
<220> FEATURE:
<223> OTHER INFORMATION: PRX protein

<400> SEQUENCE: 164

Met Ala Pro Val Ala Val Gly Asp Thr Leu Pro Asp Gly Gln Leu Gly
1               5                   10                  15

Trp Phe Asp Gly Glu Asp Lys Leu Gln Gln Val Ser Val His Gly Leu
            20                  25                  30

Ala Ala Gly Lys Lys Val Val Leu Phe Gly Val Pro Gly Ala Phe Thr
        35                  40                  45

Pro Thr Cys Ser Asn Gln His Val Pro Gly Phe Ile Asn Gln Ala Glu
    50                  55                  60

Gln Leu Lys Ala Lys Gly Val Asp Asp Ile Leu Leu Val Ser Val Asn
65                  70                  75                  80

Asp Pro Phe Val Met Lys Ala Trp Ala Lys Ser Tyr Pro Glu Asn Lys
                85                  90                  95

His Val Lys Phe Leu Ala Asp Gly Leu Gly Thr Tyr Thr Lys Ala Leu
            100                 105                 110

Gly Leu Glu Leu Asp Leu Ser Glu Lys Gly Leu Gly Ile Arg Ser Arg
        115                 120                 125

Arg Phe Ala Leu Leu Ala Asp Asn Leu Lys Val Thr Val Ala Asn Ile
    130                 135                 140

Glu Glu Gly Gly Gln Phe Thr Ile Ser Gly Ala Glu Glu Ile Leu Lys
145                 150                 155                 160

Ala Leu

<210> SEQ ID NO 165
<211> LENGTH: 162
<212> TYPE: PRT
<213> ORGANISM: Unknown
<220> FEATURE:
<223> OTHER INFORMATION: PRX protein

<400> SEQUENCE: 165

Met Ala Pro Val Ala Val Gly Asp Thr Leu Pro Asp Gly Gln Leu Gly
1               5                   10                  15

Trp Phe Asp Gly Glu Asp Lys Leu Gln Gln Val Ser Val His Gly Leu
            20                  25                  30

Ala Ala Gly Lys Lys Val Val Leu Phe Gly Val Pro Gly Ala Phe Thr
        35                  40                  45

Pro Thr Cys Ser Asn Gln His Val Pro Gly Phe Ile Asn Gln Ala Glu
    50                  55                  60

Gln Leu Lys Ala Lys Gly Val Asp Asp Ile Leu Leu Val Ser Val Asn
65                  70                  75                  80

Asp Pro Phe Val Met Lys Ala Trp Ala Lys Ser Tyr Pro Glu Asn Lys
                85                  90                  95

His Val Lys Phe Leu Ala Asp Gly Leu Gly Thr Tyr Thr Lys Ala Leu
```

```
                100                 105                 110
Gly Leu Glu Leu Asp Leu Ser Glu Lys Gly Leu Gly Ile Arg Ser Arg
            115                 120                 125

Arg Phe Ala Leu Leu Ala Asp Asn Leu Lys Val Thr Val Ala Asn Ile
        130                 135                 140

Glu Gly Gly Gln Phe Thr Ile Ser Gly Ala Glu Ile Leu Lys
145                 150                 155                 160

Ala Leu

<210> SEQ ID NO 166
<211> LENGTH: 198
<212> TYPE: PRT
<213> ORGANISM: Unknown
<220> FEATURE:
<223> OTHER INFORMATION: PRX protein

<400> SEQUENCE: 166

Met Ala Ser Ala Leu Leu Arg Lys Ala Thr Val Gly Gly Ser Ala Ala
1               5                   10                  15

Ala Ala Ala Ala Arg Trp Ala Ser Arg Gly Leu Ala Ser Val Gly Ser
            20                  25                  30

Gly Ser Asp Ile Val Ser Ala Ala Pro Gly Val Ser Leu Gln Lys Ala
        35                  40                  45

Arg Ser Trp Asp Glu Gly Val Ala Thr Asn Phe Ser Thr Thr Pro Leu
    50                  55                  60

Lys Asp Ile Phe His Gly Lys Lys Val Val Ile Phe Gly Leu Pro Gly
65                  70                  75                  80

Ala Tyr Thr Gly Val Cys Ser Gln Ala His Val Pro Ser Tyr Lys Asn
                85                  90                  95

Asn Ile Asp Lys Leu Lys Ala Lys Gly Val Asp Ser Val Ile Cys Val
            100                 105                 110

Ser Val Asn Asp Pro Tyr Ala Leu Asn Gly Trp Ala Glu Lys Leu Gln
        115                 120                 125

Ala Lys Asp Ala Ile Glu Phe Tyr Gly Asp Phe Asp Gly Ser Phe His
    130                 135                 140

Lys Ser Leu Asp Leu Glu Val Asp Leu Ser Ala Ala Leu Leu Gly Arg
145                 150                 155                 160

Arg Ser His Arg Trp Ser Ala Phe Val Asp Asp Gly Lys Ile Lys Ala
                165                 170                 175

Phe Asn Val Glu Val Ala Pro Asp Phe Lys Val Ser Gly Ala Glu
            180                 185                 190

Val Ile Leu Asp Gln Ile
        195

<210> SEQ ID NO 167
<211> LENGTH: 198
<212> TYPE: PRT
<213> ORGANISM: Unknown
<220> FEATURE:
<223> OTHER INFORMATION: PRX protein

<400> SEQUENCE: 167

Met Ala Ser Ala Leu Leu Arg Lys Ala Thr Val Gly Gly Ser Ala Ala
1               5                   10                  15

Ala Ala Ala Ala Arg Trp Ala Ser Arg Gly Leu Ala Ser Val Gly Ser
            20                  25                  30

Gly Ser Asp Ile Val Ser Ala Ala Pro Gly Val Ser Leu Gln Lys Ala
```

```
            35                  40                  45
Arg Ser Trp Asp Glu Gly Val Ala Thr Asn Phe Ser Thr Thr Pro Leu
 50                  55                  60

Lys Asp Ile Phe His Gly Lys Lys Val Val Ile Phe Gly Leu Pro Gly
 65                  70                  75                  80

Ala Tyr Thr Gly Val Cys Ser Gln Ala His Val Pro Ser Tyr Lys Asn
                 85                  90                  95

Asn Ile Asp Lys Leu Lys Ala Lys Gly Val Asp Ser Val Ile Cys Val
                100                 105                 110

Ser Val Asn Asp Pro Tyr Ala Leu Asn Gly Trp Ala Glu Lys Leu Gln
            115                 120                 125

Ala Lys Asp Ala Ile Glu Phe Tyr Gly Asp Phe Asp Gly Ser Phe His
        130                 135                 140

Lys Ser Leu Asp Leu Glu Val Asp Leu Ser Ala Ala Leu Leu Gly Arg
145                 150                 155                 160

Arg Ser His Arg Trp Ser Ala Phe Val Asp Asp Gly Lys Ile Lys Ala
                165                 170                 175

Phe Asn Val Glu Val Ala Pro Ser Asp Phe Lys Val Ser Gly Ala Glu
            180                 185                 190

Val Ile Leu Asp Gln Ile
        195

<210> SEQ ID NO 168
<211> LENGTH: 220
<212> TYPE: PRT
<213> ORGANISM: Unknown
<220> FEATURE:
<223> OTHER INFORMATION: PRX protein

<400> SEQUENCE: 168

Met Pro Gly Leu Thr Ile Gly Asp Thr Val Pro Asn Leu Glu Leu Asp
  1               5                  10                  15

Ser Thr His Gly Lys Ile Arg Ile His Asp Phe Val Gly Asp Thr Tyr
                 20                  25                  30

Val Ile Leu Phe Ser His Pro Gly Asp Phe Thr Pro Val Cys Thr Thr
            35                  40                  45

Glu Leu Ala Ala Met Ala Gly Tyr Ala Lys Glu Phe Asp Lys Arg Gly
 50                  55                  60

Val Lys Leu Leu Gly Ile Ser Cys Asp Asp Val Gln Ser His Lys Asp
 65                  70                  75                  80

Trp Ile Lys Asp Ile Glu Ala Tyr Lys Pro Gly Asn Arg Val Thr Tyr
                 85                  90                  95

Pro Ile Met Ala Asp Pro Ser Arg Glu Ala Ile Lys Gln Leu Asn Met
                100                 105                 110

Val Asp Pro Asp Glu Lys Asp Ser Asn Gly Gly His Leu Pro Ser Arg
            115                 120                 125

Ala Leu His Ile Val Gly Pro Asp Lys Lys Val Lys Leu Ser Phe Leu
        130                 135                 140

Tyr Pro Ala Cys Val Gly Arg Asn Met Asp Glu Val Val Arg Ala Val
145                 150                 155                 160

Asp Ala Leu Gln Thr Ala Ala Lys His Ala Val Ala Thr Pro Val Asn
                165                 170                 175

Trp Lys Pro Gly Glu Arg Val Val Ile Pro Pro Gly Val Ser Asp Asp
            180                 185                 190

Glu Ala Lys Glu Lys Phe Pro Gln Gly Phe Asp Thr Ala Asp Leu Pro
```

```
                195                 200                 205
Ser Gly Lys Gly Tyr Leu Arg Phe Thr Lys Val Gly
    210                 215                 220
```

<210> SEQ ID NO 169
<211> LENGTH: 220
<212> TYPE: PRT
<213> ORGANISM: Unknown
<220> FEATURE:
<223> OTHER INFORMATION: PRX protein

<400> SEQUENCE: 169

```
Met Pro Gly Leu Thr Leu Gly Asp Val Pro Asp Leu Glu Leu Asp
1               5                   10                  15

Thr Thr His Gly Lys Ile Arg Leu His Asp Phe Val Gly Asp Ala Tyr
                20                  25                  30

Val Ile Ile Phe Ser His Pro Ala Asp Phe Thr Pro Val Cys Thr Thr
            35                  40                  45

Glu Leu Ser Glu Met Ala Gly Tyr Ala Gly Phe Asp Lys Arg Gly
    50                  55                  60

Val Lys Leu Leu Gly Phe Ser Cys Asp Val Glu Ser His Lys Asp
65                  70                  75                  80

Trp Ile Lys Asp Ile Glu Ala Tyr Lys Pro Gly Arg Arg Val Gly Phe
                85                  90                  95

Pro Ile Val Ala Asp Pro Asp Arg Glu Ala Ile Arg Gln Leu Asn Met
                100                 105                 110

Ile Asp Ala Asp Glu Lys Asp Thr Ala Gly Gly Glu Leu Pro Asn Arg
            115                 120                 125

Ala Leu His Ile Val Gly Pro Asp Lys Lys Val Lys Leu Ser Phe Leu
    130                 135                 140

Phe Pro Ala Cys Thr Gly Arg Asn Met Ala Glu Val Leu Arg Ala Thr
145                 150                 155                 160

Asp Ala Leu Leu Thr Ala Ala Arg His Arg Val Ala Thr Pro Val Asn
                165                 170                 175

Trp Lys Pro Gly Glu Arg Val Val Ile Pro Pro Gly Val Ser Asp Glu
            180                 185                 190

Glu Ala Lys Ala Arg Phe Pro Ala Gly Phe Glu Thr Ala Gln Leu Pro
        195                 200                 205

Ser Asn Lys Cys Tyr Leu Arg Phe Thr Gln Val Asp
    210                 215                 220
```

<210> SEQ ID NO 170
<211> LENGTH: 198
<212> TYPE: PRT
<213> ORGANISM: Unknown
<220> FEATURE:
<223> OTHER INFORMATION: PRX protein

<400> SEQUENCE: 170

```
Met Ala Ser Gly Asn Ala Gln Ile Gly Lys Ser Ala Pro Asp Phe Thr
1               5                   10                  15

Ala Thr Ala Val Val Asp Gly Ala Phe Lys Glu Ile Lys Leu Ser Asp
                20                  25                  30

Tyr Arg Gly Lys Tyr Val Val Leu Phe Phe Tyr Pro Leu Asp Phe Thr
            35                  40                  45

Phe Val Cys Pro Thr Glu Ile Ile Ala Phe Ser Asp His Ala Glu Asp
    50                  55                  60
```

```
Phe Arg Lys Leu Gly Cys Glu Val Leu Gly Val Ser Val Asp Ser Gln
 65                  70                  75                  80

Phe Thr His Leu Ala Trp Ile Asn Thr Pro Arg Lys Glu Gly Gly Leu
                 85                  90                  95

Gly Pro Leu Asn Ile Pro Leu Leu Ala Asp Val Thr Lys Ser Leu Ser
            100                 105                 110

Gln Asn Tyr Gly Val Leu Lys Asn Asp Glu Gly Ile Ala Tyr Arg Gly
        115                 120                 125

Leu Phe Ile Ile Asp Ala Lys Gly Val Leu Arg Gln Ile Thr Val Asn
130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
        195

<210> SEQ ID NO 171
<211> LENGTH: 271
<212> TYPE: PRT
<213> ORGANISM: Unknown
<220> FEATURE:
<223> OTHER INFORMATION: PRX protein

<400> SEQUENCE: 171

Met Ala Ser Ile Ala Ser Ser Ser Thr Thr Leu Leu Ser Ser Ser Ser
1               5                   10                  15

Arg Val Leu Leu Pro Ser Lys Ser Ser Leu Leu Ser Pro Thr Val Ser
                20                  25                  30

Phe Pro Arg Ile Ile Pro Ser Ser Ala Ser Ser Ser Ser Leu Cys
             35                  40                  45

Ser Gly Phe Ser Ser Leu Gly Ser Leu Thr Thr Asn Arg Ser Ala Ser
     50                  55                  60

Arg Arg Asn Phe Ala Val Lys Ala Gln Ala Asp Asp Leu Pro Leu Val
 65                  70                  75                  80

Gly Asn Lys Ala Pro Asp Phe Glu Ala Glu Ala Val Phe Asp Gln Glu
                 85                  90                  95

Phe Ile Lys Val Lys Leu Ser Glu Tyr Ile Gly Lys Lys Tyr Val Ile
            100                 105                 110

Leu Phe Phe Tyr Pro Leu Asp Phe Thr Phe Val Cys Pro Thr Glu Ile
        115                 120                 125

Thr Ala Phe Ser Asp Arg Tyr Glu Glu Phe Glu Lys Leu Asn Thr Glu
    130                 135                 140

Val Leu Gly Val Ser Val Asp Ser Val Phe Ser His Leu Ala Trp Val
145                 150                 155                 160

Gln Thr Asp Arg Lys Ser Gly Gly Leu Gly Asp Leu Asn Tyr Pro Leu
                165                 170                 175

Val Ser Asp Ile Thr Lys Ser Ile Ser Lys Ser Phe Gly Val Leu Ile
            180                 185                 190

Pro Asp Gln Gly Ile Ala Leu Arg Gly Leu Phe Ile Ile Asp Lys Glu
        195                 200                 205

Gly Val Ile Gln His Ser Pro Ile Asn Asn Leu Gly Ile Gly Arg Ser
    210                 215                 220
```

```
Val Asp Glu Thr Met Arg Thr Leu Gln Ala Leu Gln Tyr Val Gln Glu
225                 230                 235                 240

Asn Pro Asp Glu Val Cys Pro Ala Gly Trp Lys Pro Gly Glu Lys Ser
            245                 250                 255

Met Lys Pro Asp Pro Lys Leu Ser Lys Glu Tyr Phe Ser Ala Ile
        260                 265                 270
```

<210> SEQ ID NO 172
<211> LENGTH: 154
<212> TYPE: PRT
<213> ORGANISM: Unknown
<220> FEATURE:
<223> OTHER INFORMATION: PRX protein

<400> SEQUENCE: 172

```
Met Ala Cys Ala Phe Ser Val Ser Ser Ala Ala Pro Leu Ala Ser
1               5                   10                  15

Pro Lys Gly Asp Leu Pro Leu Val Gly Asn Lys Ala Pro Asp Phe Glu
                20                  25                  30

Ala Glu Ala Met Phe Asp Gln Gly Phe Ile Lys Ser Lys Cys Met Phe
            35                  40                  45

Val Ser Ser Ala Glu Ile Thr Ala Phe Ser Arg Tyr Glu Glu Phe
50                  55                  60

Glu Lys Ile Asn Thr Glu Val Leu Gly Val Ser Ile Asp Ser Val Gly
65                  70                  75                  80

Ile Ala Leu Arg Gly Leu Phe Ile Ile Asp Lys Glu Gly Val Ile Gln
                85                  90                  95

His Ser Thr Ile Asn Asn Leu Ala Ile Gly Arg Ser Val Asp Glu Thr
            100                 105                 110

Leu Arg Thr Leu Gln Ala Leu Gln Tyr Val Gln Glu Asn Pro Asp Glu
        115                 120                 125

Val Cys Pro Ala Gly Trp Lys Pro Gly Glu Lys Ser Met Lys Pro Asp
    130                 135                 140

Pro Lys Asp Ser Lys Glu Glu Gln Glu Cys
145                 150
```

<210> SEQ ID NO 173
<211> LENGTH: 266
<212> TYPE: PRT
<213> ORGANISM: Unknown
<220> FEATURE:
<223> OTHER INFORMATION: PRX protein

<400> SEQUENCE: 173

```
Met Ala Ser Val Ala Ser Ser Thr Thr Leu Ile Ser Ser Pro Ser Ser
1               5                   10                  15

Arg Val Phe Pro Ala Lys Ser Ser Leu Ser Ser Pro Ser Val Ser Phe
                20                  25                  30

Leu Arg Thr Leu Ser Ser Pro Ser Ala Ser Ala Ser Leu Arg Ser Gly
            35                  40                  45

Phe Ala Arg Arg Ser Ser Leu Ser Ser Thr Ser Arg Arg Ser Phe Ala
    50                  55                  60

Val Lys Ala Gln Ala Asp Asp Leu Pro Leu Val Gly Asn Lys Ala Pro
65                  70                  75                  80

Asp Phe Glu Ala Glu Ala Val Phe Asp Gln Glu Phe Ile Lys Val Lys
                85                  90                  95

Leu Ser Asp Tyr Ile Gly Lys Lys Tyr Val Ile Leu Phe Phe Tyr Pro
            100                 105                 110
```

Leu Asp Phe Thr Phe Val Cys Pro Thr Glu Ile Thr Ala Phe Ser Asp
        115                 120                 125

Arg His Ser Glu Phe Glu Lys Leu Asn Thr Glu Val Leu Gly Val Ser
    130                 135                 140

Val Asp Ser Val Phe Ser His Leu Ala Trp Val Gln Thr Asp Arg Lys
145                 150                 155                 160

Ser Gly Gly Leu Gly Asp Leu Asn Tyr Pro Leu Ile Ser Asp Val Thr
                165                 170                 175

Lys Ser Ile Ser Lys Ser Phe Gly Val Leu Ile His Asp Gln Gly Ile
                180                 185                 190

Ala Leu Arg Gly Leu Phe Ile Ile Asp Lys Glu Gly Val Ile Gln His
            195                 200                 205

Ser Thr Ile Asn Asn Leu Gly Ile Gly Arg Ser Val Asp Glu Thr Met
        210                 215                 220

Arg Thr Leu Gln Ala Leu Gln Tyr Ile Gln Glu Asn Pro Asp Glu Val
225                 230                 235                 240

Cys Pro Ala Gly Trp Lys Pro Gly Glu Lys Ser Met Lys Pro Asp Pro
                245                 250                 255

Lys Leu Ser Lys Glu Tyr Phe Ser Ala Ile
            260                 265

<210> SEQ ID NO 174
<211> LENGTH: 265
<212> TYPE: PRT
<213> ORGANISM: Unknown
<220> FEATURE:
<223> OTHER INFORMATION: PRX protein

<400> SEQUENCE: 174

Met Ala Cys Val Ala Ser Ser Thr Thr Leu Ile Ser Ser Pro Ser Ser
1               5                   10                  15

Arg Val Phe Pro Ala Lys Ser Ser Leu Ser Ser Pro Ser Val Ser Phe
            20                  25                  30

Leu Arg Thr Leu Ser Ser Pro Ser Ala Ser Ala Ser Leu Arg Ser Gly
        35                  40                  45

Phe Ala Arg Arg Ser Ser Leu Ser Ser Thr Ser Arg Arg Ser Phe Ala
    50                  55                  60

Val Lys Ala Gln Ala Asp Asp Leu Pro Leu Val Gly Asn Lys Ala Pro
65                  70                  75                  80

Asp Phe Glu Ala Glu Ala Val Phe Asp Gln Glu Phe Ile Lys Val Lys
                85                  90                  95

Leu Ser Asp Tyr Ile Gly Lys Lys Tyr Val Ile Leu Phe Phe Tyr Pro
            100                 105                 110

Leu Asp Phe Thr Phe Val Cys Pro Thr Glu Ile Thr Ala Phe Ser Asp
        115                 120                 125

Arg His Ser Glu Phe Glu Lys Leu Asn Thr Glu Val Leu Gly Val Ser
    130                 135                 140

Val Asp Ser Val Phe Ser His Leu Ala Trp Val Gln Thr Asp Arg Lys
145                 150                 155                 160

Ser Gly Gly Leu Gly Asp Leu Asn Tyr Pro Leu Ile Ser Asp Val Thr
                165                 170                 175

Lys Ser Ile Ser Lys Ser Phe Gly Val Leu Ile His Asp Gln Gly Ile
                180                 185                 190

Ala Leu Arg Gly Leu Phe Ile Ile Asp Lys Glu Gly Val Ile Gln His
            195                 200                 205

```
Ser Thr Ile Asn Asn Leu Gly Ile Gly Arg Ser Val Asp Glu Thr Met
    210                 215                 220

Arg Thr Leu Gln Ala Leu Gln Tyr Thr Gly Asn Pro Asp Glu Val Cys
225                 230                 235                 240

Pro Ala Gly Trp Lys Pro Gly Glu Lys Ser Met Lys Pro Asp Pro Lys
                245                 250                 255

Leu Ser Lys Glu Tyr Phe Ser Ala Ile
            260                 265
```

<210> SEQ ID NO 175
<211> LENGTH: 265
<212> TYPE: PRT
<213> ORGANISM: Unknown
<220> FEATURE:
<223> OTHER INFORMATION: PRX protein

<400> SEQUENCE: 175

```
Met Ala Ser Val Ala Ser Ser Thr Thr Leu Ile Ser Ser Pro Ser Ser
1               5                   10                  15

Arg Val Phe Pro Ala Lys Ser Ser Leu Ser Ser Pro Ser Val Ser Phe
                20                  25                  30

Leu Arg Thr Leu Ser Ser Pro Ser Ala Ser Ala Ser Leu Arg Ser Gly
            35                  40                  45

Phe Ala Arg Arg Ser Ser Leu Ser Ser Thr Ser Arg Arg Ser Phe Ala
    50                  55                  60

Val Lys Ala Gln Ala Asp Asp Leu Pro Leu Val Gly Asn Lys Ala Pro
65                  70                  75                  80

Asp Phe Lys Ala Glu Ala Val Phe Asp Gln Glu Phe Ile Lys Val Lys
                85                  90                  95

Leu Ser Asp Tyr Asn Gly Lys Lys Tyr Val Ile Leu Phe Phe Tyr Pro
            100                 105                 110

Leu Asp Phe Thr Phe Val Cys Pro Thr Glu Ile Thr Ala Phe Ser Asp
            115                 120                 125

Arg His Ser Glu Phe Glu Lys Leu Asn Thr Glu Val Leu Gly Val Ser
    130                 135                 140

Val Asp Ser Val Phe Ser His Leu Ala Trp Val Gln Thr Asp Arg Lys
145                 150                 155                 160

Ser Gly Gly Leu Gly Asp Leu Asn Tyr Pro Leu Ile Ser Asp Val Thr
                165                 170                 175

Lys Ser Ile Ser Lys Ser Phe Gly Val Leu Ile His Asp Gln Gly Ile
            180                 185                 190

Ala Leu Arg Gly Leu Phe Ile Ile Asp Lys Glu Gly Val Ile Gln His
        195                 200                 205

Ser Thr Ile Asn Asn Leu Gly Ile Gly Arg Ser Val Asp Glu Thr Met
    210                 215                 220

Arg Thr Leu Gln Ala Leu Gln Tyr Thr Gly Asn Pro Asp Glu Val Cys
225                 230                 235                 240

Pro Ala Gly Trp Lys Ser Gly Glu Lys Ser Met Lys Pro Asp Pro Lys
                245                 250                 255

Leu Ser Lys Glu Tyr Phe Ser Ala Ile
            260                 265
```

<210> SEQ ID NO 176
<211> LENGTH: 196
<212> TYPE: PRT
<213> ORGANISM: Unknown

```
<220> FEATURE:
<223> OTHER INFORMATION: PRX protein

<400> SEQUENCE: 176

Glu Leu Pro Leu Val Gly Asn Ser Ala Pro Gly Phe Glu Ala Glu Ala
1               5                   10                  15

Val Phe Asp Gln Glu Phe Ile Lys Val Lys Leu Ser Glu Tyr Ile Gly
            20                  25                  30

Lys Lys Tyr Val Ile Leu Phe Phe Tyr Pro Leu Asp Phe Thr Phe Val
        35                  40                  45

Cys Pro Thr Glu Ile Thr Ala Phe Ser Asp Arg Tyr Ser Glu Phe Glu
    50                  55                  60

Lys Val Asn Thr Glu Val Leu Gly Val Ser Val Asp Ser Val Phe Ser
65                  70                  75                  80

His Leu Ala Trp Val Gln Thr Asp Arg Lys Ser Gly Gly Leu Gly Asp
                85                  90                  95

Leu Asn Tyr Pro Leu Val Ser Asp Val Thr Lys Ser Ile Ser Lys Ser
            100                 105                 110

Tyr Gly Val Leu Ile Pro Asp Gln Gly Ile Ala Leu Arg Gly Leu Phe
        115                 120                 125

Ile Ile Asp Lys Glu Gly Val Ile Gln His Ser Thr Ile Asn Asn Leu
    130                 135                 140

Gly Ile Gly Arg Ser Val Asp Glu Thr Met Arg Thr Leu Gln Ala Leu
145                 150                 155                 160

Gln Tyr Val Gln Glu Asn Pro Asp Glu Val Cys Pro Ala Gly Trp Lys
                165                 170                 175

Pro Gly Glu Lys Ser Met Lys Pro Asp Pro Lys Arg Ser Lys Glu Tyr
            180                 185                 190

Phe Ala Ser Ile
        195

<210> SEQ ID NO 177
<211> LENGTH: 258
<212> TYPE: PRT
<213> ORGANISM: Unknown
<220> FEATURE:
<223> OTHER INFORMATION: PRX protein

<400> SEQUENCE: 177

Met Ala Cys Ala Phe Ser Ala Ser Thr Val Ser Thr Ala Ala Ala Leu
1               5                   10                  15

Val Ala Ser Pro Lys Pro Ala Gly Ala Pro Ser Ala Cys Arg Phe Pro
            20                  25                  30

Ala Leu Arg Arg Gly Arg Ala Gly Leu Arg Cys Ala Arg Leu Glu Asp
        35                  40                  45

Ala Arg Ala Arg Ser Phe Val Ala Arg Ala Ala Glu Tyr Asp Leu
    50                  55                  60

Pro Leu Val Gly Asn Lys Ala Pro Asp Phe Ala Ala Glu Ala Val Phe
65                  70                  75                  80

Asp Gln Glu Phe Ile Asn Val Lys Leu Ser Asp Tyr Ile Gly Lys Lys
                85                  90                  95

Tyr Val Ile Leu Phe Phe Tyr Pro Leu Asp Phe Thr Phe Val Cys Pro
            100                 105                 110

Thr Glu Ile Thr Ala Phe Ser Asp Arg His Glu Glu Phe Glu Lys Ile
        115                 120                 125

Asn Thr Glu Ile Leu Gly Val Ser Val Asp Ser Val Phe Ser His Leu
```

```
                130                 135                 140
Ala Trp Val Gln Thr Glu Arg Lys Ser Gly Gly Leu Gly Asp Leu Lys
145                 150                 155                 160

Tyr Pro Leu Val Ser Asp Val Thr Lys Ser Ile Ser Lys Ser Phe Gly
                165                 170                 175

Val Leu Ile Pro Asp Gln Gly Ile Ala Leu Arg Gly Leu Phe Met Ile
                180                 185                 190

Asp Lys Glu Gly Val Ile Gln His Ser Thr Ile Asn Asn Leu Gly Ile
                195                 200                 205

Gly Arg Ser Val Asp Glu Thr Leu Arg Thr Leu Gln Ala Leu Gln Tyr
                210                 215                 220

Val Gln Glu Asn Pro Asp Glu Val Cys Pro Ala Gly Trp Lys Pro Gly
225                 230                 235                 240

Glu Lys Ser Met Lys Pro Asp Pro Lys Gly Ser Lys Glu Tyr Phe Ala
                245                 250                 255

Ala Ile

<210> SEQ ID NO 178
<211> LENGTH: 210
<212> TYPE: PRT
<213> ORGANISM: Unknown
<220> FEATURE:
<223> OTHER INFORMATION: PRX protein

<400> SEQUENCE: 178

Asp Ala Arg Ala Arg Ser Phe Val Ala Arg Ala Ala Glu Tyr Asp
1               5                   10                  15

Leu Pro Leu Val Gly Asn Lys Ala Pro Asp Phe Ala Ala Glu Ala Val
                20                  25                  30

Phe Asp Gln Glu Phe Ile Asn Val Lys Leu Ser Asp Tyr Ile Gly Lys
                35                  40                  45

Lys Tyr Val Ile Leu Phe Phe Tyr Pro Leu Asp Phe Thr Phe Val Cys
50                  55                  60

Pro Thr Glu Ile Thr Ala Phe Ser Asp Arg His Glu Glu Phe Glu Lys
65                  70                  75                  80

Ile Asn Thr Glu Ile Leu Gly Val Ser Val Asp Ser Val Phe Ser His
                85                  90                  95

Leu Ala Trp Val Gln Thr Glu Arg Lys Ser Gly Gly Leu Gly Asp Leu
                100                 105                 110

Lys Tyr Pro Leu Val Ser Asp Val Thr Lys Ser Ile Ser Lys Ser Phe
                115                 120                 125

Gly Val Leu Ile Pro Asp Gln Gly Ile Ala Leu Arg Gly Leu Phe Ile
                130                 135                 140

Ile Asp Lys Glu Gly Val Ile Gln His Ser Thr Ile Asn Asn Leu Gly
145                 150                 155                 160

Ile Gly Arg Ser Val Asp Glu Thr Leu Arg Thr Leu Gln Ala Leu Gln
                165                 170                 175

Tyr Val Lys Lys Pro Asp Glu Val Cys Pro Ala Gly Trp Lys Pro Gly
                180                 185                 190

Glu Lys Ser Met Lys Pro Asp Pro Lys Gly Ser Lys Glu Tyr Phe Ala
                195                 200                 205

Ala Ile
210

<210> SEQ ID NO 179
```

```
<211> LENGTH: 210
<212> TYPE: PRT
<213> ORGANISM: Unknown
<220> FEATURE:
<223> OTHER INFORMATION: PRX protein

<400> SEQUENCE: 179

Asp Ala Arg Ala Arg Ser Phe Val Ala Arg Ala Ala Glu Tyr Asp
1               5                   10                  15

Leu Pro Leu Val Gly Asn Lys Ala Pro Asp Phe Ala Ala Glu Ala Val
            20                  25                  30

Phe Asp Gln Glu Phe Ile Asn Val Lys Leu Ser Asp Tyr Ile Gly Lys
            35                  40                  45

Lys Tyr Val Ile Leu Phe Phe Tyr Pro Leu Asp Phe Thr Phe Val Cys
50                  55                  60

Pro Thr Glu Ile Thr Ala Phe Ser Asp Arg His Glu Glu Phe Glu Lys
65                  70                  75                  80

Ile Asn Thr Glu Ile Leu Gly Val Ser Val Asp Ser Val Phe Ser His
                85                  90                  95

Leu Ala Trp Val Gln Thr Glu Arg Lys Ser Gly Gly Leu Gly Asp Leu
            100                 105                 110

Lys Tyr Pro Leu Val Ser Asp Val Thr Lys Ser Ile Ser Lys Ser Phe
            115                 120                 125

Gly Val Leu Ile Pro Asp Gln Gly Ile Ala Leu Arg Gly Leu Phe Ile
130                 135                 140

Ile Asp Lys Glu Gly Val Ile Gln His Ser Thr Ile Asn Asn Leu Gly
145                 150                 155                 160

Ile Gly Arg Ser Val Asp Glu Thr Leu Arg Thr Leu Arg Ala Leu Gln
                165                 170                 175

Tyr Val Lys Lys Pro Asp Glu Val Cys Pro Ala Gly Trp Lys Pro Gly
            180                 185                 190

Glu Lys Ser Met Lys Pro Asp Pro Lys Gly Ser Lys Glu Tyr Phe Ala
            195                 200                 205

Ala Ile
    210

<210> SEQ ID NO 180
<211> LENGTH: 242
<212> TYPE: PRT
<213> ORGANISM: Unknown
<220> FEATURE:
<223> OTHER INFORMATION: PRX protein

<400> SEQUENCE: 180

Asp Ala Arg Ala Arg Ser Phe Val Ala Arg Ala Ala Glu Tyr Asp
1               5                   10                  15

Leu Pro Leu Val Gly Asn Lys Ala Pro Asp Phe Ala Ala Glu Ala Val
            20                  25                  30

Phe Asp Gln Glu Phe Ile Asn Val Lys Leu Ser Asp Tyr Ile Gly Lys
            35                  40                  45

Lys Tyr Val Ile Leu Phe Phe Tyr Pro Leu Asp Phe Thr Phe Val Cys
50                  55                  60

Pro Thr Glu Ile Thr Ala Phe Ser Asp Arg His Glu Glu Phe Glu Lys
65                  70                  75                  80

Ile Asn Thr Glu Ile Leu Gly Val Ser Val Asp Ser Val Phe Ser His
                85                  90                  95

Leu Ala Trp Val Gln Thr Glu Arg Lys Ser Gly Gly Leu Gly Asp Leu
```

```
                  100                 105                 110
Lys Tyr Pro Leu Val Ser Asp Val Thr Lys Ser Ile Ser Lys Ser Phe
            115                 120                 125

Gly Val Leu Ile Pro Asp Gln Gly Ile Ala Leu Arg Gly Leu Phe Ile
            130                 135                 140

Ile Asp Lys Glu Gly Val Ile Gln His Ser Thr Ile Asn Asn Leu Gly
145                 150                 155                 160

Ile Gly Arg Ser Val Asp Glu Thr Leu Arg Thr Leu Gln Ala Leu Gln
                165                 170                 175

Tyr Val Lys Lys Pro Asp Glu Val Cys Pro Ala Gly Trp Lys Pro Gly
            180                 185                 190

Glu Lys Ser Met Lys Pro Asp Leu Gly Pro Lys Arg Ser Thr Arg Cys
            195                 200                 205

Tyr Leu Glu Arg Thr Phe Ala Leu Ser Cys Gly Val Leu Ser Trp Pro
            210                 215                 220

Phe Leu Gly Tyr Met Cys Phe Cys Asp Pro Ser Cys Ser Tyr His Ala
225                 230                 235                 240

Tyr Asn

<210> SEQ ID NO 181
<211> LENGTH: 261
<212> TYPE: PRT
<213> ORGANISM: Unknown
<220> FEATURE:
<223> OTHER INFORMATION: PRX protein

<400> SEQUENCE: 181

Met Ala Ala Cys Cys Ser Ser Leu Ala Thr Ala Val Ser Ser Ser Ser
1               5                   10                  15

Ala Lys Pro Leu Ala Gly Ile Pro Pro Ala Ala Pro His Ser Leu Ser
            20                  25                  30

Leu Pro Arg Ala Pro Ala Arg Pro Leu Arg Leu Ser Ala Ser Ser
            35                  40                  45

Ser Arg Ser Ala Arg Ala Ser Ser Phe Val Ala Arg Ala Gly Gly Val
        50                  55                  60

Asp Asp Ala Pro Leu Val Gly Asn Lys Ala Pro Asp Phe Asp Ala Glu
65                  70                  75                  80

Ala Val Phe Asp Gln Glu Phe Ile Asn Val Lys Leu Ser Asp Tyr Ile
                85                  90                  95

Gly Lys Lys Tyr Val Ile Leu Phe Phe Tyr Pro Leu Asp Phe Thr Phe
            100                 105                 110

Val Cys Pro Thr Glu Ile Thr Ala Phe Ser Asp Arg Tyr Asp Glu Phe
            115                 120                 125

Glu Lys Leu Asn Thr Glu Ile Leu Gly Val Ser Ile Asp Ser Val Phe
            130                 135                 140

Ser His Leu Ala Trp Val Gln Thr Asp Arg Lys Ser Gly Gly Leu Gly
145                 150                 155                 160

Asp Leu Lys Tyr Pro Leu Ile Ser Asp Val Thr Lys Ser Ile Ser Lys
                165                 170                 175

Ser Phe Gly Val Leu Ile Pro Asp Gln Gly Ile Ala Leu Arg Gly Leu
            180                 185                 190

Phe Ile Ile Asp Lys Glu Gly Val Ile Gln His Ser Thr Ile Asn Asn
            195                 200                 205

Leu Ala Ile Gly Arg Ser Val Asp Glu Thr Met Arg Thr Leu Gln Ala
            210                 215                 220
```

-continued

```
Leu Gln Tyr Val Gln Asp Asn Pro Asp Glu Val Cys Pro Ala Gly Trp
225                 230                 235                 240

Lys Pro Gly Asp Lys Ser Met Lys Pro Asp Pro Lys Gly Ser Lys Glu
            245                 250                 255

Tyr Phe Ala Ala Ile
            260

<210> SEQ ID NO 182
<211> LENGTH: 276
<212> TYPE: PRT
<213> ORGANISM: Unknown
<220> FEATURE:
<223> OTHER INFORMATION: PRX protein

<400> SEQUENCE: 182

Met Ala Ala Cys Cys Ser Ser Leu Ala Thr Ala Val Ser Ser Ser Ser
1               5                   10                  15

Ala Lys Pro Leu Ala Gly Ile Pro Pro Ala Ser Pro His Ser Leu Ser
            20                  25                  30

Leu Pro Arg Ser Pro Ala Ala Ala Arg Pro Leu Arg Leu Ser Ala
        35                  40                  45

Ser Ser Ser Arg Ser Ala Arg Ala Ser Ser Phe Val Ala Arg Ala Gly
    50                  55                  60

Gly Val Asp Asp Ala Pro Leu Val Gly Asn Lys Ala Pro Asp Phe Asp
65                  70                  75                  80

Ala Glu Ala Val Phe Asp Gln Glu Phe Ile Asn Val Lys Leu Ser Asp
                85                  90                  95

Tyr Ile Gly Lys Lys Tyr Val Ile Leu Phe Phe Tyr Pro Leu Asp Phe
            100                 105                 110

Thr Phe Val Cys Pro Thr Glu Ile Thr Ala Phe Ser Asp Arg Tyr Asp
        115                 120                 125

Glu Phe Glu Lys Leu Asn Thr Glu Ile Leu Gly Val Ser Ile Asp Ser
    130                 135                 140

Val Phe Ser His Leu Ala Trp Val Gln Thr Asp Arg Lys Ser Gly Gly
145                 150                 155                 160

Leu Gly Asp Leu Lys Tyr Pro Leu Ile Ser Asp Val Thr Lys Ser Ile
                165                 170                 175

Ser Lys Ser Phe Gly Val Leu Ile Pro Asp Gln Gly Ile Ala Leu Arg
            180                 185                 190

Gly Leu Phe Ile Ile Asp Lys Glu Gly Val Ile Gln His Ser Thr Ile
        195                 200                 205

Asn Asn Leu Ala Ile Gly Arg Ser Val Asp Glu Thr Met Arg Thr Leu
    210                 215                 220

Gln Ala Ser Ser Leu Glu Tyr Thr Leu Leu Ser Ala His Thr Ala Leu
225                 230                 235                 240

Gln Tyr Val Gln Asp Asn Pro Asp Glu Val Cys Pro Ala Gly Trp Lys
                245                 250                 255

Pro Gly Asp Lys Ser Met Lys Pro Asp Pro Lys Gly Ser Lys Glu Tyr
            260                 265                 270

Phe Ala Ala Ile
            275

<210> SEQ ID NO 183
<211> LENGTH: 199
<212> TYPE: PRT
<213> ORGANISM: Unknown
```

<220> FEATURE:
<223> OTHER INFORMATION: PRX protein

<400> SEQUENCE: 183

| Arg | Ala | Ser | His | Ala | Glu | Lys | Pro | Leu | Val | Gly | Ser | Val | Ala | Pro | Asp |
|---|---|---|---|---|---|---|---|---|---|---|---|---|---|---|---|
| 1 | | | | 5 | | | | | 10 | | | | | 15 | |

Phe Lys Ala Gln Ala Val Phe Asp Gln Glu Phe Gln Glu Ile Thr Leu
     20       25       30

Ser Lys Tyr Arg Gly Lys Tyr Val Val Leu Phe Phe Tyr Pro Leu Asp
     35       40       45

Phe Thr Phe Val Cys Pro Thr Glu Ile Thr Ala Phe Ser Asp Arg Tyr
   50       55       60

Lys Glu Phe Lys Asp Ile Asn Thr Glu Val Leu Gly Val Ser Val Asp
65        70       75       80

Ser Gln Phe Thr His Leu Ala Trp Ile Gln Thr Asp Arg Lys Glu Gly
     85       90       95

Gly Leu Gly Asp Leu Ala Tyr Pro Leu Val Ala Asp Leu Lys Lys Glu
     100       105      110

Ile Ser Lys Ala Tyr Gly Val Leu Thr Glu Asp Gly Ile Ser Leu Arg
   115       120       125

Gly Leu Phe Ile Ile Asp Lys Glu Gly Val Val Gln His Ala Thr Ile
   130       135      140

Asn Asn Leu Ala Phe Gly Arg Ser Val Asp Glu Thr Lys Arg Val Leu
145        150       155      160

Gln Ala Ile Gln Tyr Val Gln Ser Asn Pro Asp Glu Val Cys Pro Ala
     165       170      175

Gly Trp Lys Pro Gly Asp Lys Thr Met Lys Pro Asp Pro Lys Gly Ser
     180       185      190

Lys Glu Tyr Phe Ser Ala Val
     195

<210> SEQ ID NO 184
<211> LENGTH: 259
<212> TYPE: PRT
<213> ORGANISM: Unknown
<220> FEATURE:
<223> OTHER INFORMATION: PRX protein

<400> SEQUENCE: 184

Met Glu Thr Val Ala Ser Leu Ser Arg Ala Ala Leu Ala Gly Ala Pro
1        5       10       15

Ala Ala Thr Arg Ala Thr Ala Ser Pro Val Asn Arg Ala Val Val Pro
     20       25      30

Ala Ala Ser Arg Pro Arg Gly Gly Arg Leu Cys Cys Arg Arg Ser Leu
     35       40      45

Thr Ala Val Ser Ala Ala Gly Ala Ser Pro Pro Val Ser Pro Ser
   50       55       60

Pro Ser Pro Asp Gly Gly Ser Pro Gly Val Trp Asp Ala Leu Gly Gly
65        70       75      80

Val Ser Val Leu Ala Ala Gly Thr Gly Glu Ala Val Gln Leu Arg Asp
     85       90      95

Leu Trp Asp Pro Thr Glu Gly Val Ala Val Val Ala Leu Leu Arg His
     100       105      110

Phe Gly Cys Phe Cys Cys Trp Glu Leu Ala Ser Val Leu Lys Glu Ser
   115       120      125

Met Ala Lys Phe Asp Ala Ala Gly Ala Lys Leu Ile Ala Ile Gly Val

```
            130                 135                 140
Gly Thr Pro Asp Lys Ala Arg Ile Leu Ala Asp Gly Leu Pro Phe Pro
145                 150                 155                 160

Val Asp Ser Leu Tyr Ala Asp Pro Glu Arg Lys Ala Tyr Asp Val Leu
                165                 170                 175

Gly Leu Tyr His Gly Leu Gly Arg Thr Leu Ile Ser Pro Ala Lys Met
            180                 185                 190

Tyr Ser Gly Leu Asn Ser Ile Lys Lys Val Thr Lys Asn Tyr Thr Leu
                195                 200                 205

Lys Gly Thr Pro Ala Asp Leu Thr Gly Ile Leu Gln Gln Gly Gly Met
            210                 215                 220

Leu Val Phe Arg Gly Lys Glu Leu Leu Tyr Ser Trp Lys Asp Lys Gly
225                 230                 235                 240

Thr Gly Asp His Ala Pro Leu Asp Asp Val Leu Asn Ala Cys Cys Asn
                245                 250                 255

Arg Thr Ser

<210> SEQ ID NO 185
<211> LENGTH: 258
<212> TYPE: PRT
<213> ORGANISM: Unknown
<220> FEATURE:
<223> OTHER INFORMATION: PRX protein

<400> SEQUENCE: 185

Met Ala Ala Ala Ala Ser Thr Ser Leu Pro Val Pro Arg Val Ser
1               5                   10                  15

Leu Pro Pro Ser Ala Arg Pro Ala Ala Pro Arg His Gly Leu Leu
                20                  25                  30

Ile Pro Gly Arg Arg Gly Cys Phe Arg Leu Arg Gly Ser Pro Ala Ala
            35                  40                  45

Pro Ala Ala Ala Ser Gly Ser Pro Ser Val Pro Ser Ser Ser Pro
50                  55                  60

Glu Ala Gly Ser Gly Ile Gly Asp Ala Leu Gly Gly Val Ala Ile Tyr
65                  70                  75                  80

Ser Ala Ala Thr Gly Glu Pro Val Leu Phe Arg Asp Leu Trp Asp Gln
                85                  90                  95

Asn Glu Gly Met Ala Val Val Ala Leu Leu Arg His Phe Gly Cys Pro
                100                 105                 110

Cys Cys Trp Glu Leu Ala Ser Val Leu Arg Asp Thr Lys Glu Arg Phe
            115                 120                 125

Asp Ser Ala Gly Val Lys Leu Ile Ala Val Gly Val Gly Thr Pro Asp
130                 135                 140

Lys Ala Arg Ile Leu Ala Glu Arg Leu Pro Phe Pro Leu Asp Tyr Leu
145                 150                 155                 160

Tyr Ala Asp Pro Glu Arg Lys Ala Tyr Asp Leu Leu Gly Leu Tyr Phe
                165                 170                 175

Gly Ile Gly Arg Thr Phe Phe Asn Pro Ala Ser Ala Ser Val Phe Ser
            180                 185                 190

Arg Phe Asp Ser Leu Lys Glu Ala Val Lys Asn Tyr Thr Ile Glu Ala
                195                 200                 205

Thr Pro Asp Asp Arg Ala Ser Val Leu Gln Gln Gly Gly Met Phe Val
            210                 215                 220

Phe Arg Gly Lys Glu Leu Ile Tyr Ala Arg Lys Asp Glu Gly Thr Gly
225                 230                 235                 240
```

Asp His Ala Pro Leu Asp Asp Val Leu Asn Ile Cys Cys Lys Ala Pro
             245                 250                 255

Ala Ala

<210> SEQ ID NO 186
<211> LENGTH: 217
<212> TYPE: PRT
<213> ORGANISM: Unknown
<220> FEATURE:
<223> OTHER INFORMATION: PRX protein

<400> SEQUENCE: 186

Met Ala Phe Ala Val Ser Thr Ala Cys Arg Pro Ser Leu Leu Leu Pro
1               5                   10                  15

Pro Arg Gln Arg Ser Ser Pro Pro Arg Pro Arg Pro Leu Leu Cys Thr
            20                  25                  30

Pro Ser Thr Ala Ala Phe Arg Arg Gly Ala Leu Ser Ala Thr Thr Thr
        35                  40                  45

Pro Thr Pro Ala Arg Ala Ala Leu Pro Ser Thr Thr Gly Arg Asn Arg
    50                  55                  60

Ile Val Cys Gly Lys Val Ser Lys Gly Ser Ala Ala Pro Asn Phe Thr
65                  70                  75                  80

Leu Arg Asp Gln Asp Gly Arg Ala Val Ser Leu Ser Lys Phe Lys Gly
                85                  90                  95

Arg Pro Val Val Val Tyr Phe Tyr Pro Ala Asp Glu Thr Pro Gly Cys
            100                 105                 110

Thr Lys Gln Ala Cys Ala Phe Arg Asp Ser Tyr Glu Lys Phe Lys Lys
        115                 120                 125

Ala Gly Ala Glu Val Ile Gly Ile Ser Gly Asp Asp Ala Ala Ser His
    130                 135                 140

Lys Glu Phe Lys Lys Tyr Lys Leu Pro Phe Thr Leu Leu Ser Asp Glu
145                 150                 155                 160

Glu Gly Asn Lys Val Arg Lys Glu Trp Gly Val Pro Ala Asp Leu Phe
                165                 170                 175

Gly Thr Leu Pro Gly Arg Gln Thr Tyr Val Leu Asp Lys Asn Gly Val
            180                 185                 190

Val Gln Tyr Ile Tyr Asn Asn Gln Phe Gln Pro Glu Lys His Ile Gly
        195                 200                 205

Glu Thr Leu Lys Ile Leu Gln Ser Leu
    210                 215

<210> SEQ ID NO 187
<211> LENGTH: 251
<212> TYPE: PRT
<213> ORGANISM: Unknown
<220> FEATURE:
<223> OTHER INFORMATION: PRX protein

<400> SEQUENCE: 187

Met Ala Ala Arg Ala Pro Leu Pro Val Pro His Ala Ala Ala Thr Ser
1               5                   10                  15

Pro Arg Pro Ala Ala Ala Ser Ser Leu Leu Arg Ala Arg Gly Pro Cys
            20                  25                  30

Ala Ser Leu Leu Tyr Pro Arg Arg Leu Arg Phe Ser Val Ala Pro Val
        35                  40                  45

Ala Ala Ala Lys Pro Glu Ala Val Gly Arg Ala Gly Glu Ala Ala Ala
    50                  55                  60

```
Ala Pro Val Glu Gly Leu Ala Lys Ser Leu Gln Gly Val Glu Val Phe
 65                  70                  75                  80

Asp Leu Ser Gly Lys Ala Val Pro Val Val Asp Leu Trp Lys Asp Arg
                 85                  90                  95

Lys Ala Ile Val Ala Phe Ala Arg His Phe Gly Cys Val Leu Cys Arg
            100                 105                 110

Lys Arg Ala Asp Leu Leu Ala Ala Lys Gln Asp Ala Met Glu Ala Ala
        115                 120                 125

Gly Val Ala Leu Val Leu Ile Gly Pro Gly Thr Val Glu Gln Ala Lys
    130                 135                 140

Ala Phe Tyr Asp Gln Thr Lys Phe Lys Gly Glu Val Tyr Ala Asp Pro
145                 150                 155                 160

Ser His Ser Ser Tyr Asn Ala Leu Glu Phe Ala Phe Gly Leu Phe Ser
                165                 170                 175

Thr Phe Thr Pro Ser Ala Gly Leu Lys Ile Ile Gln Leu Tyr Met Glu
            180                 185                 190

Gly Tyr Arg Gln Asp Trp Glu Leu Ser Phe Glu Lys Thr Thr Arg Thr
        195                 200                 205

Lys Gly Gly Trp Tyr Gln Gly Gly Leu Leu Val Ala Gly Pro Gly Ile
210                 215                 220

Asp Asn Ile Leu Tyr Ile His Lys Asp Lys Glu Ala Gly Asp Asp Pro
225                 230                 235                 240

Asp Met Asp Asp Val Leu Lys Ala Cys Cys Ser
                245                 250

<210> SEQ ID NO 188
<211> LENGTH: 252
<212> TYPE: PRT
<213> ORGANISM: Unknown
<220> FEATURE:
<223> OTHER INFORMATION: PRX protein

<400> SEQUENCE: 188

Met Ser Leu Ala Thr Ala Ala Gly Ala Gln Pro Phe Val Arg Ser
1               5                   10                  15

Ser Ser Ser Ala Ala Ala Ser Ser Arg Pro Leu Leu Ala Val
                20                  25                  30

Ala Ala Ala Arg His Arg Arg Pro His Gly Ser Leu Ala Ala Ala
            35                  40                  45

Ala Ala Ala Arg Arg Arg Arg Arg Pro Leu Leu Gln Val Arg Ala
        50                  55                  60

Ala Arg Thr Glu Ser Thr Gly Val Ser Val Gly Phe Arg Ala Pro Gln
 65                  70                  75                  80

Phe Glu Leu Pro Glu Pro Leu Thr Gly Lys Leu Trp Thr Leu Asp Asp
                 85                  90                  95

Phe Glu Gly Asn Pro Ala Leu Leu Val Met Phe Val Cys Asn His Cys
            100                 105                 110

Pro Phe Val Lys His Leu Lys Lys Asp Ile Ala Lys Leu Thr Ser Phe
        115                 120                 125

Tyr Met Glu Lys Gly Leu Ala Ala Val Ala Ile Ser Ser Asn Ser Ile
    130                 135                 140

Val Thr His Pro Gln Asp Gly Pro Asp Tyr Ile Ala Glu Glu Ala Lys
145                 150                 155                 160

Leu Tyr Lys Tyr Ser Phe Pro Tyr Leu Tyr Asp Glu Ser Gln Glu Val
                165                 170                 175
```

```
Ala Lys Ala Phe Arg Ala Val Cys Thr Pro Glu Phe Tyr Leu Phe Lys
            180             185             190

Lys Asp Gly Arg Arg Pro Phe Glu Leu Phe Tyr His Gly Gln Phe Asp
        195             200             205

Asp Ser Arg Pro Ser Asn Asn Val Pro Val Thr Gly Arg Asp Leu Ser
    210             215             220

Arg Ala Ile Asp Cys Ala Leu Ser Gly Gln Glu Leu Pro Phe Val Pro
225             230             235             240

Lys Pro Ser Val Gly Cys Ser Ile Lys Trp His Pro
                245             250
```